(12) United States Patent
Buck et al.

(10) Patent No.: US 8,586,546 B2
(45) Date of Patent: *Nov. 19, 2013

(54) COMBINED TREATMENT WITH AN EGFR KINASE INHIBITOR AND AN AGENT THAT SENSITIZES TUMOR CELLS TO THE EFFECTS OF EGFR KINASE INHIBITORS

(75) Inventors: Elizabeth A. Buck, Huntington, NY (US); Graeme Griffin, Buffalo Grove, IL (US); Sharon M. Barr, Huntington, NY (US)

(73) Assignee: OSI Pharmaceuticals, LLC, Farmingdale, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/370,682

(22) Filed: Feb. 10, 2012

(65) Prior Publication Data
US 2012/0207767 A1    Aug. 16, 2012

Related U.S. Application Data

(60) Continuation of application No. 12/631,116, filed on Dec. 4, 2009, now Pat. No. 8,114,846, which is a division of application No. 11/717,545, filed on Mar. 13, 2007, now Pat. No. 7,651,687.

(60) Provisional application No. 60/781,877, filed on Mar. 13, 2006.

(51) Int. Cl.
*A61K 38/00* (2006.01)

(52) U.S. Cl.
USPC .......................................... 514/21.2; 530/350

(58) Field of Classification Search
USPC ...................................................... 514/21.2
See application file for complete search history.

(56) References Cited

U.S. PATENT DOCUMENTS

| 7,651,687 B2 | 1/2010 | Buck et al. |
| 7,700,594 B2 | 4/2010 | Chen et al. |
| 8,114,846 B2 | 2/2012 | Buck et al. |
| 2002/0183239 A1 | 12/2002 | Gibbons et al. |
| 2003/0008923 A1 | 1/2003 | Dukart |
| 2005/0272688 A1 | 12/2005 | Higgins et al. |
| 2006/0035907 A1 | 2/2006 | Christensen et al. |
| 2006/0094674 A1 | 5/2006 | Neel |
| 2007/0112005 A1* | 5/2007 | Chen et al. ............ 514/243 |
| 2007/0254883 A1 | 11/2007 | Crew |

FOREIGN PATENT DOCUMENTS

| WO | 2002080975 A1 | 10/2002 |
| WO | 2004004644 A2 | 1/2004 |
| WO | WO/2004/004644 * | 1/2004 |
| WO | 2005049021 A1 | 6/2005 |
| WO | 2005080593 A2 | 9/2005 |
| WO | 2006102111 A2 | 9/2006 |
| WO | 2007019385 A2 | 2/2007 |
| WO | 2007047754 A2 | 4/2007 |
| WO | 2007075554 A2 | 7/2007 |

OTHER PUBLICATIONS

Wu et al. (Mol. Cancer Jul. 20, 2005 4:25).*
Tannock, I.F. (Experimental Chemotherapy, Ch. 19—p. 338 and 352-359, in The Basic Science of Oncology Tannock and Hill, eds., New York 1992).*
Adjei, A. (2005) J Clin Oncol 23:5386-5403.
Brunn, G. (1996) The EMBO Journal 15(19):5256-5267.
Castillo, L. (2004) Annals of Oncology 15:1007-1012.
Fan, Q. (2006) Cancer Cell 9, 341-349.
Gemmill, R M et al., (2005) British Journal of Cancer 92(12):2266-2277.
Goudar, R K et al. (2005) Mol Cancer Therapeutics 4 (1):101-112.
Hildalgo, M. (2000) Oncogene 19:6680-6686.
Jacinto, E. (2004) Nature Cell Biology 6(11):1122-1128, Suppl. info. pp. 1-3.
Johnston, S. (2005) Clin. Cancer Res 11:889s-899s (suppl.).
Kim, D. (2005) Current Opinion Investigational Drugs 2005 6(12):1250-1258.
Kokubo, Y. (2005) Brit J Cancer 92:1711-1719.
Mills, G.B. (2001) PNAS 98(18):10031-10033.
Mita, M.M. (2003) Cancer Biology Therapy 2:4 Suppl. 1, S169-S177 (Jul./Aug. 2003).
Neshat, M.S. (2001) PNAS 98(18) 10314-10319.
Rathmell, W.K. (2005) Expert Rev Anticancer Ther 5(6):1031-1040.
Sarbassov, D. (2005) Science 307:1098-1101.
Sarbassov, D. (2006) Molecular Cell 22:159-168.
Sawyers, C. (2003) Cancer Cell 5:343-348.
Signal (2003) Signal 4(3).
Thomson, S. (2005) Cancer Res 65(20):9455-9462.
Vogt, P.K. (2006) Cancer Cell 9:327-328.
Wu, L. (2005) Cancer Res 65(7):2825-2831.
Yau, C.Y.F. (2005) Cancer Res 65(4):1497-1504.
De Bono, J.S. (2002) Trends in Mol. Medicine 8:S19-S26.
Dancey, J. (2003) Nature Rev Drug Discovery 2:296-313.
Shepherd, F (2005) N Engl J Med 353(2):123-132.
Birle, D.C. (2003 2nd edn) Proc Am Assoc Cancer Res 44:932 Abs. R4692.
Knight, Z. A. (2006) Cell 125:733-747.

(Continued)

*Primary Examiner* — Laura B Goddard
*Assistant Examiner* — Meera Natarajan
(74) *Attorney, Agent, or Firm* — Alexander A. Stewart; OSI Pharmaceuticals, LLC

(57) ABSTRACT

The present invention provides a method for treating tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor that binds to and directly inhibits both mTORC1 and mTORC2 kinases. The present invention also provides a pharmaceutical composition comprising an EGFR kinase inhibitor and an mTOR inhibitor that binds to and directly inhibits both mTORC1 and mTORC2 kinases, in a pharmaceutically acceptable carrier. A preferred example of an EGFR kinase inhibitor that can be used in practicing the methods of this invention is the compound erlotinib HCl (also known as TARCEVA®).

34 Claims, 19 Drawing Sheets

(56) References Cited

OTHER PUBLICATIONS

Engelman, J. A. (2005) Proc Natl Acad Sci U.S.A. 102:3788-3793.
Moasser, M.M. (2001) Cancer Res 61:7184-718.
International Search Report and Written Opinion of the International Searching Authority in PCT/US2007/006358 date of mailing Apr. 8, 2008.
Barnett, S.F, et al. (2005) Current Topics in Medicinal Chemistry 5 pp. 109-125.
Hennessy B.T. et al. (2005) Nature Reviews, Drug Discovery 4 pp. 988-1004.
International Preliminary Report on Patentability and Written Opinion in PCT/US2007/006358 date of issuance Sep. 16, 2008.

* cited by examiner

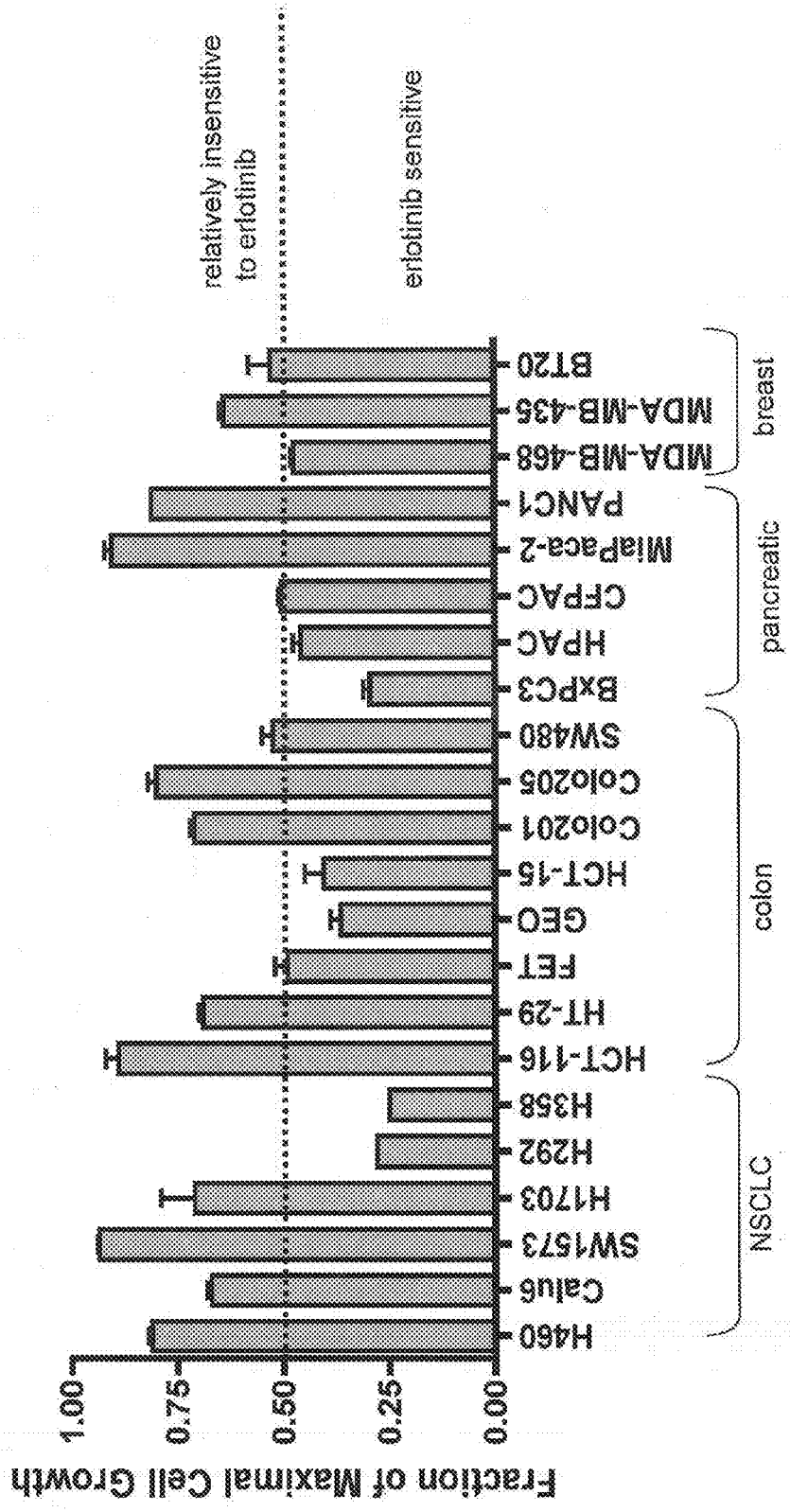
Figure 1. Erlotinib sensitivity in a panel of 22 cancer cell lines derived from 4 tumor types

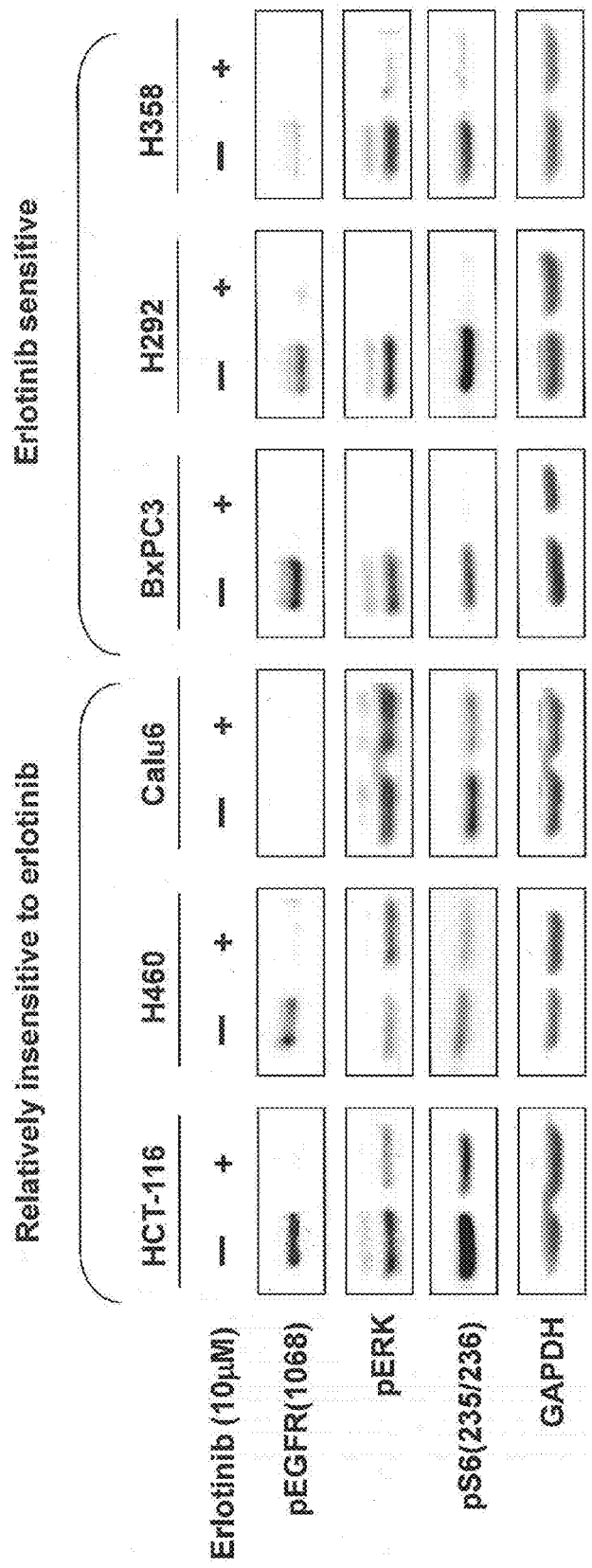
Figure 2. Effects of Erlotinib on pEGFR, pERK, and pS6 in a panel of 3 sensitive and 3 relatively insensitive cell lines

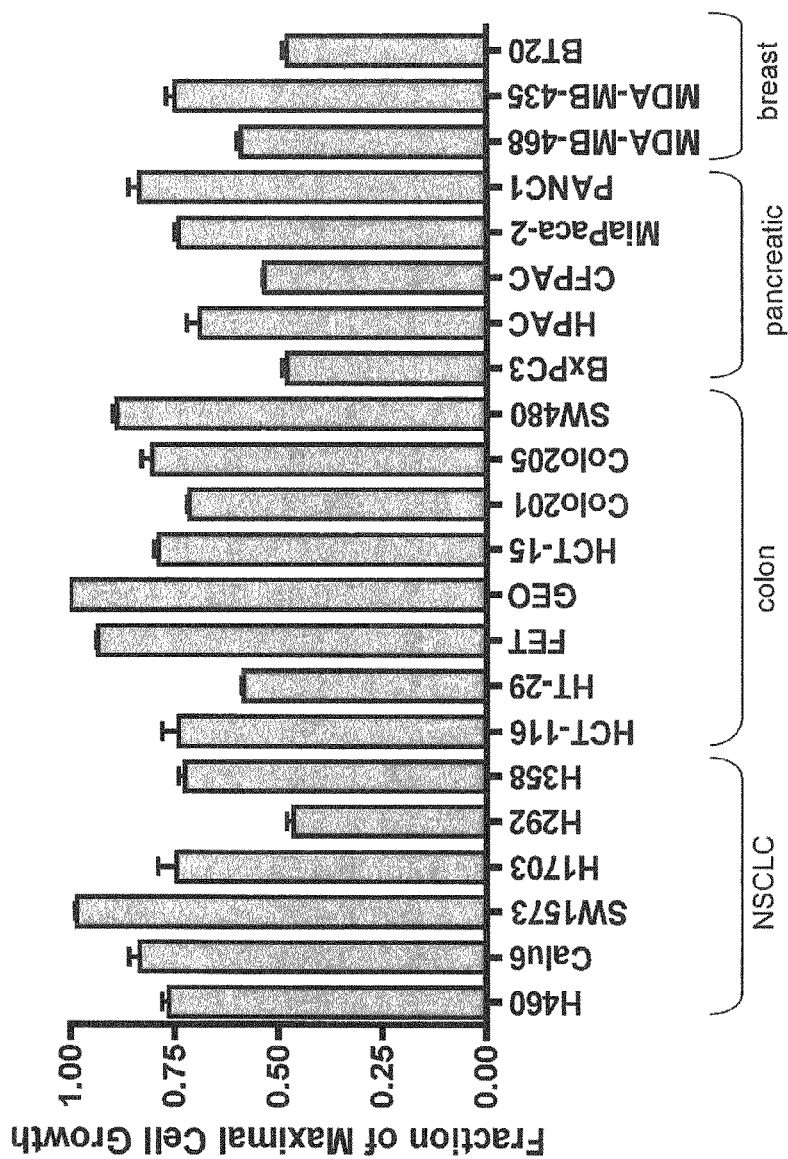
Figure 3A. Rapamycin sensitivity in a panel of 22 cancer cell lines derived from 4 tumor types

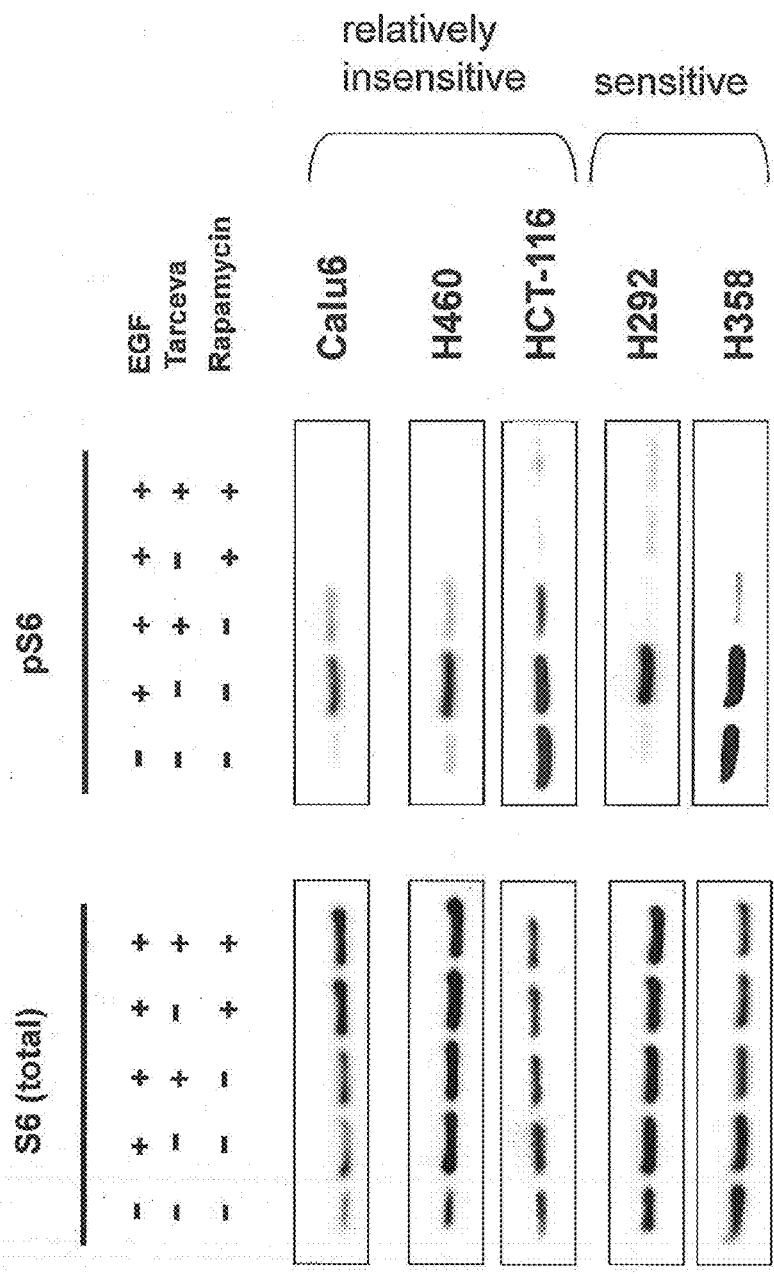
Figure 4. Rapamycin downregulates pS6 (235/236) in both erlotinib sensitive and relatively insensitive cell lines

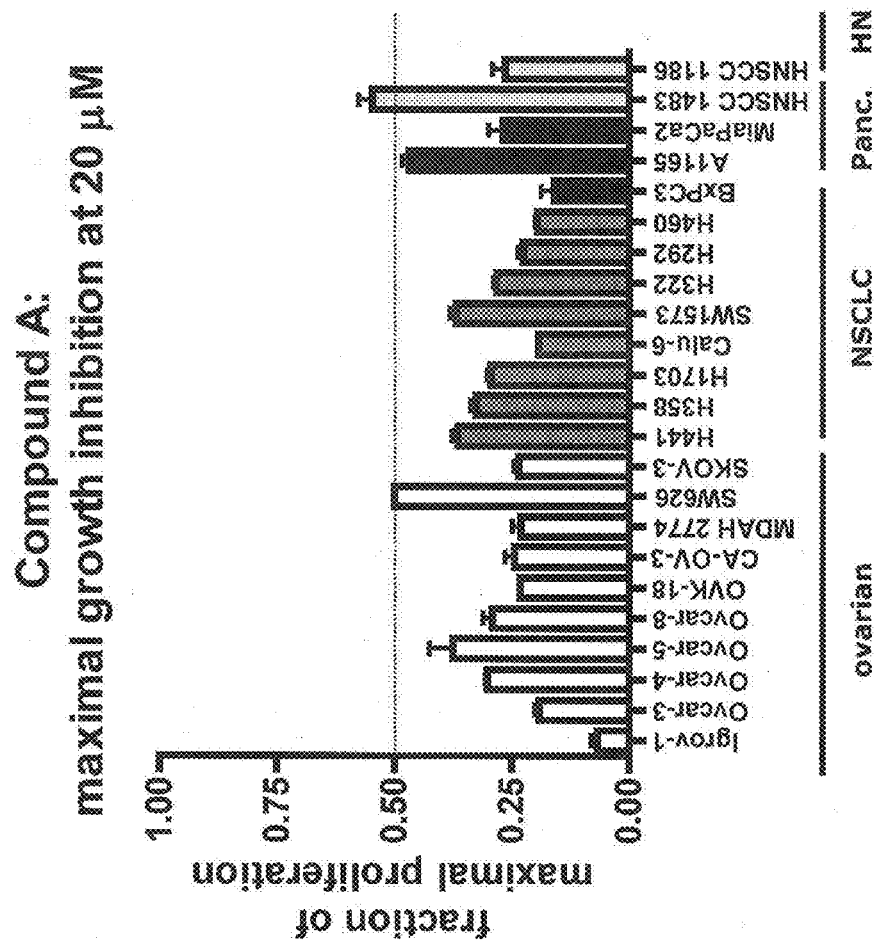
Figure 7. Compound A has single agent activity in a panel of non small cell, pancreatic lung cancer, ovarian cancer and head and neck squamous cell carcinoma cell lines.

Figure 8. The combination of compound A and erlotinib is synergistic in mesenchymal NSCLC and pancreatic cell lines

| Cell line | tumor type | EMT status | additive/ synergistic | EC50 cmpd A µM | % max inhibition, cmpd A alone | EC50, cmpd A + 10 µM erlotinib, µM | % max inhibition, cmpd A + 10 µM erlotinib |
|---|---|---|---|---|---|---|---|
| H292 | NSCLC | epithelial | additive | 0.34 | 77.4 | 0.3 | 93.52 |
| H322 | NSCLC | epithelial | additive | 0.47 | 71.7 | 0.46 | 92.4 |
| H358 | NSCLC | epithelial | additive | 1.3 | 67.4 | 1.2 | 87.2 |
| H441 | NSCLC | epithelial | additive | 0.82 | 63.4 | 0.7 | 80.12 |
| H460 | NSCLC | mesenchymal | synergistic | 1.49 | 80.5 | 0.07 | 88.63 |
| H1703 | NSCLC | mesenchymal | synergistic | 1.14 | 70.7 | 0.6 | 75.00 |
| Calu6 | NSCLC | mesenchymal | synergistic | 1.6 | 80.7 | 0.13 | 94.5 |
| SW1573 | NSCLC | mesenchymal | synergistic | 1.5 | 63.2 | 0.3 | 65.06 |
| BxPC3 | pancreatic | epithelial | additive | 0.26 | 84.1 | 0.3 | 91.2 |
| A1165 | pancreatic | mesenchymal | synergistic | 1.6 | 53.1 | 0.52 | 64.21 |
| MiaPaCa2 | pancreatic | mesenchymal | synergistic | 1.5 | 73.1 | 0.97 | 80.60 |

Figure 9. The combination of Compound A and erlotinib is synergistic in multiple tumor types

| cell line | tumor type | epithelial/ mesenchymal | additive/ synergistic | EC50, uM cmpd A | % max inhibition, cmpd A alone | EC50, uM cmpd A + 10 uM erlotinib | % max inhibition, cmpd A + 10 uM erlotinib |
|---|---|---|---|---|---|---|---|
| OVK18 | ovarian | N/D | additive | 0.78 | 76.9 | 0.78 | 88.9 |
| Igrov-1 | ovarian | epithelial | synergistic | 0.15 | 93.9 | 0.04 | 99.5 |
| CA-OV-3 | ovarian | N/D | additive | 0.73 | 75.5 | 0.24 | 78.8 |
| Ovcar-3 | ovarian | mesenchymal | synergistic | 0.14 | 80.9 | <0.01 | 86.8 |
| Ovcar-4 | ovarian | epithelial | synergistic | 0.38 | 69.7 | 0.1 | 77.5 |
| Ovcar-5 | ovarian | epithelial | additive | 0.64 | 62.4 | 0.64 | 82.7 |
| Ovcar-8 | ovarian | mesenchymal | synergistic | 2.4 | 59.6 | 1.6 | 74.6 |
| HNSCC 1186 | HNSCC | epithelial | synergistic | 0.24 | 70.3 | <.01 | 99.2 |
| HNSCC 1386 | HNSCC | mesenchymal | additive | 0.52 | 54.8 | 0.25 | 58.8 |
| HNSCC 1483 | HNSCC | epithelial | synergistic | 0.18 | 45.3 | <.01 | 58.8 |
| MDA-MB-468 | breast | epithelial | synergistic | 4.8 | 73 | 1.1 | 83 |
| MDA-MB-231 | breast | mesenchymal | synergistic | 5.3 | 73 | 1.6 | 72 |

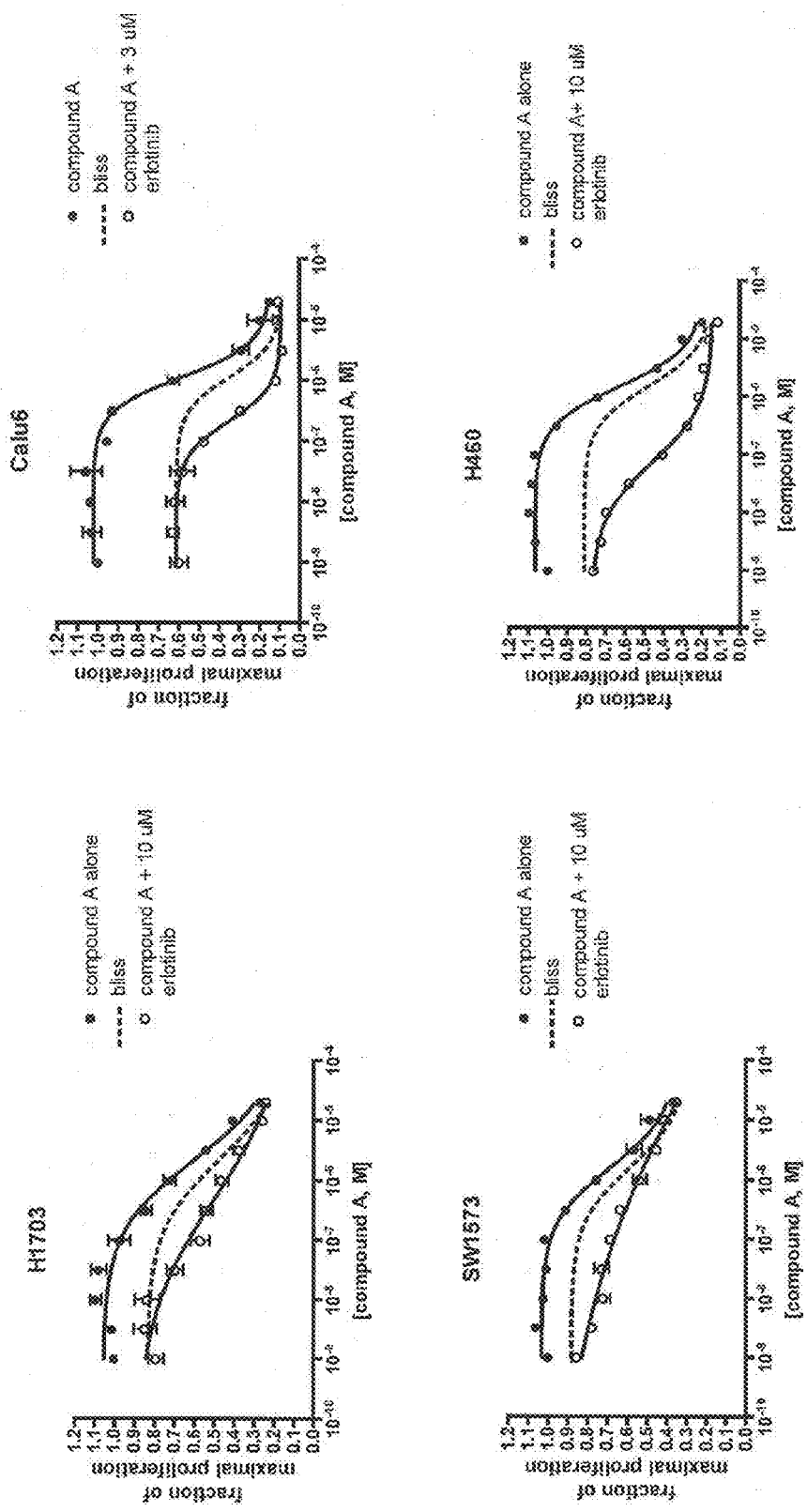
Figure 10-A. The combination of erlotinib and compound A is synergistic in mesenchymal NSCLC cell lines

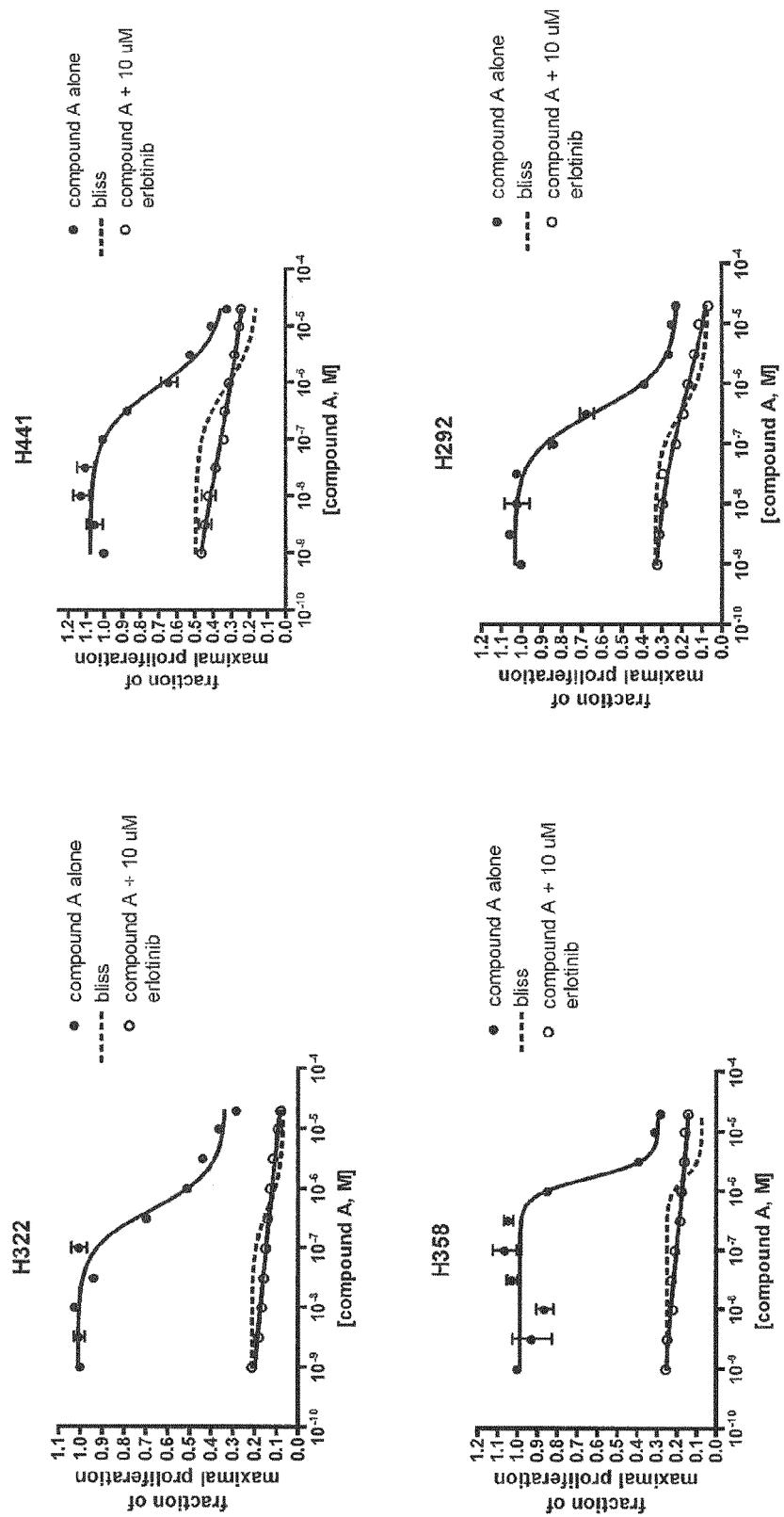
Figure 10-B. The combination of erlotinib and compound A is additive in epithelial NSCLC cell lines

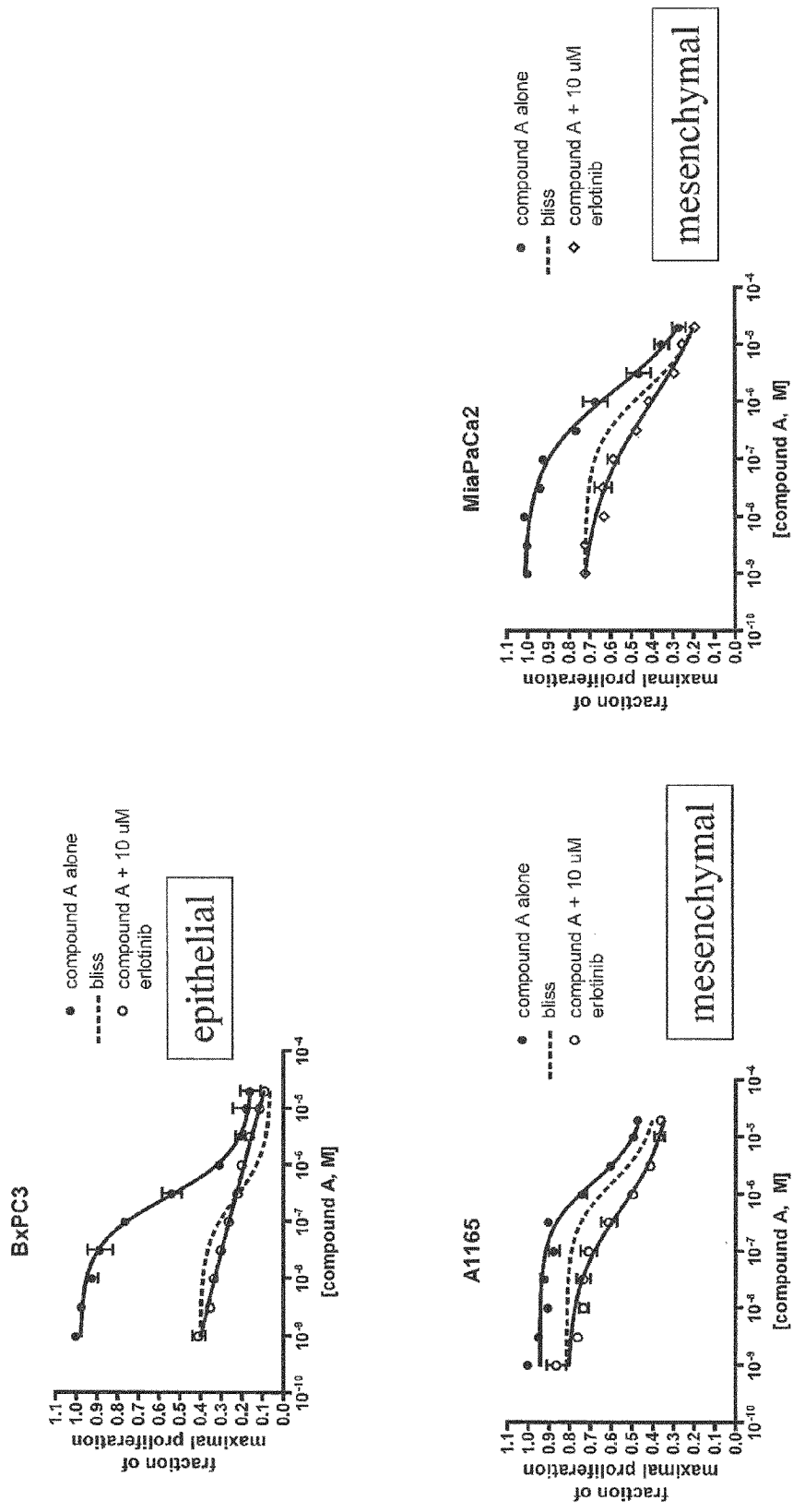
Figure 11. The combination of erlotinib and compound A is synergistic in mesenchymal pancreatic cell lines

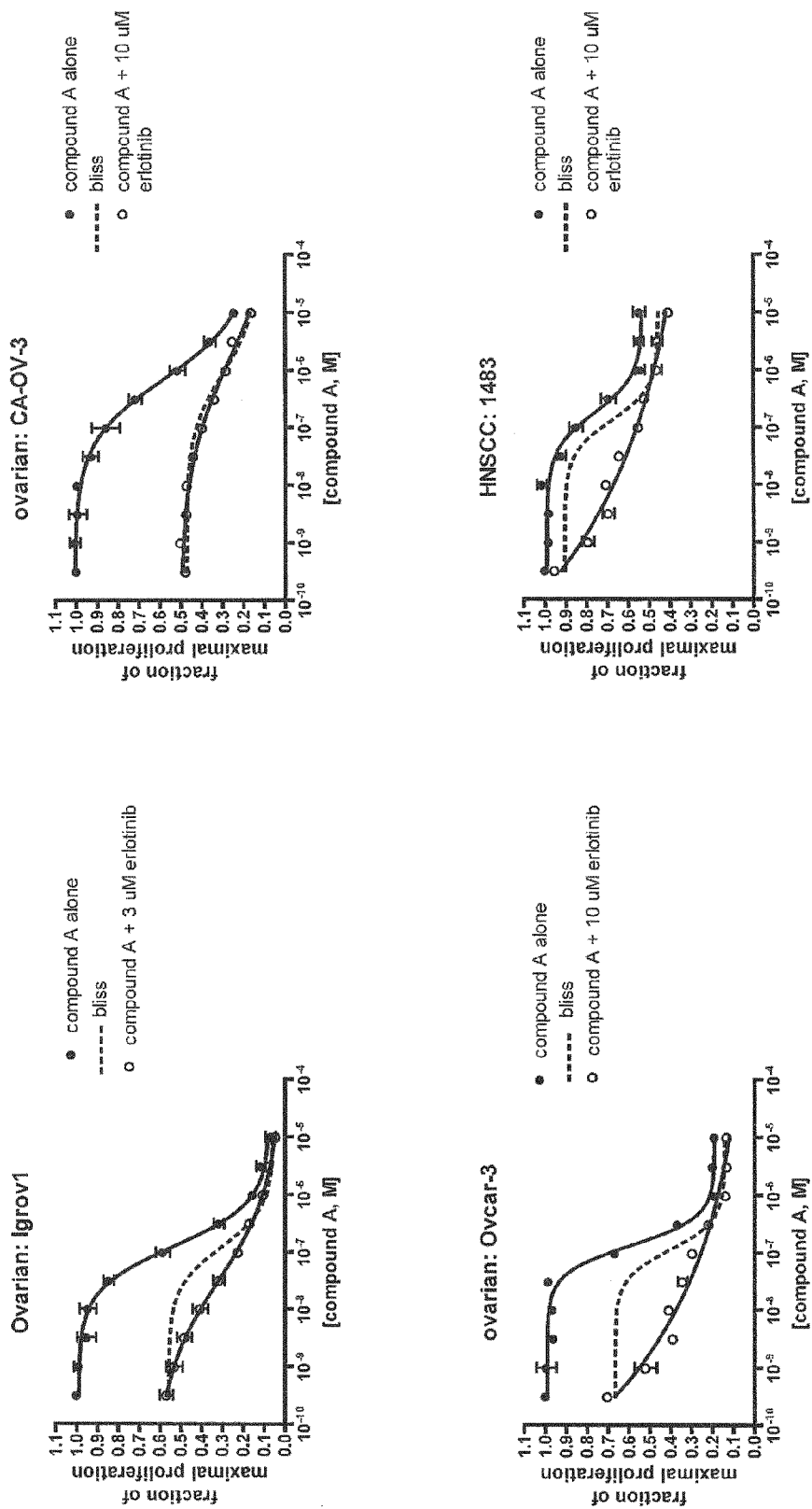
Figure 12. The combination of compound A and erlotinib is synergistic in multiple tumor types

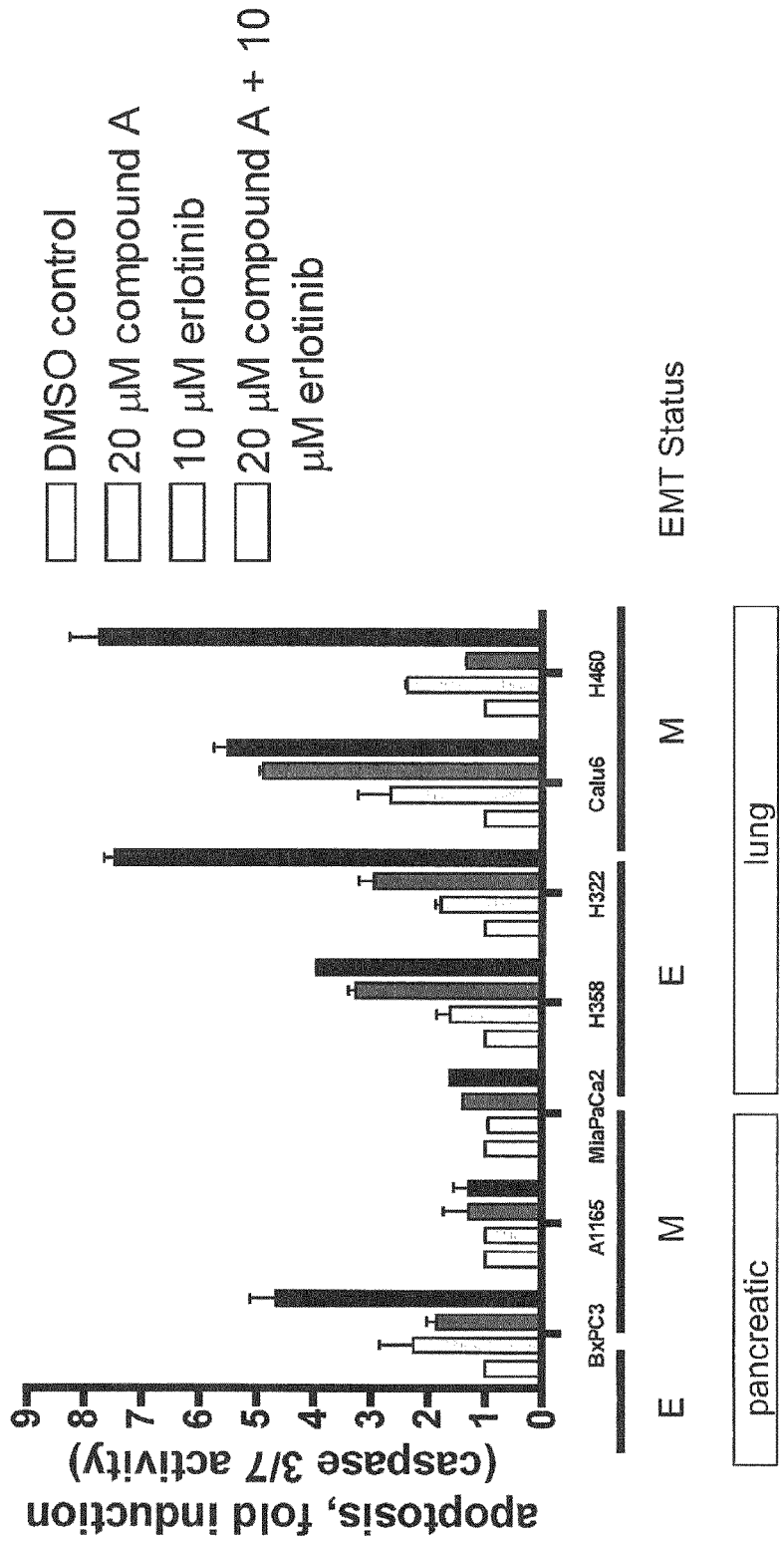
Figure 13. The combination of compound A and erlotinib enhances apoptosis in pancreatic and NSCLC cell lines

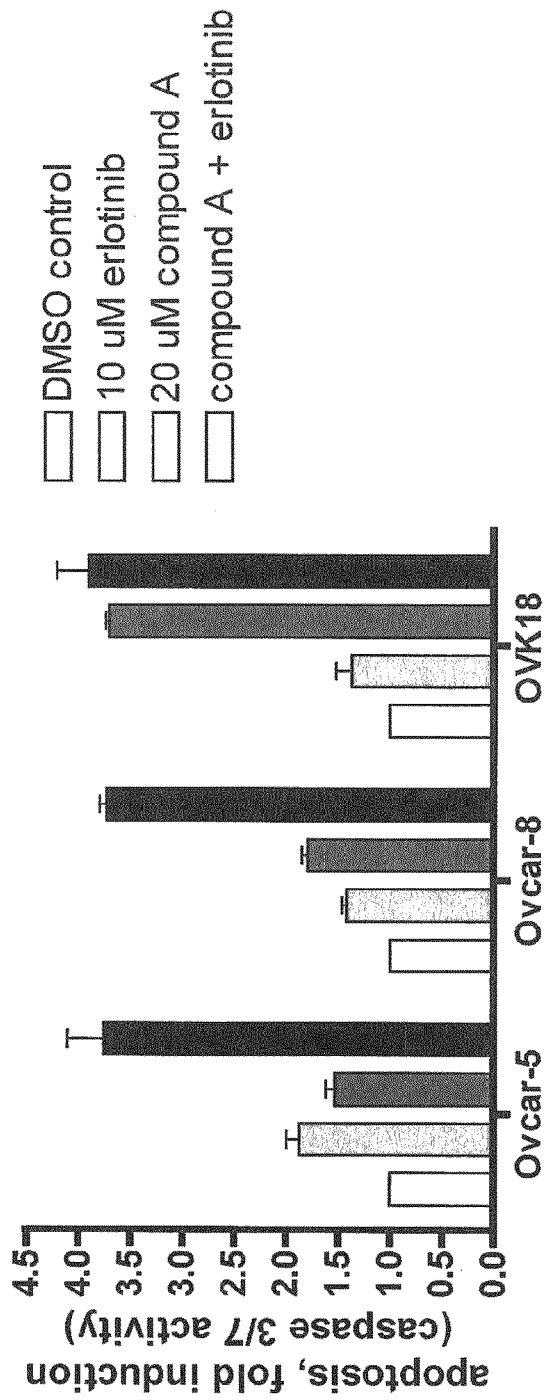
Figure 14. The combination of erlotinib and compound A enhances apoptosis in ovarian cell lines

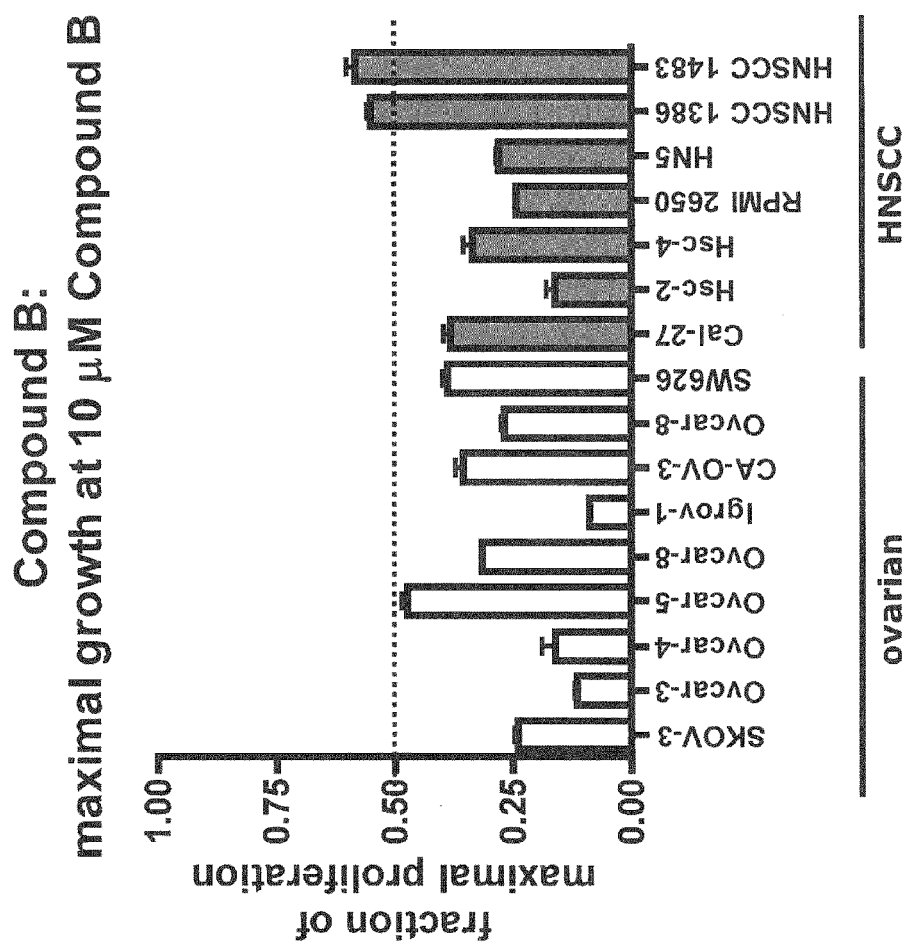
Figure 15. Compound B has single agent activity in a panel of ovarian cancer and head and neck squamous cell carcinoma cell lines.

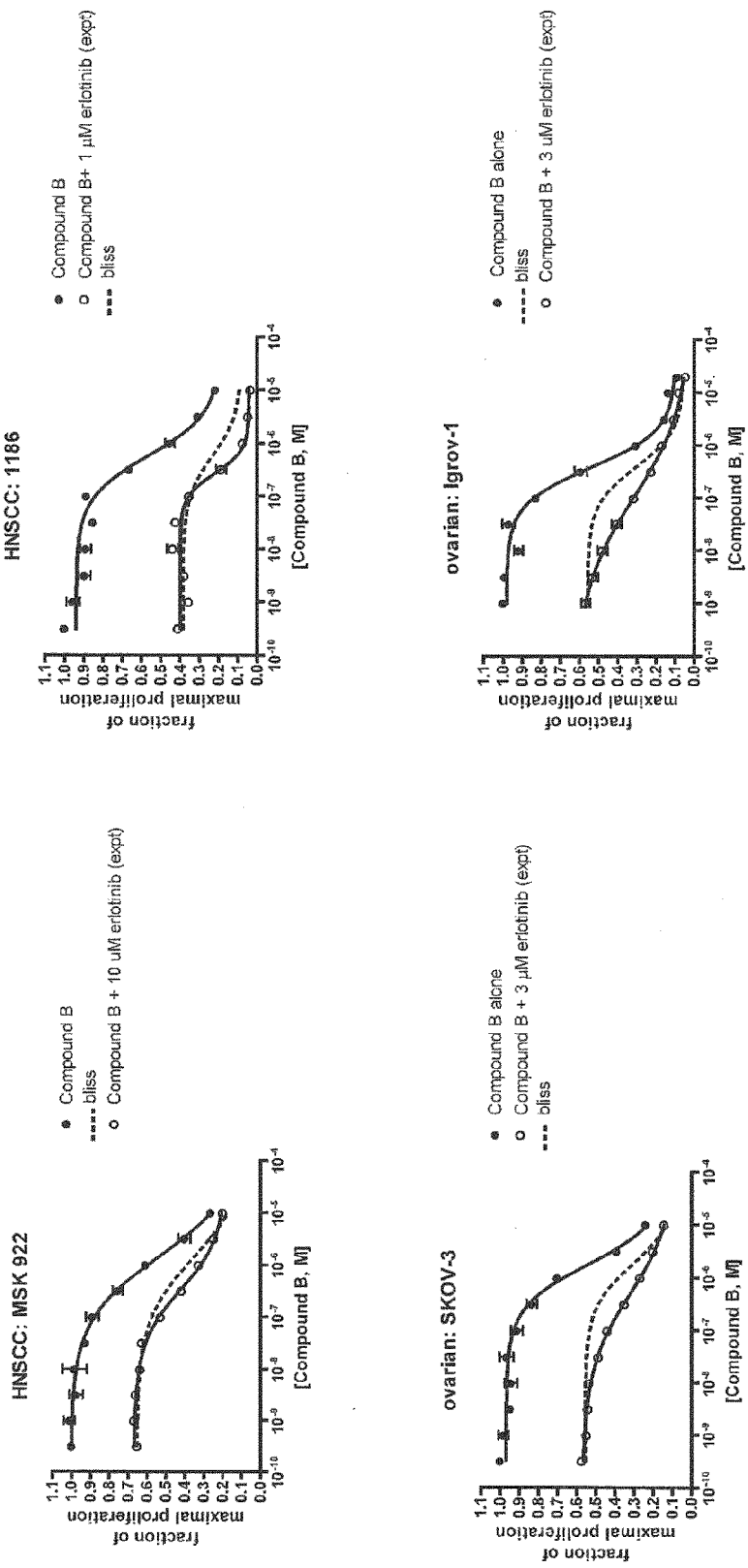
Figure 16. The combination of compound B and erlotinib is synergistic in multiple tumor types

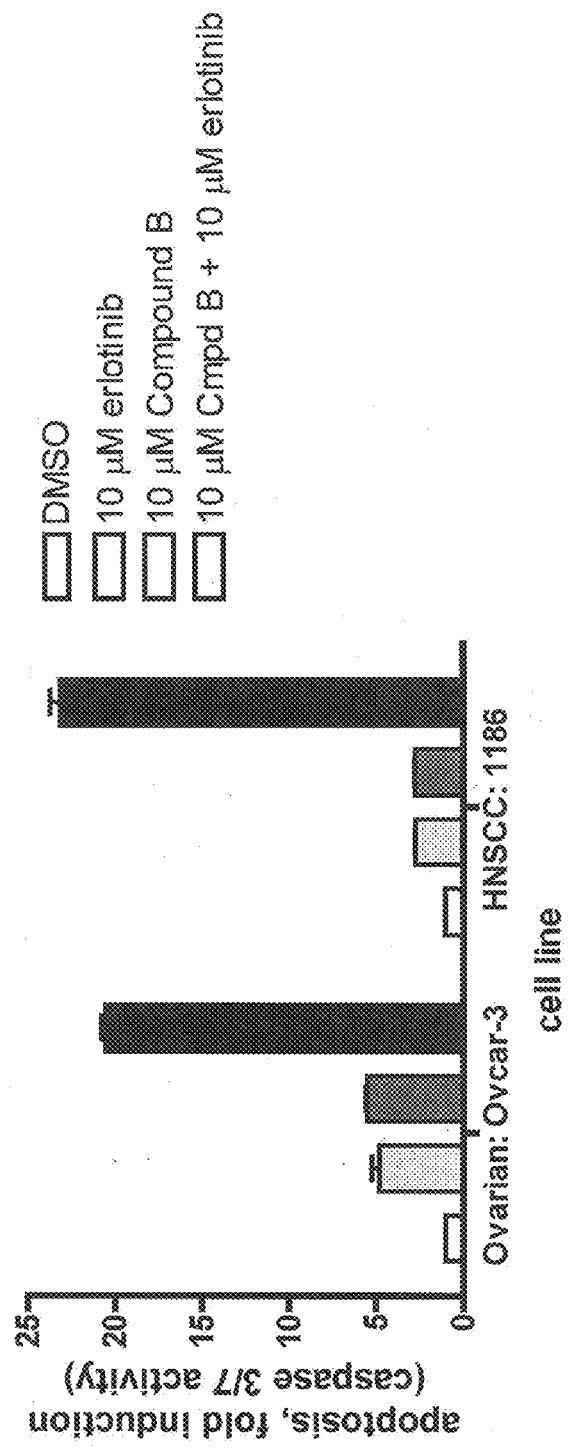
Figure 17. The combination of erlotinib and compound B enhances apoptosis in ovarian cell lines

COMBINED TREATMENT WITH AN EGFR KINASE INHIBITOR AND AN AGENT THAT SENSITIZES TUMOR CELLS TO THE EFFECTS OF EGFR KINASE INHIBITORS

CROSS-REFERENCE TO RELATED APPLICATIONS

This application is a continuation application which claims priority to U.S. application Ser. No. 12/631,116, now U.S. Pat. No. 8,114,846, which is a divisional of U.S. application Ser. No. 11/717,545, filed Mar. 13, 2007, now U.S. Pat. No. 7,651,687, which claims the benefit of U.S. Provisional Application No. 60/781,877 filed Mar. 13, 2006, all of which are herein incorporated by reference in their entirety.

BACKGROUND OF THE INVENTION

The present invention is directed to compositions and methods for treating cancer patients. Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide). More recently, gene targeted therapies, such as protein-tyrosine kinase inhibitors (e.g. imatinib; the EGFR kinase inhibitor, erlotinib) have increasingly been used in cancer therapy.

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA®) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors, but do not identify a completely non-responsive phenotype.

The development for use as anti-tumor agents of compounds that directly inhibit the kinase activity of the EGFR, as well as antibodies that reduce EGFR kinase activity by blocking EGFR activation, are areas of intense research effort (de Bono J. S. and Rowinsky, E. K. (2002) Trends in Mol. Medicine 8:S19-S26; Dancey, J. and Sausville, E. A. (2003) Nature Rev. Drug Discovery 2:92-313). Several studies have demonstrated, disclosed, or suggested that some EGFR kinase inhibitors might improve tumor cell or neoplasia killing when used in combination with certain other anti-cancer or chemotherapeutic agents or treatments (e.g. Herbst, R. S. et al. (2001) Expert Opin. Biol. Ther. 1:719-732; Solomon, B. et al (2003) Int. J. Radiat. Oncol. Biol. Phys. 55:713-723; Krishnan, S. et al. (2003) Frontiers in Bioscience 8, e1-13; Grunwald, V. and Hidalgo, M. (2003) J. Nat. Cancer Inst. 95:851-867; Seymour L. (2003) Current Opin. Investig. Drugs 4(6): 658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Ciardiello, F. et al. (2000) Clin. Cancer Res. 6:2053-2063; and Patent Publication No: US 2003/0157104).

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). More recently, erlotinib has demonstrated promising activity in phase I and II trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), CRC (Oza, M., et al. (2003) Proc. Am. Soc. Clin. Oncol. 22:196a, abstract 785) and MBC (Winer, E., et al. (2002) Breast Cancer Res. Treat. 76:5115a, abstract 445). In a phase III trial, erlotinib monotherapy significantly prolonged survival, delayed disease progression and delayed worsening of lung cancer-related symptoms in patients with advanced, treatment-refractory NSCLC (Shepherd, F. et al. (2005) N. Engl. J. Med. 353(2):123-132). While most of the clinical trial data for erlotinib relate to its use in NSCLC, preliminary results from phase I/II studies have demonstrated promising activity for erlotinib and capecitabine/erlotinib combination therapy in patients with wide range of human solid tumor types, including CRC (Oza, M., et al. (2003) Proc. Am. Soc. Clin. Oncol. 22:196a, abstract 785) and MBC (Jones, R. J., et al. (2003) Proc. Am. Soc. Clin. Oncol. 22:45a, abstract 180). In November 2004 the U.S. Food and Drug Administration (FDA) approved TARCEVA® for the treatment of patients with locally advanced or metastatic non-small cell lung cancer (NSCLC) after failure of at least one prior chemotherapy regimen. TARCEVA® is the only drug in the epidermal growth factor receptor (EGFR)

class to demonstrate in a Phase III clinical trial an increase in survival in advanced NSCLC patients.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as EGFR kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

Target-specific therapeutic approaches, such as erlotinib, are generally associated with reduced toxicity compared with conventional cytotoxic agents, and therefore lend themselves to use in combination regimens. Promising results have been observed in phase I/II studies of erlotinib in combination with bevacizumab (Mininberg, E. D., et al. (2003) Proc. Am. Soc. Clin. Oncol. 22:627a, abstract 2521) and gemcitabine (Dragovich, T., (2003) Proc. Am. Soc. Clin. Oncol. 22:223a, abstract 895). Recent data in NSCLC phase III trials have shown that first-line erlotinib or gefitinib in combination with standard chemotherapy did not improve survival (Gatzemeier, U., (2004) Proc. Am. Soc. Clin. Oncol. 23:617 (Abstract 7010); Herbst, R. S., (2004) Proc. Am. Soc. Clin. Oncol. 23:617 (Abstract 7011); Giaccone, G., et al. (2004) J. Clin. Oncol. 22:777; Herbst, R., et al. (2004) J. Clin. Oncol. 22:785). However, pancreatic cancer phase III trials have shown that first-line erlotinib in combination with gemcitabine did improve survival (OSI Pharmaceuticals/Genentech/Roche Pharmaceuticals Press Release, Sep. 20, 2004).

Activation of EGFR triggers multiple cascades of signal transduction pathways. EGFR contains at least six autophosphorylation sites that serve as docking nodes for a multitude of intracellular signaling molecules including adapter proteins and other enzymes. Therefore, rather than regulating a single linear pathway, activation of EGFR modulates entire networks of cellular signal transduction cascades. These signals affect both cell cycle progression/proliferation and apoptosis. Two signal transduction cascades that lie downstream of EGFR are the MAPK (mitogen activated protein kinase) and Akt pathways. In the MAPK pathway, EGFR activates the small GTP binding protein Ras to transfer cell growth signals through the Raf-MEK-ERK cascade, culminating in the regulation of transcription factors important for cell cycle progression.

EGFR can activate PI3K (through homodimers or heterodimers with HER3) to initiate signals through the PDK1-Akt pathway. Akt can positively regulate anti-apoptotic factors within the cell to promote cell survival. In addition Akt can activate the protein kinase mTOR (mammalian target of rapamycin) to promote cell growth and proliferation. mTOR is a major regulator of cell growth and proliferation in response to both growth factors and cellular nutrients. It is a key regulator of the rate limiting step for translation of mRNA into protein, the binding of the ribosome to mRNA. Here mTOR directly modulates the activities of a number of downstream signaling proteins involved in protein synthesis. Two substrates that are directly phosphorylated by mTOR include 4EBP1 and p70S6K. 4EBP1 is a transcriptional repressor that binds to eIF4E, blocking proper organization of the ribosome initiation complex. Phosphorylation of 4EBP1 by mTOR disrupts interactions with eIF4E, liberating eIF4E for translation. mTOR also directly phosphorylates and activates p70S6K, which in turn phosphorylates S6 ribosomal protein, leading to enhanced mRNA translation.

mTOR exists in at least 2 distinct multiprotein complexes described as raptor-mTOR complex (mTORC1) and rictor-mTOR complex (mTORC2) in mammalian cells (sometimes referred to as just TORC1 and TORC2). mTORC1 is composed of mTOR, GβL and raptor proteins and it binds to FKBP12-rapamycin. mTORC1 is a rapamycin-sensitive complex as its kinase activity is inhibited by FKB12-rapamycin in vitro. How FKBP12-rapamycin inhibits mTOR kinase activity is poorly understood. The drug rapamycin does not displace GβL or raptor from mTOR but does strongly destabilize the raptor-mTOR interaction. Extensive work with rapamycin indicates that mTORC1 complex positively regulates cell growth. The raptor branch of the mTOR pathway modulates number of processes, including mRNA translation, ribosome biogenesis, nutrient metabolism and autophagy. The two mammalian proteins, S6 Kinase 1 (S6K1) and 4E-BP1, which are linked to protein synthesis, are downstream targets of mTORC1. mTORC1 has been shown to phosphorylates S6K1 at T389 and is inhibited by FKBP12-rapamycin in vitro and by rapamycin in vivo. mTORC1 can also phosphorylate 4E-BP1 at T37/46 in vitro and in vivo.

mTORC2 is composed of mTOR, GβL and rictor proteins and it does not bind to FKBP12-rapamycin complex. mTORC2 is a rapamycin-insensitive complex as its kinase activity is not inhibited by FKBP12-rapamycin complex in vitro. It is unclear why FKBP12-rapamycin complex does not bind the rictor containing mTORC2 complex. Rictor or an unidentified component of the complex may block or occupy the FKBP12-rapamycin complex binding site or allosterically destroy the FKBP12-rapamycin complex binding pocket. It has been discovered recently that mTORC2 is a hydrophobic motif kinase for Akt/PKB and plays an important role in Akt/PKB activation. mTORC2 has been shown to phosphorylate PKB/Akt at S473 in vitro and in vivo. Akt/PKB is a key component of insulin/PI3K signaling pathway and modulates cell survival and proliferation through downstream substrates such as the FOXO class of transcription factors and p53 regulator mdm2. In addition, mTORC2 regulates the actin cytoskeleton through unknown mechanisms that involve PKCα and Rho. mTORC2 can also phosphorylate 4E-BP1 in vitro and in vivo.

Deregulation of mTOR pathway is emerging as a common theme in diverse human diseases and as a consequence drugs that target mTOR have therapeutic values. The diseases most clearly associated with deregulation of mTORC1 are tuberous sclerosis complex (TSC) and Lymphangioleiomyomatosis (LAM), both of which are cause by mutations in TSC1 or TSC2 tumor suppressors. Patients with TSC develop benign tumors that when present in brain, however, can cause seizures, mental retardation and death. LAM is a serious lung disease. Inhibition of mTORC1 may help patients with Peutz-Jeghers cancer-prone syndrome caused by LKB1 mutation.

mTORC1 may also have role in the genesis of sporadic cancers. Inactivation of several tumor suppressors, in particular PTEN, p53, VHL and NF1, has been linked to mTORC1 activation. Rapamycin and its analogues (eg CCI-779, RAD001 and AP23573) inhibit TORC1 and have shown moderate anti-cancer activity in phase II clinical trials. However, due to the negative signal from S6K1 to the insulin/PI3K/Akt pathway, it is important to note that inhibitors of mTORC1, like rapalogs, can activate PKB/Akt. If this effect persists with chronic rapamycin treatment it may provide cancer cells with an increased survival signal that may be clinically undesirable. The PI3K/Akt pathway is activated in many cancers. Activated Akt regulates cell survival, cell proliferation and metabolism by phosphorylating proteins such as BAD, FOXO, NF-ηB, $p21^{Cip1}$, $p27^{Kip1}$, GSK3β and others. AKT might also promote cell growth by phosphorylating TSC2. AKT activation probably promotes cellular transformation and resistance to apoptosis by collectively promoting growth, proliferation and survival, while inhibiting apoptotic pathways. An inhibitor of both mTORC1 and mTORC2 should be beneficial for treatment of tumors with elevated AKT phosphorylation, and should down-regulate cell growth, cell survival and cell proliferation.

Recent reports have shown that the sensitivity of cell lines to growth inhibition by EGFR inhibitors is dependent on the down-regulation of the PI3K-Akt pathway. There can be extensive overlap in signaling where an EGFR signaling pathway can also be regulated by several other receptor tyrosine kinases. This potential for multiple inputs in EGFR signaling pathways suggests that inhibiting EGFR alone may not allow for growth inhibition of all tumor cells and highlights the potential for multi-point intervention utilizing combinations of receptor tyrosine kinase inhibitors. Combining EGFR inhibitors with inhibitors of IGF1-R has shown success in some preclinical models. In addition to multiple inputs in growth factor signaling, specific mutations or protein deletions in downstream signaling pathways can affect sensitivity to EGFR inhibition. For example the MDA-468 breast tumor cell line contains a deletion of PTEN, and endogenous inhibitor of PI3K signaling. Reconstitution of PTEN in these cells enhances their sensitivity to EGFR inhibition. Such studies have suggested that combining EGFR inhibitors with agents, such as mTOR inhibitors, that antagonize downstream signaling pathways may permit enhanced sensitization in cell lines that either have redundancy in receptor tyrosine kinase signaling or contain specific mutations in downstream signaling.

Many inhibitors of mTOR have been identified and several are in clinical trials for the treatment of cancer (e.g. RAD001 (also known as Everolimus; Novartis); CCI-779 (also known as Temsirolimus; Wyeth); AP23573 (Ariad Pharmaceuticals); and KU-0059475 (Kudus Pharmaceuticals); Mita, M. M. et al. (2003) Cancer Biology & Therapy 2:4:Suppl. 1, S169-S177). The potential effectiveness of combinations of such mTOR inhibitors with other anti-cancer agents has also been suggested and is being tested in clinical trials (Adjei, A. and Hidalgo, M. (2005) J. Clin. Oncol. 23:5386-5403). Such combinations include combinations of mTOR inhibitors with protein-tyrosine kinase inhibitors (Sawyers, C. (2003) Cancer Cell 4:343-348; Gemmill, R. M. et al. (2005) Br. J. Cancer 92(12):2266-2277; Goudar, R. K. et al. (2005) Mol. Cancer Therapeutics 4(1):101-112; International Patent Publication WO 2004/004644; Birle, D. C., et al. Proc. Am. Assoc. Cancer Res. (2nd edn) (2003) 44: 932 Abs. R4692).

Despite the advances in treatment described above there remains a critical need for improved treatments for many human cancers. The invention described herein provides new anti-cancer combination therapies that are an improvement on the efficacy of either EGFR kinase inhibitors or mTOR inhibitors when administered alone. In particular, the present invention is directed to methods of combined treatment of breast, colon, NSCL or pancreatic cancer with an epidermal growth factor receptor (EGFR) kinase inhibitor and an mTOR inhibitor that sensitizes tumor cells of these cancers to the effects of EGFR kinase inhibitors, a result which has not previously been reported in the medical literature.

SUMMARY OF THE INVENTION

The present invention provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor, with or without additional agents or treatments, such as other anti-cancer drugs or radiation therapy.

The present invention also provides a method for treating tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor that binds to and directly inhibits both mTORC1 and mTORC2 kinases.

The present invention also provides a pharmaceutical composition comprising an EGFR kinase inhibitor and an mTOR inhibitor that binds to and directly inhibits both mTORC1 and mTORC2 kinases, in a pharmaceutically acceptable carrier.

A preferred example of an EGFR kinase inhibitor that can be used in this invention is the compound erlotinib HCl (also known as TARCEVA®).

BRIEF DESCRIPTION OF THE FIGURES

FIG. 1: Sensitivity of 22 cell lines derived from four tumor types to growth inhibition by erlotinib. Data are expressed as maximal cell growth at 72 hours in the presence of 10 μM erlotinib as compared to cells treated with DMSO alone. A 50% inhibition in maximal cell growth was used as a cutoff criteria for distinguishing sensitive from relatively insensitive cell lines.

FIG. 2: Immunoblot showing the effect of erlotinib on pEGFR, pERK, and pS6 in a panel of 3 sensitive and 3 relatively insensitive cell lines. Cells were treated with erlotinib or DMSO vehicle alone for 2 hours, lysates were prepared and run on gels for western blot.

FIG. 4: Immunoblot showing that rapamycin down-regulates pS6 (235/236) in cell lines are either sensitive or relatively insensitive to erlotinib. Cells were treated with rapamycin, erlotinib, or the combination for 2 hours. Where indicated 2 ng/ml EGF ligand was added for 8 minutes prior to cell lysis.

FIG. 7: The proliferation of both epithelial and mesenchymal NSCLC and pancreatic cells, and ovarian and head and neck squamous cell carcinoma cells, are sensitive to the mTOR inhibitor Compound A as a single agent. Sensitivity of 23 cell lines derived from four tumor types to growth inhibition by Compound A. Data are expressed as maximal cell growth at 72 hours in the presence of 20 µM Compound A as compared to cells treated with DMSO alone. A 50% inhibition in maximal cell growth may be used as a cutoff criteria for distinguishing sensitive from relatively insensitive cell lines.

FIG. 8: The combination of the mTOR inhibitor Compound A and the EGFR kinase inhibitor erlotinib is synergistic in mesenchymal NSCLC and pancreatic tumor cells. The effect of the combination of compound A and erlotinib in a panel of non-small cell lung cancer (NSCLC) and pancreatic cancer cell lines. The table summarizes for each cell line: the tumor type from which the cell line was derived, EMT status denotes the expression of epithelial or mesenchymal protein markers. The combination is described as additive or synergistic as assessed by the bliss additivity model. the EC50 for Compound A, the maximal growth inhibition of cells cultured in the presence of 20 µM compound A for 72 hours, expressed as a percent of cells treated with DMSO alone, the EC50 for the combination of compound A+10 µM erlotinib, and the maximal growth inhibition at 72 hours for cells cultured in the presence of 20 µM Compound A+10 µM erlotinib.

FIG. 9: The combination of the mTOR inhibitor Compound A and the EGFR kinase inhibitor erlotinib is synergistic in multiple tumor cell types. The effect of the combination of compound A and erlotinib in a panel of ovarian cancer, head and neck squamous cell carcinoma(HNSCC) and breast cancer cell lines. The table summarizes for each cell line: the tumor type from which the cell line was derived, EMT status denotes the expression of epithelial or mesenchymal protein markers. The combination is described as additive or synergistic as assessed by the bliss additivity model. the EC50 for Compound A, the maximal growth inhibition of cells cultured in the presence of 20 µM compound A for 72 hours, expressed as a percent of cells treated with DMSO alone, the EC50 for the combination of compound A+10 µM erlotinib, and the maximal growth inhibition at 72 hours for cells cultured in the presence of 20 µM Compound A+10 µM erlotinib.

FIG. 10: The combination of the EGFR kinase inhibitor erlotinib and the mTOR inhibitor Compound A is synergistic in mesenchymal NSCLC cells and additive in epithelial NSCLC cells. Effect of varying concentrations of Compound A on the proliferation of (A) four mesenchymal NSCL cell lines (H1703, Calu6, SW1573 and H460) and (B) four epithelial NSCL cell lines (H322, H441, H358 and H292) in the presence or absence of erlotinib. The dotted line denotes the Bliss additivity curve and represents the theoretical expectation if the combined effects of erlotinib with Compound A were exactly additive. Results shown are a representative of three or more independent experiments.

FIG. 11: The combination of erlotinib and the mTOR inhibitor Compound A is additive or synergistic in pancreatic cancer cells. Effect of varying concentrations of Compound A on the proliferation of three pancreatic cell lines (BxPC3, A1165 and MiaPaCa2) in the presence or absence of erlotinib. The dotted line denotes the Bliss additivity curve and represents the theoretical expectation if the combined effects of erlotinib with Compound A were exactly additive. Results shown are a representative of three or more independent experiments.

FIG. 12: The combination of the mTOR inhibitor Compound A and the EGFR kinase inhibitor erlotinib is synergistic in multiple tumor cell types. Effect of varying concentrations of Compound A on the proliferation of representative ovarian (Igrov1, CA-OV-3 and Ovcar-3) and HNSCC (1483) cell lines in the presence or absence of erlotinib. The dotted line denotes the Bliss additivity curve and represents the theoretical expectation if the combined effects of erlotinib with Compound A were exactly additive. Results shown are a representative of three or more independent experiments.

FIG. 13: The combination of the mTOR inhibitor Compound A and the EGFR kinase inhibitor erlotinib enhances apoptosis in pancreatic cancer and NSCLC cells. Effect of the combination of erlotinib with compound A on induction of apoptosis in NSCL and pancreatic cell lines. For each cell line, fold induction in caspase 3/7 activity relative to DMSO control (white bars) is shown for cells treated with 20 µM Compound A (light gray bars), 10 µM erlotinib (dark gray bars) and the combination of 20 µM Compound A plus 10 µM erlotinib (black bars). Error bars represent the standard deviation between a minimum of two replicates. Data is representative of 3 independent experiments. EMT status for each cell line is denoted as epithelial (E) or mesenchymal (M). The tumor type from which each cell line was derived is shown.

FIG. 14: The combination of the mTOR inhibitor Compound A and the EGFR kinase inhibitor erlotinib enhances apoptosis in ovarian cancer cells. Effect of the combination of erlotinib with compound A on induction of apoptosis in ovarian cell lines. For each cell line, fold induction in caspase 3/7 activity relative to DMSO control (white bars) is shown for cells treated with 20 µM Compound A (light gray bars), 10 µM erlotinib (dark gray bars) and the combination of 20 µM Compound A plus 10 µM erlotinib (black bars). Error bars represent the standard deviation between a minimum of two replicates. Data is representative of 2 independent experiments.

FIG. 15: The mTOR inhibitor Compound B has single agent activity in ovarian cancer and HNSCC cells. Sensitivity of 16 cell lines derived from two tumor types (ovarian, white bars, HNSCC, gray bars) to growth inhibition by Compound B. Data are expressed as maximal cell growth at 72 hours in the presence of 10 µM Compound B as compared to cells treated with DMSO alone. A 50% inhibition in maximal cell growth was used as a cutoff criteria for distinguishing sensitive from relatively insensitive cell lines.

FIG. 16: The combination of the mTOR inhibitor Compound B and the EGFR kinase inhibitor erlotinib is synergistic in multiple tumor cell types. Effect of varying concentrations of Compound B on the proliferation of representative HNSCC (MSK922 and 1186) and ovarian (SKOV-3 and Igrov1) cell lines in the presence or absence of erlotinib. The dotted line denotes the Bliss additivity curve and represents the theoretical expectation if the combined effects of erlotinib with Compound B were exactly additive. Results shown are a representative of three or more independent experiments.

FIG. 17: The combination of the EGFR kinase inhibitor erlotinib and the mTOR inhibitor Compound B enhances apoptosis in ovarian cancer cells. Effect of the combination of erlotinib with compound B on induction of apoptosis in a representative ovarian and HNSCC cell line. For each cell line, fold induction in caspase 3/7 activity relative to DMSO control (white bars) is shown for cells treated with 20 μM Compound A (light gray bars), 10 μM erlotinib (dark gray bars) and the combination of 20 μM Compound A plus 10 μM erlotinib (black bars). Error bars represent the standard deviation between a minimum of two replicates. Data is representative of 2 independent experiments.

DETAILED DESCRIPTION OF THE INVENTION

Figure 3B:
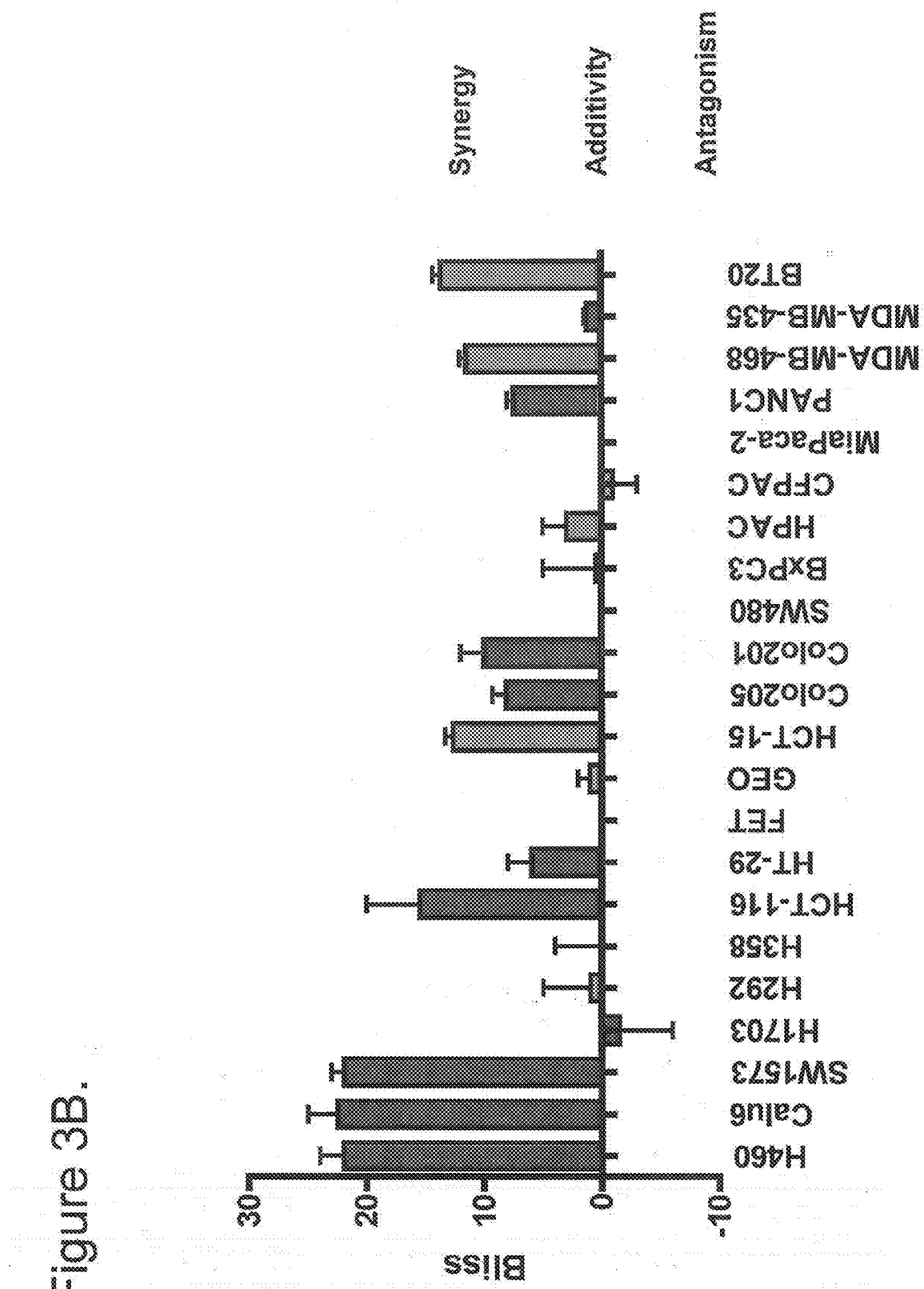
FIG. 3: A. Sensitivity of cell lines to rapamycin. Data are expressed as maximal cell growth at 72 hours in the presence of 30 nM rapamycin as compared to cells treated with DMSO alone. B. Sensitivity of cell lines to the combination of erlotinib and rapamycin. Synergy, as noted by a positive Bliss value, was observed in 13 of 22 cell lines. The calculation of Bliss values are described in the materials and methods section.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Cell growth", as used herein, for example in the context of "tumor cell growth", unless otherwise indicated, is used as commonly used in oncology, where the term is principally associated with growth in cell numbers, which occurs by means of cell reproduction (i.e. proliferation) when the rate the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

"Tumor growth" or "tumor metastases growth", as used herein, unless otherwise indicated, is used as commonly used in oncology, where the term is principally associated with an increased mass or volume of the tumor or tumor metastases, primarily as a result of tumor cell growth.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "an agent that sensitizes tumor cells to the effects of EGFR kinase inhibitors" when used herein without further qualification as to the nature of the agent, refers to an mTOR inhibitor.

The phrase "mTOR inhibitor that binds to and directly inhibits both mTORC1 and mTORC2 kinases" when used herein refers to an mTOR inhibitor that interacts with and reduces the kinase activity of both mTORC1 and mTORC2 complexes.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The present invention derives from research that provided methods for determining which tumors will respond most effectively to treatment with EGFR kinase inhibitors (Thompson, S. et al. (2005) Cancer Res. 65(20):9455-9462) based on whether the tumor cells have undergone an epithelial to mesenchymal transition ("EMT"; Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515). This work demonstrated that epithelial cells respond well to EGFR kinase inhibitors, but that after an EMT the cells become much less sensitive to such inhibitors. Such knowledge of the cellular characteristics associated with sensitivity to EGFR kinase inhibitors, and a knowledge of the biochemical pathways that regulate EMT, or the reverse process, a mesenchymal-to-epithelial transition (MET), allows one to design agents, such as the mTOR inhibitors described herein, that sensitize tumor cells to the effects of EGFR kinase inhibitors, enabling relatively insensitive cells to become sensitive, or sensitive cells to have increased sensitivity. Biomarkers can be used to determine whether tumor cells have undergone an EMT (Thomson, S. et al. (2005) Cancer Res. 65(20):9455-9462).

The data presented in the Examples herein below demonstrate that mTOR inhibitors are agents that can sensitize NSCL, pancreatic, colon or breast cancer tumor cells to the effects of EGFR kinase inhibitors. Thus the anti-tumor effects of a combination of an EGFR kinase inhibitor and such an agent are superior to the anti-tumor effects of either inhibitor by itself, and co-administration of an mTOR inhibitor with an EGFR kinase inhibitor can be effective for treatment of patients with advanced cancers such as NSCL, pancreatic, colon or breast cancers. The sensitizing effect of mTOR inhibitors is seen most frequently in tumor cells that have undergone an EMT, or are relatively insensitive to EGFR kinase inhibitors. In such cells, synergy is frequently observed when an EGFR kinase inhibitor and mTOR inhibitor are used in combination to inhibit tumor cell growth.

Accordingly, the present invention provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an mTOR inhibitor. The present invention also provides a method for treating NSCL, pancreatic, colon or breast cancer tumors or tumor metastases in a patient, comprising administering to said patient simultaneously or sequentially a synergistically effective therapeutic amount of a combination of an EGFR kinase inhibitor and an mTOR inhibitor. The present invention also provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor. In an embodiment of any of the above methods, the cells of the NSCL, pancreatic, colon or breast cancer tumors or tumor metastases have high sensitivity or are very sensitive to growth inhibition by EGFR kinase inhibitors such as erlotinib as single agents (i.e. without any agent that sensitizes the tumor cells to the effects of EGFR kinase inhibitors), such as epithelial cells that have not undergone any form of EMT (e.g. H292, H358, or BxPC3 tumor cells). In another embodiment of any of the above methods, the cells of the NSCL, pancreatic, colon or breast cancer tumors or tumor metastases have low sensitivity or are relatively insensitive or refractory to growth inhibition by EGFR kinase inhibitors such as erlotinib as single agents, such as epithelial cells that have undergone an EMT and have acquired mesenchymal characteristics (e.g. H460 or Calu6 tumor cells).

In a further embodiment of the above methods, the patient to be treated is tested prior to treatment using a diagnostic assay to determine the sensitivity of tumor cells to an EGFR kinase inhibitor. Any method known in the art that can determine the sensitivity of the tumor cells of a patient to an EGFR kinase inhibitor can be employed. For example, a method to determine a patient's likely responsiveness to an EGFR kinase inhibitor can comprise assessing whether the tumor cells have undergone an epithelial-mesenchymal transition (EMT), by for example determining the expression level of one or more tumor cell epithelial and/or mesenchymal biomarkers, thus identifying the patient as one who is less likely or not likely to demonstrate an effective response to treatment with an EGFR kinase inhibitor as a single agent if their tumor cells have undergone an EMT (e.g. see Thompson, S. et al. (2005) Cancer Res. 65(20):9455-9462 and US Published Patent Application US-2006-0211060-A1, both incorporated herein by reference). For example, the expression level of one or more tumor cell epithelial biomarkers E-cadherin, Brk, γ-catenin, α1-catenin, α2-catenin, α3-catenin, keratin 8, keratin 18, connexin 31, plakophilin 3, stratifin 1, laminin alpha-5, or ST14 can be assessed, a high level indicating that the tumor cells have probably not undergone an EMT. Similarly, the expression level of one or more tumor cell mesenchymal biomarkers vimentin, fibronectin 1, fibrillin-1, fibrillin-2, collagen alpha2(IV), collagen alpha2(V), LOXL1, nidogen, C11orf9, tenascin, N-cadherin, tubulin alpha-3, or epimorphin can be assessed, a high level indicating that the tumor cells have probably undergone an EMT. Other methods that may be utilized to assess the sensitivity of the tumor cells of a patient to an EGFR kinase inhibitor include determining the presence of mutant forms of EGFR known to confer an enhanced sensitivity to EGFR kinase inhibitors, or directly determining in a tumor cell biopsy the sensitivity of a patients tumor cells to an EGFR kinase inhibitor.

In the above embodiments where the patient is tested prior to treatment using a diagnostic assay to determine the sensitivity of tumor cells to an EGFR kinase inhibitor, in one embodiment, when the patient is identified as one whose tumor cells are predicted to have low sensitivity to an EGFR kinase inhibitor as a single agent, and thus based on the results described herein, are likely to display enhanced sensitivity in the presence of an mTOR inhibitor, the patient is administered, simultaneously or sequentially, a therapeutically effective amount of a combination of an EGFR kinase inhibitor and an mTOR inhibitor. In another embodiment, when the patient is identified as one whose tumor cells are predicted to have high sensitivity to an EGFR kinase inhibitor as a single agent, but may also display enhanced sensitivity in the presence of an mTOR inhibitor based on the results described herein, the patient is administered, simultaneously or sequentially, a therapeutically effective amount of a combination of an EGFR kinase inhibitor and an mTOR inhibitor. For these methods, an example of a preferred EGFR kinase inhibitor would be erlotinib, including pharmacologically acceptable salts or polymorphs thereof. In these methods one or more additional anti-cancer agents or treatments can be co-administered simultaneously or sequentially with the EGFR kinase inhibitor and mTOR inhibitor, as judged to be appropriate by the administering physician given the prediction of the likely responsiveness of the patient to the combination of EGFR kinase inhibitor and mTOR inhibitor, in combination with any additional circumstances pertaining to the individual patient.

Accordingly, the present invention provides a method for treating NSCL, pancreatic, colon or breast cancer tumors or tumor metastases in a patient, comprising the steps of diagnosing a patient's likely responsiveness to an EGFR kinase inhibitor, and administering to said patient simultaneously or sequentially a therapeutically effective amount of a combination of an EGFR kinase inhibitor and an mTOR inhibitor.

The present invention also provides a method for treating NSCL, pancreatic, colon or breast cancer tumors or tumor metastases in a patient, comprising the steps of diagnosing a patient's likely responsiveness to an EGFR kinase inhibitor, identifying the patient as one whose tumor or tumor metastases cells are relatively insensitive to an EGFR kinase inhibitor as a single agent, and thus likely to show an enhanced response in the presence of an mTOR inhibitor, and administering to said patient simultaneously or sequentially a therapeutically effective amount of a combination of an EGFR kinase inhibitor and an mTOR inhibitor.

The present invention also provides a method for treating NSCL, pancreatic, colon or breast cancer tumors or tumor metastases in a patient, comprising the steps of diagnosing a patient's likely responsiveness to an EGFR kinase inhibitor, identifying the patient as one whose tumor or tumor metastases cells are relatively sensitive to an EGFR kinase inhibitor as a single agent, and may thus show an enhanced response in the presence of an mTOR inhibitor, and administering to said patient simultaneously or sequentially a therapeutically effective amount of a combination of an EGFR kinase inhibitor and an mTOR inhibitor.

The present invention also provides a method for treating NSCL, pancreatic, colon or breast cancer tumors or tumor metastases in a patient, comprising the steps of diagnosing a patient's likely responsiveness to an EGFR kinase inhibitor by assessing whether the tumor cells have undergone an epithelial-mesenchymal transition, and administering to said patient simultaneously or sequentially a therapeutically effective amount of a combination of an EGFR kinase inhibitor and an mTOR inhibitor.

The present invention also provides a method for treating NSCL, pancreatic, colon or breast cancer tumors or tumor metastases in a patient, comprising the steps of diagnosing a patient's likely responsiveness to an EGFR kinase inhibitor by assessing whether the tumor cells have undergone an epithelial-mesenchymal transition, identifying the patient as one whose tumor or tumor metastases cells have undergone an epithelial-mesenchymal transition and are thus predicted to be relatively insensitive to an EGFR kinase inhibitor as a single agent, and thus likely to show an enhanced response in the presence of an mTOR inhibitor, and administering to said patient simultaneously or sequentially a therapeutically effective amount of a combination of an EGFR kinase inhibitor and an mTOR inhibitor.

The present invention also provides a method for treating NSCL, pancreatic, colon or breast cancer tumors or tumor metastases in a patient, comprising the steps of diagnosing a patient's likely responsiveness to an EGFR kinase inhibitor by assessing whether the tumor cells have undergone an epithelial-mesenchymal transition, identifying the patient as one whose tumor or tumor metastases cells have not undergone an epithelial-mesenchymal transition and are thus predicted to be relatively sensitive to an EGFR kinase inhibitor as a single agent, and may thus show an enhanced response in the presence of an mTOR inhibitor, and administering to said patient simultaneously or sequentially a therapeutically effective amount of a combination of an EGFR kinase inhibitor and an mTOR inhibitor.

In a further embodiment of the above methods, the patient to be treated is refractory to treatment with an EGFR kinase inhibitor as a single agent. Thus, for example, in one embodiment, the present invention provides a method for treating NSCL, pancreatic, colon or breast cancer tumors or tumor metastases in a patient refractory to treatment with an EGFR kinase inhibitor as a single agent, comprising administering to said patient simultaneously or sequentially a therapeutically effective amount of a combination of an EGFR kinase inhibitor and an mTOR inhibitor. In an alternative embodiment, the present invention provides a method for treating NSCL, pancreatic, colon or breast cancer tumors or tumor metastases in a patient refractory to treatment with an EGFR kinase inhibitor as a single agent, comprising the steps of diagnosing a patient's likely responsiveness to an EGFR kinase inhibitor, and administering to said patient simultaneously or sequentially a therapeutically effective amount of a combination of an EGFR kinase inhibitor and an mTOR inhibitor. It will be appreciated by one of skill in the medical arts that there are many reasons for why a patient may be refractory to treatment with an EGFR kinase inhibitor as a single agent, one of which is that the tumor cells of the patient are relatively insensitive to inhibition by the tested EGFR kinase inhibitor. It is also possible that a patient may be refractory to treatment with one type of EGFR kinase inhibitor, but be sensitive to treatment with another type of EGFR kinase inhibitor.

This invention also provides a method for treating abnormal cell growth of lung, pancreatic, colon or breast cancer cells in a patient, comprising administering to said patient simultaneously or sequentially a therapeutically effective amount of a combination of an EGFR kinase inhibitor and an mTOR inhibitor.

It will be appreciated by one of skill in the medical arts that the exact manner of administering to said patient of a therapeutically effective amount of a combination of an EGFR kinase inhibitor and mTOR inhibitor following a diagnosis of a patient's likely responsiveness to an EGFR kinase inhibitor will be at the discretion of the attending physician. The mode of administration, including dosage, combination with other anti-cancer agents, timing and frequency of administration, and the like, may be affected by the diagnosis of a patient's likely responsiveness to an EGFR kinase inhibitor, as well as the patient's condition and history. Thus, even patients diagnosed with tumors predicted to be relatively sensitive to an EGFR kinase inhibitor as a single agent may still benefit from treatment with a combination of an EGFR kinase inhibitor and mTOR inhibitor, particularly in combination with other anti-cancer agents, or other agents that may alter a tumor's sensitivity to EGFR kinase inhibitors.

In one embodiment of the methods of this invention, an mTOR inhibitor is administered at the same time as the EGFR kinase inhibitor. In another embodiment of the methods of this invention, an mTOR inhibitor is administered prior to the EGFR kinase inhibitor. In another embodiment of the methods of this invention, an mTOR inhibitor is administered after the EGFR kinase inhibitor. In another embodiment of the methods of this invention, an mTOR inhibitor is pre-administered prior to administration of a combination of an EGFR kinase inhibitor and mTOR inhibitor.

The present invention further provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, and in addition, one or more other cytotoxic, chemotherapeutic or anti-cancer agents, or compounds that enhance the effects of such agents.

In the context of this invention, other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (C is P; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, and in addition, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N-6-(3-pyridinylcarbonyl)-L-lysyl-N-6-(3-pyridinylcarbonyl)-D-lysyl-L-leucyl-N-6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide(2-methyl-N-[4,20-nitro-3-(trifluoromethyl)phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, and in addition one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 41,530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and fit-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606, 046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, and in addition one or more tumor cell pro-apoptotic or apoptosis-stimulating agents.

The present invention further provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, and in addition one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further thus provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, and in addition an anti-HER2 antibody or an immunotherapeutically active fragment thereof.

The present invention further provides a method for treating NSCL, pancreatic, colon or breast cancer tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, and in addition one or more additional anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217.

The present invention further provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, and in addition a COX II (cyclooxygenase II) inhibitor. Examples of useful COX-II inhibitors include alecoxib (e.g. CELEBREX™), valdecoxib, and rofecoxib.

The present invention further provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, and in addition treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides a method for treating NSCL, pancreatic, colon or breast cancer tumors or tumor metastases in a patient, comprising administering to the patient simultaneously or sequentially a therapeutically effective amount of a combination of an EGFR kinase inhibitor and an agent that sensitizes tumor cells to the effects of EGFR kinase inhibitors, and in addition treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The present invention further provides a method for reducing the side effects caused by the treatment of NSCL, pancreatic, colon or breast cancer tumors or tumor metastases in a patient with an EGFR kinase inhibitor or an mTOR inhibitor, comprising administering to the patient simultaneously or sequentially a therapeutically effective amount of a combination of an EGFR kinase inhibitor and an agent that sensitizes tumor cells to the effects of EGFR kinase inhibitors (i.e. an mTOR inhibitor), in amounts that are effective to produce an additive, or a superadditive or synergistic antitumor effect, and that are effective at inhibiting the growth of the tumor.

The present invention further provides a method for the treatment of NSCL, pancreatic, colon or breast cancer, comprising administering to a subject in need of such treatment (i) an effective first amount of an EGFR kinase inhibitor, or a pharmaceutically acceptable salt thereof; and (ii) an effective second amount of an agent that sensitizes tumor cells to the effects of EGFR kinase inhibitors.

The present invention also provides a method for the treatment of NSCL, pancreatic, colon or breast cancer, comprising administering to a subject in need of such treatment (i) a sub-therapeutic first amount of an EGFR kinase inhibitor, or a pharmaceutically acceptable salt thereof; and (ii) a sub-therapeutic second amount of an agent that sensitizes tumor cells to the effects of EGFR kinase inhibitors.

The present invention also provides a method for the treatment of NSCL, pancreatic, colon or breast cancer, comprising administering to a subject in need of such treatment (i) an effective first amount of an EGFR kinase inhibitor, or a pharmaceutically acceptable salt thereof; and (ii) a sub-therapeutic second amount of an agent that sensitizes tumor cells to the effects of EGFR kinase inhibitors.

The present invention also provides a method for the treatment of NSCL, pancreatic, colon or breast cancer, comprising administering to a subject in need of such treatment (i) a sub-therapeutic first amount of an EGFR kinase inhibitor, or a pharmaceutically acceptable salt thereof; and (ii) an effective second amount of an agent that sensitizes tumor cells to the effects of EGFR kinase inhibitors.

In the preceding methods the order of administration of the first and second amounts can be simultaneous or sequential, i.e. the agent that sensitizes tumor cells to the effects of EGFR kinase inhibitors can be administered before the EGFR kinase inhibitor, after the EGFR inhibitor, or at the same time as the EGFR kinase inhibitor. In an alternative embodiment of each of these methods, the NSCL, pancreatic, colon or breast cancer has low sensitivity or is relatively insensitive or refractory to inhibition by EGFR kinase inhibitors such as erlotinib as single agents.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

Additionally, the present invention provides a pharmaceutical composition comprising a combination of an EGFR kinase inhibitor and an agent that sensitizes tumor cells to the effects of EGFR kinase inhibitors in a pharmaceutically acceptable carrier.

As used herein, the term "patient" preferably refers to a human in need of treatment with an EGFR kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an EGFR kinase inhibitor.

In a preferred embodiment, the patient is a human in need of treatment for cancer, or a precancerous condition or lesion, wherein the cancer is preferably NSCL, breast, colon or pancreatic cancer. In addition, other cancers that may be treated by the methods described herein include examples of the following cancers that are treatable by administration of an EGFR kinase inhibitor: lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the ureter, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions. In addition, other cancers that may be treated by the methods described herein include examples of the following cancers that are treatable by administration of the EGFR kinase inhibitor erlotinib: cancer of the kidney or renal cell carcinoma.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

For purposes of the present invention, "co-administration of" and "co-administering" an EGFR kinase inhibitor and an agent that sensitizes tumor cells to the effects of EGFR kinase inhibitors (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The agent that sensitizes tumor cells to the effects of EGFR kinase inhibitors can be administered prior to, at the same time as, or subsequent to administration of the EGFR kinase inhibitor, or in some combination thereof. Where the EGFR kinase inhibitor is administered to the patient at repeated intervals, e.g., during a standard course of treatment, the agent that sensitizes tumor cells to the effects of EGFR kinase inhibitors can be administered prior to, at the same time as, or subsequent to, each administration of the EGFR kinase inhibitor, or some combination thereof, or at different intervals in relation to the EGFR kinase inhibitor treatment, or in a single dose prior to, at any time during, or subsequent to the course of treatment with the EGFR kinase inhibitor.

The EGFR kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the EGFR kinase inhibitor can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of EGFR kinase inhibitor being used (for example, small molecule, antibody, RNAi, ribozyme or antisense construct), and the medical judgement of the prescribing physician as based, e.g., on the results of published clinical studies.

The amount of EGFR kinase inhibitor administered and the timing of EGFR kinase inhibitor administration will depend on the type (species, gender, age, weight, etc.) and condition of the patient being treated, the severity of the disease or condition being treated, and on the route of administration. For example, small molecule EGFR kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based EGFR kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The EGFR kinase inhibitors and the agent that sensitizes tumor cells to the effects of EGFR kinase inhibitors can be administered either separately or together by the same or different routes, and in a wide variety of different dosage forms. For example, the EGFR kinase inhibitor is preferably administered orally or parenterally. The agent that sensitizes tumor cells to the effects of EGFR kinase inhibitors is preferably administered orally or parenterally. Where the EGFR kinase inhibitor is erlotinib HCl (TARCEVA®), oral administration is preferable. Both the EGFR kinase inhibitors and the agent that sensitizes tumor cells to the effects of EGFR kinase inhibitors can be administered in single or multiple doses. In one embodiment, the agent that sensitizes tumor cells to the effects of EGFR kinase inhibitors is administered first as a pretreatment, followed by administration of the combination of both agents (EGFR kinase inhibitor and the agent that sensitizes tumor cells to the effects of EGFR kinase inhibitors), either separately or combined together in one formulation.

The EGFR kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor and the agent that sensitizes tumor cells to the effects of EGFR kinase inhibitors can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous EGFR kinase inhibitors should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. Methods of preparing pharmaceutical compositions comprising mTOR inhibitors are also well known in the art (e.g. see International Patent Publication WO 2004/004644, or patents on rapamycin macrolides referred to therein). In view of the teaching of the present invention, methods of preparing pharmaceutical compositions comprising both an EGFR kinase inhibitor and the agent that sensitizes tumor cells to the effects of EGFR kinase inhibitors will be apparent from the above-cited publications and from other known references, such as Remington's Pharmaceutical Sciences, Mack Publishing Company, Easton, Pa., $18^{th}$ edition (1990).

For oral administration of EGFR kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous EGFR kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising either an EGFR kinase inhibitor or the agent that sensitizes tumor cells to the effects of EGFR kinase inhibitors in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. The agent that sensitizes tumor cells to the effects of EGFR kinase inhibitors is preferably administered in the form of liquid drench, by injection or as an implant. Such formulations are prepared in a conventional manner in accordance with standard veterinary practice.

The present invention further provides a kit comprising a single container comprising both an EGFR kinase inhibitor and the agent that sensitizes tumor cells to the effects of EGFR kinase inhibitors. The present invention further provides a kit comprising a first container comprising an EGFR kinase inhibitor and a second container comprising the agent that sensitizes tumor cells to the effects of EGFR kinase inhibitors. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer. The kit may also comprise additional containers comprising additional anti-cancer agents, agents that enhances the effect of such agents, or other compounds that improve the efficacy or tolerability of the treatment.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, peptide or RNA aptamers, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl)amine (also known as OSI-774, erlotinib, or TARCEVA® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HCl, TARCEVA®), or other salt forms (e.g. erlotinib mesylate).

EGFR kinase inhibitors also include, for example multi-kinase inhibitors that have activity on EGFR kinase, i.e. inhibitors that inhibit EGFR kinase and one or more additional kinases. Examples of such compounds include the EGFR and HER2 inhibitor CI-1033 (formerly known as PD183805; Pfizer); the EGFR and HER2 inhibitor GW-2016 (also known as GW-572016 or lapatinib ditosylate; GSK); the EGFR and JAK 2/3 inhibitor AG490 (a tyrphostin); the EGFR and HER2 inhibitor ARRY-334543 (Array BioPharma); BIBW-2992, an irreversible dual EGFR/HER2 kinase inhibitor (Boehringer Ingelheim Corp.); the EGFR and HER2 inhibitor EKB-569 (Wyeth); the VEGF-R2 and EGFR inhibitor ZD6474 (also known as ZACTIMA™; AstraZeneca Pharmaceuticals), and the EGFR and HER2 inhibitor BMS-599626 (Bristol-Myers Squibb).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be peptide or RNA aptamers. Such aptamers can for example interact with the extracellular or intracellular domains of EGFR to inhibit EGFR kinase activity in cells. An aptamer that interacts with the extracellular domain is preferred as it would not be necessary for such an aptamer to cross the plasma membrane of the target cell. An aptamer could also interact with the ligand for EGFR (e.g. EGF, TGF-), such that its ability to activate EGFR is inhibited. Methods for selecting an appropriate aptamer are well known in the art. Such methods have been used to select both peptide and RNA aptamers that interact with and inhibit EGFR family members (e.g. see Buerger, C. et al. et al. (2003) J. Biol. Chem. 278:37610-37621; Chen, C-H. B. et al. (2003) Proc. Natl. Acad. Sci. 100:9226-9231; Buerger, C. and Groner, B. (2003) J. Cancer Res. Clin. Oncol. 129(12):669-675. Epub 2003 Sep. 11.).

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

As used herein, the term "an agent that sensitizes tumor cells to the effects of EGFR kinase inhibitors" when used without further qualification as to the nature of the agent, refers to an mTOR inhibitor. An mTOR inhibitor can be any mTOR inhibitor that is currently known in the art or that will be identified in the future, and includes any chemical entity that, upon administration to a patient, results in inhibition of mTOR in the patient. An mTOR inhibitor can inhibit mTOR by any biochemical mechanism, including competition at the ATP binding site, competition elsewhere at the catalytic site of mTOR kinase, non-competitive inhibition, irreversible inhibition (e.g. covalent protein modification), or modulation of the interactions of other protein subunits or binding proteins with mTOR kinase in a way that results in inhibition of mTOR kinase activity (e.g. modulation of the interaction of mTOR with FKBP12, GβL, (mLST8), RAPTOR (mKOG1), or RICTOR (mAVO3)). Specific examples of mTOR inhibitors include: rapamycin; other rapamycin macrolides, or rapamycin analogues, derivatives or prodrugs; RAD001 (also known as Everolimus, RAD001 is an alkylated rapamycin (40-O-(2-hydroxyethyl)-rapamycin), disclosed in U.S. Pat. No. 5,665,772; Novartis); CCI-779 (also known as Temsirolimus, CCI-779 is an ester of rapamycin (42-ester with 3-hydroxy-2-hydroxymethyl-2-methylpropionic acid), disclosed in U.S. Pat. No. 5,362,718; Wyeth); AP23573 or AP23841 (Ariad Pharmaceuticals); ABT-578 (40-epi-(tetrazolyl)-rapamycin; Abbott Laboratories); KU-0059475 (Kudus Pharmaceuticals); and TAFA-93 (a rapamycin prodrug; Isotechnika). Examples of rapamycin analogs and derivatives known in the art include those compounds described in U.S. Pat. Nos. 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; all of which are incorporated herein by reference. Rapamycin derivatives are also disclosed for example in WO 94/09010, WO 95/16691, WO 96/41807, or WO 99/15530, which are incorporated herein by reference. Such analogs and derivatives include 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-0-(2-hydroxyethyl)-rapamycin, 32-deoxorapamycin and 16-pent-2-ynyloxy-32(S)-dihydro-rapamycin. Rapamycin derivatives may also include the so-called rapalogs, e.g. as disclosed in WO 98/02441 and WO01/14387 (e.g. AP23573, AP23464, AP23675 or AP23841). Further examples of a rapamycin derivative are those disclosed under the name biolimus-7 or biolimus-9 (BIOLIMUS A9™) (Biosensors International, Singapore). Any of the above rapamycin analogs or derivatives may be readily prepared by procedures as described in the above references.

Additional examples of mTOR inhibitors useful in the invention described herein include those disclosed and claimed in U.S. patent application Ser. No. 11/599,663, filed Nov. 15, 2006, a series of compounds that inhibit mTOR by binding to and directly inhibiting both mTORC1 and mTORC2 kinases. The latter application is incorporated herein in its entirety. Examples of such compounds and their synthesis are described herein in the Experimental Methods section below (under "Drugs"). Two such compounds are Compound A and Compound B, for which data indicating their utility in the methods of this invention is included and described herein. These two compounds exhibit either synergy or additivity in inhibiting tumor cell growth or proliferation when used in combination with an EGFR kinase inhibitor, depending on the tumor cell type and EMT status. Synergy is observed in the majority of tumor cell types (e.g. see Experimental Details herein). Similar results can be obtained with any compound that inhibits mTOR by binding to and directly inhibiting both mTORC1 and mTORC2 kinases, such as whose structures are disclosed herein (see Experimental Section). Additional such compounds can readily be identified by determining their ability to inhibit both mTORC1 and mTORC2 kinase activities using immunoprecipiation-kinase assays with antibodies specific to either the raptor or rictor proteins of the mTORC1 and mTORC2 complexes (for an example of such assays, see Jacinto, E. et al. (2004) Nature Cell Biol. 6(11):1122-1128).

Compounds that inhibit mTOR by binding to and directly inhibiting both mTORC1 and mTORC2 kinases have a number of important advantages over compounds like rapamycin, or its analogues, that only directly inhibit mTORC1. These include (a) superior inhibition of pAkt and concomitant induction of apoptosis in tumor cells, (b) complete inhibition of all phosphorylation of 4E-BP1, which results in greater anti-proliferative effects, (c) inhibition of pAkt (S473) in all tumor cells, thus leading to superior pro-apoptotic effects (rapamycin inhibits pAkt (S473) in only ~20% of cancer cell lines), (d) treatment does not increase pAkt (S473) in any cancer cell type tested, and so does not promote tumor cell survival (unlike rapamycin treatment, which increases pAkt (S473) in ~65% of cell lines) and (e) anti-proliferative activity in a far broader spectrum of tumor cells (N.B. approximately 50% of cell lines in a given tumor type are insensitive to rapamycin).

Also useful in the invention described herein are mTOR inhibitors that are dual PI3K/mTOR kinase inhibitors, such as for example the compound PI-103 as described in Fan, Q-W et al (2006) Cancer Cell 9:341-349 and Knight, Z. A. et al. (2006) Cell 125:733-747.

Compounds that inhibit mTOR kinase, but are non-specific kinase inhibitors that are relatively toxic to normal non-neoplastic cells and thus not suitable for administration as a therapeutic, such as for example the PI3 kinase inhibitors wortmannin and LY294002 (Brunn G. J. et al (1996) Embo J. 15:5256-5267), are not suitable for use in the methods of the invention described herein.

The present invention also encompasses the use of a combination of an EGFR kinase inhibitor and an mTOR inhibitor, for the manufacture of a medicament for the treatment of NSCL, pancreatic, colon or breast cancer tumors or tumor metastases in a patient in need thereof, wherein each inhibitor in the combination can be administered to the patient either simultaneously or sequentially. The present invention also encompasses the use of a synergistically effective combination of an EGFR kinase inhibitor and an mTOR inhibitor, for the manufacture of a medicament for the treatment of NSCL, pancreatic, colon or breast cancer tumors or tumor metastases in a patient in need thereof, wherein each inhibitor in the combination can be administered to the patient either simultaneously or sequentially. The present invention also encompasses the use of a combination of an EGFR kinase inhibitor and an agent that sensitizes tumor cells to the effects of EGFR kinase inhibitors, wherein said agent is an mTOR inhibitor, for the manufacture of a medicament for the treatment of NSCL, pancreatic, colon or breast cancer tumors or tumor metastases in a patient in need thereof, wherein each inhibitor in the combination can be administered to the patient either simultaneously or sequentially. In an embodiment of any of the above uses, the cells of the NSCL, pancreatic, colon or breast cancer tumors or tumor metastases have high sensitivity or are very sensitive to growth inhibition by EGFR kinase inhibitors such as erlotinib as single agents (i.e. without any agent that sensitizes the tumor cells to the effects of EGFR kinase inhibitors), such as epithelial cells that have not undergone any form of EMT (e.g. like H292, H358, or BxPC3 tumor cells). In another embodiment of any of the above uses, the cells of the NSCL, pancreatic, colon or breast cancer tumors or tumor metastases have low sensitivity or are relatively insensitive to growth inhibition by EGFR kinase inhibitors such as erlotinib as single agents, such as epithelial cells that have undergone an EMT and have acquired mesenchymal characteristics (e.g. like H460 or Calu6 tumor cells). In an alternative embodiment of any of the above uses the present invention also encompasses the use of an EGFR kinase inhibitor and mTOR inhibitor combination in combination with another anti-cancer agent or agent that enhances the effect of such an agent for the manufacture of a medicament for the treatment of NSCL, pancreatic, colon or breast cancer tumors or tumor metastases in a patient in need thereof, wherein each inhibitor in the combination can be administered to the patient either simultaneously or sequentially. In this context, the other anti-cancer agent or agent that enhances the effect of such an agent can be any of the agents listed above that can be added to the EGFR kinase inhibitor and mTOR inhibitor combination when treating patients.

The invention also encompasses a pharmaceutical composition that is comprised of a combination of an EGFR kinase inhibitor and an agent that sensitizes tumor cells to the effects of EGFR kinase inhibitors in combination with a pharmaceutically acceptable carrier.

Preferably the composition is comprised of a pharmaceutically acceptable carrier and a non-toxic therapeutically effective amount of a combination of an EGFR kinase inhibitor and an agent that sensitizes tumor cells to the effects of EGFR kinase inhibitors (including pharmaceutically acceptable salts of each component thereof).

Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of a combination of an EGFR kinase inhibitor and an agent that sensitizes tumor cells to the effects of EGFR kinase inhibitors (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a combination of an EGFR kinase inhibitor and an agent that sensitizes tumor cells to the effects of EGFR kinase inhibitors (including pharmaceutically acceptable salts of each component thereof) as active ingredients, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by the combination of an EGFR kinase inhibitor and an agent that sensitizes tumor cells to the effects of EGFR kinase inhibitors (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, a combination of an EGFR kinase inhibitor and an agent that sensitizes tumor cells to the effects of EGFR kinase inhibitors (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a combination of an EGFR kinase inhibitor and an agent that sensitizes tumor cells to the effects of EGFR kinase inhibitors (including pharmaceutically acceptable salts of each component thereof). A combination of an EGFR kinase inhibitor and an agent that sensitizes tumor cells to the effects of EGFR kinase inhibitors (including pharmaceutically acceptable salts of each component thereof), can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise a combination of an EGFR kinase inhibitor and an agent that sensitizes tumor cells to the effects of EGFR kinase inhibitors in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a combination of an EGFR kinase inhibitor and an agent that sensitizes tumor cells to the effects of EGFR kinase inhibitors (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a combination of an EGFR kinase inhibitor and an agent that sensitizes tumor cells to the effects of EGFR kinase inhibitors (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

The present invention also provides a method for treating tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor that binds to and directly inhibits both mTORC1 and mTORC2 kinases. In one embodiment of this method the patient is a human that is being treated for cancer. In one embodiment of this method the cells of the tumors or tumor metastases are relatively insensitive or refractory to treatment with an EGFR inhibitor as a single agent. In one embodiment of this method the EGFR kinase inhibitor and mTOR inhibitor are co-administered to the patient in the same formulation. In another embodiment of this method the EGFR kinase inhibitor and mTOR inhibitor are co-administered to the patient in different formulations. In another embodiment of this method the EGFR kinase inhibitor and mTOR inhibitor are co-administered to the patient by the same route. In another embodiment of this method the EGFR kinase inhibitor and mTOR inhibitor are co-administered to the patient by different routes. In another embodiment of this method the EGFR kinase inhibitor is a small organic molecule, an antibody or an antibody fragment that binds specifically to the EGFR. In another embodiment of this method the EGFR kinase inhibitor comprises erlotinib, or a salt thereof. In another embodiment of this method, one or more other anti-cancer agents may additionally be administered to said patient. In another embodiment of this method the administering to the patient is simultaneous. In another embodiment of this method the administering to the patient is sequential. In another embodiment of this method the cells of the tumors or tumor metastases have high sensitivity to growth inhibition by EGFR kinase inhibitors as single agents. In another embodiment of this method the cells of the tumors or tumor metastases have low sensitivity to growth inhibition by EGFR kinase inhibitors as single agents. In another embodiment of this method the cells of the tumors or tumor metastases have not undergone any form of EMT (e.g. epithelial cells). In another embodiment of this method the cells of the tumors or tumor metastases have undergone an EMT (i.e. mesenchymal or mesenchymal-like cells).

The present invention also provides a method for the treatment of cancer, comprising administering to a subject in need of such treatment an amount of the EGFR kinase inhibitor, or a pharmaceutically acceptable salt thereof; and an amount of an mTOR inhibitor that binds to and directly inhibits both mTORC1 and mTORC2 kinases, or a pharmaceutically acceptable salt thereof; wherein at least one of the amounts is administered as a sub-therapeutic amount. In one embodiment of this method the EGFR kinase inhibitor comprises erlotinib, or a salt thereof. In another embodiment of this method, one or more other anti-cancer agents may additionally be administered to said patient. In one embodiment of this method the cancer is relatively insensitive or refractory to treatment with an EGFR inhibitor as a single agent.

The present invention also provides a method for treating tumors or tumor metastases in a patient, comprising administering to said patient simultaneously or sequentially a synergistically effective therapeutic amount of a combination of an EGFR kinase inhibitor and an mTOR inhibitor that binds to and directly inhibits both mTORC1 and mTORC2 kinases. In one embodiment of this method the EGFR kinase inhibitor comprises erlotinib, or a salt thereof. In another embodiment of this method, one or more other anti-cancer agents may additionally be administered to said patient.

In one embodiment of this method the tumors or tumor metastases are relatively insensitive or refractory to treatment with an EGFR inhibitor as a single agent.

The present invention also provides a method for treating tumors or tumor metastases in a patient, comprising the steps of diagnosing a patient's likely responsiveness to an EGFR kinase inhibitor by assessing whether the tumor cells have undergone an epithelial-mesenchymal transition, identifying the patient as one whose tumor or tumor metastases cells have undergone an epithelial-mesenchymal transition and are thus predicted to be relatively insensitive to an EGFR kinase inhibitor as a single agent, and thus likely to show an enhanced response in the presence of an mTOR inhibitor, and administering to said patient simultaneously or sequentially a therapeutically effective amount of a combination of an EGFR kinase inhibitor and an mTOR inhibitor that binds to and directly inhibits both mTORC1 and mTORC2 kinases.

The present invention also provides a method for treating tumors or tumor metastases in a patient refractory to treatment with an EGFR kinase inhibitor as a single agent, comprising administering to said patient simultaneously or sequentially a therapeutically effective amount of a combination of an EGFR kinase inhibitor and an mTOR inhibitor that binds to and directly inhibits both mTORC1 and mTORC2 kinases.

The present invention also provides a pharmaceutical composition comprising an EGFR kinase inhibitor and an mTOR inhibitor that binds to and directly inhibits both mTORC1 and mTORC2 kinases, in a pharmaceutically acceptable carrier. In one embodiment of the pharmaceutical composition the EGFR kinase inhibitor comprises erlotinib. In one embodiment of the pharmaceutical composition the erlotinib in the composition is present as a hydrochloride salt. In one embodiment the pharmaceutical composition additionally comprises one or more other anti-cancer agents.

The present invention also provides a kit comprising a container, comprising an mTOR inhibitor that binds to and directly inhibits both mTORC1 and mTORC2 kinases, and an EGFR kinase inhibitor. In one embodiment of the kit the EGFR kinase inhibitor comprises erlotinib. In one embodiment the kit further comprises a sterile diluent. In one embodiment the kit further comprises a package insert comprising printed instructions directing the use of a combined treatment of an mTOR inhibitor that binds to and directly inhibits both mTORC1 and mTORC2 kinases and erlotinib to a patient as a method for treating tumors, tumor metastases or other cancers in a patient.

In the preceding methods of treatment of a patient or subject using an mTOR inhibitor that binds to and directly inhibits both mTORC1 and mTORC2 kinases, the patient or subject is preferably a human in need of treatment for cancer, or a precancerous condition or lesion, selected from the list of such conditions provided herein above. Cancers particularly suitable for these methods of treatment include for example NSCLC and pancreatic cancer, especially mesenchymal or late stage cancers of these types where a synergistic outcome is obtained, and also ovarian cancer, head and neck squamous cell carcinoma and breast cancer, in all of which a synergistic effect is also frequently observed.

In further embodiments of any of the above methods, compositions or kits of this invention where an mTOR inhibitor that binds to and directly inhibits both mTORC1 and mTORC2 kinases is used, the mTOR inhibitor comprises a compound of Formula (I) as described herein.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Recent reports in the literature have suggested that combining EGFR inhibitors with agents that antagonize downstream signaling pathways may permit sensitization in cell lines that either have redundancy in receptor tyrosine kinase signaling or contain specific mutations in downstream signaling. Herein, the present inventors have determined the correlation between erlotinib's ability to regulate the activity of the PI3K-PDK1-Akt-mTOR pathway and sensitivity to growth inhibition in a group of 22 cell lines derived from breast, colon, pancreatic and NSCL tumors. It was found that in cell lines sensitive to growth inhibition by erlotinib there is downmodulation of the activity of this pathway. In less sensitive cell lines, erlotinib is ineffective at fully down-regulating S6 ribosomal protein (below basal levels), a substrate downstream of mTOR. Here mTOR activity is likely controlled, at least to some extent, by EGFR independent mechanisms, including other growth factors or mutations.

It had not been previously determined if it was possible to combine erlotinib with another targeted agent in order to sensitize breast, colon, pancreatic or NSCL tumor cells that poorly respond to erlotinib as a single agent. Unlike cytotoxic chemotherapies that often share similar toxicities, molecular targeted agents tend to have non-overlapping toxicities and thus identifying cocktails of targeted agents to block cancer cell growth may be more clinically feasible. The present inventors have determined the effect of combining erlotinib with rapamycin, a targeted agent that acts downstream of EGFR to directly inactivate mTOR. Rapamycin is a high molecular weight polyketide natural product derived from a soil bacteria identified on the island Rapa Nui. It acts by disrupting the protein-protein interactions between raptor and mTOR. mTOR requires raptor to interact with a number of substrate proteins, including 4EBP1 and S6K, thus inhibiting this interaction blocks some of mTOR's functions. Synergistic behavior of the mTOR inhibitor rapamycin combined with EGFR inhibitors to block tumor cell growth had been previously reported for renal cell carcinoma and glioblastomas, but had not been examined in breast, colon, pancreatic or NSCL tumors.

Herein, it is demonstrated that rapamycin can re-sensitize breast, colon, pancreatic or NSCL tumor cell lines that are relatively insensitive to erlotinib as a single agent. Thus combining an mTOR inhibitor with an EGFR kinase inhibitor such as erlotinib should be useful clinically in patients with breast, colon, pancreatic or NSCL tumors.

Materials and Methods
Drugs.

The selective HER1/EGFR kinase inhibitor, erlotinib, was synthesized by OSI Pharmaceuticals, Uniondale, N.Y., USA, as the hydrochloride salt, erlotinib HCl (TARCEVA®).

Rapamycin, for in vitro experiments, was purchased from Sigma Aldrich Chemicals (St. Louis, Mo.), and for xenograft experiments, from LC Laboratories (Woburn, Mass.).

Examples of mTOR kinase inhibitors that inhibit mTOR by binding to and directly inhibiting both mTORC1 and mTORC2 kinases include compounds represented by Formula (I) as described below. Compounds A and B represent mTOR inhibitors according to Formula (I).

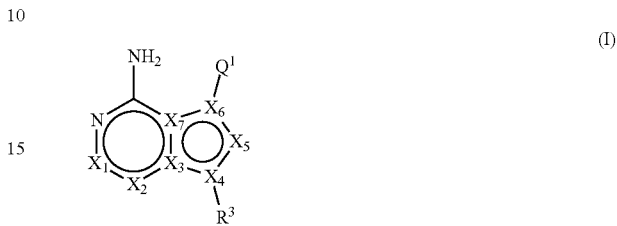

or a pharmaceutically acceptable salt thereof, wherein:
$X_1$, and $X_2$ are each independently N or C-$(E^1)_{aa}$;
$X_5$ is N, C-$(E^1)_{aa}$, or N-$(E)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;
$R^3$ is $C_{0-10}$alkyl, cyclo$C_{3-10}$alkyl, aminomethylcyclo$C_{3-10}$ alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;
$Q^1$ is -$A(R^1)_m B(W)_n$ or —$B(G^{11})_n A(Y)_m$;
A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;
or $Q^1$ is -$A(R^1)_m A(Y)_m$, wherein each A is the same or different 5-membered aromatic or heteroaromatic ring, and the two are fused together to form an 8-membered heteroaromatic system;
$R^1$ is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-$NR^{311}S(O)_{0-2}R^{321}$, —$C_{0-8}$alkyl-$NR^{311}S(O)_{0-2}$ $NR^{321}R^{331}$, —$C_{0-8}$alkyl-$S(O)_{0-2}NR^{311}R^{321}$, —$C_{0-8}$alkyl-$NR^{311}COR^{321}$, —$C_{0-8}$alkyl-$NR^{311}CO_2R^{321}$—$C_{0-8}$alkyl-$NR^{311}CONR^{321}R^{331}$, —$C_{0-8}$-alkyl-$CONR^{311}R^{321}$, —$C_{0-8}$ alkyl-$CON(R^{311})S(O)_{0-2}R^{321}$, —$C_{0-8}$alkyl-$CO_2R^{311}$, —$C_{0-8}$ alkyl-$S(O)_{0-2}R^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$ alkylheterocyclyl, —$C_{0-8}$alkyl-O—$C_{0-8}$alkylaryl, —$C_{0-8}$ alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$ alkyl-S—$C_{0-8}$alkyl$C_{3-8}$cycloalkyl, —$C_{0-8}$alkyl-S—$C_{0-8}$ alkylheterocyclyl, —$C_{0-8}$alkyl-S—$C_{0-8}$alkylaryl, —$C_{0-8}$ alkyl-S—$C_{0-8}$alkylhetaryl, —$C_{0-8}$alkyl-N($R^{311}$)—$C_{0-8}$ alkyl, —$C_{0-8}$alkyl-N($R^{311}$)—$C_{0-8}$alkyl$C_{3-8}$cycloalkyl, —$C_{0-8}$ alkyl-N($R^{311}$)—$C_{0-8}$alkylheterocyclyl, —$C_{0-8}$alkyl-N($R^{311}$)—$C_{0-8}$alkylaryl, —$C_{0-8}$alkyl-N($R^{311}$)—$C_{0-8}$alkyl-hetaryl, —$C_{0-8}$alkyl-$NR^{311}R^{321}$, —$C_{2-8}$alkenyl, —$C_{2-8}$ alkynyl, $NO_2$, CN, $CF_3$, $OCF_3$, $OCHF_2$; provided that $Q^1$ is not N-methyl-2-indolyl, N-(phenylsulfonyl)-2-indolyl, or N-tert-butoxycarbonyl W is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-$NR^{312}S(O)_{0-2}R^{322}$, —$C_{0-8}$alkyl-$NR^{311}S(O)_{0-2}$ $NR^{321}R^{331}$, —$C_{0-8}$alkyl-$NR^{311}CO_2R^{321}$, —$C_{0-8}$alkyl-CON ($R^{311}$)$S(O)_{0-2}R^{321}$, —$C_{0-8}$alkyl-$S(O)_{0-2}NR^{312}R^{322}$, —$C_{0-8}$ alkyl-$NR^{312}COR^{322}$, —$C_{0-8}$alkyl-$NR^{312}CONR^{322}R^{332}$, —$C_{0-8}$alkyl-$CONR^{312}R^{322}$, —$C_{0-8}$alkyl-$CO_2R^{312}$, —$C_{0-8}$alkyl$S(O)_{0-2}R^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, -Oaryl, —$C_{0-8}$ alkyl-O—$C_{0-8}$alkylhetaryl, —$C_{0-8}$alkylaryl, —$C_{0-8}$ alkylhetaryl, —$C_{0-8}$alkylheterocyclyl, —$C_{0-8}$alkyl-S—$C_{0-8}$ alkyl, —$C_{0-8}$alkyl-S—$C_{0-8}$alkyl$C_{3-8}$cycloalkyl, —$C_{0-8}$ alkyl-S—$C_{0-8}$alkylheterocycloalkyl, —$C_{0-8}$alkyl-S—$C_{0-8}$ alkylaryl, —$C_{0-8}$alkyl-S—$C_{0-8}$alkylhetaryl, —$C_{0-8}$alkyl-N($R^{312}$)—$C_{0-8}$ alkyl, —$C_{0-8}$alkyl-N($R^{312}$)—$C_{0-8}$alkyl$C_{3-8}$cycloalkyl, —$C_{0-8}$alkyl-N($R^{312}$)—$C_{0-8}$alkylheterocycloalkyl, —$C_{0-8}$ alkyl-N($R^{312}$)—$C_{0-8}$alkylaryl, —$C_{0-8}$alkyl-N($R^{312}$)—$C_{0-8}$ alkylhetaryl, —$C_{0-8}$alkyl-$NR^{312}R^{322}$, —$C_{2-8}$alkenyl, —$C_{2-8}$alkynyl, $NO_2$, CN, $CF_3$, $OCF_3$, $OCHF_2$; provided that $Q^1$ is not 4-benzyloxy-2-indolyl;

Y is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{0-6}$alkyl, —$C_{0-8}$alkyl$C_{3-8}$cycloalkyl, —$C_{0-8}$alkyl-$NR^{311}S(O)_{0-2}R^{321}$, —$C_{0-8}$alkyl-$NR^{311}S(O)_{0-2}$ $NR^{321}R^{331}$, —$C_{0-8}$alkyl-$NR^{311}CO_2R^{321}$, —$C_{0-8}$alkyl-CON ($R^{311}$)$S(O)_{0-2}R^{321}$, —$C_{0-8}$alkyl-$S(O)_{0-2}NR^{311}R^{321}$, —$C_{0-8}$ alkyl-$NR^{311}COR^{321}$, —$C_{0-8}$alkyl-$NR^{311}CONR^{321}R^{331}$, —$C_{0-8}$alkyl-$CONR^{311}R^{321}$, —$C_{0-8}$alkyl-$CO_2R^{311}$, —$C_{0-8}$ alkyl$S(O)_{0-2}R^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$ alkyl, —$C_{0-8}$ alkyl-S—$C_{0-8}$alkyl$C_{3-8}$cycloalkyl, —$C_{0-8}$alkyl-S—$C_{0-8}$ alkylheterocycloalkyl, —$C_{0-8}$alkyl-S—$C_{0-8}$alkylaryl, —$C_{0-8}$ alkyl-S—$C_{0-8}$alkylhetaryl, —$C_{0-8}$alkyl-N($R^{311}$)—$C_{0-8}$ alkyl, —$C_{0-8}$alkyl-N($R^{311}$)—$C_{0-8}$alkyl$C_{3-8}$cycloalkyl, —$C_{0-8}$ alkyl-N($R^{311}$)—$C_{0-8}$alkylheterocycloalkyl, —$C_{0-8}$ alkyl-N($R^{311}$)—$C_{0-8}$alkylaryl, —$C_{0-8}$alkyl-N($R^3$)—$C_{0-8}$ alkylhetaryl, —$C_{0-8}$alkyl-$NR^{311}R^{321}$, —$C_{2-8}$alkenyl, —$C_{2-8}$alkynyl, $NO_2$, CN, $CF_3$, $OCF_3$, $OCHF_2$; provided that $Q^1$ is not 2-carboxy-5-benzo[b]thiophenyl;

$G^{11}$ is halo, oxo, —$CF_3$, —$OCF_3$, —$OR^{312}$, —$NR^{312}R^{322}$, —$C(O)R^{312}$, —$C(O)C_{3-8}$cycloalkyl, —$CO_2C_{3-8}$cycloalkyl, —$CO_2R^{312}$, —$C(=O)NR^{312}R^{322}$, —$NO_2$, —CN, —$S(O)_{0-2}$ $R^{312}$, —$SO_2NR^{312}R^{322}$, $NR^{312}(C=O)R^{322}$, —$NR^{312}C(=O)$ $OR^{322}$, —$NR^{312}C(=O)NR^{322}R^{332}$, —$NR^{312}S(O)_{0-2}R^{322}$, —$C(=S)OR^{312}$, —$C(=O)SR^{312}$, —$NR^{312}C(=NR^{322})$ $NR^{332}R^{341}$, —$NR^{312}C(=NR^{322})OR^{332}$, —$NR^{312}C$ $(=NR^{322})SR^{332}$, —$OC(=O)OR^{312}$, —$OC(=O)$ $NR^{312}R^{322}$, —$OC(=O)SR^{312}$, —$SC(=O)OR^{312}$, —$SC$ $(=O)NR^{312}R^{322}$, —$P(O)OR^{312}OR^{322}$, $C_{1-10}$alkylidene, $C_{0-10}$alkyl, $C_{2-10}$alkenyl, $C_{2-10}$alkynyl, —$C_{1-10}$alkoxy$C_{0-10}$ alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$ alkenyl, -cyclo$C_{3-8}$alkyl$C_{1-10}$alkyl, -cyclo$C_{3-8}$alkenyl$C_{1-10}$ alkyl, -cyclo$C_{3-8}$alkyl$C_{2-10}$alkenyl, -cyclo$C_{3-8}$alkenyl$C_{2-10}$ alkenyl, -cyclo$C_{3-8}$alkyl$C_{2-10}$alkynyl, -cyclo$C_{3-8}$ alkenyl$C_{2-10}$alkynyl, -heterocyclyl-$C_{0-10}$alkyl, heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{313}$, —$NR^{313}R^{323}$, —$C(O)R^{313}$, —$CO_2R^{313}$, —$C(=O)NR^{313}R^{323}$, —$NO_2$, —CN, —$S(O)_{0-2}$ $R^{313}$, —$SO_2NR^{313}R^{323}$, —$NR^{313}C(=O)R^{323}$, —$NR^{313}C$ $(=O)OR^{323}$, —$NR^{313}C(=O)NR^{323}R^{333}$, —$NR^{313}S(O)_{0-2}$ $R^{323}$, —$C(=S)OR^{313}$, —$C(=O)SR^{313}$, —$NR^{313}C$ $(=NR^{323})NR^{333}R^{342}$, —$NR^{313}C(=NR^{323})OR^{333}$, —$NR^{313}C(=NR^{323})SR^{333}$, —$OC(=O)OR^{333}$, —$OC(=O)$ $NR^{313}R^{323}$, —$OC(=O)SR^{313}$, —$SC(=O)OR^{313}$, —$P(O)$ $OR^{3130}R^{323}$, or —$SC(=O)NR^{313}R^{323}$ substituents;

or $G^{11}$ is aryl-$C_{0-10}$alkyl, aryl-$C_{2-10}$alkenyl, aryl-$C_{2-10}$ alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{313}$, —$NR^{313}R^{323}$, —$C(O)R^{313}$, —$CO_2R^{313}$, —$C(=O)NR^{313}R^{323}$, —$NO_2$, —CN, —$S(O)_{0-2}R^{313}$, —$SO_2NR^{313}R^{323}$, $NR^{313}C(=O)R^{323}$, —$NR^{313}C(=O)$ $OR^{323}$, —$NR^{313}C(=O)NR^{323}R^{333}$, —$NR^{313}S(O)_{0-2}R^{323}$, —$C(=S)OR^{313}$, —$C(=O)SR^{313}$, —$NR^{323}C(=NR^{313})$ $NR^{333}R^{342}$, —$NR^{313}C(=NR^{323})OR^{333}$, —$NR^{313}C$ $(=NR^{323})SR^{333}$, —$OC(=O)OR^{313}$, —$OC(=O)$ $NR^{313}R^{323}$, —$OC(=O)SR^{313}$, —$SC(=O)OR^{313}$, —$P(O)$ $OR^{313}OR^{323}$, or —$SC(=O)NR^{313}R^{323}$ substituents; provided that $G^{11}$ is not N—$CH_2CO_2H$ when $R^3$ is 4-piperidinyl;

$R^{31}$, $R^{32}$, $R^{33}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently $C_{0-8}$alkyl optionally substituted with an aryl, heterocyclyl or hetaryl substituent, or $C_{0-8}$alkyl optionally substituted with 1-6 independent halo, —CON($C_{0-8}$alkyl)($C_{0-8}$ alkyl), —CO($C_{0-8}$alkyl), —O$C_{0-8}$alkyl, —Oaryl, —Ohetaryl, —Oheterocyclyl, —$S(O)_{0-2}$aryl, —$S(O)_{0-2}$ hetaryl, —$S(O)_{0-2}$heterocyclyl, —$S(O)_{0-2}C_{0-8}$alkyl, —N($C_{0-8}$alkyl)($C_{0-8}$alkyl), —N($C_{0-8}$alkyl)CON($C_{0-8}$ alkyl)($C_{0-8}$alkyl), —N($C_{0-8}$alkyl)CO($C_{1-8}$alkyl), —N($C_{0-8}$alkyl)CO($C_{3-8}$cycloalkyl), —N($C_{0-8}$alkyl) $CO_2(C_{1-8}$alkyl), —$S(O)_{1-2}$N($C_{0-8}$alkyl)($C_{0-8}$alkyl), —$NR^{11}S(O)_{1-2}(C_{0-8}$alkyl), —CON($C_{3-8}$cycloalkyl) ($C_{3-8}$cycloalkyl), —CON($C_{0-8}$alkyl)($C_{3-8}$cycloalkyl), —N($C_{3-8}$cycloalkyl)CON($C_{0-8}$alkyl)($C_{0-8}$alkyl), —N($C_{3-8}$cycloalkyl)CON($C_{3-8}$cycloalkyl)($C_{0-8}$alkyl), —N($C_{0-8}$alkyl)CON($C_{3-8}$cycloalkyl)($C_{0-8}$alkyl), —N($C_{0-8}$alkyl)$CO_2(C_{3-8}$cycloalkyl), —N($C_{3-8}$cycloalkyl)$CO_2(C_{3-8}$cycloalkyl), $S(O)_{1-2}$N($C_{0-8}$alkyl) ($C_{3-8}$ cycloalkyl), —$NR^{11}S(O)_{1-2}(C_{3-8}$cycloalkyl), $C_{2-8}$alkenyl, $C_{2-8}$alkynyl, CN, $CF_3$, OH, or optionally substituted aryl substituents; such that each of the above aryl, heterocyclyl, hetaryl, alkyl or cycloalkyl groups may be optionally, independently substituted with —N($C_{0-8}$alkyl)($C_{0-8}$alkyl), hydroxyl, halogen, oxo, aryl, hetaryl, $C_{0-6}$alkyl, $C_{0-8}$alkylcyclyl, —$C_{0-8}$alkyl-N ($C_{0-8}$alkyl)-$S(O)_{0-2}$—($C_{0-8}$alkyl), —$C_{0-8}$alkyl-$S(O)_{0-2}$ —N($C_{0-8}$alkyl)($C_{0-8}$alkyl), —$C_{0-8}$alkyl-N($C_{0-8}$alkyl) CO($C_{0-8}$alkyl), —$C_{0-8}$alkyl-N($C_{0-8}$alkyl)CO—N($C_{0-8}$ alkyl)($C_{0-8}$alkyl), —$C_{0-8}$alkyl-CO—N($C_{0-8}$alkyl)($C_{0-8}$ alkyl), —$C_{1-8}$alkyl-$CO_2$—($C_{0-8}$alkyl), —$C_{0-8}$alkylS $(O)_{0-2}$—($C_{0-8}$alkyl), —$C_{0-8}$alkyl-O—$C_{1-8}$alkyl, —$C_{0-8}$ alkyl-O—$C_{0-8}$alkylcyclyl, —$C_{0-8}$alkyl-O—$C_{0-8}$ alkylheterocyclyl, —$C_{0-8}$alkyl-O—$C_{0-8}$alkylaryl, —$C_{0-8}$ alkyl-O—$C_{0-8}$alkylhetaryl, —$C_{0-8}$alkyl-S—$C_{0-8}$alkyl, —$C_{0-8}$alkyl-S—$C_{0-8}$alkylcyclyl, —$C_{0-8}$alkyl-S—$C_{0-8}$ alkylheterocyclyl, —$C_{0-8}$alkyl-S—$C_{0-8}$alkylaryl, —$C_{0-8}$ alkyl-S—$C_{0-8}$alkylhetaryl, —$C_{0-8}$alkyl-N($C_{0-8}$ alkyl)-$C_{0-8}$alkyl, —$C_{0-8}$alkyl-N($C_{0-8}$alkyl)-$C_{0-8}$alkylcyclyl, —$C_{0-8}$alkyl-N($C_{0-8}$alkyl)-$C_{0-8}$alkylheterocyclyl, —$C_{0-8}$ alkyl-N($C_{0-8}$alkyl)-$C_{0-8}$ alkylaryl, —$C_{0-8}$ alkyl-N($C_{0-8}$alkyl)-$C_{0-8}$alkylhetaryl, $C_{2-8}$alkenyl, $C_{2-8}$alkynyl, $NO_2$, CN, $CF_3$, $OCF_3$, $OCHF_2$, —$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl, or
heterocyclyl optionally substituted with 1-4 independent $C_{0-8}$alkyl, cyclyl, or substituted cyclyl substituents;

E in each instance is independently halo, —$CF_3$, —$OCF_3$, —$OR^2$, —$NR^{31}R^{32}$, —C(=O)$R^{31}$, —$CO_2R^{31}$, —$CONR^{31}R^{32}$, —$NO_2$, —CN, —S(O)$_{0-2}R^{31}$, —S(O)$_{0-2}$$NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{311}$S(O)$_{0-2}R^{32}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{311}$)$SR^{31}$, —OC(=O)O OC(=O)$R^{31}$, —OC(=O)$R^{31}R^{32}$, —OC(=O)$SR^{31}$, —SC(=O)$OR^{31}$, —SC(=O)$NR^{31}R^{32}$, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$-alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{1-10}$alkyl, -heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{31}$, —$NR^{31}R^{32}$, —C(=O)$R^{31}$, —$CO_2R^{31}$, —C(=O)$NR^{31}R^{32}$, —$NO_2$, —CN, —S(=O)$_{0-2}R^{31}$, —$SO_2NR^{31}$, —$NR^{31}$C(=O)$R^{32}$, —$NR^{31}$C(=O)$OR^{31}$, —$NR^{31}$C(=O)$NR^{32}R^{33}$, —$NR^{311}$S(O)$_{0-2}R^{31}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{32}$)$SR^{33}$, —OC(=O)$OR^{31}$, —OC(=O)$NR^{31}R^{32}$, —OC(=O)$SR^{31}$, —SC(=O)$OR^{31}$, or —SC(=O)$NR^{31}R^{32}$ substituents;

or $E^1$ in each instance is independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —S(O)$_{0-2}NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{311}$S(O)$_{0-2}R^{32}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{32}$)$SR^{33}$, —OC(=O)$OR^{31}$, —OC(=O)$NR^{31}$, $R^{32}$, —OC(=O)$SR^{31}$, —SC(=O)$OR^{31}$, or —SC(=O)$NR^{31}R^{32}$ substituents;

in the cases of —$NR^{31}R^{32}$, —$NR^{311}R^{321}$, —$NR^{312}R^{322}$, —$NR^{332}R^{341}$, —$NR^{313}R^{323}$, and —$NR^{323}R^{333}$, the respective $R^{31}$ and $R^{32}$, $R^{311}$ and $R^{321}$, $R^{312}$ and $R^{322}$, $R^{331}$ and $R^{341}$, $R^{313}$ and $R^{323}$, and $R^{323}$ and $R^{333}$ are optionally taken together with the nitrogen atom to which they are attached to form a 3-10 membered saturated or unsaturated ring; wherein said ring in each instance independently is optionally substituted by one or more independent —N($C_{0-8}$alkyl)($C_{0-8}$alkyl), hydroxyl, halogen, oxo, aryl, hetaryl, $C_{0-6}$alkyl, —$C_{0-8}$alkyl$C_{3-8}$cycloalkyl, —$C_{0-8}$alkyl-N($C_{0-8}$alkyl)S(O)$_{0-2}C_{0-8}$alkyl, —$C_{0-8}$alkyl-N($C_{0-8}$alkyl)S(O)$_{0-2}$N($C_{0-8}$alkyl)($C_{0-8}$alkyl), —$C_{0-8}$alkyl-N($C_{0-8}$alkyl)$CO_2$($C_{0-8}$alkyl), —$C_{0-8}$alkyl-CON(($C_{0-8}$alkyl))S(O)$_{0-2}$($C_{0-8}$alkyl), —$C_{0-8}$alkyl-S(O)$_{0-2}$N($C_{0-8}$alkyl)($C_{0-8}$alkyl), —$C_{0-8}$alkyl-N($C_{0-8}$alkyl)CO($C_{0-8}$alkyl), —$C_{0-8}$alkyl-N($C_{0-8}$alkyl)CON($C_{0-8}$alkyl)($C_{0-8}$alkyl), —$C_{0-8}$alkyl-CON($C_{0-8}$alkyl)($C_{0-8}$alkyl), —$C_{0-8}$alkyl-$CO_2$($C_{0-8}$alkyl), —$C_{0-8}$alkylS(O)$_{0-2}$($C_{0-8}$alkyl), —$C_{0-8}$alkyl-O—$C_{0-8}$alkyl, —$C_{0-8}$alkyl-O—$C_{0-8}$alkylcyclyl, —$C_{0-8}$ alkyl-O—$C_{0-8}$alkylheterocycloalkyl, —$C_{0-8}$alkyl-O—$C_{0-8}$ alkylaryl, —Oaryl, —$C_{0-8}$alkyl-O—$C_{0-8}$alkyl-hetaryl, —$C_{0-8}$alkyl-S—$C_{0-8}$alkyl, —$C_{0-8}$alkyl-S—$C_{0-8}$ alkyl$C_{3-8}$cycloalkyl, —$C_{0-8}$alkyl-S—$C_{0-8}$ alkylheterocycloalkyl, —$C_{0-8}$alkyl-S—$C_{0-8}$alkylaryl, —$C_{0-8}$a lkyl-S—$C_{0-8}$ alkylhetaryl, —$C_{0-8}$alkyl-N($C_{0-8}$alkyl)-$C_{0-8}$alkyl, —$C_{0-8}$ alkyl-N($C_{0-8}$alkyl)-$C_{0-8}$alkyl$C_{3-8}$cycloalkyl, —$C_{0-8}$ alkyl-N($C_{0-8}$alkyl)-$C_{0-8}$alkylheterocycloalkyl, —$C_{0-8}$alkyl-N($C_{0-8}$alkyl)-$C_{0-8}$alkylaryl, —$C_{0-8}$alkyl-N($C_{0-8}$alkyl)-$C_{0-8}$ alkylhetaryl, —$C_{0-8}$alkyl-N($C_{0-8}$alkyl)($C_{0-8}$alkyl), $C_{2-8}$alkenyl, $C_{2-8}$alkynyl, $NO_2$, CN, $CF_3$, $OCF_3$, or $OCHF_2$ substituents; wherein said ring in each instance independently optionally includes one or more heteroatoms other than the nitrogen;

m is 0, 1, 2, or 3;

n is 0, 1, 2, 3, or 4;

aa is 0 or 1; and provided that Formula I is not trans-4-[8-amino-1-(7-chloro-4-hydroxy-1H-indol-2-yl)imidazo[1,5-a]pyrazin-3-yl]cyclohexanecarboxylic acid, cis-3-[8-amino-1-(7-chloro-1H-indol-2-yl)imidazo[1,5-a]pyrazin-3-yl]cyclobutanecarboxylic acid, trans-4-{8-amino-1-[7-(3-isopropyl)phenyl-1H-indol-2-yl]imidazo[1,5-a]pyrazin-3-yl}cyclohexanecarboxylic acid or trans-4-{8-amino-[7-(2,5-dichloro)phenyl-1H-indol-2-yl]imidazo[1,5-a]pyrazin-3-yl}cyclohexanecarboxylic acid.

Specific examples of compounds encompassed by Formula I, that are mTOR kinase inhibitors that inhibit mTOR by binding to and directly inhibiting both mTORC1 and mTORC2 kinases, were prepared as described in the following schemes and examples.

The following schemes, intermediates and examples serve to demonstrate how to synthesize compounds that can be used in the invention described herein, but in no way limit the invention. Additionally, the following abbreviations are used: Me for methyl, Et for ethyl, iPr or iPr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-CH3O)Ph for p-methoxyphenyl, (p-NO2)Ph for p-nitrophenyl, 4Br-Ph or (4Br)Ph for 4-bromophenyl, 2-CF3-Ph or (2CF3)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, TMP for tetramethylpiperidine, n-BuLi for n-butyllithium, CDI for 1,1'-carbonyldiimidazole, DEAD for diethyl azodicarboxylate, PS-PPh3 for polystyrene triphenylphosphine, DIEA for diisopropylethylamine, DIAD for diisopropyl azodicarboxylate, DBAD for di-tert-butyl azodicarboxylate, HPFC for high performance flash chromatography, rt or RT for room temperature, min for minute, h for hour, Bn for benzyl, and LAH for lithium aluminum hydride.

Accordingly, the following are compounds that are useful as intermediates in the formation of the mTOR inhibiting EXAMPLES.

The compounds of Formula I of this invention and the intermediates used in the synthesis of the compounds of this invention were prepared according to the following methods. Method A was used when preparing compounds of Formula I-AA

I-AA as shown below in Scheme 1:
Method A:

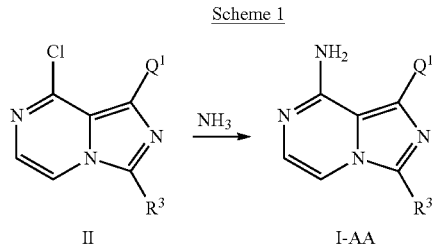

where $Q^1$ and $R^3$ are as defined previously for compound of Formula I.

In a typical preparation of compounds of Formula I-AA, compound of Formula II was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II of Scheme 1 were prepared as shown below in Scheme 2.

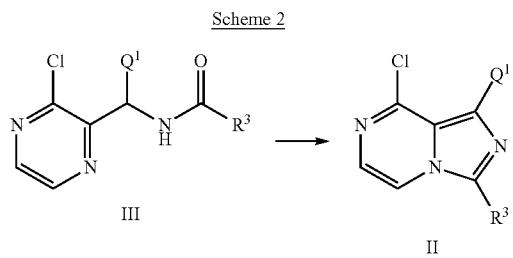

where $Q^1$ and $R^3$ are as defined previously for compound of Formula I.

In a typical preparation of a compound of Formula II, an intermediate of Formula III was treated with $POCl_3$ or the isolated "Vilsmeier salt" [CAS#33842-02-3] in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride ($CH_2Cl_2$) or chloroform ($CHCl_3$). If desired, mixtures of these solvents were used or no solvent was used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III of Scheme 2 were prepared as shown below in Scheme 3:

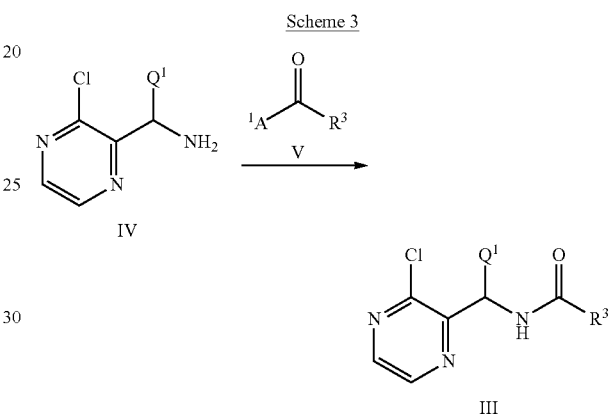

where $Q^1$ and $R^3$ are as defined previously for compound of Formula I and $A^1$=OH, alkoxy, or a leaving group such as a halogen or imidazole.

In a typical preparation, of a compound of Formula III, a compound of Formula IV and compound of Formula V were reacted under suitable amide coupling conditions. Suitable conditions include but are not limited to treating compounds of Formula IV and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvents were methylene chloride and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula IV and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV and V (where $A^1$=F, Cl, Br, I) and base and substoichiometric amounts of DMAP were preferably used although higher or lower amounts were used if desired. Additionally, other suitable reaction conditions for the conversion of a compound of Formula IV to a compound of Formula III can be found in Larock, R. C. Comprehensive Organic Transformations, 2nd ed.; Wiley and Sons: New York, 1999, pp 1941-1949.

The compounds of Formula IV of Scheme 3 were prepared as shown below in Scheme 4:

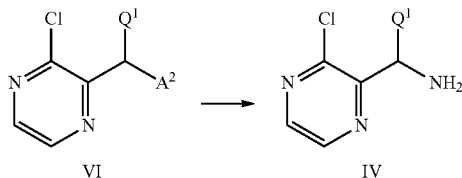

Scheme 4 where $Q^1$ is as defined previously for compound of Formula I and $A^2$=phthalimido or $N_3$.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. In the transformation of compound of Formula VI to IV, if $A^2$=$N_3$, then one skilled in the art would recognize that typical azide reduction conditions could be employed, including but not limited to $PPh_3$ and water or hydrogenation in the presence of a metal catalyst such as palladium.

The compounds of Formula VI of Scheme 4 were prepared as shown below in Scheme 5:

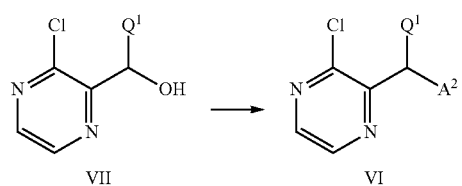

Scheme 5 where $Q^1$ is as defined previously for compound of Formula I and $A^2$=phthalimido or $N_3$.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD).

The preferred reactants were triphenylphosphine or resin-bound triphenylphosphine (PS-$PPh_3$), and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent or a slight excess, 1.1 equivalents, of triphenylphosphine, DIAD and phthalimide was used per equivalent of compound of Formula VII. Additionally, compound of Formula VII can be reacted with $Ts_2O$, $Ms_2O$, $Tf_2O$, TsCl, MsCl, or $SOCl_2$ in which the hydroxy group is converted to a leaving group such as its respective tosylate, mesylate, triflate, or halogen such as chloro and subsequently reacted with an amine equivalent such as $NH(Boc)_2$, phthalimide, potassium phthalimide, or sodium azide. Conversion of the amine equivalents by known methods such as by treating under acidic conditions (NH$(Boc)_2$), with hydrazine (phthalimide) as shown in Scheme 4, or with triphenylphosphine/water (azide) will afford the desired amine as shown in Scheme 4.

The compounds of Formula VII of Scheme 5 were prepared from aldehydes $Q^1$-CHO and a 2-chloropyrazine VIII as shown below in Scheme 6:

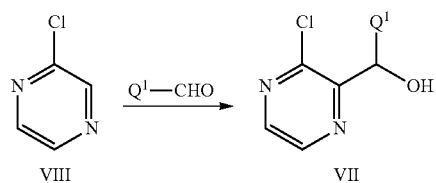

Scheme 6 where $Q^1$ is as defined previously for compound of Formula I.

In a typical preparation, of a compound of Formula VII, a compound of Formula VIII was reacted under suitable reaction conditions in a suitable solvent with a compound of Formula $Q^1$-CHO. Suitable conditions included but were not limited to treating compounds of Formula VIII with a base such as lithium tetramethylpiperidide (Li-TMP) followed by treating with compounds of Formula $Q^1$-CHO. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula I of this invention and the intermediates used in the synthesis of the compounds of this invention were also prepared according to the following methods. Method AA was used when preparing compounds of Formula I-AA from compound of Formula I-AAA as shown below in Scheme 7:

Method AA:

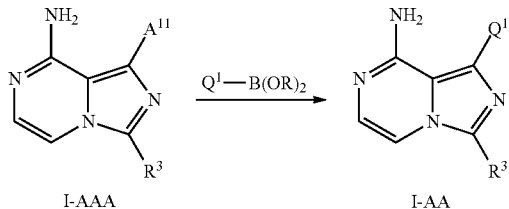

Scheme 7 where $Q^1$ and $R^3$ are as defined previously for compound of Formula I, $A^{11}$=halogen such as Cl, Br, or I and $B(OR)_2$=suitable boronic acid/ester.

In a typical preparation of compounds of Formula I-AA, compound of Formula I-AAA was reacted with a suitable boronic acid/ester ($Q^1$-$B(OR)_2$) in a suitable solvent via typical Suzuki coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AA from I-AAA. For example, compound of Formula I-AAA could be reacted with a suitable organotin reagent $Q^1$-$SnBu_3$ or the like in a suitable solvent via typical Stille coupling procedures.

The compounds of Formula I-AAA of Scheme 7 were prepared as shown below in Scheme 8.

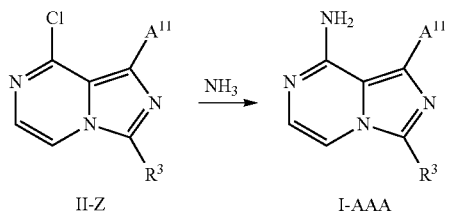

Scheme 8 where $R^3$ is as defined previously for compound of Formula I and $A^{11}$=halogen such as Cl, Br, or I.

In a typical preparation of compounds of Formula I-AAA, compound of Formula II-Z was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-Z of Scheme 8 were prepared as shown below in Scheme 9.

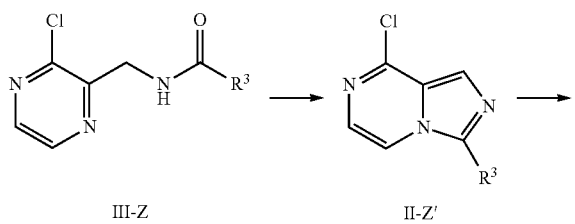

Scheme 9

-continued

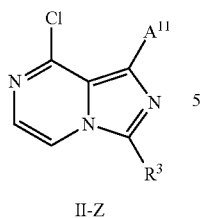

II-Z where $R^3$ is as defined previously for compound of Formula I and $A^{11}$=halogen such as Cl, Br, or I.

In a typical preparation of a compound of Formula II-Z, intermediate III-Z was converted to compound of Formula II-Z'. Intermediate of Formula III-Z was treated with POCl$_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride (CH$_2$Cl$_2$) or chloroform (CHCl$_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired. In the conversion of compound of Formula III-Z to II-Z', suitable halogenating agent were used, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Z of Scheme 9 were prepared as shown below in Scheme 10:

Scheme 10

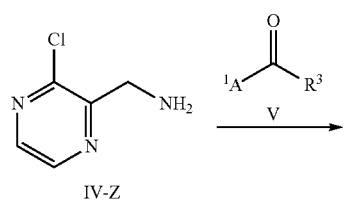

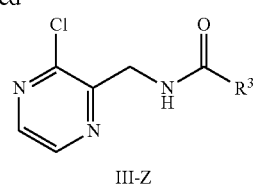

III-Z where $R^3$ is as defined previously for compound of Formula I and $A^1$=OH, alkoxy, or a leaving group such as chloro or imidazole.

In a typical preparation, of a compound of Formula III-Z, a compound of Formula IV-Z and compound of Formula V were reacted under suitable amide coupling conditions. Suitable conditions include but are not limited to treating compounds of Formula IV-Z and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Additionally, if compound of Formula IV-Z was a salt or bis-salt, a suitable base was required and included, but was not limited to, diisopropylethylamine or triethylamine. Alternatively, compounds of Formula IV-Z and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV-Z and V (where $A^1$=F, Cl, Br, I) and base and substoichiometric amounts of DMAP were preferably used although higher or lower amounts were used if desired. Additionally, other suitable reaction conditions for the conversion of an amine (compound of Formula IV-Z) to an amide (compound of Formula III-Z) can be found in Larock, R. C. Comprehensive Organic Transformations, 2nd ed.; Wiley and Sons: New York, 1999, pp 1941-1949.

The compounds of Formula IV-Z of Scheme 10 were prepared as shown below in Scheme 11:

Scheme 11

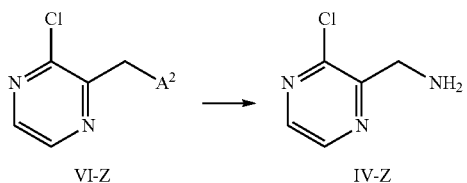

VI-Z → IV-Z where $A^2$ is phthalimido or $N_3$.

In a typical preparation, of a compound of Formula IV-Z, a compound of Formula VI-Z is reacted under suitable reaction conditions in a suitable solvent. When $A^2$=phthalimido, suitable conditions include treatment of compound of Formula VI-Z with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VI-Z of Scheme 11 were prepared as shown below in Scheme 12:

Scheme 12

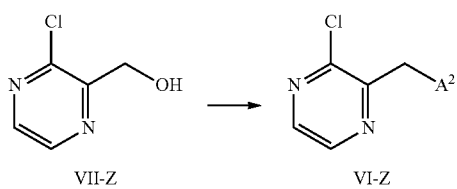

VII-Z → VI-Z where $A^2$=phthalimido or $N_3$.

In a typical preparation of a compound of Formula VI-Z (when $A^2$=phthalimido), a compound of Formula VII-Z was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS-PPh$_3$) and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Generally, 1.0 or 1.1 equivalents of triphenylphosphine, DIAD and phthalimide was used per equivalent of compound of Formula VII-Z. Additionally, compound of Formula VII-Z can be reacted with $Ts_2O$, $Ms_2O$, $Tf_2O$, TsCl, MsCl, or $SOCl_2$ in which the hydroxy group is converted to a leaving group such as its respective tosylate, mesylate, triflate, or halogen such as chloro and subsequently reacted with an amine equivalent such as $NH(Boc)_2$, phthalimide, potassium phthalimide or sodium azide. Conversion of the amine equivalents by known methods such as by treating under acidic conditions (NH(Boc)$_2$), with hydrazine (phthalimide) as shown in Scheme 4, or with triphenylphosphine/water (azide) will afford the desired amine as shown in Scheme 4.

The compounds of Formula VII-Z of Scheme 12 were prepared from 2-chloropyrazine VIII as shown below in Scheme 13:

Scheme 13

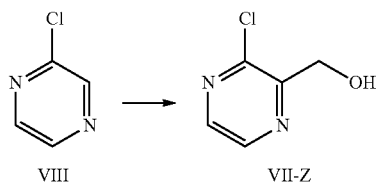

VIII → VII-Z

In a typical preparation, of a compound of Formula VII-Z, a compound of Formula VIII was reacted under suitable reaction conditions in a suitable solvent. Suitable reaction conditions included, but were not limited to, treating compounds of Formula VIII with a base such as lithium tetramethylpiperidide (Li-TMP) followed by treatment with a reagent containing a carbonyl equivalent followed by treatment with a suitable reducing agent. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. Suitable carbonyl equivalent reagents include, but are not limited to, formamides such as DMF or suitable chloroformate such as methyl or ethyl chloroformate. After addition of the suitable carbonyl equivalent reagent, the reaction if charged with a polar protic solvent such as, but not limited to, methanol or ethanol followed by treatment with a suitable reducing agent such as sodium borohydride. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula X-Z ($Q^1$-CHO) of Scheme 6 were prepared as shown below in Scheme 14:

Scheme 14

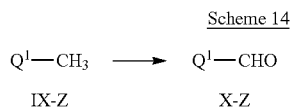

IX-Z     X-Z where Q1 is as defined previously for compound of Formula I.

In a typical preparation, of a compound of Formula X-Z ($Q^1$-CHO), a compound of Formula IX-Z ($Q^1$-$CH_3$) was reacted with a suitable oxidizing agent under suitable reaction conditions. Suitable oxidizing agents included, but were not limited to, selenium dioxide. Suitable reaction conditions for use in the above process included, but were not limited to, heating a mixture of selenium dioxide and compounds of Formula IX-Z ($Q^1$-$CH_3$) neat or in a suitable solvent such as, but not limited to, chlorobenzene or sulpholane. The above process may be carried out at temperatures between about 120° C. and about 180° C. Preferably, the reaction was carried out at 150° C. to 165° C. The above process to produce compounds of the present invention was preferably carried out at about atmospheric pressure although higher or lower pressures were used if desired. Preferably, 1-1.5 eq. selenium dioxide were used although higher or lower amounts were used if desired. Alternatively, a compound of Formula IX-Z ($Q^1$-$CH_3$) was reacted first with a halogenating agent and a radical initiator under suitable reaction conditions in a suitable solvent to give a compound of Formula $Q^1$-$CH_2$-Hal (wherein Hal=Cl or Br) that was then further reacted with DMSO and a base under suitable reaction conditions to give a compound of Formula X-Z ($Q^1$-CHO). Suitable halogenating agents included, but were not limited to, bromine, N-bromosuccinimide, and chlorine. Preferably, N-bromosuccinimide was used. Suitable radical initiators included, but were not limited to, 2,2'-azobisisobutyronitrile (AIBN) and UV light. Preferably, AIBN was used. Preferably, carbon tetrachloride was used as solvent for the halogenation step, although other halogenated solvents may be added. The halogenation may be carried out at temperatures between about 60° C. and about 100° C. Preferably, the reaction was carried out at about 80° C. Suitable bases included, but were not limited to, sodium hydrogencarbonate, sodium dihydrogenphosphate, disodium hydrogenphosphate, and collidine. Preferably, sodium hydrogencarbonate was used. DMSO was preferably used as solvent although other solvents may be added. The second step may be carried out at temperatures between about 40° C. and about 140° C. Preferably, the reaction was carried out at about 90° C. Additionally, other suitable reaction conditions for the conversion of $Q^1$-$CH_3$ to $Q^1$-CHO can be found in Larock, R. C. Comprehensive Organic Transformations, 2nd ed.; Wiley and Sons: New York, 1999, pp 1205-1207 and 1222-1224.

The compounds of Formula XIV-Z ($Q^1$-$B(OR)_2$) of Scheme 7 were prepared as shown below in Scheme 15:

Scheme 15

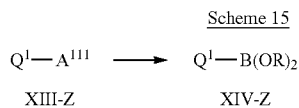

XIII-Z     XIV-Z where $Q^1$ is as defined previously for compound of Formula I, $A^{111}$=OTf or halogen such as Cl, Br, or I and $B(OR)_2$=suitable boronic acid/ester.

In a typical preparation, of a compound of Formula XIV-Z ($Q^1$-$B(OR)_2$), a compound of Formula XIII-Z ($Q^1$-$A^{111}$) was reacted with a suitable metal catalyst and a suitable boronating agent under suitable reaction conditions. Suitable metal catalyst agents included, but were not limited to, $Pd(OAc)_2$ in the presence of 1,3-bis(2,6-diisopropylphenyl)imidazolium chloride. Suitable boronating agents included, but were not limited to, bis(pinacolato)diboron. Suitable reaction conditions for use in the above process included, but were not limited to, heating a mixture of $Pd(OAc)_2$, 1,3-bis(2,6-diisopropylphenyl)imidazolium chloride, KOAc, and bis(pinacol)borane in a suitable solvent such as, but not limited to, THF. The above process may be carried out at temperatures between about 20° C. and about 100° C. Preferably, the reaction was carried out at 60° C. to 80° C. The above process to produce compounds of the present invention was preferably carried out at about atmospheric pressure although higher or lower pressures were used if desired. Preferably, 2-3 eq. KOAc, 1-1.5 eq. bis(pinacol)borane, 0.03-1 eq. $Pd(OAc)_2$, and 0.09-3 eq. 1,3-bis(2,6-diisopropylphenyl)imidazolium chloride were used although higher or lower amounts were used if desired. Additionally, other suitable reaction conditions for the conversion of $Q^1$-$A^{111}$ to $Q^1$-$B(OR)_2$ can be found in the literature which involve a variety of $Q^1$-$A^{111}$ or aryl/heteroarylhalides and a variety of conditions (Biooganic & Medicinal Chemistry Letters, 2003, 12(22), 4001; Biooganic & Medicinal Chemistry Letters, 2003, 13(18), 3059; Chemical Communications (Cambridge, UK), 2003, 23, 2924; Synthesis, 2002, 17, 2503; Angewandte Chemie, International Ed., 2002, 41(16), 3056; Journal of the American Chemical Society, 2002, 124(3), 390; Organic Letters, 2002, 4(4), 541; Tetrahedron, 2001, 57(49), 9813; Journal of Organic Chemistry, 2000, 65(1), 164; Journal of Organic Chemistry, 1997, 62(19), 6458; Journal of Organometallic Chemistry, 1983, 259(3), 269). In some cases, compounds of Formula XIII-Z ($Q^1$-$A^{111}$) and XIV-Z ($Q^1$-$B(OR)_2$) are commercially available or synthesized according to literature procedures. In cases where neither are available, compounds of Formula XIII-Z ($Q^1$-$A^{111}$) and XIV-Z ($Q^1$-$B(OR)_2$) were synthesized via procedures described in the experimental section herein.

Both $R^3$ and $Q^1$ in the compounds described herein in some instances contain functional groups that can be further manipulated. It would be appreciated by those skilled in the art that such manipulation of functional groups can be accomplished with key intermediates or with late stage compounds. Such functional group transformations are exemplified in the following Schemes 16-26 as well as in the experimental section but are in no way meant to limit the scope of such transformations. Additionally, the chemistry shown in Schemes 16-26 can also be applied to compounds of I-AAA, II-Z, and II-Z'.

The compounds of Formula I-A (compounds of Formula I-AA where $R^3$=Z—$CONR^{312}R^{322}$) were prepared as shown below in Scheme 17:

Scheme 16

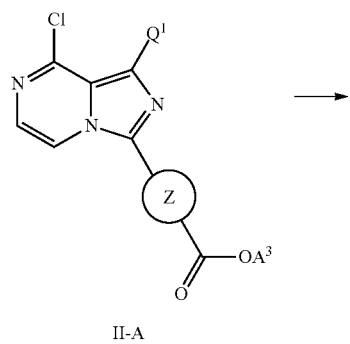

where $Q^1$, $R^{312}$ and $R^{322}$ are as defined previously for compound of Formula I and $A^3$=hydrogen or alkyl such as methyl or ethyl.

In a typical preparation of compound of Formula I-A, when $A^3$=alkyl and $R^{312}$ and $R^{322}$ were both equal to H, reaction of compound of Formula II-A (compounds of Formula II where $R^3$=Z—$CO_2A^3$) with ammonia in a suitable solvent, afforded compound of Formula I-A. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of isopropanol/THF. The above process was carried out at temperatures between about −78° C. and about 120° C. Preferably, the reaction was carried out between 80° C. and about 120° C. The above process to produce compounds of the present invention was preferably carried out at about atmospheric pressure although higher or lower pressures were used if desired. Substantially equimolar amounts of reactants were preferably used although higher or lower amounts were used if desired. Additionally, in a typical preparation of compound of Formula I-A, compound of Formula II-A (when $A^3$=H) was reacted with $HNR^{312}R^{322}$ followed by ammonia in a suitable solvent. When $A^3$=H, typical coupling procedures as described in Scheme 3 (conversion of $CO_2H$ to COCl via treatment with $SOCl_2$ or oxalyl chloride followed by reaction with $HR^{312}R^{322}$ or treatment of $CO_2H$ and $HR^{312}R^{322}$ with EDC or DCC in conjunction with DMAP, HOBT, or HOAt and the like) were employed to afford the transformation of a carboxylic acid to an amide. When $A^3$=alkyl such as methyl or ethyl, treatment of the ester with $Al(NR^{312}R^{322})$ afforded conversion of $CO_2A^3$ to $CO(NR^{312}R^{322})$. Subsequent treatment with ammonia afforded compounds of Formula I-A.

The compounds of Formula I-A' (compounds of Formula I-AA where $R^3$=Z—$CO_2A^3$) and I-A" (compounds of Formula I-AA where $R^3$=Z—$CO_2H$) were prepared as shown below in Scheme 17:

Scheme 17

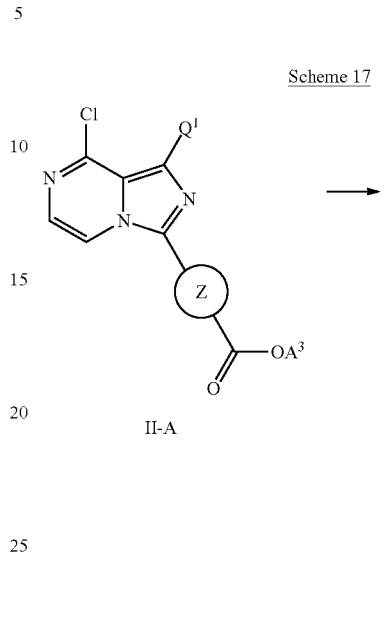

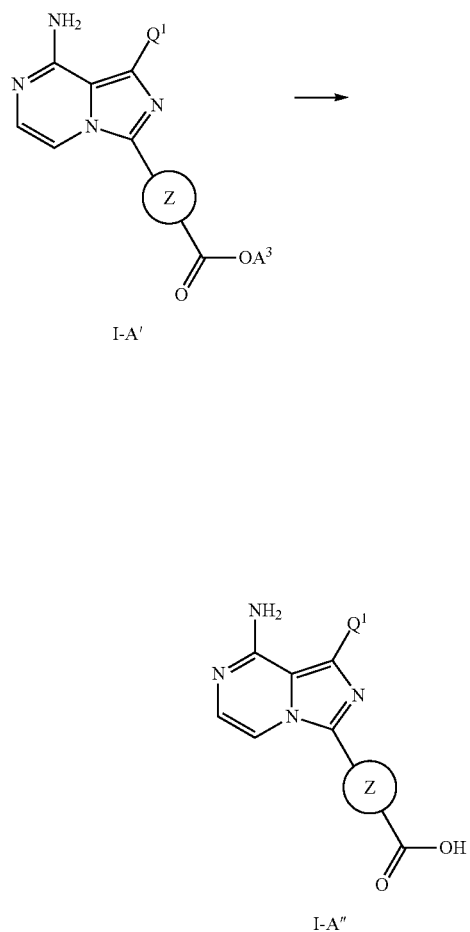

where $Q^1$ is as defined previously for compounds of Formula I and $A^3$=alkyl such as methyl or ethyl.

In a typical preparation of compound of Formula I-A', compound of Formula II-A was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 100° C. and about 120° C. The above process to produce compounds of the present invention was preferably carried out at about atmospheric pressure although higher or lower pressures were used if desired. In most cases, the reactions were run in a sealed tube. Substantially equimolar amounts of reactants were preferably used although higher or lower amounts were used if desired. Typically, an excess of ammonia was used and the reaction was monitored in order to ensure that additional ammonia to the ester moiety did not occur to an appreciable extent. Additionally, in a typical preparation of compound of Formula I-A'', compound of Formula I-A' was reacted under typical saponification conditions such as NaOH in THF/$H_2O$/MeOH. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was a mixture of THF/$H_2O$/MeOH. The above process was carried out at temperatures between about −78° C. and about 120° C. Preferably, the reaction was carried out between rt and about 60° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula II-B (compounds of Formula II where $R^3$=Z—$CH_2OH$) and I-B (compounds of Formula I-AA where $R^3$=Z—$CH_2OH$) were prepared as shown below in Scheme 18:

Scheme 18

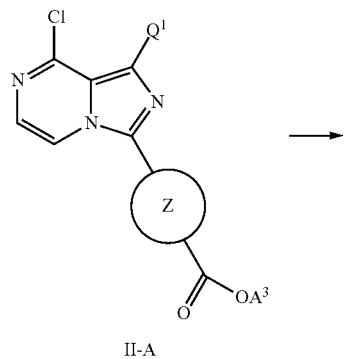

II-A

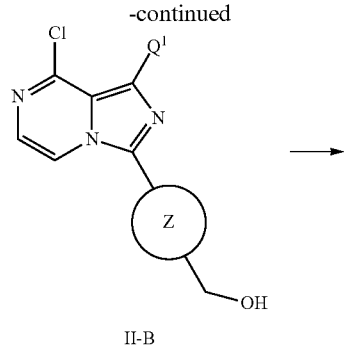

II-B

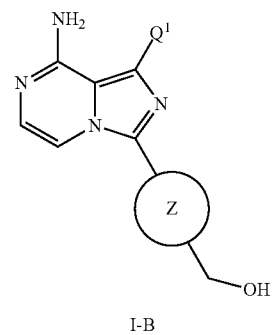

I-B where $Q^1$ is as defined previously for compound of Formula I and $A^3$=hydrogen or alkyl such as methyl or ethyl.

In a typical preparation of compound of Formula I-B, compound of Formula II-A is treated with a suitable reducing agent such as lithium aluminum hydride in a suitable solvent, such as THF to afford compound of Formula II-B. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used. The preferred solvent was THF. The above process was carried out at temperatures between about −78° C. and about 120° C. Preferably, the reaction was carried out between 0° C. and about 50° C. The above process to produce compounds of the present invention was preferably carried out at about atmospheric pressure although higher or lower pressures were used if desired. Substantially equimolar amounts of reactants were preferably used although higher or lower amounts were used if desired. Subsequent treatment of compound of Formula II-B under previously described ammonolysis conditions (ammonia in isopropanol in a sealed tube at 120° C.), afforded compound of Formula I-B.

The compounds of Formula II-C (compounds of Formula II where $R^3$=Z—$CH_2A^4$), II-D (compounds of Formula II where $R^3$=Z—$CH_2A^5(R^{313})(R^{323})_{aa}$), I-B (compounds of Formula I-AA where $R^3$=Z—$CH_2OH$) and I-C (compounds of Formula I-AA where $R^3$=Z—$CH_2A^5(R^{313})(R^{323})_{aa}$) were prepared as shown below in Scheme 19:

Scheme 19

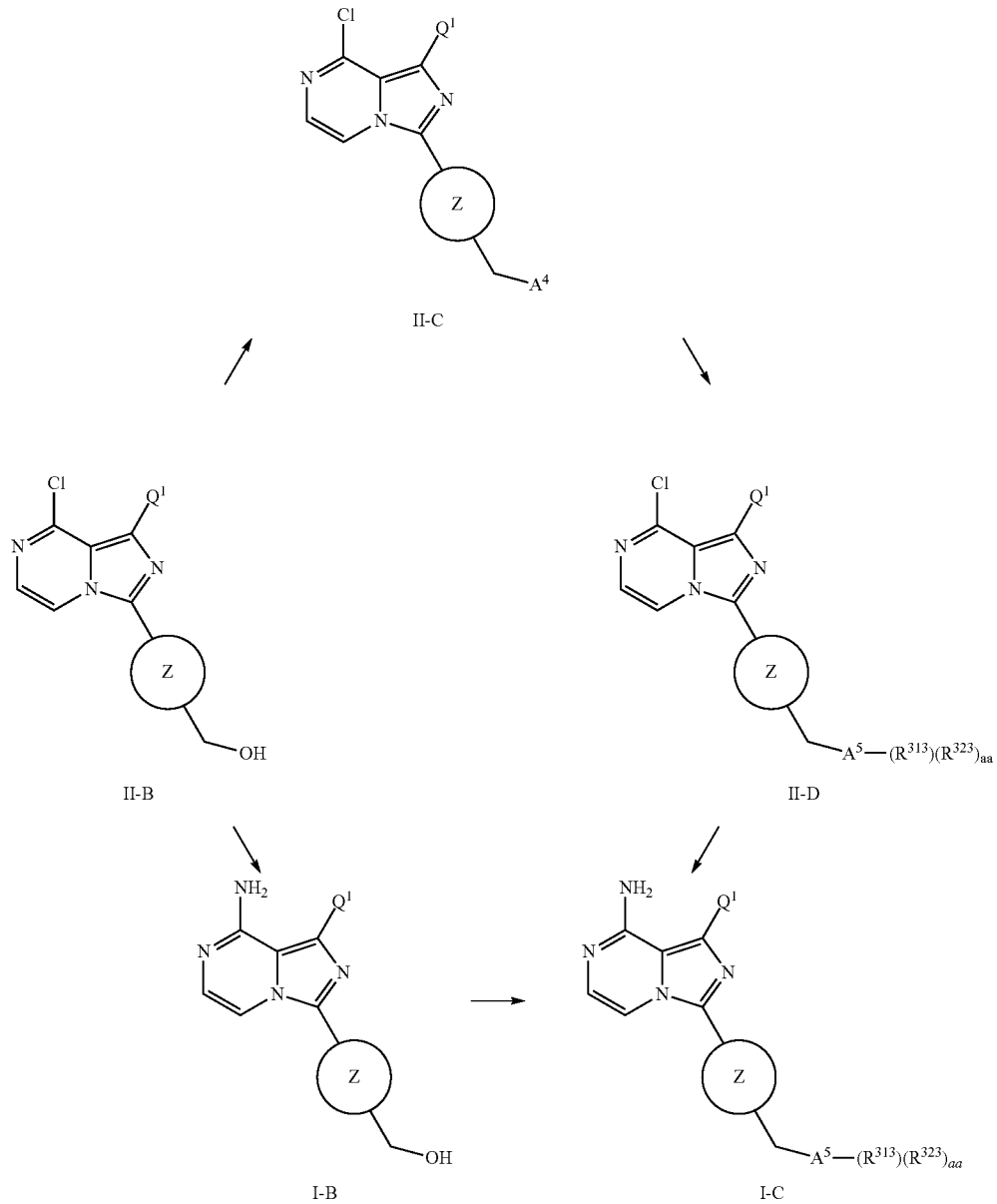

where $Q^1$, $R^{313}$, and $R^{323}$ are as defined previously for compound of Formula I; $A^4$=suitable leaving group such as OTs, OMs, OTf, or halo such as chloro, bromo, or iodo; d=0 or 1; and $A^5$=N, O or S.

In a typical preparation of compound of Formula I-C, the hydroxy group of compound of Formula II-B was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C. Reaction of compound of Formula II-C with $HA^5(R^{313})(R^{323})_{aa}$ afforded compound of Formula II-D. Subsequent reaction of compound of Formula II-D under previously described ammonolysis conditions afforded compound of Formula I-C. Additionally, compound of Formula II-B was converted to compound of Formula I-B as described previously in Scheme 18. Further conversion of compound of Formula I-B to compound of Formula I-C was accomplished by following the previously described conditions for the conversion of compound of Formula II-B to compound of Formula II-C and the further conversion of compound of Formula II-C to compound of Formula II-D (in the net conversion of OH to $A^5(R^{313})(R^{323})_{aa}$). Furthermore, compound of Formula II-B can be directly converted to compound of Formula II-D by treating compound of Formula II-B with various alkylating agent or with phenols via the Mitsunobu reaction to afford compounds Formula II-D (compounds of Formula II where $R^3$=$CH_2$—Z-$A^5(R^{313})(R^{323})_{aa}$) in which $A^5$=O, aa=0, and $R^{313}$=alkyl or aryl).

The compounds of Formula I-C' (compounds of Formula I-AA where $R^3$=Z—$CH_2$-$A^2$), I-C'' (compounds of Formula I-AA where $R^3$=Z—$CH_2$—$NH_2$), and I-C''' (compounds of Formula I-AA where $R^3$=Z—$CH_2$—$N(R^{313})(R^{323})$) were prepared as shown below in Scheme 20:

Scheme 20

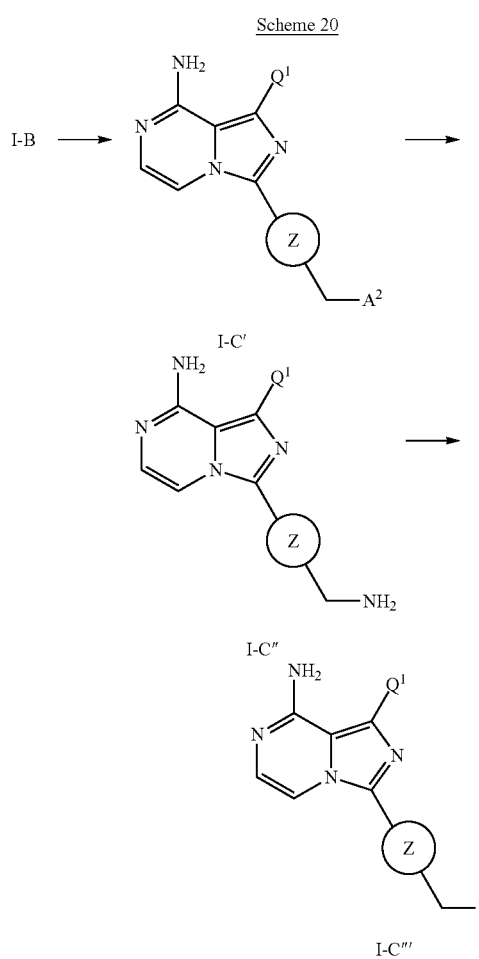

where $Q^1$, $R^{313}$, and $R^{323}$ are as defined previously for compound of Formula I and $A^2$=phthalimido or $N_3$.

In a typical preparation of compounds of Formula I-C', I-C", and I-C"', the hydroxy group of compound of Formula I-B was converted to $A^2$, following the procedures as described in Scheme 5 for the conversion of compound of Formula VII to compound of Formula VI. Reaction of compound of Formula I-C' under conditions described in Scheme 4 afforded compound of Formula I-C". Reaction of compound of Formula I-C" with, but not limited to various alkylating agents, various aldehydes/ketones under reductive amination conditions, various acylating agents such as acetic anhydride, benzoyl chlorides, or with carboxylic acids in the presence of EDC or DCC with HOBT or HOAT, or with sulphonylating agents such as $Ts_2O$ or $MeSO_2Cl$ afforded compounds of Formula I-C"'. For example, in a typical preparation of compounds of Formula I-C"', a compound of Formula I-C" is treated with a suitable acylating agent in the presence of a suitable base in a suitable solvent. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$). If desired, mixtures of these solvents were used, however, the preferred solvent was chloroform. Suitable bases for use in the above process included, but were not limited to, trialkylamines such as diisopropylethylamine, triethylamine, or resin bound trialkylamines such as PS-DIEA. The preferred base was PS-DIEA.

In the case where the suitable acylating agent was acetic anhydride, the conversion of compound of Formula I-C" to compound of Formula I-C"' where $R^{313}$=H and $R^{323}$=COCH$_3$ was accomplished. The above process was carried out at temperatures between about −78° C. and about 120° C. Preferably, the reaction was carried out between 0° C. and about 20° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula I-D (compounds of Formula I-AA where $R^3$=(CH$_2$)$_n$—Z$^2$—H and $Z^2$ is a heterocyclyl ring containing a nitrogen atom connected to H) and I-E (compounds of Formula I-AA where $R^3$=(CH$_2$)$_n$—Z$^2$—R$^{31}$ and $Z^2$ is a heterocyclyl ring containing a nitrogen atom connected to $R^{311}$) were prepared as shown below in Scheme 21:

Scheme 21

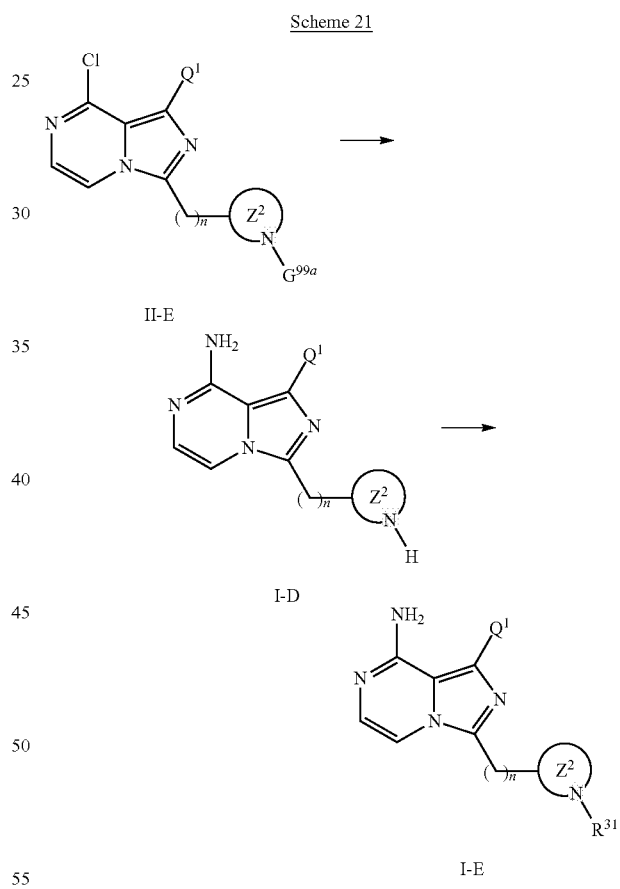

where $Q^1$ and $R^{31}$ are as defined previously for compound of Formula I, $G^{99a}$ is C(=O)A$^6$ or CO$_2$A$^6$, n=0-5, and A$^6$=alkyl, aryl, or aralkyl.

In a typical preparation of compound of Formula I-E, compound of Formula II-E is treated with suitable reagents capable of converting N-G$^{99a}$ to N—H and therefore afford compound of Formula I-D. For example, treatment of compound of Formula II-E (when $G^{99a}$ is equal to CO$_2$Bn) under previously described ammonolysis conditions followed by treatment with concentrated HCl and a suitable basic workup, affords compound of Formula I-D. Compound of Formula I-D can be subjected to various conditions including but not limited to reductive aminations, alkylations and ar(hetar)ylations, and acylations to afford amides, ureas, guanidines, carbamates, thiocarbamates, sulphonamides, and variously substituted nitrogen adducts to afford the net conversion of NH to $NR^2$.

The compounds of Formula II-G (compounds of Formula II where $R^3=Z^3$—OH), II-H (compounds of Formula II where $R^3=Z-A^5(R^{313})(R^{323})_{aa}$), I-F (compounds of Formula I-AA where $R^3=Z$—OH), and I-G (compounds of Formula I-AA where $R^3=Z\,A^5(R^{313})(R^3)_{aa}$) were prepared as shown below in Scheme 22:

compound of Formula I. Subsequent reaction of compounds of Formula II-H (compounds of Formula II where $R^3=Z-A^5(R^{313})(R^{323})_{aa}$ where d=0, $A^5$=N, and $R^{313}$ and $R^{323}$ are as previously described for compound of Formula I) with previously described ammonolysis conditions afforded compounds of Formula I-G. Furthermore, compounds of Formula II-H from II-G and I-G from I-F can be synthesized according to the conditions described in Scheme 19 for the transformations of II-B to II-D and I-B to I-C, respectively.

The compounds of Formula I-C''' (compounds of Formula I-AA where $R^3=Z$—$CH_2$—$N(R^{313})(R^{323})$) were prepared as shown below in Scheme 23:

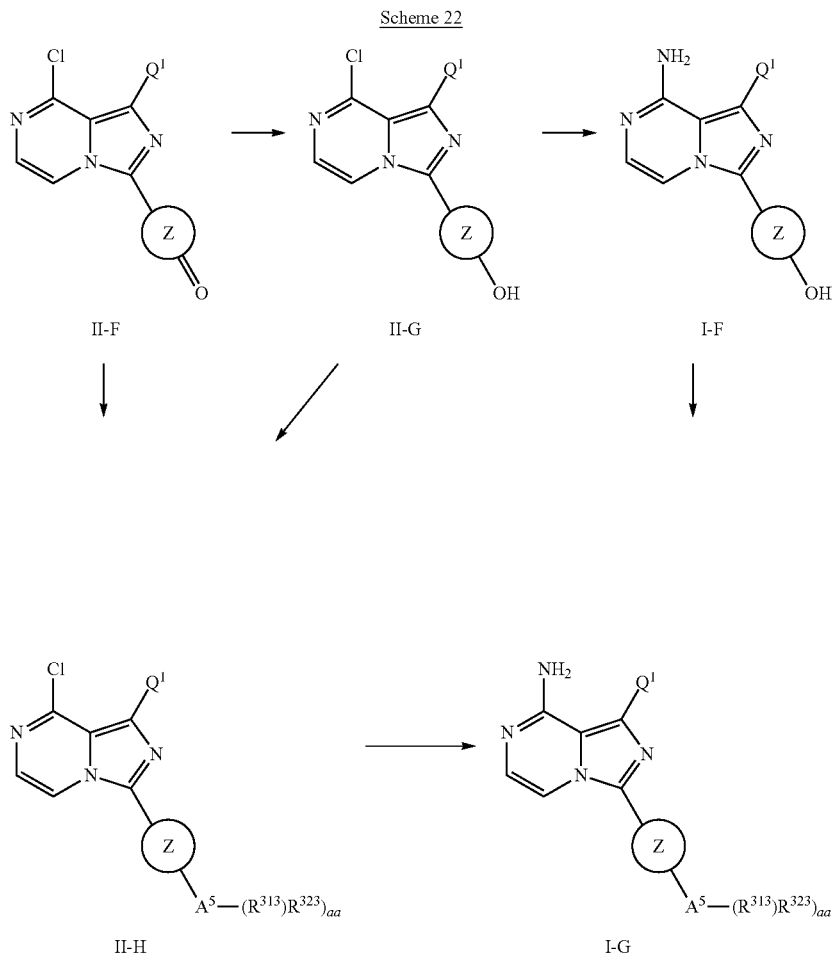

where $Q^1$, $R^{313}$, and $R^{323}$ are as defined previously for compound of Formula I; aa=0 or 1; and $A^5$=N, O or S.

In a typical preparation of compound of Formula I-F and I-G, the following transformations occurred: Compound of Formula II-F was reduced with a suitable reducing agent in a suitable solvent, such as sodium borohydride in methanol to afford compound of Formula II-G. Compound of Formula II-G was subjected to previously described ammonolysis conditions to afford compound of Formula I-F. Additionally, compounds of Formula II-F can be reacted with various amines under reductive amination conditions ($NaBH_3CN$ or $NaBH(OAc)_3$ with $HA^5(R^{313})(R^{323})_{aa}$ where d=0, $A^5$=N, and $R^{313}$ and $R^{323}$ are as previously described for compound of Formula I) to afford compounds of Formula II-H where d=0, $A^5$=N, and $R^{313}$ and $R^{323}$ are as previously described for

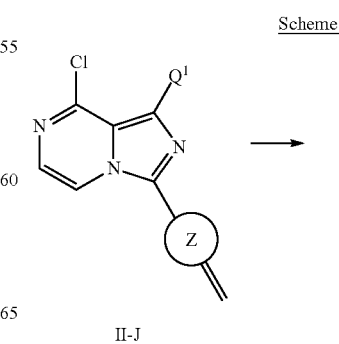

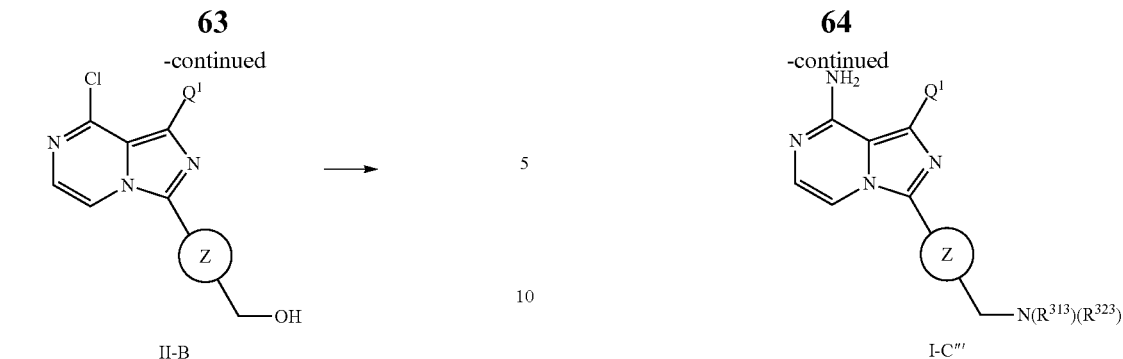

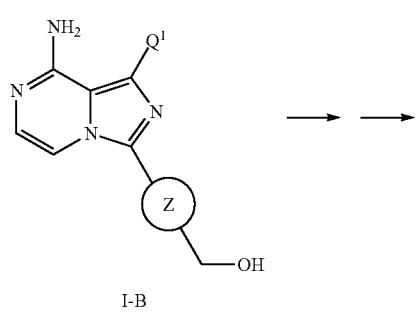

I-B

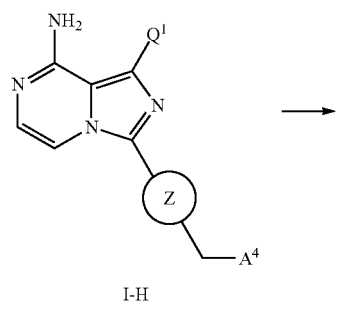

I-H where $Q^1$, $R^{313}$, and $R^{323}$ are as defined previously for compound of Formula I and $A^4$=suitable leaving group such as Cl, OTs, OMs or OTf.

In a typical preparation of compound of Formula I-C''' (compounds of Formula I-AA where $R^3$=Z—CH$_2$—N($R^{313}$)($R^{323}$)), the following transformations occurred: Compounds of Formula II-J (compounds of Formula II where $R^3$=Z=CH$_2$) were reacted with a suitable hydroborating agent such as diborane, 9-borabicyclo[3.3.1]nonane (9-BBN), catecholborane and the like, in a suitable solvent such as THF followed by treatment with an suitable oxidizing agent such as hydrogen peroxide in basic aqueous solution or NaBO$_3$.H$_2$O to afford compounds of Formula II-B. Further reaction of compounds of Formula II-B with previously described ammonolysis conditions afforded compounds of Formula I-B. The hydroxy group of compounds of Formula I-B was then converted to a suitable leaving group, $A^4$, such OTs, OMs, or OTf, by reaction with Ts$_2$O, Ms$_2$O, or Tf$_2$O, respectively, to afford compounds of Formula I-H. Further reaction of compounds of Formula I-H with HN($R^{313}$)($R^{323}$) where $R^{313}$ and $R^{323}$ are as previously described for compounds of Formula I afforded compound of Formula I-C''' (compounds of Formula I-AA where $R^3$=Z—CH$_2$—N($R^{313}$)($R^{323}$)).

The compounds of Formula I-J (compounds of Formula I-AA where $R^3$=Z—OH(CH$_2$OH)), I-K (compounds of Formula I-AA where $R^3$=Z=O), and I-L (compounds of Formula I-AA where $R^3$=Z—NR$^{313}$R$^{323}$) were prepared as shown below in Scheme 24:

Scheme 24

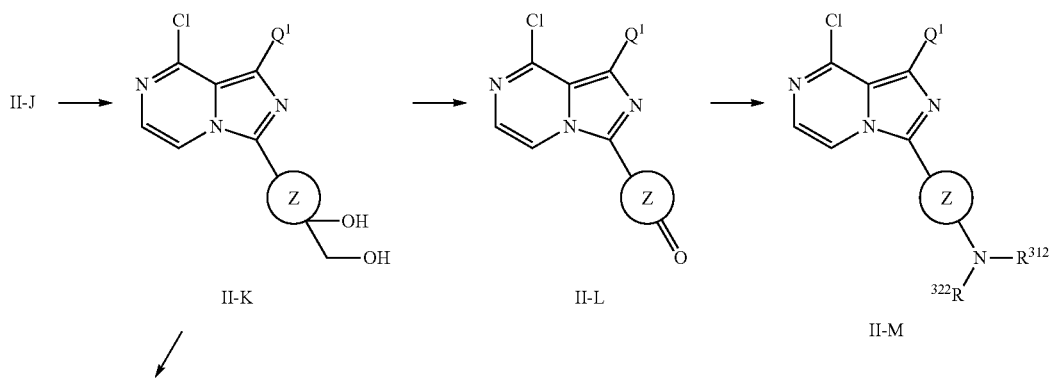

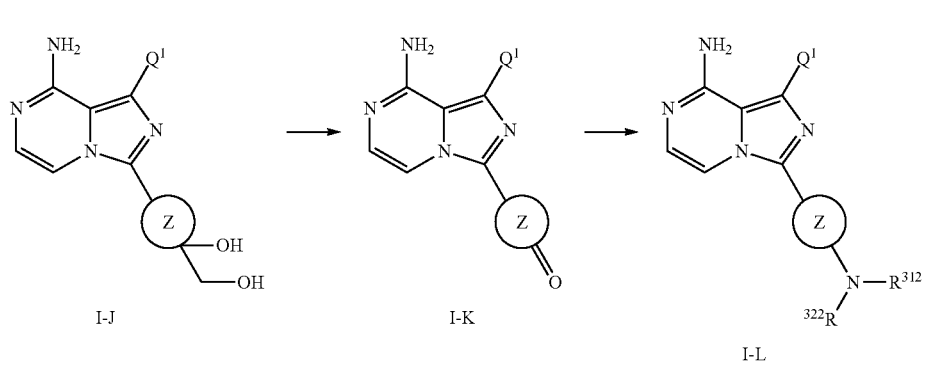

where $Q^1$, $R^{312}$ and $R^{322}$ are as defined previously for compound of Formula I.

In a typical preparation of compound of Formula I-J (compounds of Formula I-AA where $R^3$=Z—OH(CH$_2$OH)), I-K (compounds of Formula I-AA where $R^3$=Z=O), and I-L (compounds of Formula I-AA where $R^3$=Z—NR$^{312}$R$^{322}$) compound of Formula II-J was treated under (compounds of Formula II where $R^3$=Z=CH$_2$) was reacted with a suitable dihydroxylating agent such as osmium tetraoxide in the presence of NMO in a suitable solvent such as THF to afford compound of Formula II-K (compounds of Formula II where $R^3$=Z—OH(CH$_2$OH)) as a mixture of cis and trans isomers. Compounds of Formula II-K (compounds of Formula II where $R^3$=Z—OH(CH$_2$OH)) were treated with a suitable oxidizing agent, such as but not limited to, NaIO$_4$, converting the diol into a ketone moiety, affording compound of Formula II-L (compounds of Formula II where $R^3$=Z=O). Compound of Formula II-L (compounds of Formula II where $R^3$=Z=O) was then treated under typical reductive amination conditions, involving a suitable amine, HNR$^{312}$R$^{322}$ and a suitable reducing agent, such as but not limited to, NaBH(OAc)$_3$ or NaBH(CN)$_3$, affording compound of Formula II-M (compounds of Formula II where $R^3$=Z—NR$^{312}$R$^{322}$). Compound of Formula II-M (compounds of Formula II where $R^3$=Z—NR$^{312}$R$^{322}$) was treated under ammonolysis conditions, ammonia in isopropanol in a stainless steel bomb at 110° C., to afford compound of Formula I-L (compounds of Formula I-AA where $R^3$=Z—NR$^{312}$R$^{322}$). Moreover, compound of Formula II-K (compounds of Formula II where $R^3$=Z—OH(CH$_2$OH)) was treated under the ammonolysis conditions described above to afford compound of Formula I-J (compounds of Formula I-AA where $R^3$=Z—OH(CH$_2$OH)) as a mixture of isomers. Compound of Formula I-J (compounds of Formula I-AA where $R^3$=Z—OH(CH$_2$OH)) was treated with a suitable oxidizing agent, such as but not limited to, NaIO$_4$, converting the diol into a ketone moiety, affording compound of Formula I-K (compounds of Formula I-AA where $R^3$=Z=O), which was treated under the typical reductive amination conditions described above to afford compound of Formula I-L (compounds of Formula I-AA where $R^3$=Z—NR$^{312}$R$^{322}$).

The compounds of Formula I-N (compounds of Formula I-AA where $R^3$=Z—OH(CH$_2$NR$^{313}$R$^{323}$)) were prepared as shown below in Scheme 25:

Scheme 25

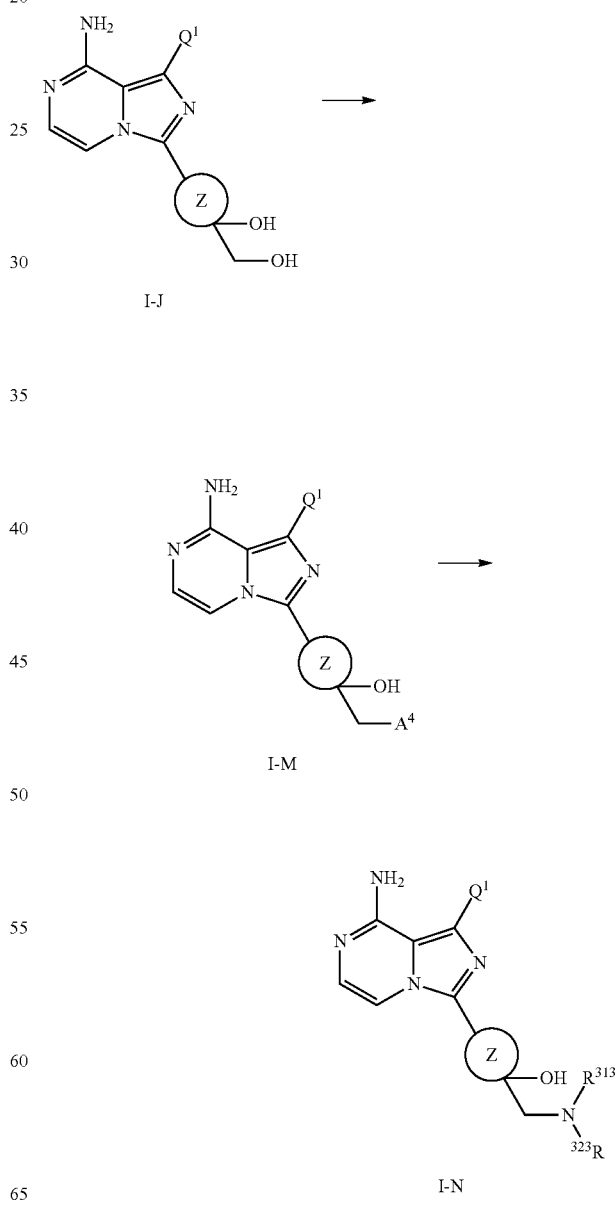

where $Q^1$, $R^{313}$, and $R^{323}$ are as defined previously for compound of Formula I; $A^4$=suitable leaving group such as OTs, OMs, or OTf.

In a typical preparation of compounds of Formula I-N (compounds of Formula I-AA where $R^3$=Z—OH ($CH_2NR^{313}R^{323}$)), the primary hydroxyl group of compound of Formula I-J (compounds of Formula I-AA where $R^3$=Z—OH($CH_2OH$)) was converted to a suitable leaving group, $A^4$, such as OTs, OMs, or OTf, by reaction with $Ts_2O$, $Ms_2O$, or $Tf_2O$ in the presence of a suitable base such as diisopropylamine or pyridine and solvent such as THF or methylene chloride to afford compound of Formula I-M (compounds of Formula I-AA where $R^3$=Z—OH($CH_2A^4$)). Reaction of compound of Formula I-M (compounds of Formula I-AA where $R^3$=Z—OH($CH_2A^4$)) with HN($R^{313}$)($R^{323}$) in a suitable solvent such as THF or methylene chloride afforded compound of Formula I-N (compounds of Formula I where $R^3$=Z—OH($CH_2NR^{313}R^{323}$)).

The compounds of Formula I-O (compounds of Formula I where $R^3$=$Z^3$—OH($G^{11}$)) were prepared as shown below in Scheme 26:

Scheme 26

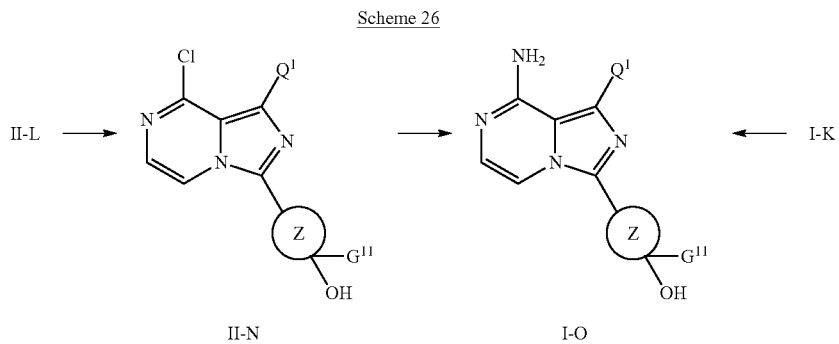

where $Q^1$ and $G^{11}$ are as defined previously for compound of Formula I.

In a typical preparation of compounds of Formula I-O (compounds of Formula I where $R^3$=Z—OH($G^{11}$)), the ketone moiety of compound of Formula II-L (compounds of Formula II where $R^3$=Z=O) was reacted with a suitable nucleophilic reagent such as MeMgBr or MeLi in a suitable solvent such as THF to afford compound of Formula II-N (compounds of Formula II where $R^3$=Z—OH($G^{11}$)). Compound of Formula II-N (compounds of Formula II where $R^3$=Z—OH($G^1$)) was reacted under ammonolysis conditions, ammonia in isopropanol in a stainless steel bomb at 110° C., to afford compound of Formula I-O (compounds of Formula I where $R^3$=Z—OH($G^{11}$)). Additionally, compound of Formula I-O (compounds of Formula I where $R^3$=Z—OH($G^{11}$)) was prepared by reacting compound of Formula I-K (compounds of Formula I-AA where $R^3$=Z=O) with a suitable nucleophilic reagent such as MeMgBr or MeLi in a suitable solvent such as THF.

The conversion of compounds of Formula I-PP' and I-P' to compounds of Formula I-RR an I-R, respectively may be accomplished by reaction with a boronic acid ester using so-called "Liebeskind-Srogl" conditions such as those described in *Organic Letters*, (2002), 4(6), 979 or *Synlett*, (2002), (3), 447.

A compound of Formula I-AB is equal to compound of Formula I wherein $X_1$=CH, $X_2$, $X_4$ and $X_5$=N, and $X_3$, $X_6$ and $X_7$=C; $Q^1$ is as defined for a compound of Formula I; $R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents; and $G^{11}$ is as defined for a compound of Formula I:

Method AB was used when preparing compounds of Formula I-AB as shown below in Scheme 28:

Method AB:

Scheme 28

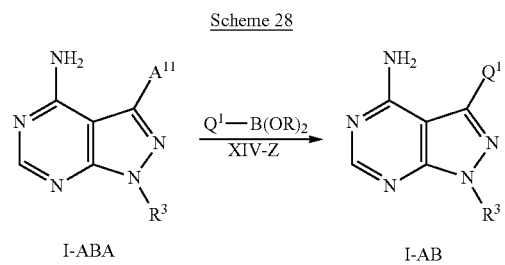

where $Q^1$ and $R^3$ are as defined previously for compound of Formula I-AB, $A^1$=halogen such as Cl, Br, or I, and $Q^1$-B(OR)$_2$=suitable boronic acid/ester.

In a typical preparation of compounds of Formula I-AB, compound of Formula I-ABA was reacted with a suitable boronic acid/ester of Formula XIV-Z ($Q^1$-B(OR)$_2$) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent systems were THF/water and DMF/water. The above process was carried out at temperatures between about 20° C. and about 120° C. Preferably, the reaction was carried out between 80° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AB from I-ABA. For example, compound of Formula I-ABA could be reacted with a suitable organotin reagent $Q^1$-SnBu$_3$ or the like in a suitable solvent via typical Stille coupling procedures.

The compounds of Formula I-ABA wherein $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents, of Scheme 28 were prepared as shown below in Scheme 29:

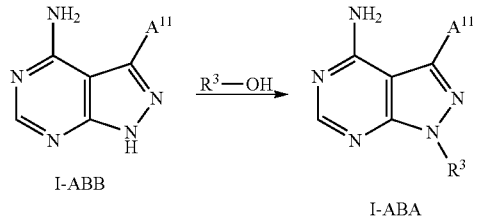

Scheme 29

I-ABB → I-ABA where $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents; $G^{11}$ is as defined previously for compound of Formula I, and $A^{11}$=halogen such as Cl, Br, or I.

In a typical preparation of a compound of Formula I-ABA, a compound of Formula I-ABB was reacted with an alcohol $R^3$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about −78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DIAD, and $R^3$—OH was used per equivalent of compound of Formula I-ABB.

Alternatively, the compounds of Formula I-ABA may be prepared by alkylating compounds of Formula I-ABB with an alkylating agent $R^3$-LG, wherein LG is a leaving group including, but not limited to, chloride, bromide, iodide, tosylate, mesylate, trifluoromethanesulfonate, under typical alkylation conditions known to someone skilled in the art.

Preferably, in compounds of Formula I-ABB, $A^{11}$=Br and I. These compounds are known ($A^{11}$=I: H. B. Cottam et al., *J. Med. Chem.* 1993, 36(22), 3424-3430; $A^{11}$=Br: T. S. Leonova et al., *Khim. Geterotsikl. Soedin.* 1982, (7), 982-984).

Compound of Formula I-AC is equal to compound of Formula I wherein $X_1$ and $X_5$=CH, $X_2$ and $X_4$=N, and $X_3$, $X_6$ and $X_7$=C; $Q^1$ is as defined for a compound of Formula I; $R^3$ is $C_{0-10}$alkyl, cycloC$_{3-10}$alkyl, bicycloC$_{5-10}$alkyl, aryl, heteroaryl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents; and $G^{11}$ is as defined for a compound of Formula I:

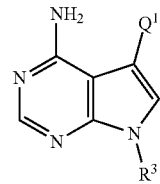

I-AC

Method AC was used when preparing compounds of Formula I-AB as shown below in Scheme 30:

Method AC:

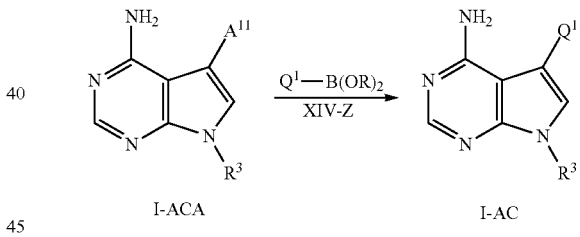

Scheme 30

I-ACA → I-AC where $Q^1$ and $R^3$ are as defined previously for compound of Formula I-AC, $A^{11}$=halogen such as Cl, Br, or I and $Q^1$-B(OR)$_2$=suitable boronic acid/ester.

In a typical preparation of compounds of Formula I-AC, compound of Formula I-ACA was reacted with a suitable boronic acid/ester XIV-Z ($Q^1$-B(OR)$_2$) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent systems were THF/water and DMF/water. The above process was carried out at temperatures between about 20° C. and about 120° C. Preferably, the reaction was carried out between 80° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of formula I-AC from I-ACA. For example, compound of Formula I-ACA could be reacted with a suitable organotin reagent $Q^1$-SnBu$_3$ or the like in a suitable solvent via typical Stille coupling procedures.

The compounds of Formula I-ACA of Scheme 30 were prepared as shown below in Scheme 31:

Scheme 31

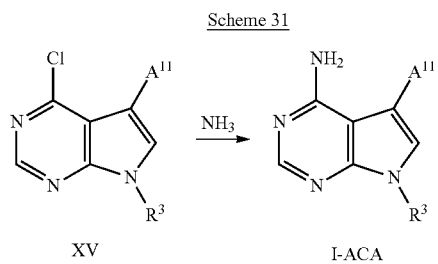

XV         I-ACA where $R^3$ is as defined previously for compound of Formula I-AC, and $A^{11}$=halogen such as Cl, Br, or I.

In a typical preparation of compounds of Formula I-ACA, compound of Formula XV was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used.

The compounds of Formula XVA (=compounds of Formula XV of Scheme 31 wherein $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents) were prepared as shown below in Scheme 32:

Scheme 32

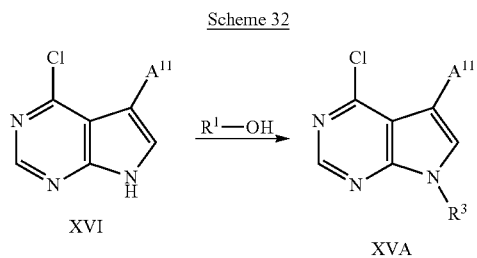

XVI         XVA where $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents; $G^{11}$ is as defined previously for compound of Formula I; and $A^{11}$=halogen such as Cl, Br, or I.

In a typical preparation of a compound of Formula XVA, a compound of Formula XVI was reacted with an alcohol $R^3$—OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about −78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DIAD, and $R^3$—OH was used per equivalent of compound of Formula XVI.

Alternatively, the compounds of Formula XVA may be prepared by alkylating compounds of Formula XVI with an alkylating agent $R^3$-LG, wherein LG is a leaving group including, but not limited to, chloride, bromide, iodide, tosylate, mesylate, trifluoromethanesulfonate, under typical alkylation conditions known to someone skilled in the art.

The compounds of Formula XVB (=compounds of Formula XV of Scheme 31 wherein $R^3$ is aryl or heteroaryl, optionally substituted by one or more independent $G^{11}$ substituents) were prepared as shown below in Scheme 33:

Scheme 33

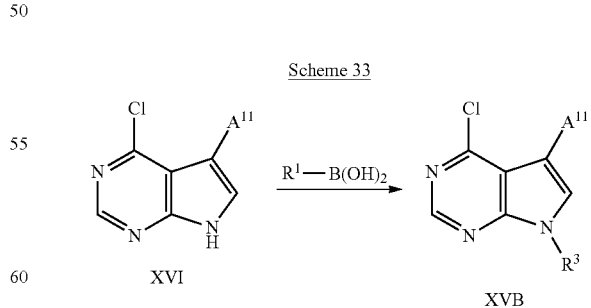

XVI         XVB where $R^3$ is aryl or heteroaryl, optionally substituted by one or more independent $G^{11}$ substituents, $G^{11}$ is as defined previously for compound of Formula I; and $A^{11}$=halogen such as Cl, Br, or I.

In a typical preparation of compounds of Formula XVB, compound of Formula XVI was reacted with a suitable boronic acid of Formula R³—B(OH)₂ in a suitable solvent via typical copper(II)-mediated coupling procedures. Suitable solvents for use in the above process included, but were not limited to, ethers such as tetrahydrofuran (THF), glyme, 1,4-dioxane, and the like; dimethylformamide (DMF); N-methylpyrrolidinone (NMP); chlorinated solvents such as methylene chloride (CH₂Cl₂). If desired, mixtures of these solvents were used, however, the preferred solvent was methylene chloride (CH₂Cl₂). Suitable reactants for use in the above process included, but were not limited to, copper(II) acetate (Cu(OAc)₂), copper(II) triflate (Cu(OTf)₂), and the like, and a base (pyridine, and the like). The preferred reactants were Cu(OAc)₂ and pyridine. The above process to produce compounds of the present invention was preferably carried out at about atmospheric pressure under air, although higher or lower pressures could be used if desired. Preferably, the reaction was carried out at about 22° C. Generally, 1.5 eq. of copper(II) acetate, 2 eq. of pyridine, and 2 eq. of boronic acid of Formula R³—B(OH)₂ were used per equivalent of compound of Formula XVI.

All compounds of Formula XVI are known in the literature (A¹¹=I: L. B. Townsend et al., *J. Med. Chem.* 1990, 33, 1984-92; A¹¹=Br, Cl: L. B. Townsend et al., *J. Med. Chem.* 1988, 31, 2086-2092). Preferably, A¹¹=Br and I.

Both R³ and Q¹ in the compounds described herein in some instances contain functional groups that can be further manipulated. It would be appreciated by those skilled in the art that such manipulation of functional groups could be accomplished with key intermediates or with late stage compounds. Such functional group transformations are exemplified in the following Schemes 34-35 as well as in the experimental section but are in no way meant to limit the scope of such transformations.

The compounds of Formula I-ACA' (=compounds of Formula I-ACA where R³=Z—CONR³¹²R³²²) were prepared from compounds of Formula XV' (=compounds of Formula XV where R³=Z—CO₂A³) as shown below in Scheme 34:

Scheme 34

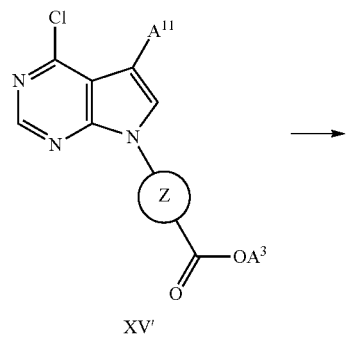

XV'

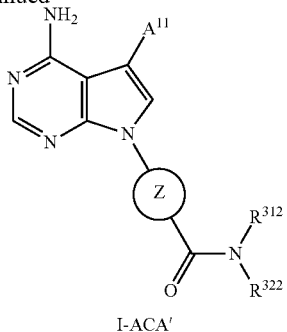

I-ACA' where R³¹² and R³²² are as defined previously for compound of Formula I; A¹¹=halogen such as Cl, Br, or I; and A³=hydrogen or alkyl such as methyl or ethyl.

In a typical preparation of compound of Formula I-ACA', when A³=alkyl and R³¹² and R³²² were both equal to H, reaction of compound of Formula XV' with ammonia in a suitable solvent, afforded compound of Formula I-ACA'. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH₂Cl₂) or chloroform (CHCl₃). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used. Additionally, in a typical preparation of compound of Formula I-ACA' (compounds of Formula I-ACA where R³=Z—CONR³¹²R³²²), compound of Formula XV' (compounds of Formula XV' where R³=Z—CO₂A³) was reacted with HNR³¹²R³²² followed by ammonia in a suitable solvent. When A³=H, typical coupling procedures (such as conversion of —CO₂H to —COCl via treatment with SOCl₂ or oxalyl chloride followed by reaction with HNR³¹²R³²² or treatment of —CO₂H and HNR³¹²R³²² with EDC or DCC in conjunction with DMAP, HOBT, or HOAt and the like) were employed to afford the transformation of a carboxylic acid to an amide. When A³=alkyl such as methyl or ethyl, treatment of the ester with Al(NR³¹²R³²²) afforded conversion of —CO₂A³ to —CO(NR³¹²R³²²). Subsequent treatment with ammonia afforded compounds of Formula I-ACA'.

The chemistry shown in Scheme 34 can also be applied to compounds with Q¹ in place of A¹.

The compounds of Formula XVIII (compounds of Formula XV, I-ACA, or I-AC where R³=Z—CH₂OH), XIX (compounds of Formula XV, I-ACA, or I-AC where R³=Z—CH₂LG), and XX (compounds of Formula XV, I-ACA, or I-AC where R³=Z—CH₂A⁵(R³¹³)(R³²³)ₐₐ) were prepared as shown below in Scheme 35:

Scheme 35

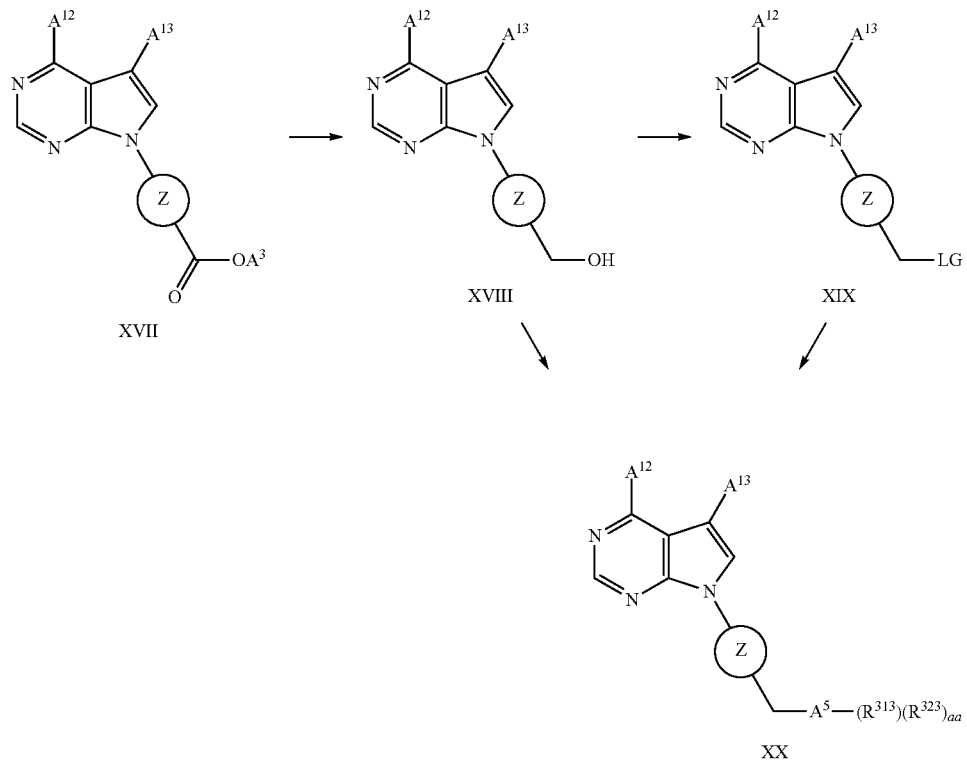

where $Q^1$, $R^{313}$, and $R^{323}$ are as defined previously for compound of Formula I; LG=suitable leaving group such as tosylate, mesylate, trifluoromethanesulfonate, or halo such as chloro, bromo, or iodo; aa=0 or 1; $A^3$=hydrogen or alkyl such as methyl or ethyl; $A^{11}$=halogen such as Cl, Br, or I; $A^{12}$=$C_1$ or $NH_2$; $A^{13}$=$A^{11}$ or $Q^1$; and $A^5$=N, O or S.

The following table indicates the relations between the compounds of Formulas XVII-XX, $A^{12}$, $A^{13}$, compounds of Formulas I-AC, I-ACA, and XV, and $R^3$.

| Compound of Formula... | wherein $A^{12}$ = | and $A^{13}$ = | ...is equal to Formula... | wherein $R^3$ = |
|---|---|---|---|---|
| XVII | Cl | $A^{11}$ | XV | Z—$CO_2A^3$ |
| XVII | $NH_2$ | $A^{11}$ | I-ACA | Z—$CO_2A^3$ |
| XVII | $NH_2$ | $Q^1$ | I-AC | Z—$CO_2A^3$ |
| XVIII | Cl | $A^{11}$ | XV | Z—$CH_2OH$ |
| XVIII | $NH_2$ | $A^{11}$ | I-ACA | Z—$CH_2OH$ |
| XVIII | $NH_2$ | $Q^1$ | I-AC | Z—$CH_2OH$ |
| XIX | Cl | $A^{11}$ | XV | Z—$CH_2LG$ |
| XIX | $NH_2$ | $A^{11}$ | I-ACA | Z—$CH_2LG$ |
| XIX | $NH_2$ | $Q^1$ | I-AC | Z—$CH_2LG$ |
| XX | Cl | $A^{11}$ | XV | Z—$CH_2A^5R^2(R^4)_d$ |
| XX | $NH_2$ | $A^{11}$ | I-ACA | Z—$CH_2A^5R^2(R^4)_d$ |
| XX | $NH_2$ | $Q^1$ | I-AC | Z—$CH_2A^5R^2(R^4)_d$ |

In a typical preparation of compound of Formula XVIII (compounds of Formula XV, I-ACA, or I-AC, where $R^3$=Z—$CH_2OH$), compound of Formula XVII (compounds of Formula XV, I-ACA, or I-AC, where $R^3$=Z—$CO_2A^3$) is treated with a suitable reducing agent, such as lithium aluminum hydride or diisobutylaluminum hydride, in a suitable solvent, such as THF or methylene chloride, to afford compound of Formula XVIII. In a typical preparation of compound of Formula XX (compounds of Formula XV, I-ACA, or I-AC, where $R^3$=Z—$CH_2A^5(R^{313})(R^{323})_{aa}$), the hydroxy group of compound of Formula XVIII was converted to a suitable leaving group, LG, such as Cl or tosylate, mesylate, or triflate, by reaction with $SOCl_2$ or $Ts_2O$, $Ms_2O$, or $Tf_2O$ to afford compound of Formula XIX (compounds of Formula XV, I-ACA, or I-AC, where $R^3$=Z—$CH_2LG$). Reaction of compound of Formula XIX with $HA^5(R^{313})(R^{323})_{aa}$ afforded compound of Formula XX. Furthermore, compound of Formula XVIII can be directly converted to compound of Formula XX by treating compound of Formula XVIII with various alkylating agents or under typical Mitsunobu reaction conditions to afford compounds of Formula XX (compounds of Formula XV, I-ACA, or I-AC, where $R^3$=Z—$CH_2A^5$ $(R^{313})(R^{323})_{aa}$) in which $A^5$=O, aa=0, and $R^{313}$=alkyl or aryl). Someone skilled in the art will choose the most appropriate stage during the sequence shown in Scheme 35 to convert $A^{12}$=Cl to $A^{12}$=$NH_2$ as described in Scheme 31, and to convert $A^{13}$=$A^1$ to $A^{13}$=$Q^1$ as described in Scheme 30, if applicable.

An alternative preparation of compounds of Formula I-AC is shown in Scheme 36.

Scheme 36

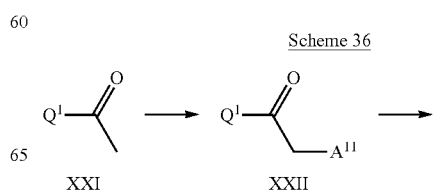

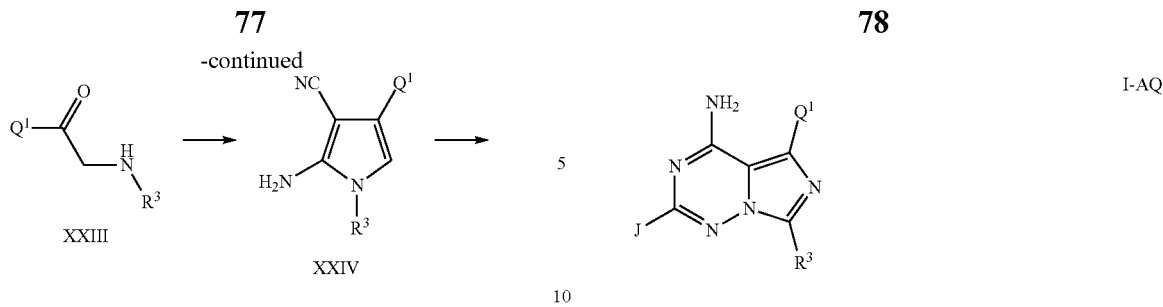

where $Q^1$ and $R^3$ are as defined previously for compound of Formula I; and $A^1$=halogen such as Cl, Br, or I.

The compounds of Formula XXI may be prepared from aldehydes $Q^1$-CHO (see Scheme 14 for their preparation) by addition of methyllithium or a methyl Grignard reagent, followed by oxidation of the resulting alcohol to the ketone of Formula XXI. Other compounds are commercially available or can be prepared by methods well known to someone skilled in the art, see: Larock, R. C. *Comprehensive Organic Transformations*, 2$^{nd}$ ed.; Wiley and Sons: New York, 1999, 1197ff. Reaction of compounds of Formula XXI under typical halogenation conditions with typical halogenating agents including, but not limited to, $Br_2$, NBS, pyridinium perbromide, or $CuBr_2$ (for $A^{11}$=Br), or NCS or $SO_2Cl_2$ (for $A^{11}$=Cl) gives the compounds of Formula XXII. Their reaction with amines of Formula $H_2N$—$R^3$ gives the aminoketones of Formula XXIII that are converted to aminocyanopyrroles of Formula XXIV by reaction with malononitrile under basic conditions. Finally, reaction of compounds of Formula XXIV under typical cyclization conditions gives the compounds of Formula I-AC. Conditions for this cyclization include, but are not limited to, heating with formamide; heating with formamide and ammonia; sequential treatment with a trialkyl orthoformate, ammonia, and a base; sequential treatment with formamidine and ammonia.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Compound of Formula I-AQ is equal to compound of Formula I wherein $X_1$=CH; $X_2$, $X_3$ and $X_5$=N; $X_4$, $X_6$, and $X_7$=C and J=H or $NH_2$ Method AQ was used when preparing compounds of Formula I-AQ as shown below in Scheme 37:

Method AQ:

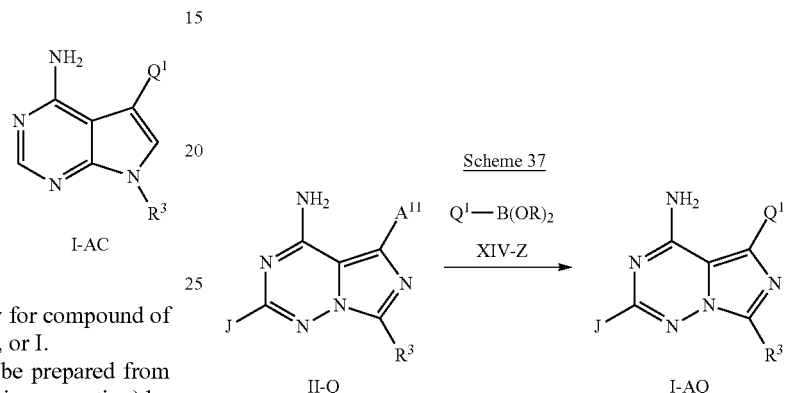

where $Q^1$ and $R^3$ are as defined previously for compound of Formula I, $A^{11}$=halogen such as Cl, Br, or I; $B(OR)_2$=suitable boronic acid/ester and J=H or $NH_2$.

In a typical preparation of compounds of Formula I-AQ, compound of Formula II-Q was reacted with a suitable boronic acid/ester ($Q^1$-$B(OR)_2$) in a suitable solvent via typical Suzuki coupling procedures. Suitable solvents for use in the above process included, but were not limited to, water, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was glyme/water. The above process was carried out at temperatures between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AQ from II-Q. For example, compound of Formula II-Q could be reacted with a suitable organotin reagent $Q^1$-$SnBu_3$ or the like in a suitable solvent via typical Stille coupling procedures.

The compounds of Formula II-Q of Scheme 37 were prepared as shown below in Scheme 38.

Scheme 38

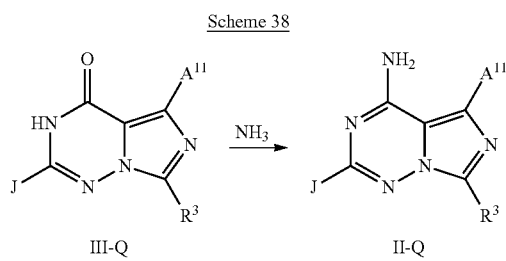

III-Q          II-Q where $R^3$ is as defined previously for compound of Formula I and $A^{11}$=halogen such as Cl, Br, or I; and J=H or $NH_2$.

In a typical preparation of compounds of Formula II-Q, compound of Formula III-Q was reacted with phosphorus oxychloride ($POCl_3$) and triazole, and pyridine followed by ammonia ($NH_3$) in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −20° C. and about 50° C. Preferably, the reaction was carried out between 0° C. and about 25° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Q of Scheme 38 were prepared as shown below in Scheme 39.

Scheme 39

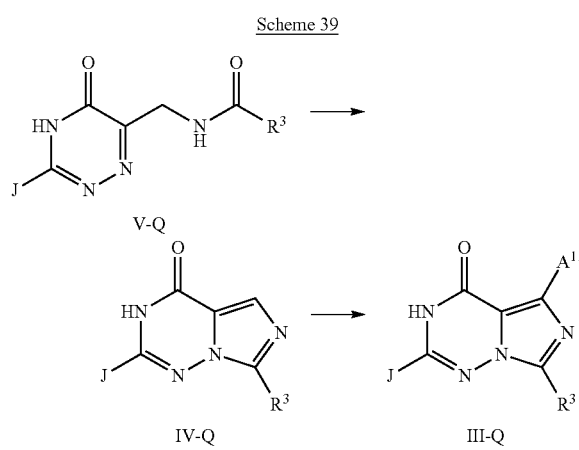

V-Q

IV-Q          III-Q where $R^3$ is as defined previously for compound of Formula I; $A^{11}$=halogen such as Cl, Br, or I; and J=H or $NH_2$.

In a typical preparation of a compound of Formula III-Q, intermediate V-Q was converted to compound of Formula IV-Q. Intermediate of Formula V-Q was treated with phosphorus oxychloride ($POCl_3$) in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile. If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Intermediate for Formula III-Q was prepared by reacting intermediate of Formula IV-Q with a suitable halogenating agent. Suitable halogenating agents included, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formulae IV-Q and III-Q where J=$NH_2$ can be respectively converted into the compounds of Formulae IV-Q and III-Q where J=H, by diazotisation procedures known to those skilled in the art. A typical procedure includes the treatment of a compound of Formula IV-Q or III-Q where J=$NH_2$ with tert-butylnitrite in a suitable solvent such a THF or DMF.

The compounds of Formula V-Q of Scheme 39 were prepared as shown below in Scheme 40:

Scheme 40

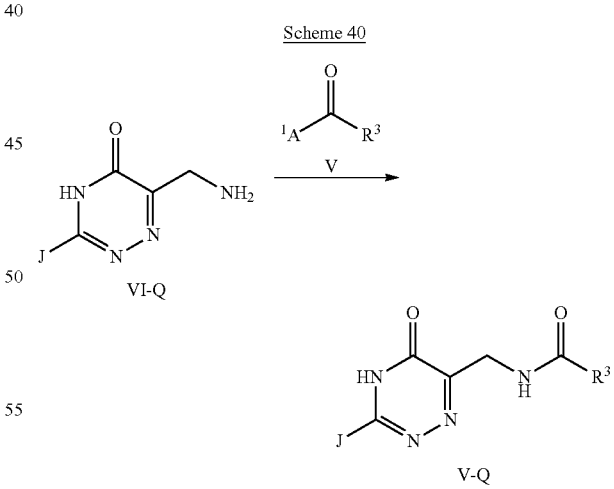

VI-Q

V-Q where $R^1$ is as defined previously for compound of Formula I; $A^1$=OH, alkoxy, or a leaving group such as chloro or imidazole; and J=H or $NH_2$.

In a typical preparation, of a compound of Formula V-Q, a compound of Formula VI-Q and compound of Formula V were reacted under suitable amide-coupling conditions. Suitable conditions include but are not limited to treating compounds of Formula VI-Q and V (when $A^1$=OH) with coupling reagents such as DCC or EDC in conjunction with DMAP, HOBt, HOAt and the like, or reagents like EEDQ. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula VI-Q and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; pyridine; halogenated solvents such as chloroform or methylene chloride. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula VI-Q and V (where $A^1$=F, Cl, Br, I) and base and substoichiometric amounts of DMAP were preferably used although higher or lower amounts were used if desired. Additionally, other suitable reaction conditions for the conversion of an amine (compound of Formula VI-Q) to an amide (compound of Formula V-Q) can be found in Larock, R. C. *Comprehensive Organic Transformations*, $2^{nd}$ ed.; Wiley and Sons: New York, 1999, pp 1941-1949.

The compounds of Formula VI-Q of Scheme 40 where J=H were prepared as shown below in Scheme 41:

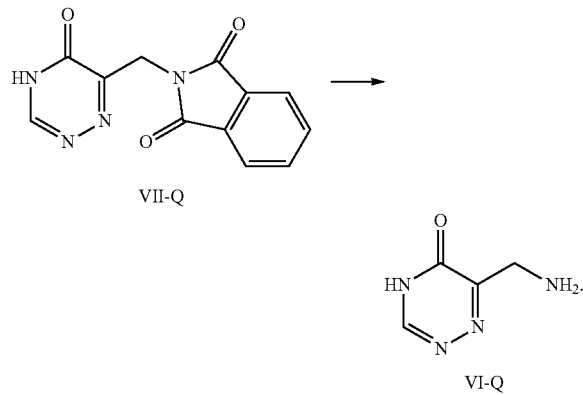

In a typical preparation, of a compound of Formula VI-Q, a compound of Formula VII-Q is reacted under suitable reaction conditions in a suitable solvent. Suitable conditions include treatment of compound of Formula VII-Q with hydrazine or methyl hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvents were ethanol and methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formula VI-Q where J=$NH_2$ may be prepared according to the procedures described in *J. Het. Chem.*, (1984), 21, 697.

The compounds of Formula VII-Q of Scheme 41 were prepared as shown below in Scheme 42:

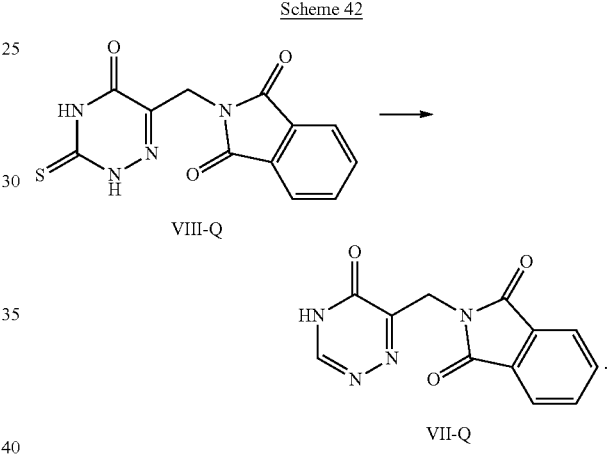

In a typical preparation of a compound of Formula VII-Q, a compound of Formula VIII-Q was reacted with Raney Nickel in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially equimolar amounts of reactants were preferably used although higher or lower amounts were used if desired. Additionally a compound of Formula VII-Q can be prepared by reacting a compound of Formula VIII-Q with a suitable oxidizing agent in a suitable solvent. A suitable oxidizing agent includes, but is not limited to hydrogen peroxide ($H_2O_2$), 3-chloro peroxybenzoic acid (mCPBA) and the like. Suitable solvents for use in the above process included, but were not limited to, ethers such as THF, glyme, and the like; DMF; DMSO; $CH_3CN$; and dimethylacetamide (DMA);

chlorinated solvents such as $CH_2Cl_2$ or $CHCl_3$. If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VIII-Q of Scheme 42 were prepared as shown below in Scheme 43:

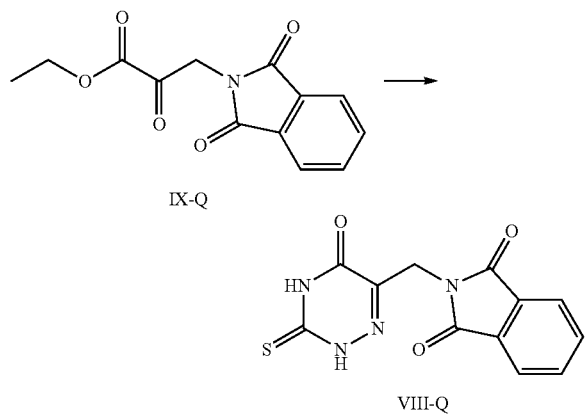

In a typical preparation of a compound of Formula VIII-Q, a compound of Formula IX-Q was reacted with thiosemicarbazide and a suitable base in a suitable solvent. Suitable bases include, but were not limited to triethylamine, ethyldiisopropylamine and the like. Suitable solvents for use in the above process included, but were not limited to, ethers such as tetrahydrofuran (THF), glyme, and the like; dimethylformamide (DMF); dimethylacetamide (DMA); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out between about 40° C. and 80° C. The above process to produce compounds of the present invention was preferably carried out at about atmospheric pressure although higher or lower pressures were used if desired. Substantially equimolar amounts of reactants were preferably used although higher or lower amounts were used if desired. Compound of Formula IX-Q can be prepared according to literature procedures Knutsen, Lars J. S. et. al., *J. Chem. Soc. Perkin Trans 1: Organic and Bio-Organic Chemistry* (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Method AW was also used when preparing compounds of Formula II-Q as shown below in Scheme 44:

Method AW:

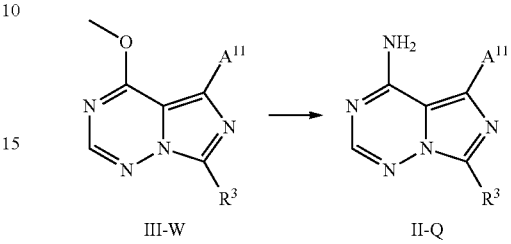

where $Q^1$ and $R^3$ are as defined previously for compound of Formula I, and $A^{11}$=halogen such as Cl, Br, or I.

In a typical preparation of compounds of Formula II-Q, compound of Formula III-W was reacted with ammonia in a suitable solvent. Suitable solvents for use in the above process included, but were not limited to, ethers such as tetrahydrofuran (THF), glyme, and the like; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about 0° C. and about 50° C. Preferably, the reaction was carried out at between 0° C. and about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-W of Scheme 44 were prepared as shown below in Scheme 45.

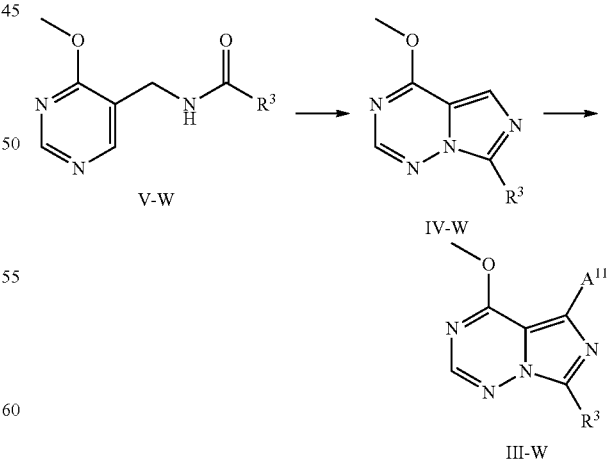

where $R^3$ is as defined previously for compound of Formula I and $A^{11}$=halogen such as Cl, Br, or I.

In a typical preparation of a compound of Formula III-W, compound V-W was converted to compound of Formula IV-W. Compound of Formula V-W was treated with phosphorus oxychloride (POCl$_3$) or the isolated "Vilsmeir salt" [CAS#33842-02-3] in a suitable solvent at a suitable reaction temperature. Suitable solvents for use in the above process included, but were not limited to, ethers such as tetrahydrofuran (THF), glyme, and the like, chlorinated solvents such as methylene chloride (CH$_2$Cl$_2$) or chloroform (CHCl$_3$), and acetonitrile (CH$_3$CN). If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Compounds of Formula III-W were prepared by reacting compound of Formula IV-W with a suitable halogenating agent. Suitable halogenating agents included, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula V-W of Scheme 45 were prepared as shown below in Scheme 46.

where R$^3$ is as defined previously for compound of Formula I, X$^{12}$=azido, or mono- or di-protected amino and A$^1$=OH, alkoxy or a leaving group such as chloro or imidazole.

In a typical preparation of a compound of Formula V-W, compound VI-W was reacted with compound V under suitable amide coupling conditions. Suitable conditions include but are not limited to those described for the conversion of compound XIII to compound XII as shown in Scheme 10. Compounds of Formula VI-W were prepared from compounds of Formula VII-W. A typical procedure for the conversion of compounds of Formula VII-W to compounds of Formula VI-W involves subjecting a compound of Formula VII-W, where X$^{12}$=azido, to reducing conditions such as, but not limited to, catalytic hydrogenation in a suitable solvent at a suitable reaction temperature. Suitable solvents for use in the above process included, but were not limited to, ethers such as tetrahydrofuran (THF), glyme, and the like, alcoholic solvents such as methanol, ethanol and the like, esters such as ethyl acetate, methyl acetate and the like. If desired, mixtures of these solvents were used. The preferred solvents were ethyl acetate and methanol. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, when X$^{12}$=azido, the reduction to compounds of Formula VI-W could be achieved by treatment of a compound of Formula VII-W with triaryl- or trialkylphosphines in the presence of water in a suitable solvent at a suitable reaction temperature. Suitable solvents for use in the above process included, but were not limited to, ethers such as tetrahydrofuran (THF), dioxane and the like, alcoholic solvents such as methanol, ethanol and the like, esters such as ethyl acetate, methyl acetate and the like, DMF, acetonitrile, and pyridine. If desired, mixtures of these solvents were used. The preferred solvents were THF and acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Where X$^{12}$=mono- or di-protected amino, the deprotection could be effected by the procedures known to those skilled in the art and as disclosed in: "Protective Groups in Organic Syntheses", T. W. Greene and P. G. M. Wuts, John Wiley and Sons, 1989.

The compounds of Formula VII-W of Scheme 46 were prepared as shown below in Scheme 47:

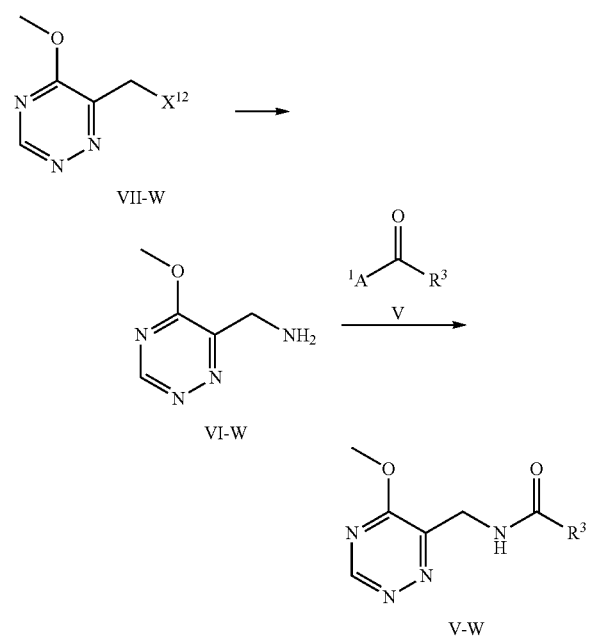

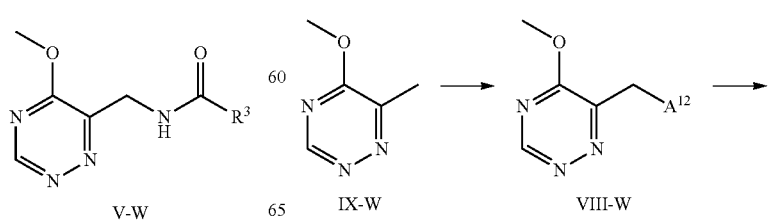

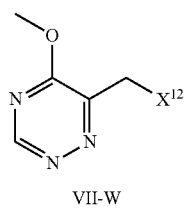

VII-W where $R_3$ is as defined previously for compound of Formula I, $X^{12}$ is as defined for a compound of Formula VII-W and $A^{12}$=iodo, bromo, chloro, tosylate, mesylate or other leaving group.

In a typical preparation of a compound of Formula VII-W where $X^{12}$=azide, compound VIII-W was reacted with an azide salt, such as lithium or sodium azide in suitable solvent at a suitable reaction temperature. Suitable solvents for use in the above process included, but were not limited to, alcoholic solvents such as ethanol, butanol and the like, esters such as ethyl acetate, methyl acetate and the like, DMF, acetonitrile, acetone DMSO. If desired, mixtures of these solvents were used. The preferred solvents were acetone and DMF. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, where $X^{12}$=mono- or di-protected amino, compounds of Formula VIII-W were reacted with suitably protected amines where the protecting group is chosen such that the nucleophilic nature of the nitrogen is either retained or where it can be enhanced by the action of a reagent such as a base. Those skilled in the art will recognize that such protecting groups include, but are not limited to, benzyl, trityl, allyl, and alkyloxycarbonyl derivatives such as BOC, CBZ and FMOC.

Compounds of Formula VIII-W where $A^{12}$=halogen, are prepared from compounds of Formula XI-W. In a typical procedure, compounds of Formula XI-W are treated with halogenating reagents such as but not limited to N-iodosuccinimide, N-bromosuccinimide, N-chlorosuccinimide, trichloroisocyanuric acid, N,N'-1,3-dibromo-5,5-dimethylhydantoin, bromine and iodine, preferably in the presence of one or more radical sources such as dibenzoyl peroxide, azobisisobutyronitrile or light in suitable solvent at a suitable reaction temperature. Suitable solvents for use in the above process included, but were not limited to, chlorinated solvents such as carbon tetrachloride, dichloromethane, α,α,α-trifluorotoluene and the like, esters such as methyl formate, methyl acetate and the like, DMF, acetonitrile. If desired, mixtures of these solvents were used. The preferred solvents were carbon tetrachloride and α,α,α-trifluorotoluene. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Alternatively, compounds of Formula VIII-W where $A^{12}$=tosylate or mesylate were prepared from compounds of Formula X-W as shown in Scheme 48. In a typical preparation of a compound of Formula VIII-W, a compound of Formula X-W was reacted with a sulfonylating reagent such as methanesulfonyl chloride or p-toluenesulfonyl chloride in the presence of a base such as, but not limited to DIPEA or triethylamine in a suitable solvent at a suitable reaction temperature. Suitable solvents for use in the above reaction included, but were not limited to, chlorinated solvents such as dichloromethane, 1,2☐-dichloroethane and the like, ethers such THF, diethylether and the like, DMF and acetonitrile. If desired, mixtures of these solvents were used. The preferred solvents were THF and dichloromethane. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Scheme 48

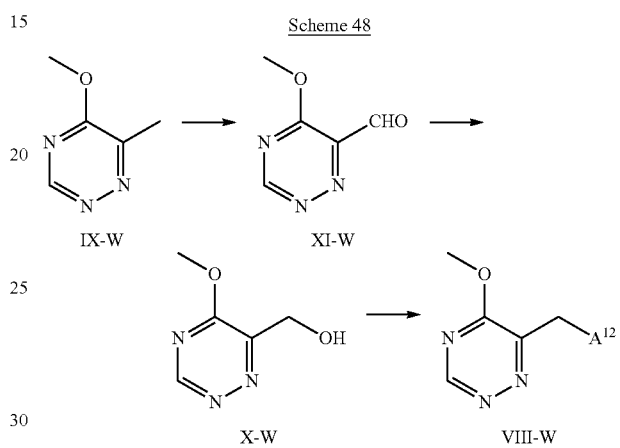

IX-W    XI-W

X-W    VIII-W

Compounds of Formula X-W were prepared from compounds of Formula XI-W. In a typical preparation of a compound of Formula X-W, a compound of Formula XI-W was reacted with a reducing reagent such as, but not limited to, sodium borohydride, lithium borohydride or lithium aluminum hydride in a suitable solvent at a suitable reaction temperature. Suitable solvents for use in the above reaction included, but were not limited to, ethers such THF, diethylether and the like, and alcohols such as ethanol, methanol, isopropanol and the like. If desired, mixtures of these solvents were used. The preferred solvents were THF and methanol. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Compounds of Formula XI-W were prepared from compounds of Formula XI-W. In a typical preparation of a compound of Formula XI-W, a compound of Formula IX-W was reacted with an oxidizing reagent such as, but not limited to, selenium dioxide, manganese dioxide, potassium permanganate and the like, in a suitable solvent at a suitable reaction temperature. Suitable solvents for use in the above reaction included, but were not limited to, chlorinated solvents such as dichloromethane, 1,2-dichloroethane and the like, water, acetic acid and sulfolane. If desired, mixtures of these solvents were used. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Those skilled in the art will appreciate that compounds of Formula IX-W can be made by routes disclosed in the literature, for example as in *Bulletin de la Societe Chimique de France*, (1973), (6) (Pt. 2), 2126.

Compounds of Formula I-AQ and/or their precursors may be subjected to various functional group interconversions as a means to access some functionalities that may not be introduced directly as a result of incompatible chemistries. Examples of such functional group manipulations applicable to compounds of Formula I-AQ and their precursors are similar, but not limited to, those described in Schemes 16-27, 34 and 35 that related to compounds of Formula I-AA, I-P, I-P', I-Q, I-R, I-AB and I-AC.

EXPERIMENTAL PROCEDURES

8-Chloro-3-cyclobutyl-imidazo[1,5-a]pyrazine

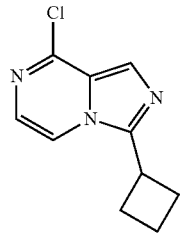 [SMILES: Clc1nccn2c(C3CCC3)ncc12]

This compound was prepared using procedures analogous to that described for trans-methyl 4-(8-chloroimidazo[1,5-a]pyrazin-3-yl)cyclohexanecarboxylate and its precursor trans-methyl 4-({[(3-chloropyrazin-2-yl)methyl]amino}carbonyl)cyclohexanecarboxylate, using cyclobutanecarboxylic acid in place of 4-(methoxycarbonyl)cyclohexanecarboxylic acid.

8-Chloro-3-cyclobutyl-1-iodoimidazo[1,5-a]pyrazine

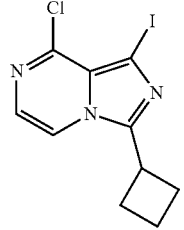 [SMILES: Clc1nccn2c(C3CCC3)nc(I)c12]

8-Chloro-3-cyclobutylimidazo[1,5-a]pyrazine (1058 mg, 5.1 mmol) and NIS (1146 mg, 5.1 mmol) in anh DMF (10 mL) were stirred at 60° C. under Ar for 6 h. The reaction was diluted with DCM (~400 mL), washed (H₂O, brine), dried (Na₂SO₄) and concentrated under reduced pressure. Purification of the crude material by flash chromatography on silica gel (50 g cartridge, 10:1-8:1-7:1-6:1 hexanes:EtOAc) afforded the title compound as a pale yellow solid; $^1$H NMR (400 MHz, CDCl₃) δ 7.51 (d, J=4.8 Hz, 1H), 7.26 (d, J=4.8 Hz, 1H), 3.75 (quintetd, J=1.2 Hz, 8.4 Hz, 1H), 2.62-2.42 (m, 4H), 2.32-1.98 (m, 2H); MS (ES+): m/z 334.0 (100) [MH⁺]; HPLC: $t_R$=3.38 min (OpenLynx, polar_5 min).

3-Cyclobutyl-1-iodoimidazo[1,5-a]pyrazin-8-amine

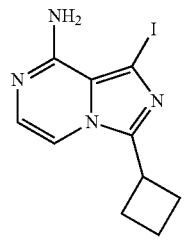 [SMILES: Nc1nccn2c(C3CCC3)nc(I)c12]

A Parr bomb containing 8-chloro-3-cyclobutyl-1-iodoimidazo[1,5-a]pyrazine (759 mg, 2.3 mmol) in IPA (100 mL) was saturated with NH₃(g) for 5 min at 0° C. then sealed and heated at 115° C. for 38 h. The reaction mixture was then concentrated under reduced pressure, partitioned between DCM (200 mL) and H₂O (50 mL) and extracted with DCM (50 mL). Combined organic fractions were washed with brine, dried (Na₂SO₄) and concentrated under reduced pressure to provide the title compound as a white solid; $^1$H NMR (400 MHz, CDCl₃) δ 7.13 (d, J=4.8 Hz, 1H), 7.01 (d, J=5.2 Hz, 1H), 5.63 (br, 2H), 3.73 (quintetd, J=0.8 Hz, 8.4 Hz, 1H), 2.60-2.38 (m, 4H), 2.20-1.90 (m, 2H); MS (ES+): m/z 315.9 (100) [MH⁺]; HPLC: $t_R$=1.75 min (OpenLynx, polar_5 min).

7-Cyclohexyl-5-iodoimidazo[5,1-f][1,2,4]triazin-4-amine

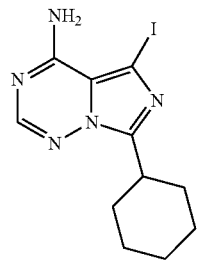 [SMILES: Nc1ncnn2c(C3CCCCC3)nc(I)c12]

To a suspension of 1H-1,2,4-triazole (1 g, 0.02 mol) in acetonitrile (23 mL) was added dropwise phosphoryl chloride (0.6 mL, 0.007 mol) and triethylamine (3 mL, 0.02 mol) at 0° C. To this mixture was added 7-cyclohexyl-5-iodoimidazo[5,1-f][1,2,4]triazin-4(3H)-one (77 mg, 0.224 mmol) and the resulting mixture refluxed overnight. The cooled mixture was then quenched with excess NH₃ in $^i$PrOH (pH 8) stirred at rt for 30 min. then filtered and the isolated solid washed with DCM. The filtrate was concentrated in vacuo and purified by chromatography over silica gel eluting with 2% MeOH in DCM to afford the 7-cyclohexyl-5-iodoimidazo[5,1-f][1,2,4]triazin-4-amine. $^1$H NMR (400 MHz-DMSO-d6) δ 1.14-1.91 (m, 10H), 3.11-3.18 (m, 1H), 6.75 (br.s, 1H), 7.84 (s, 1H) 8.42

(bs, 1H); MS (ES+): m/z: 344.01 (100) [MH+]. HPLC: $t_R$=3.10 min (OpenLynx: polar_5 min).

7-Cyclohexyl-5-iodoimidazo[5,1-f][1,2,4]triazin-4(3H)-one

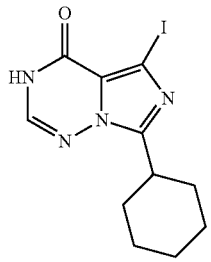 [SMILES: O=c1[nH]cnn2c(C3CCCCC3)nc(I)c12]

To a solution of 7-cyclohexylimidazo[5,1-f][1,2,4]triazin-4(3H)-one (130 mg, 0.6 mmol) in DMF (0.6 mL) was added N-iodosuccinimide (700 mg, 0.003 mol) and the reaction mixture stirred at 55° C. for 20 h. After this time the mixture was diluted with water (50 mL) and extracted with EtOAc (4×40 mL). The organic extracts were washed with water (4×40 mL), treated with sodium thiosulfate and brine, dried over $Na_2SO_4$ and concentrated in vacuo to afford 7-cyclohexyl-5-iodoimidazo[5,1-f][1,2,4]triazin-4(3H)-one. $^1$H NMR (400 MHz-DMSO-d6) δ 1.34-1.37 (m, 3H), 1.52-1.56 (m, 2H), 1.76-1.88 (m, 5H), 3.06-3.08 (m, 1H) 7.87 (s, 1H) 11.78 (s, 1H); MS (ES+): m/z: 344.95 (100) [MH+]. HPLC: tr=2.95 min (OpenLynx: polar_5 min).

7-Cyclohexylimidazo[5,1-f][1,2,4]triazin-4(3H)-one

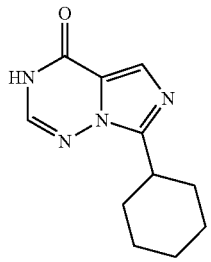 [SMILES: O=c1[nH]cnn2c(C3CCCCC3)ncc12]

To a suspension of 6-aminomethyl-4H-[1,2,4]triazin-5-one (250 mg, 1.98 mmol) in DMF (7.5 mL) was added 2-(1H-benzotriazol-1-yl)-1,1,3,3-tetramethyluronium tetrafluoroborate (760 mg, 2.38 mmol), cyclohexanecarboxylic acid (305 mg, 2.38 mmol) and N,N-diisopropylethylamine (1.5 mL, 8.6 mmol). After 1 h acetonitrile (40 mL) was added to the mixture followed by dropwise addition of phosphoryl chloride (0.28 mL, 3.0 mmol) and the reaction mixture stirred at 55° C. for 1 h. The mixture was then concentrated in vacuo chromatographed over silica gel eluting with 3% MeOH in DCM, to afford 7-cyclohexylimidazo[5,1-f][1,2,4]triazin-4(3H)-one. $^1$H NMR (400 MHz-DMSO-d6) δ 1.24-1.91 (m, 10H), 3.08-3.16 (m, 1H), 7.68 (s, 1H) 7.88 (s, 1H) 11.76 (s, 1H); MS (ES+): m/z: 219.24 (100) [MH+]. HPLC: $t_R$=2.44 min (OpenLynx: polar_5 min).

trans-[4-(8-Amino-1-iodoimidazo[1,5-a]pyrazin-3-yl)cyclohexyl]methanol

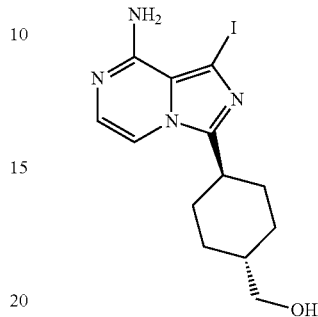

trans-[4-(8-chloro-1-iodoimidazo[1,5-a]pyrazin-3-yl)cyclohexyl]methanol (26.50 g, 67.66 mmol) was charged in a 400 mL steel bomb and was dissolved in 2M $NH_3$ in isopropanol (300 mL) and anhydrous THF (10 mL). The reaction mixture was cooled to −78° C. Ammonia gas was bubbled vigorously into the solution for 8 min; then the bomb was tightly sealed and heated to 120° C. for 20 h. The crude reaction mixture was concentrated in vacuo, then the reaction residue was taken up with MeOH/$CHCl_3$, loaded onto silica gel. The mixture was purified by a silica gel glass column chromatography [eluted with 1:1 $CH_2Cl_2$/EtOAc to 10%~7 N $NH_3$ in MeOH/$CHCl_3$] to afford the desired product as a beige cream white solid; MS (ES+): m/z 373.01 (100) [MH$^+$], 373.98 (50) [MH$^+$2]; $t_R$ (polar-5 min/openlynx) 1.57 min.

trans-[4-(8-Chloro-1-iodoimidazo[1,5-a]pyrazin-3-yl)cyclohexyl]methanol

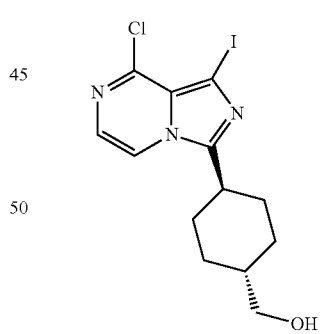

trans-[4-(8-Chloroimidazo[1,5-a]pyrazin-3-yl)cyclohexyl]methanol (18.00 g, 67.74 mmol) and N-iodosuccinimide (19.81 g, 88.06 mmol) in anhydrous DMF (360 mL) were stirred at 60° C. under $N_2$ for 6 h. The reaction was diluted with DCM (~600 mL), washed with water and brine, dried over anhydrous $Na_2SO_4$ and then concentrated in vacuo. The crude material was purified by a silica gel flash chromatography (eluted with 1:2 EtOAc/DCM to 1:1 EtOAc/DCM) to obtain the desired product as a pale yellow solid; By $^1$H NMR analysis, the product was contaminated with 0.35 eq. of NIS-impurity. The product was carried onto the next reaction without further purification; MS (ES+): m/z 391.92 (100) [MH⁺], 393.88 (50) [MH⁺2], 394.89 (10) [MH⁺3]; $t_R$ (polar-5 min/openlynx) 2.79 min.

trans-[4-(8-Chloroimidazo[1,5-a]pyrazin-3-yl)cyclohexyl]methanol

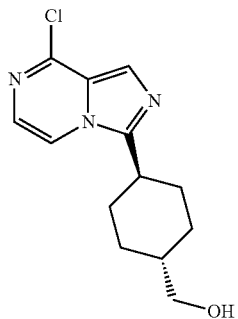 [SMILES: OC[C@H]1CC[C@H](c2ncc3c(Cl)nccn32)CC1]

A THF solution (1.00 L) of trans-methyl 4-(8-chloroimidazo[1,5-a]pyrazin-3-yl)cyclohexanecarboxylate (29.70 g, 101.1 mmol) was cooled to −78° C. and was charged with LAH (1M in THF, 25.3 mmol, 25.3 mL) dropwise. After 30 min., the reaction mixture was charged with additional LAH (25.3 mmol) at −78° C. and then, allowed to stir at −78° C. for 1.5 h. The reaction was slowly warmed up to rt and stirred for additional 30 min. Ethyl acetate, Na₂SO₄.10H₂O, and silica gel were added to the reaction mixture and concentrated in vacuo to give an orange solid. The crude mixture was purified by a silica gel glass column chromatography (eluted with 2:3 EtOAc/DCM to 100% EtOAc) to obtain the title compound as a slightly yellow-tinted white solid; ¹H NMR (CDCl₃, 400 MHz) δ 1.14-1.30 (m, 2H), 1.61-1.75 (m_c, 1H), 1.84 (ddd, J=13.2, 13.2, 13.2, 3.2 Hz, 2H), 1.98-2.13 (m, 4H), 2.19 (s, br, —OH), 2.94 (tt, J=11.6, 3.2 Hz, 1H), 3.56 (d, J=6.0 Hz, 2H), 7.31 (d, J=5.2 Hz, 1H), 7.64 (dd, J=5.2, 1.2 Hz, 1H), 7.79 (d, J=0.8 Hz, 1H); MS (ES+): m/z 266.21/268.17 (100/89) [MH⁺]. HPLC: $t_R$=2.38 min (OpenLynx, polar_5 min). MS (ES+): m/z 266.21 (100) [MH⁺], 268.17 (80) [MH⁺2], 289.18 (20) [MH⁺3]; $t_R$ (polar-5 min/openlynx) 2.36 min.

General Procedure for the Hydrolysis of Carboxylic Esters

To a solution/slurry of the carboxylic ester (30.17 mmol) in ethanol (200 mL) was added 3.0 M of sodium hydroxide in water (15.1 mL) and the mixture was stirred at 40° C. for 4 h. The solvent was removed under reduced pressure at 40° C. and to the residue was added water (10 mL) and ethanol (10 mL) and the slurry was filtered.

The filter cake was washed with ethanol (2×10 mL) and dried under vacuum to yield the sodium salt. For the isolation of the free acid, water was added to this salt and the slurry was acidified with formic acid, stirred for 10 min at RT and filtered. The filter cake was washed with water followed by ethanol to yield the carboxylic acid.

trans-Methyl 4-(8-chloroimidazo[1,5-a]pyrazin-3-yl)cyclohexanecarboxylate

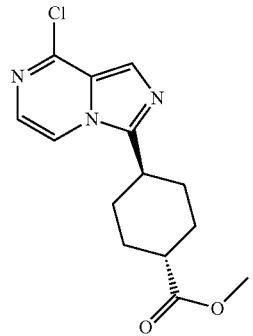 [SMILES: COC(=O)[C@H]1CC[C@H](c2ncc3c(Cl)nccn32)CC1]

trans-Methyl 4-({[(3-chloropyrazin-2-yl)methyl]amino}carbonyl)-cyclohexanecarboxylate (29.00 g, 93.02 mmol) was dissolved in anhydrous acetonitrile (930 mL) and anhydrous DMF (9 mL) and heated at 55° C. under nitrogen for 3 h. The reaction mixture was concentrated in vacuo, then, the solid residue was taken up in DCM, then, basified to pH 10 with 2M ammonia in isopropanol. The mixture was concentrated in vacuo, re-dissolved in DCM, and then loaded onto TEA-basified silica gel. The crude product was purified by a silica gel column chromatography (eluted with 2:3 EtOAc/DCM) to obtain the title compound as a yellow powder; ¹H NMR (CDCl₃, 400 MHz) δ 1.63 (ddd, J=13.2, 13.2, 13.2, 3.2 Hz, 2H), 1.85 (ddd, J=13.2, 13.2, 13.2, 2.8 Hz, 2H), 2.10 (dd, J=14.4, 3.2 Hz, 2H), 2.19 (dd, J=14.0, 3.2 Hz, 2H), 2.46 (tt, J=12.4, 3.6 Hz, 1H), 2.96 (tt, J=11.6, 3.2 Hz, 1H), 3.70 (s, 3H), 7.33 (dd, J=5.2, 1.2 Hz, 1H), 7.61 (d, J=4.8 Hz, 1H), 7.79 (s, 1H). MS (ES+): m/z 294.17/296.14 (100/86) [MH⁺]. HPLC: $t_R$=2.85 min (OpenLynx, polar_5 min).

trans-Methyl 4-({[(3-chloropyrazin-2-yl)methyl]amino}carbonyl)cyclohexanecarboxylate

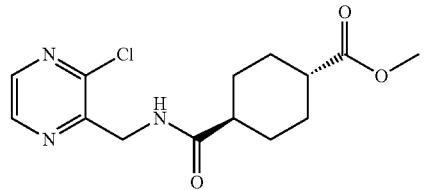 [SMILES: COC(=O)[C@H]1CC[C@H](C(=O)NCc2nccnc2Cl)CC1]

A THF (370 mL) solution of 4-(methoxycarbonyl)cyclohexanecarboxylic acid (15.14 g, 81.30 mmol) and CDI (13.18 g, 81.30 mmol) was placed under a nitrogen atmosphere and stirred at 60° C. for 4 h. The reaction mixture was cooled to rt, then, (3-chloropyrazin-2-yl)methylamine bis-hydrochloride salt (16.00 g, 73.91 mmol) and DIPEA (31.52 g, 244.00 mmol, 42.5 mL) was added. After stirring at 60° C. for 20 h, the reaction was concentrated in vacuo. The crude reaction mixture was purified by a silica gel glass column chromatography (eluted with 3:2 DCM/EtOAc) to obtain the pure desired product as a slightly yellowish creamy white powder; ¹H NMR (CDCl₃, 400 MHz) δ 1.43-1.65 (m, 4H), 2.01-2.14

(m, 4H), 2.25 (tt, J=12.0, 3.6 Hz, 1H), 2.34 (tt, J=11.6, 3.2 Hz, 1H), 3.68 (s, 3H), 4.70 (d, J=4.4 Hz, 2H), 6.81 (s, br, —NH), 8.32-8.36 (m, 1H), 8.46 (d, J=2.4 Hz, 1H); MS (ES+): m/z 312.17/314.12 (84/32) [MH$^+$]; HPLC: $t_R$=2.44 min (OpenLynx, polar_5 min).

[3-(8-Amino-1-iodoimidazo[1,5-a]pyrazin-3-yl)-cyclobutyl]methanol

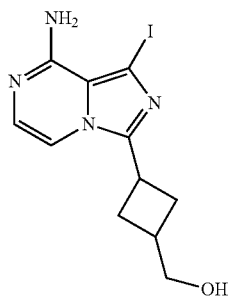 [SMILES: Nc1nccn2c(C3CC(CO)C3)nc(I)c12]

[3-(8-Chloro-1-iodoimidazo[1,5-a]pyrazin-3-yl)cyclobutyl]methanol (6.9 g) in i-PrOH (200 mL) was saturated with NH$_3$(g), by passing a slow a slow stream of ammonia for 10 min at −20° C., and then heated in a Parr bomb at 110° C. for 2d. The reaction mixture was then cooled to rt, filtered through a sintered glass and the solid residue and the Parr vessel were rinsed with i-PrOH several times. The filtrate was concentrated under reduced pressure to provide an orange solid still containing NH$_4$Cl. The material was taken up into refluxing MeCN (250 mL) and filtered hot. The step was repeated with another portion of hot MeCN (200 mL). The combined MeCN filtrates were concentrated under reduced pressure to give the title compound as an orange solid; HPLC: (polar5 min) 0.53 and 1.51 min; MS (ES+): 345.1 (100, M$^+$+1); $^1$H NMR (400 MHz, DMSO-d6) δ 7.50 (d, J=5.2 Hz, 1H), 7.44 (d, J=5.2 Hz, 0.27H, minor isomer), 6.95 (d, J=5.2 Hz, 1.29H overlapped with the minor isomer) 6.63 (br, 2H), 4.61 (t, J=5.2 Hz, 0.27H, minor isomer), 4.52 (t, J=5.2 Hz, 1H), 3.69 (quintet, J=5.6 Hz, 0.32H, minor isomer), 3.54 (quintet, J=5.6 Hz, 1H), 2.52-2.25 (m, 4H), 2.10-2.00 (m, 1H).

[3-(8-Chloro-1-iodo-imidazo[1,5-a]pyrazin-3-yl)-cyclobutyl]-methanol

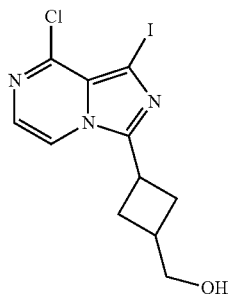 [SMILES: OCC1CC(c2nc(I)c3c(Cl)nccn23)C1]

To a solution of NIS (6.31 g, 28.0 mmol) in anh DMF (100 mL) under Ar was added dry [3-(8-chloroimidazo[1,5-a]pyrazin-3-yl)cyclobutyl]methanol (6.67 g) dissolved in anh DMF (30 mL). The flask containing [3-(8-chloroimidazo[1, 5-a]pyrazin-3-yl)cyclobutyl]methanol was rinsed with another portion of anh DMF (20 mL) and the rinse was added to the reaction mixture. The reaction was heated to 60° C. (rt→60° C.~30 min) and the stirred at this temperature for 3 h. The mixture was then cooled to rt, partitioned between 1M aq Na$_2$S$_2$O$_3$ (60 mL), brine (60 mL) and DCM (160 mL). The aq layer was extracted with DCM (3×100 mL). The combined organics were dried (Na$_2$SO$_4$), concentrated under reduced pressure and purified by flash chromatography on SiO$_2$ (0-8% MeOH in DCM) to provide a material, homogenous by UV on both TLC and HPLC, still containing DMF. The material was dissolved in DCM (200 mL) and washed with water (3×40 mL), dried (Na$_2$SO$_4$) and concentrated under reduced pressure to provide the title compound as a pale yellow solid; HPLC (polar5 min) 2.52 min; MS (ES+): m/z (rel. int.) 364.0 (100, M$^+$+1); $^1$H NMR (400 MHz, CDCl$_3$) δ 7.59 (d, J=4.8 Hz, 1 H), 7.49 (d, J=4.8 Hz, 0.22 H, minor isomer), 7.29 (d, J=4.8 Hz, 1 H), 7.28 (d, J=5.2 Hz, 0.23 H, minor isomer), 3.83-3.80 (m, 0.7 H), 3.72-3.62 (m, 3 H), 2.75-2.55 (m, 4 H), 2.42-2.32 (m, 1-2H).

[3-(8-Chloro-imidazo[1,5-a]pyrazin-3-yl)-cyclobutyl]-methanol

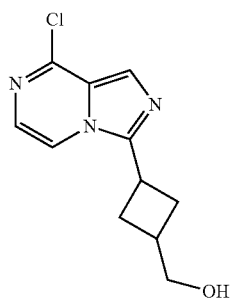 [SMILES: OCC1CC(c2ncc3c(Cl)nccn23)C1]

To a solution of 8-chloro-3-(3-methylenecyclobutyl)imidazo[1,5-a]pyrazine (4.48 g, 20.4 mmol) in anh THF (255 mL) at −78° C. under Ar, 9-BBN (61.2 mL, 0.5M in THF, 30.6 mmol) was added dropwise over 8 min (a suspension). The cooling bath was replaced with ice-H$_2$O and the reaction was allowed to warm slowly to rt. After being stirred for 17 h, H$_2$O (100 mL,) was added followed by, after ~5 min, NaBO$_3$.H$_2$O (12.2 g, 122.3 mmol) added in one lot. The reaction was stirred at rt for 5 h and then filtered through Celite. The Celite and residual solids were washed with DCM and EtOAc. The filtrate was concentrated under reduced pressure to yield an aq solution, which was saturated with NaCl and extracted with EtOAc (3×). The extracts were dried (Na$_2$SO$_4$) and concentrated under reduced pressure to yield a light yellow oil which was purified by flash chromatography on SiO$_2$ (9:1 DCM:MeOH) to afford the title compound as a light yellow oil; HPLC: $t_R$ (mass-directed HPLC, polar7 min) 2.52 min; MS (ES+): 238.0. The addition may be carried out at 0° C. Suspension quickly clears up after the exchange of cooling baths. The final product contained 1,5-cis-octanediol derived from 9-BBN. Based on $^1$H NMR estimated roughly to be 66% target material and 33% of the byproduct. The crude product was taken onto next step crude, stereoselectivity of the product was 4-5:1 as judged by ¹H NMR.

(8-Chloro-3-(3-methylene-cyclobutyl)-imidazo[1,5a]pyrazine)

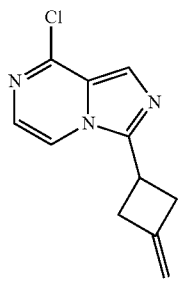

3-Methylene-cyclobutanecarboxylic acid (3-chloro-pyrazin-2-ylmethyl)-amide (52.1 g, 219.2 mmol) was dissolved in 1.0 L of anhydrous MeCN. Followed by the addition of DMF (1.0 mL) and POCl₃ (100 mL, 1.09 mol). The reaction was heated to 55° C. for 30 min. with a slow N₂ bubbling the reaction. The reaction was then concentrated in vacuo, basified with cold 2.0M NH₃ in IPA with CH₂Cl₂. The IPA/CH₂Cl₂ was concentrated in vacuo and the salts were dissolved with minimal water and extracted with CH₂Cl₂ (4×). The organic layers where combined and washed with sat. NaHCO₃ (1×), dried over sodium sulfate, filtered and concentrated in vacuo. The crude product was purified via silica gel column chromatography [eluting with 2:1 Hex:EtOAc] to yield the title compound as a light yellow solid; ¹H NMR (400 MHz, CDCl₃) δ 3.24-3.30 (4 H, m), 3.78-3.85 (1 H, m), 4.89-4.94 (2 H, m), 7.33 (1 H, d, J=4.99 Hz), 7.53 (1 H, d, J=5.09 Hz), 7.82 (1 H, s); MS (ES+): m/z 220.28/222.30 (100/80) [MH⁺]; HPLC: t_R=2.87 min (OpenLynx, polar_5 min).

3-Methylene-cyclobutanecarboxylic acid (3-chloropyrazin-2-ylmethyl)amide

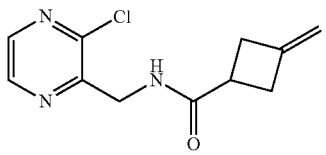 [SMILES: C=C1CC(C(=O)NCc2nccnc2Cl)C1]

C-(3-Chloropyrazin-2-yl)-methylamine bis-HCl (1.0 g, 4.62 mmol), N-ethyl-N'-(3-dimethylaminopropyl)carbodi-imide (EDC) (1.31 g, 6.47 mmol, 1.4 eq.), 4-dimethylamino pyridine (DMAP) (0.141 g, 1.15 mmol, 0.25 eq.), and diisopropylethylamine (DIPEA) (2.42 mL, 1.79 g, 13.9 mmol, 3.0 eq.) were dissolved in anhydrous CH₂Cl₂ (25 mL). To this solution, a solution of 3-methylenecyclobutanecarboxylic acid (0.622 g, 5.54 mmol, 1.2 eq.) in anhydrous CH₂Cl₂ (25 mL) was added under N₂ and the reaction was allowed to stir overnight at rt. Reaction mixture was concentrated in vacuo and the resulting residue was dissolved in EtOAc, washed with water (2×), NaHCO₃ (1×), water (1×), and brine (1×), dried over Na₂SO₄, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid. Additionally, the title compound could be prepared by the following route: 1,1'-Carbonyldiimidazole (CDI) (0.824 g, 5.08 mmol, 1.1 eq.) and 3-methylenecyclobutanecarboxylic acid (0.570 g, 5.08 mmol, 1.1 eq.) were dissolved in anhydrous THF (12 mL) and allowed to stir at 60° C. for 2 h. A solution of C-(3-chloropyrazin-2-yl)-methylamine bis-HCl (1.0 g, 4.62 mmol) and diisopropylethylamine (DIPEA) (2.42 mL, 1.79 g, 13.9 mmol, 3.0 eq.) in anhydrous CH₂Cl₂ (13 mL) was added to the acid mixture and the reaction was allowed to stir at 60° C., under N₂, overnight. The reaction mixture was concentrated in vacuo and the resulting residue was dissolved in EtOAc, washed with NaHCO₃ (2×) and brine (1×), dried over Na₂SO₄, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid; ¹H NMR (CDCl₃, 400 MHz) δ 2.86-2.96 (m, 2H), 3.03-3.19 (m, 3H), 4.72 (dd, J=4.4, 0.8 Hz, 2H), 4.79-4.84 (m, 2H), 6.78 (s, —NH), 8.32-8.34 (m, 1H), 8.46 (d, J=2.8 Hz, 1H); MS (ES+): m/z 238.19 (90) [MH⁺]; HPLC: t_R=2.67 min (OpenLynx, polar_7 min).

3-(8-Amino-1-iodoimidazo[1,5-a]pyrazin-3-yl)cyclobutanol

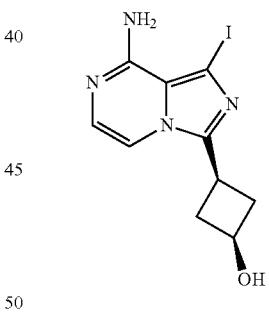

In a Parr pressure reactor 3-(8-chloro-1-iodo-imidazo[1,5-a]pyrazin-3-yl)-cyclobutanol (4.159 g, 0.0119 mol) was dissolved with 2.0M ammonia in isopropyl alcohol (40 mL). The mixture was cooled to −20° C. and saturated with ammonia. The reaction was heated at 110° C. for 63 h at which point it was cooled and concentrated in vacuo. The crude product was purified using HPFC Jones 25 g silica gel column eluting with 5-8% MeOH: CH₂Cl₂ to yield the title compounds; MS (ES+): m/z 330.88 (100) [MH⁺], 331.89 (10) [MH⁺⁺]; HPLC: t_R=0.48 min (OpenLynx, polar_5 min); ¹H NMR (CDCl₃, 400 MHz) δ 2.55-2.76 (m, 2 H) 3.06-3.22 (m, 2 H) 3.32-3.50

(m, 1 H) 4.51-4.69 (m, 1 H) 6.15 (br. s., 2 H) 7.24 (d, J=5.05 Hz, 1 H) 7.39 (d, J=5.05 Hz, 1 H).

3-(8-Chloro-1-iodoimidazo[1,5-a]pyrazin-3-yl)cyclobutanol

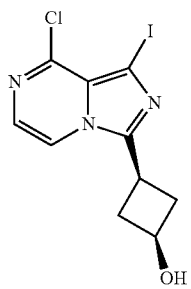 [SMILES: O[C@H]1C[C@@H](c2nc(I)c3c(Cl)nccn32)C1]

3-(8-Chloro-1-iodo-imidazo[1,5-a]pyrazin-3-yl)-cyclobutanone (5.0 g, 14 mmol) was dissolved in a 1:1 mixture of methanol (35.0 mL) and $CH_2Cl_2$ (35.0 mL). To the solution mixture sodium tetrahydroborate (560 mg, 14.0 mmol) was added slowly, gas evolution was observed. After 4.5 h at rt under nitrogen, the reaction was concentrated in vacuo. The crude mix was dissolved in EtOAc and washed with water. The organic layer was dried over sodium sulfate, filtered and concentrated in vacuo. The crude product was purified using HPFC Jones 50 gram silica gel column eluting with 50% EtOAc: Hex to 100% EtOAc, to yield the title compound as a light yellow solid; MS (ES+): m/z 349.81 (100) [MH$^+$], 351.50 (30) [MH$^{+++}$]; HPLC: $t_R$=2.49 min (OpenLynx, polar_5 min); $^1$H NMR (CDCl$_3$, 400 MHz) δ 2.41-2.54 (m, 2 H) 2.78-3.05 (m, 1 H) 3.12-3.32 (m, 1 H) 4.08-4.75 (m, 1 H) 5.30 (s, 1 H) 7.31 (d, J=5.05 Hz, 1 H) 7.57 (d, J=4.80 Hz, 1 H)

1-{4-[3-(8-Amino-1-iodoimidazo[1,5-a]pyrazin-3-yl)cyclobutyl]piperazin-1-yl}ethanone

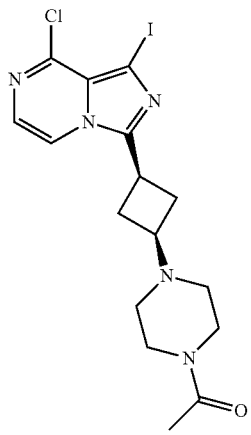 [SMILES: CC(=O)N1CCN([C@H]2C[C@@H](c3nc(I)c4c(Cl)nccn43)C2)CC1]

1-{4-[3-(8-Chloro-1-iodoimidazo[1,5-a]pyrazin-3-yl)cyclobutyl]piperazin-1-yl}ethanone (13.2 g, 0.029 mol) was dissolved in isopropyl alcohol (100 mL) into a Parr pressure reactor. The vessel was cooled to −78° C. and saturated with ammonia gas and sealed. The reaction was heated for 19 h at 110° C., at which point the reaction was cooled and the solvent concentrated in vacuo. The crude product was purified via silica gel chromatography eluting with 5-10% MeOH (7M NH$_3$): CH$_2$Cl$_2$ to yield the title compounds as an off white solid; MS (ES+): m/z 440.89 (100) [MH$^+$], 441.89 (20) [MH$^{++}$]; HPLC: $t_R$=0.46 min (OpenLynx, polar_5 min); $^1$H NMR (CDCl$_3$, 400 MHz) δ 2.09 (s, 3 H) 2.28-2.48 (m, 6 H) 2.54-2.71 (m, 2 H) 2.80-2.99 (m, 1 H) 3.27-3.43 (m, 1 H) 3.43-3.54 (m, 2 H) 3.56-3.70 (m, 2 H) 7.02 (d, J=5.05 Hz, 1 H) 7.16 (d, J=5.05 Hz, 2 H).

1-{4-[3-(8-Chloro-1-iodoimidazo[1,5-a]pyrazin-3-yl)cyclobutyl]piperazin-1-yl}ethanone

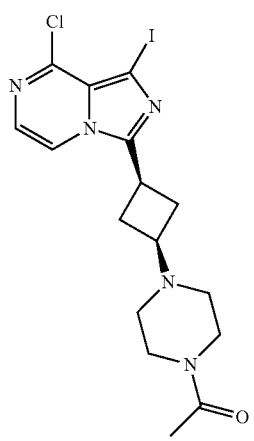 [SMILES: CC(=O)N1CCN([C@H]2C[C@@H](c3nc(I)c4c(Cl)nccn43)C2)CC1]

Into a RBF 3-(8-chloro-1-iodoimidazo[1,5-a]pyrazin-3-yl)cyclobutanone (1.00 g, 0.0029 mol) and sodium triacetoxyborohydride (1.30 g, 0.006 mol) were dissolved in 1,2-dichloroethane (65.0 mL) and a solution of 1-acetylpiperazine (0.39 g, 0.003 mol) in 1,2-dichloroethane was added to the reaction. The reaction mixture was stirred at rt for 2 h. The crude product was concentrated in vacuo and the dissolved in CH$_2$Cl$_2$ (25.0 mL) and washed with saturated NaHCO$_3$ solution (1×40 mL). The product was dried with sodium sulfate and concentrated in vacuo to yield a light yellow solid; MS (ES+): m/z 459.84 (100) [MH$^+$], 461.80 (40) [MH$^{+++}$]; HPLC: $t_R$=1.81 min (OpenLynx, polar5 min); $^1$H NMR (CDCl$_3$, 400 MHz) δ 2.04-2.15 (m, 3 H) 2.26-2.50

(m, 6 H) 2.55-2.72 (m, 2 H) 2.83-2.99 (m, 1 H) 3.29-3.52 (m, 3 H) 3.56-3.67 (m, 2 H) 7.29 (d, 1 H) 7.58 (d, 1 H).

(1-Iodo-3-[3-(4-methyl-piperazin-1-yl)-cyclobutyl]-imidazo[1,5-a]pyrazin-8-ylamine)

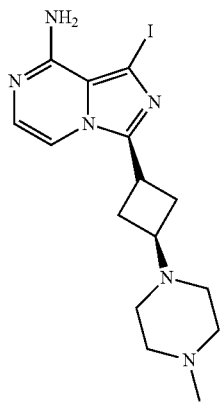

A solution of 2N ammonia in isopropyl alcohol (350 mL) and THF (30 mL, 0.4 mol) was added to 8-chloro-1-iodo-3-[3-(4-methyl-piperazin-1-yl)-cyclobutyl]-imidazo[1,5-a]pyrazine (19.91 g, 0.04612 mol) in a Parr bomb and cooled to −78° C. Ammonia was bubbled into the solution for 8-10 min. The bomb was sealed, stirred and heated to at 110° C. over 3d. The solvent was then evaporated in vacuo and purified by flash silica gel chromatography (wetted with CHCl$_3$, dried loaded with silica, and eluted with 8% (7N NH$_3$) MeOH in CHCl$_3$), which afforded the title compound; $^1$H NMR (CDCl$_3$, 400 MHz) δ 7.31 (1 H, d, J=5.01), 7.16 (1 H, d, J=6.25), 5.83 (2 H, s), 3.49 (1 H, m), 3.06 (1 H, m), 2.76 (4 H, m), 2.64 (8 H, m), 2.46 (3 H, s); MS (ES+): m/z 412.89/413.91 (50/10) [MH$^+$]; HPLC: t$_R$=0.31 min. (OpenLynx, polar_5 min.).

(8-Chloro-1-iodo-3-[3-(4-methylpiperazin-1-yl)cyclobutyl]imidazo[1,5-a]pyrazine)

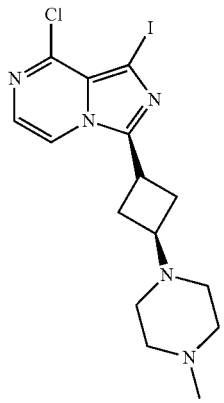

1-Methyl piperazine (5.75 mL, 0.0514 mol) in 1,2-dichloroethane (1096.7 mL, 13.892 mol) was added to 3-(8-chloro-1-iodoimidazo[1,5-a]pyrazin-3-yl)cyclobutanone (17.00 g, 0.04892 mol) and sodium triacetoxyborohydride (21.8 g, 0.0978 mol). The reaction stirred at rt for 3 h. The reaction was concentrated, dissolved in CH$_2$Cl$_2$, and then washed with saturated NaHCO$_3$ solution and brine. The product was dried over sodium sulfate, filtered, and concentrated in vacuo. The product was flushed through a quick silica gel plug (wetted with 100% CHCl$_3$, eluted with 8% (7N NH$_3$) MeOH in CHCl$_3$), to afford the title compound; $^1$H NMR (CDCl$_3$, 400 MHz) δ 7.63 (1 H, d), 7.30 (1 H, d), 3.42 (1H, m), 2.94 (1H, m), 2.65 (4 H, m), 2.44 (8 H, m), 2.32 (3H, s); MS (ES+): m/z 431.85/433.87 (100/45) [MH$^+$]; HPLC: t$_R$=1.82 min. (OpenLynx, polar_5 min.).

3-(8-Chloroimidazo[1,5-a]pyrazin-3-yl)-1-methylcyclobutanol

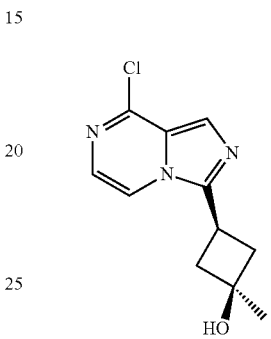

3-(8-Chloroimidazo[1,5-a]pyrazin-3-yl)cyclobutanone (1.95 g, 8.80 mmol) in anhydrous THF (77.78 mL) at −78° C. under an atmosphere of nitrogen was treated slowly with a 3.0 M solution of methylmagnesium chloride in THF (5.9 mL). The solution stirred for 3 hr at −78° C. then quenched with 40 mL of semi-saturated aqueous NH$_4$Cl (NH$_4$Cl dilution in 1:1 mixture with water) at −78° C. and allowed to warm up to rt. The mixture was then extracted with EtOAc (3×40 mL) and the combined extracts washed with brine (30 mL), dried over magnesium sulfate, filtered and concentrated in vacuo. The crude solid was purified by chromatography over silica gel eluting with 1:1 EtOAc/DCM to 4% MeOH in (1:1) EtOAc/DCM to afford desired product. $^1$H-NMR (400 MHz, CDCl$_3$) δ ppm 1.54 (s, 3 H), 2.74-2.60 (m, 4 H), 3.75-3.39 (m, 1 H), 7.35 (d, J=5.04 Hz, 1 H), 7.71 (d, J=5.00 Hz, 1 H) and 7.86 (s, 1 H). MS (ES+): m/z 238.15 and 240.17 [MH$^+$].

3-(8-Chloro-1-iodoimidazo[1,5-a]pyrazin-3-yl)-1-methylcyclobutanol

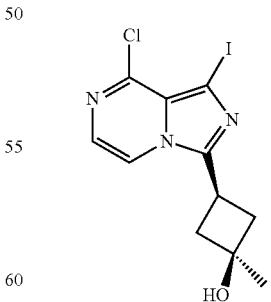

3-(8-Chloroimidazo[1,5-a]pyrazin-3-yl)-1-methylcyclobutanol (2.20 g, 9.26 mmol) and NIS (2.71 g, 12.0 mmol) were dissolved in DMF (36.6 mL, 0.472 mol) and stirred at 60° C. for 4 h. The mixture was then concentrated in vacuo and the residue reconstituted in EtOAc (100 mL). This solution was washed with sodium bicarbonate (2×20 mL) and these washes back-extracted with EtOAc (2×20 mL). The organic layers were combined, dried with sodium sulfate, filtered and concentrated in vacuo. The crude solid was purified by chromatography over silica gel eluting with 1:1 EtOAc:hexanes to afford desired product. $^1$H-NMR (400 MHz, CDCl$_3$) δ ppm 1.53 (s, 3 H), 2.72-2.59 (m, 4 H), 3.37-3.29 (m, 1 H), 7.32 (d, J=4.91 Hz, 1 H) and 7.60 (d, J=4.96 Hz, 1 H). MS (ES+): m/z 363.95 and 365.91 [MH$^+$].

3-(8-Amino-1-iodoimidazo[1,5-a]pyrazin-3-yl)-1-methylcyclobutanol

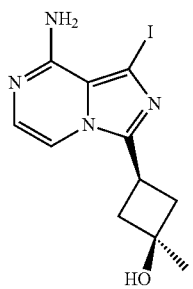 [SMILES: C[C@]1(O)C[C@@H](c2nc(I)c3c(N)nccn32)C1]

A solution of 2M ammonia in isopropanol (80 mL) and THF (5 mL) was added to 3-(8-chloro-1-iodoimidazo[1,5-a]pyrazin-3-yl)-1-methylcyclobutanol (2.77 g, 7.62 mmol) in a Parr pressure reactor. The mixture was cooled to at −78° C. then ammonia gas was bubbled into the solution for 4-6 min. The reactor was sealed then heated at 110° C. for 15 h. The solvent was then removed in vacuo and the residue purified by chromatography over silica gel eluting with 7% MeOH in DCM to afford desired product. $^1$H NMR (400 MHz, DMSO-d6) δ ppm 1.44 (s, 3 H), 2.32-2.51 (m, 4 H), 3.33-3.52 (m, 1 H), 6.61 (br.s., 2 H), 7.03 (d, J=5.05 Hz, 1 H) and 7.62 (d, J=5.05 Hz, 1 H).

(3-(8-Chloro-1-iodoimidazo[1,5-a]pyrazin-3-yl)cyclobutanone)

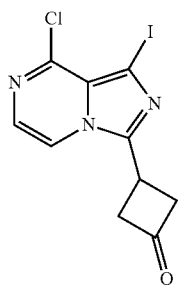 [SMILES: O=C1CC(c2nc(I)c3c(Cl)nccn23)C1]

A solution of 3-(8-chloro-1-iodoimidazo[1,5-a]pyrazin-3-yl)-1-hydroxymethylcyclobutanol (4.08 g, 0.01 μmol) in THF (120 mL) and water (40 mL) was charged with sodium periodate (2.8 g, 0.013 mol) at 0° C. The reaction warmed to rt and stirred for 5 h. The reaction mixture was diluted with ethyl acetate and then washed with brine. The organic phase was dried over Na$_2$SO$_4$, filtered, and concentrated in vacuo to afford the title compound as a yellow solid; $^1$H NMR (CDCl$_3$, 400 MHz) δ 7.56 (1 H, d, J=4.94), 7.32 (1 H, d, J=4.98), 3.64 (5 H, m); MS (ES+): m/z 347.82 and 349.85 [MH$^+$]; HPLC: t$_R$=2.89 min. (OpenLynx, polar_5 min.).

3-(8-Chloro-1-iodoimidazo[1,5-a]pyrazin-3-yl)-1-hydroxymethylcyclobutanol

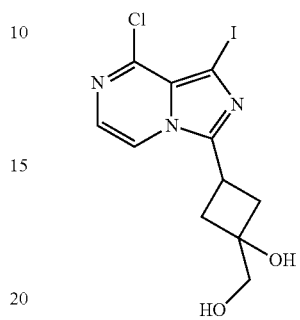

Under inert atmosphere N-iodosuccinimide (3.6 g, 0.016 mol) and 3-(8-chloroimidazo[1,5-a]pyrazin-3-yl)-1-hydroxymethylcyclobutanol (3.16 g, 0.012 mol) were dissolved in N,N-dimethylformamide (30 mL) and heated at 60° C. for 3.0 h. The reaction mixture was then concentrated in vacuo to a dark oil and purified by HPFC Jones 20 g silica gel column, eluting with 5% MeOH: CH$_2$Cl$_2$ to yield a light brown fluffy solid which was triturated with diethyl ether and hexanes to afford the title compound; MS (ES+): m/z 379.85 and 381.80 [MH$^+$]; HPLC: t$_R$=2.30 min (OpenLynx, polar_5 min).

3-(8-Chloroimidazo[1,5-a]pyrazin-3-yl)-1-hydroxymethylcyclobutanol

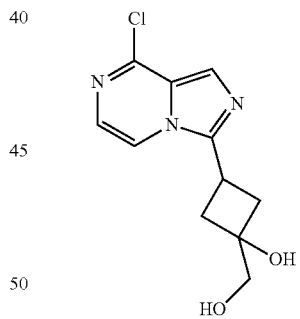

To a THF solution (170 mL) of 8-chloro-3-(3-methylenecyclobutyl)imidazo[1,5-a]pyrazine (3.1 g, 14 mmol), water (18 mL), 50% N-methylmorpholine-N-oxide in water (3.2 mL) and potassium osmate, dehydrate (200 mg, 0.70 mmol) were added and the reaction was allowed to stir at rt for 4 h.

Sodium sulfite (8.0 g, 70.0 mmol) was added to the reaction mixture and allowed to stir for 30 min at which point the reaction was concentrated in vacuo. The crude product was extracted from the aqueous with EtOAc. The organics were washed with brine and the combined aqueous washes were back extracted with EtOAc (5×50 mL). The combined organics were dried over sodium sulfate, filtered, and concentrated in vacuo to yield the title compounds as a sticky tan/off-white solid; MS (ES+): m/z 254.17 (100) [MH⁺], 256.19 (50) [MH⁺⁺⁺]; HPLC: $t_R$=1.95 min (OpenLynx, polar_5 min).

3-Methylene-cyclobutanecarboxylic acid

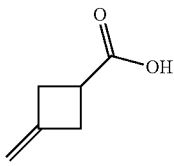

To a solution of 3-methylenecyclobutanecarbonitrile (100.0 g, 1.042 mol) in ethanol (1.00 L) and water (1.00 L) was added potassium hydroxide (230.0 g, 4.2 mol). The resulting mixture was heated at reflux for 7 hr then the EtOH was removed in vacuo and the solution was cooled to 0° C. and acidified with (300.0 mL) of conc. HCl to pH=1. The mixture was extracted with diethyl ether (4×1 L) and the combined organic phases were dried over sodium sulfate, filtered and concentrated in vacuo to yield desired product. ¹H NMR (400 MHz, CDCl₃) δ ppm 2.64-3.44 (m, 5H), 4.60-4.98 (m, 2H) and 10.64 (br. s., 1H).

Ethyl 3-methylenecyclobutanecarboxylate

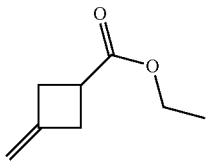

Iodoethane (7.5 mL, 93.0 mol) was added at rt to a mixture of 3-methylenecyclobutanecarboxylic acid (10.0 g, 80.0 mmol) and cesium carbonate (56.0 g, 170.0 mmol) in anhydrous N,N-dimethylformamide (500.00 mL) under an atmosphere of nitrogen. The reaction was stirred for 16 hr then partitioned between diethyl ether (1 L) and brine (1 L). The aqueous layer was extracted with diethyl ether (3×500 mL) and the combined organic phases washed with water (2×1 L), dried over sodium sulfate, filtered and concentrated in vacuo to yield desired product ¹H NMR (400 MHz, CDCl₃) δ ppm 1.26 (t, 3H), 2.71-3.27 (m, 5H), 4.15 (q, J=7.07 Hz, 2H) and 4.53-4.96 (m, 2H).

N-[(3-chloropyrazin-2-yl)methyl]-3-methylenecyclobutanecarboxamide

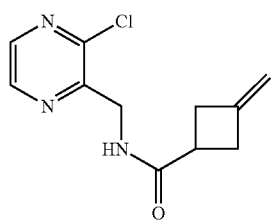 [SMILES: C=C1CC(C(=O)NCc2nccnc2Cl)C1]

1,1'-Carbonyldiimidazole (CDI) (8.24 g, 50.81 mmol) and 3-methylenecyclobutanecarboxylic acid (5.70 g, 50.81 mmol) were dissolved in anhydrous THF (100 mL) and allowed to stir at 60° C. for 4 h. A solution of C-(3-Chloropyrazin-2-yl)methylamine bis-hydrochloride (10.0 g, 46.19 mmol) and diisopropylethylamine (DIPEA) (32.30 mL, 184.76 mmol) in anhydrous CH₂Cl₂ (150 mL) was added to the mixture and the reaction was allowed to stir at rt for 24 h. The mixture was concentrated in vacuo, the residue dissolved in EtOAc and the resulting solution washed with saturated NaHCO₃ (aq.) water H₂O and Brine. The combined organic layers were dried over sodium sulfate, filtered and concentrated in vacuo to afford crude product, which was purified by chromatography over silica gel eluting with 50-70% EtOAc/hexane to yield desired product. ¹H NMR (400 MHz, CDCl₃) δ ppm 2.92-2.94 (2 H, m), 3.05-3.14 (2 H, m), 4.60 (2 H, d, J=4.24 Hz), 4.80-4.84 (2 H, m), 6.75 (1 H, brs), 8.33 (1 H, d, J=4.22 Hz) and 8.45 (1 H, d, J=2.54 Hz). MS (ES+): m/z 238 and 240 [MH+].

8-Chloro-3-(3-methylenecyclobutyl)imidazo[1,5-a]pyrazine

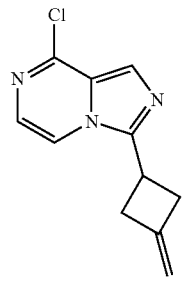

N-[(3-Chloropyrazin-2-yl)methyl]-3-methylenecyclobutanecarboxamide (52.1 g, 219.2 mmol) in anhydrous MeCN (1.0 L) was treated with DMF (1.0 mL) and POCl₃ (100 mL, 1.09 mol) and the mixture was stirred at 55° C. for 30 min. under a gentle stream of N₂. The reaction was then concentrated in vacuo and the residue reconstituted in CH₂Cl₂ and treated with cold 2.0 M NH₃ in IPA. This mixture was concentrated in vacuo, water added to dissolve the salts, and then extracted with CH₂Cl₂ (4×60 mL). The organic layers where combined and washed with sat. NaHCO₃ (1×70 mL) dried over sodium sulfate, filtered and concentrated in vacuo. The crude material was purified by chromatography over silica gel eluting with 2:1 hexane:EtOAc to yield desired product. ¹H NMR (400 MHz, CDCl₃) δ ppm 3.24-3.30 (4 H, m), 3.78-3.85 (1 H, m), 4.89-4.94 (2 H, m), 7.33 (1 H, d, J=4.99 Hz), 7.53 (1 H, d, J=5.09 Hz) and 7.82 (1 H, s). MS (ES+): m/z 220.28 and 222.30 [MH+].

C-(3-Chloropyrazin-2-yl)methylamine bis-hydrochloride

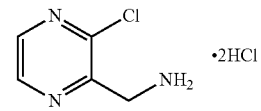

A solution of 2-(3-chloropyrazin-2-ylmethyl)-isoindole-1,3-dione (10.0 g, 36.5 mmol) in anhydrous CH₂Cl₂ (200 mL) was charged with hydrazine (2.87 mL, 2.93 g, 91.3 mmol, 2.5 eq.) at rt, under N₂ atmosphere. After 2.5 h, MeOH (300 mL)

was added and the reaction was heated until the solution was homogenous. The reaction mixture was allowed to stir for 19 h. The white ppt that had formed (2,3-dihydrophthalazine-1,4-dione byproduct), was filtered off and washed several times with ether. The clear filtrate was concentrated in vacuo and the concentrate was dissolved in EtOAc and filtered again to remove white ppt. All solvent was removed, giving a yellow oil, which was dissolved into EtOAc and ether and charged with HCl (g). The title compound, a pale yellow solid, instantly precipitated. The title compound was dried in a 40° C. oven for 72 h, affording the title compound, as a dark yellow solid; $^1$H NMR (400 MHz, CD$_3$OD) δ 4.55 (2 H, s), 8.27 (1 H, d, J=2.52 Hz), 8.54 (1 H, d, J=2.56 Hz); MS (ES+): m/z 143.96/145.96 (100/60) [MH$^+$]; HPLC: t$_R$=0.41 min (OpenLynx, polar_7 min).

1-{[(3-Oxocyclobutyl)carbonyl]oxy}pyrrolidine-2,5-dione

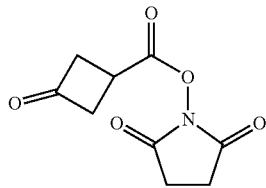 [SMILES: O=C1CC(C(=O)ON2C(=O)CCC2=O)C1]

Into a 5 L reactor equipped with a nitrogen flow and an overhead stirrer was added N-hydroxysuccinimide (250.0 g, 2.172 mol) and 3-oxo-cyclobutanecarboxylic acid (248 g, 2.17 mol). Ethyl acetate (3.4 L) was added and the reaction was cooled to 16° C. A solution of 25% DCC in EtOAc (2.17 mol) was added slowly via an addition funnel to the reaction mixture over 7 minutes then the mixture was then heated at 45° C. After 2 h, the mixture was filtered and the filtrate was washed once with EtOAc (1 L×1) and evaporated to dryness in vacuo to afford the desired product. $^1$H NMR (400 MHz, DMSO-d6) δ 2.83 (bs, 4H), 3.30-3.39 (m, 2H), 3.52-3.60 (m, 2H) and 3.67-3.73 (m, 1H).

3-(8-Chloroimidazo[1,5-a]pyrazin-3-yl)cyclobutanone

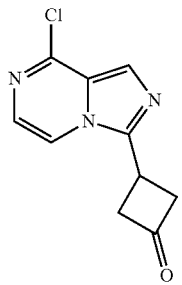 [SMILES: O=C1CC(c2ncc3c(Cl)nccn23)C1]

Into a round bottom 1-neck flask (5 L), 3-oxo-cyclobutanecarboxylic acid 2,5-dioxo-pyrrolidin-1-yl ester (217.2 g, 0.937 mol), C-(3-chloro-pyrazin-2-yl)-methylamine hydrochloride salt (153.3 g, 0.852 mol), and THF (760 mL) were added. A solution of 10% NaHCO3 (1.07 kg) was then added and after 20 min, the layers were allowed to separate and the aqueous layer was removed. The aqueous layer was back extracted with EtOAc (1×700 mL, 1×300 mL). The combined organics were washed with brine (350 mL), dried over MgSO$_4$, filtered, and concentrated in vacuo to provide the title compound. This solid was resuspended in ethyl acetate (915 mL) and DMF (132 mL) and the solution was put under an atmosphere of nitrogen and cooled to 10.5° C. Phosphorus oxychloride (159 mL, 1.70 mol) was then added over 15 minutes and the reaction was allowed to stir for 45 min. The reaction solution was then poured slowly into a 22% aqueous Na$_2$CO$_3$ solution at 10° C. Water (1 L) was added and the layers were allowed to separate. The organic layer was removed and the aqueous was back extracted with EtOAc (1×1 L, 1×0.5 L). The combined organic phases were dried over MgSO$_4$, filtered, and concentrated in vacuo until about 0.5 L of solvent remained. Heptane was added and the slurry was concentrated in vacuo until most of the EtOAc was removed. The resultant slurry was filtered to give desired product. $^1$H NMR (400 MHz, CDCl$_3$) δ 3.59-3.68 (m, 2H), 3.72-3.79 (m, 2H), 3.86-3.94 (m, 1H), 7.40 (d, 1H, J=5.2 Hz), 7.60 (d, 1H, J=5.2 Hz) and 7.85 (s, 1H).

3-(1-Bromo-8-chloroimidazo[1,5-a]pyrazin-3-yl)cyclobutanone

3-(8-Chloroimidazo[1,5-a]pyrazin-3-yl)cyclobutanone (47.7 g, 215 mmol) was dissolved in DMF (200 mL) under an atmosphere of nitrogen and cooled to −4° C. N-Bromosuccinimide (40.3 g, 226 mmol) was dissolved in DMF (140 mL) and slowly added to the reaction mixture. After 5 min, water (400 mL) was added and the resulting solid isolated by filtration and washed with solid with water to give the title compound. $^1$H NMR (DMSO-d6, 400 MHz): δ 3.45-3.53 (m, 2H), 3.58-3.67 (m, 2H), 4.08-4.16 (m, 1H), 7.45 (d, 1H, J=5.2 Hz) and 8.30 (d, 1H, J=4.8 Hz).

3-(1-Bromo-8-chloroimidazo[1,5-a]pyrazin-3-yl)-1-methylcyclobutanol

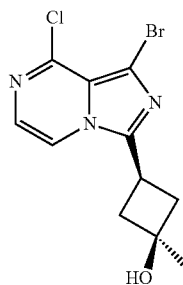

3-(1-Bromo-8-chloroimidazo[1,5-a]pyrazin-3-yl)cyclobutanone (51.988 g, 0.17 mol) in anhydrous THF (550 g, 620 mL) under nitrogen at −78° C. was treated with a 3.0 M solution of methyl magnesium chloride in THF (130 mL, 0.38 mol) over min. The mixture was stirred at −78° C. for 30 min and then the cooling bath was removed and the mixture quenched with 14% NH$_4$Cl (132 g). EtOAc was added to the aqueous phase and the pH was adjusted to ~5 with 20% HCl and the layers separated. The combined organic phases were concentrated in vacuo to a slurry and 0.5 L of toluene was added and the mixture concentrated in vacuo until the EtOAc was removed. The slurry was heated at reflux until homogeneous then allowed to cool to provide desired product, which was isolated by filtration and dried in vacuo. $^1$H NMR (DMSO-d$_6$, 400 MHz): δ 1.37 (s, 3H), 2.35-2.49 (m, 4H), 3.52 (dddd, 1H, J=9.6, 9.6, 9.6, 9.6 Hz), 5.18 (bs, 1H), 7.37 (d, 1H, J=5.2 Hz) and 8.26 (d, 1H, J=5.2 Hz).

3-(8-Amino-1-bromoimidazo[1,5-a]pyrazin-3-yl)-1-methylcyclobutanol

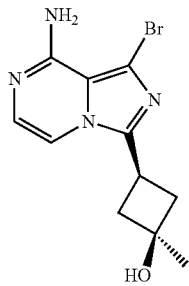 [SMILES: C[C@]1(O)C[C@@H](c2nc(Br)c3c(N)nccn32)C1]

A 35% ammonia solution (132 ml, 2.9 moles) was added to a suspension of 3-(1-bromo-8-chloroimidazo[1,5-a]pyrazin-3-yl)-1-methylcyclobutanol (22.0 g, 0.06463 mol) in 2-butanol (81 ml). The mixture was heated at 90° C. in a pressure vessel for 15 hr then concentrated to ~130 ml, cooled to room temperature and the solid collected by filtration. This material was washed with water (3×22 mL) and dried at 40° C. under vacuum. To afford the desired product. $^1$H NMR (DMSO-d$_6$, 400 MHz): δ 7.5 (d, 1H), 7.0 (d, 1H), 6.6 (bs, 2H), 5.1 (s, 1H), 3.4 (pentet, 1H), 2.3-2.4 (m, 4H) and 1.4 (s, 3H).

7-Cyclobutyl-5-iodoimidazo[5,1-f][1,2,4]triazin-4-ylamine

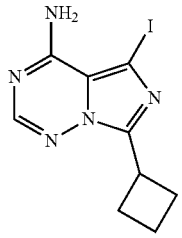 [SMILES: Nc1ncnn2c(C3CCC3)nc(I)c12]

To a solution of 1,2,4-triazole (1.28 g, 18.59 mmol) in anhydrous pyridine (10 mL) was added phosphorus oxychloride (POCl$_3$) (0.578 mL, 6.20 mmol) and stirred at rt for 15 min. This mixture was dropwise charged (3.5 min) with a solution of 7-cyclobutyl-5-iodo-3H imidazo[5,1f][1,2,4]triazin-4-one (0.653 mg, 2.07 mmol) in anhydrous pyridine (14 mL) and stirred for 1.5 h. The reaction mixture was cooled to 0° C. quenched with 2M NH$_3$ in isopropanol (IPA) until basic then allowed to reach rt and stirred for an additional 2 h. The reaction mixture was filtered through a fritted Buchner funnel and washed with DCM. The filtrate was concentrated in vacuo and purified by chromatography on silica gel [eluting with 30% EtOAc in DCM]resulting in the title compound as an off-white solid; $^1$H NMR (CDCl$_3$, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH$^+$], HPLC: t$_R$=2.59 min (MicromassZQ, polar_5 min).

7-Cyclobutyl-5-iodo-3H-imidazo[5,1-f][1,2,4]triazin-4-one

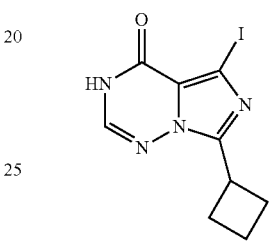

A solution of 7-cyclobutyl-3H-imidazo[5,1-f][1,2,4]triazin-4-one (789 mg, 4.15 mmol) and N-iodosuccinimide (NIS, 933 mg, 4.15 mmol) in anhydrous DMF (40 mL) was stirred overnight at rt. An additional 4 eq. of NIS was added and reaction was heated to 55° C. for 6 h. The reaction mixture was concentrated in vacuo and partitioned between DCM and H$_2$O and separated. The aqueous layer was washed with DCM (3×) and the combined organic fractions were washed with 1M sodium thiosulfate (Na$_2$S$_2$O$_3$) (1×), brine (1×), dried over sodium sulfate (Na$_2$SO$_4$), filtered, and concentrated in vacuo. The solid was triturated with 20% EtOAc in DCM and filtered through a fritted Buchner funnel resulting in the title compound as an off-white solid; $^1$H NMR (DMSO-d$_6$, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH$^+$], HPLC: t$_R$=2.62 min (MicromassZQ, polar_5 min).

7-Cyclobutyl-3H-imidazo[5,1-f][1,2,4]triazin-4-one

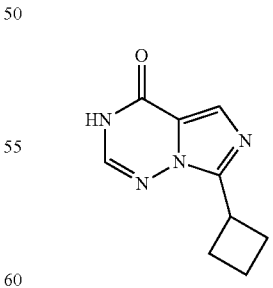

A crude solution of cyclobutanecarboxylic acid (5-oxo-4,5-dihydro-[1,2,4]triazin-6-ylmethyl)amide (1.33 g, 6.39 mmol) in phosphorus oxychloride (POCl$_3$) (10 mL) was heated to 55° C. The reaction was heated for 2 h then concentrated in vacuo and the crude oil was cooled to 0° C. in an ice-bath and quenched with 2M NH$_3$ in ispropanol (IPA) until slightly basic. This crude reaction mixture was concentrated in vacuo and was partitioned between DCM and H₂O and separated. The aqueous layer was extracted with DCM (3×) and the combined organic fractions were dried over sodium sulfate (Na₂SO₄), filtered and concentrated in vacuo. The crude material was purified by chromatography on silica gel [eluting with 5% MeOH in DCM], resulting in the title compound as an off-white solid; ¹H NMR (DMSO-d₆, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H); 11.7 (brs, 1H); MS (ES+): m/z 191.27 (100) [MH⁺], HPLC: $t_R$=2.06 min (MicromassZQ, polar_5 min).

Cyclobutanecarboxylic acid
(5-oxo-4,5-dihydro-[1,2,4]triazin-6-ylmethyl)amide

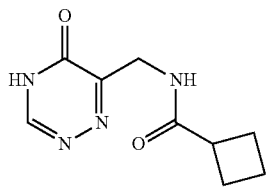 [SMILES: O=C(NCc1nnc[nH]c1=O)C1CCC1]

To a solution of 6-aminomethyl-4H-[1,2,4]triazin-5-one (500 mg, 3.96 mmol) and N,N-diisopropylethylamine (DIEA) (0.829 mL, 4.76 mmol) in anhydrous N,N-dimethylformamide (DMF) (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H₂O (2 mL) and concentrated in vacuo and was purified by chromatography on silica gel [eluting with 5% MeOH in DCM (200 mL)→10% MeOH in DCM (800 mL)], affording the title compound; ¹H NMR (DMSO-d₆, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (brt, J=5.6 Hz, 1H); 8.67 (s, 1H); MS (ES+): m/z 209.25 (100) [MH⁺], HPLC: $t_R$=1.56 min (MicromassZQ, polar_5 min).

6-Aminomethyl-4H-[1,2,4]triazin-5-one

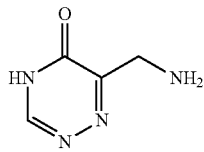

A slurry of 2-(5-oxo-4,5-dihydro-[1,2,4]triazin-6-ylmethyl)isoindole-1,3-dione (4 g, 15.6 mmol) in DCM/EtOH (1:1) (150 mL) was charged with anhydrous hydrazine (1.23 mL, 39.0 mmol) and stirred at rt for 18 h. The reaction mixture was concentrated in vacuo and the off-white solid was triturated with warm CHCl₃ and filtered through a fritted funnel. The solid was then triturated with hot boiling methanol (MeOH) and filtered through a fritted funnel resulting in an off-white solid. The material was triturated a second time as before and dried overnight resulting in the title compound as a white solid, which was taken on to the next step without further purification; ¹H NMR (DMSO-d₆, 400 MHz) δ 3.88 (s, 2H), 8.31 (2, 1H); MS (ES+): m/z 127.07 (100) [MH⁺], HPLC: $t_R$=0.34 min (MicromassZQ, polar_5 min).

2-(5-Oxo-4,5-dihydro-[1,2,4]triazin-6-ylmethyl)
isoindole-1,3-dione

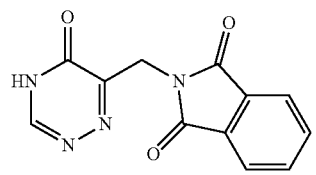 [SMILES: O=C1c2ccccc2C(=O)N1Cc1nnc[nH]c1=O]

A slurry of 2-(5-oxo-3-thioxo-2,3,4,5-tetrahydro-[1,2,4]triazin-6-ylmethyl)isoindole-1,3-dione (1.0 g, 3.47 mmol) in EtOH (40 mL) was charged with excess Raney Ni (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; ¹H NMR (DMSO-d₆, 400 MHz) δ 4.75 (s, 2H), 7.84-7.98 (m, 4H), 8.66 (s, 1H); MS (ES+): m/z 257.22 (100) [MH⁺].

2-(5-Oxo-3-thioxo-2,3,4,5-tetrahydro-[1,2,4]triazin-
6-ylmethyl)indan-1,3-dione

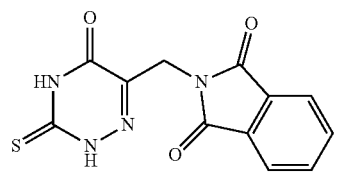 [SMILES: O=C1c2ccccc2C(=O)N1Cc1n[nH]c(=S)[nH]c1=O]

A slurry of 3-(1,3-dioxo-1,3-dihydroisoindol-2-yl)-2-oxo-propionic acid ethyl ester (20 g, 76.6 mmol) in anhydrous EtOH (300 mL) was charged with thiosemicarbazide (6.98 g, 76.6 mmol) in one portion and heated to 80° C. for 2 h. The reaction mixture was charged with N,N-diisopropylethylamine (DIEA) (26.7 mL, 76.56 mmol) and heated to 40° C. for 6 h then stirred at rt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; ¹H NMR (DMSO-d₆, 400 MHz) δ 4.68 (s, 2H), 7.85-7.95 (m, 4H); MS (ES+): m/z 289.2 (100) [MH⁺].

2-[(3-Methyl-5-oxo-4,5-dihydro-1,2,4-triazin-6-yl)
methyl]-1H-isoindole-1,3(2H)-dione

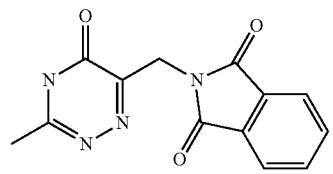 [SMILES: Cc1nnc(CN2C(=O)c3ccccc3C2=O)c(=O)[nH]1]

A solution of ethyl 3-(1,3-dioxo-1,3-dihydro-2H-isoindol-2-yl)-2-oxopropanoate [*J. Org. Chem.*, (1985), 50 (1), 91] (4.29 g, 16.4 mmol), acetamidrazone hydrochloride (1.80 g, 16.4 mmol) in anhydrous EtOH (85.8 mL) was heated to 80° C. for 3 h then cooled to rt and stirred for an additional 16 h. The reaction mixture was filtered through a fritted funnel resulting in 3.28 g, (73% yield) of the title compound as a white solid. ¹H NMR (400 MHz, DMSO-d6) δ ppm 2.28 (s, 3H), 4.73 (s, 2H) and 7.74-8.12 (m, 4H); MS (ES+): m/z 271.08 [MH+].

6-(Aminomethyl)-3-methyl-1,2,4-triazin-5(4H)-one

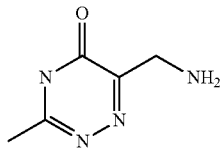

A solution of 2-[(3-methyl-5-oxo-4,5-dihydro-1,2,4-triazin-6-yl)methyl]-1H-isoindole-1,3(2H)-dione (2.00 g, 7.40 mmol) in DCM (10.0 mL) and EtOH (10.0 mL) was charged with hydrazine (0.58 mL, 18.5 mmol) and stirred at rt for 8 h, then heated to 45° C. for an additional 16 h. The reaction was charged with an additional 0.5 equiv of hydrazine (0.116 mL, 3.70 mmol) and heated to 45° C. for 4 h. The reaction mixture was allowed to cool to rt then filtered through a fritted funnel and the cake was washed with 2 portions of cold 1:1 EtOH/DCM (75 mL) and the filtrate was concentrated resulting in 622 mg of a pale yellow solid which was taken on to the next step without further purification. ¹H NMR (400 MHz, DMSO-d₆) δ ppm 2.21 (s, 3H), 3.72 (s, 2H); MS (ES+): m/z 141.06 [MH+].

trans-4-({[(Benzyloxy)carbonyl]amino}methyl)cyclohexanecarboxylic acid

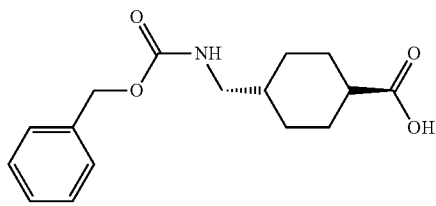

trans-4-(Aminomethyl)cyclohexanecarboxylic acid (10.00 g, 0.06361 mol), in a 10% aq solution of NaOH (5.60 g in 55 mL) was cooled to 0° C. and treated over 15 min with vigorous stirring, with benzyl chloroformate (11 mL, 0.076 mol).

After one hour the solution was acidified (1M HCl(aq)) and the resulting the white precipitate collected by filtration, washed with water and hexane then dried in vacuo oven overnight to afford 17.23 g of the title compound. ¹H NMR (400 MHz, CDCl₃): δ 0.93-0.99 (m, 2H), 1.38-1.46 (m, 2H), 1.82-1.85 (m, 2H), 2.03-2.06 (m, 2H), 2.25 (m, 1H), 3.06 (t, J=5.6 Hz, 2H), 4.83 (m, 1H), 5.09 (s, 2H), 7.31-7.36 (m, 5H). MS (ES+): m/z 292 [MH+].

Benzyl [(trans-4-{[(3-chloropyrazin-2-yl)methyl]carbamoyl}cyclohexyl)methyl]carbamate

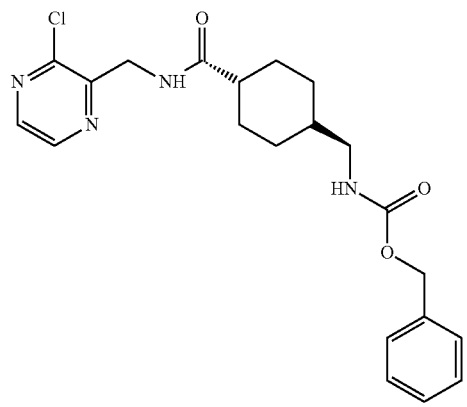

To a solution of C-(3-chloropyrazin-2-yl)methylamine hydrochloride salt (0.100 g, 0.533 mmol) in DCM (1.35 mL) was added N-(3-dimethylaminopropyl)-N-ethylcarbodiimide hydrochloride (0.16 g, 0.83 mmol), N,N-diisopropylethylamine (0.14 mL, 0.83 mmol), 1-hydroxybenzotriazole (0.075 g, 0.56 mmol) and trans-4-({[(benzyloxy)carbonyl]amino}methyl)cyclohexanecarboxylic acid (0.21 g, 0.70 mmol). The reaction was stirred at rt overnight then diluted with DCM, washed with sat. NaHCO₃ (aq) and brine, then dried over Na₂SO₄ and the solvent removed in vacuo. The residue thus isolated was chromatographed over silica gel eluting with EtOAc/hexane (1:1) to afford 0.173 g of the title compound. ¹H NMR (400 MHz, CDCl₃): δ 1.00-1.03 (m, 2H), 1.45-1.51 (m, 2H), 1.83-1.89 (m, 2H), 1.99-2.03 (m, 2H), 2.20 (m, 1H), 3.05-3.12 (m, 3H), 4.68 (d, J=4.4 Hz, 2H), 4.79 (br, 1H), 5.10 (s, 2H), 6.79 (br, 1H), 7.31-7.37 (m, 5H), 8.33 (d, J=2.8 Hz, 1H), 8.46 (d, J=2.8 Hz, 1H). MS (ES+): m/z 417.14 [MH+].

Benzyl {[trans-4-(8-chloroimidazo[1,5-a]pyrazin-3-yl)cyclohexyl]methyl}carbamate

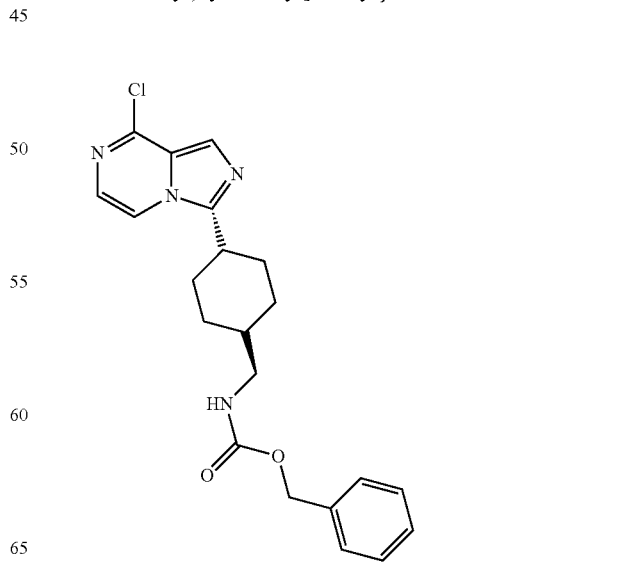

To a suspension of benzyl [(trans-4-{[(3-chloropyrazin-2-yl)methyl]carbamoyl}cyclohexyl)methyl]carbamate (0.100 g, 0.220 mmol) in EtOAc (0.9 mL) and DMF (0.068 mL) at 0° C. was added slowly POCl₃ (0.082 mL, 0.88 mmol). After stirring at rt for an hour, the mixture was cooled to 0° C. and solid NaHCO₃ was added. After a further 10 min at 0° C. and 20 min at rt, the mixture was re-cooled to 0° C. and water (20 mL) was added. The reaction mixture was extracted with EtOAc (3×20 mL) and the extracts washed with water (2×30 mL) and brine (30 mL) and then dried over Na₂SO₄ and concentrated in vacuo to afford 0.096 g of the title compound. ¹H NMR (400 MHz, CDCl₃): δ 1.15-1.19 (m, 2H), 1.76-1.87 (m, 3H), 1.93-2.00 (m, 2H), 2.04-2.08 (m, 2H), 3.07 (m, 1H), 3.15 (t, J=6.4 Hz, 2H), 4.84 (br, 1H), 5.09 (s, 2H), 7.31-7.40 (m, 6H), 7.61 (d, J=4.8 Hz, 1H), 7.79 (s, 1H). MS (ES+): m/z 399.26 [MH+].

Benzyl {[trans-4-(8-chloro-1-iodoimidazo[1,5-a]pyrazin-3-yl)cyclohexyl]methyl}carbamate

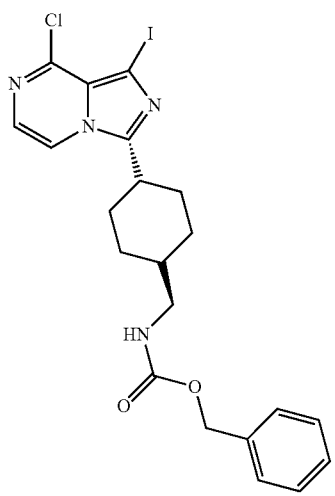

To a solution of benzyl {[trans-4-(8-chloroimidazo[1,5-a]pyrazin-3-yl)cyclohexyl]methyl}carbamate (1.49 g, 0.00374 mol) in DMF (0.6 mL) was added NIS (1.0 g, 0.0045 mol). The reaction mixture was stirred at 55° C. overnight then diluted with EtOAc (20 mL), washed with water (2×40 mL) and brine (20 mL), then dried over Na₂SO₄ and concentrated in vacuo. The crude mixture thus isolated was chromatographed over silica gel eluting with hexane→hexane:EtOAc 1:1 to afford 1.7 g of the title compound.

MS (ES+): m/z 525.01 [MH+].

Benzyl {[trans-4-(8-amino-1-iodoimidazo[1,5-a]pyrazin-3-yl)cyclohexyl]methyl}carbamate

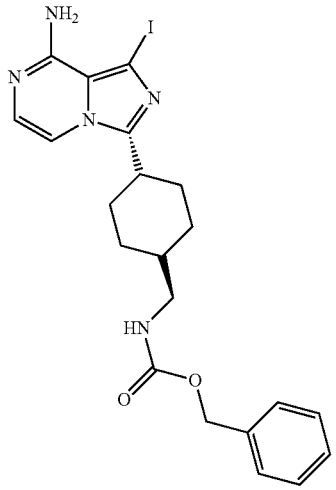

A solution of benzyl {[trans-4-(8-chloro-1-iodoimidazo[1,5-a]pyrazin-3-yl)cyclohexyl]methyl}carbamate (1.70 g, 0.00324 mol) in IPA (30 mL) was cooled to −78° C., treated with a stream of ammonia gas over 3 min. and then heated at 110° C. in a Parr vessel overnight. The reaction solution was concentrated in vacuo and residue washed with water to afford 1.37 g of desired product. ¹H NMR (400 MHz, CDCl₃): δ=1.08-1.17 (m, 2H), 1.88 (m, 1H), 1.71-1.81 (m, 2H), 1.91-1.94 (m, 2H), 2.00-2.04 (m, 2H), 2.90 (m, 1H), 3.13 (t, J=6.4 Hz, 2H), 4.86 (br, 1H), 5.11 (s, 2H), 5.76 (br, 2H), 7.00 (d, J=5.2 Hz, 1H), 7.22 (d, J=5.2 Hz, 1H), 7.31-7.37 (m, 5H). MS (ES+): m/z 5.7.36 [MH+].

Benzyl 4-{[(3-chloropyrazin-2-yl)methyl]carbamoyl}piperidine-1-carboxylate

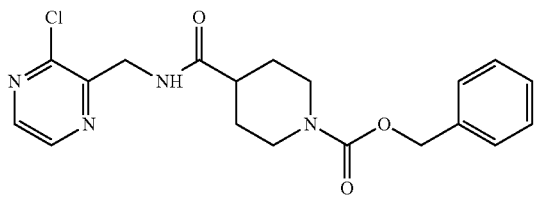 [SMILES: O=C(NCc1nccnc1Cl)C1CCN(C(=O)OCc2ccccc2)CC1]

A solution of C-(3-Chloropyrazin-2-yl)methylamine bis-hydrochloride (2.00 g, 0.0107 mol) and N,N-diisopropylethylamine (2.2 g, 0.017 mol) in DCM (27.0 mL) was treated with and N-(3-dimethylaminopropyl)-N'-ethylcarbodiimide hydrochloride (3.2 g, 0.017 mol), 1-hydroxybenzotriazole (1.5 g, 0.011 mol) and 1-[(benzyloxy)carbonyl]-4-piperidine carboxylic acid (3.8 g, 0.014 mol). The mixture was stirred at rt overnight then diluted with DCM (30 mL), washed with sat. NaHCO₃ (20 mL) and brine (20 mL), then dried over Na₂SO₄ and concentrated in vacuo. The crude material thus obtained was chromatographed over silica gel eluting with EtOAc: hexane 1:1 yielding 3.38 g of the title compound. ¹H NMR (400 MHz, CDCl₃): δ 1.68-1.78 (m, 2H), 1.91-1.94 (m, 2H), 2.44 (m, 1H), 2.89-2.92 (m, 2H), 4.24-4.26 (m, 2H), 4.70 (d, J=4.8 Hz, 2H), 5.14 (s, 2H), 6.85 (br, 1H), 7.30-7.37 (m, 5H), 8.34 (d, J=2.8 Hz, 1H), 8.45 (d, J=2.8 Hz, 1H). MS (ES+): m/z 389.17 [MH+].

Benzyl 4-(8-chloroimidazo[1,5-a]pyrazin-3-yl)piperidine-1-carboxylate

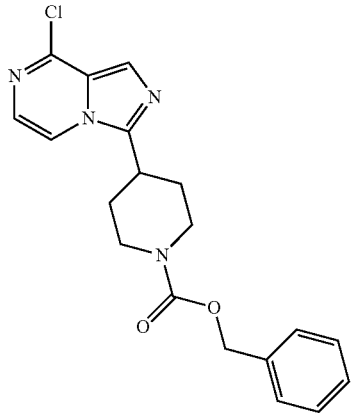 [SMILES: O=C(OCc1ccccc1)N1CCC(c2ncc3c(Cl)nccn23)CC1]

To a suspension of benzyl 4-{[(3-chloropyrazin-2-yl)methyl]carbamoyl}piperidine-1-carboxylate (0.100 g, 0.220 mmol) in EtOAc (0.9 mL) and DMF (0.068 mL) at 0° C. was slowly added POCl₃ (0.082 mL, 0.88 mmol). After stirring at rt for an hour the mixture was cooled to 0° C. then treated with solid NaHCO₃. The mixture was stirred for 20 min at rt, diluted with water and extracted with EtOAc (3×20 mL). The combined extracts were washed with water (2×30 mL) and brine (30 mL), then dried over Na₂SO₄, and concentrated in vacuo to yield 2.07 g of desired product. ¹H NMR (400 MHz, CDCl₃): δ 1.98-2.04 (m, 4H), 3.03-3.20 (m, 3H), 4.30-4.33 (m, 2H), 5.16 (s, 2H), 7.33 (d, J=5.2 Hz, 1H), 7.35-7.38 (m, 5H), 7.26 (d, J=4.4 Hz, 1H), 7.79 (s, 1H). MS (ES+): m/z 371.22 [MH+].

Benzyl 4-(8-chloro-1-iodoimidazo[1,5-a]pyrazin-3-yl)piperidine-1-carboxylate

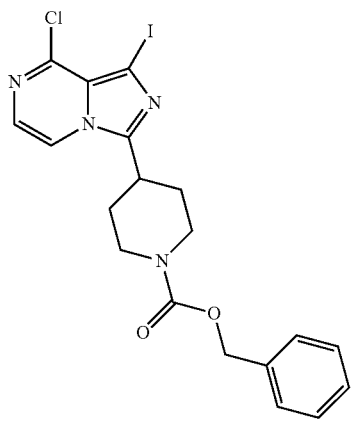 [SMILES: O=C(OCc1ccccc1)N1CCC(c2nc(I)c3c(Cl)nccn23)CC1]

To a solution of benzyl 4-(8-chloroimidazo[1,5-a]pyrazin-3-yl)piperidine-1-carboxylate (1.31 g, 0.00354 mol) in DMF (0.6 mL) was added NIS (1.6 g, 0.0071 mol). The reaction mixture was left to stir at 55° C. for 20 h. then the mixture was diluted with EtOAc (20 mL), washed with water (2×40 mL) and brine, then dried over Na₂SO₄ and concentrated in vacuo. The crude reaction mixture was chromatographed over silica gel eluting with hexane→hexane:EtOAc 1:1 yielding 1.63 g of desired product. ¹H NMR (400 MHz, CDCl₃): δ 1.95-2.04 (m, 4H), 3.02-3.15 (m, 3H), 4.29-4.32 (m, 2H), 5.15 (s, 2H), 7.32 (d, J=5.2 Hz, 1H), 7.34-7.37 (m, 5H), 7.66 (d, J=5.2 Hz, 1H). MS (ES+): m/z 497.03 [MH+].

Benzyl 4-(8-amino-1-iodoimidazo[1,5-a]pyrazin-3-yl)piperidine-1-carboxylate

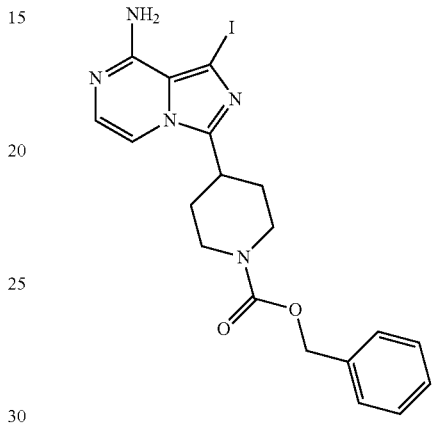

A mixture of benzyl 4-(8-chloro-1-iodoimidazo[1,5-a]pyrazin-3-yl)piperidine-1-carboxylate (0.500 g, 0.00101 mol) in IPA (20 mL) was cooled to at −78° C. and treated with a stream of ammonia gas over 3 minutes. The resulting solution was heated at 110° C. in a Parr vessel prior to concentration in vacuo, suspension in DCM and filtration through a bed of Celite. The filtrate was concentrated in vacuo to afford 0.504 g of desired product. ¹H NMR (400 MHz, CDCl₃): δ 1.88-2.02 (m, 2H), 2.99-3.10 (m, 3H), 4.24-4.41 (m, 2H), 5.15 s, 2H), 6.03 (br, 2H), 7.03 (d, J=4.8 Hz, 1H), 7.24 (d, J=5.2 Hz, 1H), 7.31-7.40 (m, 5H). MS (ES+): m/z 479.33 [MH+].

1-(2-Trimethylsilylethoxymethyl)-1H-pyrrolo[2,3-b]pyridine

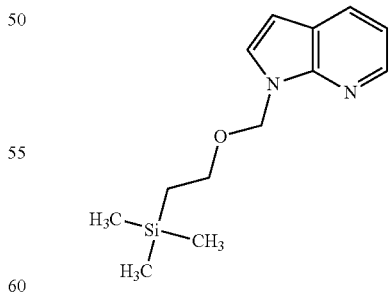

To a suspension of sodium hydride (934 mg, 0.0358 mol) in DMF (57 mL) was added dropwise under N₂, a solution of 1H-pyrrolo[2,3-b]pyridine (3.00 g, 0.0254 mol) in DMF (20 mL). The mixture was stirred at r.t. for 45 min. then cooled to 0° C. and treated dropwise with [2-(trimethylsilyl)ethoxy]methyl chloride (6.32 mL, 0.0357 mol). The mixture was stirred at rt for 12 h. then poured into water (10 mL), stirred for 30 min. and extracted with Et2O (4×10 mL). The combined extracts were washed with brine (20 mL), dried over sodium sulfate, and concentrated in vacuo to give the crude product which was chromatographed over silica gel eluting with hexane→1:9 Et₂O: hexane to afford 6 g desired product.

N-(2-Trimethylsilyl-1-ethoxymethyl)-2-(tributylstannyl)-1H-pyrrolo[2,3-b]pyridine

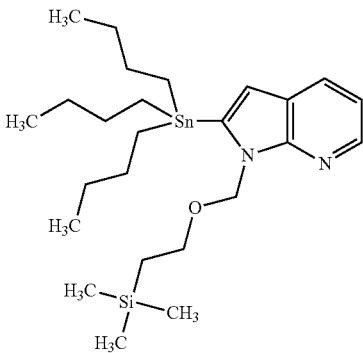 [SMILES: CCC[CH2][Sn]([CH2]CCC)([CH2]CCC)[c]1cc2cccnc2n1COCC[Si](C)(C)C]

To a solution of 1-(2-trimethylsilylethoxymethyl)-1H-pyrrolo[2,3-b]pyridine (500 mg, 0.0020129 mol) in THF (5 mL) at −10° C. was added a 2.0 M of n-BuLi in cyclohexane (1.2 mL). After 10 min at −10° C., the mixture was cooled to −20° C. and tributyltin chloride (0.65 mL, 0.0024 mol) was added. The mixture was stirred at rt for 1 h, the poured into a 5% aqueous ammonium chloride (20 mL), extracted with EtOAc (3×20 mL) and the combined extracts dried over anhydrous MgSO₄ and concentrated in vacuo. The material thus obtained was chromatographed over silica gel eluting with 1:9 EtOAc:hexane to afford 0.7 g of the title compound. $^1$H NMR (400 MHz DMSO-d6) δ 0.01 (s, 9H), 0.10 (s, 2H), 0.92-0.94 (m, 9H), 1.14-1.27 (m, 6H), 1.37-1.46 (m, 6H), 1.60-1.72 (m, 6H), 3.48-3.52 (m, 2H), 5.71 (s, 2H), 6.74 (s, 1H), 7.16-7.19 (m, 1H), 8.02 (dd, J=1.6, 7.6 Hz, 1H) and 8.31 (dd, J=1.6, 4.4 Hz, 1H).

3-Cyclobutyl-1-[1-(2-trimethylsilylethoxymethyl)-1H-pyrrolo[2,3-b]pyridin-2-yl]imidazo[1,5-a]pyrazin-8-amine

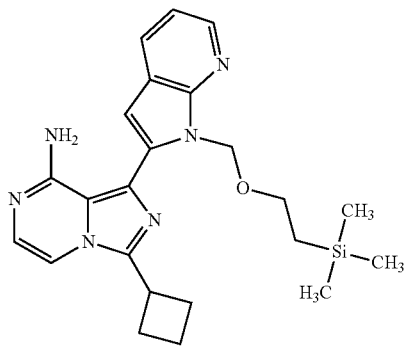 [SMILES: C[Si](C)(C)CCOCn1c(-c2nc(C3CCC3)n3ccnc(N)c23)cc2cccnc21]

A mixture of N-(2-trimethylsilyl-1-ethoxymethyl)-2-(tributylstannyl)-1H-pyrrolo[2,3-b]pyridine (110 mg, 0.20 mmol), 3-cyclobutyl-1-iodoimidazo[1,5-a]pyrazin-8-amine (50 mg, 0.1592 mmol) and bis(triphenylphosphine)palladium(II) chloride (10 mg, 0.02 mmol) in ethanol (2 mL) was heated at reflux for 48 h. The mixture was then cooled to rt, filtered through a pad of Celite and concentrated in vacuo. The residue thus obtained was chromatographed over silica gel eluting with hex:EtOAc to afford 17.2 mg of the title compound. $^1$H NMR (400 MHz CDCl₃) δ 0.22 (s, 9H), 0.70 (t, 2H), 1.87-2.19 (m, 2H), 2.49-2.64 (m, 4H), 3.37 (t, 2H), 3.81-3.86 (m, 1H), 5.51 (bs, 2H), 6.07 (s, 2H), 6.67 (s, 1H), 7.10-7.16 (m, 3H), 7.93 (dd, J=1.6, 8.0 Hz, 1H) and 8.41 (dd, J=1.6, 4.8 Hz, 1H). MS (ES+): m/z: 435.21 [MH+].

4-Bromo-2-nitro-N-phenylaniline

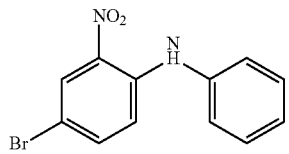 [SMILES: O=[N+]([O-])c1cc(Br)ccc1Nc1ccccc1]

A mixture of 1-bromo-4-fluoro-3-nitrobenzene (2270 mg, 10.01 mmol), aniline (3 ml) and DMF (20 ml) was heated at 100° C. under an atmosphere of Nitrogen for 7 h. The mixture was then concentrated in vacuo, and the residue triturated with heptane (30 ml) to give the desired product. $^1$H NMR (400 MHz, CDCl₃) δ=7.11 (d, 1 H, J=9.2 Hz), 7.25-7.29 (m, 3 H), 7.40-7.45 (m, 3 H), 8.35 (d, 1 H, J=2.4 Hz) and 9.45 (brs, 1 H).

4-Bromo-N-methyl-2-nitroaniline

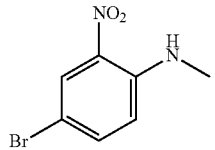

Prepared according to a procedure analogous to that described for 4-bromo-2-nitro-N-phenylaniline. $^1$H NMR (400 MHz, CDCl₃): δ=3.02 (d, 3 H, J=5.2 Hz), 6.76 (d, 1 H, J=9.6 Hz), 7.51-7.54 (m, 1 H), 8.02 (brs, 1 H) and 8.32 (d, 1 H, J=2.8 Hz). MS (ES+): m/z 231.05 and 233.08-[MH+].

4-Bromo-N-ethyl-2-nitroaniline

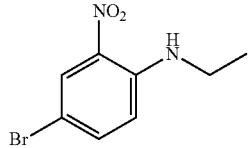

Prepared according to a procedure analogous to that described for 4-bromo-2-nitro-N-phenylaniline. $^1$H NMR (400 MHz, CDCl₃) δ=1.37 (t, 3 H, J=7.2 Hz), 3.31-3.37 (m, 2

H), 6.76 (d, 1 H, J=8.8 Hz), 7.48-7.51 (m, 1 H), 7.95 (brs, 1 H) and 8.31 (d, 1 H, J=2.4 Hz). MS (ES+): m/z 245.07 and 247.11 [MH+].

N-Benzyl-4-bromo-2-nitroaniline

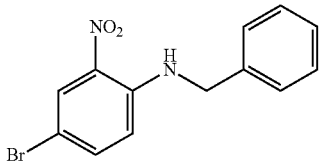 [SMILES: O=[N+]([O-])c1cc(Br)ccc1NCc1ccccc1]

Prepared according to a procedure analogous to that described for 4-bromo-2-nitro-N-phenylaniline. $^1$H NMR (400 MHz, CDCl$_3$) δ=4.54 (d, 2 H, J=5.6 Hz), 6.72 (d, 1 H, J=9.2 Hz), 7.30-7.40 (m, 5 H), 7.44 (ddd, 1 H, J=0.4 & 2.4 & 9.2 Hz), 8.34 (d, 1 H, J=2.4 Hz) and 8.41 (brs, 1 H). MS (ES+): m/z 245.07 and 247.11-[MH+].

4-Bromo-N$^1$-phenylbenzene-1,2-diamine

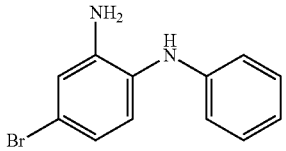

Prepared according to a procedure analogous to that described for 4-bromo-2-nitro-N-phenylaniline. $^1$H NMR (400 MHz, DMSO-d$_6$) δ=3.80 (brs, 2 H), 5.07 (br, s, 1 H), 6.70-6.75 (m, 2 H), 6.82-6.86 (m, 2 H), 6.93 (d, 1 H, J=2.4 Hz), 6.97 (d, 1 H, J=8.0 Hz) and 7.17-7.24 (m, 2 H). MS (ES+): m/z 263.17 and 265.20 [MH+].

4-Bromo-N$^1$-methylbenzene-1,2-diamine

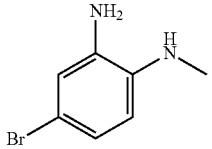

A suspension of 4-bromo-N-methyl-2-nitroaniline (5328 mg, 22.04 mmol) in EtOH (100 ml) was treated with SnCl$_2$.2H$_2$O (25.61 g, 110.2 mmol) and the resulting mixture heated at 70° C. under an atmosphere of Nitrogen for 5 h. The reaction mixture was then cooled to rt and treated with ice-water (50 ml) followed by aqueous NaOH (4 N) until pH>8. This basic mixture was then extracted with EtOAc (3×150 ml) and the combined extracts washed with brine (3×100 ml), dried over MgSO$_4$ and concentrated in vacuo to afford the title compound. $^1$H NMR (400 MHz, DMSO-d$_6$) δ ppm=2.68 (s, 3 H), 4.74 (brs, 3 H), 6.27 (d, 1 H, J=8.4 Hz), 6.61 (dd, 1 H, J=2.0 & 8.4 Hz) and 6.66 (d, 1 H, J=2.0 Hz). MS (ES+): m/z 201.10 and 203.12-[MH+].

4-Bromo-N$^1$-ethylbenzene-1,2-diamine

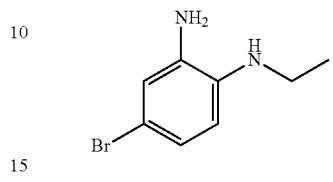

Prepared according to a procedure analogous to that described for 4-bromo-N-methylbenzene-1,2-diamine. $^1$H NMR (400 MHz, DMSO-d$_6$,) δ ppm=1.19 (t, 3H, J=6.8 Hz), 3.01 (quartet, 2H, J=6.8 Hz), 4.46 (brs, 1H), 4.81 (brs, 2H), 6.30 (d, 1H, J=8.4 Hz), 6.58 (dd, 1H, J=2.4 & 8.4 Hz) and 6.66 (d, 1H, J=2.0 Hz). MS (ES+): m/z 215.07 and 217.16 [MH+].

N$^1$-Benzyl-4-bromobenzene-1,2-diamine

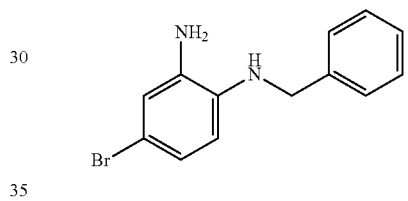

Prepared according to a procedure analogous to that described for 4-bromo-N$^1$-methylbenzene-1,2-diamine. $^1$H NMR (400 MHz, DMSO-d$_6$) δ ppm=3.39 (brs, 2 H), 3.61 (brs, 1 H), 4.28 (s, 2 H), 6.51 (d, 1 H, J=8.4 Hz), 6.85-6.89 (m, 2 H) and 7.27-7.38 (m, 5 H). MS (ES+): m/z 277.20 and 279.20 [MH+].

1-Benzyl-5-bromo-2-phenyl-1H-benzimidazole

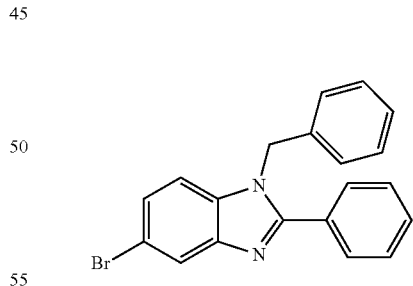

p-TsOH.H$_2$O (311.7 mg, 1.606 mmol) was added to a DCM (50 ml) solution of N$^1$-benzyl-4-bromobenzene-1,2-diamine (4451 mg, 16.06 mmol) and trimethyl orthobenzoate (3096 μl, 17.66 mmol) and the resulting mixture was stirred at rt under an atmosphere of Nitrogen for 40 h. The reaction mixture was then concentrated in vacuo to give a yellow solid which was triturated with 40% MeOH/water (375 mL), filtered, washed with saturated NaHCO$_3$ (20 ml)+H$_2$O (80 ml) twice and 40% MeOH/H$_2$O (2×50 ml), and dried to give the title compound. $^1$H NMR (400 MHz, DMSO-d$_6$) δ ppm=5.44 (s, 2 H), 7.05-7.08 (m, 3 H), 7.30-7.36 (m, 4 H), 7.44-7.50 (m, 3 H), 7.66-7.68 (m, 2 H) and 7.99 (dd, 1 H, J=0.4 & 1.6 Hz). MS (ES+): m/z 363.20 and 365.26 [MH+].

5-Bromo-1-methyl-2-phenyl-1H-benzimidazole

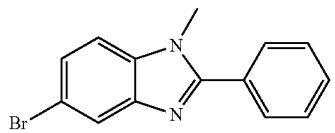 [SMILES: Cn1c(-c2ccccc2)nc2cc(Br)ccc21]

Prepared according to a procedure analogous to that described for 1-benzyl-5-bromo-2-phenyl-1H-benzimidazole. $^1$H NMR (400 MHz, CDCl$_3$) δ ppm=3.86 (s, 3 H), 7.26-7.29 (m, 1 H), 7.42 (dd, 1 H, J=2.0 & 8.4 Hz), 7.53-7.56 (m, 3H), 7.74-7.76 (m, 2 H) and 7.95 (dd, 1 H, J=0.4 & 1.6 Hz). MS (ES+): m/z 287.18 and 289.14 [MH+].

5-Bromo-1-ethyl-2-phenyl-1H-benzimidazole

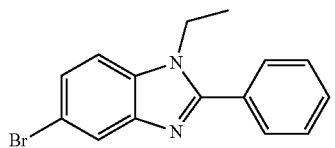 [SMILES: CCn1c(-c2ccccc2)nc2cc(Br)ccc21]

Prepared according to a procedure analogous to that described for 1-benzyl-5-bromo-2-phenyl-1H-benzimidazole. $^1$H NMR (400 MHz, CDCl$_3$) δ ppm=1.46 (t, 3 H, J=7.2 Hz), 4.27 (quartet, 2 H, J=7.2 Hz), 7.27 (m, 1 H), 7.30 (dd, 1 H, J=0.4 & 8.8 Hz), 7.42 (dd, 1 H, J=1.6 & 8.8 Hz), 7.53-7.55 (m, 3 H), 7.70-7.72 (m, 2 H) and 7.96 (dd, 1 H, J=0.4 & 1.6 Hz). MS(ES+): m/z 301.18 and 303.11 [MH+].

5-Bromo-1,2-diphenyl-1H-benzimidazole

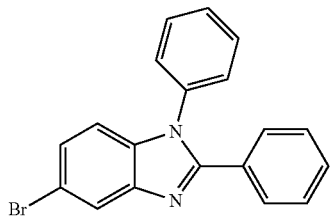 [SMILES: Brc1ccc2c(c1)nc(-c1ccccc1)n2-c1ccccc1]

Prepared according to a procedure analogous to that described for 1-benzyl-5-bromo-2-phenyl-1H-benzimidazole. $^1$H NMR (400 MHz, CDCl$_3$): δ=7.11 (dd, 1 H, J=0.4 & 8.4 Hz), 7.27-7.39 (m, 6 H), 7.48-7.56 (m, 5 H) and 8.01 (dd, 1 H, J=0.4 & 1.6 Hz). MS (ES+): m/z 349.20 and 351.22 [MH+].

1-Methyl-2-phenyl-5-(4,4,5,5-tetramethyl-[1,3,2]dioxaborolan-2-yl)-1H-benzimidazole

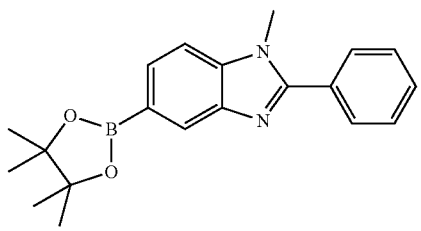 [SMILES: Cn1c(-c2ccccc2)nc2cc(B3OC(C)(C)C(C)(C)O3)ccc21]

A mixture of 5-bromo-1-methyl-2-phenyl-1H-benzimidazole (616 mg, 2.14 mmol), [1,1'-Bis(diphenylphosphino)ferrocene]dichloropalladium(II) complex with dichloromethane (1:1) (52.6 mg, 0.0644 mmol), bis(pinacolato)diboron (667 mg, 2.57 mmol), 1,1'-bis(diphenylphosphino)ferrocene (36.8 mg, 0.0644 mmol) and AcOK (638 mg, 6.44 mmol) in 1,4-dioxane (10 ml) was purged with N$_2$ for 5 min, and was then heated at 100° C. under an atmosphere of Nitrogen for 16 h. The mixture was then treated with saturated NH$_4$Cl (20 ml), extracted with EtOAc (3×20 ml) and the combined extracts washed with brine (3×20 ml), dried over MgSO$_4$ and concentrated in vacuo to afford crude product which was purified by chromatography over silica gel eluting with 30% (250 ml) and 40% (250 ml) EtOAc/Heptane to give a white solid that was triturated with 50% EtOAc/Heptane (10 ml) to yield the title compound. $^1$H NMR (400 MHz, CDCl$_3$) δ ppm=1.38 (s, 12 H), 3.86 (s, 3 H), 7.39 (dd, 1 H, J=1.2 & 8.0 Hz), 7.50-7.55 (m, 3H), 7.76-7.79 (m, 3H) and 8.29 (d, 1H, J=0.8 Hz). MS (ES+): m/z 335.29 (100) [MH+].

1-Ethyl-2-phenyl-5-(4,4,5,5-tetramethyl-[1,3,2]dioxaborolan-2-yl)-1H-benzimidazole

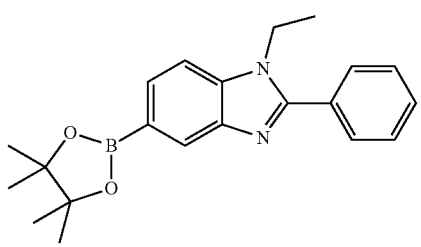 [SMILES: CCn1c(-c2ccccc2)nc2cc(B3OC(C)(C)C(C)(C)O3)ccc21]

Prepared according to a procedure analogous to that described for 1-Methyl-2-phenyl-5-(4,4,5,5-tetramethyl-[1,3,2]dioxaborolan-2-yl)-1H-benzimidazole. $^1$H NMR (400 MHz, CDCl$_3$) δ ppm=1.38 (s, 12 H), 1.45 (t, 3 H, J=7.2 Hz), 4.28 (quartet, 2 H, J=7.2 Hz), 7.42 (dd, 1 H, J=0.8 & 8.0 Hz), 7.51-7.54 (m, 3H), 7.71-7.74 (m, 2H), 7.77 (dd, 1 H, J=0.8 & 8.0 Hz) and 8.31 (s, 1 H). MS (ES+): m/z 349.33 [MH+].

1-Benzyl-2-phenyl-5-(4,4,5,5-tetramethyl-[1,3,2]dioxaborolan-2-yl)-1H-benzimidazole

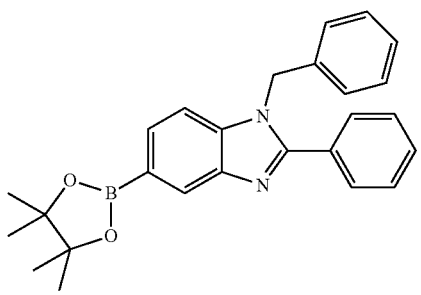 [SMILES: CC1(C)OB(c2ccc3c(c2)nc(-c2ccccc2)n3Cc2ccccc2)OC1(C)C]

Prepared according to a procedure analogous to that described for 1-Methyl-2-phenyl-5-(4,4,5,5-tetramethyl-[1,3,2]dioxaborolan-2-yl)-1H-benzimidazole. $^1$H NMR (400 MHz, CDCl$_3$) δ ppm=1.36 (s, 12 H), 5.45 (s, 2 H), 7.05-7.08 (m, 1H), 7.21 (dd, 1 H, J=0.8 & 8.0 Hz), 7.26-7.31 (m, 3H), 7.44-7.48 (m, 3H), 7.66-7.71 (m, 3H) and 8.36 (m, 1 H). MS (ES+): m/z 411.42 [MH+].

1,2-Diphenyl-5-(4,4,5,5-tetramethyl-[1,3,2]dioxaborolan-2-yl)-1H-benzimidazole

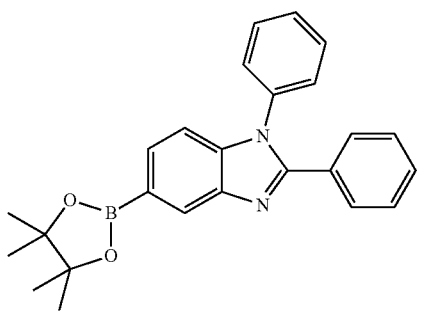 [SMILES: CC1(C)OB(c2ccc3c(c2)nc(-c2ccccc2)n3-c2ccccc2)OC1(C)C]

Prepared according to a procedure analogous to that described for 1-Methyl-2-phenyl-5-(4,4,5,5-tetramethyl-[1,3,2]dioxaborolan-2-yl)-1H-benzimidazole. $^1$H NMR (400 MHz, CDCl$_3$) δ ppm=1.38 (s, 12 H), 7.22 (dd, 1 H, J=0.8 & 8.0 Hz), 7.29-7.35 (m, 5 H), 7.47-7.50 (m, 3 H), 7.55-7.57 (m, 2 H) and 7.71 (dd, 1H, J=0.8 & 8.0 Hz), 8.38 (m, 1 H). MS (ES+): m/z 397.43 [MH+].

7-Chloro-2-(4,4,5,5-tetramethyl-[1,3,2]dioxaborolan-2-yl)-1H-indole

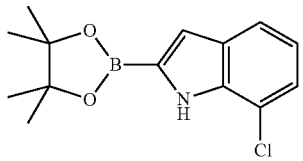 [SMILES: CC1(C)OB(c2cc3cccc(Cl)c3[nH]2)OC1(C)C]

A flask containing Ir(Ome)$_2$(COD)$_2$ [Inorganic Syntheses (1985), 23, 126] (850 mg, 0.0013 mol), 4,4'-di-tert-butyl-[2,2']bipyridinyl (686 mg, 0.00256 mol) and 4,4,4',4',5,5,5',5'-octamethyl-2,2'-bi-1,3,2-dioxaborolane (15.2 g, 0.0600 mol) was evacuated and refilled with Ar (3×), then charged with anhydrous DME (400 mL, 3 mol) and a solution of 7-chloro-1H-indole (0.086 mol) in DME (10 mL). The resulting mixture was stirred under Ar for 16 h then concentrated and chromatographed over silica gel eluting with 10% EtOAc/Heptane to afford the desired product as a waxy solid in a 96% yield. $^1$H NMR (400 MHz, CDCl$_3$) δ ppm 1.39 (s, 12 H), 7.04 (t, J=7.71 Hz, 1 H), 7.15 (d, J=2.27 Hz, 1 H), 7.21-7.30 (m, 1 H), 7.58 (d, J=8.08 Hz, 1 H) and 8.72 (br. s., 1 H).

4-Methoxy-2-(4,4,5,5-tetramethyl-[1,3,2]dioxaborolan-2-yl)-1H-indole

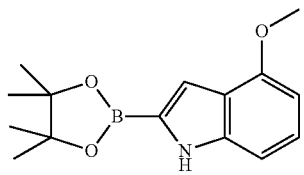

Prepared according to a procedure analogous to that described for 7-chloro-2-(4,4,5,5-tetramethyl-[1,3,2]dioxaborolan-2-yl)-1H-indole using 4-methoxy-1H-indole.

7-Bromo-4-methoxy-2-(4,4,5,5-tetramethyl-[1,3,2]dioxaborolan-2-yl)-1H-indole

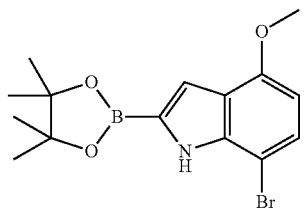

Prepared according to a procedure analogous to that described for 7-chloro-2-(4,4,5,5-tetramethyl-[1,3,2]dioxaborolan-2-yl)-1H-indole using 7-bromo-4-methoxy-1H-indole.

7-Methyl-2-(4,4,5,5-tetramethyl-[1,3,2]dioxaborolan-2-yl)-1H-indole

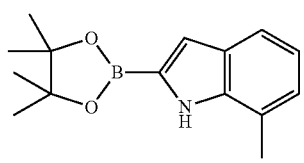 [SMILES: Cc1cccc2cc(B3OC(C)(C)C(C)(C)O3)[nH]c12]

Prepared according to a procedure analogous to that described for 7-chloro-2-(4,4,5,5-tetramethyl-[1,3,2]dioxaborolan-2-yl)-1H-indole using 7-methyl-1H-indole.

7-Fluoro-2-(4,4,5,5-tetramethyl-[1,3,2]dioxaborolan-2-yl)-1H-indole

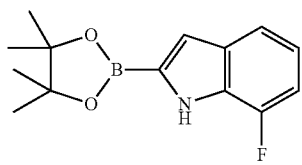 [SMILES: CC1(C)OB(c2cc3cccc(F)c3[nH]2)OC1(C)C]

Prepared according to a procedure analogous to that described for 7-chloro-2-(4,4,5,5-tetramethyl-[1,3,2]dioxaborolan-2-yl)-1H-indole using 7-fluoro-1H-indole.

4-Methyl-2-(4,4,5,5-tetramethyl-[1,3,2]dioxaborolan-2-yl)-1H-indole

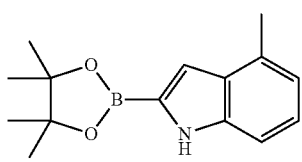 [SMILES: Cc1cccc2[nH]c(B3OC(C)(C)C(C)(C)O3)cc12]

Prepared according to a procedure analogous to that described for 7-chloro-2-(4,4,5,5-tetramethyl-[1,3,2]dioxaborolan-2-yl)-1H-indole using 4-methyl-1H-indole.

4-Methoxy-1-methyl-2-(4,4,5,5-tetramethyl-[1,3,2]dioxaborolan-2-yl)-1H-indole

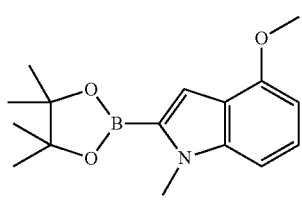

Prepared according to a procedure analogous to that described for 7-chloro-2-(4,4,5,5-tetramethyl-[1,3,2]dioxaborolan-2-yl)-1H-indole using 4-methoxy-1-methyl-1H-indole.

7-Ethyl-2-(4,4,5,5-tetramethyl-[1,3,2]dioxaborolan-2-yl)-1H-indole

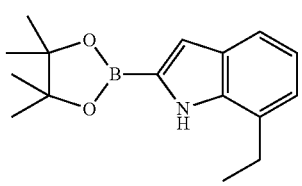

Prepared according to a procedure analogous to that described for 7-chloro-2-(4,4,5,5-tetramethyl-[1,3,2]dioxaborolan-2-yl)-1H-indole using 7-ethyl-1H-indole.

4,7-Dimethoxy-2-(4,4,5,5-tetramethyl-[1,3,2]dioxaborolan-2-yl)-1H-indole

Prepared according to a procedure analogous to that described for 7-chloro-2-(4,4,5,5-tetramethyl-[1,3,2]dioxaborolan-2-yl)-1H-indole using 4,7-dimethoxy-1H-indole.

2-(4,4,5,5-Tetramethyl-[1,3,2]dioxaborolan-2-yl)-1H-indol-4-yl acetate

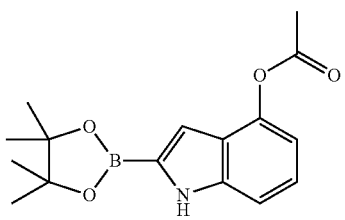 [SMILES: CC(=O)Oc1cccc2[nH]c(B3OC(C)(C)C(C)(C)O3)cc12]

Prepared according to a procedure analogous to that described for 7-chloro-2-(4,4,5,5-tetramethyl-[1,3,2]dioxaborolan-2-yl)-1H-indole using 1H-indol-4-yl acetate.

2-(4,4,5,5-Tetramethyl-[1,3,2]dioxaborolan-2-yl)-1H-indole-4-carboxylic acid, methyl ester

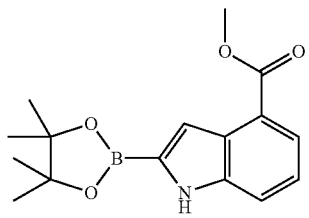 [SMILES: COC(=O)c1cccc2[nH]c(B3OC(C)(C)C(C)(C)O3)cc12]

Prepared according to a procedure analogous to that described for 7-chloro-2-(4,4,5,5-tetramethyl-[1,3,2]dioxaborolan-2-yl)-1H-indole using 1H-indole-4-carboxylic acid, methyl ester.

7-Methoxy-2-(4,4,5,5-tetramethyl-[1,3,2]dioxaborolan-2-yl)-benzofuran

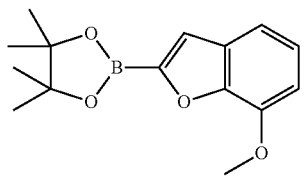 [SMILES: COc1cccc2cc(B3OC(C)(C)C(C)(C)O3)oc12]

Prepared according to a procedure analogous to that described for 7-chloro-2-(4,4,5,5-tetramethyl-[1,3,2]dioxaborolan-2-yl)-1H-indole using 7-methoxy-benzofuran.

4,4,5,5-Tetramethyl-2-(3-methyl-benzo[b]thiophen-2-yl)-[1,3,2]dioxaborolane

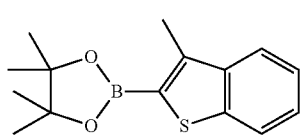 [SMILES: Cc1c(B2OC(C)(C)C(C)(C)O2)sc2ccccc12]

Prepared according to a procedure analogous to that described for 7-chloro-2-(4,4,5,5-tetramethyl-[1,3,2]dioxaborolan-2-yl)-1H-indole using 3-methyl-benzo[b]thiophene.

3-Methyl-2-(4,4,5,5-tetramethyl-[1,3,2]dioxaborolan-2-yl)-benzofuran

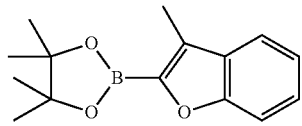 [SMILES: Cc1c(B2OC(C)(C)C(C)(C)O2)oc2ccccc12]

Prepared according to a procedure analogous to that described for 7-chloro-2-(4,4,5,5-tetramethyl-[1,3,2]dioxaborolan-2-yl)-1H-indole using 3-methyl-benzofuran.

7-Bromo-2-(4,4,5,5-tetramethyl-[1,3,2]dioxaborolan-2-yl)-1H-indole

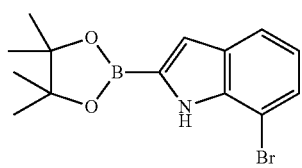 [SMILES: CC1(C)OB(c2cc3cccc(Br)c3[nH]2)OC1(C)C]

Prepared according to a procedure analogous to that described for 7-chloro-2-(4,4,5,5-tetramethyl-[1,3,2]dioxaborolan-2-yl)-1H-indole using 7-bromo-1H-indole.

3-Methyl-2-(4,4,5,5-tetramethyl-[1,3,2]dioxaborolan-2-yl)-1H-indole

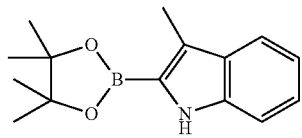 [SMILES: Cc1c(B2OC(C)(C)C(C)(C)O2)[nH]c2ccccc12]

Prepared according to a procedure analogous to that described for 7-chloro-2-(4,4,5,5-tetramethyl-[1,3,2]dioxaborolan-2-yl)-1H-indole using 3-methyl-1H-indole.

7-Methyl-2-(4,4,5,5-tetramethyl-[1,3,2]dioxaborolan-2-yl)-benzofuran

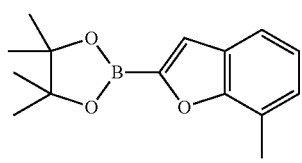 [SMILES: Cc1cccc2cc(B3OC(C)(C)C(C)(C)O3)oc12]

Prepared according to a procedure analogous to that described for 7-chloro-2-(4,4,5,5-tetramethyl-[1,3,2]dioxaborolan-2-yl)-1H-indole using 7-methyl-benzofuran.

7-Methoxy-2-(4,4,5,5-tetramethyl-[1,3,2]dioxaborolan-2-yl)-1H-indole

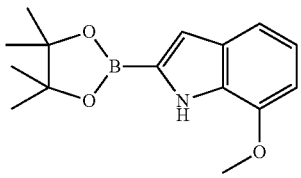

Prepared according to a procedure analogous to that described for 7-chloro-2-(4,4,5,5-tetramethyl-[1,3,2]dioxaborolan-2-yl)-1H-indole using 7-methoxy-1H-indole.

7-Ethoxy-1H-indole

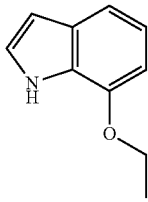

To a stirred solution of 1H-indol-7-ol (500 mg, 3.75 mmol) in acetone (10 mL) at r.t. was added potassium carbonate (3.11 g, 22.5 mmol), followed by iodoethane (0.45 mL, 5.63 mol). The mixture was stirred at r.t. for 16 h then solvent removed under reduced pressure. The crude product thus obtained was purified by chromatography over silica gel to afford 7-ethoxy-1H-indole: $^1$H NMR (400 MHz, MeOD) δ ppm 1.51 (t, J=6.95 Hz, 3 H), 4.22 (q, J=6.91 Hz, 2 H), 6.42 (d, J=3.03 Hz, 1H), 6.63 (d, J=7.58 Hz, 1 H), 6.92 (t, J=7.83 Hz, 1 H), 7.04-7.23 (m, 2 H); MS (ES+): m/z 162.20 (MH+).

7-Ethoxy-2-(4,4,5,5-tetramethyl-[1,3,2]dioxaborolan-2-yl)-1H-indole

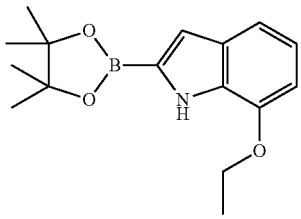 [SMILES: CCOc1cccc2cc(B3OC(C)(C)C(C)(C)O3)[nH]c12]

Prepared according to a procedure analogous to that described for 7-chloro-2-(4,4,5,5-tetramethyl-[1,3,2]dioxaborolan-2-yl)-1H-indole using 7-ethoxy-1H-indole.

7-Isopropoxy-1H-indole

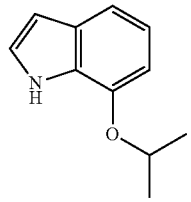

Made according to the procedure described for 7-ethoxy-1H-indole using 2-iodopropane.

7-Isopropoxy-2-(4,4,5,5-tetramethyl-[1,3,2]dioxaborolan-2-yl)-1H-indole

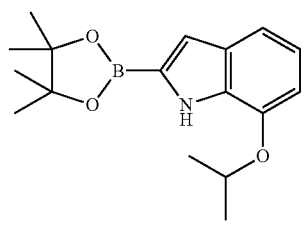 [SMILES: CC(C)Oc1cccc2cc(B3OC(C)(C)C(C)(C)O3)[nH]c12]

Prepared according to a procedure analogous to that described for 7-chloro-2-(4,4,5,5-tetramethyl-[1,3,2]dioxaborolan-2-yl)-1H-indole using 7-isopropoxy-1H-indole.

7-Trifluoromethyl-2-(4,4,5,5-tetramethyl-[1,3,2]dioxaborolan-2-yl)-1H-indole

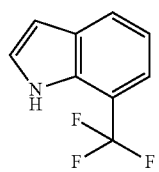 [SMILES: FC(F)(F)c1cccc2cc[nH]c12]

To a stirred mixture of 7-trifluoromethyl-1H-indole-2,3-dione (116 mg) in THF (5.00 mL) was added boron trifluoride etherate (0.205 mL, 1.62 mmol) followed by sodium borohydride (71.4 mg, 1.88 mmol). The resulting mixture was stirred at −20° C. for 2 hrs, then water (1 mL) was added and the mixture was stirred at 0° C. for 10 min. The solution was acidified to pH=1 with 2N HCl, warmed to r.t. and stirred at r.t. for 20 min prior to extraction with EtOAc. The extracts were dried over magnesium sulphate, concentrated in vacuo and the residue purified by chromatography over silica gel eluting with hexane to give 7-trifluoromethyl-1H-indole. $^1$H NMR (400 MHz, CDCl$_3$) δ ppm 6.63-6.68 (1 H, m), 7.20 (1

H, t, J=7.71 Hz), 7.30-7.35 (1 H, m), 7.47 (1 H, d, J=7.33 Hz), 7.83 (1 H, d, J=8.08 Hz), and 8.56 (1 H, br. s.).

7-Trifluoromethyl-2-(4,4,5,5-tetramethyl-[1,3,2]dioxaborolan-2-yl)-1H-indole

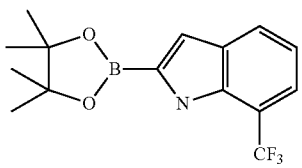 [SMILES: CC1(C)OB(c2cc3cccc(C(F)(F)F)c3[nH]2)OC1(C)C]

Prepared according to a procedure analogous to that described for 7-chloro-2-(4,4,5,5-tetramethyl-[1,3,2]dioxaborolan-2-yl)-1H-indole using 7-trifluoromethyl-1H-indole.

Ethyl N-[2(trifluoromethoxy)phenyl]carbamate

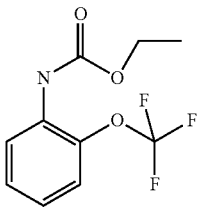 [SMILES: CCOC(=O)Nc1ccccc1OC(F)(F)F]

Ethyl chloroformate (4.4 mL, 0.046 mol) was added to a mixture of 2-(trifluoromethoxy)aniline (8.25 g, 0.0466 mol), sodium carbonate (15 g, 0.14 mol), 1,4-dioxane (70 mL) and water (70 mL) at 0° C. and the reaction mixture stirred at room temperature overnight. The reaction mixture was then washed with ether, acidified (pH 3) and the product extracted into EtOAc (3×40 mL). The combined extracts were washed with water (40 mL) and brine (40 mL), dried over Na2SO4 and the solvent removed in vacuo to give the desired product in a 84% yield. $^1$H NMR (400 MHz, CDCl$_3$): δ 1.33 (t, J=5.2 Hz, 3H), 4.25 (q, J=6.8 Hz, 2H), 6.91 (br, 1H), 7.04 (m, 1H), 7.23 (m, 1H), 7.28 (m, 1H) and 8.2 (m, 1H). MS (ES+): m/z 250.12 [MH+].

Ethyl [2-iodo-6-(trifluoromethoxy)phenyl]carbamate

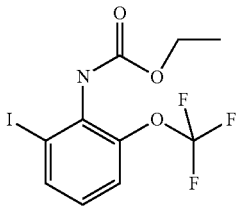 [SMILES: CCOC(=O)Nc1c(I)cccc1OC(F)(F)F]

A 1.4 M solution of sec-butyllithium in cyclohexane (3.0 mL) was added drop-wise to a solution of ethyl N-[2-(trifluoromethoxy)phenyl]carbamate (0.5000 g, 0.002006 mol) in THF (9 mL) at −70° C. After stirring for 1 hour a solution of iodine (0.51 g, 0.002 mol) in THF (1.0 mL) was added drop-wise at −70° C. Stirring was continued for another 1 hour then the mixture was quenched with saturated ammonium chloride solution. Water (50 mL) was added and the mixture extracted with diethyl ether (3×40 mL). The combined organic phases was washed with 40% sodium meta-bisulfite solution, water and brine, then dried over Na2SO4 and the solvent removed in vacuo to give the desired product in a 73% yield. $^1$H NMR (400 MHz, CDCl$_3$): δ 1.29-1.36 (m, 3H), 4.21-4.28 (m, 2H), 6.21 (br, 1H), 7.05 (t, J=8.0 Hz, 1H), 7.30 (m, 1H) and 7.80 (dd, J=6.8, 1.2 Hz, 1H). MS (ES+): m/z 375.78 [MH+].

Ethyl [2-trifluoromethoxy-6-(trimethylsilanylethynylphenyl)]carbamate

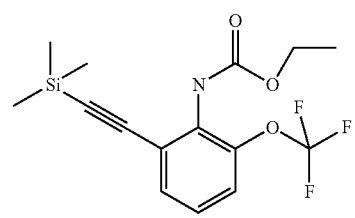 [SMILES: CCOC(=O)Nc1c(C#C[Si](C)(C)C)cccc1OC(F)(F)F]

A mixture of Pd(PPh3)2Cl2 (83 mg, 0.00012 mol) and copper (I) iodide (23 mg, 0.00012 mol) in triethylamine (44 mL, 0.32 mol) was heated at 40° C. for 20 min then cooled to rt and ethyl [2-iodo-6-(trifluoromethoxy)phenyl]carbamate (4.50 g, 0.0120 mol) was added in one portion. The mixture was stirred at room temperature for 30 min, then (trimethylsilyl)acetylene (1.6 mL, 0.011 mol) was added and the mixture stirred for a further 2 hours. The solvent was removed in vacuo and the residue was partitioned between water and diethyl ether (60 mL of each). The organic was washed with 1N HCl and brine, then dried over Na2SO4 then the solvent removed in vacuo. The reaction was chromatographed over silica gel eluting with 20% EtOAc/hexane to afford the desired product in 80% yield. MS (ES+): m/z 345.99 [MH+].

7-Trifluoromethoxy-1H-indole

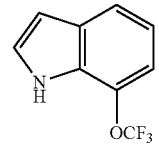 [SMILES: FC(F)(F)Oc1cccc2cc[nH]c12]

Sodium ethoxide (0.65 mL, 0.0017 mol, 2.6M) was added to a solution of ethyl [2-trifluoromethoxy-6-(trimethylsilanylethynylphenyl)]carbamate in EtOH (5.0 mL) and the mixture stirred at 72° C. for 14 hours. The solvent was removed under reduced pressure and the residue was partitioned between diethyl ether and water (30 mL of each). The ether phase was washed with brine and dried over Na$_2$SO$_4$ yielding the desired compound in 59% yield. $^1$H NMR (400 MHz, CDCl$_3$): δ 6.60-6.61 (m, 1H), 7.07-7.09 (m, 2H), 7.25 (d, J=5.6 Hz, 1H), 7.55-7.57 (m, 1H) and 8.42 (br, 1H). MS (ES+): m/z 202.18 [MH+].

7-Trifluoromethoxy-2-(4,4,5,5-tetramethyl-[1,3,2]dioxaborolan-2-yl)-1H-indole

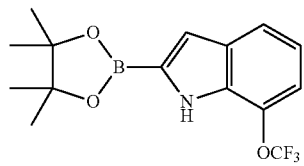 [SMILES: CC1(C)OB(c2cc3cccc(OC(F)(F)F)c3[nH]2)OC1(C)C]

Prepared according to a procedure analogous to that described for 7-chloro-2-(4,4,5,5-tetramethyl-[1,3,2]dioxaborolan-2-yl)-1H-indole using 7-trifluoromethoxy-1H-indole.

7-Phenyl-1H-indole

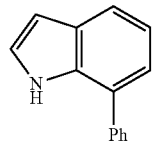 [SMILES: c1ccc(-c2cccc3cc[nH]c23)cc1]

To a suspension of 7-bromo-1H-indole (196 mg, 0.00100 mol) in 1,4-dioxane (4 mL) and water (1 mL) was added phenylboronic acid (146 mg, 0.00120 mol), potassium carbonate (414 mg, 0.00300 mol) and [1,1'-bis(diphenylphosphino)ferrocene]dichloropalladium(II), complex with dichloromethane (1:1) (82 mg, 0.00010 mol). The flask was evacuated and refilled with nitrogen, three times then the mixture was heated at 100° C. overnight. The mixture was diluted with EtOAc (30 mL), washed with sat. aq. NaHCO$_3$ (10 mL) and brine (10 mL), then dried over anhydrous sodium sulfate and the solvent removed in vacuo. The crude material was purified by chromatography over silica gel eluting with hexane/EtOAc to give the title compound (180 mg, 93% yield). $^1$H NMR (CDCl$_3$, 400 MHz): δ 6.64 (dd, J=3.0, 2.0 Hz, 1H), 7.18-7.26 (m, 3H), 7.41 (t, J=7.5 Hz, 1H), 7.48-7.57 (m, 2H), 7.61-7.70 (m, 3H) and 8.43 (br s, 1H) ppm. LC-MS (ES+.): 194 [MH$^+$].

7-Phenyl-2-(4,4,5,5-tetramethyl-[1,3,2]dioxaborolan-2-yl)-1H-indole

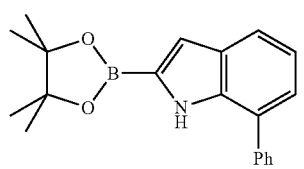 [SMILES: CC1(C)OB(c2cc3cccc(-c4ccccc4)c3[nH]2)OC1(C)C]

Prepared according to a procedure analogous to that described for 7-chloro-2-(4,4,5,5-tetramethyl-[1,3,2]dioxaborolan-2-yl)-1H-indole using 7-phenyl-1H-indole.

7-Cyclopropyl-2-(4,4,5,5-tetramethyl-[1,3,2]dioxaborolan-2-yl)-1H-indole

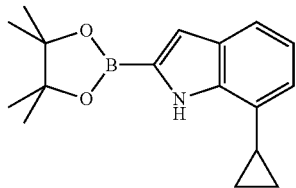 [SMILES: CC1(C)OB(c2cc3cccc(C4CC4)c3[nH]2)OC1(C)C]

Prepared according to the procedures described above for 7-phenyl-2-(4,4,5,5-tetramethyl-[1,3,2]dioxaborolan-2-yl)-1H-indole using cyclopropylboronic acid in place of phenylboronic acid. $^1$H NMR (CDCl$_3$, 400 MHz): δ 0.75-0.82 (m, 2H), 0.95-1.04 (m, 2H), 2.08 (m, 1H), 6.59 (dd, J=3.0, 2.0 Hz, 1H), 6.96 (d, J=7.1 Hz, 1H), 7.06 (t, J=7.6 Hz, 1H), 7.25 (m, 1H), 7.52 (d, J=7.8 Hz, 1H) and 8.39 (br s, 1H) ppm. LC-MS (ES, Pos.): 158 [MH$^+$].

6-Bromo-7-fluoro-1H-indole

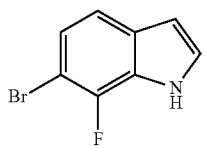 [SMILES: Fc1c(Br)ccc2cc[nH]c12]

To a solution of 1-bromo-2-fluoro-3-nitrobenzene (2.5 g, 11.3 mmol) in THF (25 mL) at −50° C. was added vinyl magnesium bromide (34 mL, 34 mmol) and the mixture was stirred at −40° C. for 1 h. The reaction was quenched with saturated ammonium chloride solution and extracted with ethyl acetate. The organic layer was washed with brine, dried over anhydrous sodium sulfate and evaporated under reduced pressure to yield a gum, which was purified by column chromatography over silica gel eluting with EtOAc/hexane to afford pure 6-bromo-7-fluoro-1H-indole. $^1$H NMR (400 MHz, CDCl$_3$) δ=6.53-6.62 (m, 1H), 7.16-7.25 (m, 2H), 7.29 (d, J=8.34 Hz, 1H) and 8.36 (br. s., 1H); MS (ES+): m/z 214.08 [MH+].

6-Bromo-7-fluoro-1-methyl-1H-indole

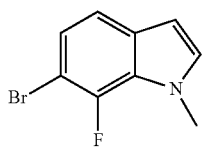

To a solution of 6-bromo-7-fluoro-1H-indole (470 mg, 2.19 mmol) in THF (7 mL) at −10° C. was added sodium hydride (175 mg, 4.39 mmol, 60% dispersion) and the mixture was stirred at 0° C. for 30 min. Methyl iodide was added at 0° C. and the reaction was allowed to warm to at 10° C. and stirred for 2 h. The reaction was quenched with saturated ammonium chloride and extracted with DCM. The DCM extract was washed with brine, dried over anhydrous sodium sulfate and evaporated under reduced pressure. The crude product was purified by column chromatography over silica gel eluting with EtOAc/hexane to afford 6-bromo-7-fluoro-1-methyl-1H-indole. $^1$H NMR (400 MHz, CDCl$_3$) δ=3.95 (d, J=2.00 Hz, 1H), 6.42 (t, J=2.78 Hz, 1H), 6.94 (d, J=3.03 Hz, 1H), 7.09-7.15 (m, 1H) and 7.20 (d, J=8.34 Hz, 1H); MS (ES+): m/z 228.04 [MH+].

7-Fluoro-1-methyl-6-(4,4,5,5-tetramethyl-[1,3,2]dioxaborolan-2-yl)-1H-indole

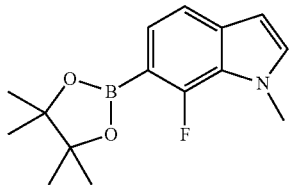 [SMILES: Cn1ccc2ccc(B3OC(C)(C)C(C)(C)O3)c(F)c21]

To a mixture of 6-bromo-7-fluoro-1-methyl-1H-indole (420 mg, 1.84 mmol), 4,4,4',4',5,5,5',5'-octamethyl-2,2'-bi-1,3,2-dioxaborolane (514 mg, 2.02 mmol), potassium acetate (542 mg, 5.52 mmol), [1,1'-bis(diphenylphosphino)ferrocene]dichloropalladium(II) complex with dichloromethane (1:1 complex, 150 mg, 0.184 mmol) and 1,1'-bis(diphenylphosphino)ferrocene (102 mg, 0.184 mmol) was added dioxane (10 mL) and the mixture was degassed by bubbling through with nitrogen for 3 min. The reaction mixture was heated at 100° C. overnight then the dioxane was removed under reduced pressure and the residue was dissolved in DCM and filtered to remove inorganics. The filtrate was concentrated and the crude product was purified by column chromatography over silica gel eluting with EtOAc/hexane to afford pure 7-fluoro-1-methyl-6-(4,4,5,5-tetramethyl-[1,3,2]dioxaborolan-2-yl)-1H-indole. $^1$H NMR (400 MHz, CDCl$_3$) δ=1.41 (s, 12H), 4.02 (d, J=2.02 Hz, 3H), 6.46 (t, J=2.65 Hz, 1H), 7.03 (d, J=3.03 Hz, 1H) and 7.28-7.47 (m, 2H); MS (ES+): m/z 276.03 [MH+].

7-Trifluoromethyl-benzo[b]thiophene

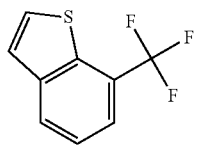 [SMILES: FC(F)(F)c1cccc2ccsc12]

To a stirred solution of 2-(trifluoromethyl)benzenethiol (5.000 g, 0.028 mol) in acetone (50 mL) was added 2-bromo-1,1-diethoxyethane (6.08 g, 0.030 mol) and potassium carbonate (7.757 g, 0.056 mol). The resulting mixture was then stirred at 45° C. for 2 hours prior to removal of the solvent in vacuo and suspension of the residue in EtOAc. The inorganic salts were filtered off and the organic phase was concentrated to give crude product, which was used in next step without further purification. This residue was dissolved in toluene (50 mL), and to this solution was added PPA (10 g) and the resulting mixture stirred at 95-100° C. for 2 hours. The mixture was allowed to cool to rt, was poured into ice-water, then extracted with EtOAc (3×50 mL). The combined extracts were washed with aqueous sodium bicarbonate followed by brine, then dried over anhydrous sodium sulfate and evaporated under reduced pressure to yield an oil. This was purified by column chromatography over silica gel eluting with hexane to give 7-trifluoromethyl-benzo[b]thiophene. $^1$H NMR (400 MHz, MeOD) δ ppm 7.49-7.57 (m, 2H), 7.70 (d, J=7.33 Hz, 1H), 7.74 (d, J=5.56 Hz, 1H) and 8.10 (d, J=8.08 Hz, 1H).

7-Trifluoromethylbenzo[b]thiophene-2-boronic acid

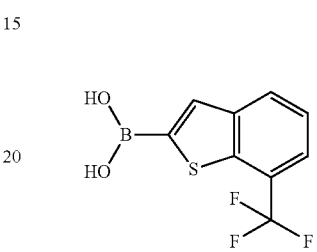

To a solution of 7-trifluoromethyl-benzo[b]thiophene (0.52 g, 0.0026 mol) in THF (30 mL) at −78° C. was added 2.5 M of n-BuLi in hexane (1.4 mL). The reaction was then slowly warmed up to −30° C. over 30 min. and stirred at this temperature for 10 min prior to recooling to −78° C. and treatment with triisopropyl borate (0.7255 g, 0.0038 mol). The reaction was then slowly warmed up to 0° C. then was quenched with saturated ammonium chloride and the solvent removed in vacuo. To the residue was added aqueous sodium hydroxide (10 mL, 2N solution) followed by water (30 mL) then this mixture was extracted with DCM. The aqueous solution was acidified using dilute sulfuric acid (2N solution), filtered and the residue dried in vacuo to yield 7-trifluoromethylbenzo[b]thiophen-2-boronic acid. $^1$H NMR (400 MHz, MeOD) δ ppm 7.55 (1 H, t, J=7.45 Hz), 7.75 (1 H, d, J=7.07 Hz), 8.02 (1 H, s) and 8.17 (1 H, d, J=7.83 Hz).

N-Methylindole-6-boronic acid

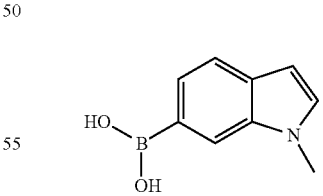

A mixture of indole-6-boronic acid (0.100 g, 0.615 mmol), sodium hydride (0.07 g, 20 mmol) and THF (5 mL, 60 mmol) was stirred at rt for 20 min. then methyl iodide (100 uL, 20 mmol) was added and the mixture was allowed ro stir at rt for 3 hours. The reaction was quenched with sat. NH$_4$Cl solution, washed with brine and dried over Na$_2$SO4, then the solvent was removed in vacuo. The crude product was purified by chromatography over silica gel eluting with 1:9 EtOAc/hexane and 1% MeOH, yielding the desired product. $^1$H NMR (400 MHz, CDCl$_3$) δ ppm 3.99 (s, 3H), 6.58 (m, 1H). 7.23 (m, 1H), 7.81 (m, 1H), 8.08 (m, 1H) and 8.34 (m, 1H). MS (ES+): m/z 176.15 [MH+].

4-Bromo-3-methyl-2-nitrophenol

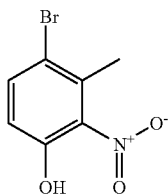

To a solution of 3-methyl-2-nitrophenol (2.0 g, 13.06 mmol) in acetic acid (40 mL) was added bromine (0.70 mL, 13.71 mmol) and the mixture was stirred at RT for 5 h. The reaction was poured in to ice water and the yellow precipitate formed was filtered and washed with water and dried in vacuo to yield 4-bromo-3-methyl-2-nitrophenol. $^1$H NMR (400 MHz, CDCl$_3$) δ=2.61 (s, 3H), 2.62 (s, 5H), 6.92 (d, J=8.84 Hz, 1H), 7.66 (d, J=9.09 Hz, 1H) and 9.28 (s, 1 H); MS (ES+): m/z 215.00 [M-17].

1-Bromo-4-methoxy-2-methyl-3-nitrobenzene

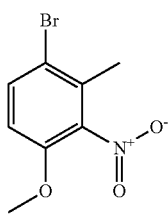

To a solution of 4-bromo-3-methyl-2-nitrophenol (2.200 g, 9.48 mmol) in acetone (35 mL) was added potassium carbonate (3.276 g, 23.70 mmol) and methyl iodide (1.47 mL, 23.70 mmol) and the mixture was heated to reflux for 4 h. The reaction was cooled to rt, filtered and the filtrate was evaporated under reduced pressure to afford the crude product. Purification of the crude product by column chromatography over silica gel eluting with EtOAc/hexane afforded pure 1-bromo-4-methoxy-2-methyl-3-nitrobenzene as pale yellow solid. $^1$H NMR (400 MHz, CDCl$_3$) δ=2.33 (s, 2H), 3.87 (s, 3H), 6.78 (d, J=8.84 Hz, 1H) and 7.58 (d, J=8.84 Hz, 1H); MS (ES+): m/z 247.26 [MH+].

1-[(E)-2-(6-bromo-3-methoxy-2-nitrophenyl)vinyl]pyrrolidine

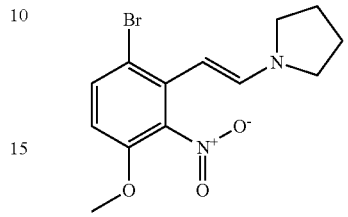

To a solution of 1-bromo-4-methoxy-2-methyl-3-nitrobenzene (1.400 g, 5.68 mmol) and 1,1-dimethoxy-N,N-dimethylmethanamine (0.884 mL, 6.657 mmol) in DMF (10.0 mL) was added pyrrolidine (0.555 mL, 6.656 mmol) and the mixture was heated to at 110° C. for 4 h. The DMF was removed and the residue was recrystallized from DCM: methanol (1:6) mixture to afford 1-[(E)-2-(6-bromo-3-methoxy-2-nitrophenyl)vinyl]pyrrolidine.

4-Bromo-7-methoxy-1H-indole

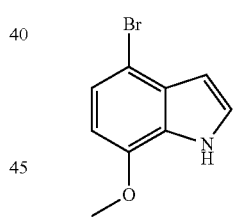

To a solution of 1-[(E)-2-(6-bromo-3-methoxy-2-nitrophenyl)vinyl]pyrrolidine (1.3 g, 3.97 mmol) in THF (6 mL) and methanol (6 mL) was added Raney Ni (≈500 mg) followed by hydrazine (0.19 mL). (CAUTION: Exothermic reaction with vigorous gas evolution). Hydrazine (0.19 mL) was added again, two times, after 30 min and 1 h. The reaction was stirred at 45° C. for 2 h, filtered through a pad of celite. The filtrate was concentrated in vacuo and the residue purified by chromatography over silica gel eluting with EtOAc/hexane to afford pure 4-bromo-7-methoxy-1H-indole. $^1$H NMR (400 MHz, CDCl$_3$) δ=3.94 (s, 3H), 6.52 (d, J=8.08 Hz, 1H), 6.56 (dd, J=3.16, 2.40 Hz, 1H), 7.17 (d, J=8.08 Hz, 1H), 7.22 (t, J=2.78 Hz, 1H) and 8.47 (br. s., 1H); MS (ES+): m/z 226.12 [MH+].

2-Phenyl-5-(4,4,5,5-tetramethyl-[1,3,2]dioxaborolan-2-yl)-1,3-benzothiazole

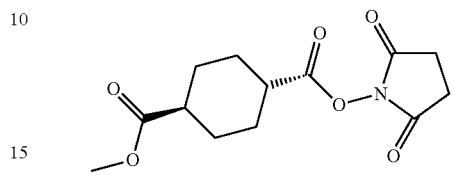

A stirred solution of 5-bromo-2-phenylbenzothiazole (0.500 g, 0.00172 mol), bis(pinacolato)diboron (0.508 g, 0.00200 mol), 1,3-bis(2,6-diisopropylphenyl)imidazol-2-ylidene hydrochloride (0.044 g, 0.10 mmol), Pd(OAc)2 (0.019 g, 0.086 mmol) and AcOK (0.423 g, 0.00431 mol) in anhydrous THF (9.78 mL, 0.121 mol) was heated at 72° C. under Argon for 29 h. The mixture was filtered through a multi-layered pad of anhydrous sodium sulfate, silica gel and celite and the filtrate was concentrated in vacuo and the solids triturated multiple times with hexanes to give the title compound. $^1$H NMR (400 MHz, CHLOROFORM-d) δ ppm=1.39 (s, 12 H), 7.49-7.56 (m, 3 H), 7.83 (dd, J=8.08, 1.01 Hz, 1 H), 7.92 (d, J=7.33 Hz, 1 H), 8.12-8.18 (m, 2 H) and 8.60 (s, 1 H); MS (ES+): m/z 337.91 [MH+].

4-(Methoxycarbonyl)-4-methylcyclohexanecarboxylic acid

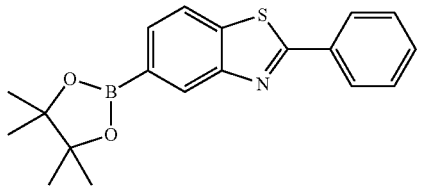 [SMILES: CC1(C)OB(c2ccc3sc(-c4ccccc4)nc3c2)OC1(C)C]

N,N-Diisopropylamine (1.18 mL, 8.35 mmol) was added dropwise to a 2M solution of $^n$butyllithium (4.18 mL, 8.4 mmol) at −78° C. under nitrogen. After 15 min at this temperature the solution was raised to and held at 0° C. for 15 min prior to re-cooling to −78° C. and treatment with a solution of 4-(methoxycarbonyl)cyclohexanecarboxylic acid (0.62 g, 3.34 mmol) in THF (8 mL). After 30 min., iodomethane (0.31 mL, 5 mmol) was added dropwise and the mixture was allowed to warm to rt over 2 hr. The mixture was cooled to at 0° C., quenched with 2 N HCl (10 mL) then was extracted with EtOAc (2×10 mL), washed with brine (3×15 mL), and dried over anhydrous magnesium sulfate. Concentration of the combined organic extracts afforded a yellow solid. NMR (CDCl$_3$) consistent with crude, desired product.

Methyl trans-4-{[(2,5-dioxopyrrolidin-1-yl)oxy]carbonyl}cyclohexanecarboxylate

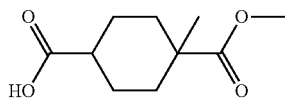

A solution of N-hydroxysuccinimide (6.18 g, 0.0537 mol) and trans-4-(methoxycarbonyl)cyclohexanecarboxylic acid (10.00 g, 0.05370 mol) in THF (100.00 mL) was charged with (N,N'-dicyclohexylcarbodiimide (11.08 g, 0.0537 mol) in THF (16 mL). This reaction was stirred at rt for an additional 16 h then stirred at 45° C. for 1 h. The reaction mixture was filtered while still warm through a fritted funnel. The cake was washed with 3 more portions of THF and the filtrate was concentrated in vacuo and was crystallized from i-PrOH (300 mL) and filtered through a fritted funnel resulting in 11.8 g, (78% yield) of the title compound as a white crystals. $^1$H NMR (400 MHz, CDCl3) δ ppm 1.45-1.69 (m, 4H), 2.07-2.16 (m, 2H), 2.18-2.28 (m, 2H), 2.29-2.39 (m, 1H), 2.59-2.71 (m, 1H) 2.84 (br. s., 4H) and 3.68 (s, 3H); MS (ES+): m/z 284.09 [MH+].

Methyl trans-4-{[(3-amino-5-oxo-4,5-dihydro-1,2,4-triazin-6-yl)methyl]carbamoyl}cyclohexanecarboxylate

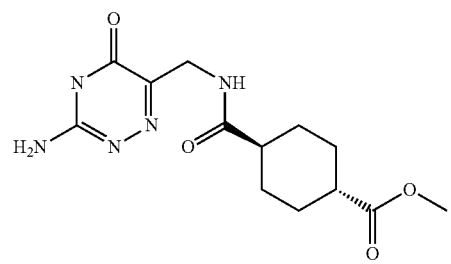 [SMILES: COC(=O)[C@H]1CC[C@H](C(=O)NCc2nnc(N)[nH]c2=O)CC1]

A solution of 3-amino-6-(aminomethyl)-1,2,4-triazin-5(4H)-one [J. Heterocyclic Chem., (1984), 21 (3), 697](2.00 g, 0.0113 mol) in H$_2$O (60.0 mL, 3.33 mol) was cooled to 0° C. and drop wise charged with 1.00 M of NaHCO$_3$ in H$_2$O (22.5 mL) and allowed to warm to rt. This mixture was charged with methyl trans-4-{[(2,5-dioxopyrrolidin-1-yl)oxy]carbonyl}cyclohexanecarboxylate (3.8 g, 0.012 mol) in 1:1 THF/MeCN (40 mL). After 30 min a precipitate began to form in the reaction. This was allowed to stir at rt for an additional 16 h and was filtered through a fritted funnel and washed with H$_2$O (2×), diethyl ether (2×), and dried in vacuo resulting in the title compound 2.92 g, (84% yield) as an off-white solid. $^1$H NMR (400 MHz, DMSO-d$_6$) δ ppm 1.24-1.55 (m, 4H), 1.83 (s, 2H), 1.98 (d, J=10.61 Hz, 2H), 2.27 (s, 2H), 3.64 (s, 3H), 4.10 (d, J=5.81 Hz, 2H), 6.81 (br. s., 2H), 7.91 (t, J=5.56 Hz, 1H) and 11.98 (br. s., 1H); MS (ES+): m/z 310.05 [MH+].

Methyl trans-4-(2-amino-4-oxo-3,4-dihydroimidazo[5,1-f][1,2,4]triazin-7-yl)cyclohexanecarboxylate

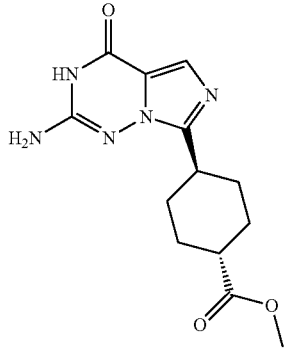 [SMILES: COC(=O)[C@H]1CC[C@H](c2ncc3c(=O)[nH]c(N)nn32)CC1]

A solution of methyl trans-4-{[(3-amino-5-oxo-4,5-dihydro-1,2,4-triazin-6-yl)methyl]carbamoyl}cyclohexanecarboxylate (2.00 g, 0.00646 mol) in 1,2-dichloroethane (130 mL) was charged with POCl₃ (4.2 mL, 0.045 mol) and heated to reflux for 3 h. The reaction mixture was concentrated in vacuo then partitioned between EtOAc and sat. NaHCO₃ and separated. The aqueous was re-extracted with EtOAc (3×) and the combined organic fractions were dried over Na₂SO₄, filtered, and concentrated in vacuo resulting in 1.43 g, (76% yield) of the title compound as an off-white solid. ¹H NMR (400 MHz, DMSO-d₆) δ ppm 1.43 (q, J=11.79 Hz, 2H), 1.61 (q, J=12.55 Hz, 2H), 1.85-2.11 (m, 4H), 2.38 (t, J=11.87 Hz, 1H), 2.98 (t, J=11.75 Hz, 1H), 3.61 (s, 3H), 6.17 (br. s., 2 H), 7.49 (s, 1H) and 10.90 (br. s., 1H); MS (ES+): m/z 292.25 [MH+].

Methyl trans-4-(2-amino-5-iodo-4-oxo-3,4-dihydroimidazo[5,1-f][1,2,4]triazin-7-yl)cyclohexanecarboxylate

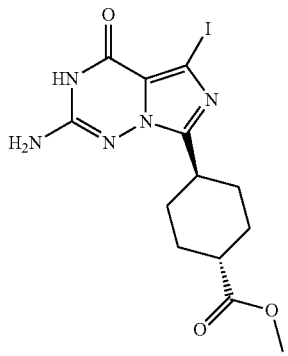 [SMILES: COC(=O)[C@H]1CC[C@H](c2nc(I)c3c(=O)[nH]c(N)nn32)CC1]

A solution of methyl trans-4-(2-amino-4-oxo-3,4-dihydroimidazo[5,1-f][1,2,4]triazin-7-yl)cyclohexanecarboxylate (0.200 g, 0.000686 mol) and N-iodosuccinimide (0.278 g, 0.00124 mol) in anhydrous DMF (4.0 mL) was stirred at rt for 48 h. The reaction was concentrated in vacuo then partitioned between H₂O and EtOAc. The aqueous material was re-extracted with EtOAc (3×) and the combined organic fractions were washed with H₂O (2×), Na₂S₂O₃ (2×) and brine (1×). The aqueous was re-extracted with CHCl₃ and combined with the EtOAc fractions dried over Na₂SO₄, filtered and concentrated in vacuo resulting in 229 mg, (79.9% yield) of the title compound as a light orange solid. ¹H NMR (400 MHz, DMSO-d₆) δ ppm 1.34-1.65 (m, 4H), 1.88-2.06 (m, 4H), 2.33-2.45 (m, 1H), 2.91-3.01 (m, 1H), 3.61 (s, 3H), 6.17 (s, 2H) and 10.82 (br. s., 1H); MS (ES+): m/z 417.82 [MH+].

Methyl trans-4-(5-iodo-4-oxo-3,4-dihydroimidazo[5,1-f][1,2,4]triazin-7-yl)cyclohexanecarboxylate

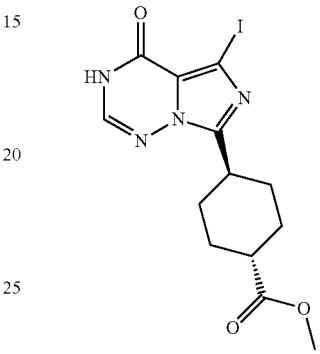

A solution of methyl trans-4-(2-amino-5-iodo-4-oxo-3,4-dihydroimidazo[5,1-f][1,2,4]triazin-7-yl)cyclohexanecarboxylate (0.880 g, 0.00211 mol) in anhydrous THF (74 mL) and DMF (13.2 mL) was charged with tert-butyl nitrite (1.2 mL, 0.010 mol) and stirred at rt for 2 h. The reaction was concentrated in vacuo and was purified by chromatography over silica gel [eluting with 5% MeOH in CHCl₃] resulting in 570 mg, (67% yield) of the title compound as a pale orange solid. (¹H NMR (400 MHz, DMSO-d₆) δ ppm 1.40-1.54 (m, 2H), 1.56-1.69 (m, 2H), 1.92-2.06 (m, 4H), 2.36-2.46 (m, 1H), 3.02-3.14 (m, 1H), 3.61 (s, 3H), 7.89 (d, J=3.28 Hz, 1 H) and 11.79 (br. s., 1H); MS (ES+): m/z 402.86 [MH+].

Methyl trans-4-(4-amino-5-iodoimidazo[5,1-f][1,2,4]triazin-7-yl)cyclohexanecarboxylate

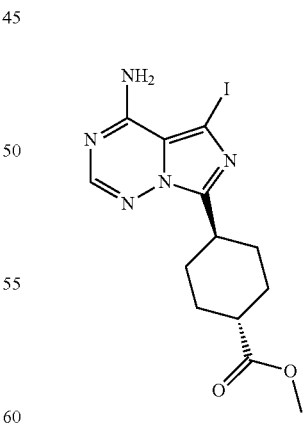

A solution of 1H-1,2,4-triazole (0.881 g, 0.0128 mol) in pyridine (3.00 mL) was charged with POCl₃ (0.396 mL, 0.00425 mol) and stirred at rt for 15 min. To this mixture was drop wise added methyl trans-4-(5-iodo-4-oxo-3,4-dihydroimidazo[5,1-f][1,2,4]triazin-7-yl)cyclohexanecarboxylate (0.570 g, 0.00142 mol) in pyridine (6.00 mL) and stirred at rt for an additional 2.45 h. The reaction was quenched with excess 2 M of NH₃ in i-PrOH (40.00 mL) at 0° C. and allowed to stir at rt for an additional 3 h. The reaction was concentrated in vacuo and partitioned between EtOAc and sat. NaHCO₃ and separated. The aqueous was washed with EtOAc (3×) and the combined organic fractions were washed with brine (1×). The aqueous was re-extracted with CHCl₃ (3×) and the organic was added to the EtOAc fractions. The combined organic fractions were dried over Na₂SO₄, filtered and concentrated in vacuo. The crude brown/red solid was purified by chromatography over silica gel [eluting with 5% MeOH in CHCl₃]resulting in 438 mg, (76% yield) of the title compound as a light yellow solid. ¹H NMR (400 MHz, DMSO-d₆) δ ppm 1.39-1.54 (m, 2H), 1.55-1.71 (m, 2H), 1.92-2.07 (m, 4H), 2.35-2.46 (m, 1H), 3.06-3.19 (m, 1H), 3.61 (s, 3H), 6.77 (br. s., 1H) 7.86 (s, 1H) and 8.44 (br. s., 1H); MS (ES+): m/z 401.85 [MH+].

1-Chloro-2-[(2,2-diethoxyethyl)thio]benzene

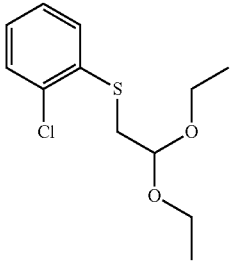 [SMILES: CCOC(CSc1ccccc1Cl)OCC]

To a solution of 2-chlorobenzenethiol (5.0 g, 34.5 mmol) in acetone (35 mL) was added 2-bromo-1,1-diethoxyethane (7.15 g, 36.3 mmol) followed by potassium carbonate (9.55 g, 69.1 mmol). The mixture was heated at reflux for 3 h. then cooled to rt, filtered and the filtrate evaporated under reduced pressure to yield the crude product. This material was purified by chromatography over silica gel eluting with ethyl acetate in hexanes (0→2%) to afford pure 1-chloro-2-(2,2-diethoxyethylsulfanyl)benzene (7.3, 80%). ¹H NMR (400 MHz, CDCl₃) δ=1.20 (t, J=7.07 Hz, 6H), 3.15 (d, J=5.56 Hz, 2H), 3.51-3.61 (m, 2H), 3.63-3.74 (m, 2H), 4.69 (t, J=5.56 Hz, 1H), 7.12 (td, J=7.58, 1.52 Hz, 1H), 7.20 (td, J=7.58, 1.52 Hz, 1H), 7.36 (dd, J=7.83, 1.52 Hz, 1H), 7.39 (dd, J=8.08, 1.52 Hz, 1H); MS (ES+): m/z 187.17 [M-74].

7-Chlorobenzo[b]thiophene

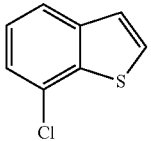

To a solution of 1-chloro-2-(2,2-diethoxyethylsulfanyl) benzene (3.95 g, 15.14 mmol) in toluene (40 mL) was added polyphosphoric acid (15 g, 137.5 mmol).

The mixture was heated at reflux for 4 h. then was poured in to ice water, stirred for min and extracted with toluene. The combined toluene extracts were washed with aqueous sodium bicarbonate followed by brine, dried over anhydrous sodium sulfate and evaporated under reduced pressure to yield the crude product. This material was purified by chromatography over silica gel eluting with hexane to afford pure 7-chlorobenzo[b]thiophene (1.72 g, 67.5%). ¹H NMR (400 MHz, CDCl₃) δ=7.13-7.30 (m, 3H), 7.38 (d, J=5.31 Hz, 1H), 7.62 (dd, J=7.33, 1.52 Hz, 1H); MS (ES+): m/z 169.06 [MH+].

7-Chlorobenzo[b]thiophene-2-boronic acid

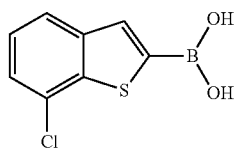 [SMILES: OB(O)c1cc2cccc(Cl)c2s1]

To a solution of 7-chlorobenzo[b]thiophene (1.0 g, 5.92 mmol) in THF (25 mL) at −78° C. was added ⁿbutyllithium (7.41 mL, 11.8 mmol, 1.6 M solution). The reaction was allowed to warm to −30° C. then was cooled back to −78° C. and triisopropyl borate (2.23 g, 11.8 mmol) was added. The mixture was allowed to warm to 0° C., saturated ammonium chloride added and the organic phase separated off and concentrated in vacuo. To the residue was added aqueous sodium hydroxide (10 mL, 2N solution) followed by water (30 mL) and the mixture was washed with DCM. The aqueous phase was acidified with 2N sulfuric acid, and the resulting precipitate isolated by filtration and dried under vacuum to yield 7-chlorobenzo[b]thiophene-2-boronic acid (1.21 g, 96%) as white solid. ¹H NMR (400 MHz, CDCl₃) δ=7.41 (t, J=7.70 Hz, 1H), 7.50 (d, J=7.70 Hz, 1H), 7.91 (d, J=7.70 Hz, 1H), 8.03 (s, 1H), 8.63 (s, 2H); MS (ES+): m/z 211.86 [M+].

7-(methylthio)-1H-indole

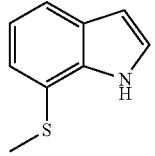

To a solution of 7-bromo-1H-indole (3.0 g, 15.3 mmol) in THF (60 mL) at −78° C. was added ᵗBuLi (1.7 M, 33.8 mL, 57.4 mmol) and the mixture was allowed to warm to 0° C. The reaction was re-cooled to −78° C. and a solution of dimethyl disulfide (2.0 mL, 22.9 mmol) was added and the reaction was allowed to warm to 0° C. The reaction was quenched with saturated ammonium chloride and extracted with ethyl acetate. The organic layer was washed with brine, dried over anhydrous sodium sulfate and evaporated under reduced pressure to yield the crude product. This material was purified by chromatography over silica gel eluting with ethyl acetate in hexanes (0→2%) to afford pure 7-(methylthio)-1H-indole (1.4 g, 55%). ¹H NMR (400 MHz, CDCl₃) δ=2.50 (s, 3 H), 6.58 (dd, J=3.03, 2.02 Hz, 1H), 7.09 (t, J=7.58 Hz, 1H), 7.18-7.31 (m, 2H), 7.56 (d, J=7.83 Hz, 1H), 8.45 (br. s., 1 H); MS (ES+): m/z 164.15 [MH+].

7-(Methylsulfonyl)-1H-indole

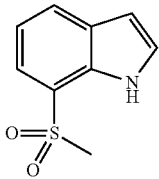

To a solution of 7-(methylthio)-1H-indole (1.1 g, 6.7 mmol) in DCM (25 ml) at −40° C. was added m-chloroperbenzoic acid (3.02 g, 13.4 mmol) and the reaction was stirred at −40° C. for 30 min. The reaction mixture was then quenched with saturated sodium bicarbonate and extracted with DCM. The DCM extracts was washed with water, brine, dried over anhydrous sodium sulfate and evaporated under reduced pressure to yield the crude product. This material was purified by chromatography over silica gel eluting with hexanes (0->10%) to afford pure 7-(methylsulfonyl)-1H-indole (987 mg, 75%). $^1$H NMR (400 MHz, CDCl$_3$) δ=3.12 (s, 1H), 6.66 (d, J=2.53 Hz, 1H), 7.24 (t, J=7.71 Hz, 1H), 7.35 (d, J=1.77 Hz, 1H), 7.68 (d, J=7.07 Hz, 1H), 7.90 (d, J=7.83 Hz, 1H), 9.68 (br. s., 1H); MS (ES+): m/z 196.08 [MH+].

Methyl trans-4-cyanocyclohexanecarboxylate

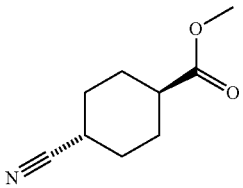

Chlorosulfonyl isocyanate (1.0 mL, 0.012 mol) was added to a solution of trans-4-(methoxycarbonyl)cyclohexanecarboxylic acid (2.00 g, 0.0107 mol) in DCM cooled to 0° C. The resulting solution was heated at reflux for 15 minutes and then cooled 0° C. and treated dropwise with DMF. The mixture was stirred at room temperature overnight then poured onto ice water and the organic phase separated and washed with a saturated solution of sodium bicarbonate. The solvent was removed in vacuo and the crude material was taken up in ethyl acetate, washed with 1N aq. NaOH (10 mL) and the ethyl acetate removed in vacuo. The resulting crude product was used in subsequent steps without further purification. $^1$H NMR (400 MHz, CHLOROFORM-d) δ ppm 1.36-1.70 (4 H, m), 2.01-2.18 (4 H, m), 2.24-2.54 (2 H, m) and 3.68 (3 H, s).

Trans-4-cyanocyclohexanecarboxylic acid

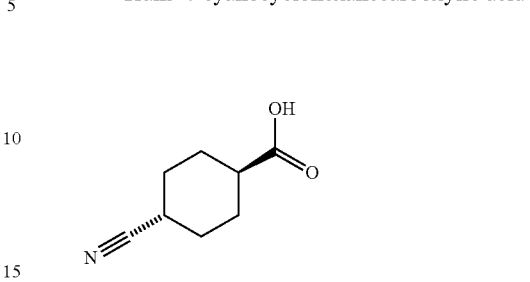

To a solution of methyl trans-4-cyanocyclohexanecarboxylate (996 mg, 5.96 mmol) in THF (37 mL) was added a solution of 0.5 M lithium hydroxide in water (20 mL). The mixture was stirred overnight then the THF was removed in vacuo and the residual aqueous solution acidified to pH 4. The resulting mixture was extracted with ether (2×30 mL), EtOAc (2×30 mL) and CHCl$_3$ (2×30 mL) then the combined extracts, dried over anhydrous sodium sulfate and concentrated in vacuo. This material was taken to the next step without any purification. $^1$H NMR (400 MHz, CHLOROFORM-d) δ ppm 1.43-1.73 (4 H, m), 2.05-2.22 (4 H, m) and 2.36-2.59 (2 H, m).

2-[Trans-4-(8-chloroimidazo[1,5-a]pyrazin-3-yl)cyclohexyl]propan-2-ol

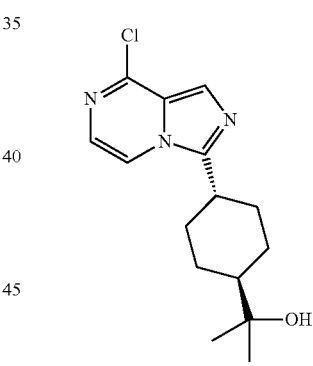

A solution of methyl trans-4-(8-chloroimidazo[1,5-a]pyrazin-3-yl)cyclohexanecarboxylate (4.0 g, 0.014 mol) in toluene (300 mL) and THF (70 mL) was cooled to 0° C. and treated with a 3.0 M solution of methylmagnesium bromide in ether (14 mL) maintaining the temperature at 0° C. The mixture was stirred at rt for 1.5 hours then cooled to 0° C. and an additional 3 eq of 3.0 M of methylmagnesium bromide in ether was added. The mixture was stirred at rt for 15 minutes then cooled to 0° C. and quenched with 1:1 NH$_4$Cl sat.: H$_2$O (50 mL total volume). The organic layer was separated and the aqueous layer was extracted with EtOAc (3×30 mL). The combined organic layers were dried over sodium sulfate and concentrated in vacuo and the crude product thus obtained, chromatographed over silica gel eluting with EtOAc to afford desired 2-[trans-4-(8-chloroimidazo[1,5-a]pyrazin-3-yl)cyclohexyl]propan-2-ol. $^1$H NMR (400 MHz, CHLOROFORM-d) δ ppm 1.14-1.39 (m, 8 H), 1.41-1.60 (m, 1 H), 1.77-1.98 (m, 2 H), 2.01-2.20 (m, 4 H), 2.78-3.06 (m, 1 H), 7.35 (d, J=5.05 Hz, 1 H), 7.64 (d, J=5.05 Hz, 1 H) and 7.83 (s, 1 H).

EXAMPLE 1

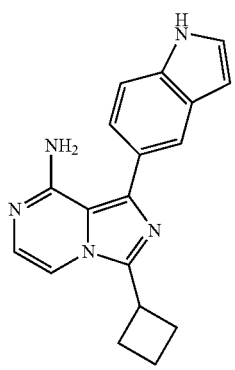 [SMILES: Nc1nccn2c(C3CCC3)nc(-c3ccc4[nH]ccc4c3)c12]

3-Cyclobutyl-1-(1H-indol-5-yl)imidazo[1,5-a]pyrazin-8-amine

A dry mixture of 8-amino-3-cyclobutyl-1-iodoimidazo[3,4-a]pyrazine (30 mg, 0.096 mmol), cesium carbonate (38 mg, 0.117 mmol) and 5-(4,4,5,5-tetramethyl-1,3,2-dioxaborolan-2-yl)-1H-indole (26 mg, 0.107 mmol) was purged with Argon 3 times prior to the addition of tetrakistriphenylphosphino palladium (0) (6 mg, 0.005 mmol). The mixture was purged twice more and then treated with a degassed mixture of DME:water (5:1, 2 mL). The resulting solution was degassed twice more and then heated at 80° C. overnight. The resulting reaction mixture was concentrated in vacuo, the residue dissolved in 1:1 MeCN:MeOH (1.5 mL) and purified by mass directed preparative HPLC to afford 3-cyclobutyl-1-(1H-indol-5-yl)imidazo[1,5-a]pyrazin-8-amine. $^1$H NMR (400 MHz, DMSO-d$_6$) δ ppm 1.82-1.92 (1 H, m) 1.95-2.08 (1 H, m) 2.32-2.41 (4 H, m) 3.82-3.93 (1 H, m) 5.91 (2 H, br. s.) 6.45 (1 H, d, J=3.03 Hz) 6.90 (1 H, d, J=5.05 Hz) 7.26 (1 H, dd, J=8.34, 1.52 Hz) 7.34 (1 H, d, J=5.05 Hz) 7.35-7.39 (1 H, m) 7.45 (1 H, d, J=8.34 Hz) 7.64-7.68 (1 H, m) 11.20 (1 H, br. s.); MS (ES+): m/z 304.15 [MH+]. HPLC: t$_R$ 6.18 min (XTerra C18 5 uM, 4.6×15 mm, A: MeCN & B:10 mmol NH$_4$OAc in 0.05% HOAc/aq., method Polar15).

EXAMPLE 2

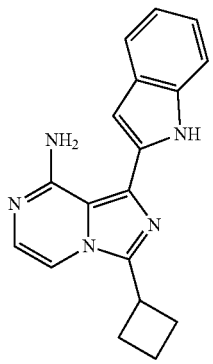 [SMILES: Nc1nccn2c(C3CCC3)nc(-c3cc4ccccc4[nH]3)c12]

3-Cyclobutyl-1-(1H-indol-2-yl)imidazo[1,5-a]pyrazin-8-amine

Prepared as described above for EXAMPLE 1 using 1-(tert-butoxycarbonyl)-1H-indole-2-boronic acid in place of 5-(4,4,5,5-tetramethyl-1,3,2-dioxaborolan-2-yl)-1H-indole. The reaction conditions used effected significant cleavage of the N-(tert-butoxycarbamoyl) functionality. MS (ES+): m/z 304.10 [MH+].

EXAMPLE 3

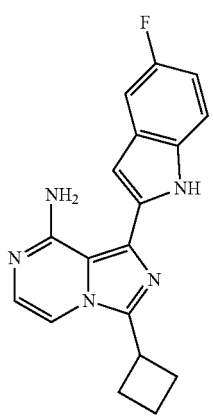 [SMILES: Nc1nccn2c(C3CCC3)nc(-c3cc4cc(F)ccc4[nH]3)c12]

3-Cyclobutyl-1-(5-fluoro-1H-indol-2-yl)imidazo[1,5-a]pyrazin-8-amine

Prepared as described above for EXAMPLE 1 using 1-(tert-butoxycarbonyl)-5-fluoro-1H-indole-2-boronic acid in place of 5-(4,4,5,5-tetramethyl-1,3,2-dioxaborolan-2-yl)-

1H-indole. The reaction conditions used effected significant cleavage of the N-(tert-butoxycarbamoyl) functionality. MS (ES+): m/z 322.06 [MH+].

EXAMPLE 4

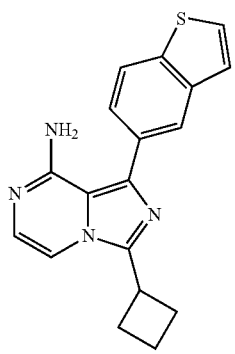 [SMILES: Nc1nccn2c(C3CCC3)nc(-c3ccc4sccc4c3)c12]

1-(1-Benzothien-5-yl)-3-cyclobutylimidazo[1,5-a]pyrazin-8-amine

Prepared as described above for EXAMPLE 1 using 2-(1-benzothiophen-5-yl)-4,4,5,5-tetramethyl-1,3,2-dioxaborolane in place of 5-(4,4,5,5-tetramethyl-1,3,2-dioxaborolan-2-yl)-1H-indole. MS (ES+): m/z 321.10 [MH+].

EXAMPLE 5

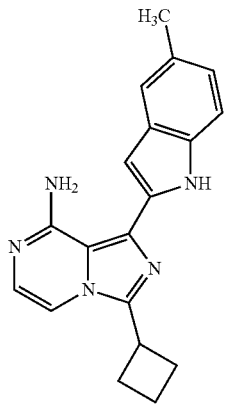 [SMILES: Cc1ccc2[nH]c(-c3nc(C4CCC4)n4ccnc(N)c34)cc2c1]

3-Cyclobutyl-1-(5-methyl-1H-indol-2-yl)imidazo[1,5-a]pyrazin-8-amine

Prepared as described above for EXAMPLE 1 using 1-(tert-butoxycarbonyl)-5-methyl-1H-indole-2-boronic acid in place of 5-(4,4,5,5-tetramethyl-1,3,2-dioxaborolan-2-yl)-1H-indole. MS (ES+): m/z 318.05 [MH+].

EXAMPLE 6

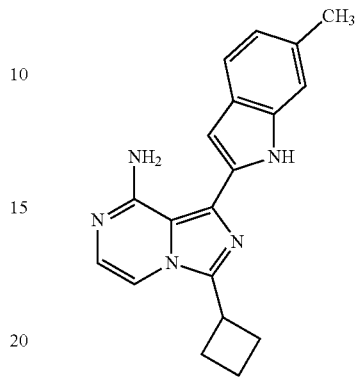

3-Cyclobutyl-1-(6-methyl-1H-indol-2-yl)imidazo[1,5-a]pyrazin-8-amine

Prepared as described above for EXAMPLE 1 using 1-(tert-butoxycarbonyl)-6-methyl-1H-indole-2-boronic acid in place of 5-(4,4,5,5-tetramethyl-1,3,2-dioxaborolan-2-yl)-1H-indole. MS (ES+): m/z 318.05 [MH+].

EXAMPLE 7

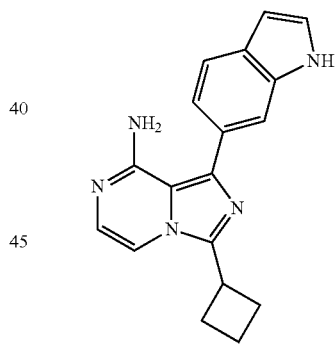

3-Cyclobutyl-1-(1H-indol-6-yl)imidazo[1,5-a]pyrazin-8-amine

A mixture of 6-bromo-1H-indole (2 g, 10.00 mmol), 4,4,4',4',5,5,5',5'-octamethyl-2,2'-bi-1,3,2-dioxaborolane (2.00 g, 7.87 mmol) and potassium acetate (3.0 g, 31.00 mmol) was degassed three times, treated with (1,1'-bis(diphenylphosphino)ferrocene) palladium dichloride (0.20 g, 0.28 mmol) and degassed twice more. 1,2-dimethoxyethane (28 mL) was added and the mixture was heated at 75° C. overnight. The cooled reaction mixture was then diluted with water, extracted with EtOAc and the extracts washed with water and brine, then dried over magnesium sulphate, and concentrated in vacuo to afford a brown/black semi-solid. This was triturated with ether to afford a brown powder, which was identified by LCMS to be desired indole-6-boronic acid, pinacol ester. ¹H NMR (400 MHz, CHLOROFORM-d) δ ppm 1.37 (s, 12 H), 6.54-6.58 (m, 1 H), 7.26-7.28 (m, 1 H), 7.55 (dd, J=7.83, 1.01 Hz, 1 H), 7.62-7.68 (m, 1 H), 7.90 (s, 1 H), 8.19 (br. s., 1 H); MS (ES+): m/z 244.25 [MH⁺]; HPLC: $t_R$=3.52 min (OpenLynx, polar_5 min).

This material was used in place of 5-(4,4,5,5-tetramethyl-1,3,2-dioxaborolan-2-yl)-1H-indole under the conditions described in EXAMPLE 1 to afford 3-cyclobutyl-1-(1H-indol-6-yl)imidazo[1,5-a]pyrazin-8-amine. MS (ES+): m/z 304.15 [MH+].

EXAMPLE 8

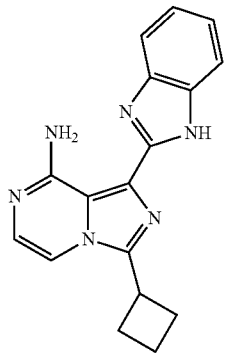

1-(1H-Benzimidazol-2-yl)-3-cyclobutylimidazo[1,5-a]pyrazin-8-amine

3-Cyclobutyl-1-iodoimidazo[1,5-a]pyrazin-8-amine (500 mg, 2 mmol) and tetrakis(triphenylphosphine)palladium(0) (100 mg, 0.1 mmol) was degassed dry three times then treated with methanol (20 mL) and N,N-diisopropylethylamine (0.7 mL, 4.0 mmol) and the mixture heated at 70° C. under an atmosphere of carbon monoxide, with intermittent bubbling of this gas under the surface of the reaction mixture. After 3d heating with extensive bubbling through of the solution with carbon monoxide and some addition of fresh catalyst after day 2, TLC (10% MeOH/DCM) indicated the reaction to be complete. The reaction mixture was diluted with water, extracted with DCM and the extracts washed with water and brine, then dried over magnesium sulphate, and concentrated in vacuo to afford an orange solid which was recrystallised from acetonitrile to afford methyl 8-amino-3-cyclobutylimidazo[1,5-a]pyrazine-1-carboxylate. ¹ H NMR (400 MHz, CHLOROFORM-d) δ ppm 1.97-2.06 (m, 1 H), 2.10-2.26 (m, 1 H), 2.43-2.54 (m, 2 H), 2.53-2.68 (m, 2 H), 3.78 (dd, J=9.09, 8.08 Hz, 1 H), 4.01 (s, 3 H), 7.08 (d, J=4.80 Hz, 1 H), 7.22 (d, J=4.80 Hz, 1 H), 7.38 (br. s., 1 H), 7.69 (br. s., 1 H).

A suspension of 1,2-phenylenediamine (60 mg, 0.6 mmol) in toluene (2.0 mL) was treated with a 2M solution of trimethylaluminum in toluene (0.5 mL) effecting the formation of a pink solution. After 5 min this solution was treated with solid methyl 8-amino-3-cyclobutylimidazo[1,5-a]pyrazine-1-carboxylate (30 mg, 0.1 mmol) and the mixture heated at 120° C. for 30 min then stirred at rt overnight. The mixture was then partitioned between 2M NaOH (10 mL) & EtOAc (10 mL) and stirred for 15 min. The organic layer was separated and the aqueous layer extracted further with EtOAc (3×10 mL). The combined organics were washed with brine, dried and concentrated in vacuo to give ~85% pure 8-amino-N-(2-aminophenyl)-3-cyclobutylimidazo[1,5-a]pyrazine-1-carboxamide which was used without purification.

A solution of 8-amino-N-(2-aminophenyl)-3-cyclobutylimidazo[1,5-a]pyrazine-1-carboxamide (40.0 mg, 0.124 mmol) in acetic acid (1.2 mL) was microwaved at 120° C. for 10 min (300W). The resulting solution was purified mass directed preparative HPLC to afford 1-(1H-benzimidazol-2-yl)-3-cyclobutylimidazo[1,5-a]pyrazin-8-amine. 1H NMR (400 MHz, DMSO-d6) δ ppm 1.92-2.05 (m, 1 H) 2.07-2.21 (m, 1 H) 2.53-2.59 (m, 4 H) 3.91-4.06 (m, 1 H) 7.08 (d, J=4.80 Hz, 1 H) 7.16-7.26 (m, 2 H) 7.38 (d, J=4.80 Hz, 1 H) 7.44 (br. s., 1 H) 7.55 (d, J=8.08 Hz, 1 H) 7.62 (d, J=6.82 Hz, 1 H) 10.49 (br. s., 1 H) 12.76 (s, 1 H); MS (ES+): m/z 305.15 [MH⁺].

EXAMPLE 9

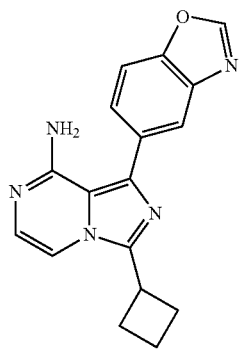 [SMILES: Nc1nccn2c(C3CCC3)nc(-c3ccc4ocnc4c3)c12]

1-(1,3-Benzoxazol-5-yl)-3-cyclobutylimidazo[1,5-a]pyrazin-8-amine

A mixture of 5-chlorobenzoxazole (0.129 g, 0.84 mmol), 4,4,4',4',5,5,5',5'-octamethyl-2,2'-bi-1,3,2-dioxaborolane (0.4956 g, 1.95 mmol), potassium acetate (0.41 g, 4.2 mmol), 1,3-bis(2,6-diisopropylphenyl)imidazol-2-ylidene hydrochloride (43 mg, 0.10 mmol) and palladium acetate (11 mg, 0.05 mmol) was degassed, treated with tetrahydrofuran (10 mL) and the resulting mixture heated at 80° C. overnight. The mixture was diluted with water (100 mL), acidified to pH 6 and extracted with EtOAc (3×40 mL). The extracts were washed with water, dried and concentrated in vacuo. The residue so obtained was purified by chromatography over silica gel eluting with DCM to 10% MeCN/DCM to afford 1,3-benzoxazole-5-boronic acid, pinacol ester. ¹H NMR (400 MHz, CHLOROFORM-d) δ ppm 1.37-1.39 (m, 12 H) 7.59 (d, J=8.34 Hz, 1 H) 7.86 (dd, J=8.08, 1.01 Hz, 1 H) 8.10 (s, 1 H) 8.26 (s, 1 H); MS (ES+): m/z 246.23 [MH⁺].

This material was used in place of 5-(4,4,5,5-tetramethyl-1,3,2-dioxaborolan-2-yl)-1H-indole under the conditions

EXAMPLE 10

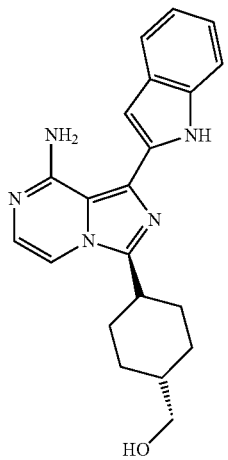

{trans-4-[8-Amino-1-(1H-indol-2-yl)imidazo[1,5-a]pyrazin-3-yl]cyclohexyl}methanol Prepared according to the procedure described in EXAMPLE 2 using trans-[4-(8-amino-1-iodoimidazo[1,5-a]pyrazin-3-yl)cyclohexyl]methanol in place of 8-amino-3-cyclobutyl-1-iodoimidazo[3,4-a]pyrazine. $^1$H NMR (DMSO-d6, 400 MHz) δ 1.12-1.23 (m,), 1.38-1.54 (m, 1H); 1.58-1.78 (m, 2H); 1.82-1.92 (m, 2H); 1.96-2.06 (m, 2H); 3.03-3.16 (m, 1H); 3.29 (t, J=5.6 Hz, 2H); 4.46 (t, J=5.3 Hz, 1H); 6.45 (brs, 2H); 6.63 (d, J=1.38 Hz, 1H); 7.02 (t, J=7.50 Hz, 1H); 7.06 (d, J=4.99 Hz, 1H); 7.12 (t, J=7.52 Hz, 1H), 7.46 (d, J=8.02 Hz, 1H), 7.58 (d, J=7.83 Hz, 1H), 7.66 (d, J=5.06 Hz, 1H), 11.43 (s, 1H); MS (ES+): m/z 362.07 (100) [MH+], HPLC: tR=1.97 min (MicromassZQ, polar_5 min).

EXAMPLE 11

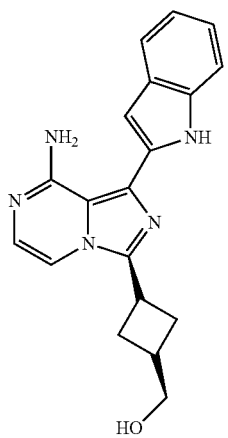

{cis-3-[8-Amino-1-(1H-indol-2-yl)imidazo[1,5-a]pyrazin-3-yl]cyclobutyl}methanol

Prepared according to the procedure described in EXAMPLE 2 using [3-(8-chloro-1-iodoimidazo[1,5-a]pyrazin-3-yl)cyclobutyl]methanol in place of 8-amino-3-cyclobutyl-1-iodoimidazo[3,4-a]pyrazine. MS (ES+): m/z 334.10 [MH+].

EXAMPLE 12

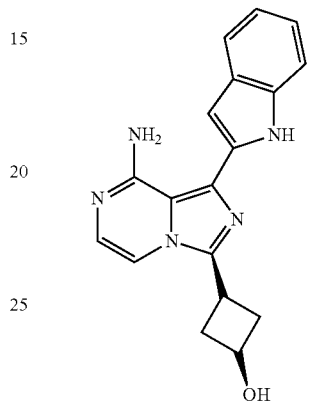

cis-3-[8-Amino-1-(1H-indol-2-yl)imidazo[1,5-a]pyrazin-3-yl]cyclobutanol

Prepared according to the procedure described in EXAMPLE 2 using 3-(8-amino-1-iodoimidazo[1,5-a]pyrazin-3-yl)cyclobutanol in place of 8-amino-3-cyclobutyl-1-iodoimidazo[3,4-a]pyrazine. MS (ES+): m/z 320.03 [MH+].

EXAMPLE 13

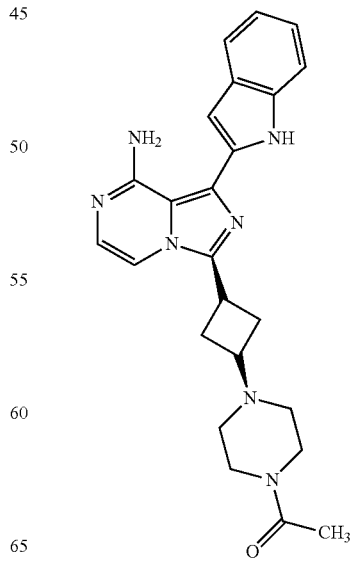

3-[cis-3-(4-Acetylpiperazin-1-yl)cyclobutyl]-1-(1H-indol-2-yl)imidazo[1,5-a]pyrazin-8-amine Prepared according to the procedure described in EXAMPLE 2 using 1-{4-[3-(8-amino-1-iodoimidazo[1,5-a]pyrazin-3-yl)cyclobutyl]piperazin-1-yl}ethanone in place of 8-amino-3-cyclobutyl-1-iodoimidazo[3,4-a]pyrazine. MS (ES+): m/z 430.08 [MH+].

EXAMPLE 14

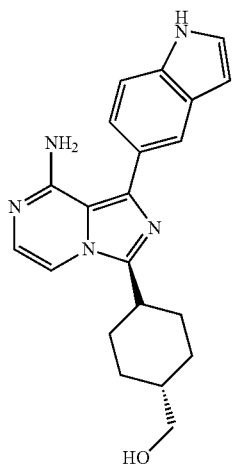

{trans-4-[8-Amino-1-(1H-indol-5-yl)imidazo[1,5-a]pyrazin-3-yl]cyclohexyl}methanol Prepared according to the procedure described in EXAMPLE 1 using trans-[4-(8-amino-1-iodoimidazo[1,5-a]pyrazin-3-yl)cyclohexyl]methanol in place of 8-amino-3-cyclobutyl-1-iodoimidazo[3,4-a]pyrazine. MS (ES+): m/z 362.07 [MH+].

EXAMPLE 15

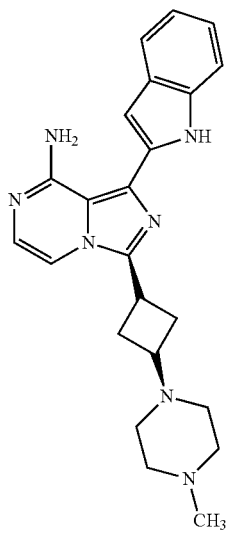

1-(1H-Indol-2-yl)-3-[cis-3-(4-methylpiperazin-1-yl)cyclobutyl]imidazo[1,5-a]pyrazin-8-amine Prepared according to the procedure described in EXAMPLE 2 using 1-iodo-3-[3-(4-methyl-piperazin-1-yl)cyclobutyl]imidazo[1,5-a]pyrazin-8-ylamine in place of 8-amino-3-cyclobutyl-1-iodoimidazo[3,4-a]pyrazine. MS (ES+): m/z 402.10 [MH+].

EXAMPLE 16

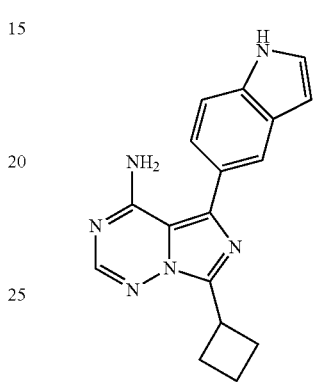

7-Cyclobutyl-5-(1H-indol-5-yl)imidazo[5,1-f][1,2,4]triazin-4-amine

Prepared according to the procedure described in EXAMPLE 1 using 7-cyclobutyl-5-iodoimidazo[5,1-f][1,2,4]triazin-4-ylamine in place of 8-amino-3-cyclobutyl-1-iodoimidazo[3,4-a]pyrazine. MS (ES+): m/z 305.16 [MH+].

EXAMPLE 17

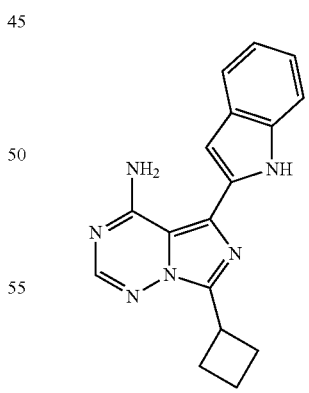

7-Cyclobutyl-5-(1H-indol-2-yl)imidazo[5,1-f][1,2,4]triazin-4-amine

Prepared according to the procedure described in EXAMPLE 2 using 7-cyclobutyl-5-iodoimidazo[5,1-f][1,2, 4]triazin-4-ylamine in place of 8-amino-3-cyclobutyl-1-iodoimidazo[3,4-a]pyrazine. MS (ES+): m/z 305.07 [MH⁺].

EXAMPLE 18

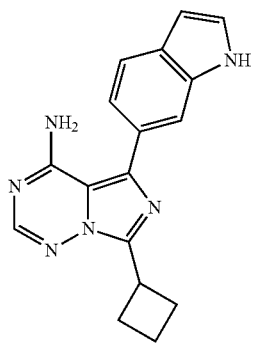 [SMILES: Nc1ncnn2c(C3CCC3)nc(-c3ccc4cc[nH]c4c3)c12]

7-Cyclobutyl-5-(1H-indol-6-yl)imidazo[5,1-f][1,2,4]triazin-4-amine

Prepared according to the procedure described in EXAMPLE 7 using 7-cyclobutyl-5-iodoimidazo[5,1-f][1,2,4]triazin-4-ylamine in place of 8-amino-3-cyclobutyl-1-iodoimidazo[3,4-a]pyrazine. MS (ES+): m/z 305.07 [MH+].

EXAMPLE 19

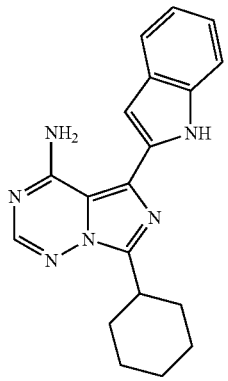 [SMILES: Nc1ncnn2c(C3CCCCC3)nc(-c3cc4ccccc4[nH]3)c12]

7-Cyclohexyl-5-(1H-indol-2-yl)imidazo[5,1-f][1,2,4]triazin-4-amine

Prepared according to the procedure described in EXAMPLE 2 using 7-cyclohexyl-5-iodoimidazo[5,1-f][1,2,4]triazin-4-amine in place of 8-amino-3-cyclobutyl-1-iodoimidazo[3,4-a]pyrazine. ¹H NMR (400 MHz-DMSO-d6) δ 1.40-1.54 (m, 4H), 1.72-1.82 (m, 2H), 1.87-1.92 (m, 2H), 2.02-2.09 (m, 2H) 3.31-3.38 (m, 1H) 6.26 (bs, 2H) 6.73-6.74 (m, 1H), 7.13-7.17 (m, 1H), 7.22-7.25 (m, 1H), 7.44 (d, J=8.0 Hz, 1H) 7.64 (d, J=8.0 Hz, 1H), 7.91 (s, 1H), 9.18 (s, 1H). MS (ES+): m/z: 333.16 (100) [MH+]. HPLC: t$_R$=3.46 min (OpenLynx: polar_5 min).

EXAMPLE 20

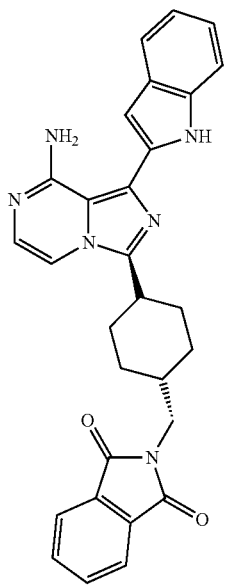

A mixture of {trans-4-[8-amino-1-(1H-indol-2-yl)imidazo[1,5-a]pyrazin-3-yl]cyclohexyl}methanol (400 mg, 0.001 mol), phthalimide (211.7 mg, 0.001439 mol), and triphenylphosphine resin (2.14 mmol/g loading; 1.03 g, 0.00221 mol; Argonaut) in THF (22 mL, 0.27 mol; Aldrich) was placed under nitrogen atmosphere and charged dropwise with diisopropyl azodicarboxylate (290.9 mg, 0.001439 mol). After 16 h, the resin was filtered off, washed with chloroform (5×20 mL) and the filtrate concentrated in vacuo to yield an orange oil which was chromatographed over silica gel eluting with chloroform→5% MeOH/chloroform to afford the title compound. ¹H NMR (CDCl₃, 400 MHz): δ 7.90-7.85 (m, 2H), 7.77-7.70 (m, 2H), 7.64 (m, 1H), 7.43 (dd, J=8.0, 0.8 Hz, 1H), 7.27-7.15 (m, 2H), 7.14 (m, 1H), 7.09 (d, J=4.8 Hz, 1H), 6.77 (br s, 1H), 3.64 (d, J=6.4 Hz, 2H), 2.91 (m, 1H), 2.09 (m, 2H), 2.25-1.90 (m, 4H), 1.80 (ddd, J=13.2, 12.4, 2.4 Hz, 2H), 1.27 (ddd, J=13.2, 12.4, 2.4 Hz, 2H). MS (ES+): m/z 491.09 [MH+].

EXAMPLE 21

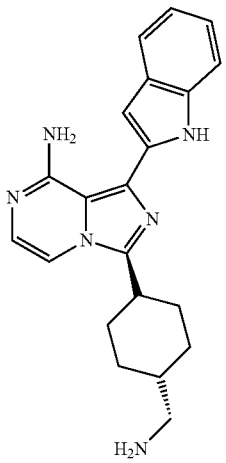

1-{trans-4-[8-Amino-1-(1H-indol-2-yl)imidazo[1,5-a]pyrazin-3-yl]cyclohexyl}methanamine A solution of benzyl {[trans-4-(8-amino-1-(1H-indol-2-yl)imidazo[1,5-a]pyrazin-3-yl)cyclohexyl]methyl}carbamate (0.163 g, 0.330 mmol) in conc. HCl (5 ml) was stirred at rt overnight. The reaction mixture was diluted with H₂O (20 mL), washed with Et₂O (30 mL), then basified with 1N NaOH (aq) and extracted with DCM (3×20 mL). The combined extracts were washed with water then dried over Na₂SO₄ and concentrated in vacuo To afford 0.085 g of desired compound. MS (ES+): m/z 361.30 [MH+].

EXAMPLE 22

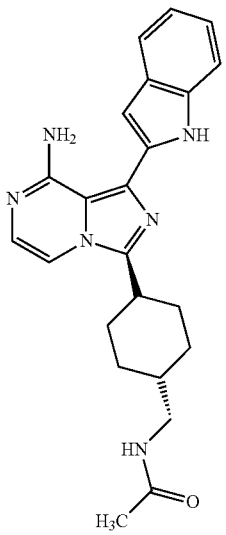

N-({trans-4-[8-Amino-1-(1H-indol-2-yl)imidazo[1,5-a]pyrazin-3-yl]cyclohexyl}methyl)acetamide To a suspension of 1-{trans-4-[8-amino-1-(1H-indol-2-yl)imidazo[1,5-a]pyrazin-3-yl]cyclohexyl}methanamine (100.00 mg, 0.27 mmol), N-(3-dimethylaminopropyl)-N'-ethylcarbodiimide hydrochloride (0.0798 g, 0.416 mmol), N,N-diisopropylethylamine (0.097 mL, 0.55 mmol), 1-hydroxbenzotriaxole Hydrate (0.0425 g, 0.277 mmol), and DMF (600 uL) in DCM (5 mL) was added AcOH (24 uL). The mixture was stirred at rt for 3 h under an atmosphere of nitrogen then diluted with DCM (20 mL), washed with saturated NaHCO₃ (aq) (2×25 mL) and brine (2×25 mL), then dried over Na₂SO₄, filtered and concentrated in vacuo. The residue was chromatographed over silica gel eluting with DCM→2% 2M NH₃ in MeOH/DCM to afford 0.02 g of the title compound. MS (ES+): m/z 403.31 [MH+]. ¹H NMR (400 MHz, CDCl₃): δ 1.12-1.31 (m, 3H), 1.79-1.86 (m, 2H), 1.94-1.97 (m, 2H), 2.02 (s, 3H), 2.04-2.09 (m, 2H), 2.91 (m, 1H), 3.20 (t, J=6.4 Hz, 2H), 5.51 (br, 1H), 5.66 (br, 2H), 6.79 (s, 1H), 7.10-7.16 (m, 2H), 7.20-7.25 (m, 2H), 7.43 (d, J=8.4 Hz, 1H), 7.44 (d, J=7.6 Hz, 1H), 9.07 (br, 1H).

EXAMPLE 23

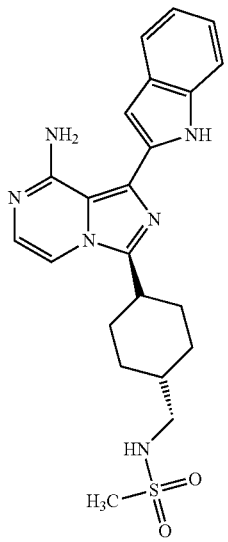

N-({4-[8-amino-1-(1H-indol-2-yl)imidazo[1,5-a]pyrazin-3-yl]cyclohexyl}methyl)methanesulfonamide Methanesulfonyl chloride (4.40 μL, 0.057 mmol was added to a mixture of 1-{trans-4-[8-amino-1-(1H-indol-2-yl)imidazo[1,5-a]pyrazin-3-yl]cyclohexyl}methanamine (20.5 mg, 0.057 mol) and PS-DIEA (3.90 mmol/g loading; 60 mg, 0.2 mmol) in DCM (1.14 mL). The reaction mixture was stirred for 30 min at r.t. for 18 h. The crude reaction mixture was then concentrated and residue purified by mass directed preparative HPLC to afford 4 mg of desired product. MS (ES+): m/z 439.10 (100) [MH+]. ¹H NMR (CD3OD, 400 MHz): δ 8.24 (br s, 2H), 7.61 (m, 2H), 7.46 (dd, J=8.4, 0.8 Hz, 1H), 7.19 (ddd, J=7.2, 1.2, 1.2 Hz, 1H), 7.08 (ddd, J=7.2, 1.2, 1.2 Hz, 1H), 6.75 (d, J=0.8 Hz, 1H), 3.14 (m, 1H), 2.07 (m, 4H), 1.85 (m, 2H), 1.64 (m, 1H), 1.26 (m, 2H).

EXAMPLE 24

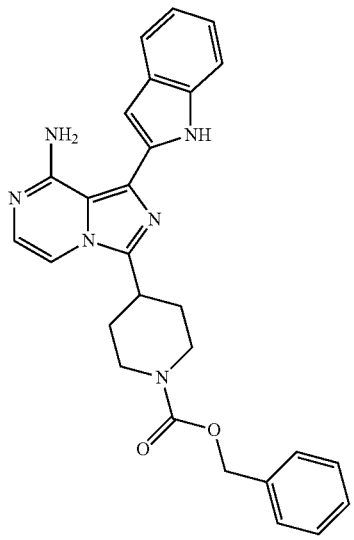 [SMILES: Nc1nccn2c(C3CCN(C(=O)OCc4ccccc4)CC3)nc(-c3cc4ccccc4[nH]3)c12]

Benzyl 4-[8-amino-1-(1H-indol-2-yl)imidazo[1,5-a]pyrazin-3-yl]piperidine-1-carboxylate A mixture of benzyl 4-(8-amino-1-iodoimidazo[1,5-a]pyrazin-3-yl)piperidine-1-carboxylate (1.149 g, 0.002191 mol), 1-(tert-butoxycarbonyl)-1H-indole-2-boronic acid (0.629 g, 0.00241 mol), 1,2-dimethoxyethane (9.3 mL), water (1.8 mL) and cesium carbonate (1.43 g, 0.00438 mol) was degassed three times and then treated with tetrakis(triphenyl phosphine)palladium(0) (200 mg, 0.0002 mol). The mixture was once more degassed and then heated at 100° C. overnight. The resulting reaction mixture was diluted with EtOAc (30 mL) then washed with water (2×30 mL) and brine, dried over $Na_2SO_4$ and concentrated in vacuo. The crude product was chromatographed over silica gel eluting with hexane→EtOAc:hexane 1:1:0.05 2M $NH_3$/MeOH to afford the desired product. $^1$H NMR (400 MHz, $CDCl_3$): δ 2.02-2.06 (m, 4H), 3.03-3.17 (m, 3H), 4.29-4.33 (m, 2H), 5.16 (s, 2H), 5.66 (br, 2H), 6.79-6.80 (m, 1H), 7.11-7.16 (m, 2H), 7.20-7.25 (m, 2H), 7.31-7.45 (m, 5H), 7.44 (m, 1H), 7.64 (d, J=7.6 Hz, 1H), 8.96 (br, 1H). MS (ES+): m/z 467.12 [MH+].

EXAMPLE 25

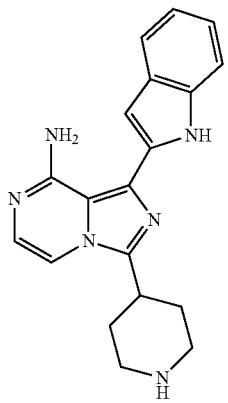 [SMILES: Nc1nccn2c(C3CCNCC3)nc(-c3cc4ccccc4[nH]3)c12]

1-(1H-Indol-2-yl)-3-piperidin-4-ylimidazo[1,5-a]pyrazin-8-amine

A solution of benzyl 4-[8-amino-1-(1H-indol-2-yl)imidazo[1,5-a]pyrazin-3-yl]piperidine-1-carboxylate (3.61 g, 0.00774 mol) in conc. HCl (100 ml) was stirred at rt overnight. The mixture was then diluted with water (200 mL), washed with $Et_2O$ (2×30 mL) then the aqueous layer concentrated in vacuo yielding 2.62 g of desired product as the trihydrochloride salt. $^1$H NMR (400 MHz, MeOD): δ 2.19-2.32 (m, 4H), 3.26-3.30 (m, 2H), 3.53-3.36 (m, 2H), 3.70 (m, 1H), 7.06 (d, J=5.6 Hz, 1H), 7.10-7.14 (m, 1H), 7.23-7.26 (m, 2H), 7.50-7.52 (m, 1H), 7.67 (m, 1H), 7.93 (m, 1H). MS (ES+): m/z 333.27 [MH+].

EXAMPLE 26

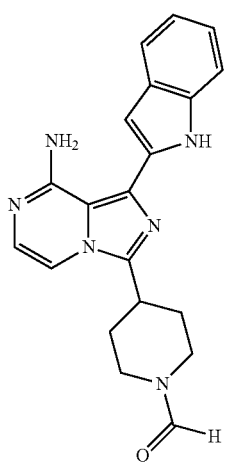 [SMILES: Nc1nccn2c(C3CCN(C=O)CC3)nc(-c3cc4ccccc4[nH]3)c12]

4-[8-Amino-1-(1H-indol-2-yl)imidazo[1,5-a]pyrazin-3-yl]piperidine-1-carbaldehyde To a solution of 1-(1H-Indol-2-yl)-3-piperidin-4-ylimidazo[1,5-a]pyrazin-8-amine hydrochloride (30.00 mg, 0.0068 mmol) in DCM (0.5 mL, 0.008 mol) was added N-(3-dimethylaminopropyl)-N-ethylcarbodiimide hydrochloride (0.0195 g, 0.102 mmol), N,N-diisopropylethylamine (0.047 mL), 1-hydroxbenzotriaxole hydrate (0.0104 g, 0.0679 mmol) and formic acid (4.7 mg, 0.10 mmol). The reaction was stirred at rt overnight then diluted with DCM, washed with saturated NaHCO$_3$ (2×25 mL) and brine (2×25), then dried over Na$_2$SO$_4$ and concentrated in vacuo. The material thus isolated was crystallized from EtOAc to afford 10.6 mg of desired product. $^1$H NMR (400 MHz, CDCl$_3$): δ 2.04-2.12 (m, 4H), 2.99-3.00 (m, 1H), 3.27-3.32 (m, 2H), 3.85 (m, 1H), 4.49 (m, 1H), 5.70 (br, 2H), 6.80 (s, 1H), 7.13-7.24 (m, 4H), 7.45 (d, J=8.4 Hz, 1H), 7.65 (d, J=8.0 Hz, 1H), 8.10 (s, 1H), 8.97 (br, 1H). MS (ES+): m/z 361.16 [MH+].

EXAMPLE 27

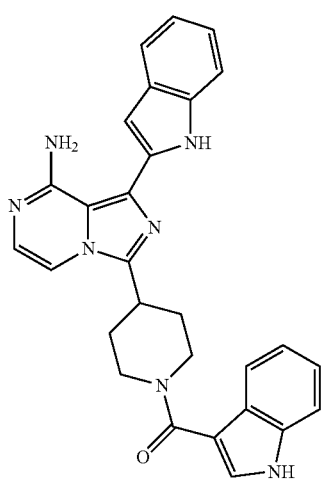 [SMILES: Nc1nccn2c(C3CCN(C(=O)c4c[nH]c5ccccc45)CC3)nc(-c3cc4ccccc4[nH]3)c12]

3-[1-(1H-Indol-3-ylcarbonyl)piperidin-4-yl]-1-(1H-indol-2-yl)imidazo[1,5-a]pyrazin-8-amine Prepared according to the procedure described above for EXAMPLE 26, except using indole-3-carboxylic acid in place of formic acid. MS (ES+): m/z 476.18 [MH+].

EXAMPLE 28

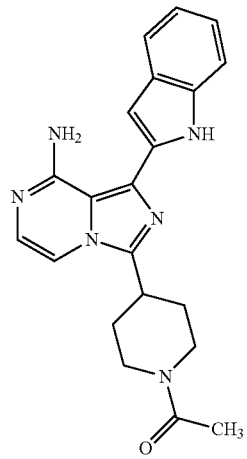 [SMILES: CC(=O)N1CCC(c2nc(-c3cc4ccccc4[nH]3)c3c(N)nccn23)CC1]

3-(1-Acetylpiperidin-4-yl)-1-(1H-indol-2-yl)imidazo[1,5-a]pyrazin-8-amine

Prepared according to the procedure described above for EXAMPLE 26, except using acetic acid in place of formic acid. MS (ES+): m/z 375.17 [MH+].

EXAMPLE 29

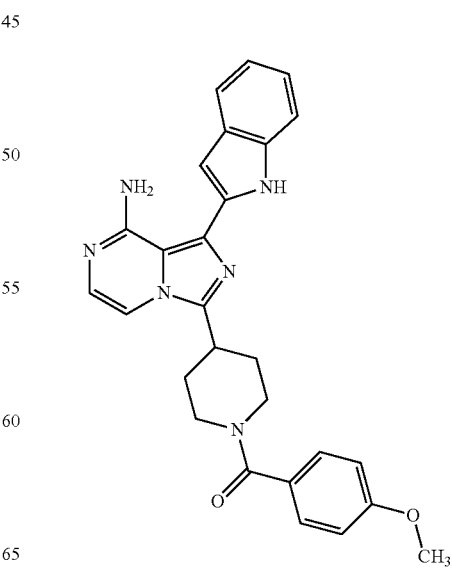

167

3-[1-(4-Methoxybenzoyl)piperidin-4-yl]-1-(1H-indol-2-yl)imidazo[1,5-a]pyrazin-8-amine Prepared according to the procedure described above for EXAMPLE 26, except using 4-methoxybenzoic acid in place of formic acid. MS (ES+): m/z 467.27 [MH+].

EXAMPLE 30

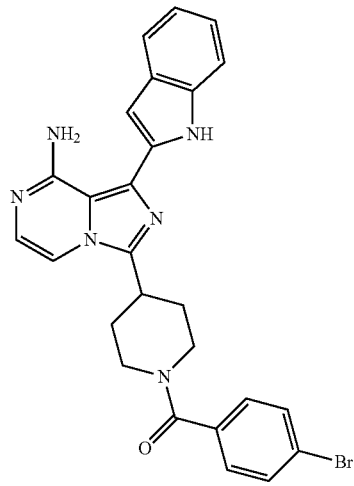 [SMILES: Nc1nccn2c(C3CCN(C(=O)c4ccc(Br)cc4)CC3)nc(-c3cc4ccccc4[nH]3)c12]

3-[1-(4-Bromobenzoyl)piperidin-4-yl]-1-(1H-indol-2-yl)imidazo[1,5-a]pyrazin-8-amine Prepared according to the procedure described above for EXAMPLE 26, except using 4-methoxybenzoic acid in place of formic acid. MS (ES+): m/z 515.17 & 517.17 [MH+].

EXAMPLE 31

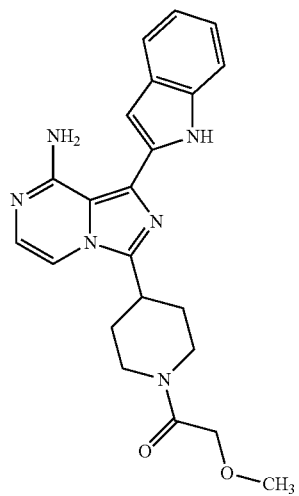 [SMILES: COCC(=O)N1CCC(c2nc(-c3cc4ccccc4[nH]3)c3c(N)nccn23)CC1]

168

1-(1H-Indol-2-yl-3-[1-(methoxyacetyl)piperidin-4-yl]imidazo[1,5-a]pyrazin-8-amine Prepared according to the procedure described above for EXAMPLE 26, except using 2-methoxyacetic acid in place of formic acid. MS (ES+): m/z 405.10 [MH+].

EXAMPLE 32

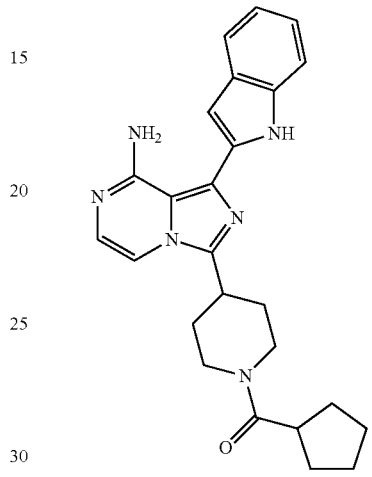

3-[1-(Cyclopentylcarbonyl)piperidin-4-yl]-1-(1H-indol-2-yl)imidazo[1,5-a]pyrazin-8-amine Prepared according to the procedure described above for EXAMPLE 26, except using cyclopentanecarboxylic acid in place of formic acid. MS (ES+): m/z 429.07 [MH+].

EXAMPLE 33

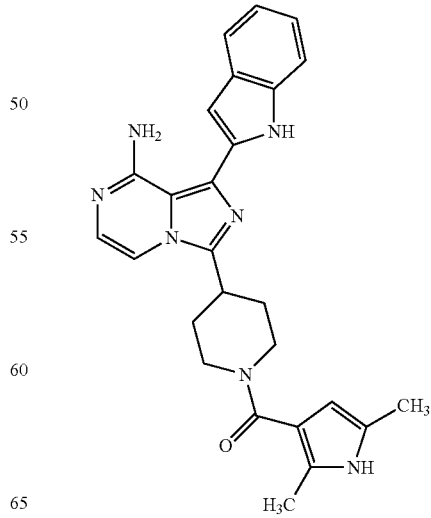

3-{1-[(2,5-Dimethyl-1H-pyrrol-3-yl)carbonyl]piperidin-4-yl}-1-(1H-indol-2-yl)imidazo[1,5-a]pyrazin-8-amine Prepared according to the procedure described above for EXAMPLE 26, except using 2,5-dimethylpyrrolecarboxylic acid in place of formic acid. MS (ES+): m/z 454.19 [MH+].

EXAMPLE 34

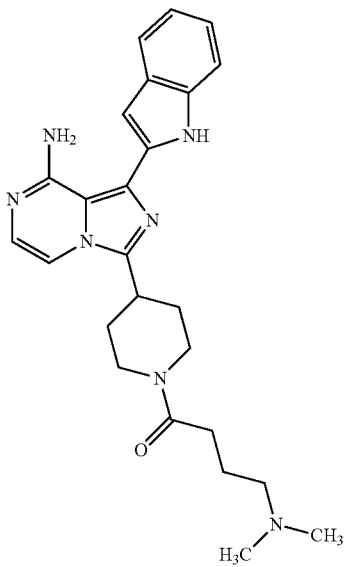 [SMILES: CN(C)CCCC(=O)N1CCC(c2nc(-c3cc4ccccc4[nH]3)c3c(N)nccn23)CC1]

3-{1-[4-(Dimethylamino)butanoyl]piperidin-4-yl}-1-(1H-indol-2-yl) imidazo[1,5-a]pyrazin-8-amine Prepared according to the procedure described above for EXAMPLE 26, except using 4-(dimethylamino)butanoic acid in place of formic acid. MS (ES+): m/z 446.22 [MH+].

EXAMPLE 35

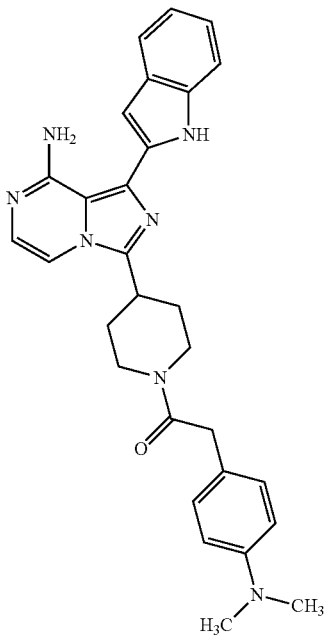 [SMILES: CN(C)c1ccc(CC(=O)N2CCC(c3nc(-c4cc5ccccc5[nH]4)c4c(N)nccn34)CC2)cc1]

3-{1-[4-(Dimethylamino)phenacyl]piperidin-4-yl}-1-(1H-indol-2-yl)imidazo[1,5-a]pyrazin-8-amine Prepared according to the procedure described above for EXAMPLE 26, except using 4-(dimethylamino)phenylacetic acid in place of formic acid. MS (ES+): m/z 480.22 [MH+].

EXAMPLE 36

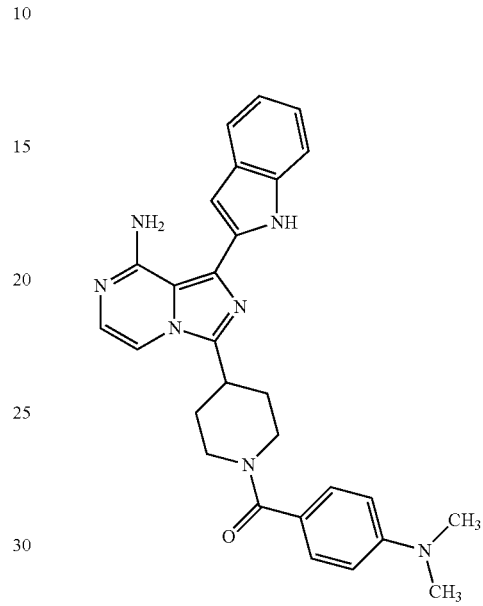

3-{1-[4-(Dimethylamino)benzoyl]piperidin-4-yl}-1-(1H-indol-2-yl)imidazo[1,5-a]pyrazin-8-amine Prepared according to the procedure described above for EXAMPLE 26, except using 4-(dimethylamino)benzoic acid in place of formic acid. MS (ES+): m/z 480.22 [MH+].

EXAMPLE 37

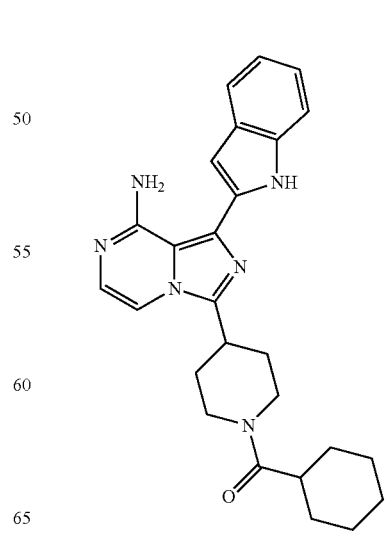

3-[1-(Cyclohexylcarbonyl)piperidin-4-yl]-1-(1H-indol-2-yl)imidazo[1,5-a]pyrazin-8-amine Prepared according to the procedure described above for EXAMPLE 26, except using cyclohexanecarboxylic acid in place of formic acid. MS (ES+): m/z 443.20 [MH+].

EXAMPLE 38

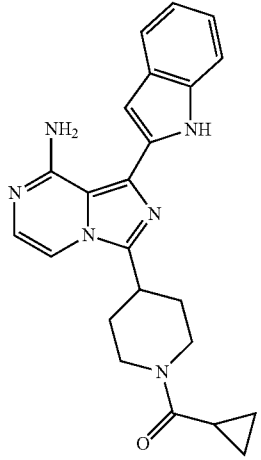 [SMILES: Nc1nccn2c(C3CCN(C(=O)C4CC4)CC3)nc(-c3cc4ccccc4[nH]3)c12]

3-[1-(Cyclopropylcarbonyl)piperidin-4-yl]-1-(1H-indol-2-yl)imidazo[1,5-a]pyrazin-8-amine Prepared according to the procedure described above for EXAMPLE 26, except using cyclopropanecarboxylic acid in place of formic acid. MS (ES+): m/z 401.19 [MH+].

EXAMPLE 39

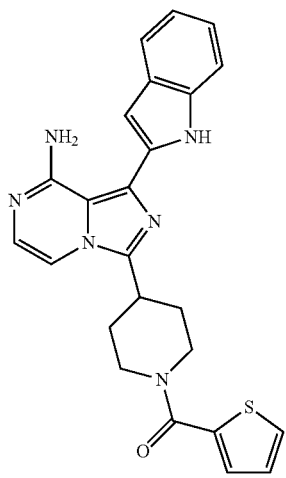

1-(1H-Indol-2-yl)-3-[1-(2-thienylcarbonyl)piperidin-4-yl]imidazo[1,5-a]pyrazin-8-amine Prepared according to the procedure described above for EXAMPLE 26, except using thiophene-2-carboxylic acid in place of formic acid. MS (ES+): m/z 443.22 [MH+].

EXAMPLE 40

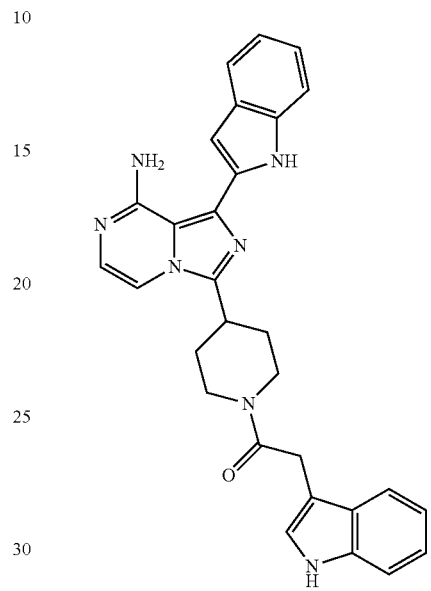

3-[1-(1H-Indol-3-ylacetyl)piperidin-4-yl]-1-(1H-indol-2-yl)imidazo[1,5-a]pyrazin-8-amine Prepared according to the procedure described above for EXAMPLE 26, except using indole-3-acetic acid in place of formic acid. MS (ES+): m/z 490.10 [MH+].

EXAMPLE 41

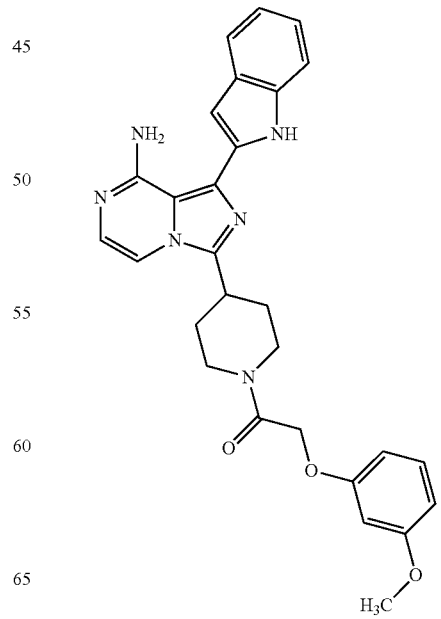

1-(1H-Indol-2-yl)-3-{1-[(3-methoxyphenoxy)acetyl]piperidin-4-yl}imidazo[1,5-a]pyrazin-8-amine Prepared according to the procedure described above for EXAMPLE 26, except using (3-methoxyphenoxy)acetic acid in place of formic acid. MS (ES+): m/z 497.11 [MH+].

EXAMPLE 42

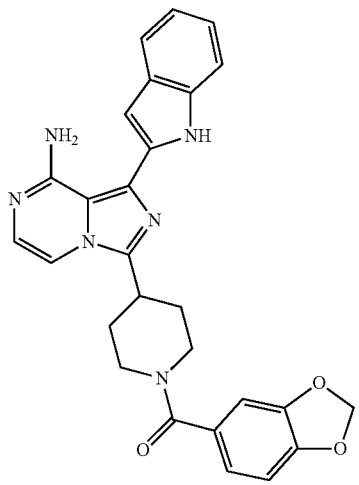 [SMILES: Nc1nccn2c(C3CCN(C(=O)c4ccc5c(c4)OCO5)CC3)nc(-c3cc4ccccc4[nH]3)c12]

3-[1-(1,3-Benzodioxol-5-ylcarbonyl)piperidin-4-yl]-1-(1H-indol-2-yl)imidazo[1,5-a]pyrazin-8-amine Prepared according to the procedure described above for EXAMPLE 26, except using 1,3-benzodioxole-5-carboxylic acid in place of formic acid. MS (ES+): m/z 481.05 [MH+].

EXAMPLE 43

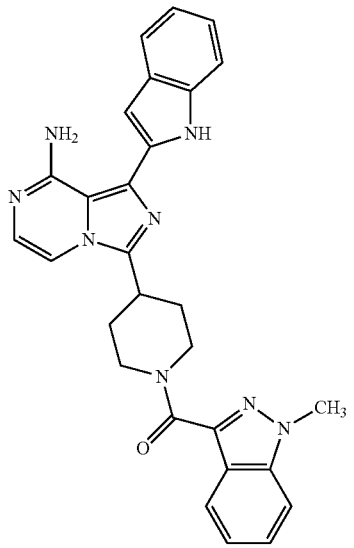 [SMILES: Cn1nc(C(=O)N2CCC(c3nc(-c4cc5ccccc5[nH]4)c4c(N)nccn34)CC2)c2ccccc21]

1-(1H-Indol-2-yl)-3-{1-[(1-methyl-1H-indazol-3-yl)carbonyl]piperidin-4-yl}imidazo[1,5-a]pyrazin-8-amine Prepared according to the procedure described above for EXAMPLE 26, except using 1-methyl-1H-indazole-3-carboxylic acid in place of formic acid. MS (ES+): m/z 491.04 [MH+].

EXAMPLE 44

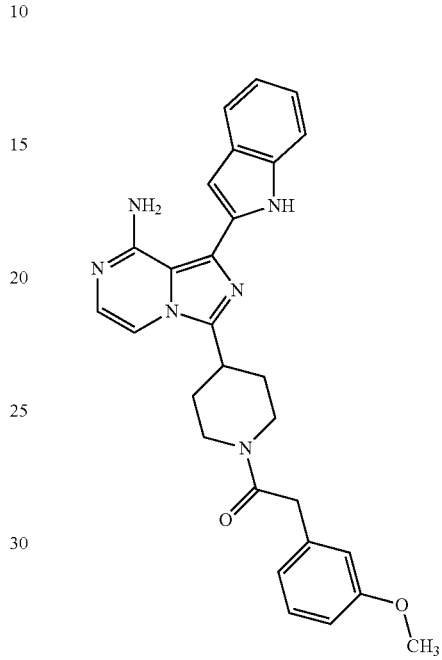

1-(1H-Indol-2-yl)-3-{1-[(3-methoxyphenyl)acetyl]piperidin-4-yl}imidazo[1,5-a]pyrazin-8-amine Prepared according to the procedure described above for EXAMPLE 26, except using 3-methoxyphenylacetic acid in place of formic acid. MS (ES+): m/z 481.09 [MH+].

EXAMPLE 45

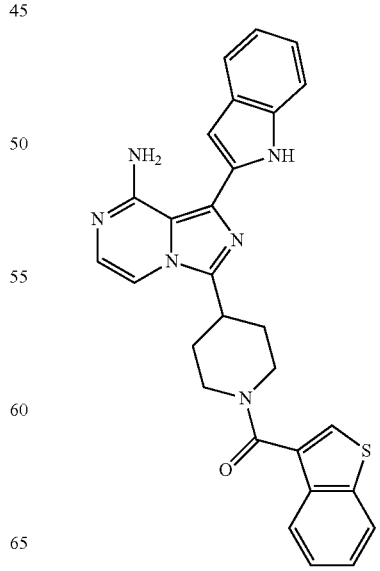

3-[1-(1-Benzothien-3-ylcarbonyl)piperidin-4-yl]-1-iodoimidazo[1,5-a]pyrazin-8-amine Prepared according to the procedure described above for EXAMPLE 26, except using benzothiophene-3-carboxylic acid in place of formic acid. MS (ES+): m/z 493.01 [MH+].

EXAMPLE 46

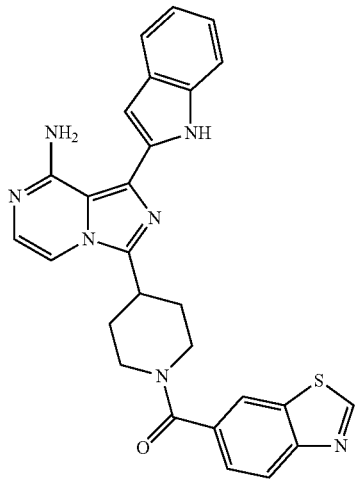 [SMILES: Nc1nccn2c(C3CCN(C(=O)c4ccc5ncsc5c4)CC3)nc(-c3cc4ccccc4[nH]3)c12]

3-[1-(1,3-Benzothiazol-6-ylcarbonyl)piperidin-4-yl]-1-iodoimidazo[1,5-a]pyrazin-8-amine Prepared according to the procedure described above for EXAMPLE 26, except using benzothiazole-6-carboxylic acid in place of formic acid. MS (ES+): m/z 494.01 [MH+].

EXAMPLE 47

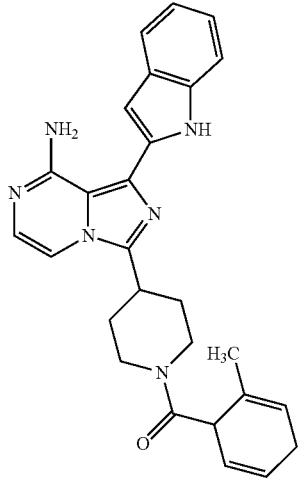 [SMILES: CC1=CCC=CC1C(=O)N1CCC(c2nc(-c3cc4ccccc4[nH]3)c3c(N)nccn23)CC1]

1-(1H-Indol-2-yl)-3-{1-[(2-methylcyclohexa-2,5-dien-1-yl)carbonyl]piperidin-4-yl}imidazo[1,5-a]pyrazin-8-amine Prepared according to the procedure described above for EXAMPLE 26, except using 2-methylcyclohexa-2,5-diene-1-carboxylic acid in place of formic acid. MS (ES+): m/z 453.08 [MH+].

EXAMPLE 48

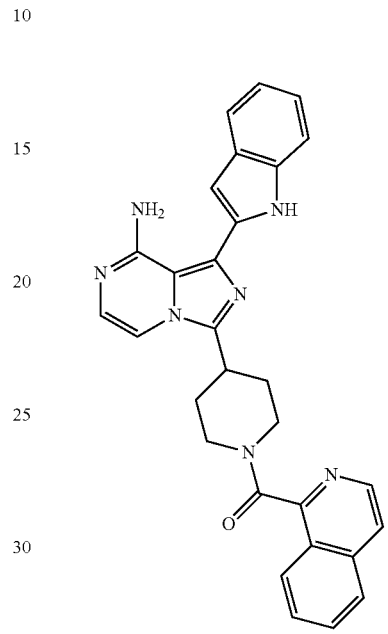

1-(1H-Indol-2-yl)-3-[1-(isoquinolin-1-ylcarbonyl)piperidin-4-yl]imidazo[1,5-a]pyrazin-8-amine Prepared according to the procedure described above for EXAMPLE 26, except using isoquinoline-1-carboxylic acid in place of formic acid. MS (ES+): m/z 488.01 [MH+].

EXAMPLE 49

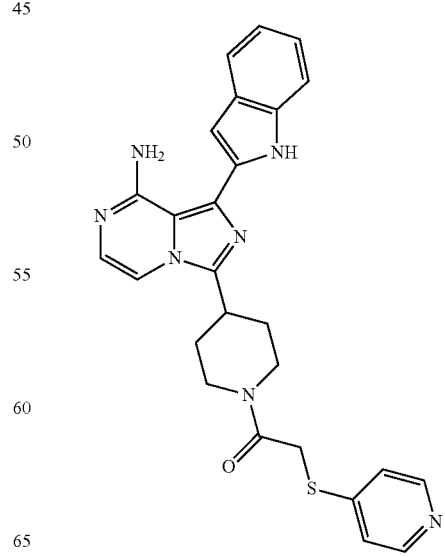

1-(1H-Indol-2-yl)-3-{1-[(pyridin-4-ylthio)acetyl]piperidin-4-yl}imidazo[1,5-a]pyrazin-8-amine Prepared according to the procedure described above for EXAMPLE 26, except using (pyridin-4-ylthio)acetic acid in place of formic acid. MS (ES+): m/z 484.04 [MH+].

EXAMPLE 50

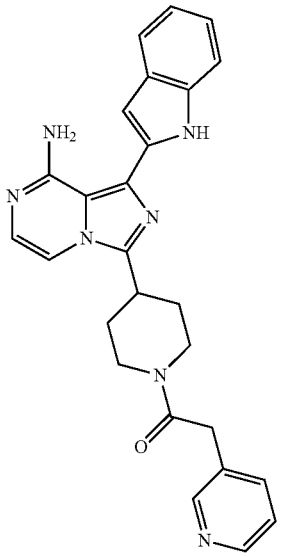 [SMILES: Nc1nccn2c(C3CCN(C(=O)Cc4cccnc4)CC3)nc(-c3cc4ccccc4[nH]3)c12]

1-(1H-Indol-2-yl)-3-[1-(pyridin-3-ylacetyl)piperidin-4-yl]imidazo[1,5-a]pyrazin-8-amine Prepared according to the procedure described above for EXAMPLE 26, except using pyridin-3-ylacetic acid in place of formic acid. MS (ES+): m/z 452.07 [MH+].

EXAMPLE 51

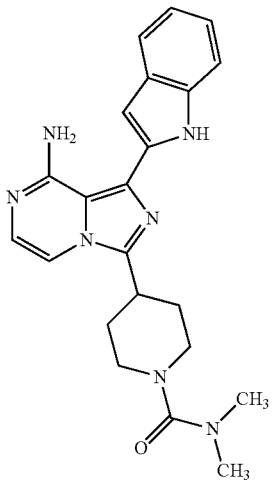 [SMILES: CN(C)C(=O)N1CCC(c2nc(-c3cc4ccccc4[nH]3)c3c(N)nccn23)CC1]

4-(8-Amino-1-(1H-indol-2-yl)imidazo[1,5-a]pyrazin-3-yl)-N,N-dimethylpiperidine-1-carboxamide A mixture of 1-(1H-indol-2-yl)-3-piperidin-4-ylimidazo[1,5-a]pyrazin-8-amine hydrochloride (30.0 mg, 0.0679 mmol), N,N-diisopropylethylamine (59.1 μL, 0.340 mmol) and DMF (1.00 mL) was treated with N,N-dimethylcarbamoyl chloride (6.23 μL, 0.0679 mmol) and stirred at rt for 1 h prior to semi-preparative HPLC to afford the isolated title compound. $^1$H NMR (400 MHz, CD$_3$OD) ppm: 8.32 (br. s., 1H), 7.59-7.66 (m, 2H), 7.46 (d, 1H, J=8.3 Hz), 7.15-7.22 (m, 1H), 7.01-7.10 (m, 2H), 6.74 (s, 1H), 3.82 (d, 2H, J=12.6 Hz), 3.34-3.42 (m, 1H), 2.97-3.09 (m, 2H), 2.87 (s, 6H), 1.95-2.09 (m, 4H); MS (ES+): m/z 404.14 [MH+].

EXAMPLE 52

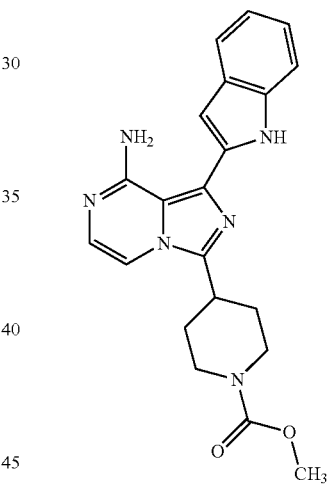

Methyl 4-(8-amino-1-(1H-indol-2-yl)imidazo[1,5-a]pyrazin-3-yl)piperidine-1-carboxylate A mixture of 1-(1H-indol-2-yl)-3-piperidin-4-ylimidazo[1,5-a]pyrazin-8-amine hydrochloride (30.0 mg, 0.0679 mmol), N,N-diisopropylethylamine (59.1 μL, 0.340 mmol) and DMF (1.00 mL) was treated with methyl chloroformate (5.25 μL, 0.0679 mmol) and stirred at rt for 1 h prior to semi-preparative HPLC to afford the isolation of the title compound. $^1$H NMR (400 MHz, CD$_3$OD) ppm: 8.32 (br. s., 1H), 7.58-7.66 (m, 2H), 7.46 (d, 1H, J=8.1 Hz), 7.14-7.22 (m, 1H), 7.00-7.12 (m, 2H), 6.73 (s, 1H), 4.26 (d, 2H, J=12.9 Hz), 3.71 (s, 3H), 3.33-3.37 (m, 1H), 2.9-3.17 (m, 2H), 1.85-2.06 (m, 4H); MS (ES+): m/z 391.06 [MH+].

EXAMPLE 53

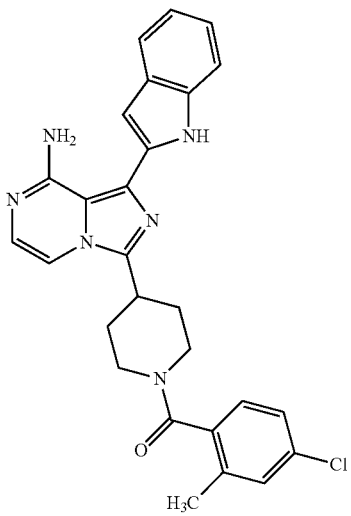 [SMILES: Cc1cc(Cl)ccc1C(=O)N1CCC(c2nc(-c3cc4ccccc4[nH]3)c3c(N)nccn23)CC1]

3-[1-(4-Chloro-2-methylbenzoyl)piperidin-4-yl]-1-(1H-indol-2-yl)imidazo[1,5-a]pyrazin-8-amine Prepared according to the procedure described above for EXAMPLE 26, except using 4-chloro-2-methylbenzoic acid in place of formic acid. MS (ES+): m/z 485.05 [MH+].

EXAMPLE 54

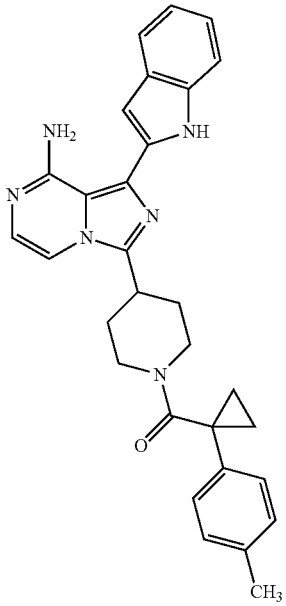 [SMILES: Cc1ccc(C2(C(=O)N3CCC(c4nc(-c5cc6ccccc6[nH]5)c5c(N)nccn45)CC3)CC2)cc1]

1-(1H-Indol-2-yl)-3-(1-{[1-(4-methylphenyl)cyclopropyl]carbonyl}piperidin-4-yl)imidazo[1,5-a]pyrazin-8-amine Prepared according to the procedure described above for EXAMPLE 26, except using 1-(4-methylphenyl)cyclopropanecarboxylic acid in place of formic acid. MS (ES+): m/z 491.11 [MH+].

EXAMPLE 55

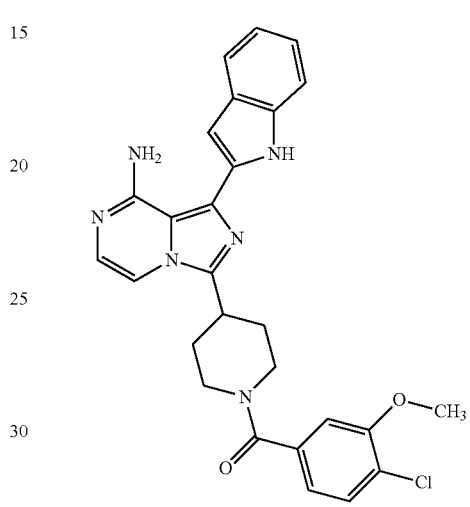

3-[1-(4-Chloro-3-methoxybenzoyl)piperidin-4-yl]-1-(1H-indol-2-yl)imidazo[1,5-a]pyrazin-8-amine Prepared according to the procedure described above for EXAMPLE 26, except using 4-chloro-3-methoxybenzoic acid in place of formic acid. MS (ES+): m/z 501.04 [MH+].

EXAMPLE 56

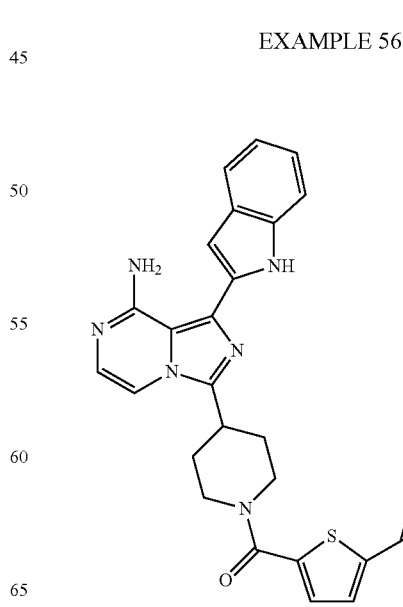

1-(5-{[4-(8-Amino-1-(1H-indol-2-yl)imidazo[1,5-a]pyrazin-3-yl)piperidin-1-yl]carbonyl}-2-thienyl)ethanone Prepared according to the procedure described above for EXAMPLE 26, except using 5-acetylthiophene-2-carboxylic acid in place of formic acid. MS (ES+): m/z 485.04 [MH+].

EXAMPLE 57

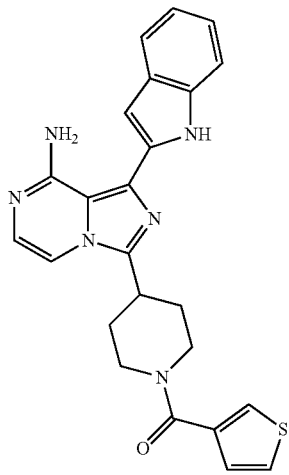 [SMILES: Nc1nccn2c(C3CCN(C(=O)c4ccsc4)CC3)nc(-c3cc4ccccc4[nH]3)c12]

1-(1H-Indol-2-yl)-3-[1-(3-thienylcarbonyl)piperidin-4-yl]imidazo[1,5-a]pyrazin-8-amine Prepared according to the procedure described above for EXAMPLE 26, except using thiophene-3-carboxylic acid in place of formic acid. MS (ES+): m/z 443.04 [MH+].

EXAMPLE 58

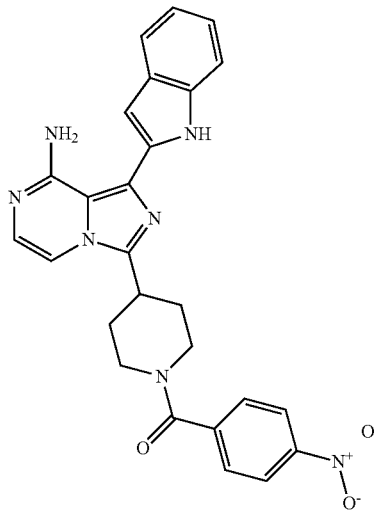

1-(1H-Indol-2-yl)-3-[1-(4-nitrobenzoyl)piperidin-4-yl]-imidazo[1,5-a]pyrazin-8-amine Prepared according to the procedure described above for EXAMPLE 26, except using 4-nitrobenzoic acid in place of formic acid. MS (ES+): m/z 482.07 [MH+].

EXAMPLE 59

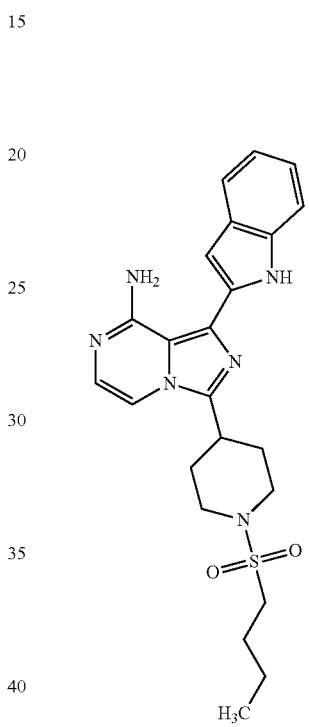

3-[1-(Butylsulfonyl)piperidin-4-yl]-1-(1H-indol-2-yl)imidazo[1,5-a]pyrazin-8-amine A solution of 1-(1H-indol-2-yl)-3-piperidin-4-ylimidazo[1,5-a]pyrazin-8-amine hydrochloride (33.23 mg, 0.075 mmol) in DMF (1 mL) was treated with N,N-diisopropylethylamine (0.05 mL, 0.3 mmol) and a solution of "butanesulfonyl chloride (9.42 mg, 0.0602 mmol) in 1 mL of DMF. The mixture was left to stir at rt for 1 h and then subjected to mass-directed preparative HPLC to afford the title compound. $^1$H NMR (400 MHz-DMSO-d6) δ 0.91 (t, 3H), 1.40-1.45 (m, 2H), 1.66-1.69 (m, 2H), 1.86-1.90 (m, 2H) 2.04-2.09 (m, 2H) 3.02-3.11 (m, 5H) 3.73-3.77 (m, 2H), 6.47 (bs, 2H), 6.64 (s, 1H), 7.00-7.05 (m, 1H) 7.09-7.12 (m, 2H), 7.45 (d, J=8.4 Hz, 1H), 7.58 (d, J=8.0 Hz, 1H), 7.69 (d, J=5.2 Hz, 1H). MS (ES+): m/z: 453.24 [MH+].

EXAMPLE 60

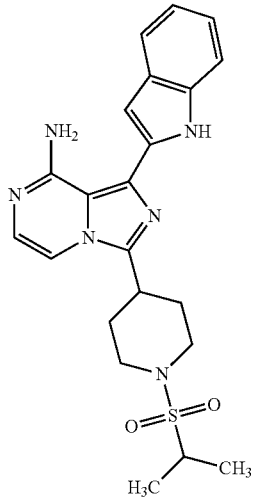 [SMILES: CC(C)S(=O)(=O)N1CCC(c2nc(-c3cc4ccccc4[nH]3)c3c(N)nccn23)CC1]

1-(1H-Indol-2-yl)-3-[1-(isopropylsulfonyl)piperidin-4-yl]imidazo[1,5-a]pyrazin-8-amine Prepared according to the procedure described above for EXAMPLE 59, except using isopropane-2-sulfonyl chloride in place of "butanesulfonyl chloride. MS (ES+): m/z 439.27 [MH+].

EXAMPLE 61

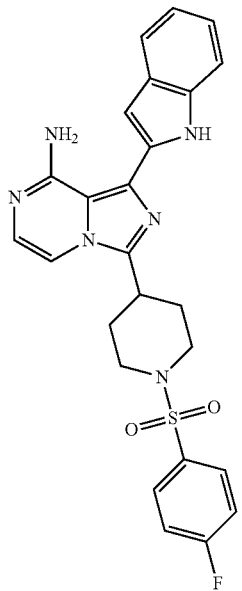 [SMILES: Nc1nccn2c(C3CCN(S(=O)(=O)c4ccc(F)cc4)CC3)nc(-c3cc4ccccc4[nH]3)c12]

3-{1-[(4-Fluorophenyl)sulfonyl]piperidin-4-yl}-1-(1H-indol-2-yl)imidazo[1,5-a]pyrazin-8-amine Prepared according to the procedure described above for EXAMPLE 59, except using 4-fluorobenzenesulfonyl chloride in place of "butanesulfonyl chloride. MS (ES+): m/z 491.15 [MH+].

EXAMPLE 62

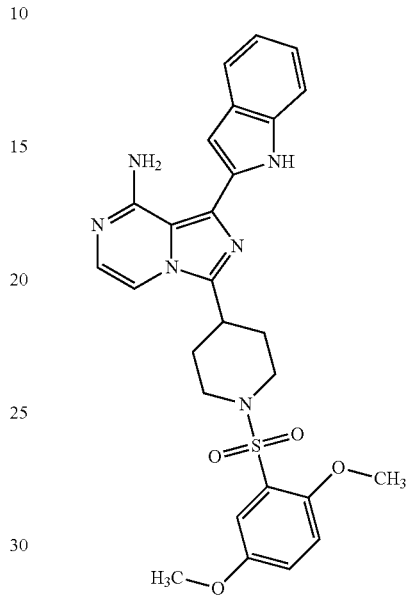

3-{1-[(2,5-Dimethoxyphenyl)sulfonyl]piperidin-4-yl}-1-(1H-indol-2-yl)imidazo[1,5-a]pyrazin-8-amine Prepared according to the procedure described above for EXAMPLE 59, except using 2,5-dimethoxybenzenesulfonyl chloride in place of "butanesulfonyl chloride. MS (ES+): m/z 533.17 [MH+].

EXAMPLE 63

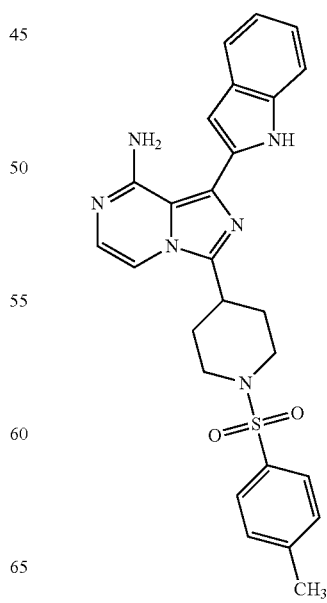

1-(1H-Indol-2-yl)-3-{1-[(4-methylphenyl)sulfonyl]piperidin-4-yl}imidazo[1,5-a]pyrazin-8-amine Prepared according to the procedure described above for EXAMPLE 59, except using 4-methylbenzenesulfonyl chloride in place of ⁿbutanesulfonyl chloride. MS (ES+): m/z 487.94 [MH+].

EXAMPLE 64

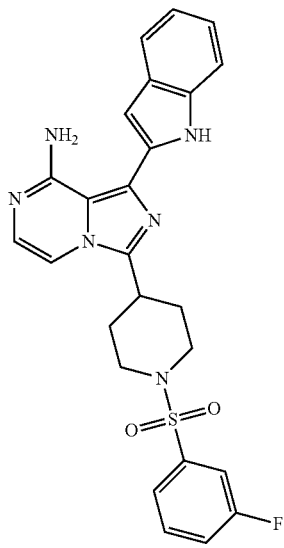 [SMILES: Nc1nccn2c(C3CCN(S(=O)(=O)c4cccc(F)c4)CC3)nc(-c3cc4ccccc4[nH]3)c12]

3-{1-[(3-Fluorophenyl)sulfonyl]piperidin-4-yl}-1-(1H-indol-2-yl)imidazo[1,5-a]pyrazin-8-amine Prepared according to the procedure described above for EXAMPLE 59, except using 3-fluorobenzenesulfonyl chloride in place of ⁿbutanesulfonyl chloride. MS (ES+): m/z 491.92 [MH+].

EXAMPLE 65

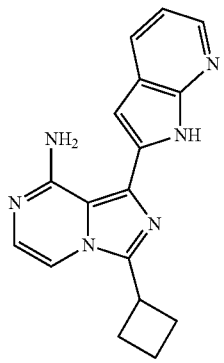 [SMILES: Nc1nccn2c(C3CCC3)nc(-c3cc4cccnc4[nH]3)c12]

3-Cyclobutyl-1-(1H-pyrrolo[2,3-b]pyridin-2-yl)imidazo[1,5-a]pyrazin-8-amine

3-Cyclobutyl-1-[1-(2-trimethylsilylethoxymethyl)-1H-pyrrolo[2,3-b]pyridin-2-yl]imidazo[1,5-a]pyrazin-8-amine (35 mg, 0.08 mmol) was stirred with concentrated HCl for 15 min. The mixture was then concentrated in vacuo and purified via mass directed preparative HPLC to afford the title compound. $^1$H NMR (400 MHz DMSO-d6) δ 1.92-2.00 (m, 1H), 2.07-2.14 (m, 1H), 2.43-2.47 (m, 4H), 3.93-4.01 (m, 1H), 6.35-6.49 (bs, 2H), 6.64-6.70 (m, 1H), 7.03-7.10 (m, 2H), 7.39-7.49 (m, 1H), 7.95-8.00 (m, 1H), 8.18-8.23 (m, 1H), 11.91 (bs, 1H). MS (ES+): m/z: 305.17 [MH+].

EXAMPLE 66

Methyl trans-4-(8-amino-1-(1H-indol-2-yl)imidazo[1,5-a]pyrazin-3-yl)cyclohexanecarboxylate Starting from trans-methyl 4-(8-chloroimidazo[1,5-a]pyrazin-3-yl)cyclohexanecarboxylate, the title compound was prepared according to procedures analogous to those described for EXAMPLE 10. $^1$H NMR (d$_6$-DMSO, 400 MHz): δ 11.42 (br s, 1H), 7.70 (d, J=4.0 Hz, 1H), 7.58 (d, J=8.0 Hz, 1H), 7.46 (d, J=8.0 Hz, 1H), 7.30-6.90 (m, 3H), 6.63 (br s, 1H), 6.44 (br s, 1H), 3.64 (s, 3H), 3.18 (m, 1H), 2.44 (m, 1H), 2.03 (m, 4H), 1.80-1.50 (m, 4H). MS (ES+): m/z 390.28 [MH+].

EXAMPLE 67

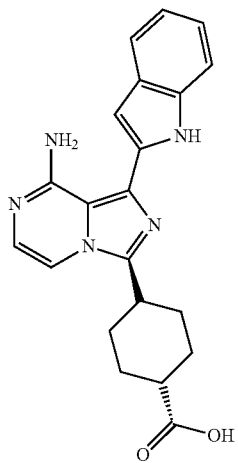

trans-4-(8-Amino-1-(1H-indol-2-yl)imidazo[1,5-a]pyrazin-3-yl)cyclohexanecarboxylic acid A mixture of 37% HCl (30 mL) and methyl trans-4-(8-amino-1-(1H-indol-2-yl)imidazo[1,5-a]pyrazin-3-yl)cyclohexanecarboxylate (500.0 mg, 1.28 mmol) was stirred for 18 h at rt. The reaction mixture was then concentrated in vacuo, and the residue washed with diethyl ether (3×10 mL) and ethyl acetate (2×10 mL), then with ice-cold acetonitrile (10 mL) to afford 0.3 g of the desired product. $^1$H NMR ($d_6$-DMSO, 400 MHz): δ 12.15 (br s, 1H), 11.69 (s, 1H), 8.45 (br s, 2H), 7.97 (d, J=6.4 Hz, 1H), 7.63 (d, J=8.0 Hz, 1H), 7.50 (dd, J=8.0, 0.4 Hz, 1H), 7.19 (m, 1H), 7.13 (d, J=6.0 Hz, 1H), 7.06 (m, 1H), 6.83 (d, J=1.6 Hz, 1H), 3.27 (td, J=11.6, 3.2, 3.2 Hz, 1H), 2.33 (td, J=10.8, 3.2, 3.2 Hz, 1H), 2.05 (m, 4H), 1.73 (m, 2H) and 1.58 (m/z, 2H). MS (ES+): m/z 376.05 [MH+].

EXAMPLE 68 trans-4-(8-Amino-1-(1H-indol-2-yl)imidazo[1,5-a]pyrazin-3-yl)-N-pyridin-3-ylcyclohexanecarboxamide A suspension of 3-aminopyridine (40 mg, 0.43 mmol) in toluene (1.3 mL) was treated with a 2M toluene solution of trimethylaluminum (0.3 mL, 0.60 mmol).

After 25 min, the resulting solution was treated with methyl trans-4-(8-amino-1-(1H-indol-2-yl)imidazo[1,5-a]pyrazin-3-yl)cyclohexanecarboxylate (30 mg, 0.08 mol) and the mixture stirred at rt overnight. The mixture was then stirred with 2M NaOH (20 mL) and ethyl acetate (20 mL) for 10 min., then the organic phase was separated and the aqueous extracted EtOAc (3×15 mL). The combined organic extracts were washed with water (20 mL) and brine (20 mL), then dried over $Na_2SO_4$ and concentrated in vacuo to give crude product which was subjected to mass-directed preparative HPLC to afford pure desired product. $^1$H NMR ($d_6$-DMSO, 400 MHz): δ 11.45 (br s, 1H), 10.12 (s, 1H), 8.77 (d, J=2.4 Hz, 1H), 8.25 (d, J=4.8 Hz, 1H), 8.14 (s, 1H), 8.08 (dd, J=8.0, 1.6 Hz, 1H), 7.71 (d, J=5.2 Hz, 1H), 7.59 (d, J=7.6 Hz, 1H), 7.46 (d, J=8.4 Hz, 1H), 7.34 (m, 1H), 7.15-7.00 (m, 3H), 6.65 (s, 1H), 6.42 (br s, 2H), 3.22 (m, 1H), 2.47 (m, 1H), 2.15-1.95 (m, 4H), and 1.85-1.65 (m, 4H). MS (ES+): m/z 452.17 [MH+].

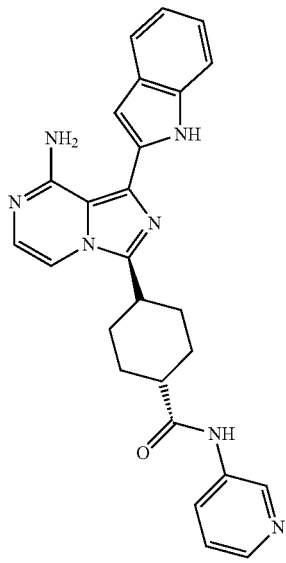

EXAMPLE 69

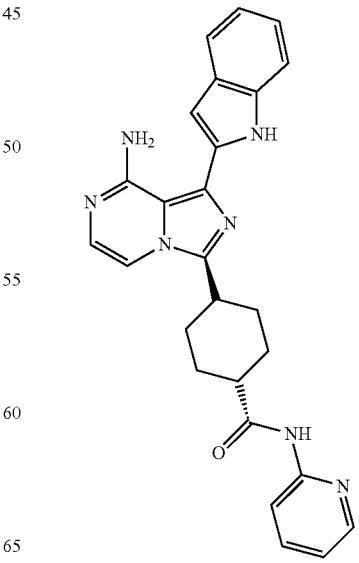

trans-4-(8-Amino-1-(1H-indol-2-yl)imidazo[1,5-a]pyrazin-3-yl)-N-pyridin-2-ylcyclohexanecarboxamide Prepared according to the procedure described above for EXAMPLE 68, except using 2-aminopyridine in place of 3-aminopyridine. MS (ES+): m/z 452.17 [MH+].

EXAMPLE 70

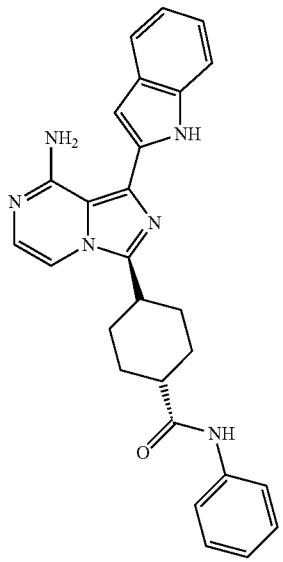

trans-4-(8-Amino-1-(1H-indol-2-yl)imidazo[1,5-a]pyrazin-3-yl)-N-phenylcyclohexane carboxamide Prepared according to the procedure described above for EXAMPLE 68, except using aniline in place of 3-aminopyridine. MS (ES+): m/z 451.16 [MH+].

EXAMPLE 71

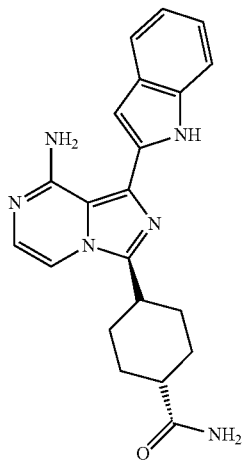

trans-4-[8-Amino-1-(1H-indol-2-yl)imidazo[1,5-a]pyrazin-3-yl]cyclohexanecarboxamide trans-4-(8-Amino-1-iodoimidazo[1,5-a]pyrazin-3-yl)cyclohexanecarboxamide (40 mg, 0.10 mmol), 1-(tert-butoxycarbonyl)-1H-indole-2-boronic acid (33 mg, 0.12 mmol), and sodium carbonate (33 mg, 0.3 mmol) were added to DME:Water (5:1) (2 mL) and the mixture degassed with Argon for 10 min. Tetrakis(triphenylphosphine)palladium(0) (8.0 mg, 0.007 mmol) was then added and the reaction mixture microwaved at 110° C. for 1 h, The mixture was concentrated in vacuo, taken up in DMSO, and purified by mass-directed preparative HPLC to afford desired product. $^1$H NMR (d$_6$-DMSO, 400 MHz): ☐ 11.50 (br s, 1H), 7.72 (m, 1H), 7.58 (m, 1H), 7.46 (dd, J=7.6, 0.4 Hz, 1H), 7.25 (br s, 1H), 7.13 (m, 1H), 7.08-7.00 (m, 2H), 6.70 (br s, 1H), 6.69 (br s, 1H), 3.16 (m, 1H), 2.20 (m, 1H), 2.10-1.80 (m, 4H) and 1.65 (m, 4H). MS (ES+): m/z 375.17 [MH+].

EXAMPLE 72

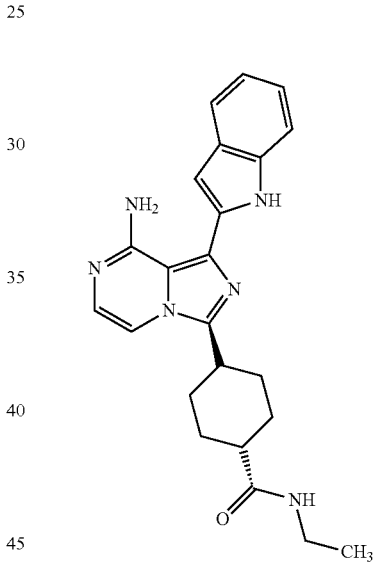

trans-4-(8-Amino-1-(1H-indol-2-yl)imidazo[1,5-a]pyrazin-3-yl)-N-ethylcyclohexanecarboxamide Ethylamine hydrochloride (30 mg, 0.37 mmol), 2-(1H-benzotriazol-1-yl)-1,1,3,3-tetramethyluronium tetrafluoroborate (35 mg, 0.1 mmol), and N,N-diisopropylethylamine (80 μL, 0.53 mmol) were added to a solution of trans-4-(8-Amino-1-(1H-indol-2-yl)imidazo[1,5-a]pyrazin-3-yl)cyclohexanecarboxylic acid (25 mg, 0.07 mmol) in anhydrous DMF (2 mL). Upon completion of reaction (as monitored by LCMS), the mixture was added to a saturated aqueous sodium bicarbonate solution (10 mL). The resulting precipitate was collected by filtration and washed with cold acetonitrile (3×10 mL) to afford 13 mg of the desired product. $^1$H NMR (d$_6$-DMSO, 400 MHz): δ 11.41 (br s, 1H), 7.75 (dd, J=4.0, 4.0 Hz, 1H), 7.69 (d, J=4.0 Hz, 1H), 7.58 (d, J=8.0, 4.0 Hz, 1H), 7.45 (d, J=4.0, 4.0 Hz, 1H), 7.12 (dd, J=8.0, 8.0 Hz, 1H), 7.08-7.00 (m, 2H), 6.63 (m, 1H), 6.43 (br s, 2H), 3.16 (m, 1H), 3.07 (m, 2H), 2.18 (m, 1H), 2.02 (m, 2H), 1.84 (m, 2H), 1.66 (m, 4H) and 1.02 (t, J=4.0 Hz, 3H). MS (ES+): m/z 403.09 [MH+].

EXAMPLE 73

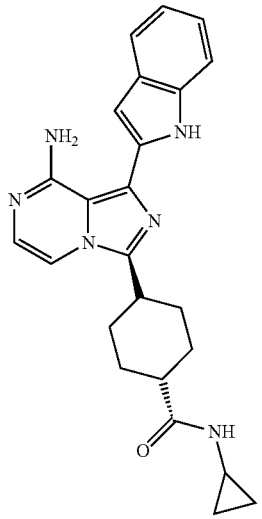

trans-4-(8-Amino-1-(1H-indol-2-yl)imidazo[1,5-a]pyrazin-3-yl)-N-cyclopropylcyclo hexanecarboxamide Prepared according to the procedure described above for EXAMPLE 72, except using cyclopropylamine in place of ethylamine. MS (ES+): m/z 415.22 [MH+].

EXAMPLE 74

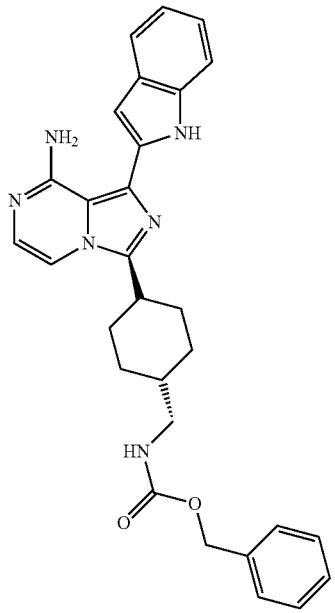

Benzyl {[trans-4-(8-amino-1-(1H-indol-2-yl)imidazo[1,5-a]pyrazin-3-yl)cyclohexyl]methyl}carbamate A mixture of benzyl {[trans-4-(8-amino-1-iodoimidazo[1,5-a]pyrazin-3-yl)cyclohexyl]methyl}carbamate (1.00 g, 0.00180 mol), 1-(tert-butoxycarbonyl)-1H-indole-2-boronic acid (0.517 g, 0.00198 mol), 1,2-dimethoxyethane (7.7 mL), water (1.4 mL, 0.081 mol) and Cesium Carbonate (1.17 g, 0.00360 mol) degassed three times, treated with tetrakis(triphenylphosphine)palladium(0) (200 mg, 0.0002 mol) and degassed once more. The resulting mixture was heated at 100° C. overnight before being diluted with EtOAc (40 mL), washed with water (2×30 mL) and brine (20 mL) then dried over $Na_2SO_4$ and concentrated in vacuo. The crude product thus isolated was chromatographed over silica gel eluting with hexane→EtOAc:hexane: 5% 2M $NH_3$ in MeOH 1:1: 0.05 to afford the title compound. $^1$H NMR (400 MHz, $CDCl_3$): δ 1.13-1.22 (m, 2H), 1.75-1.86 (m, 2H), 1.94-1.97 (m, 2H), 2.11-2.13 (m, 2H), 2.86 (m, 1H), 3.12-3.16 (m, 2H), 4.82 (m, 1H), 5.12 (s, 2H), 5.69 (br, 2H), 6.78 (s, 1H), 7.13-7.15 (m, 2H), 7.19-7.25 (m, 2H), 7.32-7.38 (m, 5H), 7.42 (d, J=8.0 Hz, 1H), 7.64 (d, J=8.4 Hz, 1H), 9.09 (br, 1H). MS (ES+): m/z 495 [MH+].

EXAMPLE 75

N-{[trans-4-(8-Amino-1-(1H-indol-2-yl)imidazo[1,
5-a]pyrazin-3-yl)cyclohexyl]methyl}-3-furamide Prepared according to the procedure described above for EXAMPLE 22, except using 2-furoic acid in place of acetic acid. MS (ES+): m/z 455.20 [MH+].

EXAMPLE 76

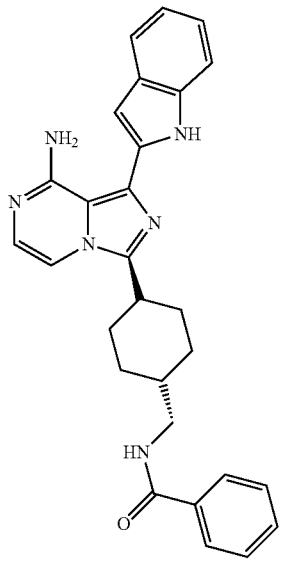

N-{[trans-4-(8-Amino-1-(1H-indol-2-yl)imidazo[1,
5-a]pyrazin-3-yl)cyclohexyl]methyl}benzamide Prepared according to the procedure described above for EXAMPLE 22, except using benzoic acid in place of acetic acid. MS (ES+): m/z 465.25 [MH+].

EXAMPLE 77

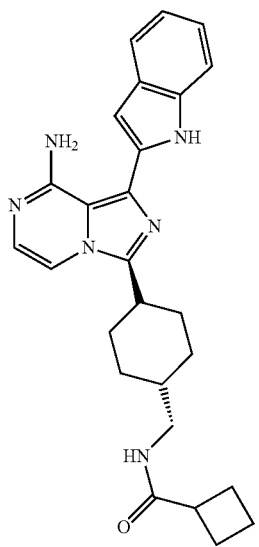

N-{[trans-4-(8-Amino-1-(1H-indol-2-yl)imidazo[1,
5-a]pyrazin-3-yl)cyclohexyl]
methyl}cyclobutanecarboxamide Prepared according to the procedure described above for EXAMPLE 22, except using cyclobutanecarboxylic acid in place of acetic acid. MS (ES+): m/z 443.25 [MH+].

EXAMPLE 78

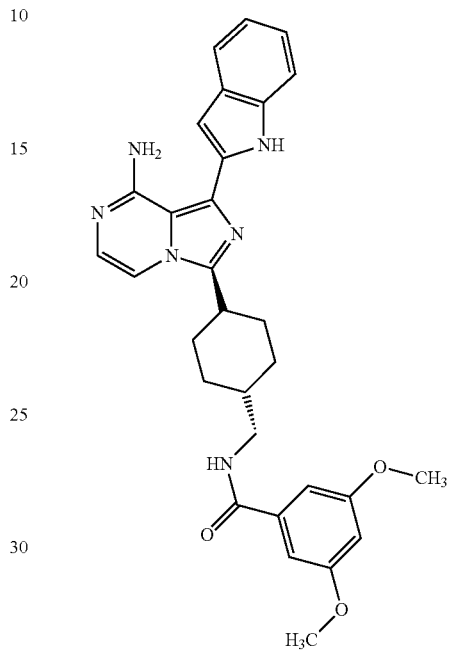

N-{[trans-4-(8-Amino-1-(1H-indol-2-yl)imidazo[1,
5-a]pyrazin-3-yl)cyclohexyl]methyl}-3,5-
dimethoxybenzamide Prepared according to the procedure described above for EXAMPLE 22, except using 3,5-dimethoxybenzoic acid in place of acetic acid. MS (ES+): m/z 525.35 [MH+].

EXAMPLE 79

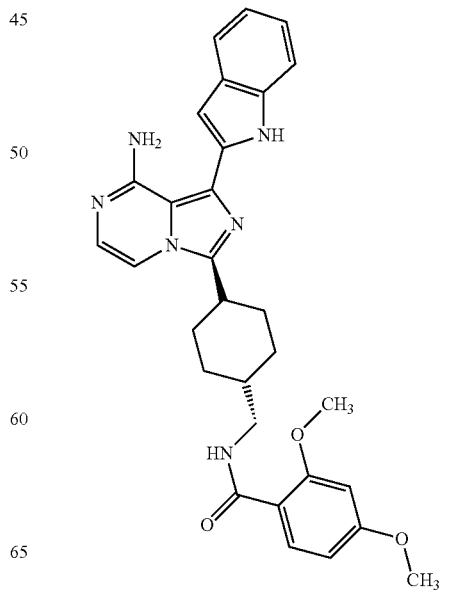

N-{[trans-4-(8-Amino-1-(1H-indol-2-yl)imidazo[1,5-a]pyrazin-3-yl)cyclohexyl]methyl}-2,4-dimethoxybenzamide Prepared according to the procedure described above for EXAMPLE 22, except using 2,4-dimethoxybenzoic acid in place of acetic acid. MS (ES+): m/z 525.33 [MH+].

EXAMPLE 80

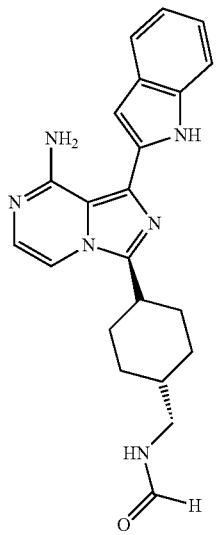

N-{[trans-4-(8-Amino-1-(1H-indol-2-yl)imidazo[1,5-a]pyrazin-3-yl)cyclohexyl]methyl}formamide Prepared according to the procedure described above for EXAMPLE 22, except using formic acid in place of acetic acid. MS (ES+): m/z 389.10 [MH+].

EXAMPLE 81

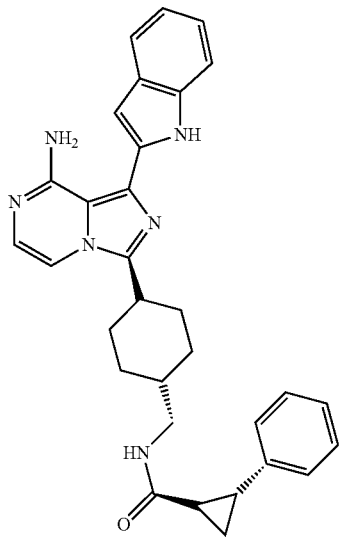

(1R,2R)—N-{[trans-4-(8-amino-1-(1H-indol-2-yl)imidazo[1,5-a]pyrazin-3-yl)cyclohexyl]methyl}-2-phenylcyclopropanecarboxamide Prepared according to the procedure described above for EXAMPLE 22, except using (1R,2R)-2-phenylcyclopropanecarboxylic acid in place of acetic acid. MS (ES+): m/z 505.30 [MH+].

EXAMPLE 82

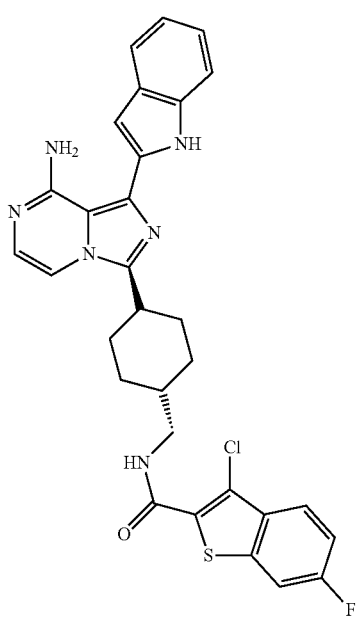

N-{[trans-4-(8-Amino-1-(1H-indol-2-yl)imidazo[1,5-a]pyrazin-3-yl)cyclohexyl]methyl}-3-chloro-6-fluorobenzo[b]thiophene-2-carboxamide Prepared according to the procedure described above for EXAMPLE 22, except using 3-chloro-6-fluorobenzo[b]

thiophene-2-carboxylic acid in place of acetic acid. MS (ES+): m/z 573.35 & 575.31 [MH+].

EXAMPLE 83

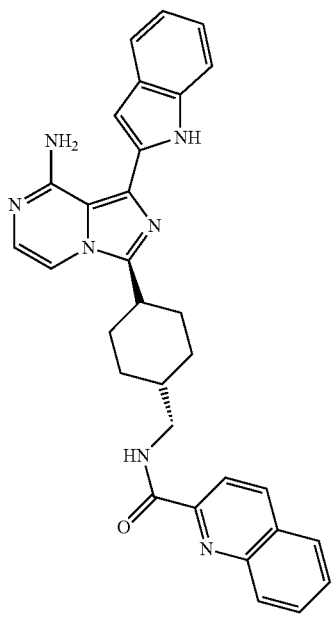

N-{[trans-4-(8-Amino-1-(1H-indol-2-yl)imidazo[1,5-a]pyrazin-3-yl)cyclohexyl]methyl}isoquinoline-2-carboxamide Prepared according to the procedure described above for EXAMPLE 22, except using isoquinoline-2-carboxylic acid in place of acetic acid. MS (ES+): m/z 516.40 [MH+].

EXAMPLE 84

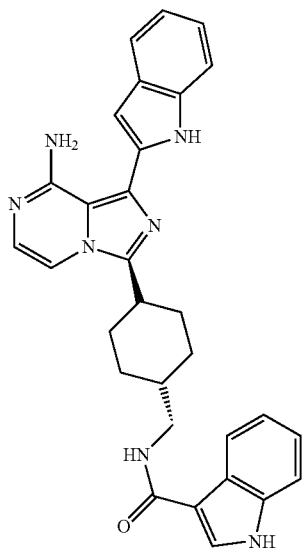

N-{[trans-4-(8-Amino-1-(1H-indol-2-yl)imidazo[1,5-a]pyrazin-3-yl)cyclohexyl]methyl}indole-3-carboxamide Prepared according to the procedure described above for EXAMPLE 22, except using indole-3-carboxylic acid in place of acetic acid. MS (ES+): m/z 505.46 [MH+].

EXAMPLE 85

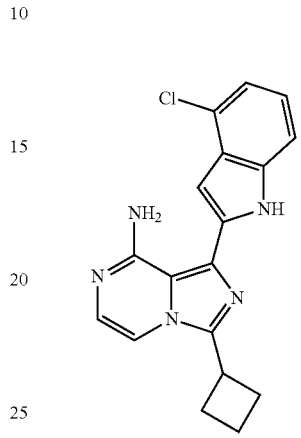

1-(4-Chloro-1H-indol-2-yl)-3-cyclobutylimidazo[1,5-a]pyrazin-8-amine

Prepared according to the procedure described above for EXAMPLE 2, except using 1-(tert-butoxycarbonyl)-4-chloro-1H-indole-2-boronic acid in place of 1-(tert-butoxycarbonyl)-1H-indole-2-boronic acid. $^1$H NMR (400 MHz-DMSO-d6) δ 1.91-1.98 (m, 1H), 2.08-2.15 (m, 1H), 2.42-2.46 (m, 4H), 3.97-4.00 (m, 1H), 6.42 (bs, 2H), 6.67 (s, 1H), 7.09-7.14 (m, 3H), 7.43-7.47 (m, 2H) and 11.83 (bs, 1H). MS (ES+): m/z 338.26 [MH+].

EXAMPLE 86

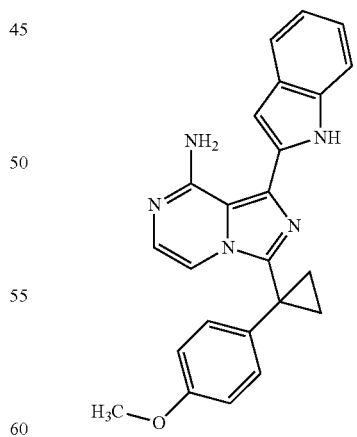

1-(1H-Indol-2-yl)-3-[1-(4-methoxyphenyl)cyclopropyl]imidazo[1,5-a]pyrazin-8-amine Prepared according to the procedure described above for EXAMPLE 2, except using 4-methoxyphenylcyclopropanecarboxylic acid in place of cyclobutanecarboxylic acid. $^1$H NMR (400 MHz, CHLOROFORM-d) δ ppm 1.46 (s, 2 H), 1.58 (s, 2 H), 3.76 (s, 3 H), 6.78 (d, J=8.80 Hz, 2 H), 6.77 (s, 1 H), 6.82 (s, 1 H), 6.98 (d, J=5.13 Hz, 1 H), 7.03 (d, J=8.80 Hz, 2 H), 7.15 (t, J=7.52 Hz, 1 H), 7.23 (s, 2 H), 7.44 (d, J=8.07 Hz, 1 H), 7.65 (d, J=8.07 Hz, 1 H) and 9.36 (br. s., 1 H). MS (ES+): m/z 396.15 [MH+].

EXAMPLE 87

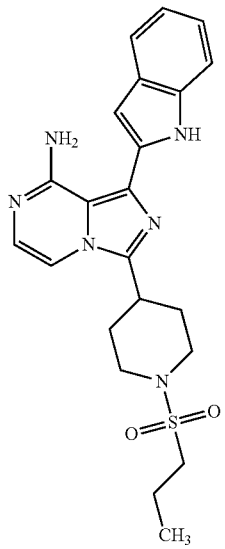 [SMILES: CCCS(=O)(=O)N1CCC(c2nc(-c3cc4ccccc4[nH]3)c3c(N)nccn23)CC1]

1-(1H-Indol-2-yl)-3-[1-(propylsulfonyl)piperidin-4-yl]imidazo[1,5-a]pyrazin-8-amine Prepared according to the procedure described above for EXAMPLE 59, except using propane-2-sulfonyl chloride in place of ″butanesulfonyl chloride. MS (ES+): m/z 439.06 [MH+].

EXAMPLE 88

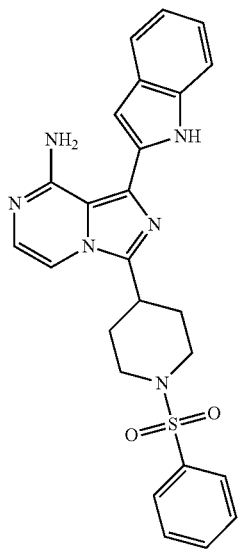 [SMILES: Nc1nccn2c(C3CCN(S(=O)(=O)c4ccccc4)CC3)nc(-c3cc4ccccc4[nH]3)c12]

1-(1H-Indol-2-yl)-3-[1-(phenylsulfonyl)piperidin-4-yl]imidazo[1,5-a]pyrazin-8-amine Prepared according to the procedure described above for EXAMPLE 59, except using benzenesulfonyl chloride in place of ″butanesulfonyl chloride. MS (ES+): m/z 473.29 [MH+].

EXAMPLE 89

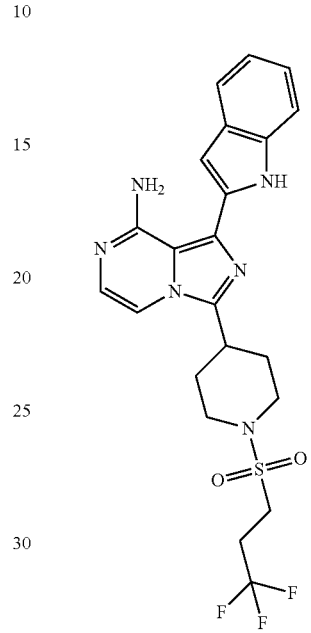

1-(1H-Indol-2-yl)-3-{1-[(3,3,3-trifluoropropyl)sulfonyl]piperidin-4-yl}imidazo[1,5-a]pyrazin-8-amine Prepared according to the procedure described above for EXAMPLE 59, except using 3,3,3-trifluoropropane-1-sulfonyl chloride in place of ″butanesulfonyl chloride. MS (ES+): m/z 493.19 [MH+].

EXAMPLE 90

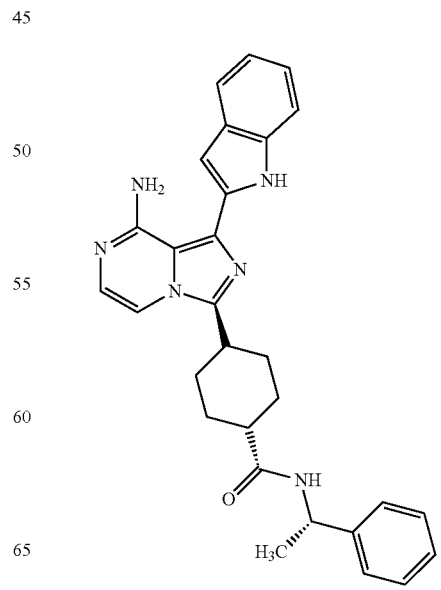

201 trans-3-(8-Amino-1-(1H-indol-2-yl)imidazo[1,5-a]pyrazin-3-yl)-N-[(1S)-1-phenylethyl]cyclohexanecarboxamide Prepared according to the procedure described above for EXAMPLE 72, except using (1S)-1-phenylethanamine in place of cyclopropylamine. MS (ES+): m/z 479.11 [MH+].

EXAMPLE 91

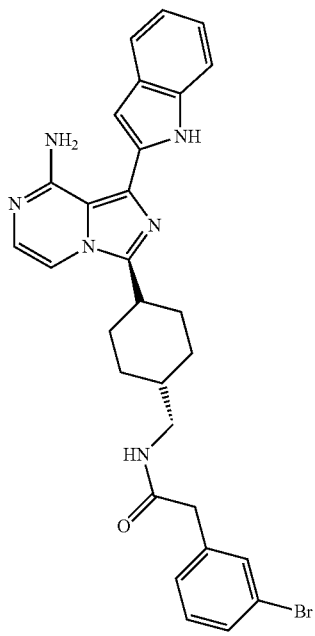

202

N-{[trans-4-(8-Amino-1-(1H-indol-2-yl)imidazo[1,5-a]pyrazin-3-yl)cyclohexyl]methyl}(3-bromophenyl)acetamide Prepared according to the procedure described above for EXAMPLE 22, except using 3-bromophenylacetic acid in place of acetic acid. MS (ES+): m/z 557.21 and 559.20 [MH+].

EXAMPLE 92

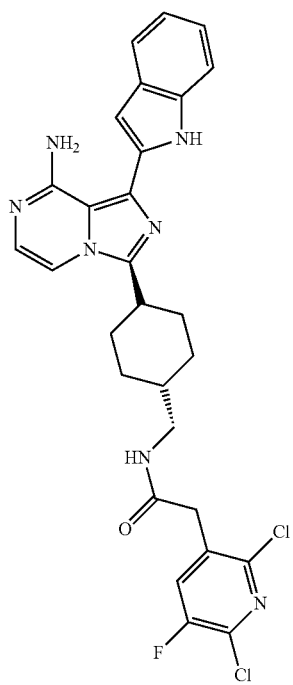

N-{[trans-4-(8-Amino-1-(1H-indol-2-yl)imidazo[1,5-a]pyrazin-3-yl)cyclohexyl]methyl}(2,6-dichloro-5-fluoropyridin-3-yl)acetamide Prepared according to the procedure described above for EXAMPLE 22, except using (2,6-dichloro-5-fluoropyridin-3-yl)acetic acid in place of acetic acid. MS (ES+): m/z 522.21 [MH+].

EXAMPLE 93

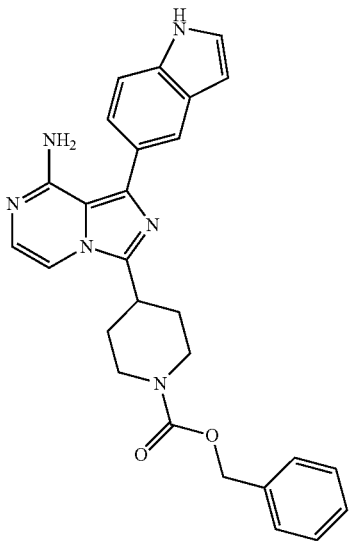 [SMILES: Nc1nccn2c(C3CCN(C(=O)OCc4ccccc4)CC3)nc(-c3ccc4[nH]ccc4c3)c12]

Benzyl 4-[8-amino-1-(1H-indol-5-yl)imidazo[1,5-a]pyrazin-3-yl]piperidine-1-carboxylate Prepared according to the procedure described above for EXAMPLE 24, except using indole-5-boronic acid in place of 1-(tert-butoxycarbonyl)-1H-indole-2-boronic acid. MS (ES+): m/z 494.97 [MH+].

EXAMPLE 94

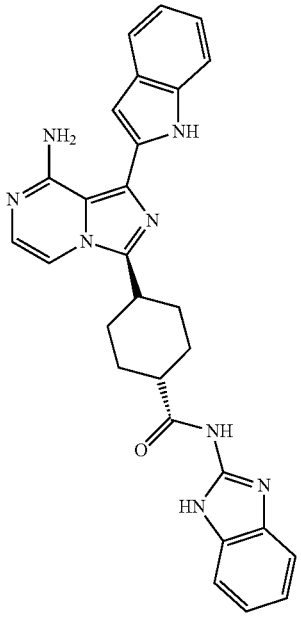

trans-4-(8-Amino-1-(1H-indol-2-yl)imidazo[1,5-a]pyrazin-3-yl)-N-benzimidazol-2-ylcyclohexanecarboxamide Prepared according to the procedure described above for EXAMPLE 68, except using 2-aminobenzimidazole in place of 3-aminopyridine. MS (ES+): m/z 490.97 [MH+].

EXAMPLE 95

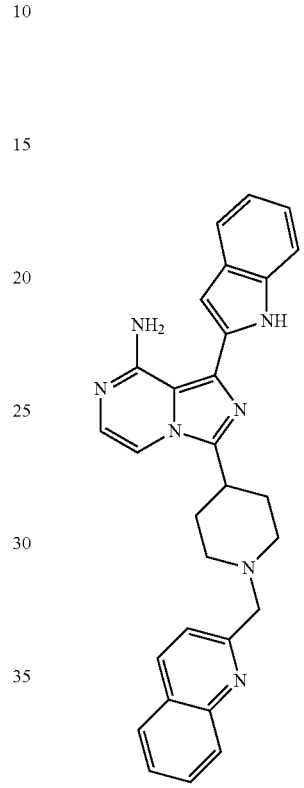

1-(1H-Indol-2-yl)-3-[1-(quinolin-2-ylmethyl)piperidin-4-yl]imidazo[1,5-a]pyrazin-8-amine A solution of 1-(1H-Indol-2-yl)-3-piperidin-4-ylimidazo[1,5-a]pyrazin-8-amine hydrochloride (30 mg, 0.09 mmol), 2-formylquinoline (17 mg, 0.11 mmol) and triethylamine (0.019 mL, 0.14 mmol) in 1,4-dioxane (1 mL) was treated with sodium cyanoborohydride (5.7 mg, 0.090 mmol) and microwaved at 300 watts, 120° C. for 20 min. The mixture was concentrated in vacuo, the residue was dissolved in methanol loaded onto an SCX ion exchange cartridge, and then eluted with 1M NH$_4$OH in methanol. The semi-pure material thus obtained was then subjected to semi-preparative HPLC to afford desired product. $^1$H NMR (400 MHz, MeOD) δ ppm 2.13-2.33 (m, 4 H), 2.90 (t, J=10.86, 9.60 Hz, 2 H), 3.47 (d, J=10.11 Hz, 2 H), 4.29 (s, 2 H), 6.74 (s, 1 H), 7.02-7.11 (m, 2 H), 7.19 (t, J=8.08, 7.07 Hz, 1 H), 7.47 (d, J=9.09 Hz, 1 H), 7.58-7.65 (m, 3 H), 7.69 (d, J=8.59 Hz, 1 H), 7.80 (t, J=8.34, 6.82 Hz, 1 H), 7.96 (d, J=7.33 Hz, 1 H), 8.08 (d, J=8.34 Hz, 1H) and 8.39 (d, J=8.59 Hz, 1 H). MS (ES+): m/z 474.23 [MH+].

EXAMPLE 96

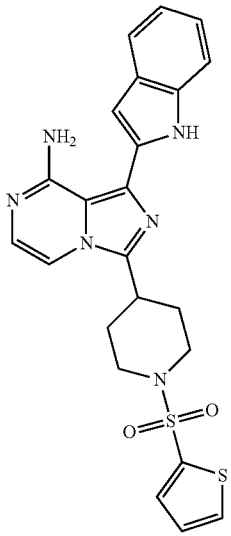 [SMILES: Nc1nccn2c(C3CCN(S(=O)(=O)c4cccs4)CC3)nc(-c3cc4ccccc4[nH]3)c12]

1-(1H-Indol-2-yl)-3-[1-(2-thienylsulfonyl)piperidin-4-yl]imidazo[1,5-a]pyrazin-8-amine Prepared according to the procedure described above for EXAMPLE 59, except using thiophene-2-sulfonyl chloride in place of "butanesulfonyl chloride. MS (ES+): m/z 479.16 [MH+].

EXAMPLE 97

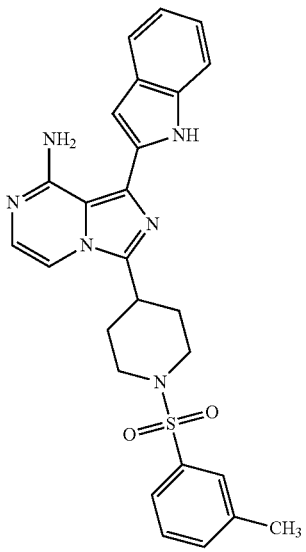 [SMILES: Cc1cccc(S(=O)(=O)N2CCC(c3nc(-c4cc5ccccc5[nH]4)c4c(N)nccn34)CC2)c1]

1-(1H-Indol-2-yl)-3-{1-[(3-methylphenyl)sulfonyl]piperidin-4-yl}imidazo[1,5-a]pyrazin-8-amine Prepared according to the procedure described above for EXAMPLE 59, except using 3-methylbenzenesulfonyl chloride in place of "butanesulfonyl chloride. MS (ES+): m/z 487.94 [MH+].

EXAMPLE 98

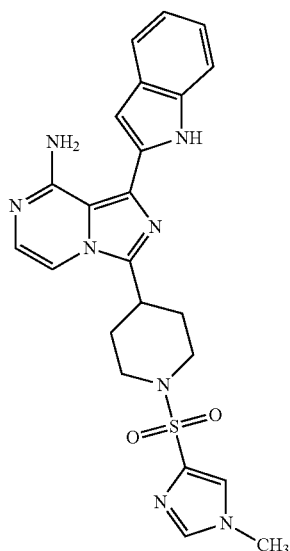 [SMILES: Cn1cnc(S(=O)(=O)N2CCC(c3nc(-c4cc5ccccc5[nH]4)c4c(N)nccn34)CC2)c1]

1-(1H-Indol-2-yl)-3-{1-[(1-methyl-1H-imidazol-4-yl)sulfonyl]piperidin-4-yl}imidazo[1,5-a]pyrazin-8-amine Prepared according to the procedure described above for EXAMPLE 59, except using 1-methyl-1H-imidazole-4-sulfonyl chloride in place of "butanesulfonyl chloride. MS (ES+): m/z 477.20 [MH+].

The following examples were prepared according to procedures analogous to those described above, utilizing where necessary known literature chemistries.

| Ex # | Structure | MH+ | Ex # | Structure | MH+ |
|---|---|---|---|---|---|
| 99 | 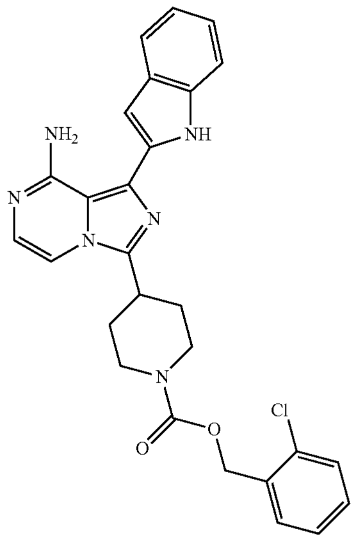 [SMILES: Nc1nccn2c(C3CCN(C(=O)OCc4ccccc4Cl)CC3)nc(-c3cc4ccccc4[nH]3)c12] | 500.93 502.91 | 100 | 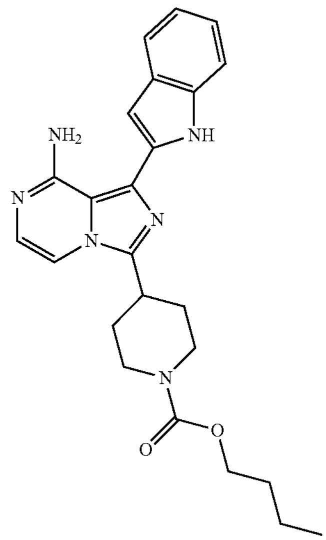 [SMILES: CCCCOC(=O)N1CCC(c2nc(-c3cc4ccccc4[nH]3)c3c(N)nccn23)CC1] | 433.06 |
| 101 | 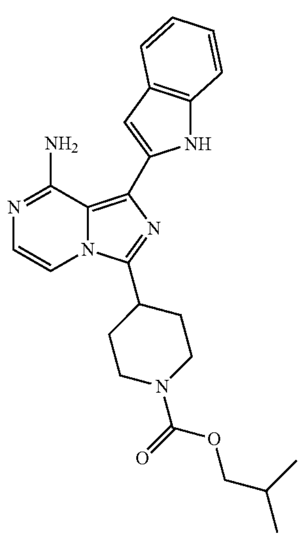 [SMILES: CC(C)COC(=O)N1CCC(c2nc(-c3cc4ccccc4[nH]3)c3c(N)nccn23)CC1] | 433.02 | 102 | 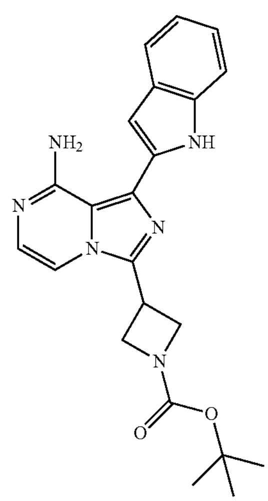 [SMILES: CC(C)(C)OC(=O)N1CC(c2nc(-c3cc4ccccc4[nH]3)c3c(N)nccn23)C1] | 404.96 |

| Ex # | Structure | MH+ | Ex # | Structure | MH+ |
|---|---|---|---|---|---|
| 103 | 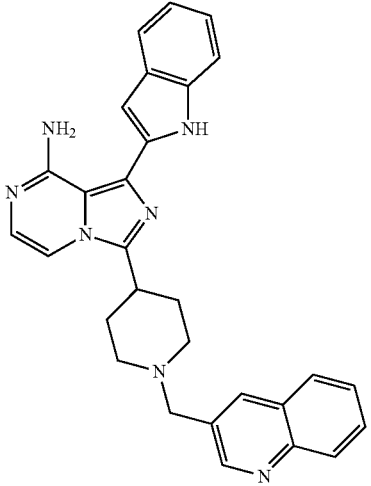 [SMILES: Nc1nccn2c(C3CCN(Cc4cnc5ccccc5c4)CC3)nc(-c3cc4ccccc4[nH]3)c12] | 474.23 | 104 | 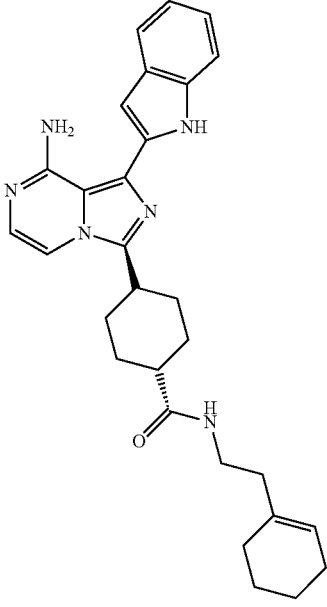 | 483.00 |
| 105 | 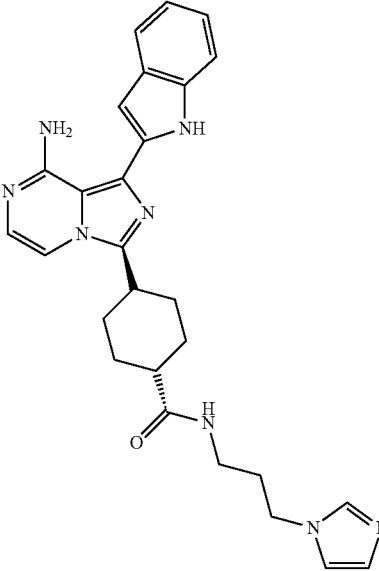 | 483.27 | 106 | 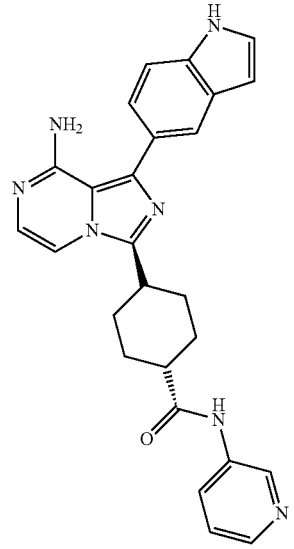 | 452.04 |

-continued

| Ex # | Structure | MH+ | Ex # | Structure | MH+ |
|---|---|---|---|---|---|
| 107 | 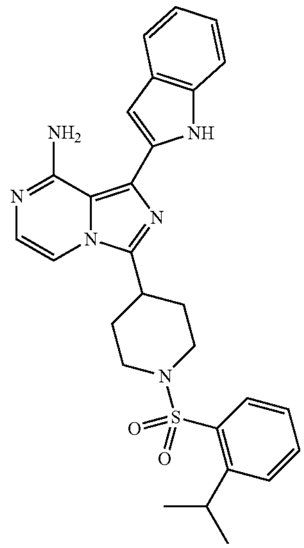 [SMILES: CC(C)c1ccccc1S(=O)(=O)N1CCC(c2nc(-c3cc4ccccc4[nH]3)c3c(N)nccn23)CC1] | 514.92 | 108 | 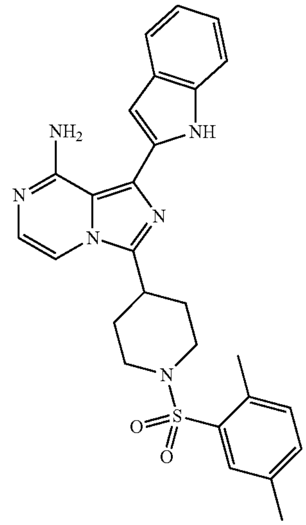 [SMILES: Cc1ccc(C)c(S(=O)(=O)N2CCC(c3nc(-c4cc5ccccc5[nH]4)c4c(N)nccn34)CC2)c1] | 500.89 |
| 109 | 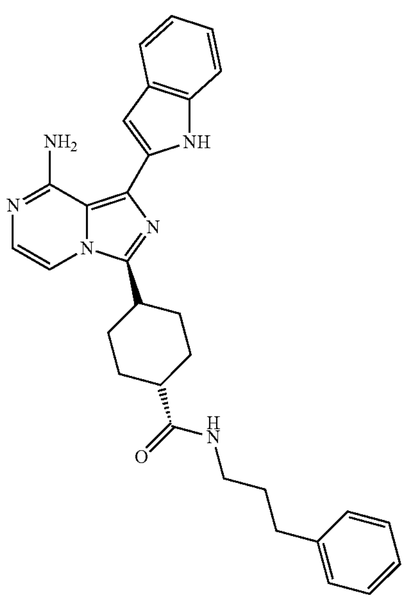 | 492.92 | 110 | 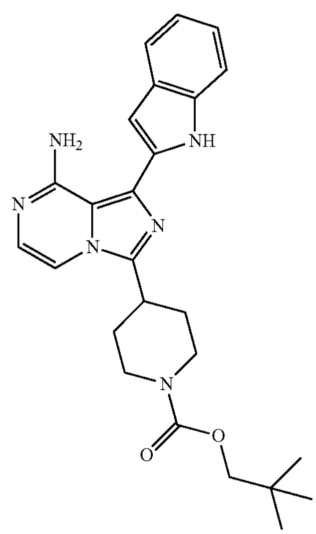 [SMILES: CC(C)(C)COC(=O)N1CCC(c2nc(-c3cc4ccccc4[nH]3)c3c(N)nccn23)CC1] | 447.01 |

-continued

| Ex # | Structure | MH+ | Ex # | Structure | MH+ |
|---|---|---|---|---|---|
| 111 | 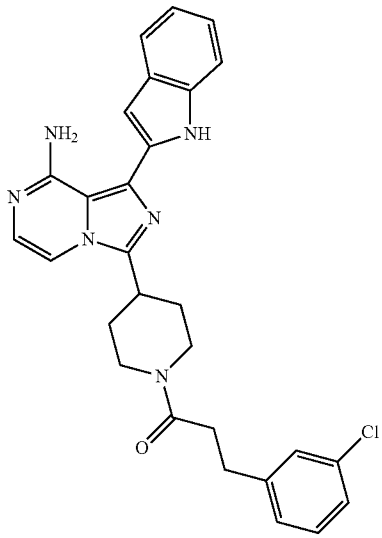 [SMILES: Nc1nccn2c(C3CCN(C(=O)CCc4cccc(Cl)c4)CC3)nc(-c3cc4ccccc4[nH]3)c12] | 498.93 500.94 | 112 | 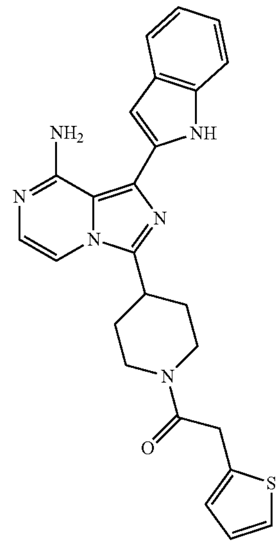 [SMILES: Nc1nccn2c(C3CCN(C(=O)Cc4cccs4)CC3)nc(-c3cc4ccccc4[nH]3)c12] | 456.90 |
| 113 | 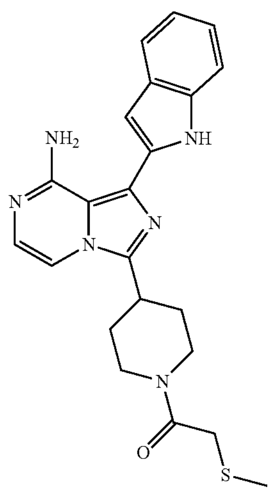 [SMILES: CSCC(=O)N1CCC(c2nc(-c3cc4ccccc4[nH]3)c3c(N)nccn23)CC1] | 420.97 | 114 | 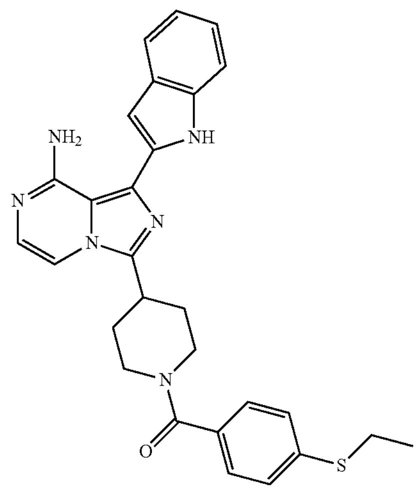 [SMILES: CCSc1ccc(C(=O)N2CCC(c3nc(-c4cc5ccccc5[nH]4)c4c(N)nccn34)CC2)cc1] | 496.91 |
| 115 | 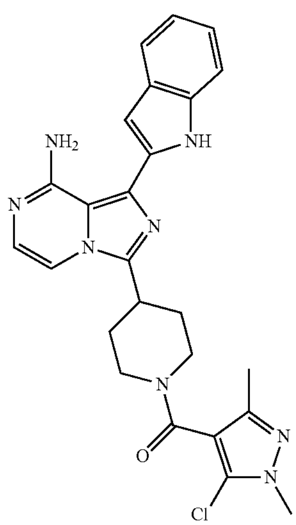 [SMILES: Cc1nn(C)c(Cl)c1C(=O)N1CCC(c2nc(-c3cc4ccccc4[nH]3)c3c(N)nccn23)CC1] | 488.91 | 116 | 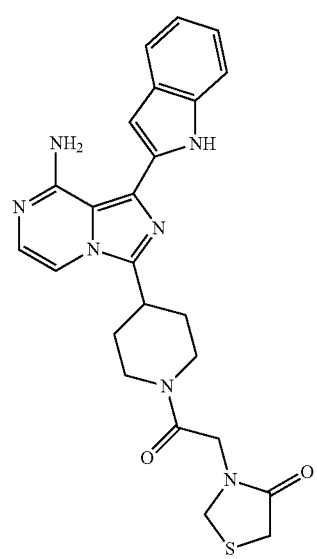 [SMILES: Nc1nccn2c(C3CCN(C(=O)CN4CSCC4=O)CC3)nc(-c3cc4ccccc4[nH]3)c12] | 475.91 |

-continued

| Ex # | Structure | MH+ | Ex # | Structure | MH+ |
|---|---|---|---|---|---|
| 117 | 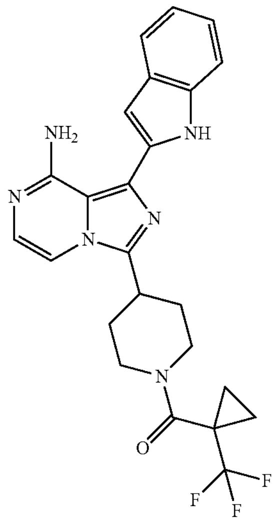 [SMILES: Nc1nccn2c(C3CCN(C(=O)C4(C(F)(F)F)CC4)CC3)nc(-c3cc4ccccc4[nH]3)c12] | 468.84 | 118 | 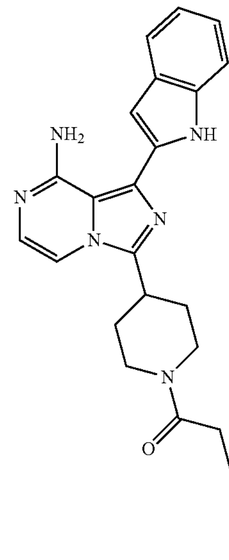 | 426.99 |
| 119 | 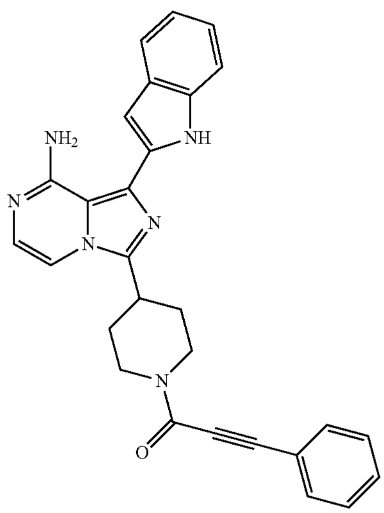 [SMILES: Nc1nccn2c(C3CCN(C(=O)C#Cc4ccccc4)CC3)nc(-c3cc4ccccc4[nH]3)c12] | 461.00 | 120 | 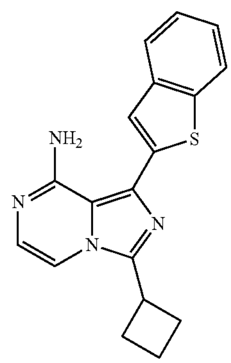 | 320.86 |
| 121 | 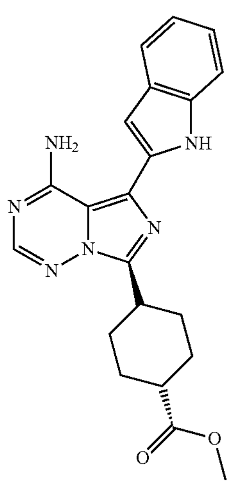 | 391.23 | 122 | 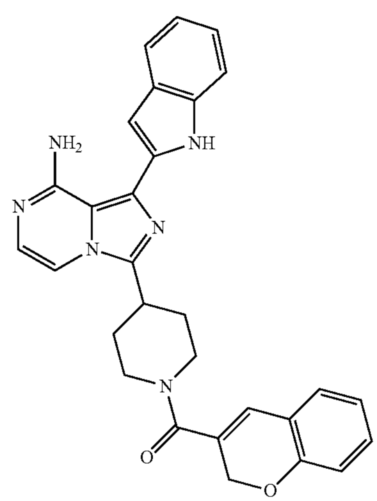 [SMILES: Nc1nccn2c(C3CCN(C(=O)C4=Cc5ccccc5OC4)CC3)nc(-c3cc4ccccc4[nH]3)c12] | 490.97 |

-continued
| Ex # | Structure | MH+ | Ex # | Structure | MH+ |
|---|---|---|---|---|---|
| 123 | 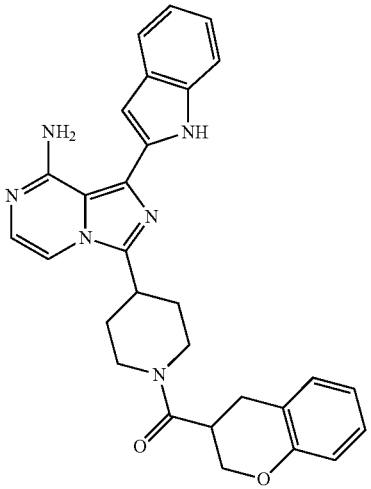 [SMILES: Nc1nccn2c(C3CCN(C(=O)C4COc5ccccc5C4)CC3)nc(-c3cc4ccccc4[nH]3)c12] | 493.18 | 124 | 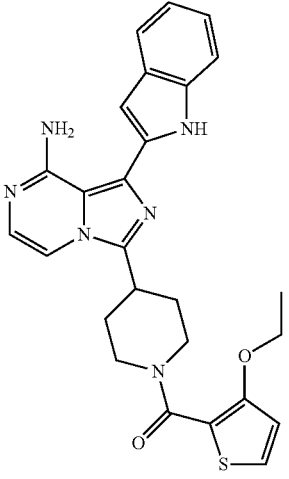 [SMILES: CCOc1ccsc1C(=O)N1CCC(c2nc(-c3cc4ccccc4[nH]3)c3c(N)nccn23)CC1] | 487.09 |
| 125 | 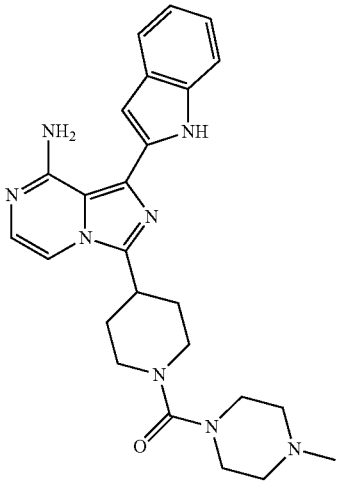 [SMILES: CN1CCN(C(=O)N2CCC(c3nc(-c4cc5ccccc5[nH]4)c4c(N)nccn34)CC2)CC1] | 459.01 | 126 | 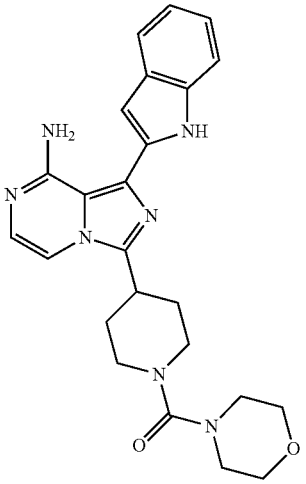 [SMILES: Nc1nccn2c(C3CCN(C(=O)N4CCOCC4)CC3)nc(-c3cc4ccccc4[nH]3)c12] | 446.15 |
| 127 | 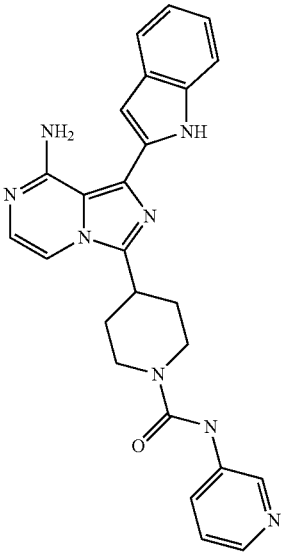 [SMILES: Nc1nccn2c(C3CCN(C(=O)Nc4cccnc4)CC3)nc(-c3cc4ccccc4[nH]3)c12] | 452.98 | 128 | 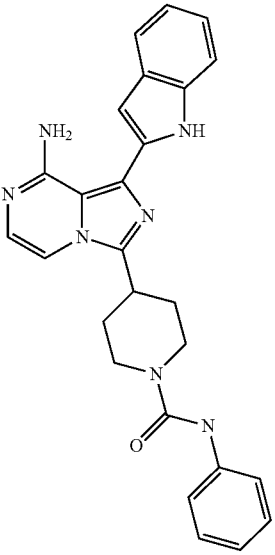 [SMILES: Nc1nccn2c(C3CCN(C(=O)Nc4ccccc4)CC3)nc(-c3cc4ccccc4[nH]3)c12] | 451.97 |

-continued

| Ex # | Structure | MH+ | Ex # | Structure | MH+ |
|---|---|---|---|---|---|
| 129 | 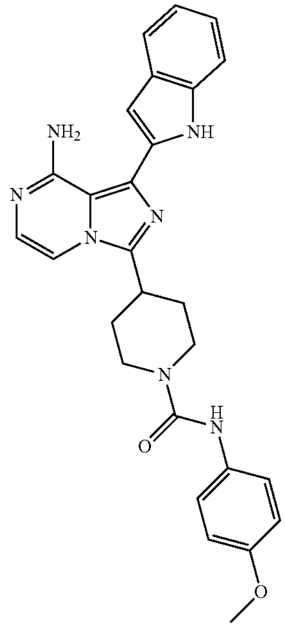 [SMILES: COc1ccc(NC(=O)N2CCC(c3nc(-c4cc5ccccc5[nH]4)c4c(N)nccn34)CC2)cc1] | 481.95 | 130 | 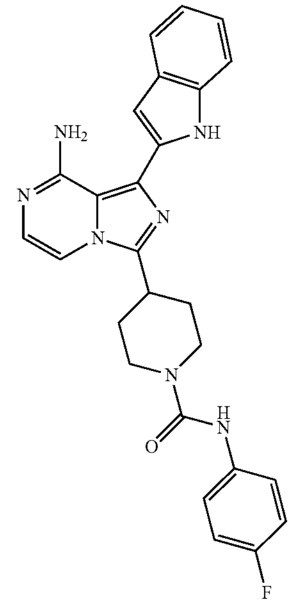 [SMILES: Nc1nccn2c(C3CCN(C(=O)Nc4ccc(F)cc4)CC3)nc(-c3cc4ccccc4[nH]3)c12] | 470.00 |
| 131 | 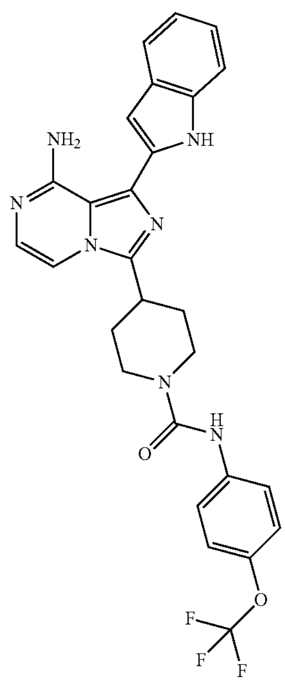 [SMILES: Nc1nccn2c(C3CCN(C(=O)Nc4ccc(OC(F)(F)F)cc4)CC3)nc(-c3cc4ccccc4[nH]3)c12] | 535.91 | 132 | 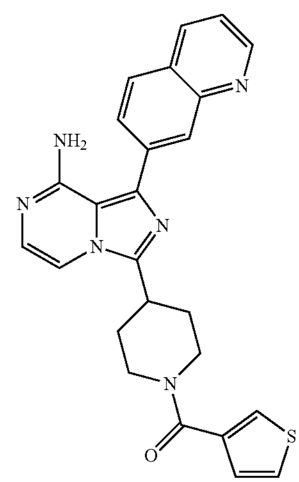 [SMILES: Nc1nccn2c(C3CCN(C(=O)c4ccsc4)CC3)nc(-c3ccc4cccnc4c3)c12] | 454.97 |

-continued
| Ex # | Structure | MH+ | Ex # | Structure | MH+ |
|---|---|---|---|---|---|
| 133 | 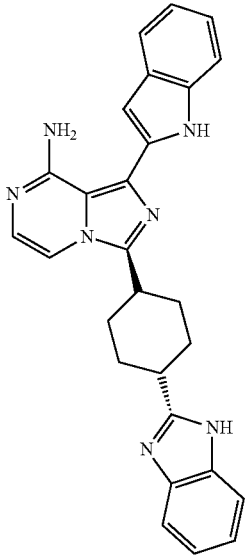 | 448.02 | 134 | 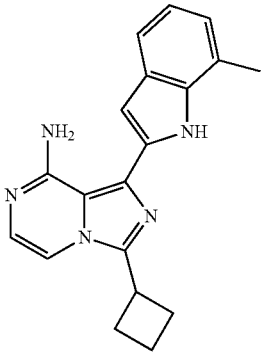 [SMILES: Cc1cccc2cc(-c3nc(C4CCC4)n4ccnc(N)c34)[nH]c12] | 318.03 |
| 135 | 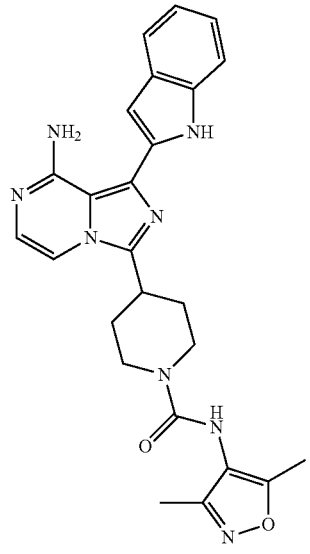 [SMILES: Cc1noc(C)c1NC(=O)N1CCC(c2nc(-c3cc4ccccc4[nH]3)c3c(N)nccn23)CC1] | 470.96 | 136 | 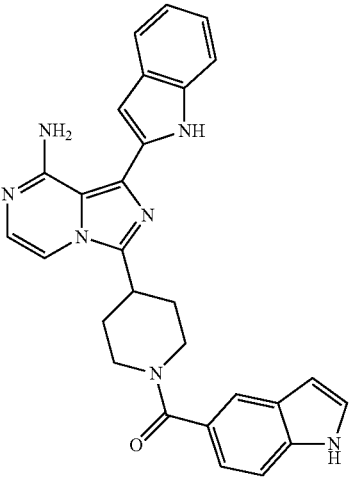 [SMILES: Nc1nccn2c(C3CCN(C(=O)c4ccc5[nH]ccc5c4)CC3)nc(-c3cc4ccccc4[nH]3)c12] | 475.92 |

| Ex # | Structure | MH+ | Ex # | Structure | MH+ |
|---|---|---|---|---|---|
| 137 | 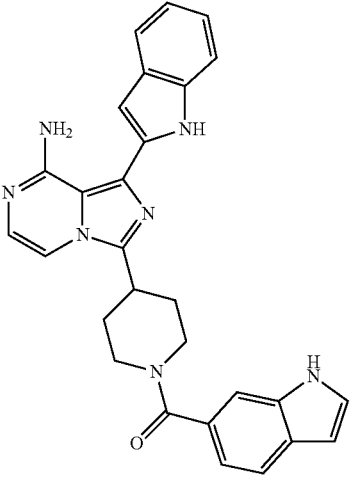 [SMILES: Nc1nccn2c(C3CCN(C(=O)c4ccc5cc[nH]c5c4)CC3)nc(-c3cc4ccccc4[nH]3)c12] | 475.92 | 138 | 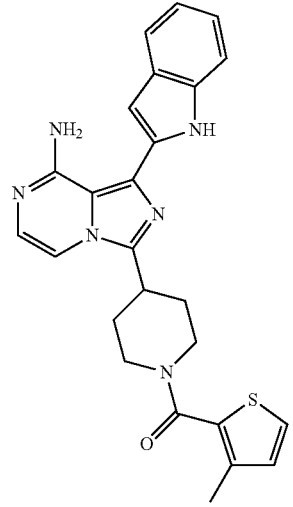 [SMILES: Cc1ccsc1C(=O)N1CCC(c2nc(-c3cc4ccccc4[nH]3)c3c(N)nccn23)CC1] | 457.08 |
| 139 | 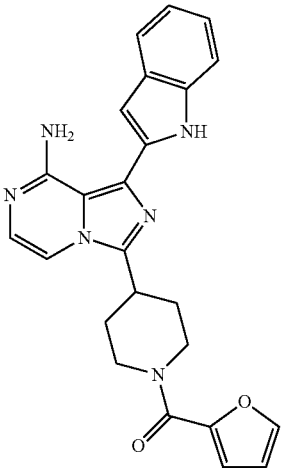 [SMILES: Nc1nccn2c(C3CCN(C(=O)c4ccco4)CC3)nc(-c3cc4ccccc4[nH]3)c12] | 426.92 | 140 | 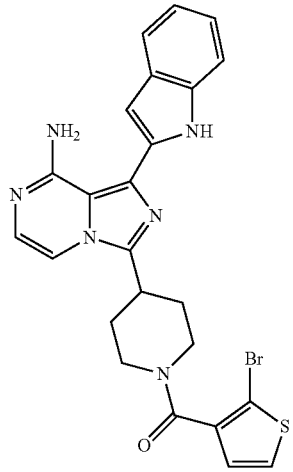 [SMILES: Nc1nccn2c(C3CCN(C(=O)c4ccsc4Br)CC3)nc(-c3cc4ccccc4[nH]3)c12] | 521.03<br>523.08 |
| 141 | 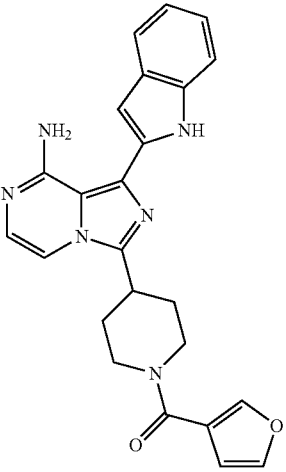 [SMILES: Nc1nccn2c(C3CCN(C(=O)c4ccoc4)CC3)nc(-c3cc4ccccc4[nH]3)c12] | 427.05 | 142 | 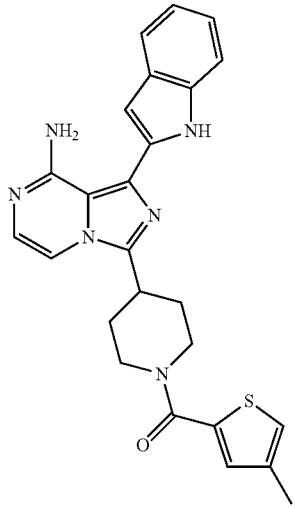 [SMILES: Cc1csc(C(=O)N2CCC(c3nc(-c4cc5ccccc5[nH]4)c4c(N)nccn34)CC2)c1] | 457.02 |

| Ex # | Structure | MH+ | Ex # | Structure | MH+ |
|---|---|---|---|---|---|
| 143 | 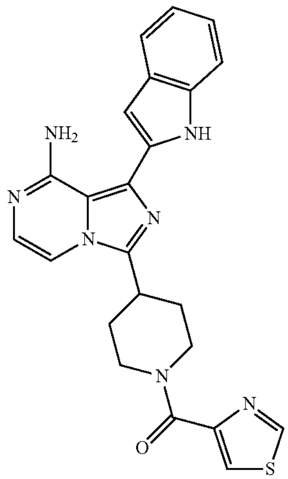 [SMILES: Nc1nccn2c(C3CCN(C(=O)c4cscn4)CC3)nc(-c3cc4ccccc4[nH]3)c12] | 444.20 | 144 | 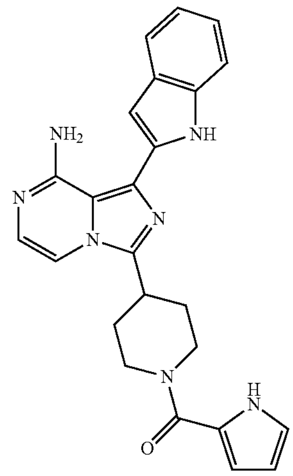 [SMILES: Nc1nccn2c(C3CCN(C(=O)c4ccc[nH]4)CC3)nc(-c3cc4ccccc4[nH]3)c12] | 425.91 |
| 145 | 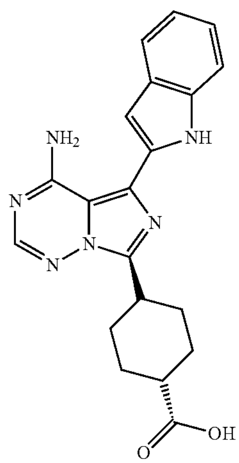 | 376.98 | 146 | 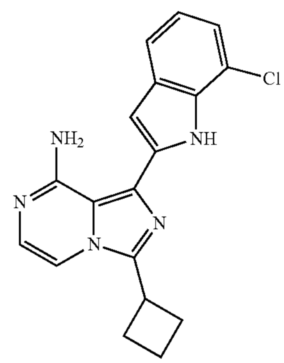 [SMILES: Nc1nccn2c(C3CCC3)nc(-c3cc4cccc(Cl)c4[nH]3)c12] | 337.97 339.92 |
| 147 | 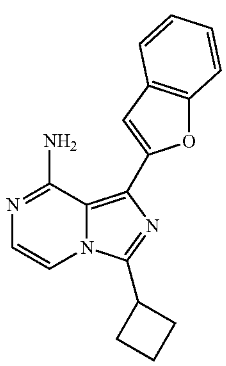 [SMILES: Nc1nccn2c(C3CCC3)nc(-c3cc4ccccc4o3)c12] | 304.95 | 148 | 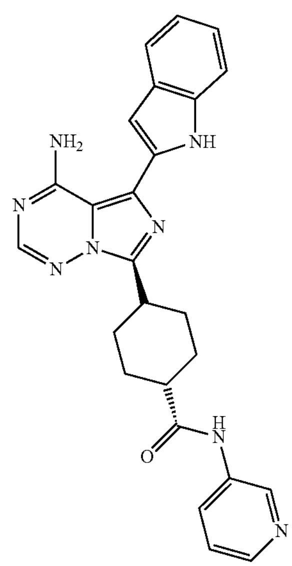 | 452.95 |

-continued

| Ex # | Structure | MH+ | Ex # | Structure | MH+ |
|---|---|---|---|---|---|
| 149 | 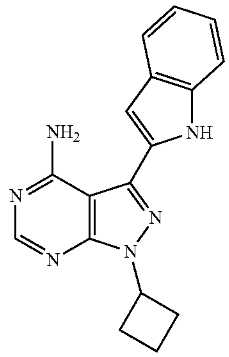 [SMILES: Nc1ncnc2c1c(-c1cc3ccccc3[nH]1)nn2C1CCC1] | 305.20 | 150 | 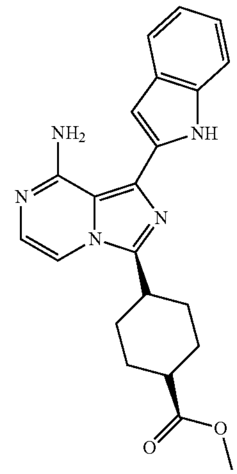 | 389.83 |
| 151 | 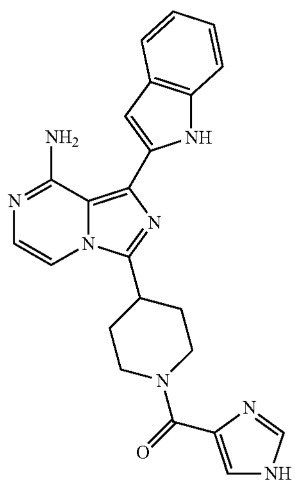 [SMILES: Nc1nccn2c(C3CCN(C(=O)c4c[nH]cn4)CC3)nc(-c3cc4ccccc4[nH]3)c12] | 426.97 | 152 | 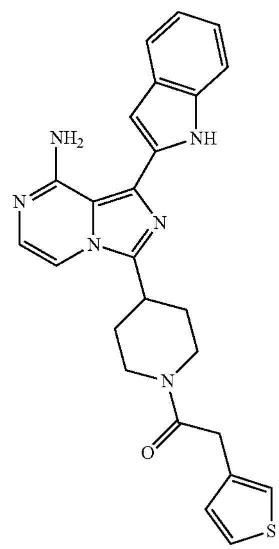 [SMILES: Nc1nccn2c(C3CCN(C(=O)Cc4ccsc4)CC3)nc(-c3cc4ccccc4[nH]3)c12] | 456.79 |
| 153 | 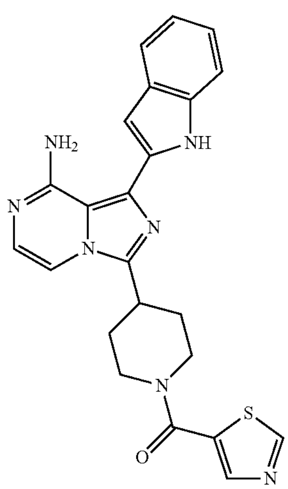 [SMILES: Nc1nccn2c(C3CCN(C(=O)c4cncs4)CC3)nc(-c3cc4ccccc4[nH]3)c12] | 443.97 | 154 | 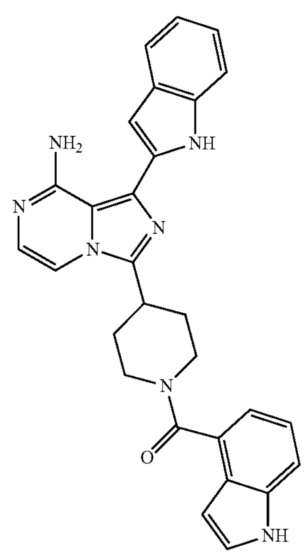 [SMILES: Nc1nccn2c(C3CCN(C(=O)c4cccc5[nH]ccc45)CC3)nc(-c3cc4ccccc4[nH]3)c12] | 475.94 |

-continued

| Ex # | Structure | MH+ | Ex # | Structure | MH+ |
|---|---|---|---|---|---|
| 155 | 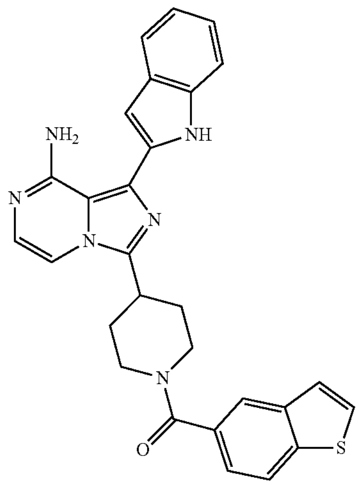 [SMILES: Nc1nccn2c(C3CCN(C(=O)c4ccc5sccc5c4)CC3)nc(-c3cc4ccccc4[nH]3)c12] | 492.76 | 156 | 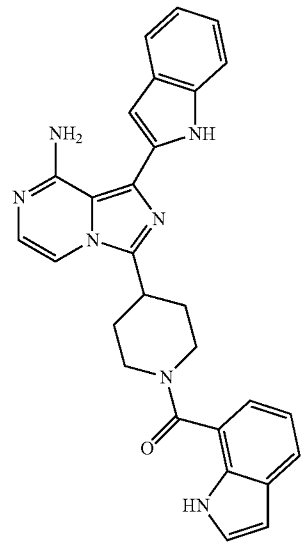 [SMILES: Nc1nccn2c(C3CCN(C(=O)c4cccc5cc[nH]c45)CC3)nc(-c3cc4ccccc4[nH]3)c12] | 475.85 |
| 157 | 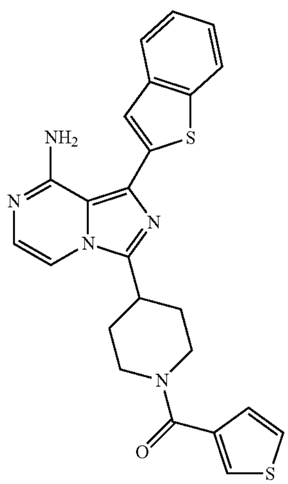 [SMILES: Nc1nccn2c(C3CCN(C(=O)c4ccsc4)CC3)nc(-c3cc4ccccc4s3)c12] | 460.13 | 158 | 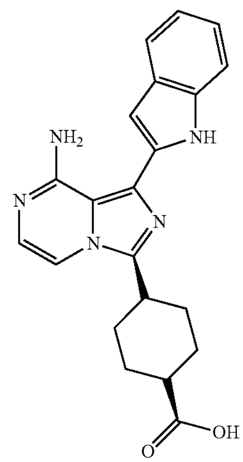 | 375.98 |
| 159 | 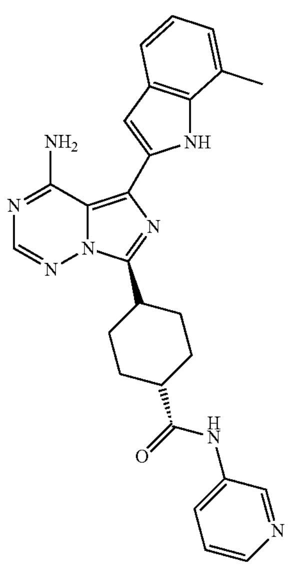 | 466.97 | 160 | 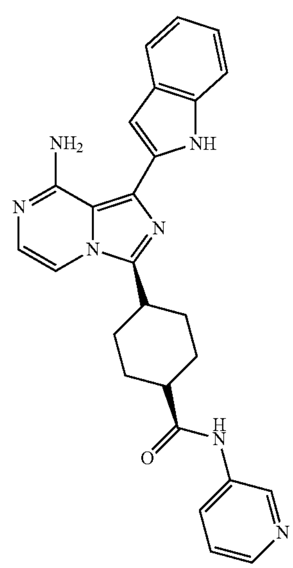 | 451.98 |

-continued

| Ex # | Structure | MH+ | Ex # | Structure | MH+ |
|---|---|---|---|---|---|
| 161 | 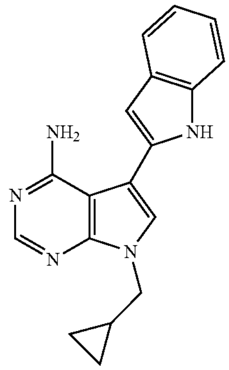 [SMILES: Nc1ncnc2c1c(-c1cc3ccccc3[nH]1)cn2CC1CC1] | 304.19 | 162 | 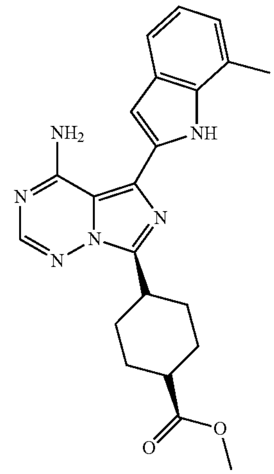 | 405.02 |
| 163 | 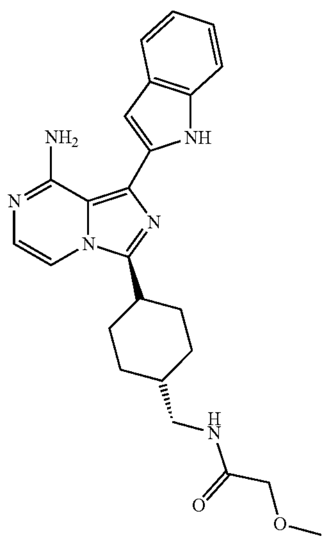 | 433.18 | 164 | 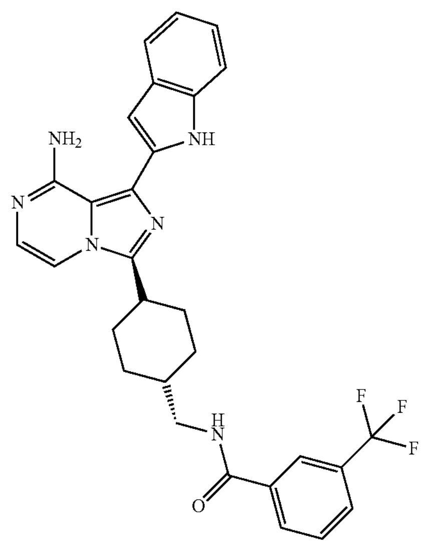 | 532.90 |
| 165 | 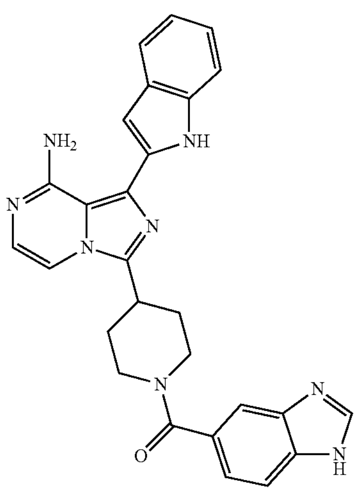 [SMILES: Nc1nccn2c(C3CCN(C(=O)c4ccc5[nH]cnc5c4)CC3)nc(-c3cc4ccccc4[nH]3)c12] | 476.95 | 166 | 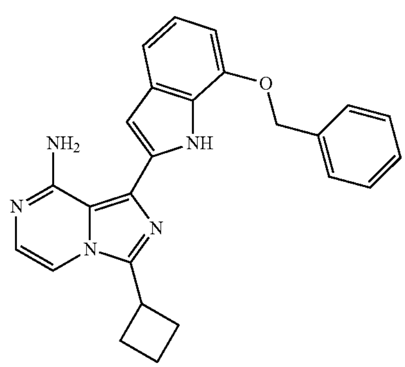 [SMILES: Nc1nccn2c(C3CCC3)nc(-c3cc4cccc(OCc5ccccc5)c4[nH]3)c12] | 410.02 |

| Ex # | Structure | MH+ | Ex # | Structure | MH+ |
|---|---|---|---|---|---|
| 167 | 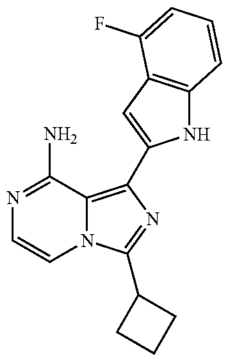 [SMILES: Nc1nccn2c(C3CCC3)nc(-c3cc4c(F)cccc4[nH]3)c12] | 321.92 | 168 | 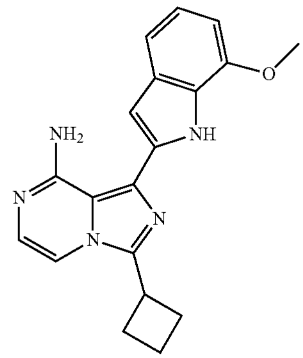 [SMILES: COc1cccc2cc(-c3nc(C4CCC4)n4ccnc(N)c34)[nH]c12] | 333.87 |
| 169 | 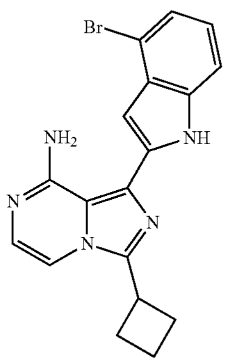 [SMILES: Nc1nccn2c(C3CCC3)nc(-c3cc4c(Br)cccc4[nH]3)c12] | 381.83 383.72 | 170 | 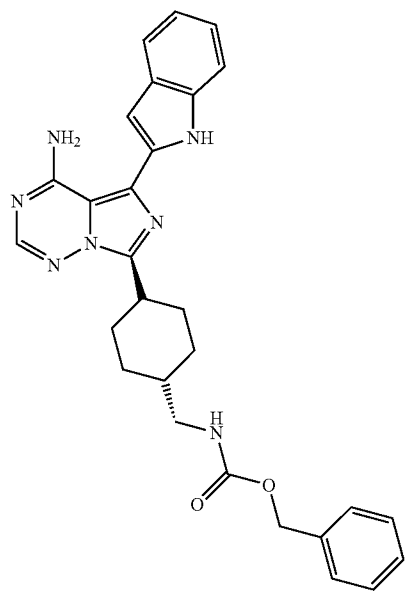 | 495.97 |
| 171 | (Chiral) | 465.96 | 232 | 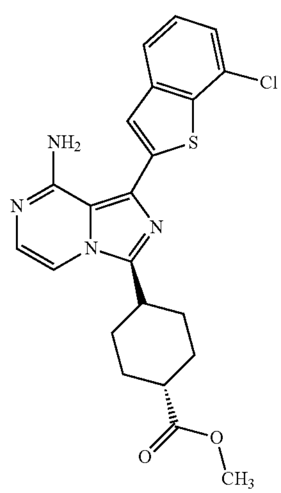 | 440.89 442.86 |

-continued
| Ex # | Structure | MH+ | Ex # | Structure | MH+ |
|---|---|---|---|---|---|
| 172 | 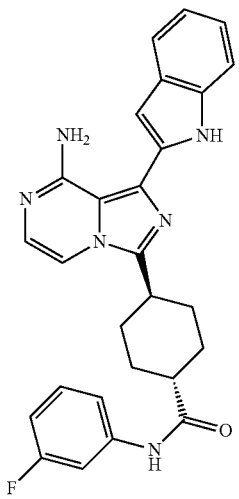 Chiral | 468.84 470.50 | 233 | 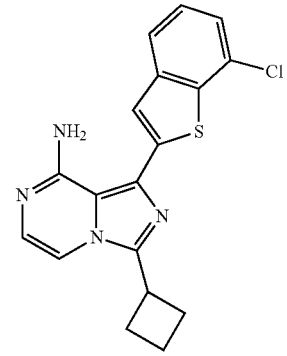 [SMILES: Nc1nccn2c(C3CCC3)nc(-c3cc4cccc(Cl)c4s3)c12] | 354.74 356.98 |
| 173 | 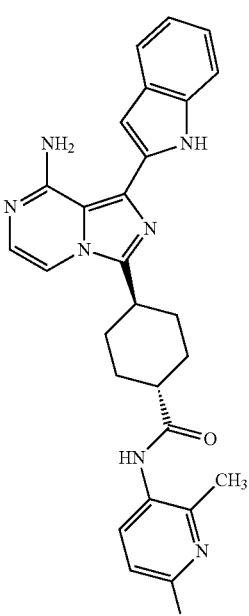 Chiral | 480.20 | 234 | 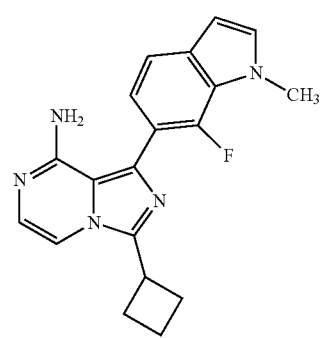 [SMILES: Cn1ccc2ccc(-c3nc(C4CCC4)n4ccnc(N)c34)c(F)c21] | 335.84 |

-continued

| Ex # | Structure | MH+ | Ex # | Structure | MH+ |
|---|---|---|---|---|---|
| 174 | Chiral | 452.97 | 235 | 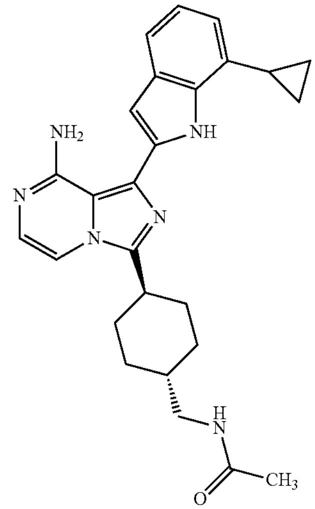 [SMILES: CC(=O)NC[C@H]1CC[C@H](c2nc(-c3cc4cccc(C5CC5)c4[nH]3)c3c(N)nccn32)CC1] | 442.96 |
| 175 | Chiral | 466.20 | 236 | 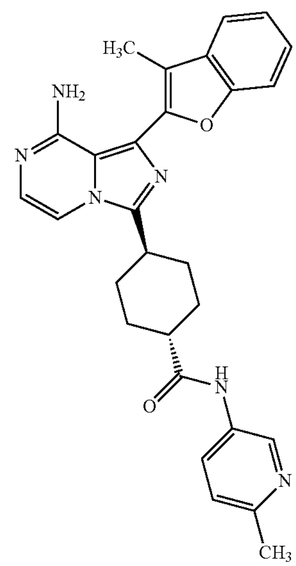 [SMILES: Cc1ccc(NC(=O)[C@H]2CC[C@H](c3nc(-c4oc5ccccc5c4C)c4c(N)nccn43)CC2)cn1] | 480.98 |
| 176 | 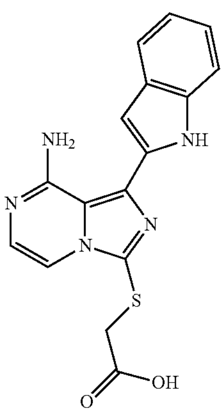 [SMILES: Nc1nccn2c(SCC(=O)O)nc(-c3cc4ccccc4[nH]3)c12] | 399.92 | 237 | 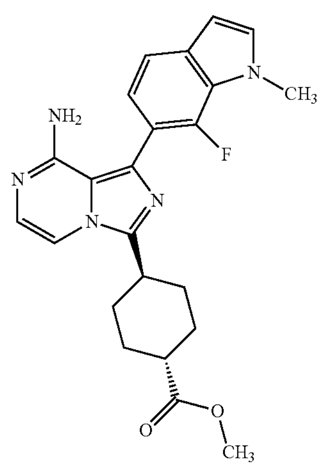 [SMILES: COC(=O)[C@H]1CC[C@H](c2nc(-c3ccc4ccn(C)c4c3F)c3c(N)nccn32)CC1] | 421.83 |

| Ex # | Structure | MH+ | Ex # | Structure | MH+ |
|---|---|---|---|---|---|
| 177 | 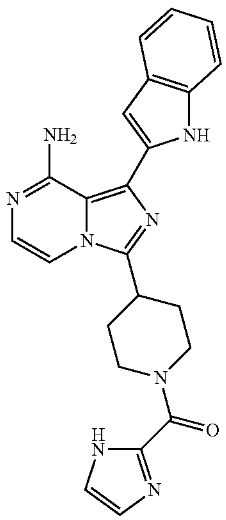 [SMILES: Nc1nccn2c(C3CCN(C(=O)c4ncc[nH]4)CC3)nc(-c3cc4ccccc4[nH]3)c12] | 426.91 | 238 | 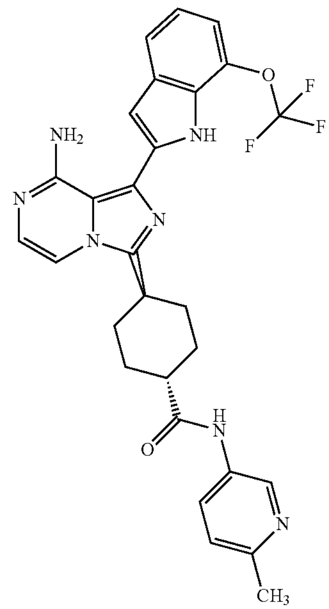 [SMILES: Cc1ccc(NC(=O)[C@H]2CC[C@H](c3nc(-c4cc5cccc(OC(F)(F)F)c5[nH]4)c4c(N)nccn43)CC2)cn1] | 549.91 |
| 178 | 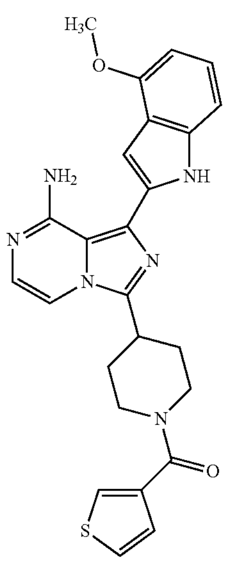 [SMILES: COc1cccc2[nH]c(-c3nc(C4CCN(C(=O)c5ccsc5)CC4)n4ccnc(N)c34)cc12] | 472.62 | 239 | 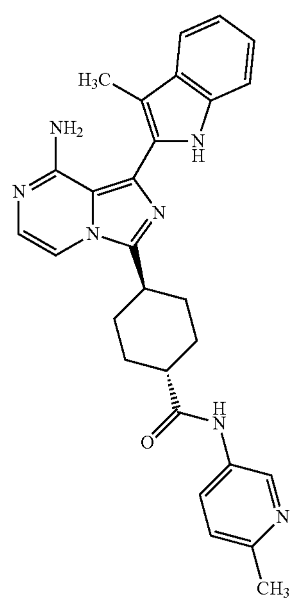 [SMILES: Cc1ccc(NC(=O)[C@H]2CC[C@H](c3nc(-c4[nH]c5ccccc5c4C)c4c(N)nccn43)CC2)cn1] | 482.02 |

| Ex # | Structure | MH+ | Ex # | Structure | MH+ |
|---|---|---|---|---|---|
| 179 | 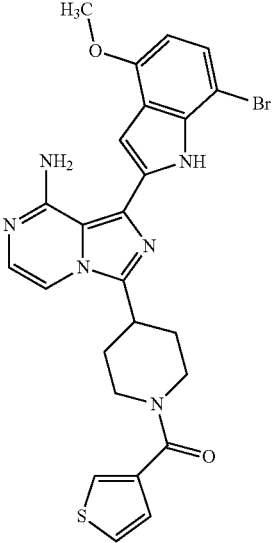 [SMILES: COc1ccc(Br)c2[nH]c(-c3nc(C4CCN(C(=O)c5ccsc5)CC4)n4ccnc(N)c34)cc12] | 550.68 552.50 | 240 | 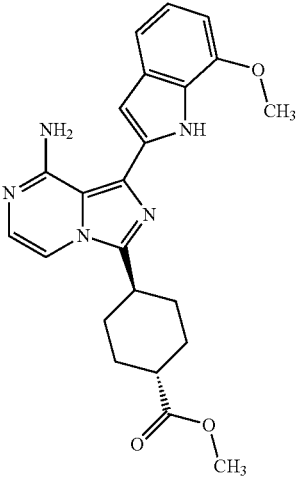 [SMILES: COc1cccc2cc(-c3nc([C@H]4CC[C@H](C(=O)OC)CC4)n4ccnc(N)c34)[nH]c12] | 419.89 |
| 180 | 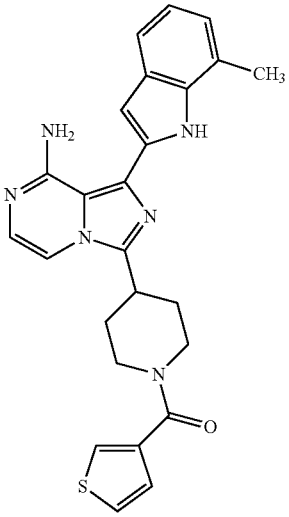 [SMILES: Cc1cccc2cc(-c3nc(C4CCN(C(=O)c5ccsc5)CC4)n4ccnc(N)c34)[nH]c12] | 456.63 | 241 | 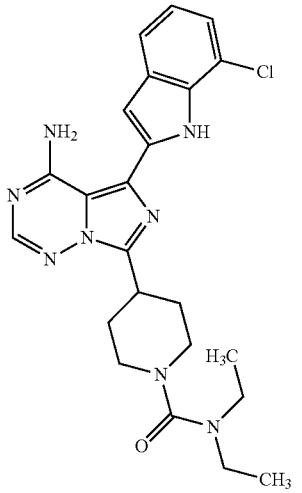 [SMILES: CCN(CC)C(=O)N1CCC(c2nc(-c3cc4cccc(Cl)c4[nH]3)c3c(N)ncnn23)CC1] | 467.92 |

-continued

| Ex # | Structure | MH+ | Ex # | Structure | MH+ |
|---|---|---|---|---|---|
| 181 | Chiral | 471.89 | 242 | 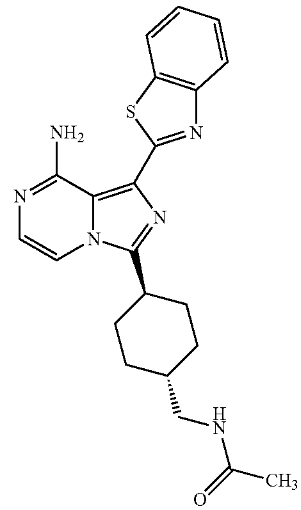 | 420.97 |
| 182 | 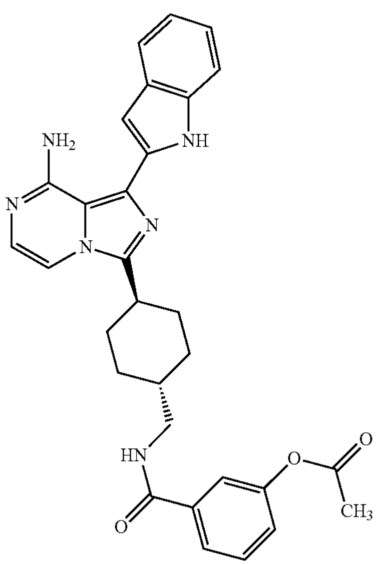 [SMILES: CC(=O)Oc1cccc(C(=O)NC[C@H]2CC[C@H](c3nc(-c4cc5ccccc5[nH]4)c4c(N)nccn43)CC2)c1] | 523.93 | 243 | 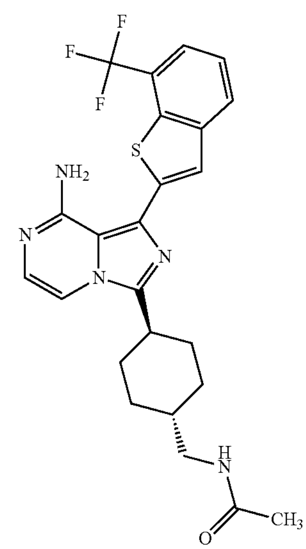 [SMILES: CC(=O)NC[C@H]1CC[C@H](c2nc(-c3cc4cccc(C(F)(F)F)c4s3)c3c(N)nccn32)CC1] | 487.97 |

-continued

| Ex # | Structure | MH+ | Ex # | Structure | MH+ |
|---|---|---|---|---|---|
| 183 | 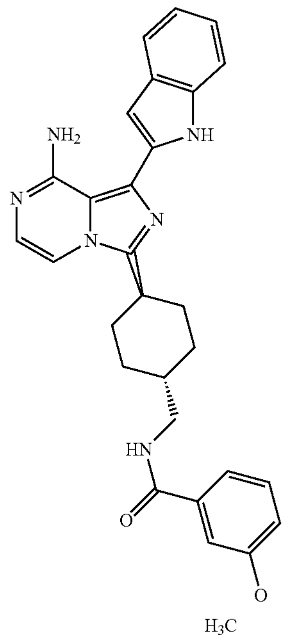 | 496.05 | 244 | 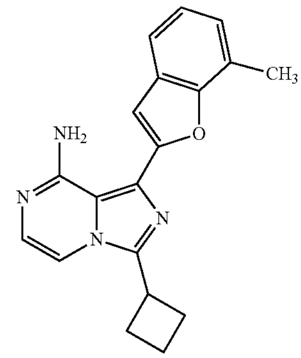 [SMILES: Cc1cccc2cc(-c3nc(C4CCC4)n4ccnc(N)c34)oc12] | 319.00 |
| 184 | 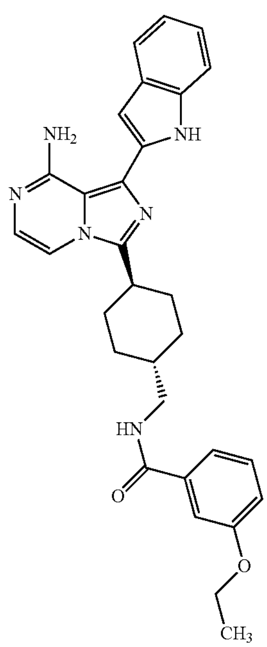 [SMILES: CCOc1cccc(C(=O)NC[C@H]2CC[C@H](c3nc(-c4cc5ccccc5[nH]4)c4c(N)nccn43)CC2)c1] | 510.00 | 245 | 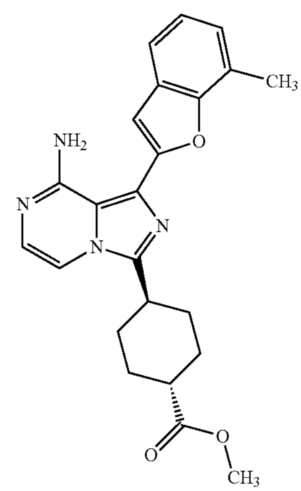 [SMILES: COC(=O)[C@H]1CC[C@H](c2nc(-c3cc4cccc(C)c4o3)c3c(N)nccn32)CC1] | 405.03 |

-continued

| Ex # | Structure | MH+ | Ex # | Structure | MH+ |
|---|---|---|---|---|---|
| 185 | 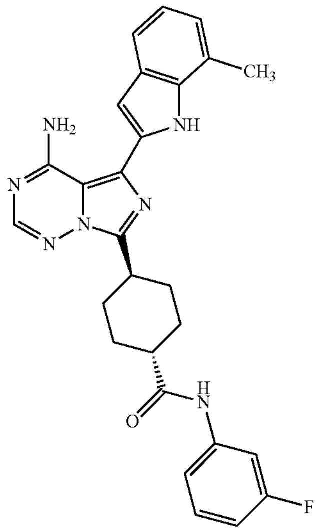 [SMILES: Cc1cccc2cc(-c3nc([C@H]4CC[C@H](C(=O)Nc5cccc(F)c5)CC4)n4ncnc(N)c34)[nH]c12] | 483.89 | 246 | 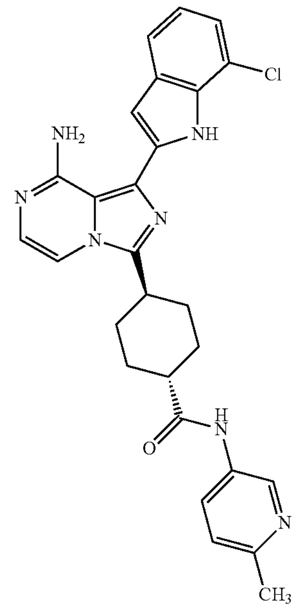 [SMILES: Cc1ccc(NC(=O)[C@H]2CC[C@H](c3nc(-c4cc5cccc(Cl)c5[nH]4)c4c(N)nccn43)CC2)cn1] | 499.95 501.96 |
| 186 | 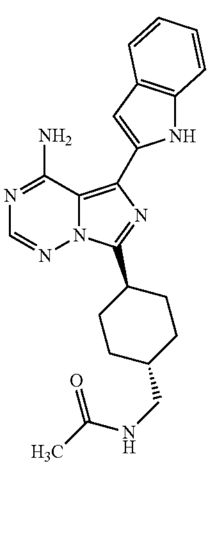 | 404.18 | 247 | 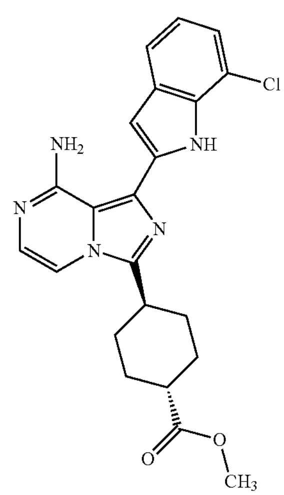 [SMILES: COC(=O)[C@H]1CC[C@H](c2nc(-c3cc4cccc(Cl)c4[nH]3)c3c(N)nccn32)CC1] | 423.83 425.93 |

-continued

| Ex # | Structure | MH+ | Ex # | Structure | MH+ |
|---|---|---|---|---|---|
| 187 | 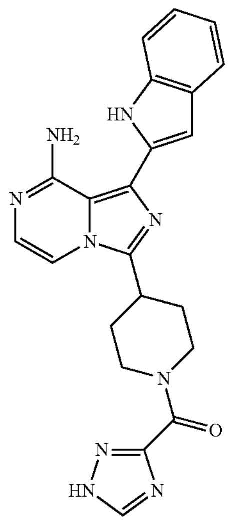 [SMILES: Nc1nccn2c(C3CCN(C(=O)c4nc[nH]n4)CC3)nc(-c3cc4ccccc4[nH]3)c12] | 427.93 | 248 | Chiral | 409.95 411.90 |
| 188 | 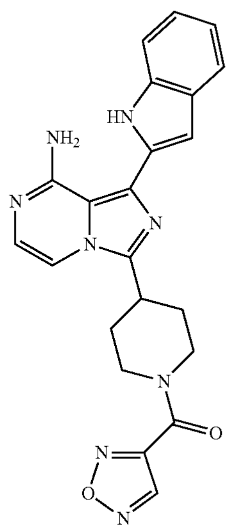 [SMILES: Nc1nccn2c(C3CCN(C(=O)c4cnon4)CC3)nc(-c3cc4ccccc4[nH]3)c12] | 428.88 | 249 | Chiral | 376.99 |
| 189 | 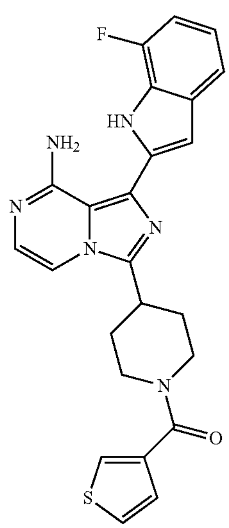 [SMILES: Nc1nccn2c(C3CCN(C(=O)c4ccsc4)CC3)nc(-c3cc4cccc(F)c4[nH]3)c12] | 460.66 | 250 | Chiral | 412.06 414.03 |

| Ex # | Structure | MH+ | Ex # | Structure | MH+ |
|---|---|---|---|---|---|
| 191 | 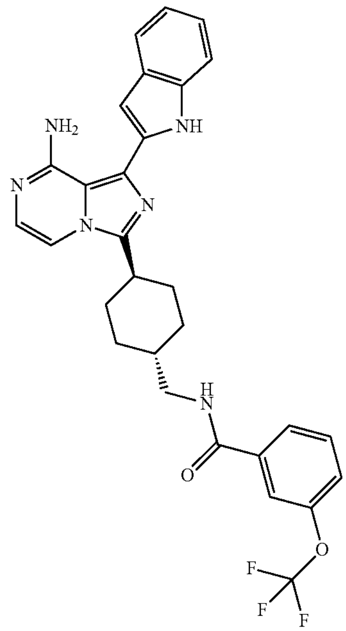 | Chiral 548.72 | 251 | 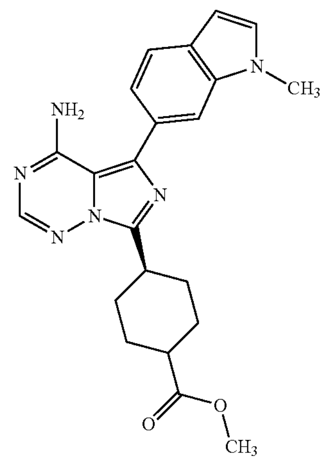 | 404.96 |
| 192 | 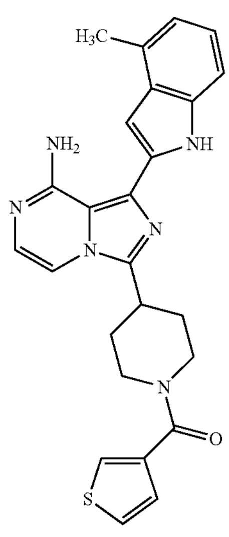 [SMILES: Cc1cccc2[nH]c(-c3nc(C4CCN(C(=O)c5ccsc5)CC4)n4ccnc(N)c34)cc12] | 456.86 | 252 | 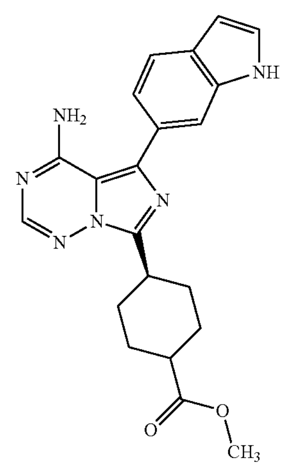 | 391.01 |

-continued

| Ex # | Structure | MH+ | Ex # | Structure | MH+ |
|---|---|---|---|---|---|
| 193 | 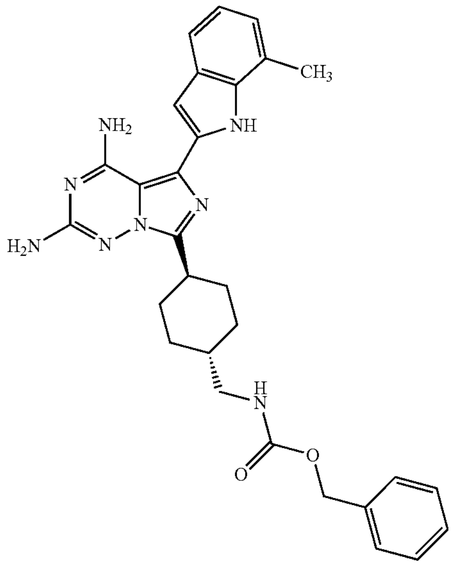 [SMILES: Cc1cccc2cc(-c3nc([C@H]4CC[C@H](CNC(=O)OCc5ccccc5)CC4)n4nc(N)nc(N)c34)[nH]c12] | 525.25 | 253 | 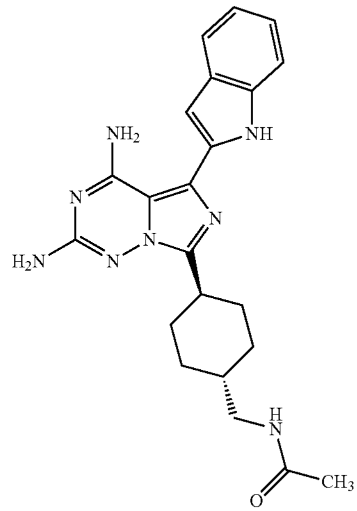 [SMILES: CC(=O)NC[C@H]1CC[C@H](c2nc(-c3cc4ccccc4[nH]3)c3c(N)nc(N)nn32)CC1] | 419.12 |
| 194 | Chiral | 467.21 | 254 | 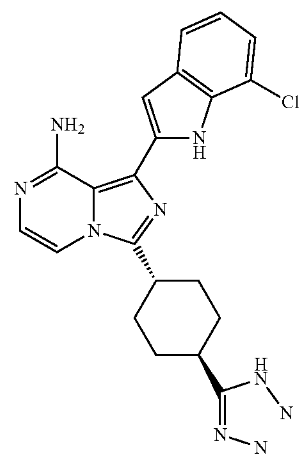 [SMILES: N/N=C(\NN)[C@H]1CC[C@H](c2nc(-c3cc4cccc(Cl)c4[nH]3)c3c(N)nccn32)CC1] | 434.04 |
| 195 | 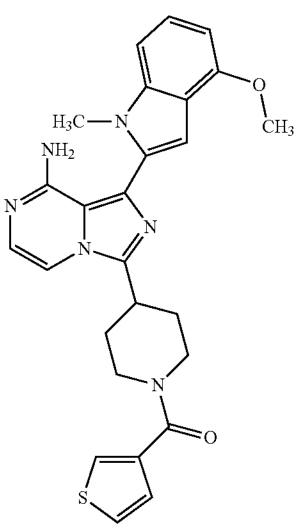 [SMILES: COc1cccc2c1cc(-c1nc(C3CCN(C(=O)c4ccsc4)CC3)n3ccnc(N)c13)n2C] | 486.96 | 255 | 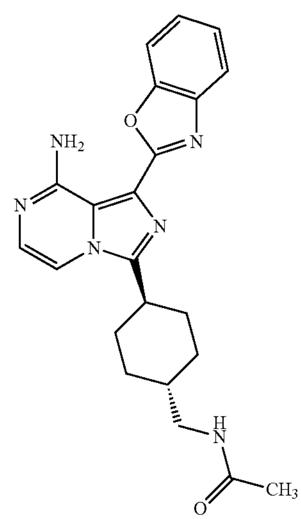 [SMILES: CC(=O)NC[C@H]1CC[C@H](c2nc(-c3nc4ccccc4o3)c3c(N)nccn32)CC1] | 405.03 |

-continued

| Ex # | Structure | MH+ | Ex # | Structure | MH+ |
|---|---|---|---|---|---|
| 196 | 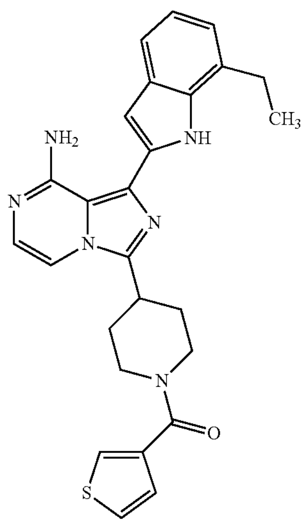 [SMILES: CCc1cccc2cc(-c3nc(C4CCN(C(=O)c5ccsc5)CC4)n4ccnc(N)c34)[nH]c12] | 470.97 | 256 | 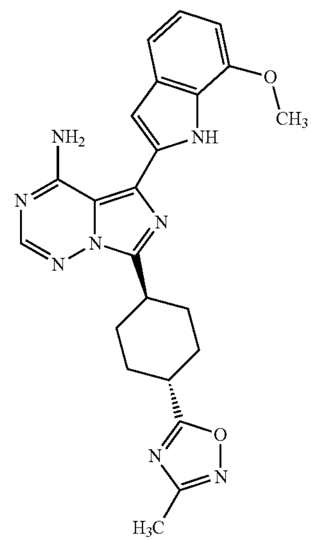 [SMILES: COc1cccc2cc(-c3nc([C@H]4CC[C@H](c5nc(C)no5)CC4)n4ncnc(N)c34)[nH]c12] | 445.01 |
| 197 | 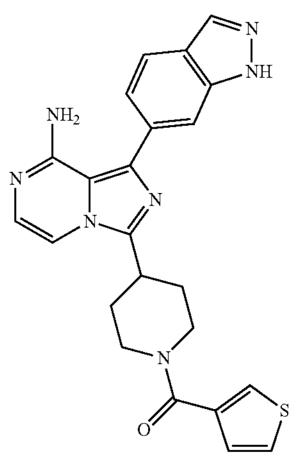 [SMILES: Nc1nccn2c(C3CCN(C(=O)c4ccsc4)CC3)nc(-c3ccc4cn[nH]c4c3)c12] | 444.00 | 257 | 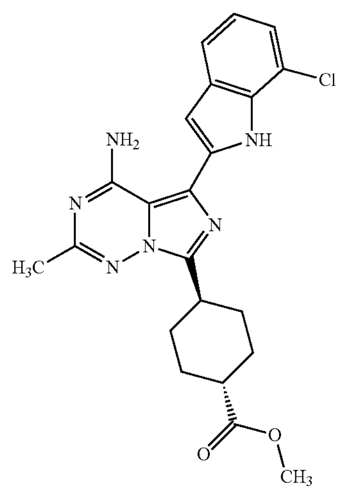 [SMILES: COC(=O)[C@H]1CC[C@H](c2nc(-c3cc4cccc(Cl)c4[nH]3)c3c(N)nc(C)nn32)CC1] | 438.94<br>440.89 |
| 198 | 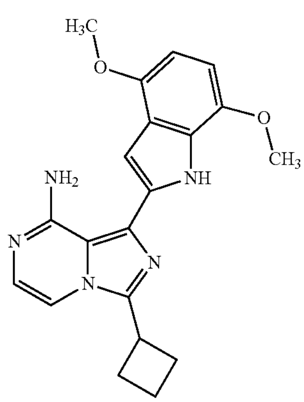 [SMILES: COc1ccc(OC)c2[nH]c(-c3nc(C4CCC4)n4ccnc(N)c34)cc12] | 363.89 | 258 | 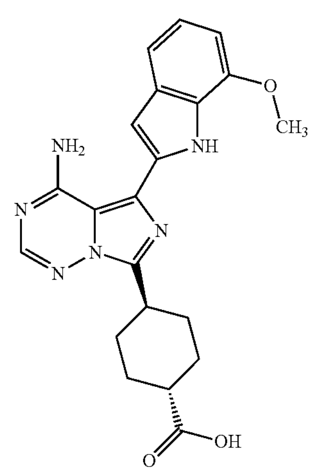 [SMILES: COc1cccc2cc(-c3nc([C@H]4CC[C@H](C(=O)O)CC4)n4ncnc(N)c34)[nH]c12] | 406.98<br>406.99 |

-continued

| Ex # | Structure | MH+ | Ex # | Structure | MH+ |
|---|---|---|---|---|---|
| 199 | 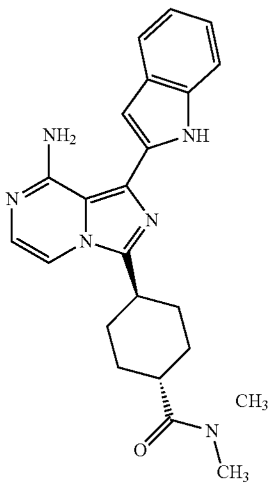 | 403.07 Chiral | 259 | 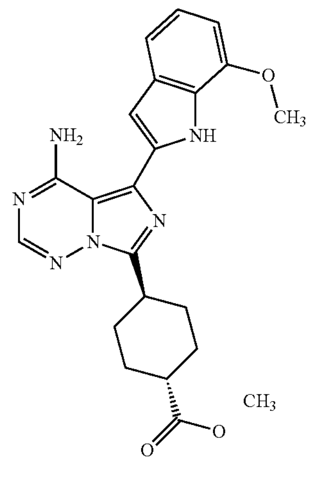 | 421.00 |
| 200 | 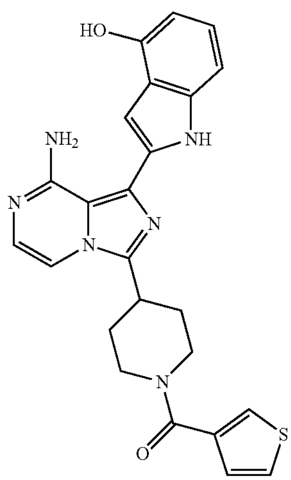 [SMILES: Nc1nccn2c(C3CCN(C(=O)c4ccsc4)CC3)nc(-c3cc4c(O)cccc4[nH]3)c12] | 458.97 | 260 | 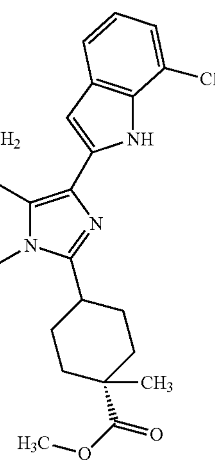 | 437.93 439.95 |
| 201 | 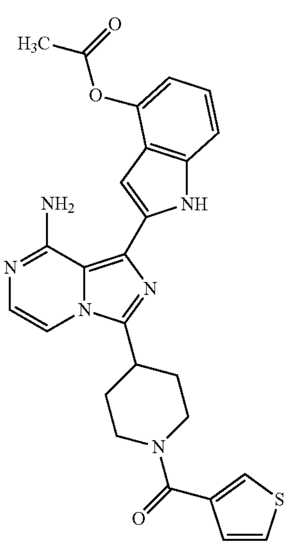 [SMILES: CC(=O)Oc1cccc2[nH]c(-c3nc(C4CCN(C(=O)c5ccsc5)CC4)n4ccnc(N)c34)cc12] | 500.96 | 261 | 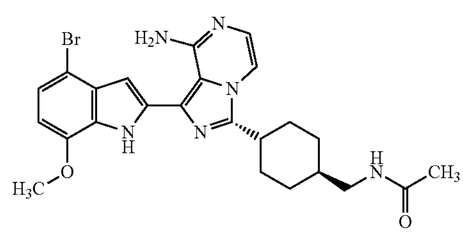 | 511.21 513.14 |

-continued

| Ex # | Structure | MH+ | Ex # | Structure | MH+ |
|---|---|---|---|---|---|
| 202 | 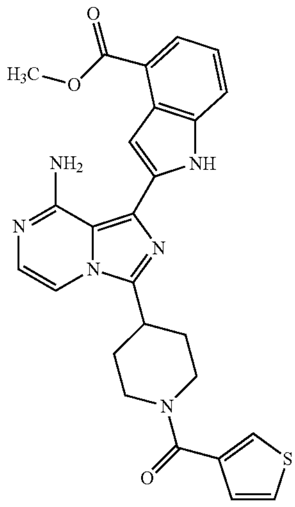 [SMILES: COC(=O)c1cccc2[nH]c(-c3nc(C4CCN(C(=O)c5ccsc5)CC4)n4ccnc(N)c34)cc12] | 500.94 | 262 | 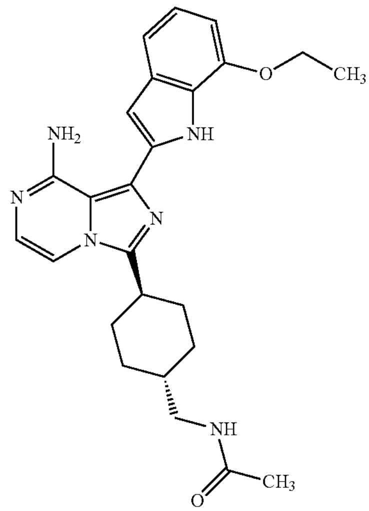 | Chiral 447.03 |
| 203 | 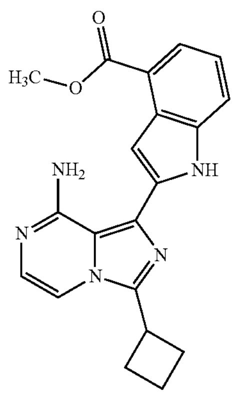 [SMILES: COC(=O)c1cccc2[nH]c(-c3nc(C4CCC4)n4ccnc(N)c34)cc12] | 362.03 | 263 | 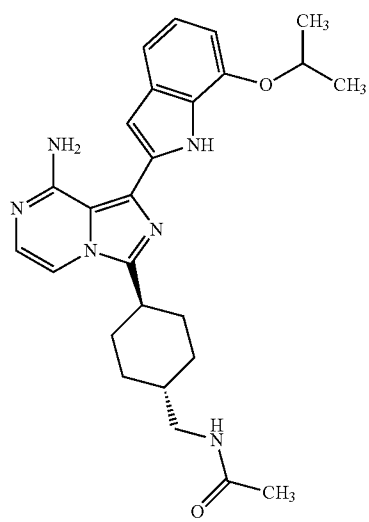 | Chiral 461.05 |
| 204 | 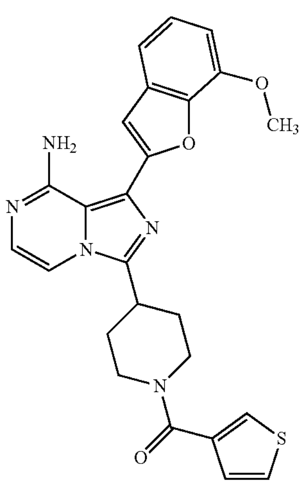 [SMILES: COc1cccc2cc(-c3nc(C4CCN(C(=O)c5ccsc5)CC4)n4ccnc(N)c34)oc12] | 473.95 | 264 | 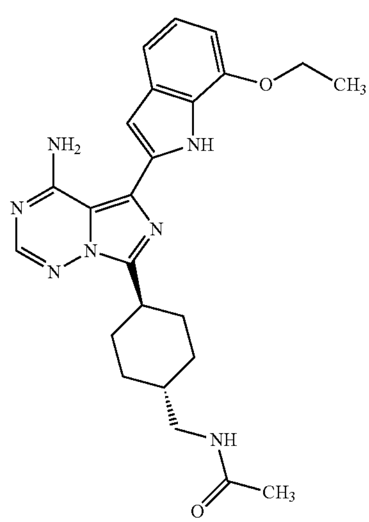 | Chiral 447.99 |

-continued
| Ex # | Structure | MH+ | Ex # | Structure | MH+ |
|---|---|---|---|---|---|
| 205 | 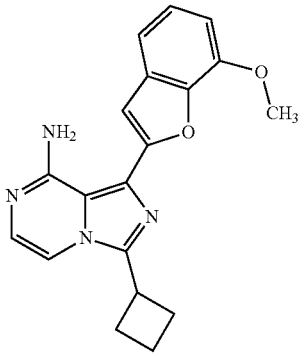 [SMILES: COc1cccc2cc(-c3nc(C4CCC4)n4ccnc(N)c34)oc12] | 335.06 | 265 | 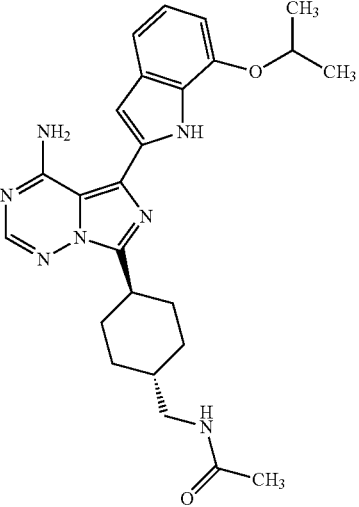 Chiral | 462.00 |
| 206 | 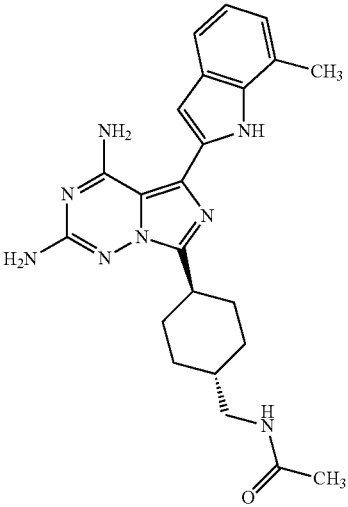 [SMILES: CC(=O)NC[C@H]1CC[C@H](c2nc(-c3cc4cccc(C)c4[nH]3)c3c(N)nc(N)nn32)CC1] | 433.07 | 266 | 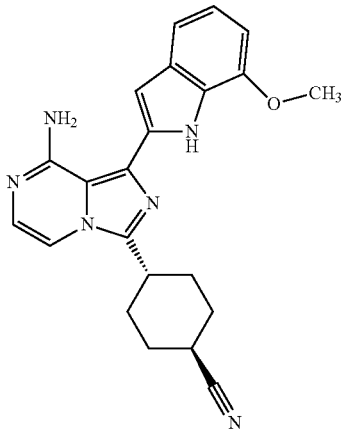 [SMILES: COc1cccc2cc(-c3nc([C@H]4CC[C@H](C#N)CC4)n4ccnc(N)c34)[nH]c12] | 387.20 |
| 207 | 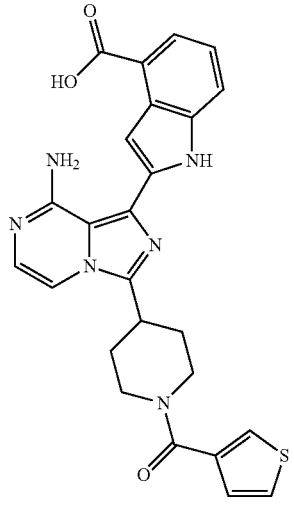 [SMILES: Nc1nccn2c(C3CCN(C(=O)c4ccsc4)CC3)nc(-c3cc4c(C(=O)O)cccc4[nH]3)c12] | 486.96 | 267 | 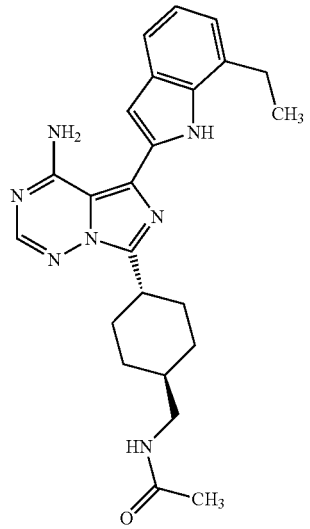 [SMILES: CCc1cccc2cc(-c3nc([C@H]4CC[C@H](CNC(C)=O)CC4)n4ncnc(N)c34)[nH]c12] | 432.06 |

263 264
-continued
| Ex # | Structure | MH+ | Ex # | Structure | MH+ |
|---|---|---|---|---|---|
| 208 | 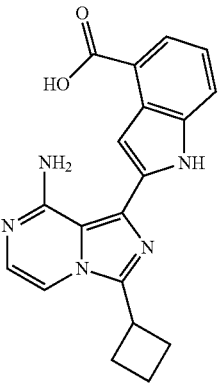 [SMILES: Nc1nccn2c(C3CCC3)nc(-c3cc4c(C(=O)O)cccc4[nH]3)c12] | 348.02 | 268 | 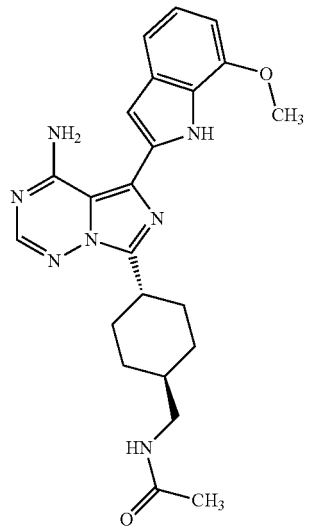 [SMILES: COc1cccc2cc(-c3nc([C@H]4CC[C@H](CNC(C)=O)CC4)n4ncnc(N)c34)[nH]c12] | 434.02 434.06 |
| 209 | 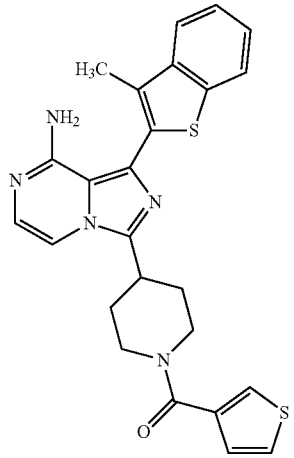 [SMILES: Cc1c(-c2nc(C3CCN(C(=O)c4ccsc4)CC3)n3ccnc(N)c23)sc2ccccc12] | 473.87 | 269 | 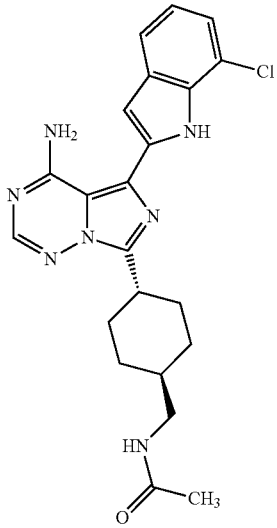 [SMILES: CC(=O)NC[C@H]1CC[C@H](c2nc(-c3cc4cccc(Cl)c4[nH]3)c3c(N)ncnn32)CC1] | 437.97 439.95 |
| 210 | 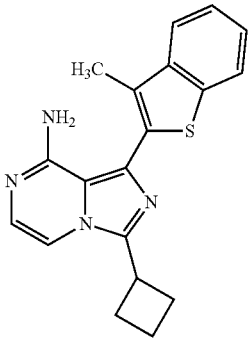 | 334.88 | 270 | 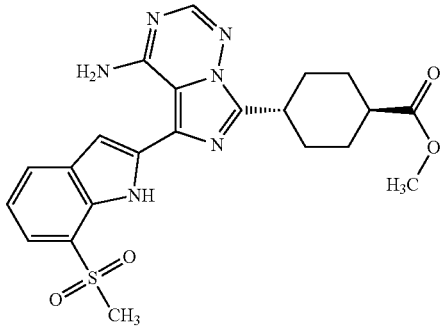 [SMILES: COC(=O)[C@H]1CC[C@H](c2nc(-c3cc4cccc(S(C)(=O)=O)c4[nH]3)c3c(N)ncnn32)CC1] | 468.95 |

-continued
| Ex # | Structure | MH+ | Ex # | Structure | MH+ |
|---|---|---|---|---|---|
| 211 | 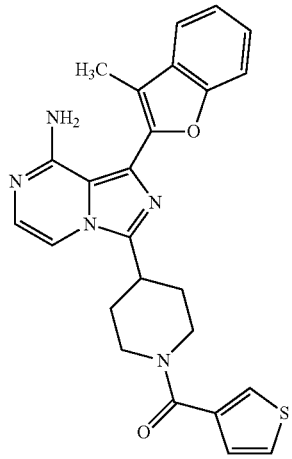 [SMILES: Cc1c(-c2nc(C3CCN(C(=O)c4ccsc4)CC3)n3ccnc(N)c23)oc2ccccc12] | 457.95 | 271 | 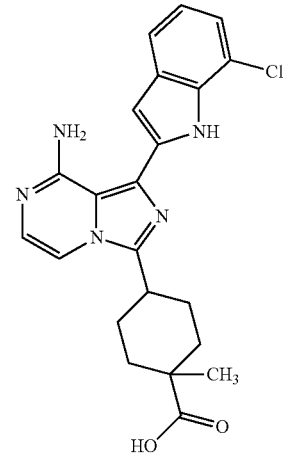 [SMILES: CC1(C(=O)O)CCC(c2nc(-c3cc4cccc(Cl)c4[nH]3)c3c(N)nccn23)CC1] | 423.97 425.93 |
| 212 | 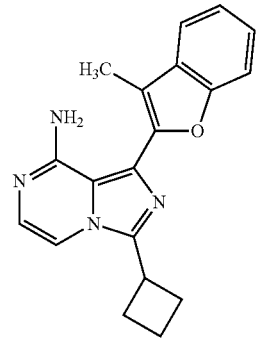 [SMILES: Cc1c(-c2nc(C3CCC3)n3ccnc(N)c23)oc2ccccc12] | 318.92 | 272 | 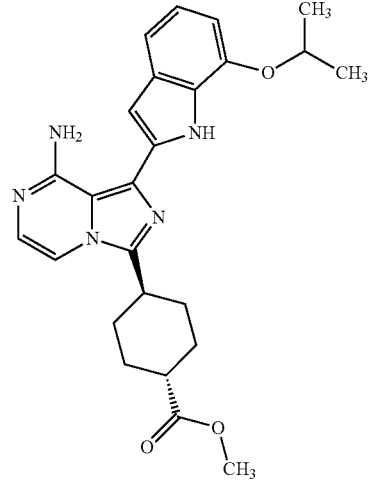 [SMILES: COC(=O)[C@H]1CC[C@H](c2nc(-c3cc4cccc(OC(C)C)c4[nH]3)c3c(N)nccn32)CC1] | 448.05 |
| 213 | 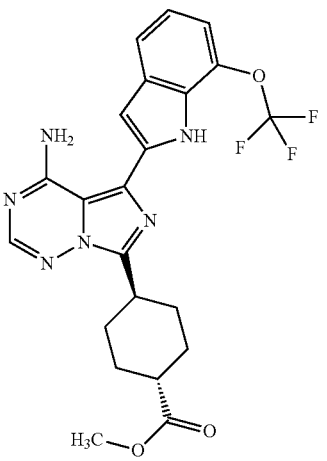 Chiral | 475.02 | 273 | 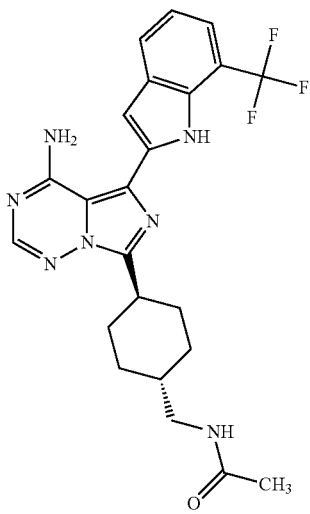 [SMILES: CC(=O)NC[C@H]1CC[C@H](c2nc(-c3cc4cccc(C(F)(F)F)c4[nH]3)c3c(N)ncnn32)CC1] | 471.98 |

-continued

| Ex # | Structure | MH+ | Ex # | Structure | MH+ |
|---|---|---|---|---|---|
| 214 | *(structure)* Chiral | 425.17 427.06 | 274 | *(structure)* | 418.09 |
| 215 | *(structure)* | 518.83 | 275 | *(structure)* | 405.03 |
| 216 | *(structure)* | 379.87 | 276 | *(structure)* Chiral | 363.98 |

| Ex # | Structure | MH+ | Ex # | Structure | MH+ |
|---|---|---|---|---|---|
| 217 | 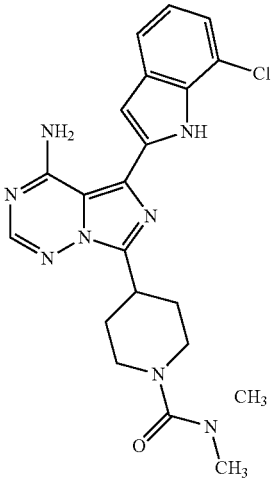 | 439.19 | 277 | 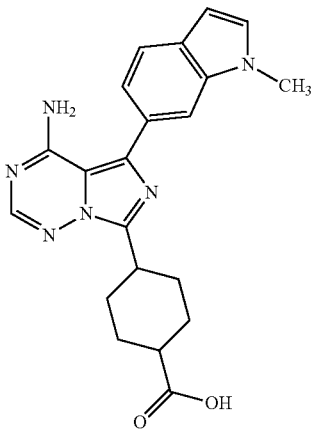 [SMILES: Cn1ccc2ccc(-c3nc(C4CCC(C(=O)O)CC4)n4ncnc(N)c34)cc21] Chiral | 423.97 425.99 |
| 218 | 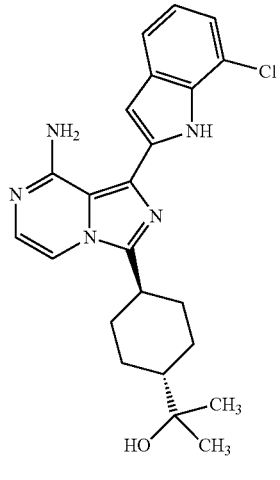 | 526.77 | 278 | 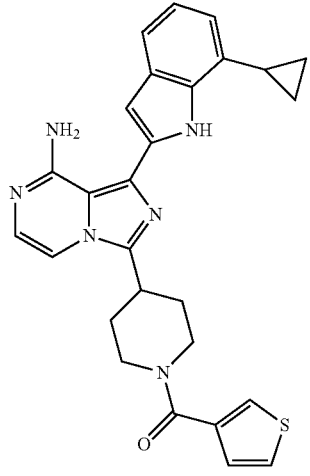 [SMILES: Nc1nccn2c(C3CCN(C(=O)c4ccsc4)CC3)nc(-c3cc4cccc(C5CC5)c4[nH]3)c12] | 391.01 |
| 219 | 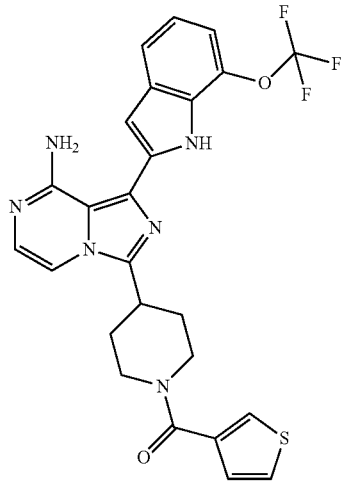 | 483.04 | 279 | 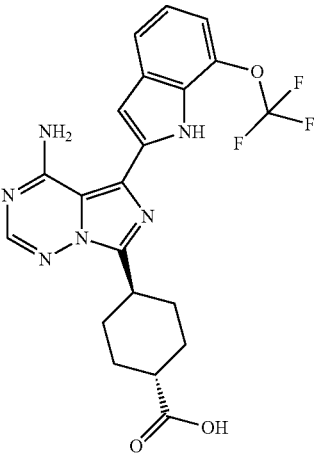 [SMILES: Nc1ncnn2c1c(-c1cc3cccc(OC(F)(F)F)c3[nH]1)nc2[C@H]1CC[C@H](C(=O)O)CC1] | 460.94 |

US 8,586,546 B2
271 272
-continued
| Ex # | Structure | MH+ | Ex # | Structure | MH+ |
|---|---|---|---|---|---|
| 220 | 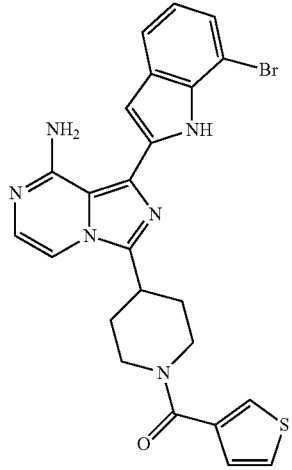 [SMILES: Nc1nccn2c(C3CCN(C(=O)c4ccsc4)CC3)nc(-c3cc4cccc(Br)c4[nH]3)c12] | 520.89 | 280 | 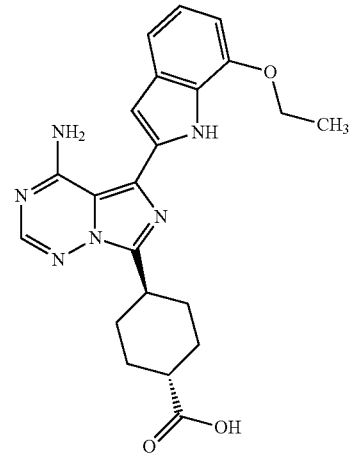 [SMILES: CCOc1cccc2cc(-c3nc([C@H]4CC[C@H](C(=O)O)CC4)n4ncnc(N)c34)[nH]c12] | 421.00 |
| 221 | 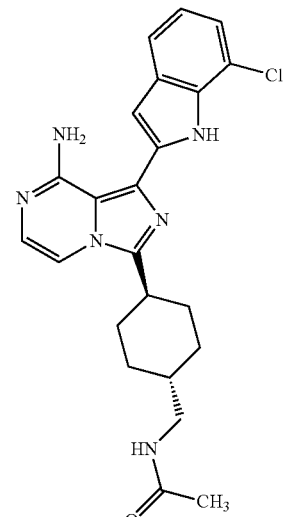 | 436.98 438.94 | 281 | 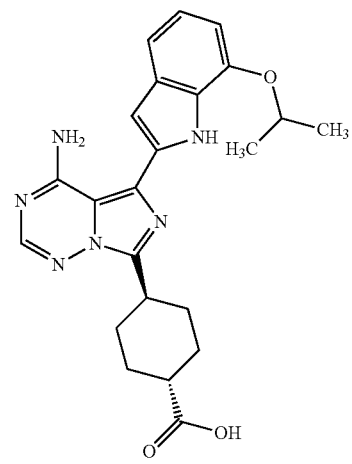 [SMILES: CC(C)Oc1cccc2cc(-c3nc([C@H]4CC[C@H](C(=O)O)CC4)n4ncnc(N)c34)[nH]c12] | 435.03 |
| 222 | 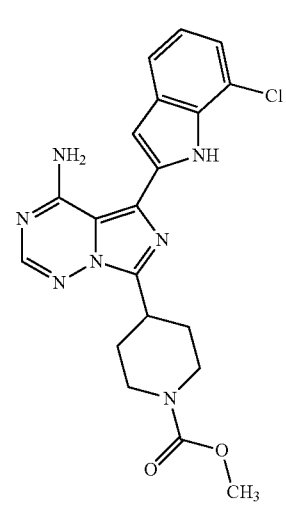 [SMILES: COC(=O)N1CCC(c2nc(-c3cc4cccc(Cl)c4[nH]3)c3c(N)ncnn23)CC1] | 425.93 | 282 | 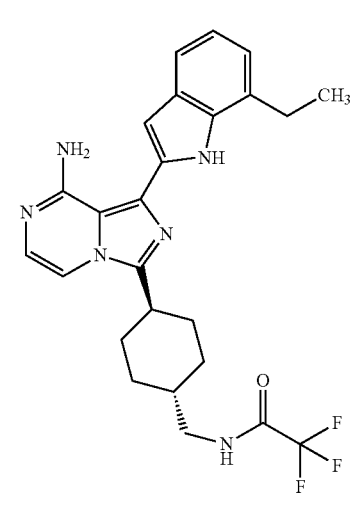 Chiral | 485.32 |

-continued

| Ex # | Structure | MH+ | Ex # | Structure | MH+ |
|---|---|---|---|---|---|
| 223 | 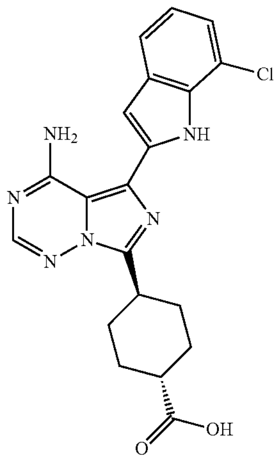 | 411.13 413.02 Chiral | 283 | 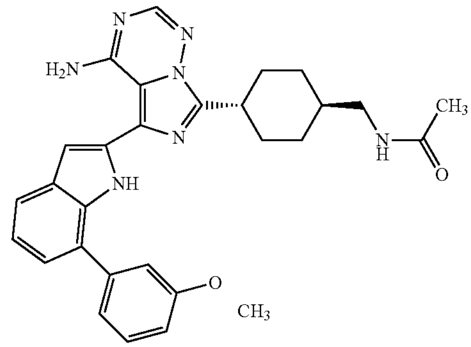 | 510.38 |
| 224 | 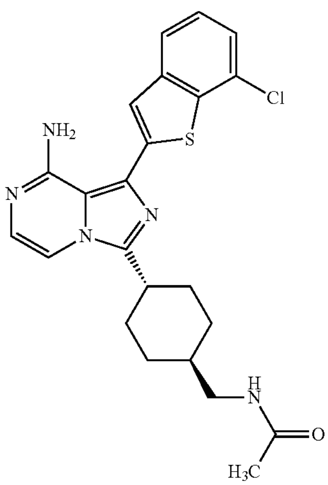 [SMILES: CC(=O)NC[C@H]1CC[C@H](c2nc(-c3cc4cccc(Cl)c4s3)c3c(N)nccn32)CC1] | 453.99 | 284 | 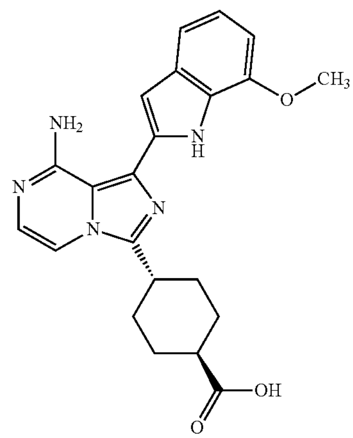 [SMILES: COc1cccc2cc(-c3nc([C@H]4CC[C@H](C(=O)O)CC4)n4ccnc(N)c34)[nH]c12] | 406.29 |
| 225 | 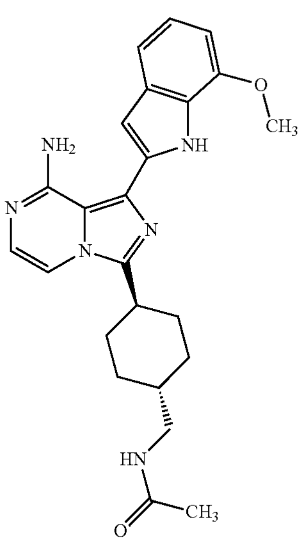 [SMILES: COc1cccc2cc(-c3nc([C@H]4CC[C@H](CNC(C)=O)CC4)n4ccnc(N)c34)[nH]c12] | 433.02 | 285 | 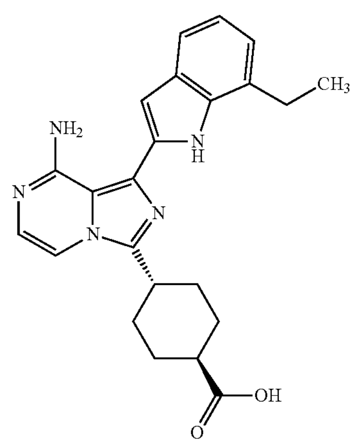 [SMILES: CCc1cccc2cc(-c3nc([C@H]4CC[C@H](C(=O)O)CC4)n4ccnc(N)c34)[nH]c12] | 404.21 |

-continued

| Ex # | Structure | MH+ | Ex # | Structure | MH+ |
|---|---|---|---|---|---|
| 226 | 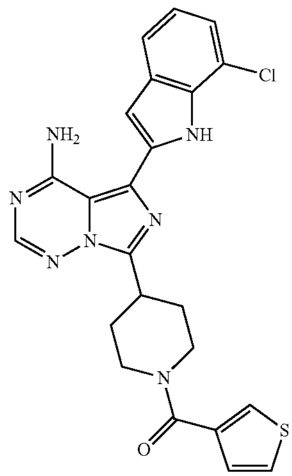 [SMILES: Nc1ncnn2c(C3CCN(C(=O)c4ccsc4)CC3)nc(-c3cc4cccc(Cl)c4[nH]3)c12] | 479.85 | 286 | Chiral | 420.53 |
| 227 | 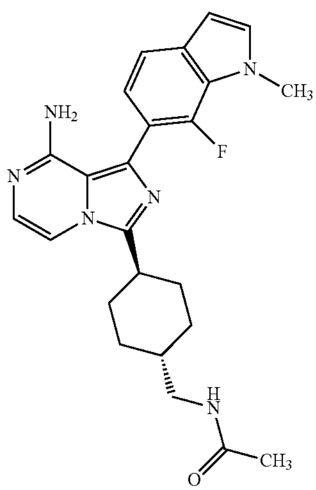 [SMILES: CC(=O)NC[C@H]1CC[C@H](c2nc(-c3ccc4ccn(C)c4c3F)c3c(N)nccn32)CC1] | 434.95 | 287 | 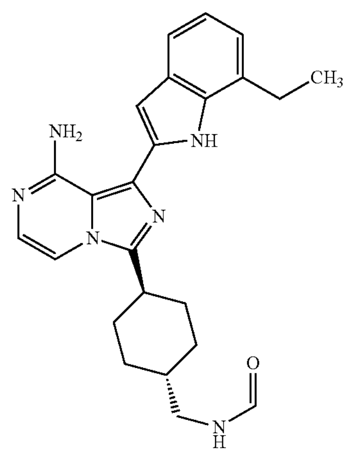 [SMILES: CCc1cccc2cc(-c3nc([C@H]4CC[C@H](CNC=O)CC4)n4ccnc(N)c34)[nH]c12] | 417.29 |
| 228 | 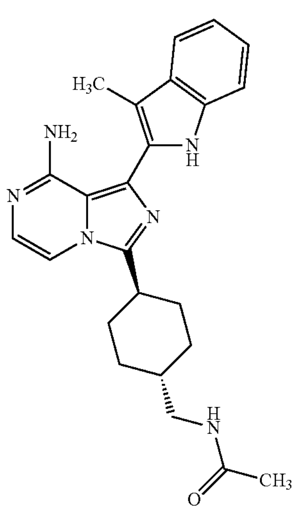 [SMILES: CC(=O)NC[C@H]1CC[C@H](c2nc(-c3[nH]c4ccccc4c3C)c3c(N)nccn32)CC1] | 417.21 | 288 | Chiral | 423.29 |

-continued

| Ex # | Structure | MH+ | Ex # | Structure | MH+ |
|---|---|---|---|---|---|
| 229 | Chiral | 500.99 502.88 | 289 | 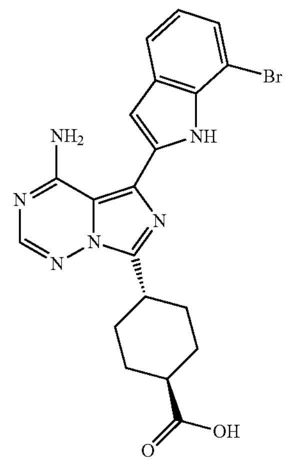 [SMILES: Nc1ncnn2c1c(-c1cc3cccc(Br)c3[nH]1)nc2[C@H]1CC[C@H](C(=O)O)CC1] | 455.11 457.09 |
| 230 | 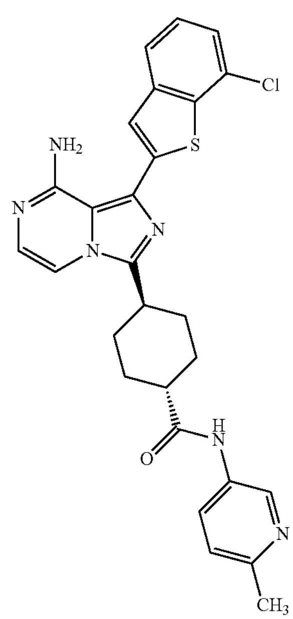 [SMILES: Cc1ccc(NC(=O)[C@H]2CC[C@H](c3nc(-c4cc5cccc(Cl)c5s4)c4c(N)nccn43)CC2)cn1] | 516.91 518.90 | 290 | 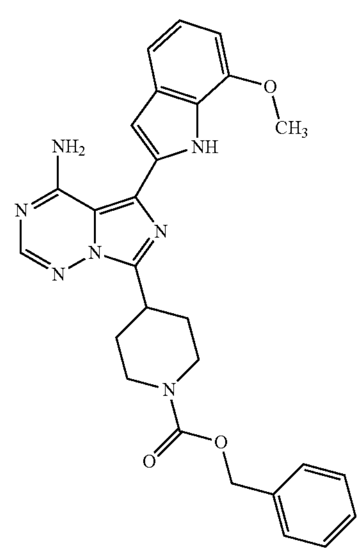 [SMILES: COc1cccc2cc(-c3nc(C4CCN(C(=O)OCc5ccccc5)CC4)n4ncnc(N)c34)[nH]c12] | 497.93 |

-continued

| Ex # | Structure | MH+ | Ex # | Structure | MH+ |
|---|---|---|---|---|---|
| 231 | 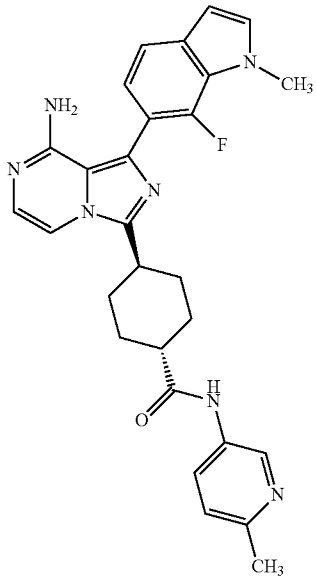 [SMILES: Cc1ccc(NC(=O)[C@H]2CC[C@H](c3nc(-c4ccc5ccn(C)c5c4F)c4c(N)nccn43)CC2)cn1] | 498.02 | 291 | Chiral | 424.04 425.99 |
| 292 | Chiral | 434.08 | 333 | 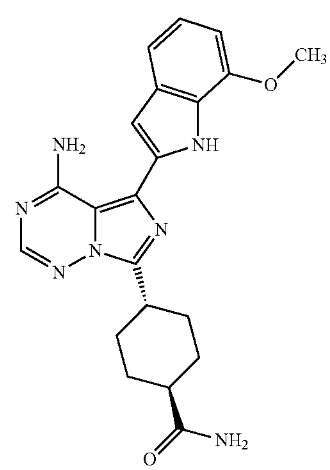 [SMILES: COc1cccc2cc(-c3nc([C@H]4CC[C@H](C(N)=O)CC4)n4ncnc(N)c34)[nH]c12] | 406.35 406.42 |

-continued

| Ex # | Structure | MH+ | Ex # | Structure | MH+ |
|---|---|---|---|---|---|
| 293 | 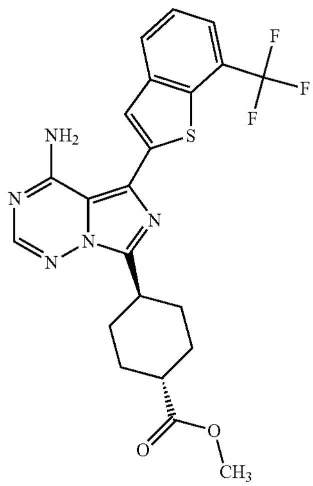 | Chiral 475.89 | 334 | 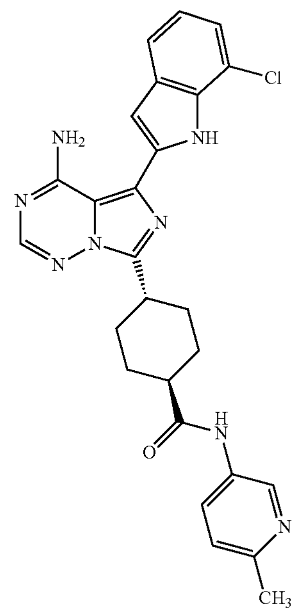 [SMILES: Cc1ccc(NC(=O)[C@H]2CC[C@H](c3nc(-c4cc5cccc(Cl)c5[nH]4)c4c(N)ncnn43)CC2)cn1] | 501.31 |
| 294 | 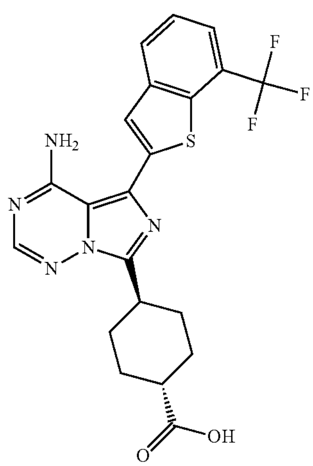 | Chiral 461.94 | 335 | 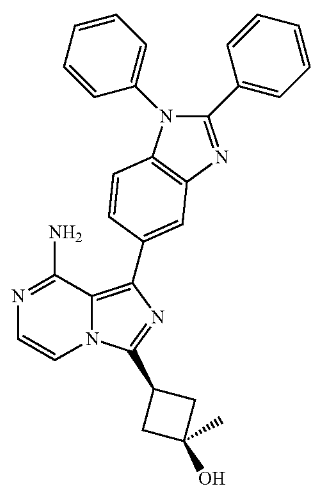 [SMILES: C[C@]1(O)C[C@@H](c2nc(-c3ccc4c(c3)nc(-c3ccccc3)n4-c3ccccc3)c3c(N)nccn32)C1] | 487.44 |
| 295 | 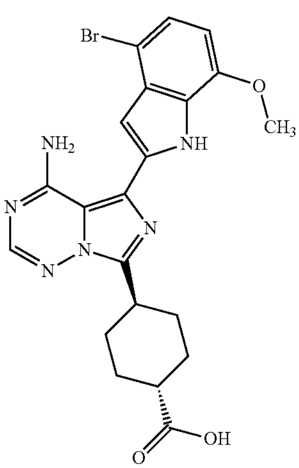 [SMILES: COc1ccc(Br)c2cc(-c3nc([C@H]4CC[C@H](C(=O)O)CC4)n4ncnc(N)c34)[nH]c12] | 485.14 487.10 | 336 | 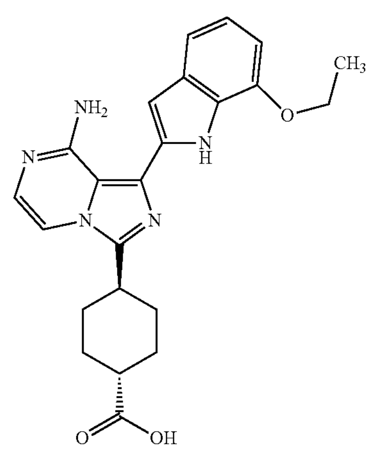 [SMILES: CCOc1cccc2cc(-c3nc([C@H]4CC[C@H](C(=O)O)CC4)n4ccnc(N)c34)[nH]c12] | 420.15 420.18 |

-continued

| Ex # | Structure | MH+ | Ex # | Structure | MH+ |
|---|---|---|---|---|---|
| 296 | 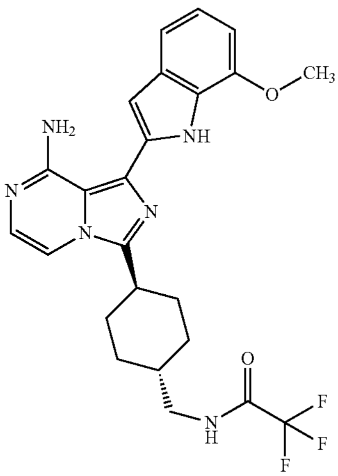 | Chiral 491.18 | 337 | 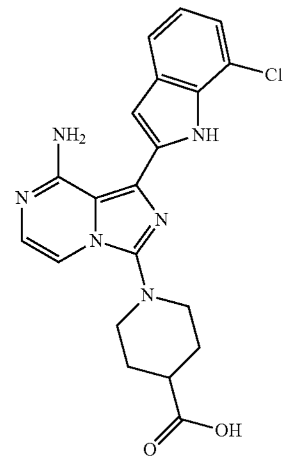 [SMILES: Nc1nccn2c(N3CCC(C(=O)O)CC3)nc(-c3cc4cccc(Cl)c4[nH]3)c12] | 411.06 413.07 |
| 297 | 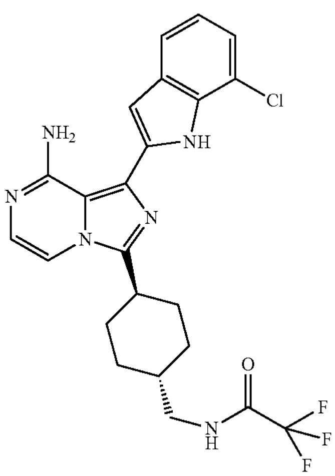 | Chiral 488.63 | 338 | 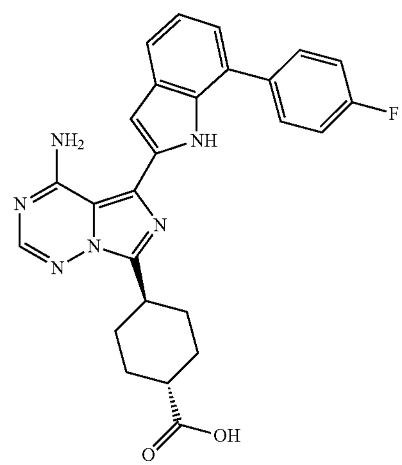 | Chiral 471.35 |
| 298 | 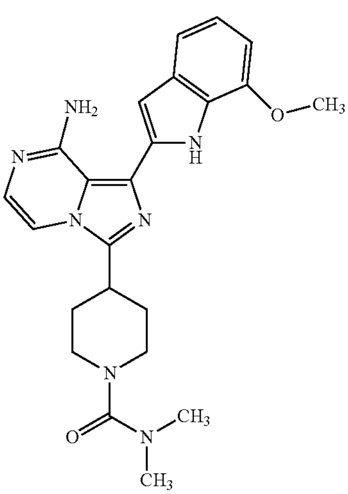 [SMILES: COc1cccc2cc(-c3nc(C4CCN(C(=O)N(C)C)CC4)n4ccnc(N)c34)[nH]c12] | 434.08 | 339 | 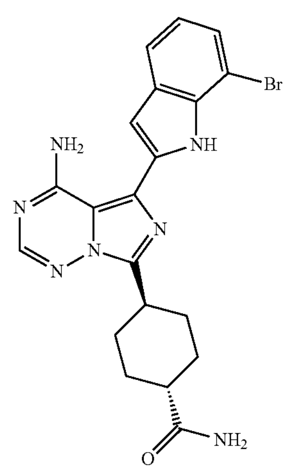 | Chiral 454.07 456.03 |

-continued

| Ex # | Structure | MH+ | Ex # | Structure | MH+ |
|---|---|---|---|---|---|
| 299 | 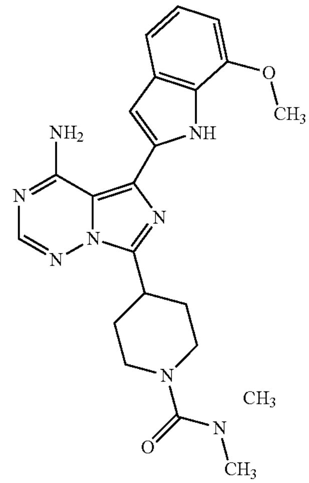 | 435.10 | 340 | 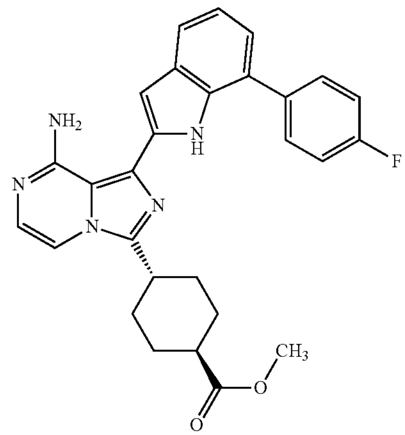 [SMILES: COC(=O)[C@H]1CC[C@H](c2nc(-c3cc4cccc(-c5ccc(F)cc5)c4[nH]3)c3c(N)nccn32)CC1] | 484.44 |
| 300 | Chiral | 505.10 | 341 | 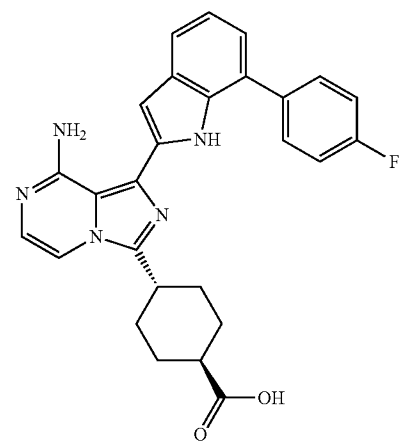 [SMILES: Nc1nccn2c1c(-c1cc3cccc(-c4ccc(F)cc4)c3[nH]1)nc2[C@H]1CC[C@H](C(=O)O)CC1] | 470.41 |
| 301 | 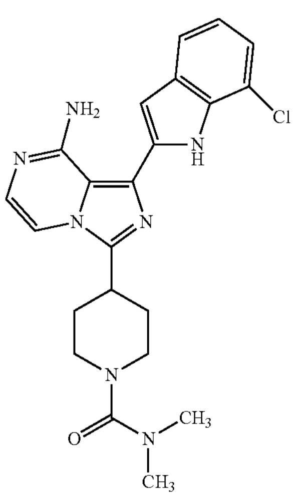 [SMILES: CN(C)C(=O)N1CCC(c2nc(-c3cc4cccc(Cl)c4[nH]3)c3c(N)nccn23)CC1] | 438.00 | 342 | 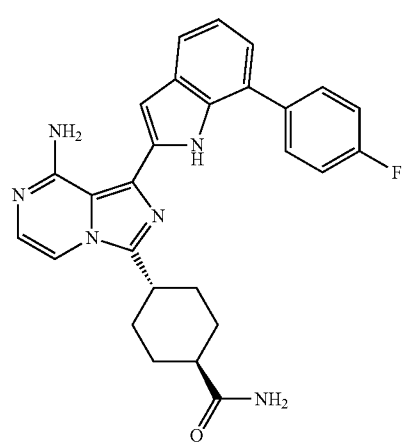 [SMILES: Nc1nccn2c1c(-c1cc3cccc(-c4ccc(F)cc4)c3[nH]1)nc2[C@H]1CC[C@H](C(N)=O)CC1] | 469.46 |

| Ex # | Structure | MH+ | Ex # | Structure | MH+ |
|---|---|---|---|---|---|
| 302 | 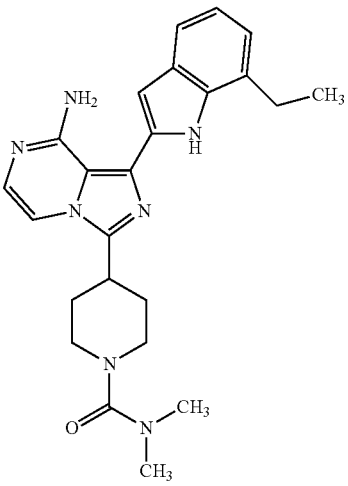 | 432.02 | 343 | 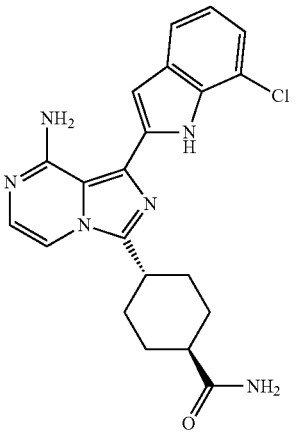 [SMILES: Nc1nccn2c1c(-c1cc3cccc(Cl)c3[nH]1)nc2[C@H]1CC[C@H](C(N)=O)CC1] | 409.35 |
| 303 | 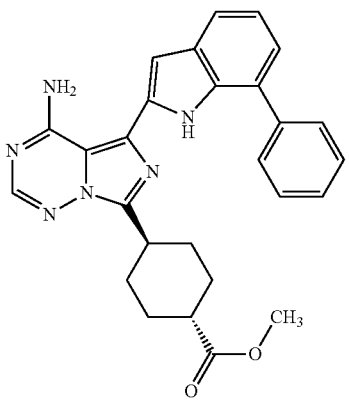 [SMILES: COC(=O)[C@H]1CC[C@H](c2nc(-c3cc4cccc(-c5ccccc5)c4[nH]3)c3c(N)ncnn32)CC1] | 467.30 | 344 | 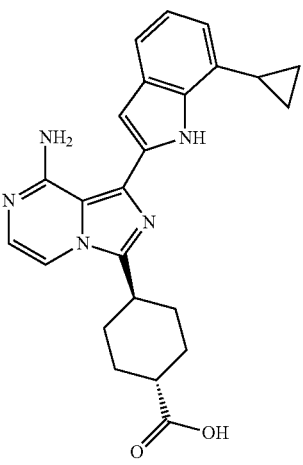 [SMILES: Nc1nccn2c1c(-c1cc3cccc(C4CC4)c3[nH]1)nc2[C@H]1CC[C@H](C(=O)O)CC1] | 416.17 |
| 304 | 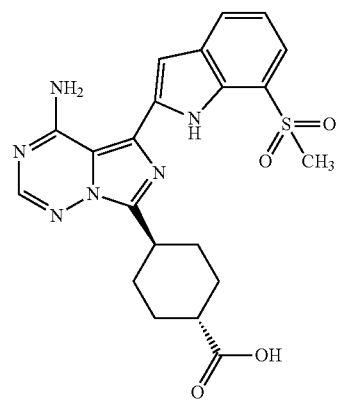 [SMILES: CS(=O)(=O)c1cccc2cc(-c3nc([C@H]4CC[C@H](C(=O)O)CC4)n4ncnc(N)c34)[nH]c12] | 455.23 | 345 | 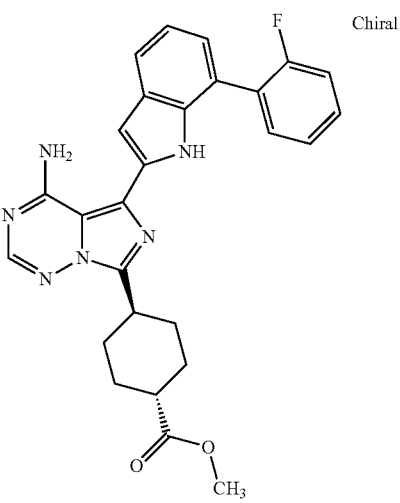 [SMILES: COC(=O)[C@H]1CC[C@H](c2nc(-c3cc4cccc(-c5ccccc5F)c4[nH]3)c3c(N)ncnn32)CC1] | 485.39 |

-continued

| Ex # | Structure | MH+ | Ex # | Structure | MH+ |
|---|---|---|---|---|---|
| 305 | 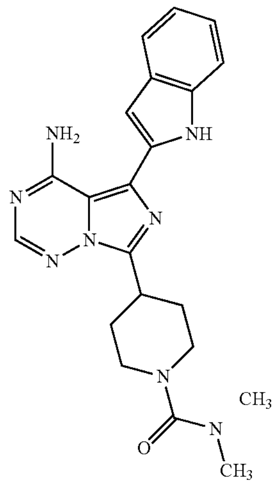 | 405.09 | 346 | Chiral | 444.10 |
| 306 | Chiral | 424.13 426.23 | 347 | 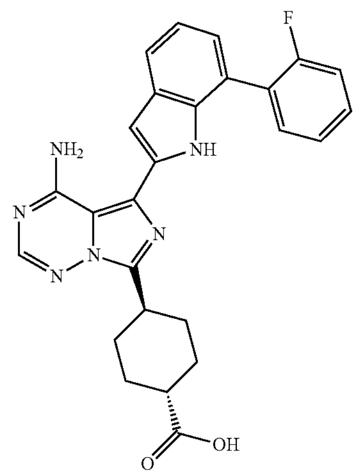 [SMILES: Nc1ncnn2c1c(-c1cc3cccc(-c4ccccc4F)c3[nH]1)nc2[C@H]1CC[C@H](C(=O)O)CC1] | 471.41 |
| 307 | Chiral | 458.99 | 348 | 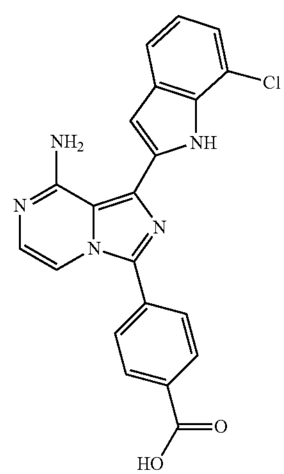 [SMILES: Nc1nccn2c(-c3ccc(C(=O)O)cc3)nc(-c3cc4cccc(Cl)c4[nH]3)c12] | 404.04 406.06 |

-continued

| Ex # | Structure | MH+ | Ex # | Structure | MH+ |
|---|---|---|---|---|---|
| 308 | 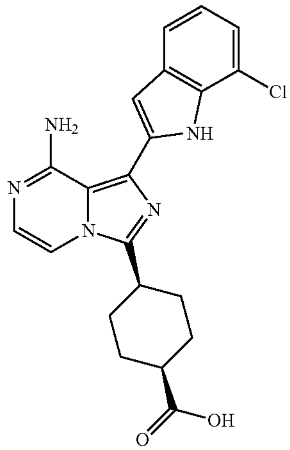 | Chiral 409.97 411.96 | 349 | 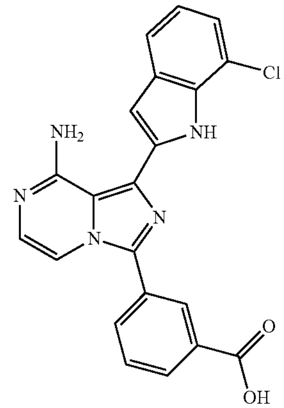 [SMILES: Nc1nccn2c(-c3cccc(C(=O)O)c3)nc(-c3cc4cccc(Cl)c4[nH]3)c12] | 404.27 406.29 |
| 309 | 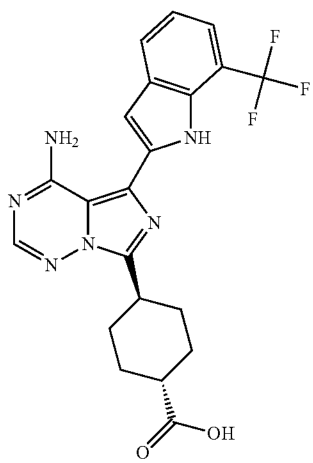 | Chiral 445 445.1 | 350 | 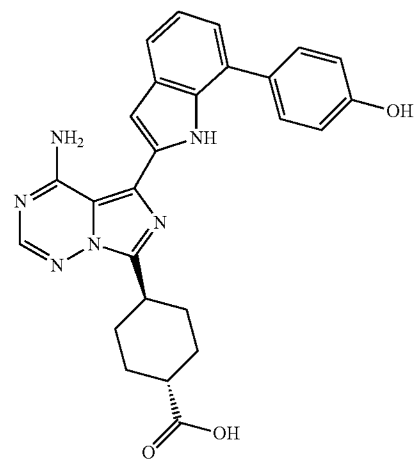 | Chiral 469.39 |
| 310 | 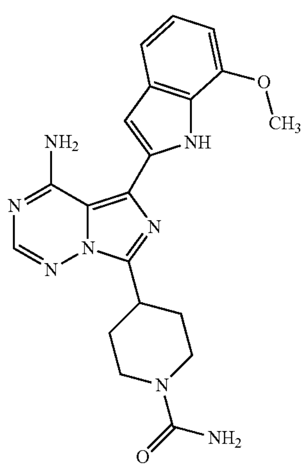 [SMILES: COc1cccc2cc(-c3nc(C4CCN(C(N)=O)CC4)n4ncnc(N)c34)[nH]c12] | 407.05 | 351 | 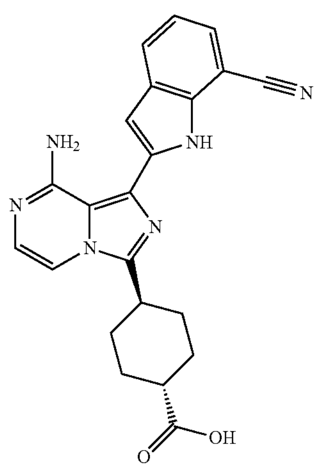 [SMILES: N#Cc1cccc2cc(-c3nc([C@H]4CC[C@H](C(=O)O)CC4)n4ccnc(N)c34)[nH]c12] | 401.39 |

| Ex # | Structure | MH+ | Ex # | Structure | MH+ |
|---|---|---|---|---|---|
| 311 | 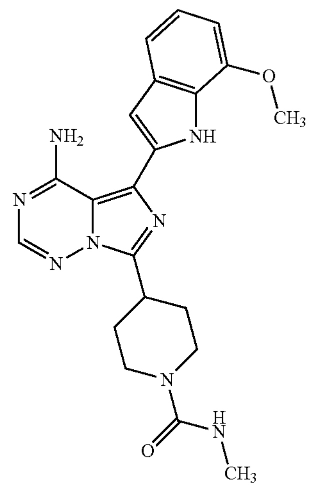 [SMILES: CNC(=O)N1CCC(c2nc(-c3cc4cccc(OC)c4[nH]3)c3c(N)ncnn23)CC1] | 421.00 | 352 | Chiral | 444.16 |
| 312 | 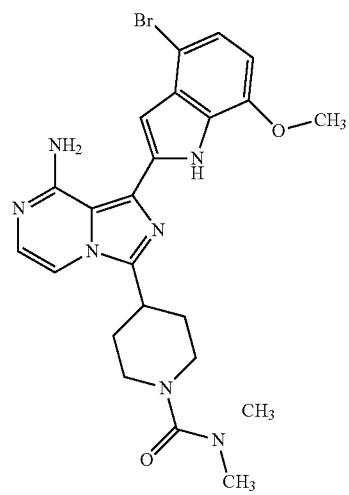 | 512.40 | 353 | Chiral | 481.12 483.14 |
| 313 | 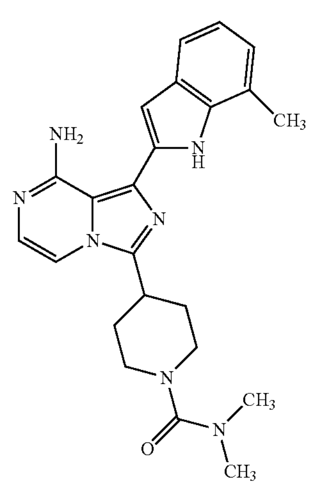 [SMILES: Cc1cccc2cc(-c3nc(C4CCN(C(=O)N(C)C)CC4)n4ccnc(N)c34)[nH]c12] | 418.03 | 354 | 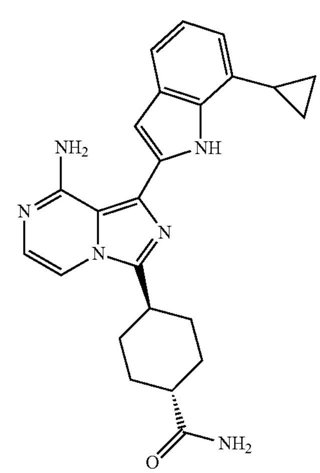 [SMILES: Nc1nccn2c1c(-c1cc3cccc(C4CC4)c3[nH]1)nc2[C@H]1CC[C@H](C(N)=O)CC1] | 415.17 |

-continued

| Ex # | Structure | MH+ | Ex # | Structure | MH+ |
|---|---|---|---|---|---|
| 314 | 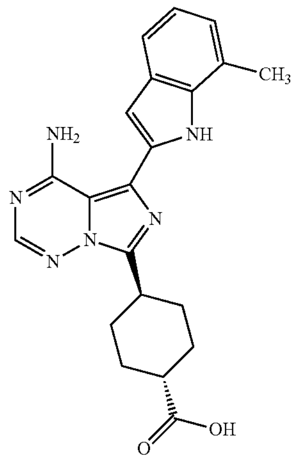 [SMILES: Cc1cccc2cc(-c3nc([C@H]4CC[C@H](C(=O)O)CC4)n4ncnc(N)c34)[nH]c12] | 391.06 | 355 | 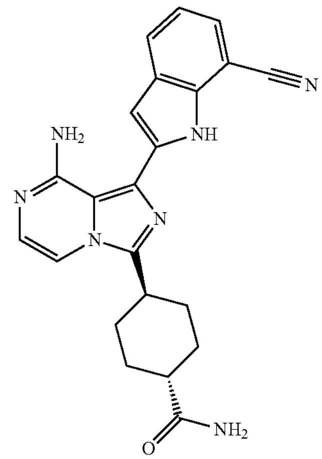 [SMILES: N#Cc1cccc2cc(-c3nc([C@H]4CC[C@H](C(N)=O)CC4)n4ccnc(N)c34)[nH]c12] | 400.09 |
| 315 | 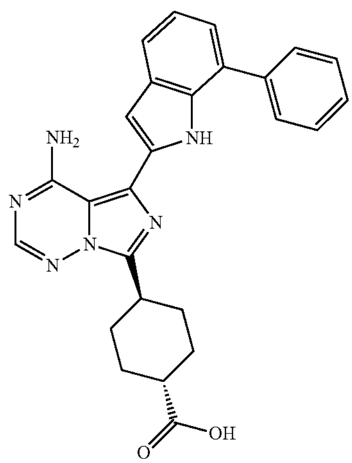 [SMILES: Nc1ncnn2c1c(-c1cc3cccc(-c4ccccc4)c3[nH]1)nc2[C@H]1CC[C@H](C(=O)O)CC1] | 453.04 453.17 453.39 | 356 | 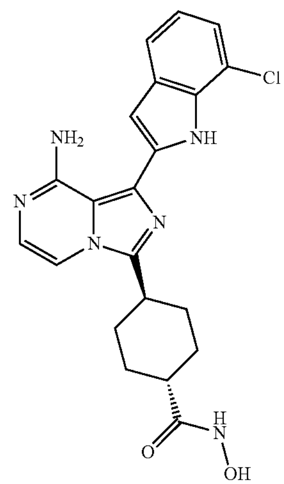 [SMILES: Nc1nccn2c1c(-c1cc3cccc(Cl)c3[nH]1)nc2[C@H]1CC[C@H](C(=O)NO)CC1] | 425.34 427.33 |
| 316 | 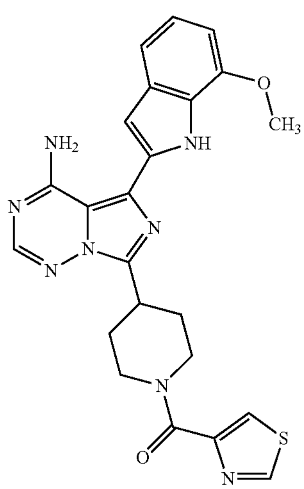 [SMILES: COc1cccc2cc(-c3nc(C4CCN(C(=O)c5cscn5)CC4)n4ncnc(N)c34)[nH]c12] | 474.95 | 357 | 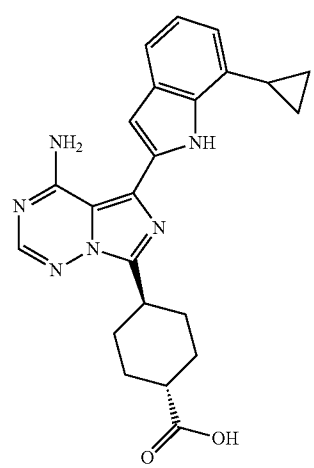 | Chiral 417.36 |

| Ex # | Structure | MH+ | Ex # | Structure | MH+ |
|---|---|---|---|---|---|
| 317 | 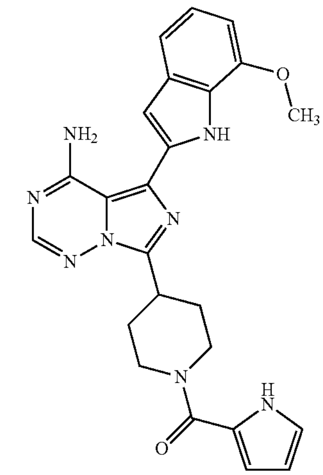 [SMILES: COc1cccc2cc(-c3nc(C4CCN(C(=O)c5ccc[nH]5)CC4)n4ncnc(N)c34)[nH]c12] | 457.08 | 358 | Chiral | 402.33 |
| 318 | 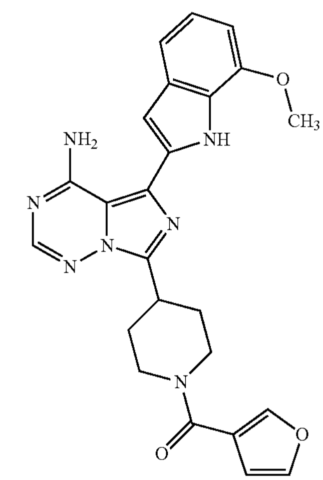 [SMILES: COc1cccc2cc(-c3nc(C4CCN(C(=O)c5ccoc5)CC4)n4ncnc(N)c34)[nH]c12] | 457.95 | 359 | 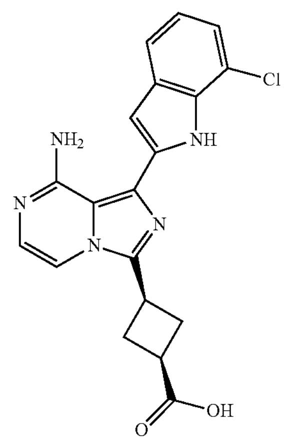 [SMILES: Nc1nccn2c1c(-c1cc3cccc(Cl)c3[nH]1)nc2[C@H]1C[C@@H](C(=O)O)C1] | 381.96 384.01 |
| 319 | 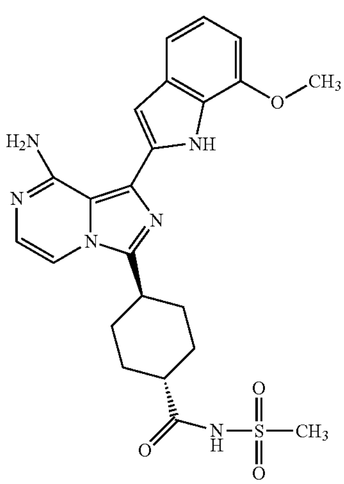 [SMILES: COc1cccc2cc(-c3nc([C@H]4CC[C@H](C(=O)NS(C)(=O)=O)CC4)n4ccnc(N)c34)[nH]c12] | 482.96 | 360 | Chiral | 487.01 489.03 |

| Ex # | Structure | MH+ | Ex # | Structure | MH+ |
|---|---|---|---|---|---|
| 320 | 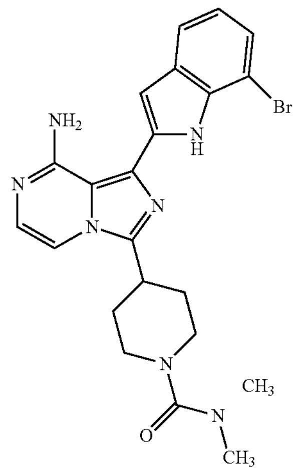 | 483.90 | 361 | 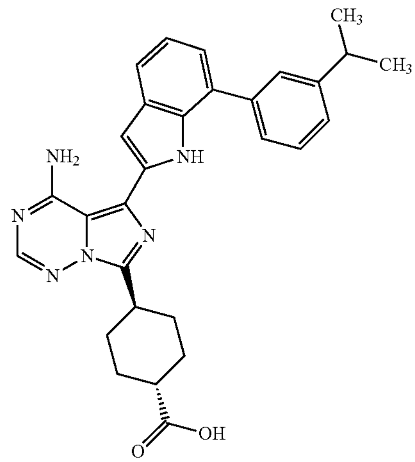 | Chiral 495.03 |
| 321 | 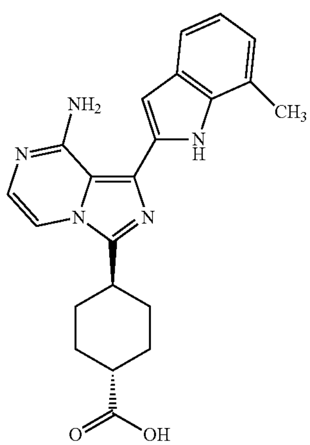 [SMILES: Cc1cccc2cc(-c3nc([C@H]4CC[C@H](C(=O)O)CC4)n4ccnc(N)c34)[nH]c12] | 390.02 | 362 | 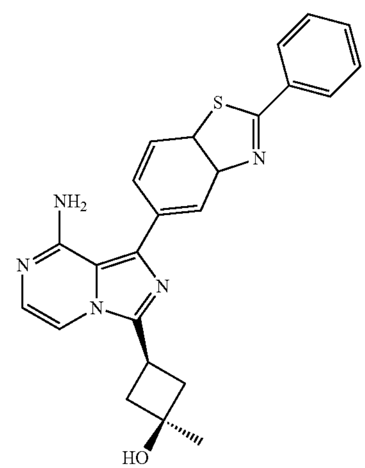 [SMILES: C[C@]1(O)C[C@@H](c2nc(C3=CC4N=C(c5ccccc5)SC4C=C3)c3c(N)nccn32)C1] | 428.02 |
| 322 | 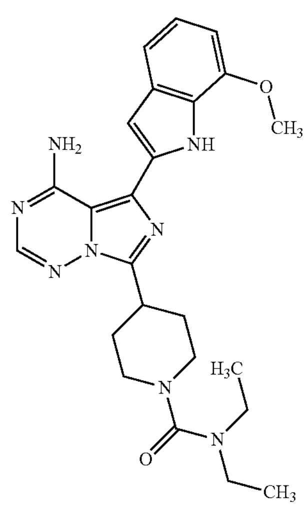 [SMILES: CCN(CC)C(=O)N1CCC(c2nc(-c3cc4cccc(OC)c4[nH]3)c3c(N)ncnn23)CC1] | 463.08 | 363 | 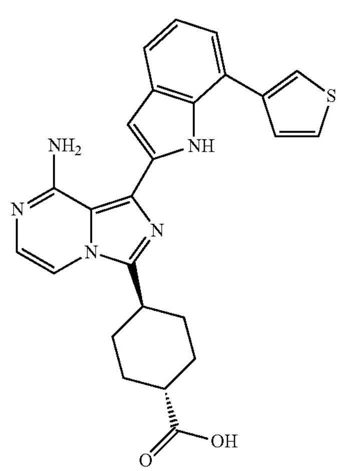 | Chiral 458.32 |

| Ex # | Structure | MH+ | Ex # | Structure | MH+ |
|---|---|---|---|---|---|
| 323 | 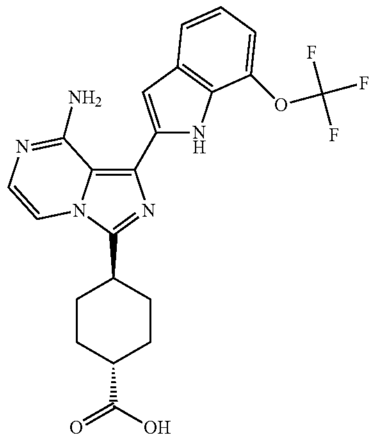 [SMILES: Nc1nccn2c1c(-c1cc3cccc(OC(F)(F)F)c3[nH]1)nc2[C@H]1CC[C@H](C(=O)O)CC1] | 460.09 | 364 | 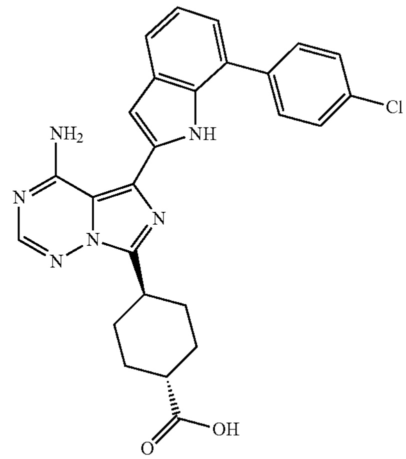 | Chiral 487.01 488.90 |
| 324 | 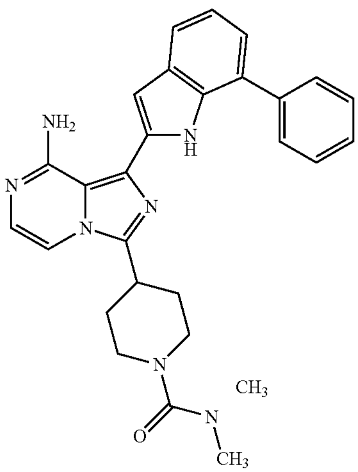 | 480.21 | 365 | 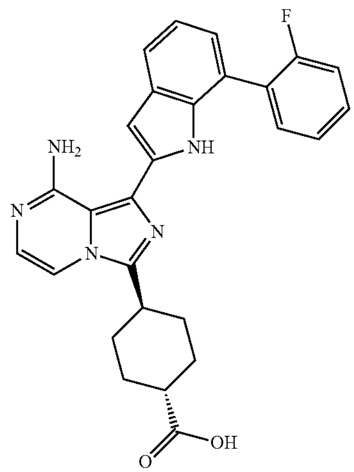 | Chiral 470.37 |
| 325 | 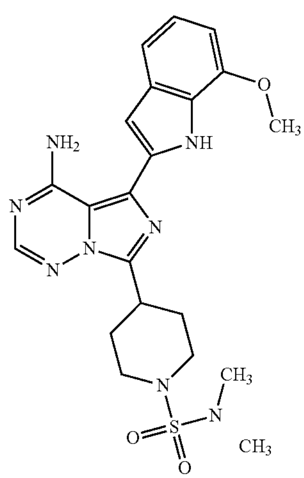 | 471.11 | 366 | 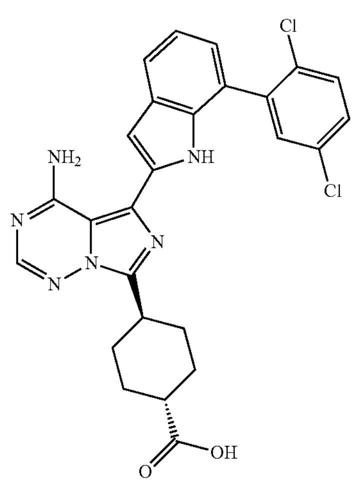 | Chiral 521.27 523.27 |

-continued

| Ex # | Structure | MH+ | Ex # | Structure | MH+ |
|---|---|---|---|---|---|
| 326 | 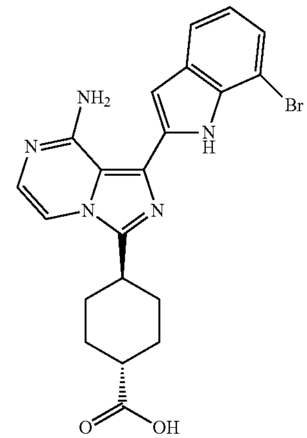 [SMILES: Nc1nccn2c1c(-c1cc3cccc(Br)c3[nH]1)nc2[C@H]1CC[C@H](C(=O)O)CC1] | 455.94 | 367 | 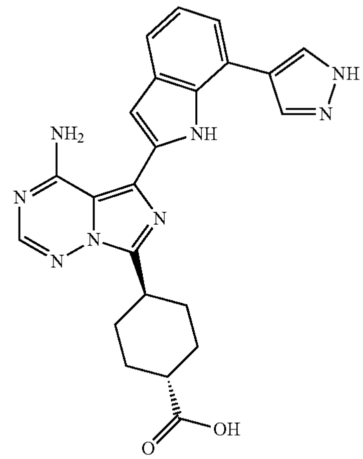 [SMILES: Nc1ncnn2c1c(-c1cc3cccc(-c4cn[nH]c4)c3[nH]1)nc2[C@H]1CC[C@H](C(=O)O)CC1] | 443.22 |
| 327 | 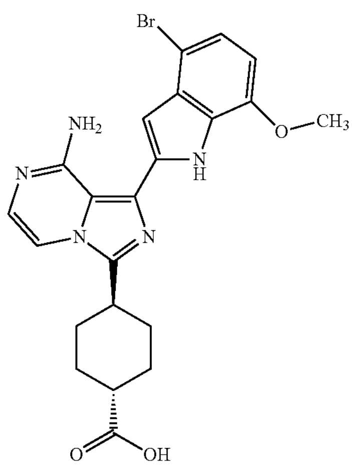 [SMILES: COc1ccc(Br)c2cc(-c3nc([C@H]4CC[C@H](C(=O)O)CC4)n4ccnc(N)c34)[nH]c12] | 486.20 | 368 | 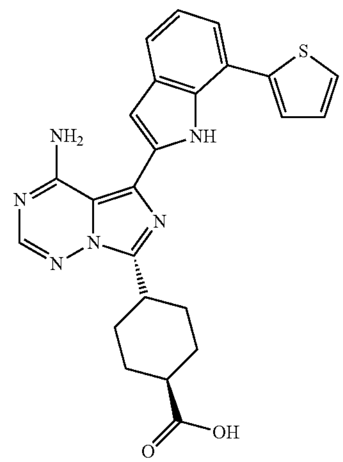 | 459.28 |
| 328 | 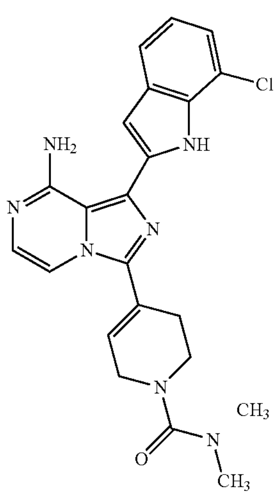 | 436.23 438.26 | 369 | 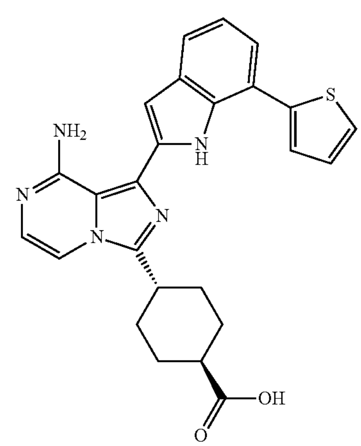 [SMILES: Nc1nccn2c1c(-c1cc3cccc(-c4cccs4)c3[nH]1)nc2[C@H]1CC[C@H](C(=O)O)CC1] | 458.37 |

-continued

| Ex # | Structure | MH+ | Ex # | Structure | MH+ |
|---|---|---|---|---|---|
| 329 | 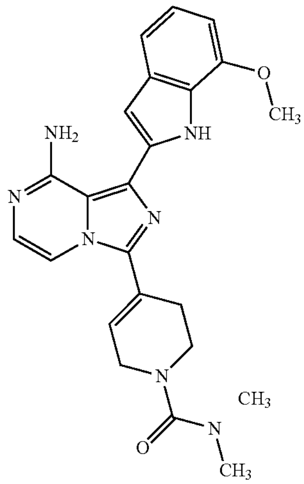 | 432.02 | 370 | 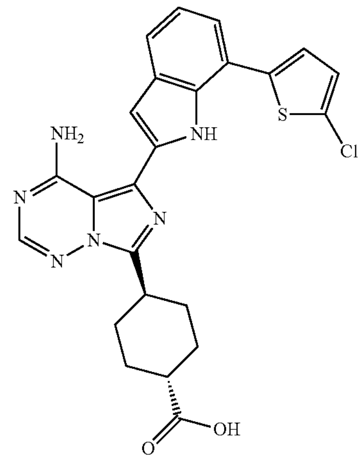 [SMILES: Nc1ncnn2c1c(-c1cc3cccc(-c4ccc(Cl)s4)c3[nH]1)nc2[C@H]1CC[C@H](C(=O)O)CC1] | 493.22 495.18 |
| 330 | 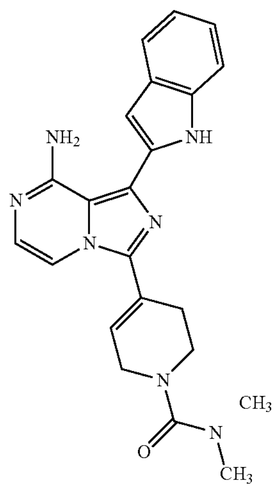 | 402.06 | 371 | 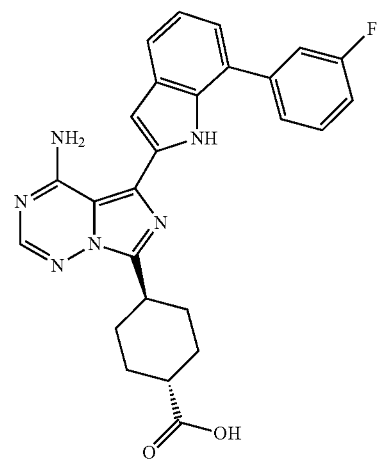 | 471.03 |
| 331 | 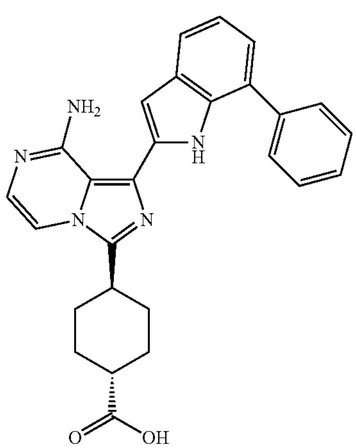 [SMILES: Nc1nccn2c1c(-c1cc3cccc(-c4ccccc4)c3[nH]1)nc2[C@H]1CC[C@H](C(=O)O)CC1] | 452.12 | 372 | 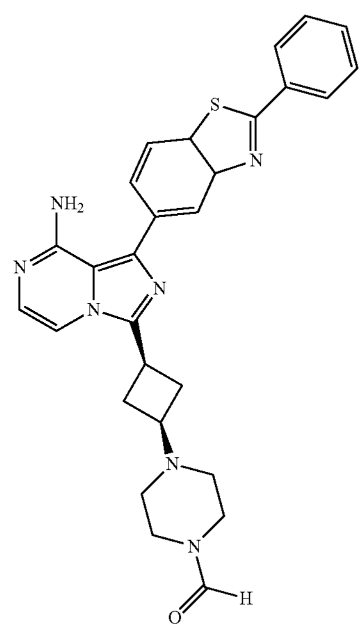 [SMILES: Nc1nccn2c1c(C1=CC3N=C(c4ccccc4)SC3C=C1)nc2[C@H]1C[C@@H](N2CCN(C=O)CC2)C1] | 510.03 |

-continued

| Ex # | Structure | MH+ | Ex # | Structure | MH+ |
|---|---|---|---|---|---|
| 332 | 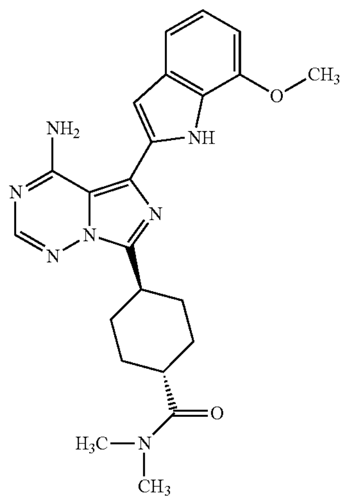 | Chiral 434.25 | 373 | 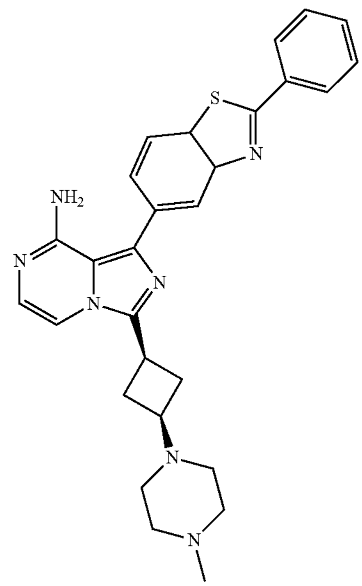 [SMILES: CN1CCN([C@H]2C[C@@H](c3nc(C4=CC5N=C(c6ccccc6)SC5C=C4)c4c(N)nccn43)C2)CC1] | 496.06 |
| 374 | 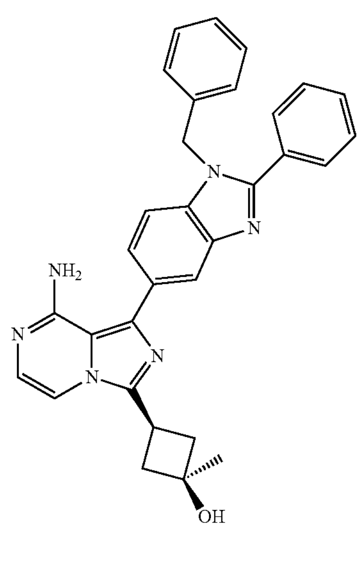 [SMILES: C[C@]1(O)C[C@@H](c2nc(-c3ccc4c(c3)nc(-c3ccccc3)n4Cc3ccccc3)c3c(N)nccn32)C1] | 501.45 | 375 | 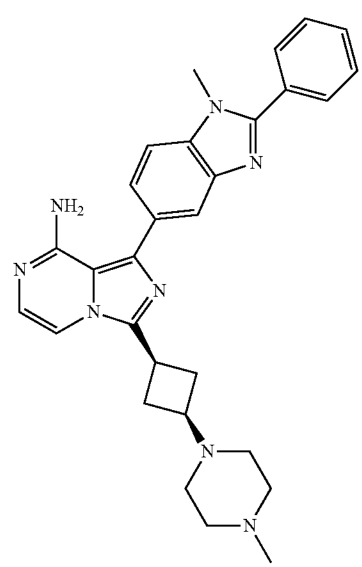 [SMILES: CN1CCN([C@H]2C[C@@H](c3nc(-c4ccc5c(c4)nc(-c4ccccc4)n5C)c4c(N)nccn43)C2)CC1] | 493.49 |

| Ex # | Structure | MH+ | Ex # | Structure | MH+ |
|---|---|---|---|---|---|
| 376 | 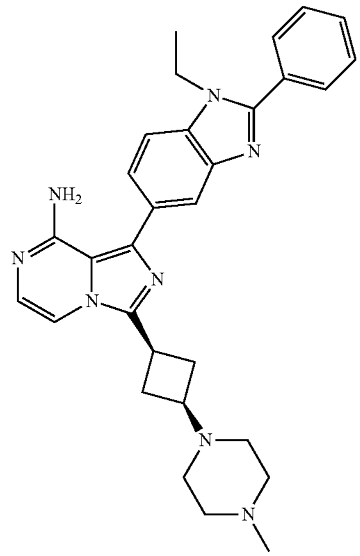 [SMILES: CCn1c(-c2ccccc2)nc2cc(-c3nc([C@H]4C[C@@H](N5CCN(C)CC5)C4)n4ccnc(N)c34)ccc21] | 507.46 | 377 | 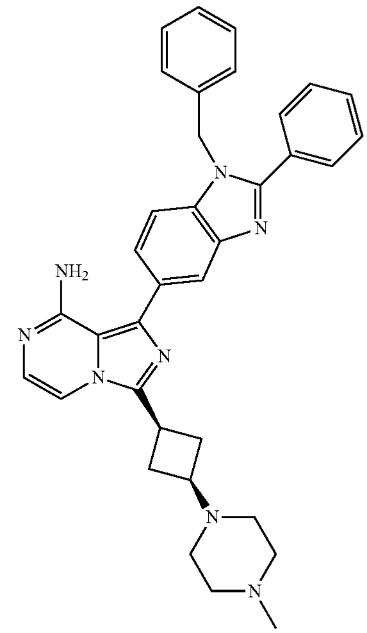 [SMILES: CN1CCN([C@H]2C[C@@H](c3nc(-c4ccc5c(c4)nc(-c4ccccc4)n5Cc4ccccc4)c4c(N)nccn43)C2)CC1] | 569.56 |
| 378 | 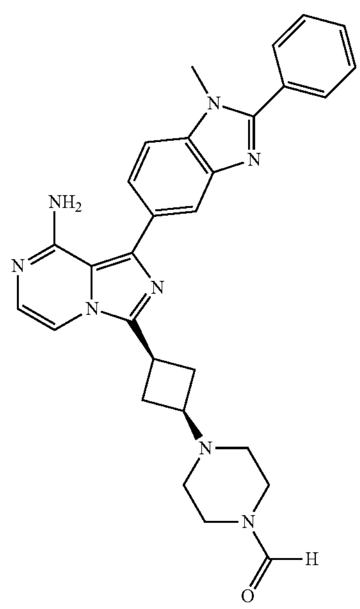 [SMILES: Cn1c(-c2ccccc2)nc2cc(-c3nc([C@H]4C[C@@H](N5CCN(C=O)CC5)C4)n4ccnc(N)c34)ccc21] | 507.46 | 379 | 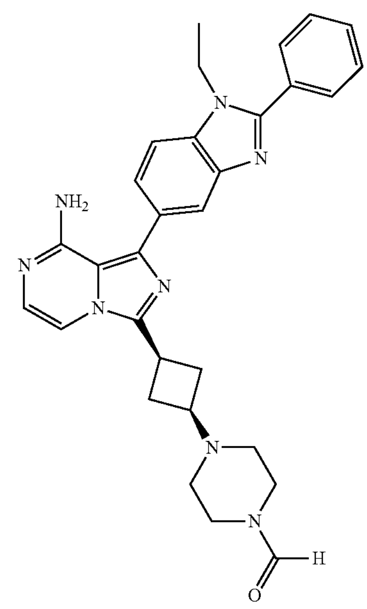 [SMILES: CCn1c(-c2ccccc2)nc2cc(-c3nc([C@H]4C[C@@H](N5CCN(C=O)CC5)C4)n4ccnc(N)c34)ccc21] | 521.50 |

-continued

| Ex # | Structure | MH+ | Ex # | Structure | MH+ |
|---|---|---|---|---|---|
| 380 | 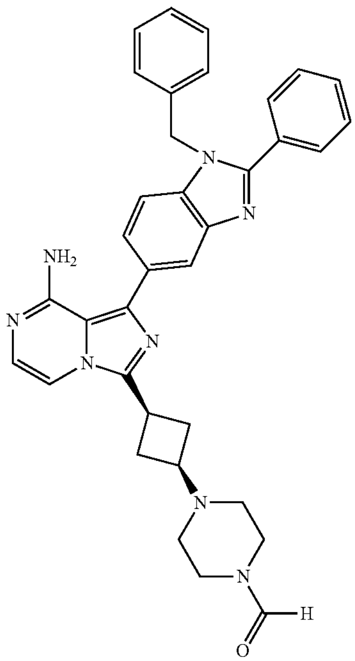 [SMILES: Nc1nccn2c1c(-c1ccc3c(c1)nc(-c1ccccc1)n3Cc1ccccc1)nc2[C@H]1C[C@@H](N2CCN(C=O)CC2)C1] | 583.53 | 381 | 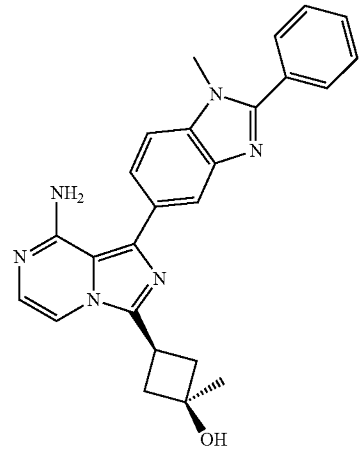 [SMILES: Cn1c(-c2ccccc2)nc2cc(-c3nc([C@H]4C[C@@](C)(O)C4)n4ccnc(N)c34)ccc21] | 425.39 |
| 382 | 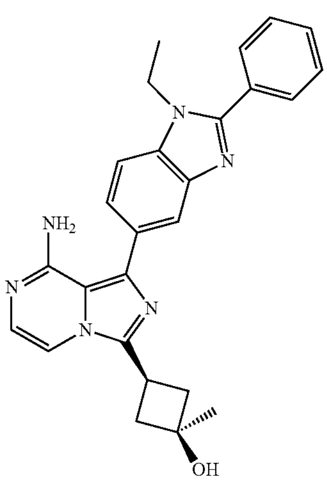 [SMILES: CCn1c(-c2ccccc2)nc2cc(-c3nc([C@H]4C[C@@](C)(O)C4)n4ccnc(N)c34)ccc21] | 439.42 | 383 | 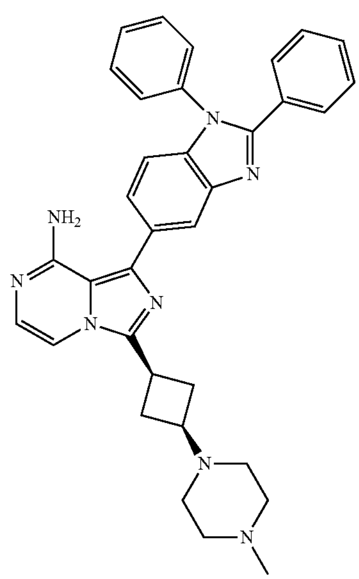 [SMILES: CN1CCN([C@H]2C[C@@H](c3nc(-c4ccc5c(c4)nc(-c4ccccc4)n5-c4ccccc4)c4c(N)nccn43)C2)CC1] | 555.55 |

| Ex # | Structure | MH+ |
|---|---|---|
| 384 | | 569.55 |
The following compounds are expected to be active as inhibitors of mTOR. Where shown, X can be N or CH.
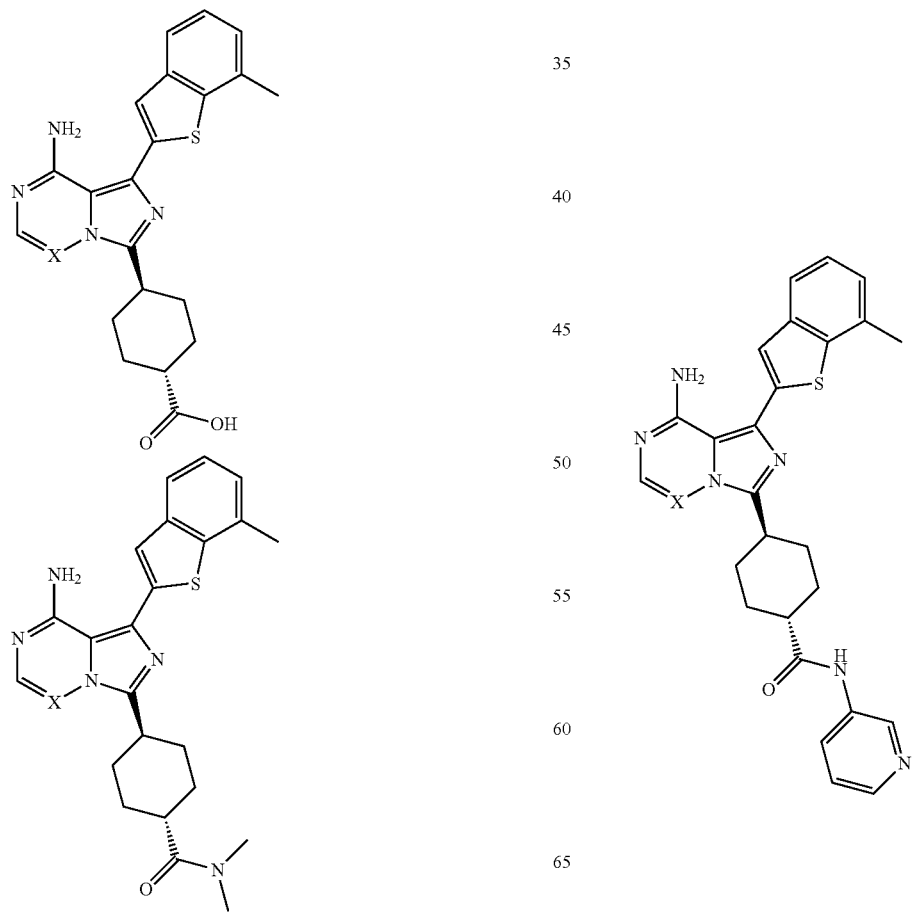

315
-continued
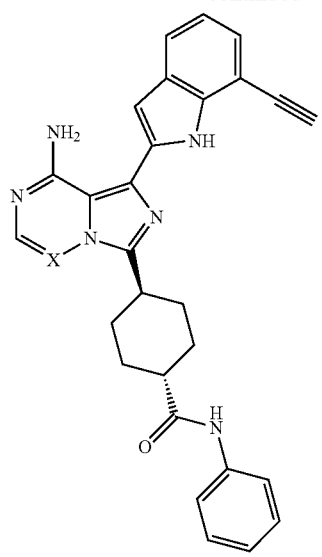
316
-continued
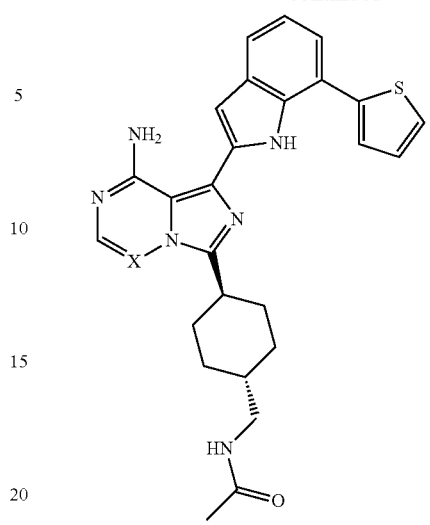
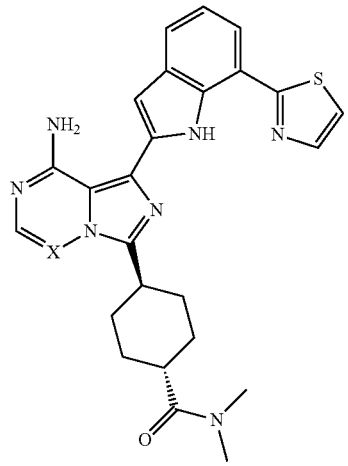
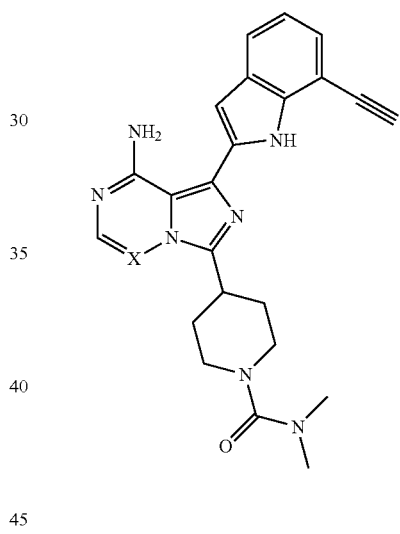
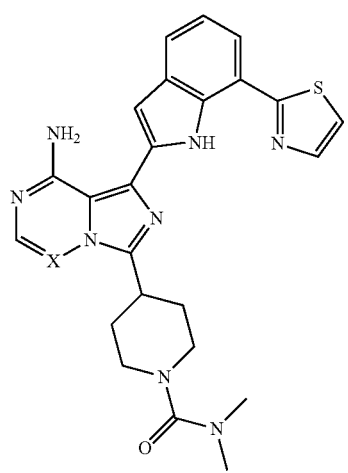
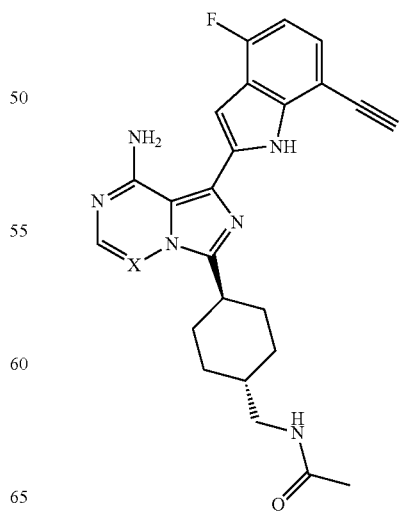

317
-continued
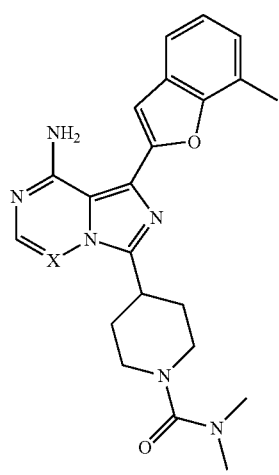
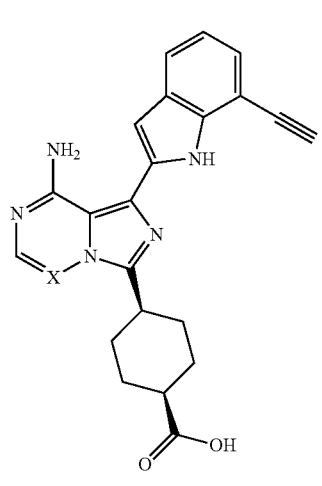
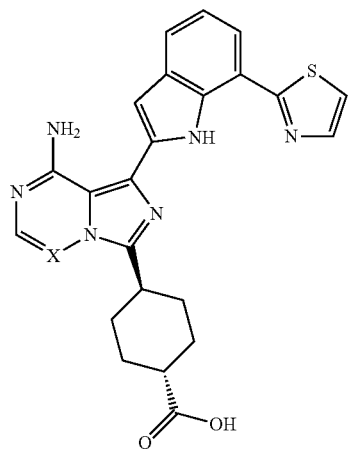
318
-continued
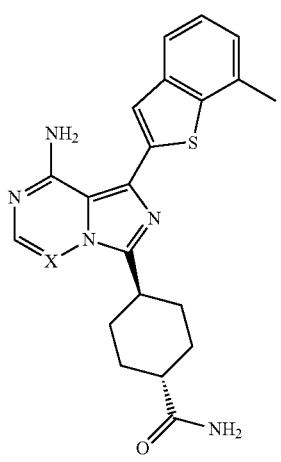
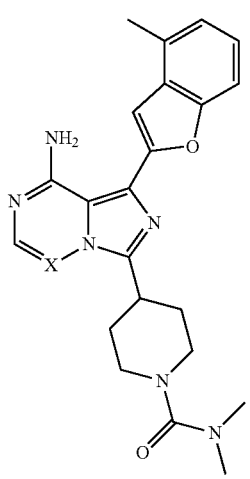
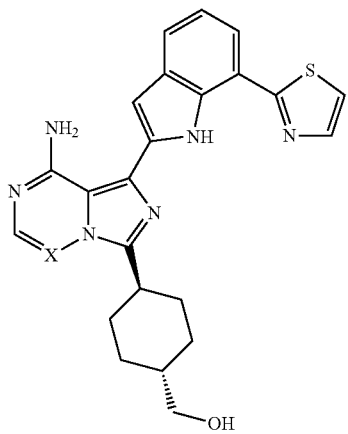

319
-continued
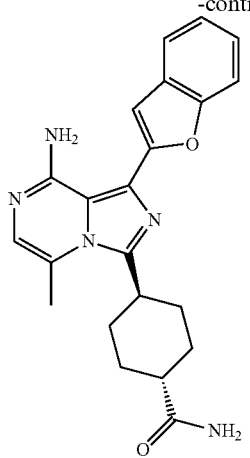
320
-continued
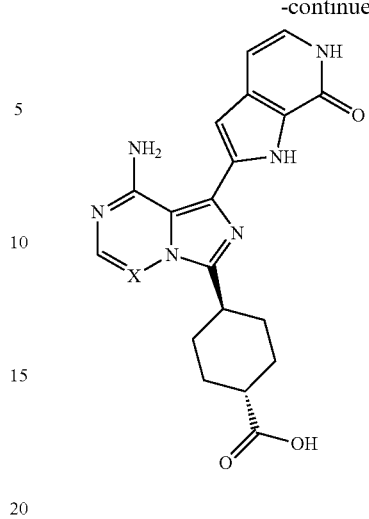
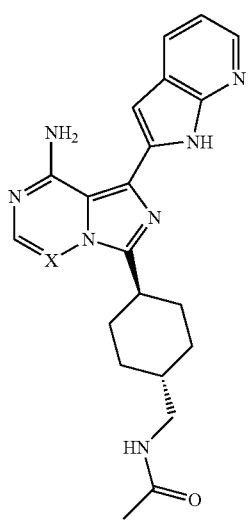
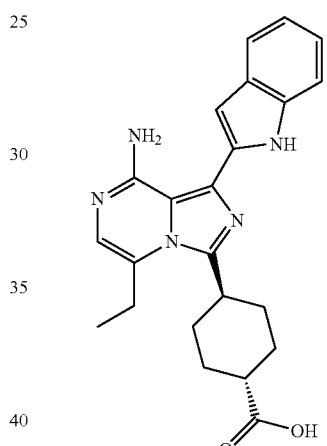
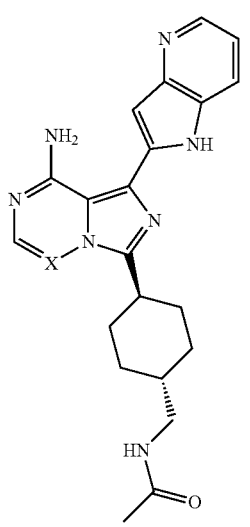
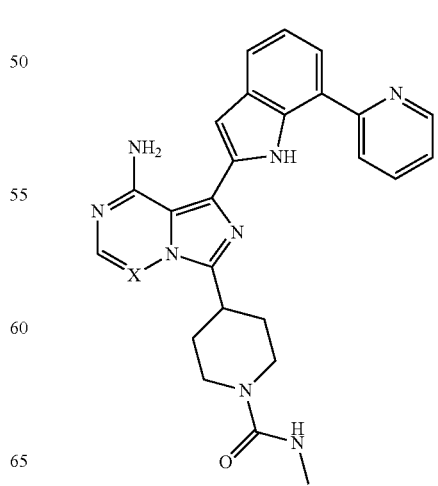

-continued

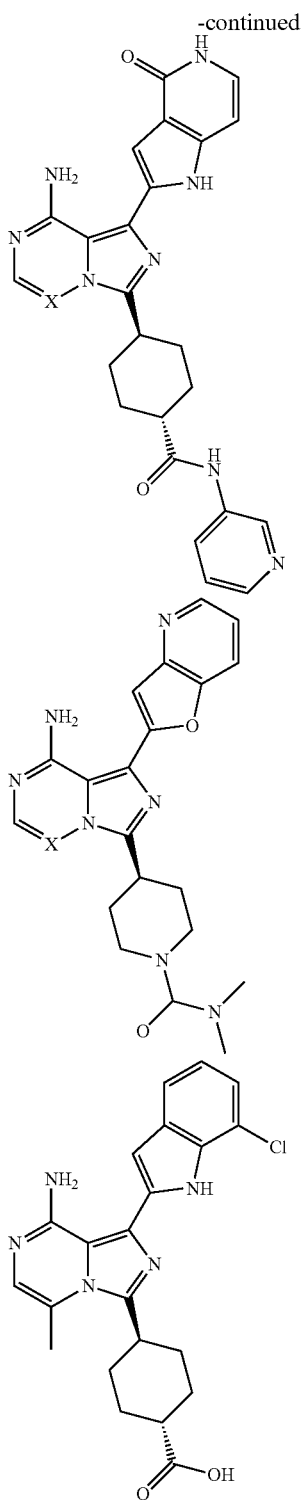

Cell lines: Human cancer cell lines were purchased from the American Type Culture Collection (ATCC). The cell lines H460, Calu6, SW1573, H1703, H292, H358, HCT-116, HT-29, FET, GEO, SW480, Colo205 CBS, BxPC3, HPAC, CFPAC, MiaPaca-2, Panc1, MDA-MB-468, BT-20, MDA-MB-435 H441, H322, A1165, Igrov-1, Ovcar-3, CA-OV-3, MDAH2774, SW626, SKOV-3, Cal-27, RPMI 2650, and MDA-MB-231 were grown in media as prescribed by the ATCC, containing 10% FCS. Hsc-2, Hsc-4 and OVK-18 were obtained from the Riken Cell Bank and were cultured according to the Riken Cell Bank recommended conditions. HNSCC 1483, HNSCC 1386, HNSCC 1186 were a gift from Memorial Sloan Kettering and were cultured in 1:1 DMEM: Hams F12 with 10% FCS. Ovcar-4, Ovcar-5 and Ovcar-8 were obtained from the NCI and were grown in RPMI with 10% FCS. HN5 was a gift from an academic investigator and was cultured in DMEM plus 10% FCS.

Measurement of Cell Proliferation: Cell proliferation was determined using the Cell Titer Glo assay (Promega Corporation, Madison, Wis.). Cell lines were seeded at a density of 3000 cells per well in a 96-well plate. 24 Hours after plating cells were dosed with varying concentrations of drug, either as a single agent or in combination. The signal for Cell Titer Glo was determined 72 Hours after dosing.

Measurement of apoptosis: Induction of apoptosis as measured by increased Caspase 3/7 activity was determined using the Caspase 3/7 Glo assay (Promega Corporation, Madison, Wis.). Cell lines were seeded at a density of 3000 cells per well in a 96-well plate. 24 Hours after plating cells were dosed with varying concentrations of drug, either as a single agent or in combination. The signal for Caspase 3/7 Glo was determined 24 Hours after dosing. The caspase 3/7 activity was normalized to cell number per well, using a parallel plate treated with Cell Titer Glo (Promega Corporation, Madison, Wis.). Signal for each well was normalized using the following formula: Caspase 3/7 Glo luminescence units/Cell Titer Glo fraction of DMSO control. All graphs were generated using PRISM® software (Graphpad Software, San Diego, Calif.).

Analysis of Additivity and Synergy: The Bliss additivism model was used to classify the effect of combining rapamycin and erlotinib as additive, synergistic, or antagonistic. A theoretical curve was calculated for combined inhibition using the equation: $E_{bliss}=E_A+E_B-E_A*E_B$, where $E_A$ and $E_B$ are the fractional inhibitions obtained by drug A alone and drug B alone at specific concentrations. Here, $E_{bliss}$ is the fractional inhibition that would be expected if the combination of the two drugs was exactly additive. If the experimentally measured fractional inhibition is less than $E_{bliss}$ the combination was said to be synergistic. If the experimentally measured fractional inhibition is greater than $E_{bliss}$ the combination was said to be antagonistic. For dose response curves, the Bliss additivity value was calculated for varying doses of drug A when combined with a constant dose of drug B. This allowed an assessment as to whether drug B affected the potency of drug A or shifted its intrinsic activity. All plots were generated using PRISM® software (Graphpad Software, San Diego, Calif.).

Preparation of Protein Lysates and Western Blotting:

Cell extracts were prepared by detergent lysis (50 mM Tris-HCl, pH 8.0, 150 mM NaCl, 1% NP-40, 0.5% sodium deoxycholate, 0.1% SDS, containing protease inhibitor (P8340, Sigma, St. Louis, Mo.) and phosphatase inhibitor (P5726, Sigma, St. Louis, Mo.) cocktails. The soluble protein concentration was determined by micro-BSA assay (Pierce, Rockford Ill.). Protein immunodetection was performed by electrophoretic transfer of SDS-PAGE separated proteins to nitrocellulose, incubation with antibody, and chemiluminescent second step detection (PicoWest; Pierce, Rockford, Ill.). The antibodies included: EGFR, phospho-EGFR (Y1068), ErbB2, phospho-erbB2, ErbB3, phospho-ErbB3, ErbB4, phospho-p42/p44, phospho-Akt(473), phospho-Akt(308), total Akt, phosho-S6 (235/236), and total S6. With the exception of total ErbB3 (obtained from Santa Cruz Biotechnology, Inc., Santa Cruz, Calif.), all antibodies were obtained from Cell Signaling Technology, Inc. (Danvers, Mass.). For analysis of erlotinib's effect on the phosphorylation of downstream signaling proteins, cell lines were grown to approximately 70% confluency, at which time erlotinib was added at the indicated concentration, and cells were incubated at 37° C. for two hours. Where indicated, 10 ng/ml EGF ligand was added for 5 minutes. The media was removed, cells were washed two times with PBS, and cells were lysed as previously described.

Xenograft Experiments:

Female CD-1 nu/nu mice (Charles River Laboratories, Wilmington, Mass.) were implanted with harvested Calu-6 NSCLC tumor cells in a single subcutaneous site on the flank of the mice in the axillary region. Tumors were allowed to grow to 200+50 mm$^3$, at which time the animals were sorted into treatment groups (see below) of 8 animals per group, having approximately equal body weight (+/−1 g) within a group, and tattooed on the tail for permanent identification. Tumor volumes and body weights were determined twice weekly. The tumor volume was determined by measuring in two directions with vernier calipers and calculated using the formula: Tumor volume=(length×width$^2$)/2. The data were plotted as the % change in mean values of tumor volume and body weight for each group. The tumor growth inhibition (% TGI) was determined as % TGI=100(1−W$_t$/W$_c$): where Wt is the median tumor volume of the treated group at time x and We is the median tumor volume of the control group at time x. Tarceva was dosed in a 6% Captisol (CyDex, Inc) in WFI (Water for Injection) solution and all control animals were dosed with an equal volume of the vehicle. Tarceva animals were dosed by oral gavage once a day for 18 days and the % TGI measured on day 19. Rapamycin was dosed in 4% ethanol/5% PEG400/5% Tween 80 in WFI. Rapamycin animals were dosed by intraperitoneal injection on day 1, 8 and 15, and all control animals were dosed with an equal volume of the vehicle.

Treatment groups:
set 1=vehicle control.
set 2=Tarceva® alone 100 mg/kg daily.
set 3=rapamycin alone 4 mg/kg (day 1/8/15).
set 4=Tarceva®+Rapamycin (4 mg/kg)–(day 1/8/15).

Results

Studies on the effect of a combination of an EGFR kinase inhibitor and an mTOR inhibitor on NSCLC, colon, pancreatic, and breast tumor cells.

The sensitivities to erlotinib of 22 cell lines derived from NSCLC, colon, pancreatic, and breast tumors was determined. The ability of 10 µM erlotinib to inhibit the growth of these cell lines is shown in FIG. 1. It was found that these cell lines display a range of sensitivities to erlotinib, and a maximal growth inhibition of greater than 50% was chosen as a cutoff criteria for indicating high sensitivity. Erlotinib's effects on the PI3K-Akt-mTOR pathway in this group of cell lines was analyzed. The three most sensitive cell lines (H292, H358, and BxPC3) and three relatively insensitive cell lines (H460, Calu6, and HCT-116) were selected for further investigation. Xenografts experiments have previously confirmed our in vitro classification of sensitivity for this group of cell lines (data not shown, and Thompson, S. et al. (2005) Cancer Res. 65(20):9455-9462, for H460 and Calu6). Phosphorylation of S6 was chosen as a readout for the activity of mTOR. In the three sensitive epithelial cell lines it was found that erlotinib can efficiently down-regulate the phosphorylation of pS6, while in the relatively insensitive cell lines, which have undergone EMT, a less pronounced down-regulation of S6 phosphorylation was observed. These results are consistent with previous reports describing signaling pathways in other cell lines that are sensitive or relatively insensitive to EGFR inhibition (Engelman, J. A. et al. (2005) Proc. Natl. Acad. Sci. U.S.A. 102:3788-3793; Moasser, M. M. et al. (2001) Cancer Res. 61:7184-718).

Previous studies with glioblastoma and renal cell carcinoma have demonstrated the potential of combining EGFR inhibitors with rapamycin for these two cancer types (Engelman, J. A. et al. (2005) Proc. Natl. Acad. Sci. U.S.A. 102: 3788-3793; Moasser, M. M. et al. (2001) Cancer Res. 61:7184-718; Gemmill, R. M. et al. (2005) Br. J. Cancer 92:2266-2277; Goudar, R. K. et al. (2005) Mol. Cancer Ther. 4:101-112). For example, renal cell carcinomas harboring a mutation in the von Hippel-Lindau gene (VHL) or those with tuberous sclerosis (TSC) mutations were sensitized to the combination of gefitinib and rapamycin (Gemmill, R. M. et al. (2005) Br. J. Cancer 92:2266-2277). The combination of EGFR inhibitors with inhibitors of mTOR has also shown promise in glioblastoma, a tumor type that is characterized by a very high frequency of truncating mutations for the EGFR (EGFRvIII). The present inventors sought to determine if other tumor types that are not characterized by these groups of specific mutations might also respond to the combination of EGFR inhibitors with mTOR inhibitors. Cell lines derived from colon, lung, breast, and pancreatic cancers were chosen for further analysis. The effect of low doses of rapamycin alone on the growth of the cell line panel was initially tested. FIG. 3A shows the maximal inhibition of the cell lines to rapamycin. Several cell lines, including H292 and BxPC3, show some growth inhibition by rapamycin alone. In all cell lines it was verified that rapamycin could effectively down-regulate the phosphorylation of S6. A representative panel is shown in FIG. 4. These results demonstrate how inhibition of the mTOR pathway alone might not be sufficient to substantially affect cell proliferation.

The effect that combining rapamycin with erlotinib had on two criteria: 1. potency and 2. intrinsic efficacy was determined. Our assessment of additivity, synergy, or antagonism was based on the Bliss additivism model described in the materials and methods section. This model was chosen over isobologram or combination index (CI) analyses as it would allow the evaluation of the nature of drug interactions even in cases where the maximal effects for rapamycin or erlotinib as single agents were low enough such that a reliable IC$_{50}$ value could not be obtained. For cell lines that are relatively insensitive to erlotinib as a single agent, the IC$_{50}$ value is often greater than 10 µM, the solubility limit for the drug. In addition, as both isobologram and combination index analyses are based upon a single criteria, IC$_{50}$ value, and do not directly reflect variability within data, they do not necessarily always indicate whether the extent of synergy is significant. The Bliss additivism model also allows us to evaluate changes in intrinsic efficacy. Both isobologram and CI analyses reflect only changes in potency, but shifts in intrinsic efficacy also have the potential to be clinically meaningful. This approach has been described previously for high throughput studies involving drug combinations (Borisy, A. A. et al. (2003) Proc. Natl. Acad. Sci. U.S.A. 100:7977-7982).

The data for combination of erlotinib with rapamycin are summarized in FIG. 3B. The fractional increase in maximal intrinsic efficacy when erlotinib is combined with rapamycin is shown (FIG. 3B). The data are expressed as percentage decrease in cell growth above what would be expected if the combination was strictly additive in nature. Here Bliss=0 would indicate the combination was directly additive, Bliss>0 would indicate the percentage increase in maximal inhibition above additivity (synergy), and Bliss<0 would indicate the percentage decrease in maximal inhibition from additivity (antagonism). Synergy, as noted by a positive Bliss value, was observed in 13 of 22 cell lines. Six of the nine erlotinib-sensitive cell lines showed pure additivity (Bliss=0, approximately) with rapamycin, the exceptions being HCT15, MDA-MB-468 and HPAC, which showed synergy. The three cell lines that are most sensitive to erlotinib (i.e. H292, H358, and BxPC3) showed pure additivity. However, these two targeted agents act synergistically to inhibit cell growth in 10 out of 13 of the cell lines that are relatively insensitive to erlotinib. In no cell line tested was the combination of erlotinib and rapamycin antagonistic. HCT-116 and MDA-468 were among those that showed synergy. Both of these cell lines have been reported to contain genetic defects that result in activation of mTOR in an EGFR-independent manner. HCT-116 Has a mutation in PI3K, leading to constitutive activity that is growth factor independent. MDA-468 has been reported to have a deletion of PTEN. The loss of this PI3K pathway inhibitor leads to sustained activation of mTOR that is partially independent of EGFR. By targeting the Akt-mTOR pathway downstream of these mutations one can effectively shut it down. Indeed, rapamycin can fully shut down this pathway as shown by its ability to fully block S6 phosphorylation. The sum of inhibition is greater than the effect of each targeted agent alone.

Figure 5:
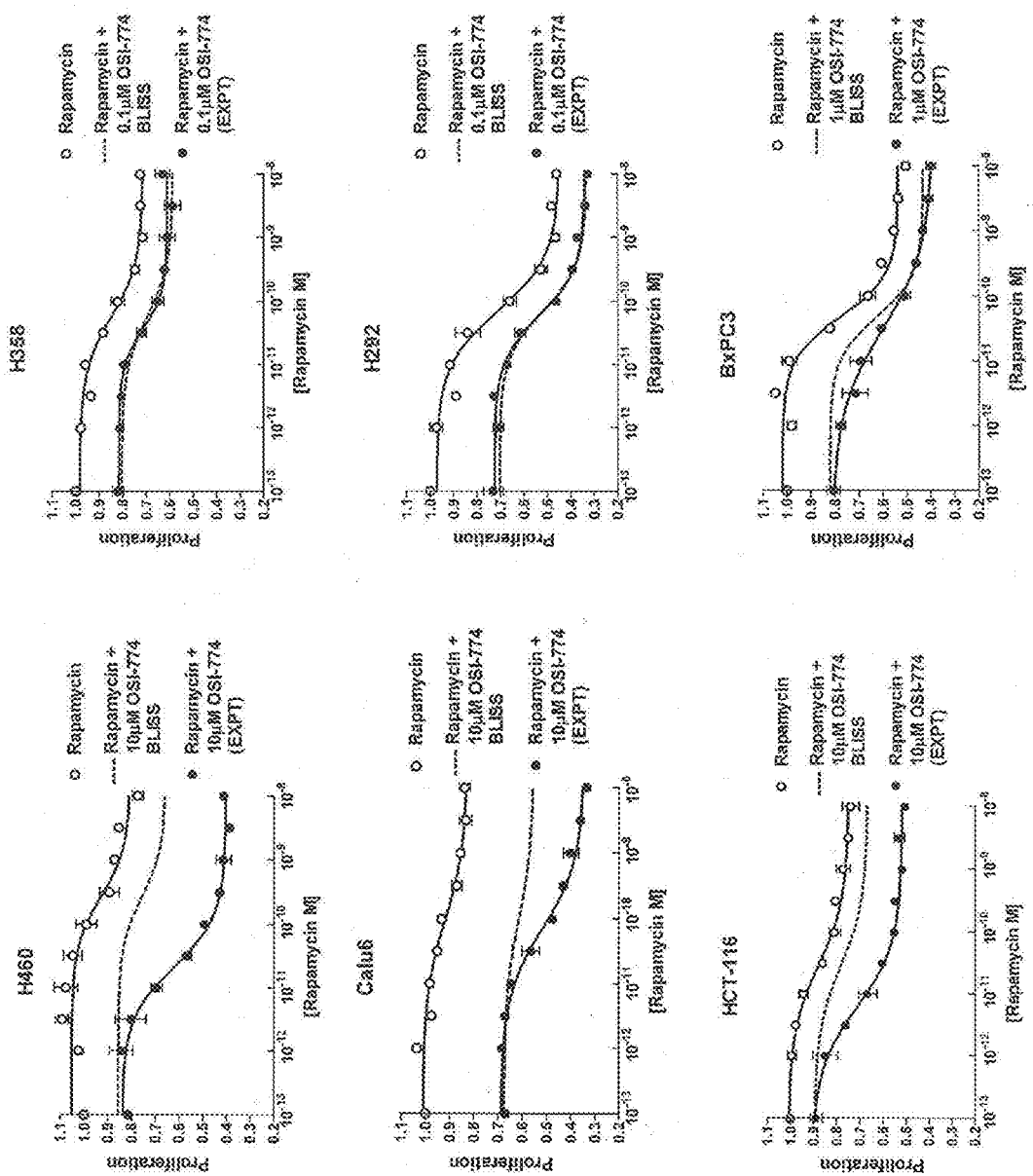
FIG. 5: Effect of varying concentrations of rapamycin on the proliferation of three sensitive cell lines (H358, H292, and BxPC3) and three relatively insensitive cell lines (H460, Calu6, and HCT-116) in the presence or absence of erlotinib. The dashed line represents the Bliss additivity curve and represents the theoretical expectation if the combined effects of erlotinib with rapamycin were exactly additive. Results shown are a representative of three or more independent experiments.

The effect of varying concentrations of rapamycin on growth inhibition in the presence and absence of 10 µM erlotinib is shown in FIG. 5. Here Bliss represents the theoretical curve that should be expected if the combination of erlotinib and rapamycin was purely additive in nature. For the three most sensitive cell lines (H292, H358, and BxPC3) Bliss analysis shows that erlotinib is exactly additive with rapamycin. This was confirmed by isobologram analysis of the data (not shown). For the three cell lines selected above that are relatively insensitive to erlotinib (H460, Calu6, and HCT-116) it was found that the combination shows synergy. This is reflected by both an increase in potency and a gain in maximal intrinsic efficacy. For example, H460 cells show an increase in maximal efficacy of approximately 60% (34% to 56%) as well as a 10-fold shift in potency (267 µM to 21 µM) when rapamycin is combined with erlotinib.

Figure 6:
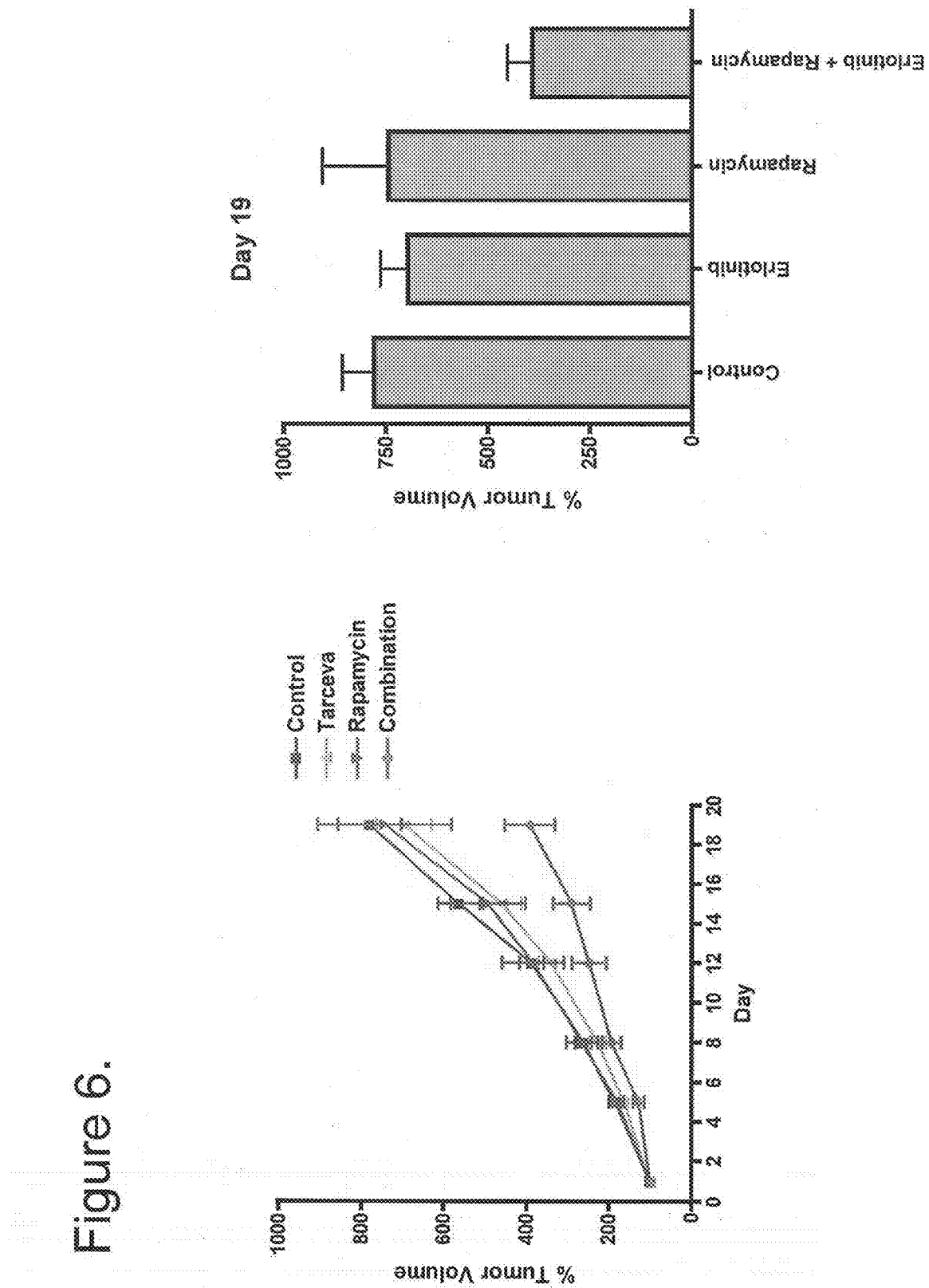
FIG. 6: Effect of a combination of erlotinib with rapamycin to synergistically inhibit growth in a Calu6 xenograft model. In the left panel the synergistic effect of the combination on tumor volume is monitored over a period of 19 days. In the right panel the data for day 19 are presented separately.

To investigate whether the above in vitro observations would extend to xenograft models in vivo, the combination of erlotinib and rapamycin was tested in a Calu6 xenograft model. As predicted by the cell culture studies, neither erlotinib or rapamycin had a substantial effect on inhibiting tumor growth as a single agent. However, when these two targeted agents were combined they showed better than additive effects in inhibiting tumor growth. These results are shown in FIG. 6. On day 19 there is a 56% reduction in tumor growth with the erlotinib and rapamycin combination while there is no statistically significant reduction in tumor growth by either drug when they are administered as single agents. By day 19 tumors in control animals as well as tumors in animals treated with either erlotinib or rapamycin alone had grown to the point that animals had to be sacrificed while animals receiving the combination continued to survive for greater than 29 days (data not shown).

Discussion:

Molecularly targeted agents acting on EGFR down modulate a number of different signaling cascades within the cell. The down-regulation of any single pathway may be necessary but not sufficient to inhibit tumor cell growth. For EGFR inhibitors down-regulation of the PI3K-Akt-mTOR pathway appears to track with sensitivity to growth inhibition. In cell lines that are relatively insensitive to blockade of the EGFR, the mTOR pathway appears to be insufficiently inhibited. Mechanisms potentially leading to the sustained activity of the mTOR pathway include: other growth factor receptors including IGF1R and FGFR, specific mutations such as constitutively activating PI3K mutations, or loss of PTEN activity. Therefore, in cell lines that are relatively insensitive to EGFR kinase inhibitor, intervention at multiple points may be necessary. The effects of combining the small molecule EGFR kinase inhibitor erlotinib with the mTOR inhibitor rapamycin were determined. It was found that cell lines that are relatively insensitive to erlotinib are sensitized to erlotinib by treatment with rapamycin. This is reflected in both a shift in potency and increase in maximal intrinsic activity.

The rapamycin and erlotinib combination was further characterized in a Calu6 xenograft model. Neither rapamycin or erlotinib showed significant reduction in tumor growth as single agents but show pronounced reduction in tumor growth in combination.

The above results provide an improved understanding of the mechanism of action of EGFR inhibitors to inhibitor tumor growth and will assist physicians in selecting patient populations who are most likely to benefit from combined therapy compared to single agent therapy.

In summary, in this study it was demonstrated that a combination of an EGFR kinase inhibitor and an mTOR inhibitor can have a synergistic or supra-additive inhibitory effect on the growth of human breast, colon, NSCL or pancreatic cancer cells. Thus mTOR inhibitors can act as agents that can sensitize tumor cells to the effects of EGFR kinase inhibitors.

Studies on the effects on tumor cells of a combination of an EGFR kinase inhibitor and an mTOR inhibitor that binds to and directly inhibits both mTORC1 and mTORC2 kinases.

The sensitivities to Compound A of 23 cell lines derived from ovarian, NSCLC, pancreatic, and HNSCC tumors was determined. The ability of 20 µM Compound A to inhibit the growth of these cell lines is shown in FIG. 7. A maximal growth inhibition of greater than 50% was chosen as the criteria for high sensitivity and all but one of these can be categorized as very sensitive. When combined with erlotinib, Compound A synergistically inhibits cellular proliferation in the majority of cell lines tested. These findings are summarized in FIG. 8 (NSCLC and pancreatic) and FIG. 9 (ovarian, HNSCC and breast). In every cell line tested, the combination improved maximal efficacy and, where synergistic, the combination resulted in a reduced EC50. Synergy was assessed using the bliss additivity model as previously described. In a panel of NSCLC and pancreatic cell lines, the combination of compound A and erlotinib was synergistic in the four mesenchymal cell lines and additive in the four epithelial cell lines tested. The effect of varying concentrations of Compound A on growth inhibition in the presence and absence of erlotinib is shown in FIG. 10 (NSCLC) and FIG. 11 (pancreatic). Here Bliss represents the theoretical curve that would be predicted if the combination of erlotinib and Compound A was purely additive. For the four mesenchymal NSCLC cell lines (FIG. 10A) Bliss analysis indicates that the combination of erlotinib and Compound A is synergistic. This is reflected by both an increase in potency and a gain in maximal intrinsic efficacy. For the four epithelial NSCLC cell lines (FIG. 10B), the combination is additive. In a panel of pancreatic cancer cell lines, the combination of erlotinib and Compound A was synergistic in the two mesenchymal cell lines and additive in the epithelial cell line tested (FIG. 11). For the set of ovarian cancer and HNSCC cell lines tested, representative dose-response curves are shown (FIG. 12). Within the panel of ovarian and HNSCC cell lines, the combination of erlotinib and Compound A was synergistic in the majority of cell lines tested (e.g. Igrov-1 Ovcar-3, HNSCC 1483) and additive in the remainder (e.g. CA-OV-3) although a strict correlation between mesenchymal phenotype and synergistic inhibition of proliferation was not observed. In no cell line tested was the combination of erlotinib and Compound A antagonistic.

In a set of NSCLC and pancreatic cell lines, the combination of Compound A and erlotinib was shown to potentiate the induction of apoptosis to a greater degree than either single agent in all but one cell line tested (FIG. 13). In that cell line, A1165, the level of apoptosis was equal to that resulting from treatment with Compound A alone.

The combination enhanced apoptosis in both the mesenchymal and epithelial cell lines. Similarly, in a set of three ovarian cell lines, both erlotinib and Compound A increased apoptosis relative the DMSO treated cells, and the combination of erlotinib and Compound A enhanced induction of apoptosis to a greater degree than either single agent (FIG. 14).

Compound B has significant anti-proliferative activity in a panel of HNSCC and ovarian cell lines (FIG. 14). The ability of 10 µM Compound B to inhibit the growth of these cell lines is shown in FIG. 15. A maximal growth inhibition of greater than 50% was chosen as the criteria for high sensitivity and all but two of these can be categorized as very sensitive. When combined with erlotinib, Compound B synergistically inhibits cellular proliferation in the majority of cell lines tested. The effect of varying concentrations of Compound B on growth inhibition in the presence and absence of erlotinib is shown for four representative cell lines in FIG. 16. Synergy was determined using the Bliss model as described above. In no cell line tested was the combination of erlotinib and Compound B antagonistic.

The combination of erlotinib and Compound B was also shown to enhance apoptosis to a greater degree than either single agent in one ovarian and one HNSCC cell line (FIG. 17). In these cell lines erlotinib and Compound B were each capable of inducing a modest increase in apoptosis relative to DMSO treated cells, and the combination of the two targeted agents resulted in a greater than 20 fold induction of apoptosis.

Abbreviations

EGF, epidermal growth factor; EGFR, epidermal growth factor receptor; EMT, epithelial-to-mesenchymal transition; MET, mesenchymal-to-epithelial transition; NSCL, non-small cell lung; NSCLC, non-small cell lung cancer; HNSCC, head and neck squamous cell carcinoma; CRC, colorectal cancer; MBC, metastatic breast cancer; Brk, Breast tumor kinase (also known as protein tyrosine kinase 6 (PTK6)); FCS, fetal calf serum; LC, liquid chromatography; MS, mass spectrometry; IGF-1, insulin-like growth factor-1; TGFat, transforming growth factor alpha; HB-EGF, heparin-binding epidermal growth factor; LPA, lysophosphatidic acid; $IC_{50}$, half maximal inhibitory concentration; pY, phosphotyrosine; wt, wild-type; PI3K, phosphatidyl inositol-3 kinase; GAPDH, glyceraldehyde 3-phosphate dehydrogenase; MAPK, mitogen-activated protein kinase; PDK-1,3-Phosphoinositide-Dependent Protein Kinase 1; Akt, also known as protein kinase B, is the cellular homologue of the viral oncogene v-Akt; mTOR, mammalian target of rapamycin; 4EBP 1, eukaryotic translation initiation factor-4E (mRNA cap-binding protein) Binding Protein-1, also known as PHAS-I; p70S6K, 70 kDa ribosomal protein-S6 kinase; eIF4E, eukaryotic translation initiation factor-4E (mRNA cap-binding protein); Raf, protein kinase product of Raf oncogene; MEK, ERK kinase, also known as mitogen-activated protein kinase kinase; ERK, Extracellular signal-regulated protein kinase, also known as mitogen-activated protein kinase; PTEN, "Phosphatase and Tensin homologue deleted on chromosome 10", a phosphatidylinositol phosphate phosphatase; pPROTEIN, phospho-PROTEIN, "PROTEIN" can be any protein that can be phosphorylated, e.g. EGFR, ERK, S6 etc; PBS, Phosphate-buffered saline; TGI, tumor growth inhibition; WFI, Water for Injection; SDS, sodium dodecyl sulfate; ErbB2, "v-erb-b2 erythroblastic leukemia viral oncogene homolog 2", also known as HER-2; ErbB3, "v-erb-b2 erythroblastic leukemia viral oncogene homolog 3", also known as HER-3; ErbB4, "v-erb-b2 erythroblastic leukemia viral oncogene homolog 4", also known as HER-4; FGFR, Fibroblast Growth Factor Receptor; DMSO, dimethyl sulfoxide.

Incorporation By Reference

All patents, published patent applications and other references disclosed herein are hereby expressly incorporated herein by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating tumors or tumor metastases in a patient, comprising administering to said patient simultaneously or sequentially a therapeutically effective amount of a combination of an EGFR kinase inhibitor and an agent that sensitizes tumor cells to the effects of EGFR kinase inhibitors, wherein said agent is an mTOR inhibitor that binds to and directly inhibits both mTORC1 and mTORC2 kinases, and is a compound represented by Formula (I),

or a pharmaceutically acceptable salt thereof, wherein:
$X_1$, and $X_2$ are each independently N or C-$(E^1)_{aa}$;
$X_5$ is N, C-$(E^1)_{aa}$, or N-$(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;
$R^3$ is $C_{0-10}$alkyl, cyclo$C_{3-10}$alkyl, aminomethylcyclo $C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;
$Q^1$ is -A($R^1$)$_m$B(W)$_n$ or —B($G^{11}$)$_n$A(Y)$_m$;
A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;
or $Q^1$ is -A($R^1$)$_m$A(Y)$_m$, wherein each A is the same or different 5-membered aromatic or heteroaromatic ring, and the two are fused together to form an 8-membered heteroaromatic system;
$R^1$ is independently, hydrogen, —N($C_{0-8}$alkyl)($C_{0-8}$ alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cyclyoalkyl, —$C_{0-8}$alkyl-$NR^{311}$S$(O)_{0-2}R^{321}$, —$C_{0-8}$alkyl-$NR^{311}$S$(O)_{0-2}NR^{321}R^{331}$, —$C_{0-8}$alkyl-$S(O)_{0-2}NR^{311}R^{321}$, —$C_{0-8}$alkyl-$NR^{311}COR^{321}$, —$C_{0-8}$alkyl-$NR^{311}CO_2R^{321}$, —$C_{0-8}$alkyl-$NR^{311}CONR^{321}R^{331}$, —$C_{0-8}$alkyl-$CONR^{311}R^{321}$, —$C_{0-8}$alkyl-$CON(R^{311})S(O)_{0-2}R^{321}$, $C_{0-8}$alkyl-$CO_2R^{311}$, —$C_{0-8}$alkyl-$S(O)_{0-2}R^{311}$, $C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cyclyoalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N($R^{311}$)—$C_{0-8}$alkyl, —$C_{0-8}$alkyl-N($R^{311}$)—$C_{0-8}$alkyl$C_{3-8}$cycloalkyl, —$C_{0-8}$alkyl-N($R^{311}$)—$C_{0-8}$alkylheterocyclyl, —$C_{0-8}$alkyl-N($R^{311}$)—$C_{0-8}$alkylaryl, —$C_{0-8}$alkyl-N($R^{311}$)—$C_{0-8}$alkylhetaryl, —$C_{0-8}$alkyl-$NR^{311}R^{321}$—$C_{2-8}$alkenyl, —$C_{2-8}$alkynyl, $NO_2$, CN, $CF_3$, $OCF_3$, $OCHF_2$; provided that $Q^1$ is not N-methyl-2-indolyl, N-(phenylsulfonyl)-2-indolyl, or N-tert-butoxycarbonyl W is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-$NR^{312}$S$(O)_{0-2}R^{322}$, —$C_{0-8}$alkyl-$NR^{311}$S$(O)_{0-2}NR^{321}R^{331}$—$C_{0-8}$alkyl-$NR^{311}CO_2R^{321}$, —$C_{0-8}$alkyl-$CON(R^{311})$S$(O)_{0-2}R^{321}C_{0-8}$alkyl-$S(O)_{0-2}NR^{312}R^{322}$, —$C_{0-8}$alkyl-$NR^{312}COR^{322}$, —$C_{0-8}$alkyl-$NR^{312}CONR^{322}R^{332}$, —$C_{0-8}$alkyl-$CONR^{312}R^{322}$, —$C_{0-8}$alkyl-$CO_2R^{312}$, —$C_{0-8}$alkylS$(O)_{0-2}R^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocyloalkyl, —$C_{0-8}$alkyl-O—$C_{0-8}$alkylaryl, —Oaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocyloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N($R^{312}$)—$C_{0-8}$alkyl, —$C_{0-8}$alkyl-N($R^{312}$)—$C_{0-8}$alkyl$C_{3-8}$cyclyoalkyl, —$C_{0-8}$alkyl-N($R^{312}$)—$C_{0-8}$ alkylheterocyclyoalkyl, —$C_{0-8}$alkyl-N($R^{312}$)—$C_{0-8}$ alkylaryl, —$C_{0-8}$alkyl-N($R^{312}$)—$C_{0-8}$alkylhetaryl, —$C_{0-8}$alkyl-$NR^{312}R^{322}$, —$C_{2-8}$alkenyl, —$C_{2-8}$alkynyl, $NO_2$, CN, $CF_3$, $OCF_3$, $OCHF_2$; provided that $Q^1$ is not 4-benzyloxy-2-indolyl;

Y is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{0-6}$alkyl, —$C_{0-8}$alkyl$C_{3-8}$cycloalkyl, —$C_{0-8}$alkyl-$NR^{311}$S$(O)_{0-2}R^{321}$, —$C_{0-8}$alkyl-$NR^{311}$S$(O)_{0-2}NR^{321}R^{331}$, —$C_{0-8}$alkyl-$NR^{311}CO_2R^{321}$, —$C_{0-8}$alkyl-CON($R^{311}$)S$(O)_{0-2}R^{321}$, —$C_{0-8}$alkyl-$S(O)_{0-2}NR^{311}R^{321}$, —$C_{0-8}$alkyl-$NR^{311}COR^{321}$, —$C_{0-8}$alkyl-$NR^{311}CONR^{321}R^{331}$, —$C_{0-8}$alkyl-$CONR^{311}R^{321}$, —$C_{0-8}$alkyl-$CO_2R^{311}$, —$C_{0-8}$alkylS$(O)_{0-2}R^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$ alkylhetaryl, —$C_{0-8}$alkylheterocyclyl, $C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocloalkyl, —$C_{0-8}$alkyl-S—$C_{0-8}$alkylaryl, —$C_{0-8}$alkyl-S—$C_{0-8}$alkylhetaryl, $C_{0-8}$alkyl-N($R^{311}$)—$C_{0-8}$alkyl, —$C_{0-8}$alkyl-N($R^{311}$)—$C_{0-8}$alkyl$C_{3-8}$cycloalkyl, —$C_{0-8}$alkyl-N($R^{311}$)—$C_{0-8}$alkylheterocloalkyl, —$C_{0-8}$alkyl-N($R^{311}$)—$C_{0-8}$alkylaryl, —$C_{0-8}$alkyl-N($R^{311}$)—$C_{0-8}$alkylhetaryl, —$C_{0-8}$alkyl-$NR^{311}R^{321}$, —$C_{2-8}$ alkenyl, —$C_{2-8}$alkynyl, $NO_2$, CN, $CF_3$, $OCF_3$, $OCHF_2$; provided that $Q^1$ is not 2-carboxy-5-benzo[b]thiophenyl;

$G^{11}$ is halo, oxo, —$CF_3$, —$OCF_3$, —$OR^{312}$, —$NR^{312}R^{322}$, —C(O)$R^{312}$, —C(O)$C_{3-8}$cycloalkyl, —$CO_2C_{3-8}$cycloalkyl, —$CO_2R^{312}$, —C(=O)$NR^{312}R^{322}$, —$NO_2$, —CN, —S$(O)_{0-2}R^{312}$, —$SO_2NR^{312}R^{322}$, $NR^{312}$C(=O)$R^{322}$, $NR^{312}$C(=O)$OR^{322}$, $NR^{312}$C(=O)$NR^{322}R^{332}$, $NR^{312}$S$(O)_{0-2}R^{322}$, —C(=S)$OR^{312}$, —C(=O)$SR^{312}$, —$NR^{312}$C(=$NR^{322}$)$NR^{332}R^{341}$, —$NR^{312}$C(=$NR^{322}$)$OR^{332}$, —$NR^{312}$C(=$NR^{322}$)$SR^{332}$, —OC(=O)$OR^{312}$, —OC(=O)$NR^{312}R^{322}$, —OC(=O)$SR^{312}$, —SC(=O)$OR^{312}$, —SC(=O)$NR^{312}R^{322}$, —P(O)$OR^{312}OR^{322}$, $C_{1-10}$alkylidene, $C_{0-10}$alkyl, $C_{2-10}$alkenyl, $C_{2-10}$alkynyl, $C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{0-10}$alkyl, heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{313}$, —$NR^{313}R^{323}$, —C(O)$R^{313}$, —$CO_2R^{313}$, —C(=O)$NR^{313}R^{323}$, —$NO_2$, —CN, —S$(O)_{0-2}R^{313}$, —$SO_2NR^{313}R^{323}$, —$NR^{313}$C(=O)$R^{323}$, —$NR^{313}$C(=O)$OR^{323}$, —$NR^{313}$C(=O)$NR^{323}R^{333}$—$NR^{313}$S$(O)_{0-2}R^{323}$, —C(=S)$OR^{313}$—C(=O)$SR^{313}$—$NR^{313}$C(=$NR^{323}$)$NR^{333}R^{342}$, —$NR^{313}$C(=$NR^{323}$)$OR^{333}$, —$NR^{313}$C(=$NR^{323}$)$SR^{333}$, —OC(=O)$OR^{333}$, —OC(=O)$NR^{313}R^{323}$, —OC(=O)$SR^{313}$, —SC(=O)$OR^{313}$, —P(O)$OR^{313}OR^{323}$, or —SC(=O)$NR^{313}R^{323}$ substituents;

or $G^{11}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{313}$, —$NR^{313}R^{323}$, —C(O)$R^{313}$, —$CO_2R^{313}$, —C(=O)$NR^{313}R^{323}$, —$NO_2$, —CN, —S$(O)_{0-2}R^{313}$—$SO_2NR^{313}R^{323}$, —$NR^{313}$C(=O)$R^{323}$, —$NR^{313}$C(=O)$OR^{323}$, —$NR^{313}$C(=O)$NR^{323}R^{333}$, —$NR^{313}$S$(O)_{0-2}R^{323}$, —C(=S)$OR^{313}$, —C(=O)$SR^{313}$, —$NR^{323}$C(=$NR^{313}$)$NR^{333}R^{342}$, —$NR^{313}$C(=$NR^{323}$)$OR^{333}$, —$NR^{313}$C(=$NR^{323}$)$SR^{333}$, —OC(=O)$OR^{313}$, —OC(=O)$NR^{313}R^{323}$, —OC(=O)$SR^{313}$, —SC(=O)$OR^{313}$, —P(O)$OR^{313}OR^{323}$, or —SC(=O)$NR^{313}R^{323}$ substituents; provided that $G^{11}$ is not N—$CH_2CO_2H$ when $R^3$ is 4-piperidinyl;

$R^{31}$, $R^{32}$, $R^{33}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently $C_{0-8}$alkyl optionally substituted with an aryl, heterocyclyl or hetaryl substituent, or $C_{0-8}$alkyl optionally substituted with 1-6 independent halo, —CON($C_{0-8}$alkyl)($C_{0-8}$alkyl), —CO($C_{0-8}$alkyl), —O$C_{0-8}$alkyl, —Oaryl, —Ohetaryl, —Oheterocyclyl, —S(O)$_{0-2}$aryl, —S(O)$_{0-2}$hetaryl, —S(O)$_{0-2}$heterocyclyl, —S(O)$_{0-2}$C$_{0-8}$alkyl, —N($C_{0-8}$alkyl)($C_{0-8}$alkyl), —N($C_{0-8}$alkyl)CON($C_{0-8}$alkyl)($C_{0-8}$alkyl)-N($C_{0-8}$alkyl)CO($C_{1-8}$alkyl), —N($C_{0-8}$alkyl)CO($C_{3-8}$cycloalkyl), —N($C_{0-8}$alkyl)CO$_2$($C_{1-8}$alkyl), —S(O)$_{1-2}$N($C_{0-8}$alkyl)($C_{0-8}$alkyl), —NR$^{11}$S(O)$_{1-2}$($C_{0-8}$alkyl), —CON($C_{3-8}$cycloalkyl)($C_{3-8}$cycloalkyl), —CON($C_{0-8}$alkyl)($C_{3-8}$cycloalkyl), —N($C_{3-8}$cycloalkyl)CON($C_{0-8}$alkyl)($C_{0-8}$alkyl), —N($C_{3-8}$cycloalkyl)CON($C_{3-8}$cycloalkyl)($C_{0-8}$alkyl), —N($C_{0-8}$alkyl)CON($C_{3-8}$cycloalkyl)($C_{0-8}$alkyl), —N($C_{0-8}$alkyl)CO$_2$($C_{3-8}$cycloalkyl), —N($C_{3-8}$cycloalkyl)CO$_2$($C_{3-8}$cycloalkyl), S(O)$_{1-2}$N($C_{0-8}$alkyl)($C_{3-8}$cycloalkyl), —NR$^{11}$S(O)$_{1-2}$($C_{3-8}$cycloalkyl), $C_{2-8}$alkenyl, $C_{2-8}$alkynyl, CN, CF$_3$, OH, or optionally substituted aryl substituents; such that each of the above aryl, heterocyclyl, hetaryl, alkyl or cycloalkyl groups may be optionally, independently substituted with —N($C_{0-8}$alkyl)($C_{0-8}$alkyl), hydroxyl, halogen, oxo, aryl, hetaryl, $C_{0-6}$alkyl, $C_{0-8}$alkylcyclyl, —$C_{0-8}$alkyl-N($C_{0-8}$alkyl)-S(O)$_{0-2}$—($C_{0-8}$alkyl), —$C_{0-8}$alkyl-S(O)$_{0-2}$—N($C_{0-8}$alkyl)($C_{0-8}$alkyl), —$C_{0-8}$alkyl-N($C_{0-8}$alkyl)CO($C_{0-8}$alkyl), —$C_{0-8}$alkyl-N($C_{0-8}$alkyl)CO—N($C_{0-8}$alkyl)($C_{0-8}$alkyl), —$C_{0-8}$alkyl-CO—N($C_{0-8}$alkyl)($C_{0-8}$alkyl), —$C_{1-8}$alkyl-CO$_2$—($C_{0-8}$alkyl), —$C_{0-8}$alkylS(O)$_{0-2}$—($C_{0-8}$alkyl), —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$ alkyl-heterocyclyl, —$C_{0-8}$alkyl-O—$C_{0-8}$alkylaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkylcyclyl, —$C_{0-8}$alkyl-S—$C_{0-8}$alkylheterocyclyl, —$C_{0-8}$alkyl-S—$C_{0-8}$alkylaryl, —$C_{0-8}$ alkyl-S—$C_{0-8}$alkylhetaryl, —$C_{0-8}$alkyl-N($C_{0-8}$alkyl)-$C_{0-8}$alkyl, —$C_{0-8}$alkyl-N($C_{0-8}$alkyl)-$C_{0-8}$alkyl-cyclyl, —$C_{0-8}$alkyl-N($C_{0-8}$alkyl)-$C_{0-8}$alkylheterocyclyl, —$C_{0-8}$ alkyl-N($C_{0-8}$alkyl)-$C_{0-8}$alkylaryl, —$C_{0-8}$alkyl-N($C_{0-8}$ alkyl)-$C_{0-8}$alkylhetaryl, $C_{2-8}$alkenyl, $C_{2-8}$alkynyl, NO$_2$, CN, CF$_3$, OCF$_3$, OCHF$_2$,
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl, or heterocyclyl optionally substituted with 1-4 independent $C_{0-8}$alkyl, cyclyl, or substituted cyclyl substituents;

$E^1$ in each instance is independently halo, —CF$_3$, —OCF$_3$, —OR$^2$, —NR$^{31}$R$^{32}$, —C(=O)R$^{31}$, —CO$_2$R$^{31}$, —CONR$^{31}$R$^{32}$, —NO$_2$, —CN, —S(O)$_{0-2}$R$^{31}$—S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{31}$)SR$^{31}$, —OC(=O)OR$^{31}$, —OC(=O)NR$^{31}$R$^{32}$, —OC(=O)SR$^{31}$, —SC(=O)OR$^{31}$, —SC(=O)NR$^{31}$R$^{32}$, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{0-10}$alkyl, -heterocyclyl-$C_{2-10}$alkenyl, or -heterocyclyl-$C_{2-10}$alkynyl, any of which is optionally substituted with one or more independent halo, oxo, —CF$_3$, —OCF$_3$, —OR$^{31}$, —NR$^{31}$R$^{32}$, —C(=O)R$^{31}$, —CO$_2$R$^{31}$, —C(=O)NR$^{31}$R$^{32}$, —NO$_2$, —CN, —S(=O)$_{0-2}$, R$^{31}$, —SO$_2$NR$^{31}$, —NR$^{31}$C(=O)R$^{32}$, —NR$^{31}$C(=O)OR$^{31}$, —NR$^{31}$C(=O)NR$^{32}$R$^{33}$, —NR$^{31}$S(O)$_{0-2}$R$^{31}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

or $E^1$ in each instance is independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —CF$_3$, —OCF$_3$, —OR$^{31}$, —NR$^{13}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)OR$^{32}$, —NR C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{13}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

in the cases of —NR$^{31}$R$^{32}$, —NR$^{311}$R$^{321}$, —NR$^{312}$R$^{322}$, —NR$^{332}$R$^{341}$, —NR$^{313}$R$^{323}$, and —NR$^{323}$R$^{333}$, the respective R$^{31}$ and R$^{32}$, R$^{311}$ and R$^{321}$, R$^{312}$ and R$^{322}$, R$^{331}$ and R$^{341}$, R$^{313}$ and R$^{323}$, and R$^{323}$ and R$^{333}$ are optionally taken together with the nitrogen atom to which they are attached to form a 3-10 membered saturated or unsaturated ring; wherein said ring in each instance independently is optionally substituted by one or more independent —N($C_{0-8}$alkyl)($C_{0-8}$alkyl), hydroxyl, halogen, oxo, aryl, hetaryl, $C_{0-6}$alkyl, —$C_{0-8}$alkyl$C_{3-8}$cycloalkyl, —$C_{0-8}$alkyl-N($C_{0-8}$alkyl)S(O)$_{0-2}$$C_{0-8}$alkyl, —$C_{0-8}$alkyl-N($C_{0-8}$alkyl)S(O)$_{0-2}$N($C_{0-8}$alkyl)($C_{0-8}$alkyl), —$C_{0-8}$alkyl-N($C_{0-8}$alkyl)CO$_2$($C_{0-8}$alkyl), —$C_{0-8}$alkyl-CON(($C_{0-8}$alkyl))S(O)$_{0-2}$($C_{0-8}$alkyl), —$C_{0-8}$alkyl-S(O)$_{0-2}$N($C_{0-8}$ alkyl)($C_{0-8}$alkyl), —$C_{0-8}$alkyl-N($C_{0-8}$alkyl)CO($C_{0-8}$ alkyl), —$C_{0-8}$alkyl-N($C_{0-8}$alkyl)CON($C_{0-8}$alkyl)($C_{0-8}$alkyl), —$C_{0-8}$alkyl-CON($C_{0-8}$alkyl)($C_{0-8}$alkyl), —$C_{0-8}$alkyl-CO$_2$($C_{0-8}$alkyl), —$C_{0-8}$alkylS(O)$_{0-2}$($C_{0-8}$alkyl), —$C_{0-8}$alkyl-O—$C_{0-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, —Oaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl-$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N($C_{0-8}$alkyl)-$C_{0-8}$alkyl, —$C_{0-8}$alkyl-N($C_{0-8}$alkyl)-$C_{0-8}$alkyl$C_{3-8}$cycloalkyl, —$C_{0-8}$alkyl-N($C_{0-8}$alkyl)-$C_{0-8}$alkylheterocycloalkyl, —$C_{0-8}$alkyl-N($C_{0-8}$alkyl)-Calkylaryl, —$C_{0-8}$alkyl-N($C_{0-8}$alkyl)-$C_{0-8}$alkyl-hetaryl, —$C_{0-8}$alkyl-N($C_{0-8}$alkyl)($C_{0-8}$alkyl), $C_{2-8}$alkenyl, $C_{2-8}$alkynyl, NO$_2$, CN, CF$_3$, OCF$_3$, or OCHF$_2$ substituents; wherein said ring in each instance independently optionally includes one or more heteroatoms other than the nitrogen;

m is 0, 1, 2, or 3;
n is 0, 1, 2, 3, or 4;
aa is 0 or 1; and provided that Formula I is not trans-4-[8-amino-1-(7-chloro-4-hydroxy-1H-indol-2-yl)imidazo[1,5-a]pyrazin-3-yl]cyclohexanecarboxylic acid, cis-3-[8-amino-1-(7-chloro-1H-indol-2-yl)imidazo[1,5-a]pyrazin-3-yl]cyclobutanecarboxylic acid, trans-4-{8-amino-1-[7-(3-isopropyl)phenyl-1H-indol-2-yl]imidazo[1,5-a]pyrazin-3-yl}cyclohexanecarboxylic acid or trans-4-{8-amino-1-[7-(2,5-dichloro)phenyl-1H-indol-2-yl]imidazo[1,5-a]pyrazin-3-yl}cyclohexanecarboxylic acid.

2. The method of claim 1, wherein the patient is a human that is being treated for cancer.

3. The method of claim 1, wherein the EGFR kinase inhibitor and mTOR inhibitor are co-administered to the patient in the same formulation.

4. The method of claim 1, wherein the EGFR kinase inhibitor and mTOR inhibitor are co-administered to the patient in different formulations.

5. The method of claim 1, wherein the EGFR kinase inhibitor and mTOR inhibitor are co-administered to the patient by the same route.

6. The method of claim 1, wherein the EGFR kinase inhibitor and mTOR inhibitor are co-administered to the patient by different routes.

7. The method of claim 1, wherein the EGFR kinase inhibitor is a small organic molecule, an antibody or an antibody fragment that binds specifically to the EGFR.

8. The method of claim 1, wherein the EGFR kinase inhibitor comprises erlotinib, or a salt thereof.

9. The method of claim 1, additionally comprising administering to said patient one or more other anti-cancer agents.

10. The method of claim 1, wherein the administering to the patient is simultaneous.

11. The method of claim 1, wherein the administering to the patient is sequential.

12. The method of claim 1, wherein the cells of the tumors or tumor metastases have high sensitivity to growth inhibition by EGFR kinase inhibitors as single agents.

13. The method of claim 1, wherein the cells of the tumors or tumor metastases have low sensitivity to growth inhibition by EGFR kinase inhibitors as single agents.

14. The method of claim 1, wherein the cells of the tumors or tumor metastases have not undergone any form of EMT.

15. The method of claim 1, wherein the cells of the tumors or tumor metastases have undergone an EMT.

16. A method for the treatment of cancer, comprising administering to a subject in need of such treatment an amount of the EGFR kinase inhibitor, or a pharmaceutically acceptable salt thereof; and an amount of an mTOR inhibitor that binds to and directly inhibits both mTORC1 and mTORC2 kinases, or a pharmaceutically acceptable salt thereof; wherein at least one of the amounts is administered as a sub-therapeutic amount, and is a compound represented by Formula (I),

or a pharmaceutically acceptable salt thereof, wherein:

$X_1$, and $X_2$ are each independently N or C-$(E^1)_{aa}$;

$X_5$ is N, C-$(E^1)_{aa}$, or N-$(E^1)_{aa}$;

$X_3$, $X_4$, $X_6$, and $X_7$ are each independently N or C;

wherein at least one of $X_3$, $X_4$, $X_5$, $X_6$, and $X_7$ is independently N or N-$(E^1)_{aa}$;

$R^3$ is $C_{0-10}$alkyl, cyclo$C_{3-10}$alkyl, aminomethylcyclo $C_{3-10}$ alkyl, bicyclo$C_{5-10}$alkyl, aryl, heteroaryl, aralkyl, heteroaralkyl, heterocyclyl or heterobicyclo$C_{5-10}$ alkyl any of which is optionally substituted by one or more independent $G^{11}$ substituents;

$Q^1$ is -A$(R^1)_m$B(W)$_n$ or —B$(G^{11})_n$A(Y)$_m$;

A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;

or $Q^1$ is -A$(R^1)_m$A(Y)$_m$, wherein each A is the same or different 5-membered aromatic or heteroaromatic ring, and the two are fused together to form an 8-membered heteroaromatic system;

$R^1$ is independently, hydrogen, —N($C_{0-8}$alkyl)($C_{0-8}$ alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CO$_2$R$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CON(R$^{311}$)S(O)$_{0-2}$R$^{321}$, —$C_{0-8}$alkyl-CO$_2$R$^{311}$, —$C_{0-8}$alkyl-S(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocyclyl, —$C_{0-8}$alkyl-O—$C_{0-8}$alkylaryl, —$C_{0-8}$alkylaryl, —$C_{0-8}$alkylhetaryl, —$C_{0-8}$ alkylheterocyclyl, —$C_{0-8}$alkyl-O—$C_{0-8}$ alkylhetaryl, —$C_{0-8}$alkyl-S—$C_{0-8}$alkyl, —$C_{0-8}$ alkyl-S—$C_{0-8}$alkyl$C_{3-8}$cycloalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$ alkylhetaryl, —$C_{0-8}$alkyl-N(R$^{311}$)—$C_{0-8}$alkyl, —$C_{0-8}$ alkyl-N(R$^{311}$)—$C_{0-8}$alkyl$C_{3-8}$cycloalkyl, —$C_{0-8}$ alkyl-N(R$^{311}$)—$C_{0-8}$alkylheterocyclyl, —$C_{0-8}$ alkyl-N(R$^{311}$)—$C_{0-8}$alkylaryl, —$C_{0-8}$alkyl-N (R$^{311}$)—$C_{0-8}$ alkylhetaryl, —$C_{0-8}$alkyl-NR$^{311}$R$^{321}$, —$C_{2-8}$ alkenyl, —$C_{2-8}$alkynyl, NO$_2$, CN, CF$_3$, OCF$_3$, OCHF$_2$ provided that $Q^1$ is not N-methyl-2-indolyl, N-(phenylsulfonyl)-2-indolyl, or N-tert-butoxycarbonyl W is independently, hydrogen, —N($C_{0-8}$alkyl)($C_{0-8}$ alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-$NR^{312}$S$(O)_{0-2}R^{322}$, —$C_{0-8}$alkyl-$NR^{311}$S$(O)_{0-2}NR^{321}R^{331}$, —$C_{0-8}$alkyl-$NR^{311}CO_2R^{321}$, —$C_{0-8}$alkyl-CON$(R^{311})$S$(O)_{0-2}R^{321}$, —$C_{0-8}$alkyl-S$(O)_{0-2}NR^{312}R^{322}$, —$C_{0-8}$alkyl-$NR^{312}COR^{322}$, —$C_{0-8}$alkyl-$NR^{312}CONR^{322}R^{332}$, —$C_{0-8}$alkyl-CONR$^{312}R^{322}$, —$C_{0-8}$alkyl-CO$_2R^{312}$, —$C_{0-8}$alkylS$(O)_{0-2}R^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, —Oaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N$(R^{312})$—$C_{0-8}$alkyl, —$C_{0-8}$alkyl-N$(R^{312})$—$C_{0-8}$alkyl$C_{0-8}$cycloalkyl, —$C_{0-8}$alkyl-N$(R^{312})$—$C_{0-8}$ alkylheterocycloalkyl, —$C_{0-8}$alkyl-N$(R^{312})$—$C_{0-8}$ alkylaryl, —$C_{0-8}$alkyl-N$(R^{312})$—$C_{0-8}$alkylhetaryl, —$C_{0-8}$alkyl-$NR^{312}R^{322}$, —$C_{2-8}$alkenyl, —$C_{2-8}$alkynyl, $NO_2$, CN, $CF_3$, $OCF_3$, $OCHF_2$; provided that $Q^1$ is not 4-benzyloxy-2-indolyl;

Y is independently, hydrogen, —$N(C_{0-8}$alkyl)$(C_{0-8}$alkyl), hydroxyl, halogen, oxo, aryl (optionally substituted with 1 or more $R^{31}$ groups), hetaryl (optionally substituted with 1 or more $R^{31}$ groups), $C_{0-6}$alkyl, —$C_{0-8}$alkyl$C_{3-8}$cycloalkyl, —$C_{0-8}$alkyl-$NR^{311}$S$(O)_{0-2}R^{321}$, —$C_{0-8}$alkyl-$NR^{311}$S$(O)_{0-2}NR^{321}R^{331}$, —$C_{0-8}$alkyl-$NR^{311}CO_2R^{321}$, —$C_{0-8}$alkyl-CON$(R^{311})$S$(O)_{0-2}R^{321}$, —$C_{0-8}$alkyl-S$(O)_{0-2}NR^{311}R^{321}$, —$C_{0-8}$alkyl-$NR^{311}COR^{321}$, —$C_{0-8}$alkyl-$NR^{311}CONR^{321}R^{331}$, —$C_{0-8}$alkyl-CONR$^{311}R^{321}$, —$C_{0-8}$alkyl-CO$_2R^{311}$, —$C_{0-8}$alkylS$(O)_{0-2}R^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N$(R^{311})$—$C_{0-8}$alkyl, —$C_{0-8}$ alkyl-N$(R^{311})$—$C_{0-8}$alkyl$C_{3-8}$cycloalkyl, —$C_{0-8}$ alkyl-N$(R^{311})$—$C_{0-8}$alkylheterocycloalkyl, —$C_{0-8}$ alkyl-N$(R^{311})$—$C_{0-8}$alkylaryl, —$C_{0-8}$alkyl-N$(R^{311})$—$C_{0-8}$alkylhetaryl, —$C_{0-8}$alkyl-$NR^{311}R^{321}$, —$C_{2-8}$alkenyl, —$C_{2-8}$alkynyl, $NO_2$, CN, $CF_3$, $OCF_3$, $OCHF_2$; provided that $Q^1$ is not 2-carboxy-5-benzo[b]thiophenyl;

$G^{11}$ is halo, oxo, —$CF_3$, —$OCF_3$, —$OR^{312}$, —$NR^{312}R^{322}$, —$C(O)R^{312}$, —$C(O)C_{3-8}$cycloalkyl, —$CO_2C_{3-8}$cycloalkyl, —$CO_2R^{312}$, —$C(=O)NR^{312}R^{322}$, —$NO_2$, —CN, —$S(O)_{0-2}R^{312}$, —$SO_2NR^{312}R^{322}$, $NR^{312}C(=O)R^{322}$, $NR^{312}C(=O)OR^{322}$, $NR^{312}C(=O)NR^{322}R^{332}$, $NR^{312}S(O)_{0-2}R^{322}$, —$C(=S)OR^{312}$, —$C(=O)SR^{312}$, —$NR^{312}C(=NR^{322})NR^{332}R^{341}$, —$NR^{312}C(=NR^{322})OR^{332}$, —$NR^{312}C(=NR^{322})SR^{332}$, —$OC(=O)OR^{312}$, —$OC(=O)NR^{312}R^{322}$, —$OC(=O)SR^{312}$, —$SC(=O)OR^{312}$, —$SC(=O)NR^{312}R^{322}$, —$P(O)OR^{312}OR^{322}$, $C_{1-10}$alkylidene, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{1-10}$alkyl, heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{313}$, —$NR^{313}R^{323}$, —$C(O)R^{313}$, —$CO_2R^{313}$, —$C(=O)NR^{313}R^{323}$—$NO_2$, —CN, —$S(O)_{0-2}R^{313}$, —$SO_2NR^{313}R^{323}$, —$NR^{313}C(=O)R^{323}$, —$NR^{313}C(=O)OR^{323}$, —$NR^{313}C(=O)NR^{323}R^{333}$, —$NR^{313}S(O)_{0-2}R^{323}$, —$C(=S)OR^{313}$, —$C(=O)SR^{313}$, —$NR^{313}C(=NR^{323})NR^{333}R^{342}$, —$NR^{313}C(=NR^{323})OR^{333}$, —$NR^{313}C(=NR^{323}SR)SR^{333}$, —$OC(=O)OR^{333}$, —$OC(=O)NR^{313}R^{323}$, —$OC(=O)SR^{313}$, —$SC(=O)OR^{313}$, —$P(O)OR^{313}OR^{323}$, or —$SC(=O)NR^{313}R^{323}$ substituents;

or $G^{11}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{313}$, —$NR^{313}R^{323}$, —$C(O)R^{313}$, —$CO_2R^{313}$, —$C(=O)NR^{313}R^{323}$, —$NO_2$, —CN, —$S(O)_{0-2}R^{313}$, —$SO_2NR^{313}R^{323}$, —$NR^{313}C(=O)R^{323}$, —$NR^{313}C(=O)OR^{323}$, —$NR^{313}C(=O)NR^{323}R^{333}$, —$NR^{313}S(O)_{0-2}R^{323}$, —$C(=S)OR^{313}$, —$C(=O)SR^{313}$, —$NR^{323}C(=NR^{313})NR^{333}R^{342}$, —$NR^{313}C(=NR^{323})OR^{333}$, —$NR^{313}C(=NR^{323})SR^{333}$, —$OC(=O)OR^{313}$, —$OC(=O)NR^{313}R^{323}$, —$OC(=O)SR^{313}$, —$SC(=O)OR^{313}$, —$P(O)OR^{313}OR^{323}$, or —$SC(=O)NR^{313}R^{323}$ substituents; provided that $G^{11}$ is not N—$CH_2CO_2H$ when $R^3$ is 4-piperidinyl;

$R^{31}$, $R^{32}$, $R^{33}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently $C_{0-8}$alkyl optionally substituted with an aryl, heterocyclyl or hetaryl substituent, or $C_{0-8}$alkyl optionally substituted with 1-6 independent halo, —CON$(C_{0-8}$alkyl)$(C_{0-8}$alkyl), —CO$(C_{0-8}$alkyl), —O$C_{0-8}$alkyl, —Oaryl, —Ohetaryl, —Oheterocyclyl, —$S(O)_{0-2}$aryl, —$S(O)_{0-2}$hetaryl, —$S(O)_{0-2}$heterocyclyl, —$S(O)_{0-2}C_{0-8}$alkyl, —N$(C_{0-8}$alkyl)$(C_{0-8}$alkyl), —N$(C_{0-8}$alkyl)CON$(C_{0-8}$alkyl)$(C_{0-8}$alkyl), —N$(C_{0-8}$alkyl)CO$(C_{1-8}$alkyl), —N$(C_{0-8}$alkyl)CO$(C_{3-8}$cycloalkyl), —N$(C_{0-8}$alkyl)CO$_2(C_{1-8}$alkyl)-S$(O)_{1-2}$N$(C_{0-8}$alkyl)$(C_{0-8}$alkyl), —$NR^{11}$S$(O)_{1-2}(C_{0-8}$alkyl), —CON$(C_{3-8}$cycloalkyl)$(C_{3-8}$cycloalkyl), —CON$(C_{0-8}$alkyl)$(C_{3-8}$cycloalkyl), —N$(C_{3-8}$cycloalkyl)CON$(C_{0-8}$alkyl)$(C_{0-8}$alkyl), —N$(C_{3-8}$cycloalkyl)CON$(C_{3-8}$cycloalkyl)$(C_{0-8}$alkyl), —N$(C_{0-8}$alkyl)CON$(C_{3-8}$cyclyoalkyl)$(C_{0-8}$alkyl), —N$(C_{0-8}$alkyl)CO$_2(C_{3-8}$cycloalkyl), —N$(C_{3-8}$cyclyoalkyl)CO$_2(C_{3-8}$cycloalkyl), S$(O)_{1-2}$N$(C_{0-8}$alkyl)$(C_{3-8}$cycloalkyl), —$NR^{11}$S$(O)_{1-2}(C_{3-8}$cyclyoalkyl), $C_{2-8}$alkenyl, $C_{2-8}$alkynyl, CN, $CF_3$, OH, or optionally substituted aryl substituents; such that each of the above aryl, heterocyclyl, hetaryl, alkyl or cyclyoalkyl groups may be optionally, independently substituted with —N$(C_{0-8}$alkyl)$(C_{0-8}$alkyl), hydroxyl, halogen, oxo, aryl, hetaryl, $C_{0-6}$alkyl, $C_{0-8}$alkylcyclyl, —$C_{0-8}$alkyl-N$(C_{0-8}$alkyl)S$(O)_{0-2}$—$(C_{0-8}$alkyl), —$C_{0-8}$alkyl-S$(O)_{0-2}$—N$(C_{0-8}$alkyl)$(C_{0-8}$alkyl), —$C_{0-8}$alkyl-N$(C_{0-8}$alkyl)CO$(C_{0-8}$alkyl), —$C_{0-8}$alkyl-N$(C_{0-8}$alkyl)CO—N$(C_{0-8}$alkyl)$(C_{0-8}$alkyl), —$C_{0-8}$alkyl-CO—N$(C_{0-8}$alkyl)$(C_{0-8}$alkyl), —$C_{1-8}$alkyl-CO$_2$—$(C_{0-8}$alkyl), —$C_{0-8}$alkylS$(O)_{0-2}$—$(C_{0-8}$alkyl), —$C_{0-8}$alkyl-O—$C_{1-8}$alkyl, —$C_{0-8}$ alkyl-O—$C_{0-8}$alkylcyclyl, —$C_{0-8}$alkyl-O—$C_{0-8}$alkyl-heterocyclyl, —$C_{0-8}$alkyl-O—$C_{0-8}$alkylaryl, —$C_{0-8}$ alkyl-O—$C_{0-8}$alkylhetaryl, —$C_{0-8}$alkyl-S—$C_{0-8}$alkyl, —$C_{0-8}$alkyl-S—$C_{0-8}$alkylcyclyl, —$C_{0-8}$alkyl-S—$C_{0-8}$alkylheterocyclyl, —$C_{0-8}$alkyl-S—$C_{0-8}$alkylaryl, —$C_{0-8}$ alkyl-S—$C_{0-8}$alkylhetaryl, —$C_{0-8}$alkyl-N($C_{0-8}$alkyl)-$C_{0-8}$, —$C_{0-8}$alkyl-N($C_{0-8}$alkyl)-$C_{0-8}$alkylcyclyl, —$C_{0-8}$ alkyl-N($C_{0-8}$alkyl)-$C_{0-8}$alkylheterocyclyl, —$C_{0-8}$ alkyl-N($C_{0-8}$alkyl)-$C_{0-8}$ alkylaryl, —$C_{0-8}$alkyl-N($C_{0-8}$alkyl)-$C_{0-8}$alkylhetaryl, $C_{2-8}$alkenyl, $C_{2-8}$alkynyl, $NO_2$, CN, $CF_3$, $OCF_3$, $OCHF_2$, —$C_{0-8}$alkyl-$C_{3-8}$cycloalkyl, —$C_{0-8}$alkyl-O—$C_{0-8}$alkyl, —$C_{0-8}$alkyl-N($C_{0-8}$alkyl)($C_{0-8}$alkyl), —$C_{0-8}$alkyl-$SO_{0-2}C_{0-8}$alkyl, or heterocyclyl optionally substituted with 1-4 independent $C_{0-8}$alkyl, cyclyl, or substituted cyclyl substituents;

$E^1$ in each instance is independently halo, —$CF_3$, —$OCF_3$, —$OR^2$, —$NR^{31}R^{32}$, —C(=O)$R^{31}$, —$CO_2R^{31}$, —$CONR^{31}R^{32}$, —$NO_2$, —CN, —S(O)$_{0-2}R^{31}$, —S(O)$_{0-2}NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{31}$)$SR^{31}$, —OC(=O)$OR^{31}$, —OC(=O)$NR^{31}R^{32}$, —OC(=O)$SR^{31}$, —SC(=O)$OR^{31}$, —SC(=O)$NR^{31}R^{32}$, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{0-10}$alkyl, -heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{31}$, —$NR^{31}R^{32}$, —C(=O)$R^{31}$, —$CO_2R^{31}$, —C(=O)$NR^{31}R^{32}$, —$NO_2$, —CN, —S(=O)$_{0-2}R^{31}$, —$SO_2NR^{31}$, —$NR^{31}$C(=O)$R^{32}$, —$NR^{31}$C(=O)$OR^{31}$, —$NR^{31}$C(=O)$NR^{32}R^{33}$, —$NR^{31}$S(O)$_{0-2}R^{31}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{32}$)$SR^{33}$, —OC(=O)$OR^{31}$, —OC(=O)$NR^{31}R^{32}$, —OC(=O)$SR^{31}$, or —SC(=O)$NR^{31}R^{32}$ substituents;

or $E^1$ in each instance is independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —S(O)$_{0-2}NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{31}$, —$NR^{31}$C(=$NR^{32}$)$OR^{33}$, —$NR^{31}$C(=$NR^{32}$)$SR^{33}$, —OC(=O)$OR^{31}$, —OC(=O)$NR^{31}R^{32}$, —OC(=O)$SR^{31}$, —SC(=O)$OR^{31}$, or —SC(=O)$NR^{31}R^{32}$ substituents;

in the cases of —$NR^{13}R^{32}$, —$NR^{311}R^{321}$, —$NR^{312}R^{322}$, —$NR^{332}R^{341}$, —$NR^{313}R^{323}$, and —$NR^{323}R^{333}$, the respective $R^{31}$ and $R^{32}$, $R^{311}$ and $R^{321}$, $R^{312}$ and $R^{322}$, $R^{331}$ and $R^{341}$, $R^{313}$ and $R^{323}$, and $R^{323}$ and $R^{333}$ are optionally taken together with the nitrogen atom to which they are attached to form a 3-10 membered saturated or unsaturated ring; wherein said ring in each instance independently is optionally substituted by one or more independent —N($C_{0-8}$alkyl)($C_{0-8}$alkyl), hydroxyl, halogen, oxo, aryl, hetaryl, $C_{0-6}$alkyl, —$C_{0-8}$alkyl$C_{3-8}$cycloalkyl, —$C_{0-8}$alkyl-N($C_{0-8}$alkyl)S(O)$_{0-2}C_{0-8}$alkyl, —$C_{0-8}$alkyl-N($C_{0-8}$alkyl)S(O)$_{0-2}$N($C_{0-8}$alkyl)($C_{0-8}$alkyl), —$C_{0-8}$alkyl-N($C_{0-8}$alkyl)$CO_2$($C_{0-8}$alkyl), —$C_{0-8}$alkyl-CON(($C_{0-8}$alkyl))S(O)$_{0-2}$($C_{0-8}$alkyl), —$C_{0-8}$alkyl-S(O)$_{0-2}$N($C_{0-8}$ alkyl)($C_{0-8}$alkyl), —$C_{0-8}$alkyl-N($C_{0-8}$alkyl)CO($C_{0-8}$ alkyl), —$C_{0-8}$alkyl-N($C_{0-8}$alkyl)CON($C_{0-8}$alkyl)($C_{0-8}$alkyl), —$C_{0-8}$alkyl-CON($C_{0-8}$alkyl)($C_{0-8}$alkyl), —$C_{0-8}$alkyl $CO_2$($C_{0-8}$alkyl), —$C_{0-8}$alkyl S(O)$_{0-2}$($C_{0-8}$alkyl), —$C_{0-8}$alkyl-O—$C_{0-8}$alkyl-$C_{0-8}$alkyl-O—$C_{0-8}$alkylcyclyl, —$C_{0-8}$alkyl-O—$C_{0-8}$alkylheterocyclyoalkyl, —$C_{0-8}$alkyl-O—$C_{0-8}$alkylaryl, —Oaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, $C_{0-8}$alkyl-N($C_{0-8}$alkyl)-$C_{0-8}$alkyl, —$C_{0-8}$alkyl-N($C_{0-8}$alkyl)-$C_{0-8}$alkyl$C_{3-8}$cycloalkyl, —$C_{0-8}$alkyl-N($C_{0-8}$alkyl)-$C_{0-8}$ alkylheterocycloalkyl, —$C_{0-8}$alkyl-N($C_{0-8}$alkyl), —$C_{0-8}$alkylaryl, —$C_{0-8}$alkyl-N($C_{0-8}$alkyl)-$C_{0-8}$alkylhetaryl, —$C_{0-8}$alkyl-N($C_{0-8}$alkyl)($C_{0-8}$alkyl) $C_{2-8}$alkenyl, $C_{2-8}$alkynyl, $NO_2$, CN, $CF_3$, $OCF_3$, or $OCHF_2$, substituents; wherein said ring in each instance independently optionally includes one or more heteroatoms other than the nitrogen;

m is 0, 1, 2, or 3:

n is 0, 1, 2, 3, or 4:

aa is 0 or 1; and provided that Formula I is not trans-4-[8-amino-1-(7-chloro-4-hydroxy-1H-indol-2-yl)imidazo[1,5-a]pyrazin-3-yl]cyclohexanecarboxylic acid, cis-3-[8-amino-1-(7-chloro-1H-indol-2-yl)imidazo[1,5-a]pyrazin-3-yl]cyclobutanecarboxylic acid, trans-4-{8-amino-1-[7-(3-isopropyl)phenyl-1H-indol-2-yl]imidazo[1,5-a]pyrazin-3-yl}cyclohexanecarboxylic acid or trans-4-{8-amino-1-[7-(2,5-dichloro)phenyl-1H-indol-2-yl]imidazo[1,5-a]pyrazin-3-yl}cyclohexanecarboxylic acid.

17. The method of claim 16, wherein the EGFR kinase inhibitor comprises erlotinib, or a salt thereof.

18. The method of claim 16, additionally comprising administering to said subject one or more other anti-cancer agents.

19. A method for treating tumors or tumor metastases in a patient, comprising administering to said patient simultaneously or sequentially a synergistically effective therapeutic amount of a combination of an EGFR kinase inhibitor and an mTOR inhibitor that binds to and directly inhibits both mTORC1 and mTORC2 kinases, and is a compound represented by Formula (I),

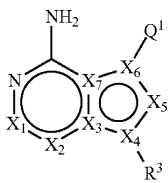

(I)

or a pharmaceutically acceptable salt thereof, wherein:

$X_1$, and $X_2$ are each independently N or C-$(E^1)_{aa}$;

$X_5$ is N, C-$(E^1)_{aa}$, or N-$(E^1)_{aa}$;

$X_3$, $X_4$, $X_6$, and $X_7$ are each independently N or C;

wherein at least one of $X_3$, $X_4$, $X_5$, $X_6$, and $X_7$ is independently N or N-$(E^1)_{aa}$;

$R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;

$Q^1$ is -A($R^1$)$_m$B(W)$_n$ or —B($G^{11}$)$_n$A(Y)$_m$;

A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;

or $Q^1$ is -A($R^1$)$_m$A(Y)$_m$, wherein each A is the same or different 5-membered aromatic or heteroaromatic ring, and the two are fused together to form an 8-membered heteroaromatic system;

$R^1$ is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, $C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-S(O)$_{0-8}$NR$^{311}$R$^{321}$, —$C_{0-8}$alkyl-NR$^{311}$COR$^{321}$, —$C_{0-8}$alkyl-NR$^{311}$CO$_2$R$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CON(R$^{311}$)S(O)$_{0-2}$R$^{321}$, —$C_{0-8}$alkyl-CO$_2$R$^{311}$, —$C_{0-8}$alkyl-S(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocyclyl, —$C_{0-8}$alkyl-O—$C_{0-8}$alkylaryl, —$C_{0-8}$alkylaryl, —$C_{0-8}$alkylhetaryl, —$C_{0-8}$ alkylheterocyclyl, —$C_{0-8}$alkyl-O—$C_{0-8}$ alkylhetaryl, —$C_{0-8}$alkyl-S—$C_{0-8}$alkyl, —$C_{0-8}$ alkyl-S—$C_{0-8}$alkyl$C_{3-8}$cycloalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$ alkyl-N(R$^{311}$)—$C_{0-8}$alkyl$C_{3-8}$cyclyoalkyl, —$C_{0-8}$ alkyl-N(R$^{311}$)—$C_{0-8}$alkylheterocyclyl, —$C_{0-8}$ alkyl-N(R$^{311}$)—$C_{0-8}$alkylaryl, —$C_{0-8}$alkyl-N(R$^{311}$)—$C_{0-8}$ alkylhetaryl, —$C_{0-8}$alkyl-NR$^{311}$R$^{321}$, —$C_{2-8}$ alkenyl, —$C_{2-8}$alkynyl, NO$_2$, CN, CF$_3$, OCF$_3$, OCHF$_2$; provided that $Q^1$ is not N-methyl-2-indolyl, N-(phenylsulfonyl)-2-indolyl, or N-tert-butoxycarbonyl W is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, $C_{0-8}$alkyl-NR$^{312}$S(O)$_{0-2}$R$^{322}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{312}$R$^{322}$, —$C_{0-8}$alkyl-NR$^{312}$COR$^{322}$, —$C_{0-8}$alkyl-NR$^{311}$CONR$^{322}$R$^{332}$, —$C_{0-8}$alkyl-CONR$^{312}$R$^{322}$, —$C_{0-8}$alkyl-CO$_2$R$^{312}$, —$C_{0-8}$alkylS(O)$_{0-2}$R$^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocyloalkyl, —$C_{0-8}$alkyl-O—$C_{0-8}$alkylaryl, —Oaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocyloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{312}$)—$C_{0-8}$alkyl, —$C_{0-8}$alkyl-N(R$^{312}$)—$C_{0-8}$alkyl$C_{3-8}$cyclyoalkyl, —$C_{0-8}$alkyl-N(R$^{312}$)—$C_{0-8}$alkylheterocycloalkyl, —$C_{0-8}$alkyl-N(R$^{312}$)—$C_{0-8}$alkylaryl, —$C_{0-8}$alkyl-N(R$^{312}$)—$C_{0-8}$alkylhetaryl, —$C_{0-8}$alkyl-NR$^{312}$R$^{322}$, —$C_{2-8}$alkenyl, —$C_{2-8}$alkynyl, NO$_2$, CN, CF$_3$, OCF$_3$, OCHF$_2$; provided that $Q^1$ is not 4-benzyloxy-2-indolyl;

Y is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{0-6}$alkyl, —$C_{0-8}$alkyl$C_{3-8}$cycloalkyl, —$C_{0-8}$alkyl-NR$^{311}$SO$_{0-2}$R$^{321}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CO$_2$R$^{311}$, —$C_{0-8}$alkylS(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$ alkylheterocycloalkyl, —$C_{0-8}$alkyl-S—$C_{0-8}$alkaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkyl$C_{3-8}$cycloalkyl, —$C_{0-8}$alkyl-N(R$^{311}$)—$C_{0-8}$ alkylheterocycloalkyl, —$C_{0-8}$alkyl-N(R$^{311}$)—$C_{0-8}$ alkylaryl, —$C_{0-8}$alkyl-N(R$^{311}$)—$C_{0-8}$alkylhetaryl, —$C_{0-8}$alkyl-NR$^{311}$R$^{321}$, —$C_{0-8}$alkenyl, —$C_{2-8}$alkynyl, NO$_2$, CN, CF$_3$, OCF$_3$, OCHF$_2$; provided that $Q^1$ is not 2-carboxy-5-benzo[b]thiophenyl;

$G^{11}$ is halo, oxo, —CF$_3$, —OCF$_3$, —OR$^{312}$, —NR$^{312}$R$^{322}$, —C(O)R$^{312}$—CO)$_{3-8}$cycloalkyl, —CO$_2$C$_{3-8}$cycloalkyl, —CO$_2$R$^{312}$, —C(=O)NR$^{312}$R$^{322}$, —NO$_2$, —CN, —S(O)$_{0-2}$R$^{312}$, —SO$_2$NR$^{312}$R$^{322}$, NR$^{312}$(C=O)R$^{322}$, NR$^{312}$C(=O)OR$^{322}$, NR$^{312}$C(=O)NR$^{322}$R$^{332}$, NR$^{312}$S(O)$_{0-2}$R$^{322}$, C(=S)OR$^{312}$, —C(=O)SR$^{312}$, —NR$^{312}$C(=NR$^{322}$)NR$^{332}$R$^{341}$, —NR$^{312}$C(=NR$^{322}$)OR$^{332}$, —NR$^{312}$C(=NR$^{322}$)SR$^{332}$, —OC(=O)OR$^{312}$, —OC(=O)NR$^{312}$R$^{322}$, —OC(=O)SR$^{312}$, —SC(=O)OR$^{312}$, —SC(=O)NR$^{312}$R$^{322}$, —P(O)OR$^{312}$OR$^{322}$, $C_{1-10}$alkylidene, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cycloC$_{3-8}$alkenylC$_{1-10}$alkyl, -cycloC$_{3-8}$alkylC$_{2-10}$alkenyl, -cycloC$_{3-8}$alkenylC$_{2-10}$alkenyl, -cycloC$_{3-8}$alkylC$_{2-10}$alkynyl, -cycloC$_{3-8}$alkenylC$_{2-10}$alkynyl, -heterocyclyl-C$_{0-10}$alkyl, heterocyclyl-C$_{2-10}$alkenyl, or -heterocyclyl-C$_{2-10}$alkynyl, any of which is optionally substituted with one or more independent halo, oxo, —CF$_3$, —OCF$_3$, —OR$^{313}$, —NR$^{313}$R$^{323}$, —C(O)R$^{313}$, —CO$_2$R$^{313}$, —C(=O)NR$^{313}$R$^{323}$, —NO$_2$, —CN, —S(O)$_{0-2}$R$^{313}$, —SO$_2$NR$^{313}$R$^{323}$, —NR$^{313}$C=)R$^{323}$, NR$^{313}$C(=O)OR$^{323}$, —R$^{313}$C(=O)R$^{323}$R$^{333}$, —NR$^{313}$S(O)$_{0-2}$R$^{323}$, —C(=S)OR$^{313}$, —C(=O)SR$^{313}$, —NR$^{313}$C(=NR$^{323}$)NR$^{333}$R$^{342}$, —NR$^{313}$C(=NR$^{323}$)OR$^{333}$, —NR$^{313}$C(=NR$^{323}$)SR$^{333}$, —OC(=O)OR$^{333}$, —OC(=O)NR$^{313}$R$^{323}$, —OC(=O)SR$^{313}$, —SC(=O)OR$^{313}$, —P(O)OR$^{313}$R$^{323}$, or —SC(=O)NR$^{313}$R$^{323}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, where the attachment point is from either the left or right as written, where any of which is optionally substituted with one or more independent halo, —CF$_3$, —OCF$_3$, —OR$^{313}$, —NR$^{313}$R$^{323}$, —C(O)R$^{313}$, —CO$_2$R$^{313}$, —C(=O)NR$^{313}$R$^{323}$, —NO$_2$, —CN, —S(O)$_{0-2}$R$^{313}$, —SO$_2$NR$^{313}$R$^{323}$, —NR$^{311}$C(=O)R$^{323}$, —NR$^{313}$C(=O)OR$^{323}$, —NR$^{313}$C(=O)NR$^{323}$R$^{333}$, —NR$^{313}$S(O)$_{0-2}$R$^{333}$, —C(=S)OR$^{313}$, —C(=O)SR$^{313}$, —NR$^{323}$C(=NR$^{313}$)NR$^{333}$R$^{342}$, —NR$^{313}$C(=NR$^{323}$)OR$^{333}$, —NR$^{313}$C(=NR$^{323}$)SR$^{333}$, —OC(=O)OR$^{313}$, —OC(=O)NR$^{313}$R$^{323}$, —OC(=O)SR$^{313}$, —SC(=O)OR$^{313}$, —P(O)OR$^{313}$OR$^{323}$, or —SC(=O)NR$^{313}$R$^{323}$ substituents; provided that G$^{11}$ is not N—CH$_2$CO$_2$H when R$^3$ is 4-piperidinyl;

R$^{31}$, R$^{32}$, R$^{33}$, R$^{311}$, R$^{321}$, R$^{331}$, R$^{312}$, R$^{322}$, R$^{332}$, R$^{341}$, R$^{313}$, R$^{323}$, R$^{333}$, and R$^{342}$, in each instance, is independently C$_{0-8}$alkyl optionally substituted with an aryl, heterocyclyl or hetaryl substituent, or C$_{0-8}$alkyl optionally substituted with 1-6 independent halo, —CON(C$_{0-8}$alkyl)(C$_{0-8}$alkyl), —CO(C$_{0-8}$alkyl), —OC$_{0-8}$alkyl, —Oaryl, —Ohetaryl, —Oheterocyclyl, —S(O)$_{0-2}$aryl, —S(O)$_{0-2}$hetaryl, —SO$_{0-2}$heterocyclyl, S(O)$_{0-2}$C$_{0-8}$alkyl, —N(C$_{0-8}$alkyl)(C$_{0-8}$alkyl), —N(C$_{0-8}$alkyl)CON(C$_{0-8}$alkyl)(C$_{0-8}$alkyl), —N(C$_{0-8}$alkyl)CO(C$_{1-8}$alkyl), —N(C$_{0-8}$alkyl)CO(C$_{3-8}$cycloalkyl), —N(C$_{0-8}$alkyl)CO$_2$(C$_{1-8}$alkyl), —S(O)$_{1-2}$N(C$_{0-8}$alkyl)(C$_{0-8}$alkyl), —NR$^{11}$S(O)$_{1-2}$(C$_{0-8}$alkyl), —CON(C$_{3-8}$cycloalkyl)(C$_{3-8}$cycloalkyl), —CON(C$_{0-8}$alkyl)(C$_{3-8}$cyclyoalkyl), —N(C$_{3-8}$cycloalkyl)CON(C$_{0-8}$alkyl)(C$_{0-8}$alkyl), —N(C$_{3-8}$cycloalkyl)CON(C$_{3-8}$cycloalkyl)(C$_{0-8}$alkyl), —N(C$_{0-8}$alkyl)CON(C$_{3-8}$cycloalkyl)(C$_{0-8}$alkyl), —N(C$_{0-8}$alkyl)CO$_2$(C$_{3-8}$cycloalkyl), —N(C$_{3-8}$cycloalkyl)CO$_2$(C$_{3-8}$cycloalkyl), S(O)$_{1-2}$N(C$_{0-8}$alkyl)(C$_{3-8}$ cycloalkyl), —NR$^{11}$S(O)$_{1-2}$(C$_{3-8}$cycloalkyl), C$_{2-8}$alkenyl, C$_{2-8}$alkynyl, CN, CF$_3$, OH, or optionally substituted aryl substituents; such that each of the above aryl, heterocyclyl, hetaryl, alkyl or cycloalkyl groups may be optionally, independently substituted with —N(C$_{0-8}$alkyl)(C$_{0-8}$alkyl), hydroxyl, halogen, oxo, aryl, hetaryl, C$_{0-6}$alkyl, C$_{0-8}$alkylcyclyl, —C$_{0-8}$alkyl-N(C$_{0-8}$alkyl)-S(O)$_{0-2}$C$_{0-8}$alkyl), —C$_{0-8}$alkyl-S(O)$_{0-2}$—N(C$_{0-8}$alkyl)(C$_{0-8}$alkyl), —C$_{0-8}$alkyl-N(C$_{0-8}$alkyl)CO(C$_{0-8}$alkyl), —C$_{0-8}$alkyl-N(C$_{0-8}$alkyl)CO—N(C$_{0-8}$alkyl)(C$_{0-8}$alkyl), —C$_{0-8}$alkyl-CO—N(C$_{0-8}$alkyl)(C$_{0-8}$alkyl), —C$_{1-8}$alkyl-CO$_2$—(C$_{0-8}$alkyl), —C$_{0-8}$alkylS(O)$_{0-2}$—(C$_{0-8}$alkyl), —C$_{0-8}$alkyl-O—C$_{1-8}$alkyl, —C$_{0-8}$alkyl-O—C$_{0-8}$alkylcyclyl, —C$_{0-8}$alkyl-O—C$_{0-8}$ alkyl-heterocyclyl, —C$_{0-8}$alkyl-O—C$_{0-8}$alkylaryl, —C$_{0-8}$alkyl-O—C$_{0-8}$alkylhetaryl, —C$_{0-8}$alkyl-S—C$_{0-8}$alkyl, —C$_{0-8}$alkyl-S—C$_{0-8}$alkylcyclyl, —C$_{0-8}$alkyl-S—C$_{0-8}$alkylheterocyclyl, —C$_{0-8}$alkyl-S—C$_{0-8}$alkylaryl, —C$_{0-8}$ alkyl-S—C$_{0-8}$alkylhetaryl, —C$_{0-8}$alkyl-N(C$_{0-8}$alkyl), —C$_{0-8}$alkyl, —C$_{0-8}$alkyl-N(C$_{0-8}$alkyl)-C$_{0-8}$alkylcyclyl, —C$_{0-8}$alkyl-N(C$_{0-8}$alkyl)-C$_{0-8}$alkylheterocyclyl, —C$_{0-8}$alkyl-N(C$_{0-8}$alkyl)-C$_{0-8}$alkylaryl, —C$_{0-8}$alkyl-N(C$_{0-8}$alkyl)-C$_{0-8}$alkylhetaryl, C$_{2-8}$alkenyl, C$_{2-8}$alkynyl, NO$_2$, CN, CF$_3$, OCF$_3$, OCHF$_2$, —C$_{0-8}$alkyl-C$_{3-8}$cycloalkyl, —C$_{0-8}$alkyl-O—C$_{0-8}$alkyl, —C$_{0-8}$alkyl-N(C$_{0-8}$alkyl)(C$_{0-8}$alkyl), —C$_{0-8}$alkyl-S(O)$_{0-2}$—C$_{0-8}$alkyl, or heterocyclyl optionally substituted with 1-4 independent C$_{0-8}$alkyl, cyclyl, or substituted cyclyl substituents;

E$^1$ in each instance is independently halo, —CF$_3$, —OCF$_3$, —OR$^2$, —NR$^{31}$R$^{32}$, —C(=O)R$^{31}$, —CO$_2$R$^{31}$, —CONR$^{31}$R$^{32}$, —NO$_2$, —CN, —S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{31}$)SR$^{31}$, —OC(=O)OR$^{31}$, —OC(=O)NR$^{31}$R$^{32}$, —OC(=O)SR$^{31}$, —SC(=O)OR$^{31}$, —SC(=O)NR$^{31}$R$^{32}$, C$_{0-10}$alkyl, C$_{2-10}$alkenyl, C$_{2-10}$alkynyl, —C$_{1-10}$alkoxyC$_{1-10}$alkyl, —C$_{1-10}$alkoxyC$_{2-10}$alkenyl, —C$_{1-10}$alkoxyC$_{2-10}$alkynyl, —C$_{1-10}$alkylthioC$_{1-10}$alkyl, —C$_{1-10}$alkylthioC$_{2-10}$alkenyl, —C$_{1-10}$alkylthioC$_{2-10}$alkynyl, cycloC$_{3-8}$alkyl, cycloC$_{3-8}$alkenyl, -cycloC$_{3-8}$alkylC$_{1-10}$alkyl, -cycloC$_{3-8}$alkenylC$_{1-10}$alkyl, -cycloC$_{3-8}$alkylC$_{2-10}$alkenyl, -cycloC$_{3-8}$alkenylC$_{2-10}$alkenyl, -cycloC$_{3-8}$alkylC$_{2-10}$alkynyl, -cycloC$_{3-8}$alkenylC$_{2-10}$alkynyl, -heterocyclyl-C$_{0-10}$alkyl, -heterocyclyl-C$_{2-10}$alkenyl, or -heterocyclyl-C$_{2-10}$alkynyl, any of which is optionally substituted with one or more independent halo, oxo, —CF$_3$, —OCF$_3$, —OR$^{31}$, —NR$^{31}$R$^{32}$, —C(=O)R$^{31}$, —CO$_2$R$^{31}$, —C(=O)NR$^{31}$R$^{32}$, —NO$_2$, —CN, —S(=O)$_{0-2}$R$^{31}$—SO$_2$NR$^{31}$, —NR$^{31}$C(=O)R$^{32}$, —NR$^{31}$C(=O)OR$^{31}$, —NR$^{31}$C(=O)NR$^{32}$R$^{33}$, —NR$^{31}$S(O)$_{0-2}$R$^{31}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

or E$^1$ in each instance is independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, where the attachment point is from either the left or right as written, where any of which is optionally substituted with one or more independent halo, —CF, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

in the cases of —NR$^{31}$R$^{32}$, —NR$^{311}$R$^{321}$, —NR$^{312}$R$^{222}$, —NR$^{332}$R$^{341}$, —NR$^{313}$R$^{323}$, and —NR$^{323}$R$^{333}$, the respective R$^{31}$ and R$^{32}$, R$^{311}$ and R$^{321}$, R$^{312}$ and R$^{322}$, R$^{331}$ and R$^{341}$, R$^{313}$ and R$^{323}$, and R$^{323}$ and R$^{333}$ are optionally taken together with the nitrogen atom to which they are attached to form a 3-10 membered saturated or unsaturated ring; wherein said ring in each instance independently is optionally substituted by one or more independent —N($C_{0-8}$alkyl)($C_{0-8}$alkyl), hydroxyl, halogen, oxo, aryl, hetaryl, $C_{0-6}$alkyl, —$C_{0-8}$alkyl$C_{3-8}$cycloalkyl, —$C_{0-8}$alkyl-N($C_{0-8}$alkyl)S(O)$_{0-2}$$C_{0-8}$alkyl, —$C_{0-8}$alkyl-N($C_{0-8}$alkyl)S(O)$_{0-2}$N($C_{0-8}$alkyl)($C_{0-8}$alkyl), —$C_{0-8}$alkyl-N($C_{0-8}$alkyl)CO$_2$($C_{0-8}$alkyl), —$C_{0-8}$—CON(($C_{0-8}$alkyl))S(O)$_{0-2}$($C_{0-8}$alkyl), —$C_{0-8}$alkyl-S(O)$_{0-2}$N($C_{0-8}$ alkyl)($C_{0-8}$alkyl), —$C_{0-8}$alkyl-N($C_{0-8}$alkyl)CO($C_{0-8}$ alkyl), —$C_{0-8}$alkyl-N($C_{0-8}$alkyl)CON($C_{0-8}$ alkyl)($C_{0-8}$alkyl), —$C_{0-8}$alkyl-CON($C_{0-8}$alkyl)($C_{0-8}$ alkyl), —$C_{0-8}$alkyl-CO$_2$($C_{0-8}$alkyl), —$C_{0-8}$alkylS(O)$_{0-2}$($C_{0-8}$alkyl), —$C_{0-8}$alkyl-O—$C_{0-8}$alkyl, —$C_{0-8}$ alkyl-O—$C_{0-8}$alkylcyclyl, —$C_{0-8}$alkyl-O—$C_{0-8}$ alkylheterocycloalkyl, —$C_{0-8}$alkyl-O—$C_{0-8}$ alkylaryl, —Oaryl, —$C_{0-8}$alkyl-O—$C_{0-8}$ alkylhetaryl, —$C_{0-8}$alkyl-S—$C_{0-8}$alkyl, —$C_{0-8}$ alkyl-S—$C_{0-8}$ alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$ alkyl-S—$C_{0-8}$alkylhetaryl, —$C_{0-8}$alkyl-N($C_{0-8}$ alkyl)-$C_{0-8}$alkyl, —$C_{0-8}$alkyl-N($C_{0-8}$alkyl)-$C_{0-8}$ alkyl$C_{3-8}$cycloalkyl, —$C_{0-8}$alkyl-N($C_{0-8}$alkyl)-$C_{0-8}$ alkylheterocycloalkyl, —$C_{0-8}$alkyl-N($C_{0-8}$alkyl)-$C_{0-8}$ alkylaryl, —$C_{0-8}$alkyl-N($C_{0-8}$alkyl)-$C_{0-8}$alkylhetaryl, —$C_{0-8}$alkyl-N($C_{0-8}$alkyl)($C_{0-8}$alkyl), $C_{2-8}$alkenyl, $C_{2-8}$alkynyl, NO$_2$, CN, CF$_3$, OCF$_3$, or OCHF$_2$ substituents; wherein said ring in each instance independently optionally includes one or more heteroatoms other than the nitrogen;

m is 0, 1, 2, or 3;
n is 0, 1, 2, 3, or 4:
aa is 0 or 1; and
provided that Formula I is not
trans-4-[8-amino-1-(7-chloro-4-hydroxy-1H-indol-2-yl)imidazo[1,5-a]pyrazin-3-yl]cyclohexanecarboxylic acid,
cis-3-[8-amino-1-(7-chloro-1H-indol-2-yl)imidazo[1,5-a]pyrazin-3-yl]cyclobutanecarboxylic acid,
trans-4-{8-amino-1-[7-(3-isopropyl)phenyl-1H-indol-2-yl]imidazo[1,5-a]pyrazin-3-yl}cyclohexanecarboxylic acid or
trans-4-{8-amino-1-[7-(2,5-dichloro)phenyl-1H-indol-2-yl]imidazo[1,5-a]pyrazin-3-yl}cyclohexanecarboxylic acid.

20. The method of claim 19, wherein the EGFR kinase inhibitor comprises erlotinib, or a salt thereof.

21. The method of claim 19, additionally comprising administering to said subject one or more other anti-cancer agents.

22. The method of claim 1, wherein the cells of the tumors or tumor metastases are relatively insensitive or refractory to treatment with an EGFR inhibitor as a single agent.

23. The method of claim 16, wherein the cancer is relatively insensitive or refractory to treatment with an EGFR inhibitor as a single agent.

24. The method of claim 19, wherein the cells of the tumors or tumor metastases are relatively insensitive or refractory to treatment with an EGFR inhibitor as a single agent.

25. The method of claim 1, wherein the patient is in need of treatment for a cancer selected from NSCLC, head and neck squamous cell carcinoma, melanoma, pancreatic, breast and ovarian cancers.

26. The method of claim 25, wherein the EGFR kinase inhibitor comprises erlotinib, or a salt thereof.

27. The method of claim 16, wherein the cancer is selected from NSCLC, head and neck squamous cell carcinoma, melanoma, pancreatic, breast and ovarian cancers.

28. The method of claim 19, wherein the patient is in need of treatment for a cancer selected from NSCLC, head and neck squamous cell carcinoma, melanoma, pancreatic, breast and ovarian cancers.

29. The method of claim 1, wherein the compound represented by Formula (I) comprises:

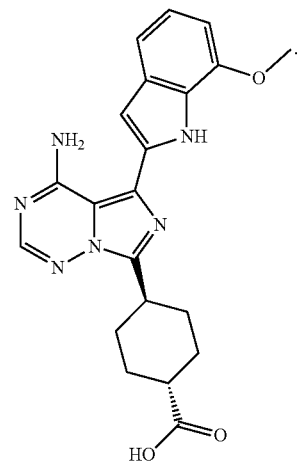 [SMILES: COc1cccc2cc(-c3nc([C@H]4CC[C@H](C(=O)O)CC4)n4ncnc(N)c34)[nH]c12]

30. The method of claim 16, wherein the compound represented by Formula (I) comprises:

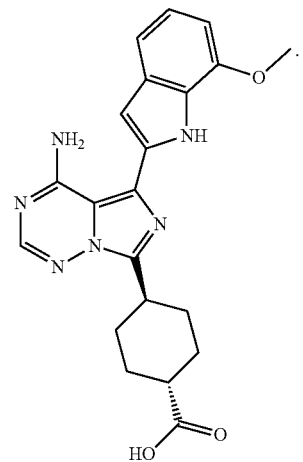 [SMILES: COc1cccc2cc(-c3nc([C@H]4CC[C@H](C(=O)O)CC4)n4ncnc(N)c34)[nH]c12]

31. The method of claim 19, wherein the compound represented by Formula (I) comprises:
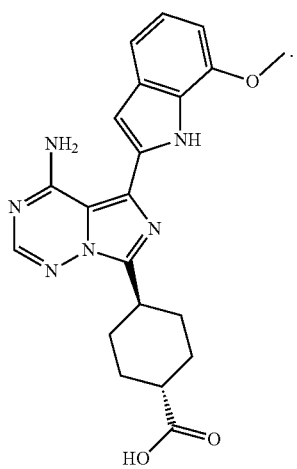
32. The method of claim 1, wherein the compound represented by Formula (I) comprises:
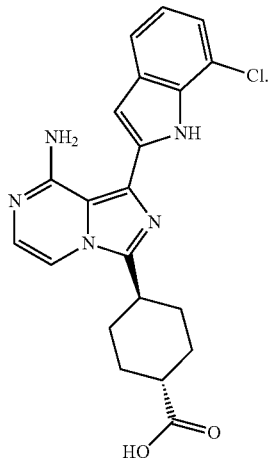 [SMILES: Nc1nccn2c1c(-c1cc3cccc(Cl)c3[nH]1)nc2[C@H]1CC[C@H](C(=O)O)CC1]
33. The method of claim 16, wherein the compound represented by Formula (I) comprises:
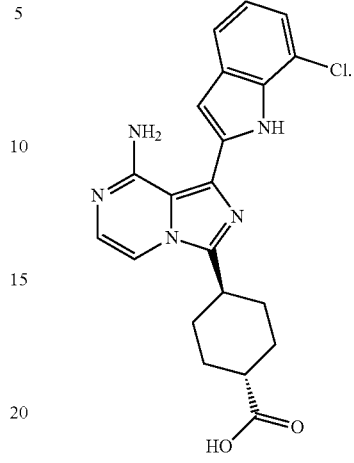
34. The method of claim 19, wherein the compound represented by Formula (I) comprises:
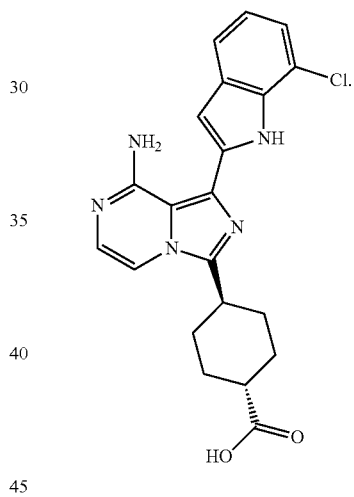
* * * * *